United States Patent
Cao et al.

(10) Patent No.: US 9,662,327 B2
(45) Date of Patent: May 30, 2017

(54) PHENYL AND PYRIDINYL SUBSTITUTED PIPERIDINES AND PIPERAZINES AS INHIBITORS OF IDH1 MUTANTS AND THEIR USE IN TREATING CANCER

(75) Inventors: Sheldon Cao, San Diego, CA (US); Janeta Popovici-Muller, Windham, NH (US); Francesco G. Salituro, Marlborough, MA (US); Jeffrey O. Saunders, Lincoln, MA (US); Xuefei Tan, Shanghai (CN); Jeremy Travins, Southborough, MA (US); Shunqi Yan, Irvine, CA (US); Zhixiong Ye, West Windsor, NJ (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 320 days.

(21) Appl. No.: 14/126,791

(22) PCT Filed: Jun. 18, 2012

(86) PCT No.: PCT/CN2012/077096
§ 371 (c)(1),
(2), (4) Date: Mar. 14, 2014

(87) PCT Pub. No.: WO2012/171506
PCT Pub. Date: Dec. 20, 2012

(65) Prior Publication Data
US 2014/0206673 A1 Jul. 24, 2014

Related U.S. Application Data

(60) Provisional application No. 61/584,209, filed on Jan. 6, 2012, provisional application No. 61/509,084, filed on Jul. 18, 2011.

(30) Foreign Application Priority Data

Jun. 17, 2011 (CN) .......................... 2011 1 0172357

(51) Int. Cl.
| | |
|---|---|
| C07D 491/052 | (2006.01) |
| C07D 401/04 | (2006.01) |
| C07D 519/00 | (2006.01) |
| C07D 217/22 | (2006.01) |
| C07D 471/04 | (2006.01) |
| C07D 405/12 | (2006.01) |
| A61K 31/496 | (2006.01) |
| A61K 31/519 | (2006.01) |
| C07D 217/26 | (2006.01) |
| C07D 413/04 | (2006.01) |
| A61K 31/551 | (2006.01) |

(52) U.S. Cl.
CPC .......... *A61K 31/496* (2013.01); *A61K 31/519* (2013.01); *A61K 31/551* (2013.01); *C07D 217/22* (2013.01); *C07D 217/26* (2013.01); *C07D 401/04* (2013.01); *C07D 405/12* (2013.01); *C07D 413/04* (2013.01); *C07D 471/04* (2013.01); *C07D 491/052* (2013.01); *C07D 519/00* (2013.01)

(58) Field of Classification Search
CPC combination set(s) only.
See application file for complete search history.

(56) References Cited

U.S. PATENT DOCUMENTS

| | | | |
|---|---|---|---|
| 2,390,529 A | 12/1945 | Friedheim | |
| 3,755,322 A | 8/1973 | Winter et al. | |
| 3,867,383 A | 2/1975 | Winter | |
| 4,084,053 A | 4/1978 | Desai et al. | |
| 5,021,421 A | 6/1991 | Hino et al. | |
| 5,489,591 A | 2/1996 | Kobayashi et al. | |
| 5,807,876 A | 9/1998 | Armistead et al. | |
| 5,834,485 A | 11/1998 | Dyke et al. | |
| 5,965,559 A | 10/1999 | Faull et al. | |
| 5,965,569 A | 10/1999 | Camps Garcia et al. | |
| 5,984,882 A | 11/1999 | Rosenschein et al. | |
| 6,262,113 B1 | 7/2001 | Widdowson et al. | |
| 6,274,620 B1 | 8/2001 | Labrecque et al. | |
| 6,313,127 B1 | 11/2001 | Waterson et al. | |
| 6,399,358 B1 | 6/2002 | Williams et al. | |
| 6,723,730 B2 | 4/2004 | Bakthavatchalam et al. | |
| 6,979,675 B2 | 12/2005 | Tidmarsh | |
| 7,173,025 B1 | 2/2007 | Stocker et al. | |
| 7,858,782 B2 | 12/2010 | Tao et al. | |
| 8,133,900 B2 | 3/2012 | Hood et al. | |
| 8,465,673 B2 | 6/2013 | Yasuda et al. | |
| 2002/0188027 A1 | 12/2002 | Robinson et al. | |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Chemical Abstract Service (CAS) STN Registry Database No. 134538-28-6 [entered STN: Jun. 28, 1991].*
Chemical Abstract Service (CAS) STN Registry Database No. 199785-02-9 [entered STN: Jan. 15, 1998].*
Chemical Abstract Service STN Registry Database No. 371136-50-4 [entered STN: Nov. 20, 2001].*
Bartmann et al. "Synthesis and Reactions of Isoquinoline Derivatives. V. Synthesis and Reactions of 3-Chloroisoquinoline-4-carboxylic Acids." Heterocycles, 1989, 29, 707-718.*
International Search Report and Written Opinion for International Application No. PCT/US2015/020346 dated Jun. 18 2015.
International Search Report for International Application No. PCT/CN2013/079184 dated Jan. 12, 2015.

(Continued)

*Primary Examiner* — Michael Barker
*Assistant Examiner* — Amanda L Aguirre
(74) *Attorney, Agent, or Firm* — Lando & Anastasi, LLP

(57) ABSTRACT

Provided are compounds of formula (I), wherein X, Y, Z, W, V, $R^2$, $R^3$ and m are defined as in the description. Their pharmaceutical compositions and their uses for treating cancers are also provided.

22 Claims, No Drawings

(56) References Cited

U.S. PATENT DOCUMENTS

| | | |
|---|---|---|
| 2003/0095958 A1 | 5/2003 | Bhisetti et al. |
| 2003/0109527 A1 | 6/2003 | Jin et al. |
| 2003/0207882 A1 | 11/2003 | Stocker et al. |
| 2003/0213405 A1 | 11/2003 | Harada et al. |
| 2004/0067234 A1 | 4/2004 | Einat et al. |
| 2004/0248221 A1 | 12/2004 | Stockwell |
| 2006/0084645 A1 | 4/2006 | Pal et al. |
| 2006/0281122 A1 | 12/2006 | Bryant et al. |
| 2007/0244088 A1 | 10/2007 | Brickmann et al. |
| 2008/0300208 A1 | 12/2008 | Einat et al. |
| 2009/0093526 A1 | 4/2009 | Miller et al. |
| 2009/0163508 A1 | 6/2009 | Kori et al. |
| 2009/0163545 A1* | 6/2009 | Goldfarb ............. A61K 31/122 514/312 |
| 2010/0129350 A1 | 5/2010 | Zacharie et al. |
| 2010/0144722 A1 | 6/2010 | Alexander et al. |
| 2010/0273808 A1 | 10/2010 | Armitage et al. |
| 2010/0331307 A1 | 12/2010 | Salituro et al. |
| 2011/0073007 A1 | 3/2011 | Yasuda et al. |
| 2011/0086088 A1 | 4/2011 | Berry |
| 2011/0288065 A1 | 11/2011 | Fujihara et al. |
| 2012/0121515 A1 | 5/2012 | Dang et al. |
| 2012/0129865 A1 | 5/2012 | Wang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2013/0197106 A1 | 8/2013 | Fantin et al. |
| 2014/0187435 A1 | 7/2014 | Dang et al. |
| 2014/0213580 A1 | 7/2014 | Cao et al. |
| 2015/0018328 A1 | 1/2015 | Konteatis et al. |
| 2015/0031627 A1 | 1/2015 | Lemieux et al. |
| 2015/0044716 A1 | 2/2015 | Balss et al. |
| 2015/0087600 A1 | 3/2015 | Popovici-Muller et al. |
| 2015/0240286 A1 | 8/2015 | Dang et al. |
| 2015/0299115 A1 | 10/2015 | Popovici-Muller et al. |

FOREIGN PATENT DOCUMENTS

| | | | |
|---|---|---|---|
| CN | 102659765 A | 9/2012 | |
| CN | 103097340 A | 5/2013 | |
| DE | 3314663 A1 | 10/1983 | |
| DE | 3512630 A1 | 10/1986 | |
| EP | 0022958 A1 | 1/1981 | |
| EP | 0384228 A1 | 8/1990 | |
| EP | 0385237 A2 | 9/1990 | |
| EP | 0945446 A1 | 9/1999 | |
| FR | 2735127 A1 | 12/1996 | |
| JP | EP 0385237 A2 * | 9/1990 | ............ C07D 215/38 |
| JP | 4099768 | 3/1992 | |
| JP | 9291034 A | 11/1997 | |
| JP | 11158073 | 6/1999 | |
| JP | 2004107220 A | 4/2004 | |
| JP | 2009237115 A | 10/2009 | |
| JP | 2010079130 A | 4/2010 | |
| JP | 2010181540 A | 8/2010 | |
| JP | 4753336 B2 | 8/2011 | |
| WO | 9630343 A1 | 10/1996 | |
| WO | 97/28128 A1 | 8/1997 | |
| WO | 97/28129 A1 | 8/1997 | |
| WO | 9744322 A1 | 11/1997 | |
| WO | 9932463 A1 | 7/1999 | |
| WO | 0116097 A1 | 3/2001 | |
| WO | 0119788 A2 | 3/2001 | |
| WO | 0119798 A2 | 3/2001 | |
| WO | 0164642 A2 | 9/2001 | |
| WO | 0164643 A2 | 9/2001 | |
| WO | 0200822 A1 | 12/2002 | |
| WO | 02102313 A2 | 12/2002 | |
| WO | 030016289 A1 | 2/2003 | |
| WO | 2004009562 A1 | 1/2004 | |
| WO | 2004046120 A2 | 6/2004 | |
| WO | 2004050033 A2 | 6/2004 | |
| WO | 2004/073619 A2 | 9/2004 | |
| WO | 2004/074438 A2 | 9/2004 | |
| WO | 2004089470 A2 | 10/2004 | |
| WO | 2005035507 A2 | 4/2005 | |
| WO | 2005060956 A1 | 7/2005 | |
| WO | 2005065691 A1 | 7/2005 | |
| WO | 2005120474 A2 | 12/2005 | |
| WO | 2006034341 A2 | 3/2006 | |
| WO | 2006-038594 A1 | 4/2006 | |
| WO | 2006070198 A1 | 7/2006 | |
| WO | 2006079791 A1 | 8/2006 | |
| WO | 2007003934 A2 | 1/2007 | |
| WO | 2007023186 A1 | 3/2007 | |
| WO | 2008/050168 A1 | 5/2008 | |
| WO | 2008052190 A2 | 5/2008 | |
| WO | 2008070661 A1 | 6/2008 | |
| WO | 2008073670 A2 | 6/2008 | |
| WO | 2008076883 A2 | 6/2008 | |
| WO | 2008131547 A1 | 11/2008 | |
| WO | 2008154026 A1 | 12/2008 | |
| WO | 2009013126 A1 | 1/2009 | |
| WO | 2009016410 A2 | 2/2009 | |
| WO | 2009118567 A2 | 10/2009 | |
| WO | 2009126863 A2 | 10/2009 | |
| WO | 2009150248 A1 | 12/2009 | |
| WO | 2010007756 A1 | 1/2010 | |
| WO | 2010 028099 A1 | 3/2010 | |
| WO | 2010105243 A1 | 9/2010 | |
| WO | 2010/129596 A1 | 11/2010 | |
| WO | 2010130638 A1 | 11/2010 | |
| WO | 2010144338 A1 | 12/2010 | |
| WO | 2010144404 A1 | 12/2010 | |
| WO | 2011002817 A1 | 1/2011 | |
| WO | 2011032169 A2 | 3/2011 | |
| WO | 2011047432 A1 | 4/2011 | |
| WO | 2011050210 A1 | 4/2011 | |
| WO | 2011/072174 A1 | 6/2011 | |
| WO | 2012/009678 A1 | 1/2012 | |
| WO | 2012074999 A1 | 6/2012 | |
| WO | 2012/092442 A1 | 7/2012 | |
| WO | 2012151452 A1 | 11/2012 | |
| WO | 2012160034 A1 | 11/2012 | |
| WO | 2012171506 A1 | 12/2012 | |
| WO | 2013102431 A1 | 7/2013 | |
| WO | 2013107291 A1 | 7/2013 | |
| WO | 2013107405 A1 | 7/2013 | |
| WO | 2013133367 A1 | 9/2013 | |
| WO | 2014015422 A1 | 1/2014 | |

OTHER PUBLICATIONS

International Search Report for International Application No. PCT/CN2013/079200 dated Jan. 12, 2015.

International Search Report for International Application No. PCT/CN2014/082869 dated Sep. 30, 2014.

International Search Report for International Application No. PCT/US2014/046204 dated Oct. 1, 2014.

International Search Report for PCT/CN2012/000841 dated Sep. 27, 2012.

International Search Report for PCT/CN2012/077096 dated Oct. 4, 2012.

International Search Report for PCT/CN2013/000009 dated Apr. 18, 2013.

International Search Report for PCT/CN2013/000068 dated Apr. 25, 2013.

International Search Report for PCT/US10/040486 dated Sep. 1, 2010.

International Search Report for PCT/US201/030692 dated Jul. 27, 2011.

International Search Report for PCT/US2010/027253 mailed Aug. 19, 2010.

(56) References Cited

OTHER PUBLICATIONS

International Search Report for PCT/US2010/059778 dated Mar. 17, 2011.
International Search Report for PCT/US2010/53623 dated Jan. 18, 2011.
International Search Report for PCT/US2010053624 dated Apr. 7, 2011.
International Search Report for PCT/US2011/067752 dated Feb. 22, 2012.
International Search Report for PCT/US2011044254 dated May 10, 2011.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jennings et al. "Expression and mutagenesis of mammalian cytosolic NADP+-specific isocitrate dehydrogenase" Biochemistry (1997) vol. 36, pp. 13743-13747.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou, "IDH1: function follows form" SciBX (2009) vol. 2, No. 48, pp. 1-2.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science (2008) vol. 321, pp. 1807-1812 and Supplemental Data.
Pollard et al, "Cancer. Puzzling patterns of predisposition." Science (2009) vol. 324, pp. 192-194.

Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.
Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shih et al. "The Role of Mutations in Epigenetic Regulators in Myeloid Malignancies" Nature Reviews Cancer (2012) vol. 12, No. 9, pp. 599-612.
Sirkanyan et al "Synthesis of new derivatives of piperazine-substituted pyrano[3,4-c]pyridines" Hayastani Kimiakan Handes—Chemical Journal of Armenia (2009) vol. 62, No. 3-4 pp. 378-385. English Abstract Only.
Sosnovik et al. "Emerging concepts in molecular MRI" Current Opinions in Biotechnology (2007) vol. 18, pp. 4-10.
STN File CA, Registry No. 1023444-33-8, entered STN on May 29, 2008, Chemical Abstracts Index Name "Benzenesulfonamide, 34[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile, 3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile, 3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile, 6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile, 6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethy10-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-

(56) References Cited

OTHER PUBLICATIONS ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP 10751525 Mailed Dec. 14, 2012.
Supplementary European Search Report for EP Application No. 10825707.2 dated Jun. 28, 2013.
Supplementary Search Report for EP10794668 Mailed Oct. 18, 2012.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-Pyrimidine Derivatives" Journal of Heterocyclic Chemistry (2010) vol. 47 pp. 1056-1061.
Wang et al. "A novel ligand N,N'-di(2-pyridyl)-2,4-diamino-6-phenyl-1,3,5-triazine (dpdapt) and its complexes: [Cu(dpdapt)Cl2] and [Cu(dpdapt)(NO3)(H2O)]•NO3 •H2O" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 mailed Aug. 19, 2010.
Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.
Meng et al. "Synthesis and antitumor evaluation of a novel series of triaminotriazine derivatives" Bioorganic & Medicinal Chemistry (2007) vol. 15, pp. 1815-1827.
Aghili et al. "Hydroxyglutaric aciduria and malignant brain tumor: a case report and literature review", Journal of Neuroncology (2008) 91 pp. 233-236.

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acta Neuropathol (2008) vol. 116, pp. 597-602.
Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p. R132 (IDH1 (R132)) occur frequently in high-grade 18-22 gliomas but not in other solid tumors." Hum Muta1., (2009) vol. 30, No. 1, pp. 7-11.
Braun et al. "Triazine-based polymers: 4. MALDI-MS of triazine-based polyamines" Polymer (1996) vol. 37, No. 5, pp. 777-783.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Text Book of Medicine, edited by Bennet and Plum, (1997) 20th edition, vol. 1, pp. 1004-1010.
Chan et al. "Multi-domain hydrogen-bond forming metal chelates: X-ray crystal structures of dicyclopalladated 2,3-bis[6-(2-amino-4-phenylamino-1 ,3,5-triazinyl)]pyrazine (H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitors show activity against Mycobacterium tuberculosis" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry (1995) vol. 32, pp. 543-545.
Dang et al., "Cancer-associated IDH1 mutations produce 2-hydroxyglutarate." Nature (2009) vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer "another Anniversary for the War on Cancer" Bio/Technology (1994) vol. 12, p. 320.
Dohner et al. "Impact of Genetic Features on Treatment Decisions in AML" American Society of Hematology (2011) pp. 36-42.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
EP Search Report & Written Opinion for EP 10825706 Dated Mar. 20, 2013.
European Search Report for Application No. 10751525.6 dated Dec. 14, 2012.
European Search Report for European Application No. 12799802.9 dated Sep. 24, 2014.
European Search Report for European Application No. EP 12800001.5 dated Oct. 10, 2014.
Eurpoean Search Report for EP Application No. 117634253 dated Sep. 23, 2013.
Freshney et al. "Culture of Animal Cells, A Manual of Basic Techniques" Alan R. Liss, Inc. (1983) pp. 1-6.
Genetics Home Reference, "L2HGDH". <http:..ghr.nlm.nih.gove/gene/L2HGDH> accessed on Sep. 4, 2015.
Gewald et al. "Discovery of triazines as potent, selective and orally active PDE4 inhibitors" Bioorganic & medicinal Chemistry Letters (2013) vol. 23, pp. 4308-4314.

(56) References Cited

OTHER PUBLICATIONS

Golub et al. "Molecular Classification of Cancer: Class Discovery and Class Prediction by Gene Expression Monitoring" Science (1999) vol. 286, pp. 531-537.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.
International Preliminary Report for related application No. PCT/US2010/059778 dated Jun. 12, 2012.
International Preliminary Report on Patentability for International Application No. PCT/CN2012/000841 dated Sep. 10, 2012.
International Preliminary Report on Patentability for International Application No. PCT/CN2012/077096 dated Sep. 17, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 mailed Sep. 13, 2011.
International Preliminary Report on Patentability for PCT/US2010/040486 dated Jan. 12, 2012.
International Preliminary Report on Patentability for PCT/US2010/053623 dated Apr. 24, 2012.
International Preliminary Report on Patentability for PCT/US2010/053624 dated Apr. 7, 2011.
International Preliminary Report on Patentability for PCT/US2011/030692 dated Oct. 2, 2012.
International Preliminary Report on Patentability for PCT/US2011/067752 dated Apr. 11, 2013.
International Search Report & Written Opinion for PCT/CN2013/070755 dated Apr. 25, 2013.
International Search Report and Written Opinion for Intematinal Application No. PCT/US2013/064601 dated Feb. 24, 2014.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US15/020349 dated Jun. 15, 2015.
International Search Report and Written Opinion for International Application No. PCT/US2014/046202 dated Sep. 30, 2014.
International Search Report and Written Opinion for International Application No. PCT/US2014/049469 dated Jan. 22, 2015.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Sonoda et al. "Analysis of IDH1 and IDH2 mutations in Japanese glioma patients" Cancer Science, vol. 100, No. 10, pp. 1996-1998, 2009.
Struys, EA. et al. "Measurement of Urinary D- and L-2-Hydroxyglutarate Enantiomers by Stable-Isotope-DilutionLiquidChromatography-Tandem Mass Spectrometry after Derivatization with Diacetyi-L-Tartaric Anhydride." Clinical Chemistry (2004) 501391-1395.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Rao et al., "Polymorphism in Drugs and its Significance in Therapeutics". Journal of Scientific & Industrial Research vol. 46 Oct. 1987 pp. 450-455.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Extended European Search Report for European application No. 16152308.9 dated Jul. 18, 2016.

\* cited by examiner

PHENYL AND PYRIDINYL SUBSTITUTED PIPERIDINES AND PIPERAZINES AS INHIBITORS OF IDH1 MUTANTS AND THEIR USE IN TREATING CANCER

CLAIM OF PRIORITY

This application is a national stage application under 35 U.S.C. §371 of International Application No. PCT/CN2012/077096, filed Jun. 18, 2012, published as International Publication No. WO 2012/171506 on Dec. 20, 2012, which claims priority from Chinese Patent Application No. CN 201110172357.4, filed Jun. 17, 2011, U.S. Ser. No. 61/509,084, filed Jul. 18, 2011 and U.S. Ser. No. 61/584,209, filed Jan. 6, 2012, each of which is incorporated by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (DEC-2008) to UniProtKB; Kullmann et al., Submitted (JUN-1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate thereby reducing NAD+ (NADP+) to NADP (NADPH), e.g., in the forward reaction:

Isocitrate+NAD+(NADP+)→α-KG+CO$_2$+NADH (NADPH)+H+.

It has been discovered that mutations of IDH1 present in certain cancer cells result in a new ability of the enzyme to catalyze the NAPH-dependent reduction of α-ketoglutarate to R(−)-2-hydroxy glutarate (2HG). 2HG is not formed by wild-type IDH1. The production of 2HG is believed to contribute to the formation and progression of cancer (Dang, L et al, Nature 2009, 462:739-44).

The inhibition of mutant IDH1 and its neoactivity is therefore a potential therapeutic treatment for cancer. Accordingly, there is an ongoing need for inhibitors of IDH1 mutants having alpha hydroxyl neoactivity.

SUMMARY OF INVENTION

Described herein are compounds of Structural Formula I:

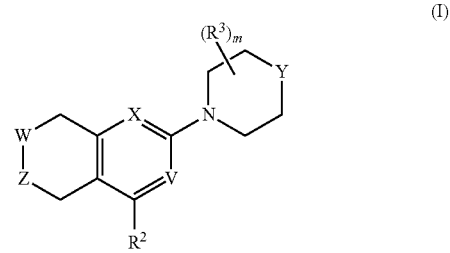

or a pharmaceutically acceptable salt thereof, wherein:
X is CR$^4$ or N;
Y is —N(R$^5$)— or —CH(R$^5$)—;
Z is —O—, —S—, —C(R)$_2$— or N(R$^7$);
W is C(R$^1$)(R$^1$) or N(R$^7$); provided that Z and W are not both N(R$^7$) at the same time;
V is N or C(R);
each R is independently selected from hydrogen, methyl or CF$_3$;
each R$^1$ is independently selected from hydrogen, alkoxy, or alkyl optionally substituted with OH or SH;
or two R$^1$ are taken together with the carbon atom to which they are bound to form a 3-7 membered cycloalkyl, or a 4-7 membered saturated heterocyclyl ring wherein said cycloalkyl or heterocyclyl is optionally substituted with methyl, halo or CF$_3$;
R$^2$ is selected from phenyl, a 3-7 membered cycloalkyl, C$_2$-C$_4$ alkyl, or CF$_3$, wherein the phenyl or cycloalkyl is optionally substituted with a single substituent selected from methyl, CF$_3$ or fluoro;
each R$^3$ is independently selected from —(C$_1$-C$_4$ alkylene)-O—(C$_1$-C$_4$ alkyl), —C$_1$-C$_4$ fluoroalkyl, —C(O)—O—(C$_1$-C$_4$ alkyl), -phenyl, -heteroaryl, C$_3$-C$_7$ cycloalkyl, —CH$_2$—N(C$_1$-C$_4$ alkyl)$_2$, C(O)—N—(C$_1$-C$_4$ alkyl)$_2$, —C(O)—NH—(C$_1$-C$_4$ alkyl), —C$_1$-C$_4$ alkyl optionally substituted with halo or —OH, or two R$^3$s are taken together to form a 3-8 saturated ring or a fused phenyl wherein said saturated ring or fused phenyl is optionally substituted with 1 to 2 methyl;
R$^4$ is selected from hydrogen, —CN, halo, C$_1$-C$_4$ alkoxy, —CH$_2$NH(C$_1$-C$_4$ alkyl), C$_2$-C$_4$ alkenyl, C$_2$-C$_4$ alkynyl, —(C$_1$-C$_4$ alkyl)-O—(C$_1$-C$_4$ alkyl), C$_1$-C$_4$ fluoroalkyl, C(O)—N—(C$_1$-C$_4$ alkyl)$_2$, —C(O)—NH—(C$_1$-C$_4$ alkyl), —S(O)$_2$—(C$_1$-C$_4$ alkyl), or a 5-membered heteroaryl;
R$^5$ is selected from: C$_1$-C$_4$ alkyl, —C(O)—(C$_1$-C$_4$ alkyl), —C(O)—(C$_0$-C$_2$ alkylene)-Q, —C(O)—(C$_0$-C$_2$ alkylene)-N(R$^6$)—(C$_0$-C$_2$ alkylene)-Q, —C(O)—O—(C$_0$-C$_2$ alkylene)-Q, —C(O)—(C$_1$-C$_2$ alkylene)-O—(C$_0$-C$_2$ alkylene)-Q, —C(O)—C(O)-Q, —S(O)$_2$-Q, —C(O)—(C$_1$-C$_4$ alkylene)-O—C(O)—(C$_1$-C$_4$ alkyl), —C(O)—(C$_1$-C$_4$ alkylene)-C(O)—O—(C$_1$-C$_4$ alkyl), —C(O)—N(R$^6$)—(C$_1$-C$_4$ alkylene)-O—C(O)—(C$_1$-C$_4$ alkyl), —C(O)—N(R$^6$)—(C$_1$-C$_4$ alkylene)-C(O)—O—(C$_1$-C$_4$ alkyl), —C(O)—(C$_0$-C$_2$ alkylene)-N(R$^6$)—(C$_1$-C$_6$ alkyl), —C(O)—(C$_0$-C$_2$ alkylene)-C(O)N(R$^6$)—(C$_1$-C$_6$ alkyl), —C(O)—(C$_0$-C$_2$ alkylene)-C(O)—(C$_1$-C$_6$ alkyl), —C(O)—(C$_0$-C$_2$ alkylene)-N(R$^6$)C(O)

O—($C_1$-$C_6$ alkyl), —C(O)—($C_0$-$C_2$ alkylene)-N($R^6$)—($C_2$-$C_6$ alkynyl), —C(O)—($C_0$-$C_2$ alkylene)-N($R^6$)—($C_2$-$C_6$ alkenyl), C(O)—($C_0$-$C_2$ alkylene)-N($R^6$)—($C_0$-$C_2$ alkylene)-O—($C_1$-$C_4$ alkyl), —C(O)—($C_1$-$C_4$ alkylene)-O—($C_1$-$C_4$ alkyl), —C(O)—($C_1$-$C_2$ alkylene)-C(O)C(O)N(R) ($C_1$-$C_4$ alkyl), —C(O)—O—($C_1$-$C_4$ alkylene)-O—($C_1$-$C_4$ alkyl), —($C_0$-$C_4$ alkylene)-O—C(O)—($C_1$-$C_4$ alkyl), —($C_0$-$C_4$ alkylene)-C(O)—O—($C_1$-$C_4$ alkyl), —($C_0$-$C_4$ alkylene)-O—($C_1$-$C_4$ alkyl), —C(O)—($C_1$-$C_2$ alkylene)-S(O)$_{0-2}$—($C_1$-$C_4$ alkyl), —S(O)$_2$—($C_1$-$C_4$ alkyl), —C(O)—($C_1$-$C_4$ alkylene)-C(O)C(O)N($R^6$) ($C_1$-$C_6$ alkyl), —C(O)—($C_1$-$C_4$ alkylene)-N($R^6$)S(O)$_2$—($C_1$-$C_6$ alkyl), or —C(O)—($C_1$-$C_4$ alkylene)-N($R^6$)S(O)$_2$Q, wherein:

any alkylene moiety present in $R^5$ is optionally substituted with OH or F;

any terminal methyl moiety present in $R^5$ is optionally replaced with —$CH_2OH$, $CF_3$, —$CH_2F$, —$CH_2Cl$, C(O)$CH_3$, C(O)$CF_3$, CN, —OH or $CO_2H$;

each $R^6$ is independently selected from hydrogen and methyl;

Q is selected from aryl, heteroaryl, carbocyclyl and heterocyclyl; and Q is optionally substituted with up to 3 substituents independently selected from $C_1$-$C_4$ alkyl optionally substituted by —OH, $C_1$-$C_4$ alkoxy, —($C_1$-$C_4$ alkylene)-OC(O)O—($C_1$-$C_4$ alkyl), —C(O)O—($C_1$-$C_4$ alkyl), —CN, fluoro, chloro, and bromo;

each $R^7$ is independently -G-L-M;

G is a bond or a bivalent $C_1$-$C_6$ saturated or unsaturated, straight or branched hydrocarbon chain wherein optionally one, two or three methylene units of the hydrocarbon chain are independently replaced by —$NR^8$—, —O—, —C(O)—, —OC(O)—, —C(O)O—, —S—, —SO—, —SO$_2$—, —C(=S)—, —C(=$NR^8$)—, —N=N—, or —C(=$N_2$)—;

L is a covalent bond or a bivalent $C_{1-8}$ saturated or unsaturated, straight or branched, hydrocarbon chain, wherein one, two, or three methylene units of L are optionally and independently replaced by cyclopropylene, —$NR^8$—, —N($R^8$)C(O)—, —C(O)N($R^8$)—, —N($R^8$)SO$_2$—, SO$_2$N($R^8$)—, —O—, —C(O)—, —OC(O)—, —C(O)O—, —S—, —SO—, —SO$_2$—, —C(=S)—, —C(=$NR^8$)—, —N=N—, or —C(=$N_2$)—;

M is E, or a 3-10 membered monocyclic or bicyclic, saturated, partially unsaturated, or aromatic ring having 0-3 heteroatoms independently selected from nitrogen, oxygen or sulfur, and wherein said ring is substituted with at 1-4 groups independently selected from -D-E, oxo, $NO_2$, halogen, CN, $C_1$-$C_6$ alkyl, $C_2$-$C_6$ alkenyl, or $C_2$-$C_6$ alkynyl;

D is a covalent bond or a bivalent $C_1$-$C_6$ saturated or unsaturated, straight or branched, hydrocarbon chain, wherein one or two methylene units of D are optionally and independently replaced by —$NR^8$—, —S—, —O—, —C(O)—, —SO—, or —SO$_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN;

each $R^8$ is independently hydrogen, $C_1$-$C_6$ alkyl, $C_2$-$C_6$ alkenyl, $C_2$-$C_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; and m is 0, 1, 2 or 3.

The compound of formula I inhibits mutant IDH1, particularly mutant IDH1 having alpha hydroxyl neoactivity. Also described herein are pharmaceutical compositions comprising a compound of formula I and methods of using such compositions to treat cancers characterized by the presence of a mutant IDH1.

DETAILED DESCRIPTION OF THE INVENTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DEFINITIONS

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, —$CH_2CH_2CH_2$— and —$CH_2CH(CH_3)CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

The term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, $S(O)$ and $S(O)_2$).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, $S(O)$ and $S(O)_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings wherein the point of attachment from the ring system to the rest of the molecule is through a non-aromatic ring are considered to be heterocyclyl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —$OR^b$, —$OR^{b'}$, —$SR^b$, —$SR^{b'}$, —($C_1$-$C_4$ alkyl)-$N(R^b)(R^b)$, —($C_1$-$C_4$ alkyl)-$N(R^b)$ ($R^{b'}$), —$N(R^b)(R^b)$, —$N(R^b)(R^{b'})$, —O—($C_1$-$C_4$ alkyl)-N $(R^b)(R^b)$, —O—($C_1$-$C_4$ alkyl)-$N(R^b)(R^{b'})$, —($C_1$-$C_4$ alkyl)-O—($C_1$-$C_4$ alkyl)-$N(R^b)(R^b)$, —($C_1$-$C_4$ alkyl)-O—($C_1$-$C_4$ alkyl)-$N(R^b)(R^{b'})$, —C(O)—$N(R^b)(R^b)$, —($C_1$-$C_4$ alkyl)-C (O)—$N(R^b)(R^b)$, —($C_1$-$C_4$ alkyl)-C(O)—$N(R^b)(R^{b'})$, —$OR^{b'}$, $R^{b'}$, —$C(O)(C_1$-$C_4$ alkyl), —$C(O)R^{b'}$, —C(O)N $(R^{b'})(R^b)$, —$N(R^b)C(O)(R^b)$, —$N(R^b)C(O)(R^{b'})$, —$N(R^b)$ $SO_2(R^b)$, —$SO_2N(R^b)(R^b)$, —$N(R^b)SO_2(R^{b'})$, and —$SO_2N$ $(R^b)(R^{b'})$, wherein any alkyl substituent is optionally further substituted with one or more of —OH, —O—($C_1$-$C_4$ alkyl), halo, —$NH_2$, —$NH(C_1$-$C_4$ alkyl), or —$N(C_1$-$C_4$ alkyl)$_2$;
  each $R^b$ is independently selected from hydrogen, and
    —$C_1$-$C_4$ alkyl; or
  two $R^b$s are taken together with the nitrogen atom to which they are bound to form a 4- to 8-membered heterocyclyl optionally comprising one additional heteroatom selected from N, S, and O; and
  each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O— ($C_1$-$C_4$ alkyl), —O—($C_1$-$C_4$ fluoroalkyl), halo, —$NH_2$, —$NH(C_1$-$C_4$ alkyl), or —$N(C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group.

As used herein, the term "elevated levels of 2HG" means 10%, 20% 30%, 50%, 75%, 100%, 200%, 500% or more 2HG then is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound of structural Formula I:

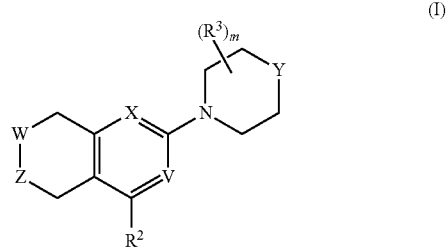

or a pharmaceutically acceptable salt thereof, wherein:
X is $CR^4$ or N;
Y is —$N(R^5)$— or —$CH(R^5)$—;
Z is —O—, —S—, —$C(R)_2$— or $N(R^7)$;
W is $C(R^1)(R^1)$ or $N(R^7)$; provided that Z and W are not both $N(R^7)$ at the same time;

V is N or C(R);

each R is independently selected from hydrogen, methyl or $CF_3$;

each $R^1$ is independently selected from hydrogen, alkoxy, or alkyl optionally substituted with OH or SH;

or two $R^1$ are taken together with the carbon atom to which they are bound to form a 3-7 membered cycloalkyl, or a 4-7 membered saturated heterocyclyl ring wherein said cycloalkyl or heterocyclyl is optionally substituted with methyl, halo or $CF_3$;

$R^2$ is selected from phenyl, a 3-7 membered cycloalkyl, $C_2$-$C_4$ alkyl, or $CF_3$, wherein the phenyl or cycloalkyl is optionally substituted with a single substituent selected from methyl, $CF_3$ or fluoro;

each $R^3$ is independently selected from —($C_1$-$C_4$ alkylene)-O—($C_1$-$C_4$ alkyl), —$C_1$-$C_4$ fluoroalkyl, —C(O)—O—($C_1$-$C_4$ alkyl), -phenyl, -heteroaryl, $C_3$-$C_7$ cycloalkyl, —$CH_2$—N($C_1$-$C_4$ alkyl)$_2$, C(O)—N—($C_1$-$C_4$ alkyl)$_2$, —C(O)—NH—($C_1$-$C_4$ alkyl), —$C_1$-$C_4$ alkyl optionally substituted with halo or —OH, or two $R^3$s are taken together to form a 3-8 saturated ring or a fused phenyl wherein said saturated ring or fused phenyl is optionally substituted with 1 to 2 methyl;

$R^4$ is selected from hydrogen, —CN, halo, $C_1$-$C_4$ alkoxy, —$CH_2$NH($C_1$-$C_4$ alkyl), $C_2$-$C_4$ alkenyl, $C_2$-$C_4$ alkynyl, —($C_1$-$C_4$ alkyl)-O—($C_1$-$C_4$ alkyl), $C_1$-$C_4$ fluoroalkyl, C(O)—N—($C_1$-$C_4$ alkyl)$_2$, —C(O)—NH—($C_1$-$C_4$ alkyl), —S(O)$_2$—($C_1$-$C_4$ alkyl), or a 5-membered heteroaryl;

$R^5$ is selected from: $C_1$-$C_4$ alkyl, —C(O)—($C_1$-$C_4$ alkyl), —C(O)—($C_0$-$C_2$ alkylene)-Q, —C(O)—($C_0$-$C_2$ alkylene)-N($R^6$)—($C_0$-$C_2$ alkylene)-Q, —C(O)—O—($C_0$-$C_2$ alkylene)-Q, —C(O)—($C_1$-$C_2$ alkylene)-O—($C_0$-$C_2$ alkylene)-Q, —C(O)—C(O)-Q, —S(O)$_2$-Q, —C(O)—($C_1$-$C_4$ alkylene)-O—C(O)—($C_1$-$C_4$ alkyl), —C(O)—($C_1$-$C_4$ alkylene)-C(O)—O—($C_1$-$C_4$ alkyl), —C(O)—N($R^6$)—($C_1$-$C_4$ alkylene)-O—C(O)—($C_1$-$C_4$ alkyl), —C(O)—N($R^6$)—($C_1$-$C_4$ alkylene)-C(O)—O—($C_1$-$C_4$ alkyl), —C(O)—($C_0$-$C_2$ alkylene)-N($R^6$)—($C_1$-$C_6$ alkyl), —C(O)—($C_0$-$C_2$ alkylene)-C(O)N($R^6$)—($C_1$-$C_6$ alkyl), —C(O)—($C_0$-$C_2$ alkylene)-C(O)—($C_1$-$C_6$ alkyl), —C(O)—($C_0$-$C_2$ alkylene)-N($R^6$)C(O)O—($C_1$-$C_6$ alkyl), —C(O)—($C_0$-$C_2$ alkylene)N($R^6$)—($C_2$-$C_6$ alkynyl), —C(O)—($C_0$-$C_2$ alkylene)-N($R^6$)—($C_2$-$C_6$ alkenyl), C(O)—($C_0$-$C_2$ alkylene)-N($R^6$)—($C_0$-$C_2$ alkylene)-O—($C_1$-$C_4$ alkyl), —C(O)—($C_1$-$C_4$ alkylene)-O—($C_1$-$C_4$ alkyl), —C(O)—($C_1$-$C_4$ alkylene)-C(O)C(O)N(R)($C_1$-$C_4$ alkyl), —C(O)—O—($C_1$-$C_4$ alkylene)-O—($C_1$-$C_4$ alkyl), —($C_0$-$C_4$ alkylene)-O—C(O)—($C_1$-$C_4$ alkyl), —($C_0$-$C_4$ alkylene)-C(O)—O—($C_1$-$C_4$ alkyl), —($C_0$-$C_4$ alkylene)-O—($C_1$-$C_4$ alkyl), —C(O)—($C_1$-$C_2$ alkylene)-S(O)$_{0-2}$—($C_1$-$C_4$ alkyl), —S(O)$_2$—($C_1$-$C_4$ alkyl), —C(O)—($C_1$-$C_4$ alkylene)-C(O)C(O)N($R^6$) ($C_1$-$C_6$ alkyl), —C(O)—($C_1$-$C_4$ alkylene)-N($R^6$)S(O)$_2$—($C_1$-$C_6$ alkyl), or —C(O)—($C_1$-$C_4$ alkylene)-N($R^6$)S(O)$_2$Q, wherein:

any alkylene moiety present in $R^5$ is optionally substituted with OH or F;

any terminal methyl moiety present in $R^5$ is optionally replaced with —$CH_2$OH, $CF_3$, —$CH_2$F, —$CH_2$Cl, C(O)$CH_3$, C(O)$CF_3$, CN, —OH or $CO_2$H;

each $R^6$ is independently selected from hydrogen and methyl;

Q is selected from aryl, heteroaryl, carbocyclyl and heterocyclyl; and Q is optionally substituted with up to 3 substituents independently selected from $C_1$-$C_4$ alkyl optionally substituted by —OH, $C_1$-$C_4$ alkoxy, —($C_1$-$C_4$ alkylene)-OC(O)O—($C_1$-$C_4$ alkyl), —C(O)O—($C_1$-$C_4$ alkyl), —CN, fluoro, chloro, and bromo;

each $R^7$ is independently -G-L-M;

G is a bond or a bivalent $C_1$-$C_6$ saturated or unsaturated, straight or branched hydrocarbon chain wherein optionally one, two or three methylene units of the hydrocarbon chain are independently replaced by —$NR^8$—, —O—, —C(O)—, —OC(O)—, —C(O)O—, —S—, —SO—, —$SO_2$—, —C(=S)—, —C(=$NR^8$)—, —N=N—, or —C(=$N_2$)—;

L is a covalent bond or a bivalent $C_{1-8}$ saturated or unsaturated, straight or branched, hydrocarbon chain, wherein one, two, or three methylene units of L are optionally and independently replaced by cyclopropylene, —$NR^8$—, —N($R^8$)C(O)—, —C(O)N($R^8$)—, —N($R^8$)$SO_2$—, $SO_2$N($R^8$)—, —O—, —C(O)—, —OC(O)—, —C(O)O—, —S—, —SO—, —$SO_2$—, —C(=S)—, —C(=$NR^8$)—, —N=N—, or —C(=$N_2$)—;

M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, $NO_2$, halogen, CN, $C_1$-$C_6$ alkyl, $C_2$-$C_6$ alkenyl, or $C_2$-$C_6$ alkynyl;

D is a covalent bond or a bivalent $C_1$-$C_6$ saturated or unsaturated, straight or branched, hydrocarbon chain, wherein one or two methylene units of D are optionally and independently replaced by —$NR^8$—, —S—, —O—, —C(O)—, —SO—, or —$SO_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN;

each $R^8$ is independently hydrogen, $C_1$-$C_6$ alkyl, $C_2$-$C_6$ alkenyl, $C_2$-$C_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; and m is 0, 1, 2 or 3.

In some embodiments, provided is a compound of Structural Formula I:

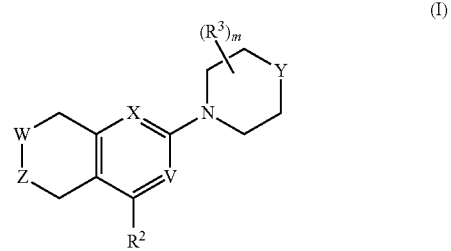

(I) or a pharmaceutically acceptable salt thereof, wherein:

X is $CR^4$ or N;

Y is —N($R^5$)— or —CH($R^5$)—;

Z is —O—, —S—, —C(R)$_2$— or N($R^7$);

W is C($R^1$)($R^1$) or N($R^7$); provided that (1) when Z is —C(R)$_2$—, then W is not C($R^1$)($R_1$); and (2) Z and W are not both N($R^7$) at the same time;

V is N or C(R);

each R is independently selected from hydrogen, methyl or $CF_3$;

each $R^1$ is independently selected from hydrogen, alkoxy, or alkyl optionally substituted with OH or SH;

or two $R^1$ are taken together with the carbon atom to which they are bound to form a 3-7 membered cycloalkyl, or a 4-7 membered saturated heterocyclyl ring wherein said cycloalkyl or heterocyclyl is optionally substituted with methyl, halo or $CF_3$;

$R^2$ is selected from phenyl, a 3-7 membered cycloalkyl, or $C_2$-$C_4$ alkyl, wherein the phenyl or cycloalkyl is optionally substituted with a single substituent selected from methyl, $CF_3$ or fluoro;

each $R^3$ is independently selected from —$C_1$-$C_4$ alkyl optionally substituted with halo, —($C_1$-$C_4$ alkyl)-O—($C_1$-$C_4$ alkyl), —$C_1$-$C_4$ fluoroalkyl, —C(O)—O—($C_1$-$C_4$ alkyl), -phenyl, -heteroaryl, $C_3$-$C_7$ cycloalkyl, —$CH_2$—N($C_1$-$C_4$ alkyl)$_2$, C(O)—N—($C_1$-$C_4$ alkyl)$_2$, —C(O)—NH—($C_1$-$C_4$ alkyl), or two $R^3$s are taken together to form a 3-8 saturated ring or a fused phenyl wherein said saturated ring or fused phenyl is optionally substituted with 1 to 2 methyl;

$R^4$ is selected from hydrogen, —CN, halo, $C_1$-$C_4$ alkoxy, —$CH_2NH(C_1$-$C_4$ alkyl), $C_2$-$C_4$ alkenyl, $C_2$-$C_4$ alkynyl, —($C_1$-$C_4$ alkyl)-O—($C_1$-$C_4$ alkyl), $C_1$-$C_4$ fluoroalkyl, C(O)—N—($C_1$-$C_4$ alkyl)$_2$, —C(O)—NH—($C_1$-$C_4$ alkyl), —S(O)$_2$—($C_1$-$C_4$ alkyl), and a 5-membered heteroaryl;

$R^5$ is selected from: —C(O)—($C_1$-$C_4$ alkyl), —C(O)—($C_0$-$C_2$ alkylene)-Q, —C(O)—($C_0$-$C_2$ alkylene)-N($R^6$)—($C_0$-$C_2$ alkylene)-Q, —C(O)—O—($C_1$-$C_2$ alkylene)-Q, —C(O)—($C_1$-$C_2$ alkylene)-O—($C_0$-$C_2$ alkylene)-Q, —C(O)—C(O)-Q, —S(O)$_2$-Q, —C(O)—($C_1$-$C_4$ alkylene)-O—C(O)—($C_1$-$C_4$ alkyl), —C(O)—($C_1$-$C_4$ alkylene)-C(O)—O—($C_1$-$C_4$ alkyl), —C(O)—N($R^6$)—($C_1$-$C_4$ alkylene)-O—C(O)—($C_1$-$C_4$ alkyl), —C(O)—N($R^6$)—($C_1$-$C_4$ alkylene)-C(O)—O—($C_1$-$C_4$ alkyl), —C(O)—($C_0$-$C_2$ alkylene)-N($R^6$)—($C_1$-$C_6$ alkyl), —C(O)—($C_0$-$C_2$ alkylene)N($R^6$)—($C_2$-$C_6$ alkynyl), —C(O)—($C_0$-$C_2$ alkylene)-N($R^6$)—($C_2$-$C_6$ alkenyl), —C(O)—($C_0$-$C_2$ alkylene)-N($R^6$)—($C_0$-$C_2$ alkylene)-O—($C_1$-$C_4$ alkyl), —C(O)—($C_1$-$C_2$ alkylene)-O—($C_1$-$C_4$ alkyl), —C(O)—($C_1$-$C_2$ alkylene)-C(O)C(O)N(R)($C_1$-$C_4$ alkyl), —C(O)—O—($C_1$-$C_4$ alkylene)-O—($C_1$-$C_4$ alkyl), —($C_0$-$C_4$ alkylene)-O—C(O)—($C_1$-$C_4$ alkyl), —($C_0$-$C_4$ alkylene)-C(O)—O—($C_1$-$C_4$ alkyl), —($C_0$-$C_4$ alkylene)-O—($C_1$-$C_4$ alkyl), —C(O)—($C_1$-$C_2$ alkylene)-S(O)$_{0-2}$—($C_1$-$C_4$ alkyl), —S(O)$_2$—($C_1$-$C_4$ alkyl), —C(O)—($C_1$-$C_4$ alkylene)-C(O)C(O)N($R^6$) ($C_1$-$C_6$ alkyl), —C(O)—($C_1$-$C_4$ alkylene)-N($R^6$)S(O)$_2$—($C_1$-$C_6$ alkyl), and —C(O)—($C_1$-$C_4$ alkylene)-N($R^6$)S(O)$_2$Q, wherein:

any alkylene moiety present in $R^5$ is optionally substituted with OH or F;

any terminal methyl moiety present in $R^5$ is optionally replaced with —$CH_2OH$, $CF_3$, —$CH_2F$, —$CH_2Cl$, C(O)$CH_3$, or C(O)$CF_3$;

each $R^6$ is independently selected from hydrogen and methyl;

Q is selected from aryl, heteroaryl, carbocyclyl and heterocyclyl; and Q is optionally substituted with up to 3 substituents independently selected from $C_1$-$C_4$ alkyl, $C_1$-$C_4$ alkoxy, —CN, fluoro, chloro, and bromo;

each $R^7$ is independently -G-L-M;

G is a bond or a bivalent $C_1$-$C_6$ saturated or unsaturated, straight or branched hydrocarbon chain wherein optionally one, two or three methylene units of the hydrocarbon chain are independently replaced by —$NR^8$—, —O—, —C(O)—, —OC(O)—, —C(O)O—, —S—, —SO—, —SO$_2$—, —C(=S)—, —C(=$NR^8$)—, —N=N—, or —C(=$N_2$)—;

L is a covalent bond or a bivalent $C_{1-8}$ saturated or unsaturated, straight or branched, hydrocarbon chain, wherein one, two, or three methylene units of L are optionally and independently replaced by cyclopropylene, —$NR^8$—, —N($R^8$)C(O)—, —C(O)N($R^8$)—, —N($R^8$)SO$_2$—, SO$_2$N($R^8$)—, —O—, —C(O)—, —OC(O)—, —C(O)O—, —S—, —SO—, —SO$_2$—, —C(=S)—, —C(=$NR^8$)—, —N=N—, or —C(=$N_2$)—;

M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, NO$_2$, halogen, CN, $C_1$-$C_6$ alkyl, $C_2$-$C_6$ alkenyl, or $C_2$-$C_6$ alkynyl;

D is a covalent bond or a bivalent $C_1$-$C_6$ saturated or unsaturated, straight or branched, hydrocarbon chain, wherein one or two methylene units of D are optionally and independently replaced by —$NR^8$—, —S—, —O—, —C(O)—, —SO—, or —SO$_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN;

each $R^8$ is independently hydrogen, $C_1$-$C_6$ alkyl, $C_2$-$C_6$ alkenyl, $C_2$-$C_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; and m is 0, 1, 2 or 3.

In some embodiments, when X is —C(CN)—, Y is —N($R^5$)—, m is 0, $R^2$ is phenyl or $C_2$-$C_4$ alkyl, and Z is —O— or —S—, then each $R^1$ is not simultaneously methyl; and when X is —C(CN)—, Y is —N($R^5$)—, m is 0, $R^2$ is phenyl or $C_2$-$C_4$ alkyl, Z is —$CH_2$— and W is C($R^1$)($R^1$), then each $R^1$ is not simultaneously hydrogen.

In some embodiments X is —C(CN)—.

In some embodiments, each $R^1$ is the same and selected from methyl and hydrogen. In one aspect of these embodiments, Z is —O—. In an alternate aspect of these embodiments, Z is —N($R^7$)—. In an alternate aspect of these embodiments, Z is —C(CH$_3$)$_2$— and each $R^1$ is hydrogen. In still another aspect of these embodiments, Z is —$CH_2$—.

In some embodiments, Y is —N($R^5$)—.

In some embodiments, $R^2$ is selected from phenyl optionally substituted with a single fluoro or a single methyl, cyclohexyl, cyclopentyl, cyclobutyl, cyclopropyl optionally substituted with a single methyl, isopropyl, ethyl and methyl. In one aspect of this embodiment, $R^2$ is selected from cyclohexyl, cyclobutyl, cyclopropyl, ethyl and isopropyl. In one aspect of these embodiments, $R^2$ is cyclohexyl, Z is —O— and each $R^1$ is hydrogen. In another aspect of these embodiments, $R^2$ is selected from cyclopropyl and isopropyl, Z is —O— and each $R^1$ is methyl.

In some embodiments, each $R^3$ is independently selected from hydrogen, methyl, ethyl, isobutyl, isopropyl, phenyl, —C(O)—O—$CH_2CH_3$, —C(O)—O—$CH_3$, and —$CH_2$—O—$CH_3$.

$R^{3c}$ is selected from hydrogen and methyl;
$R^{3d}$ is selected from hydrogen, phenyl and methyl
In some embodiments, $R^4$ is selected from:

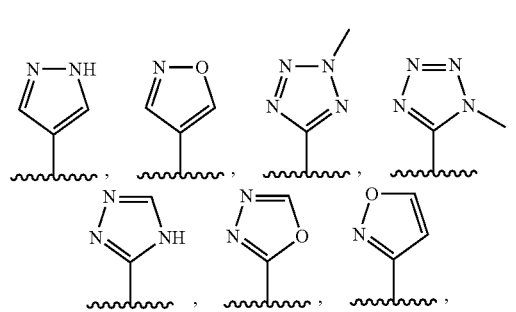

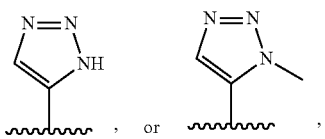, or

In some embodiments, R[5] is selected from —C(O)—(C$_1$-C$_4$ alkyl), —C(O)—(CH$_2$)$_{0-2}$-Q, —C(O)—(CH$_2$)$_{1-2}$—O—(CH$_2$)$_{0-2}$-Q, —C(O)—(C$_1$-C$_4$ alkylene)-C(O)—O—(C$_1$-C$_4$ alkyl), —C(O)—N(R[6])—(C$_1$-C$_4$ alkylene)-C(O)—O—(C$_1$-C$_4$ alkyl), —C(O)—(CH$_2$)$_{0-2}$—N(R[6])—(C$_2$-C$_6$ alkenyl), —C(O)—(CH$_2$)$_{1-2}$—O—(C$_1$-C$_4$ alkyl), —C(O)—O—(C$_1$-C$_4$ alkylene)-O—(C$_1$-C$_4$ alkyl), —(CH$_2$)$_{0-4}$—C(O)—O—(C$_1$-C$_4$ alkyl), and —C(O)—(CH$_2$)$_{1-2}$—S—(C$_1$-C$_4$ alkyl).

In some embodiments, each R[7] is independently selected from:

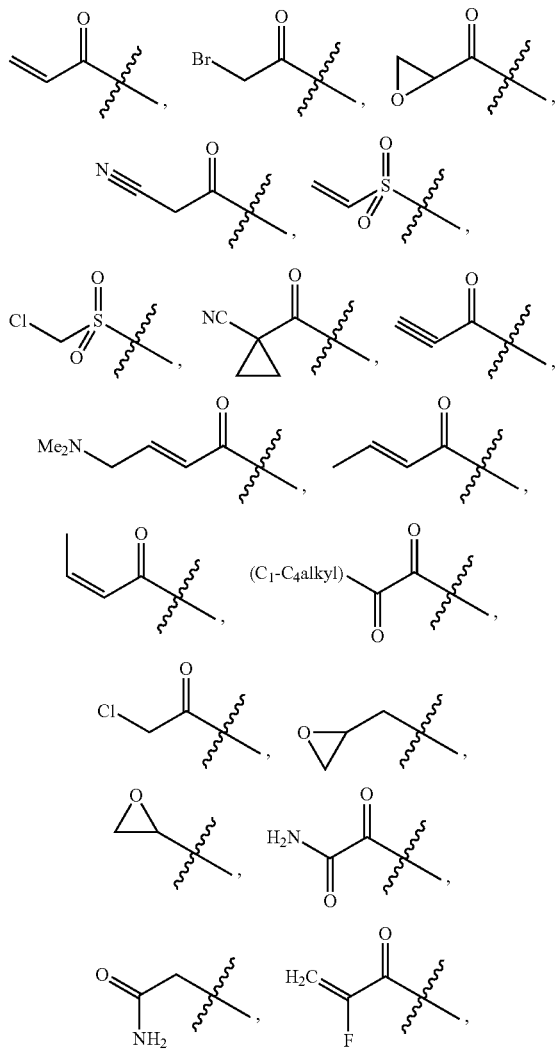

—C(O)—CH$_3$, —SO$_2$CH$_3$, —CH$_2$CH$_2$OH, —(CH$_2$)$_{1-4}$ SH, or —(CH$_2$)$_{1-4}$—OH.

In some embodiments, the compound is depicted by Structural Formula II:

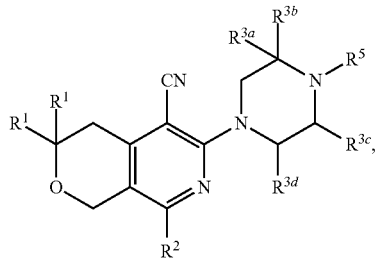

wherein:

each R[1] is the same and is selected from hydrogen and methyl;

R[2] is selected from phenyl optionally substituted with a single fluoro or a single methyl, cyclohexyl, cyclopentyl, cyclobutyl, cyclopropyl optionally substituted with a single methyl, isopropyl and methyl;

R[3a] is selected from hydrogen and methyl;

R[3b] is selected from hydrogen, methyl, ethyl, isobutyl, isopropyl, cyclopropyl, phenyl, —C(O)—O—CH$_2$CH$_3$, —C(O)—O—CH$_3$, and —CH$_2$—O—CH$_3$, wherein each of methyl, ethyl, isobutyl, and isopropyl is optionally substituted with fluoro;

R[3c] is selected from hydrogen and methyl;

R[3d] is selected from hydrogen, phenyl and methyl; and

R[5] is defined as for Structural Formula I.

In certain embodiments of Structural Formula II, each R[1] is methyl; and R[2] is selected from ethyl, isopropyl, cyclopropyl and cyclobutyl. In one aspect of these embodiments, R[3a], R[3c] and R[3d] are simultaneously hydrogen; and R[3b] is selected from (R)-methyl, (R)-ethyl, (R)-isopropyl, and C(O)—O—CH$_2$CH$_3$. In some embodiments, one or more of the hydrogens in the piperidine ring of Structural Formula II or in R[3a], R[3b], R[3c], or R[3d] is a deuterium isotope.

In certain embodiments of Structural Formula II, each R[1] is methyl; and R[2] is cyclopropyl. In one aspect of these embodiments, R[3a], R[3c] and R[3d] are simultaneously hydrogen; and R[3b] is selected from (R)-methyl, (R)-ethyl, (R)-isopropyl, (R)-cyclopropyl, and C(O)—O—CH$_2$CH$_3$. In some embodiments, one or more of the hydrogens in the piperidine ring of Structural Formula II or in R[3a], R[3b], R[3c], or R[3d] is a deuterium isotope.

In an alternate embodiment of Structural Formula II, each R[1] is hydrogen; and R[2] is cyclohexyl. In one aspect of these embodiments R[3a], R[3c] and R[3d] are simultaneously hydrogen; and R[3b] is (R)-methyl.

In some embodiments of Structural Formula I or II, R[5] is selected from —C(O)—(C$_1$-C$_4$ alkyl), —C(O)—(CH$_2$)$_{0-2}$-Q, —C(O)—(CH$_2$)$_{1-2}$—O—(CH$_2$)$_{0-2}$-Q, —C(O)—(CH$_2$)$_{0-2}$-Q-C(O)—(C$_1$-C$_2$ alkyl), —C(O)—(CH$_2$)$_{0-2}$-Q-(C$_1$-C$_4$ alkyl), —C(O)—(CH$_2$)$_{0-2}$-Q-OC(O)O—(C$_1$-C$_4$ alkyl), —C(O)—(C$_1$-C$_4$ alkylene)-C(O)—O—(C$_1$-C$_4$ alkyl), —C(O)—N(R[6])—(C$_1$-C$_4$ alkylene)-C(O)—O—(C$_1$-C$_4$ alkyl), —C(O)—(CH$_2$)$_{0-2}$—N(R[6])—(C$_2$-C$_6$ alkenyl), —C(O)—(CH$_2$)$_{1-2}$—O—(C$_1$-C$_4$ alkyl), —C(O)—O—(C$_1$-C$_4$ alkylene)-O—(C$_1$-C$_4$ alkyl), —(CH$_2$)$_{0-4}$—C(O)—O—(C$_1$-C$_4$ alkyl), and —C(O)—(CH$_2$)$_{1-2}$—S—(C$_1$-C$_4$ alkyl). In one aspect of these embodiments, R[5] is selected from —C(O)—(CH2)$_{0-3}$—OCH$_3$, —C(O)—(CH$_2$)$_{0-3}$—OCH$_2$CH$_3$, —C(O)-furanyl, —C(O)—NH—CH$_2$—CH=CH$_2$, —C(O)—(CH$_2$)$_{1-4}$—C(O)—OCH$_3$, C(O)—(CH$_2$)$_2$—C(O)—OC$_2$-C$_3$alkyl, —C(O)—(CH$_2$)$_2$C(O)CH$_3$, C(O)—(CH$_2$)$_2$—C(O)—OC(CH$_2$)$_2$OH, —C(O)—(CH$_2$)$_{1-2}$—SCH$_3$, —C(O)-cyclopropyl, —C(O)— isoxazolyl, —C(O)—CH$_2$-cyclopropyl, —C(O)—CH$_2$CH$_3$, —C(O)—(CH$_2$)$_2$CH$_3$, —C(O)—CH$_2$Cl, —C(O)—NH—CH$_3$, —C(O)—CH$_2$-thienyl, —C(O)—NH—(CH$_2$)$_2$—C(O)—OCH$_3$, —C(O)—CH$_2$-pyridinyl, —C(O)—(CH$_2$)$_2$—O-phenyl, —C(O)—CH$_2$-pyrazolyl, —C(O)—CH$_2$-oxadiazolyl, —C(O)-oxazolyl, —C(O)CH$_2$CF$_3$, C(O)(CH$_2$)$_{2-3}$OH, —C(O)(CH$_2$)C(O)CH$_3$, —C(O)CH$_2$CH(OH)CH$_3$, —C(O)CH$_2$CH$_2$F, —C(O)cyclopropyl-C(O)O—C$_1$-C$_2$ alkyl, —C(O)cyclopropyl-CH$_2$—OC(O)O—C$_1$-C$_2$ alkyl, and C(O)cyclopropyl-CH$_2$OH.

In another embodiment, the compound is selected from any one of the compounds set forth in Table 1, below.

| Cmpd No | Structure |
|---------|-----------|
| 101 | 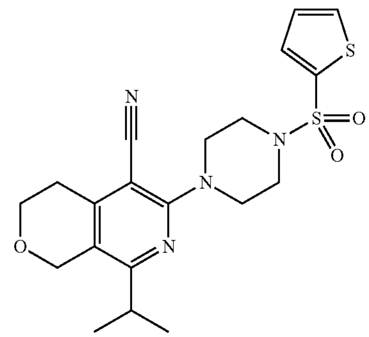 [SMILES: CC(C)c1nc(N2CCN(S(=O)(=O)c3cccs3)CC2)c(C#N)c2c1COCC2] |
| 102 | 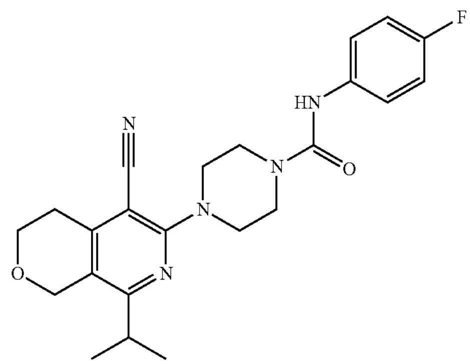 [SMILES: CC(C)c1nc(N2CCN(C(=O)Nc3ccc(F)cc3)CC2)c(C#N)c2c1COCC2] |
| 103 | 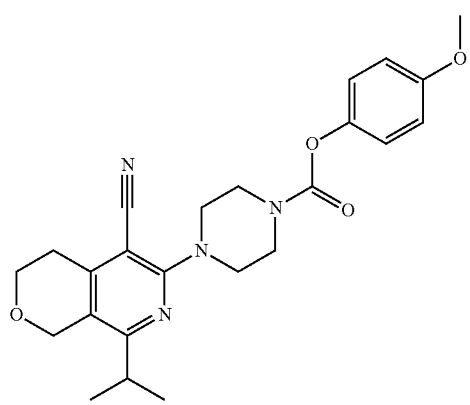 [SMILES: COc1ccc(OC(=O)N2CCN(c3nc(C(C)C)c4c(c3C#N)CCOC4)CC2)cc1] |
| 104 | 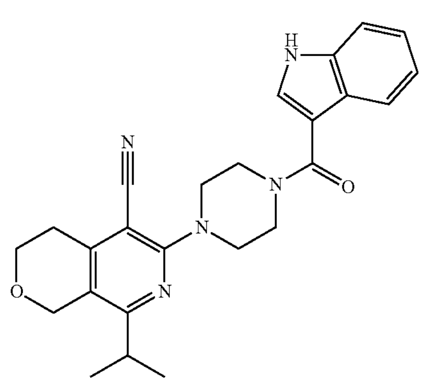 [SMILES: CC(C)c1nc(N2CCN(C(=O)c3c[nH]c4ccccc34)CC2)c(C#N)c2c1COCC2] |

-continued
| Cmpd No | Structure |
| --- | --- |
| 105 | 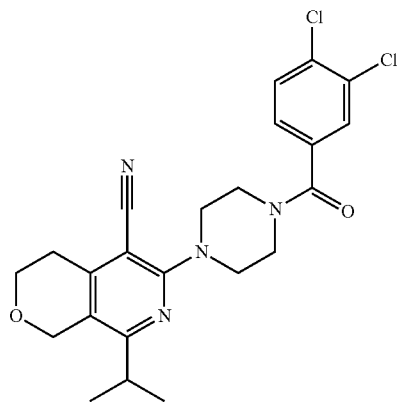 [SMILES: CC(C)c1nc(N2CCN(C(=O)c3ccc(Cl)c(Cl)c3)CC2)c(C#N)c2c1COCC2] |
| 106 | 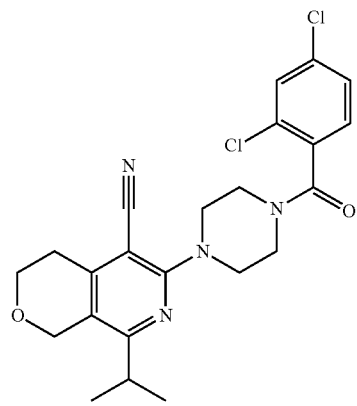 [SMILES: CC(C)c1nc(N2CCN(C(=O)c3ccc(Cl)cc3Cl)CC2)c(C#N)c2c1COCC2] |
| 107 | 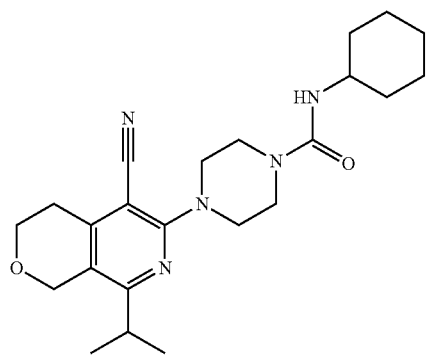 [SMILES: CC(C)c1nc(N2CCN(C(=O)NC3CCCCC3)CC2)c(C#N)c2c1COCC2] |
| 108 | 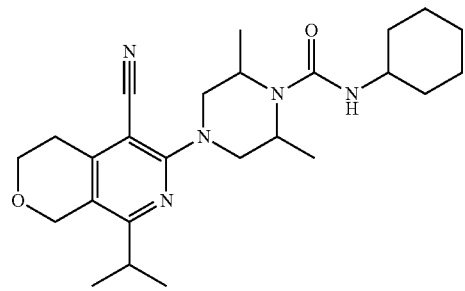 [SMILES: CC(C)c1nc(N2CC(C)N(C(=O)NC3CCCCC3)C(C)C2)c(C#N)c2c1COCC2] |

-continued
| Cmpd No | Structure |
|---------|-----------|
| 109 | 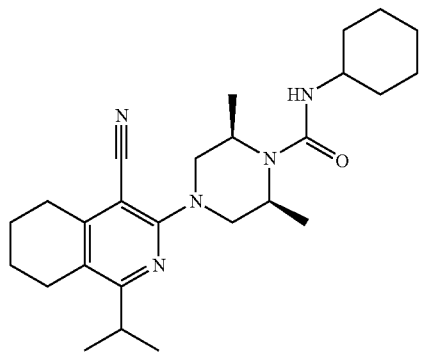 [SMILES: CC(C)c1nc(N2C[C@@H](C)N(C(=O)NC3CCCCC3)[C@@H](C)C2)c(C#N)c2c1CCCC2] |
| 110 | 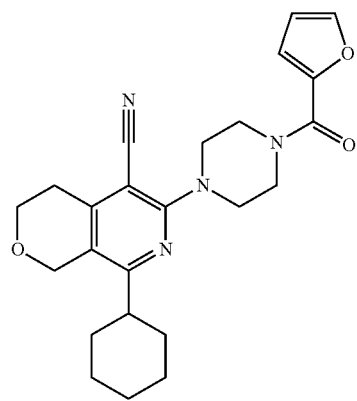 [SMILES: N#Cc1c(N2CCN(C(=O)c3ccco3)CC2)nc(C2CCCCC2)c2c1CCOC2] |
| 111 | 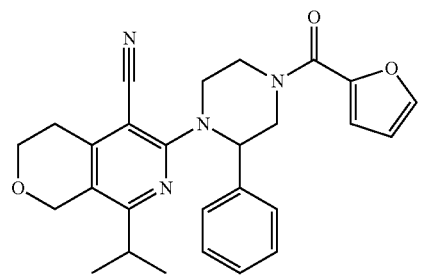 [SMILES: CC(C)c1nc(N2CCN(C(=O)c3ccco3)CC2c2ccccc2)c(C#N)c2c1COCC2] |
| 112 | 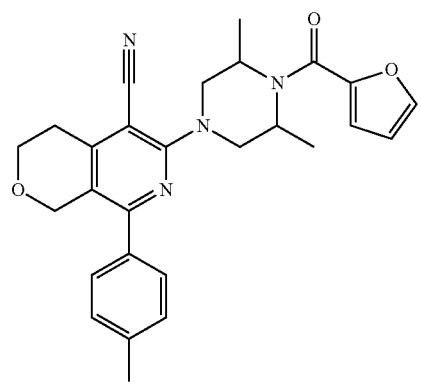 [SMILES: Cc1ccc(-c2nc(N3CC(C)N(C(=O)c4ccco4)C(C)C3)c(C#N)c3c2COCC3)cc1] |

-continued
| Cmpd No | Structure |
|---------|-----------|
| 113 | 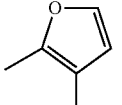 |
| 114 | 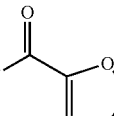 |
| 115 | 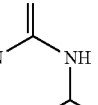 |
| 116 | 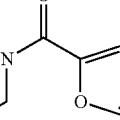 |
| 117 | 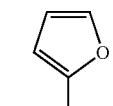 |

-continued
| Cmpd No | Structure |
|---|---|
| 118 | 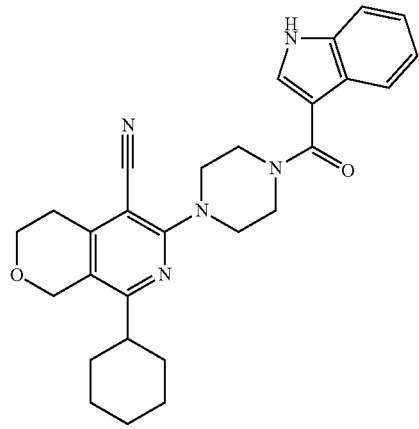 [SMILES: N#Cc1c(N2CCN(C(=O)c3c[nH]c4ccccc34)CC2)nc(C2CCCCC2)c2c1CCOC2] |
| 119 | 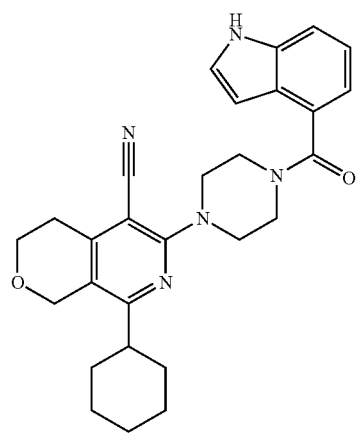 [SMILES: N#Cc1c(N2CCN(C(=O)c3cccc4[nH]ccc34)CC2)nc(C2CCCCC2)c2c1CCOC2] |
| 120 | 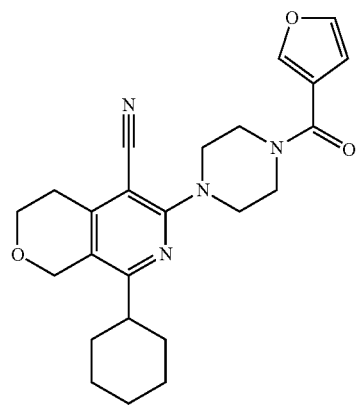 [SMILES: N#Cc1c(N2CCN(C(=O)c3ccoc3)CC2)nc(C2CCCCC2)c2c1CCOC2] |

-continued
| Cmpd No | Structure |
|---|---|
| 121 | 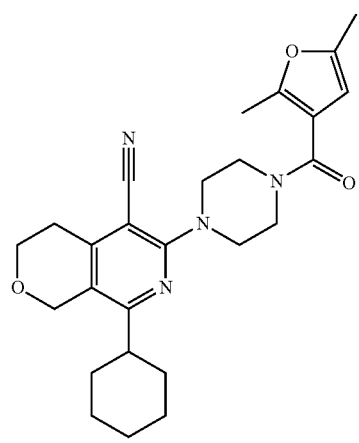 [SMILES: Cc1cc(C(=O)N2CCN(c3nc(C4CCCCC4)c4c(c3C#N)CCOC4)CC2)c(C)o1] |
| 122 | 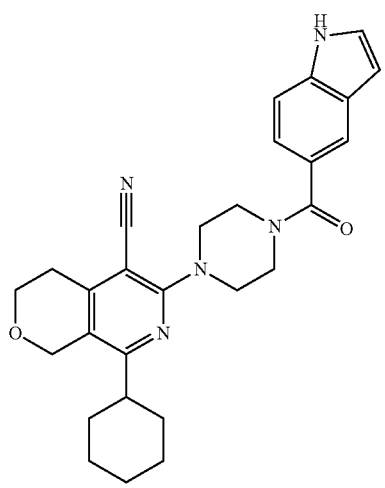 [SMILES: N#Cc1c(N2CCN(C(=O)c3ccc4[nH]ccc4c3)CC2)nc(C2CCCCC2)c2c1CCOC2] |
| 123 | 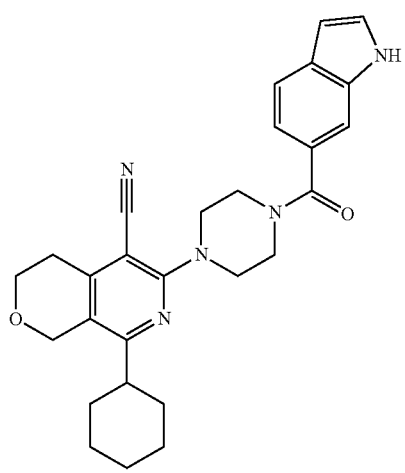 [SMILES: N#Cc1c(N2CCN(C(=O)c3ccc4cc[nH]c4c3)CC2)nc(C2CCCCC2)c2c1CCOC2] |

| Cmpd No | Structure |
|---------|-----------|
| 124 | 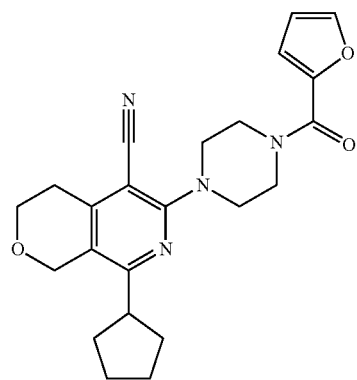 [SMILES: N#Cc1c(N2CCN(C(=O)c3ccco3)CC2)nc(C2CCCC2)c2c1CCOC2] |
| 125 | 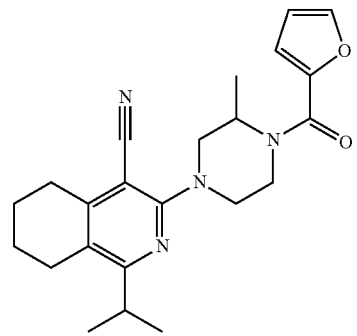 [SMILES: CC(C)c1nc(N2CCN(C(=O)c3ccco3)C(C)C2)c(C#N)c2c1CCCC2] |
| 126 | 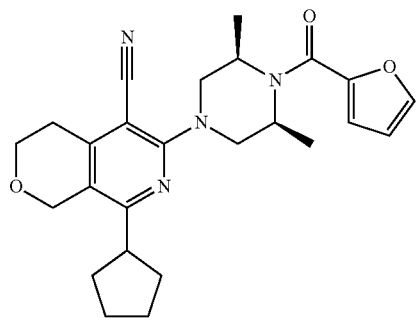 [SMILES: C[C@@H]1CN(c2nc(C3CCCC3)c3c(c2C#N)CCOC3)C[C@H](C)N1C(=O)c1ccco1] |
| 127 | 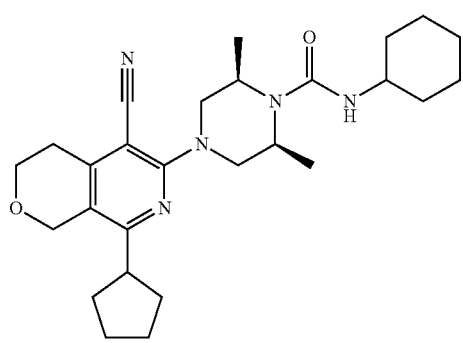 [SMILES: C[C@@H]1CN(c2nc(C3CCCC3)c3c(c2C#N)CCOC3)C[C@H](C)N1C(=O)NC1CCCCC1] |

| Cmpd No | Structure |
|---|---|
| 128 | 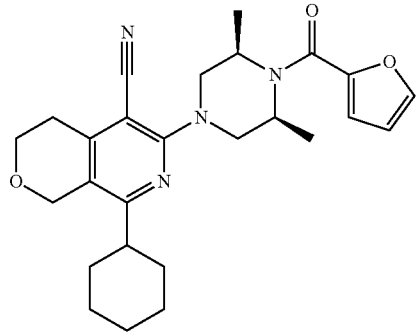 [SMILES: C[C@@H]1CN(c2nc(C3CCCCC3)c3c(c2C#N)CCOC3)C[C@H](C)N1C(=O)c1ccco1] |
| 129 | 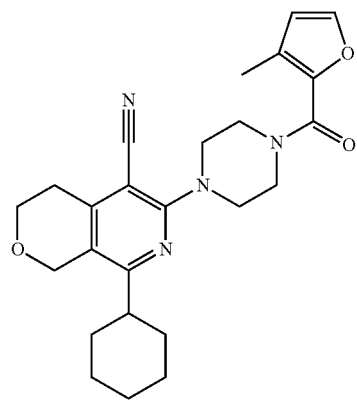 [SMILES: Cc1ccoc1C(=O)N1CCN(c2nc(C3CCCCC3)c3c(c2C#N)CCOC3)CC1] |
| 130 | 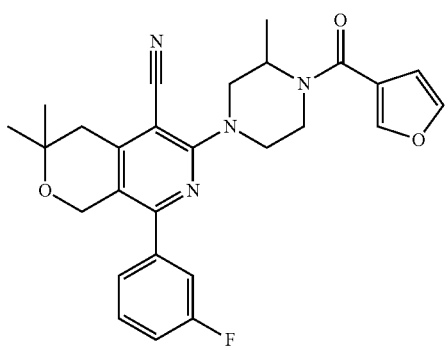 [SMILES: CC1CN(c2nc(-c3cccc(F)c3)c3c(c2C#N)CC(C)(C)OC3)CCN1C(=O)c1ccoc1] |
| 131 | 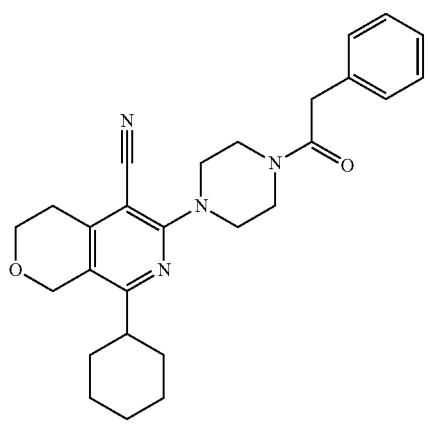 [SMILES: N#Cc1c(N2CCN(C(=O)Cc3ccccc3)CC2)nc(C2CCCCC2)c2c1CCOC2] |

| Cmpd No | Structure |
|---|---|
| 132 | 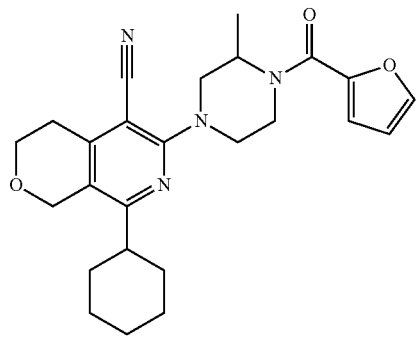 [SMILES: CC1CN(c2nc(C3CCCCC3)c3c(c2C#N)CCOC3)CCN1C(=O)c1ccco1] |
| 133 | 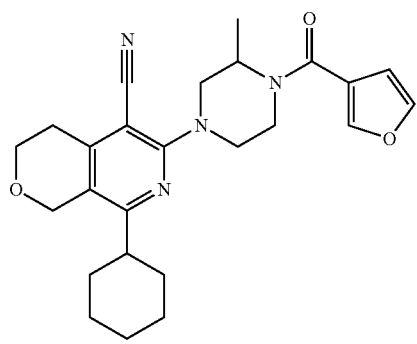 [SMILES: CC1CN(c2nc(C3CCCCC3)c3c(c2C#N)CCOC3)CCN1C(=O)c1ccoc1] |
| 134 | 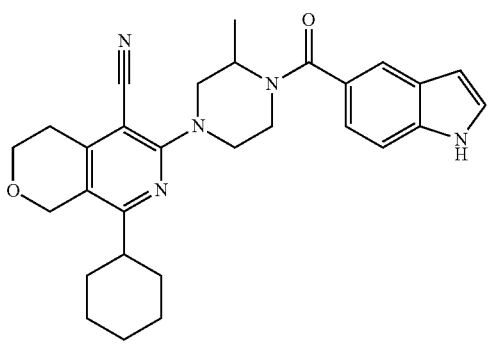 [SMILES: CC1CN(c2nc(C3CCCCC3)c3c(c2C#N)CCOC3)CCN1C(=O)c1ccc2[nH]ccc2c1] |
| 135 | 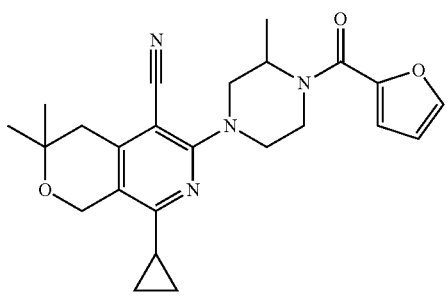 [SMILES: CC1CN(c2nc(C3CC3)c3c(c2C#N)CC(C)(C)OC3)CCN1C(=O)c1ccco1] |

| Cmpd No | Structure |
|---|---|
| 136 | 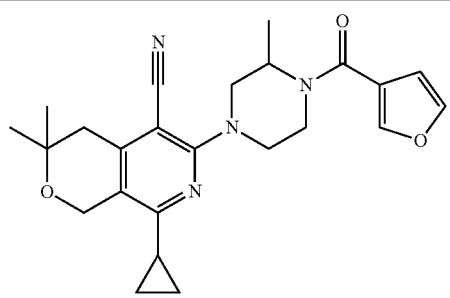 [SMILES: CC1CN(c2nc(C3CC3)c3c(c2C#N)CC(C)(C)OC3)CCN1C(=O)c1ccoc1] |
| 137 | 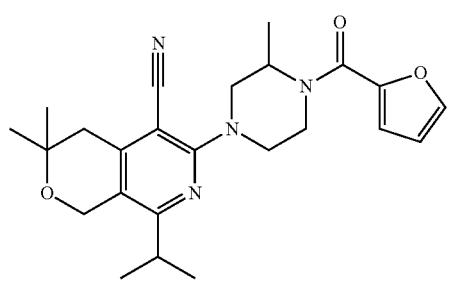 [SMILES: CC(C)c1nc(N2CCN(C(=O)c3ccco3)C(C)C2)c(C#N)c2c1COC(C)(C)C2] |
| 138 | 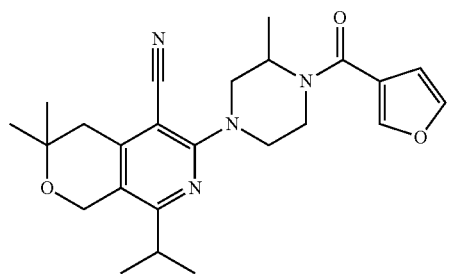 [SMILES: CC(C)c1nc(N2CCN(C(=O)c3ccoc3)C(C)C2)c(C#N)c2c1COC(C)(C)C2] |
| 139 | 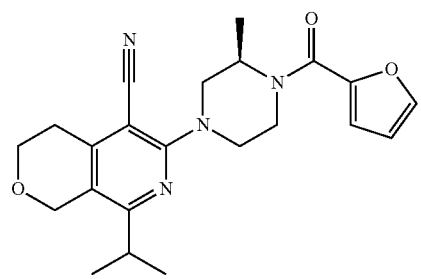 [SMILES: CC(C)c1nc(N2CCN(C(=O)c3ccco3)[C@H](C)C2)c(C#N)c2c1COCC2] |
| 140 | 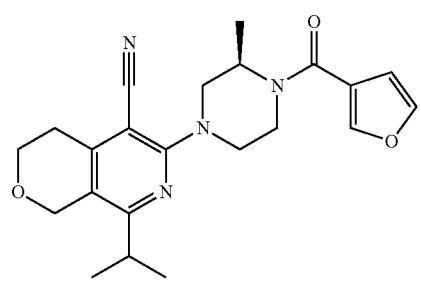 [SMILES: CC(C)c1nc(N2CCN(C(=O)c3ccoc3)[C@H](C)C2)c(C#N)c2c1COCC2] |

| Cmpd No | Structure |
|---|---|
| 141 | 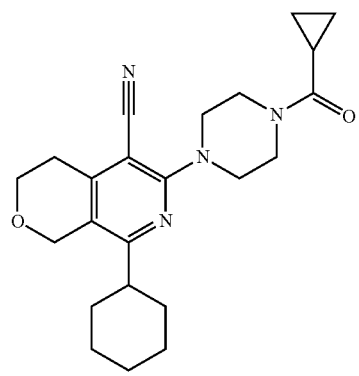 [SMILES: N#Cc1c(N2CCN(C(=O)C3CC3)CC2)nc(C2CCCCC2)c2c1CCOC2] |
| 142 | 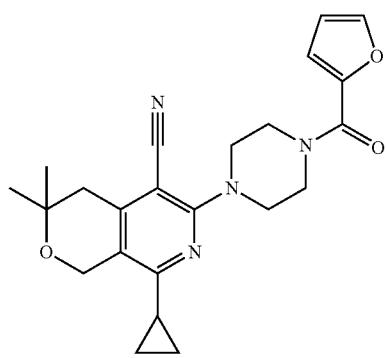 [SMILES: CC1(C)Cc2c(C#N)c(N3CCN(C(=O)c4ccco4)CC3)nc(C3CC3)c2CO1] |
| 143 | 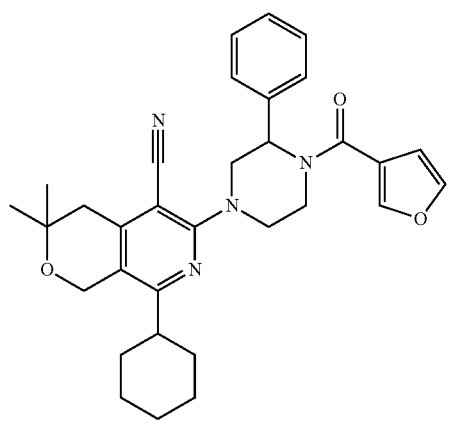 [SMILES: CC1(C)Cc2c(C#N)c(N3CCN(C(=O)c4ccoc4)C(c4ccccc4)C3)nc(C3CCCCC3)c2CO1] |
| 144 | 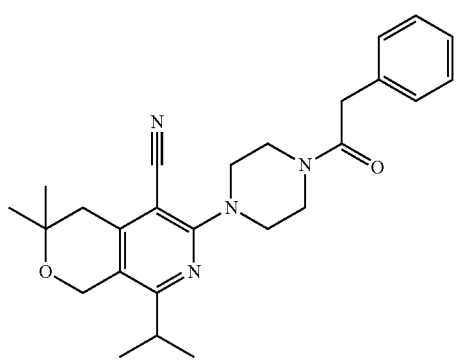 [SMILES: CC(C)c1nc(N2CCN(C(=O)Cc3ccccc3)CC2)c(C#N)c2c1COC(C)(C)C2] |

| Cmpd No | Structure |
|---|---|
| 145 | 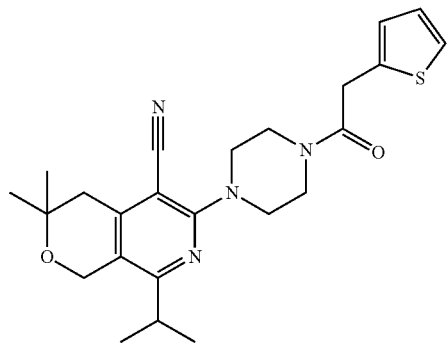 [SMILES: CC(C)c1nc(N2CCN(C(=O)Cc3cccs3)CC2)c(C#N)c2c1COC(C)(C)C2] |
| 146 | 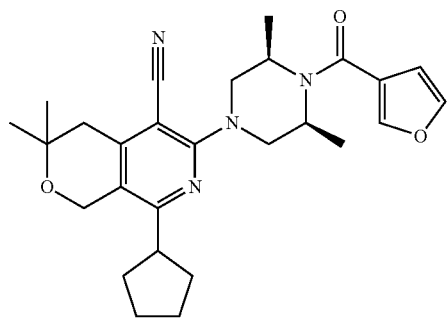 [SMILES: C[C@@H]1CN(c2nc(C3CCCC3)c3c(c2C#N)CC(C)(C)OC3)C[C@H](C)N1C(=O)c1ccoc1] |
| 147 | 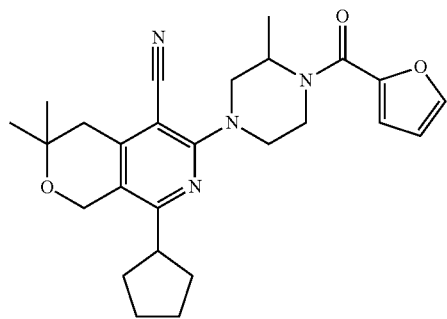 [SMILES: CC1CN(c2nc(C3CCCC3)c3c(c2C#N)CC(C)(C)OC3)CCN1C(=O)c1ccco1] |
| 148 | 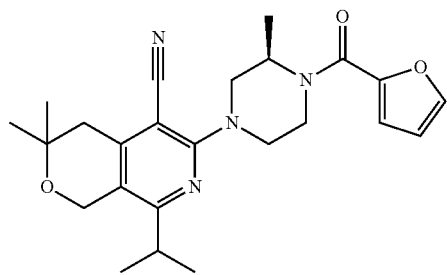 [SMILES: CC(C)c1nc(N2CCN(C(=O)c3ccco3)[C@H](C)C2)c(C#N)c2c1COC(C)(C)C2] |
| 149 | 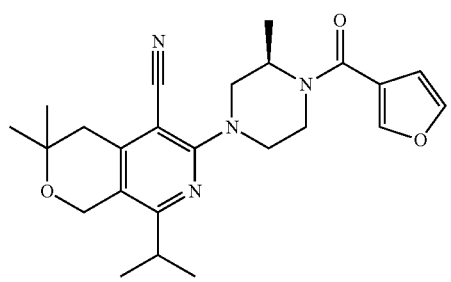 [SMILES: CC(C)c1nc(N2CCN(C(=O)c3ccoc3)[C@H](C)C2)c(C#N)c2c1COC(C)(C)C2] |

| Cmpd No | Structure |
|---|---|
| 150 | 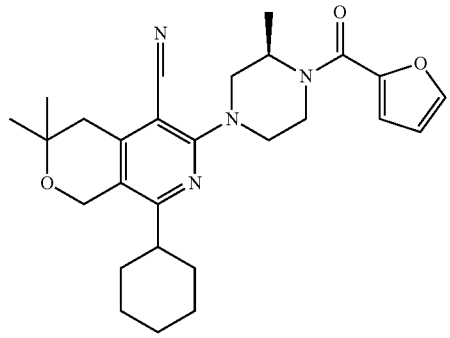 [SMILES: C[C@@H]1CN(c2nc(C3CCCCC3)c3c(c2C=N)CC(C)(C)OC3)CCN1C(=O)c1ccco1] |
| 151 | 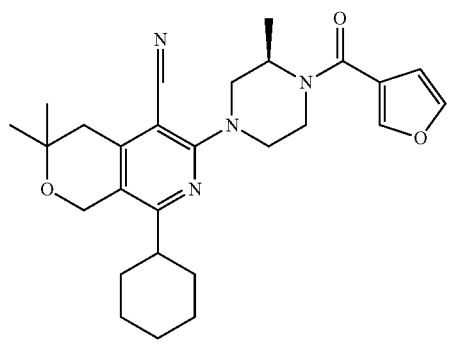 [SMILES: C[C@@H]1CN(c2nc(C3CCCCC3)c3c(c2C=N)CC(C)(C)OC3)CCN1C(=O)c1ccoc1] |
| 152 | 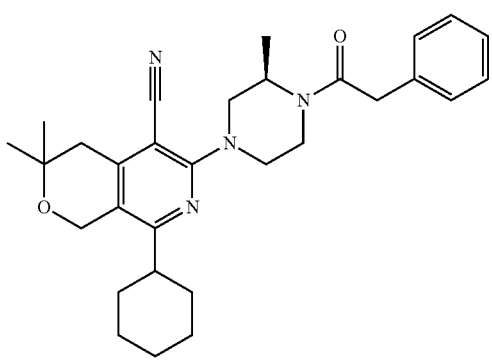 [SMILES: C[C@@H]1CN(c2nc(C3CCCCC3)c3c(c2C#N)CC(C)(C)OC3)CCN1C(=O)Cc1ccccc1] |
| 153 | 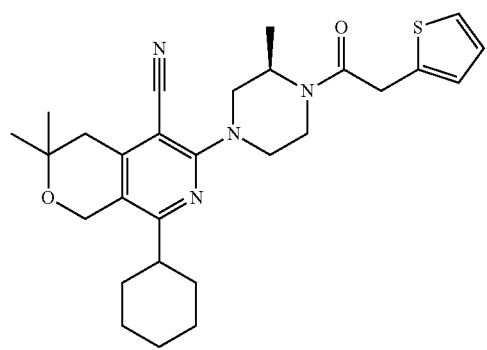 [SMILES: C[C@@H]1CN(c2nc(C3CCCCC3)c3c(c2C#N)CC(C)(C)OC3)CCN1C(=O)Cc1cccs1] |

| Cmpd No | Structure |
|---|---|
| 154 | 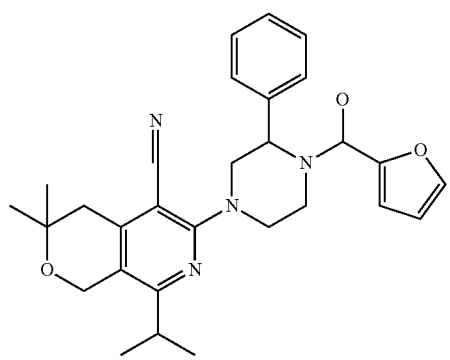 [SMILES: CC(C)c1nc(N2CCN(C(O)c3ccco3)C(c3ccccc3)C2)c(C=N)c2c1COC(C)(C)C2] |
| 155 | 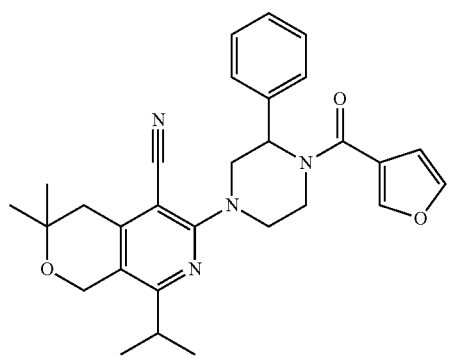 [SMILES: CC(C)c1nc(N2CCN(C(=O)c3ccoc3)C(c3ccccc3)C2)c(C#N)c2c1COC(C)(C)C2] |
| 156 | 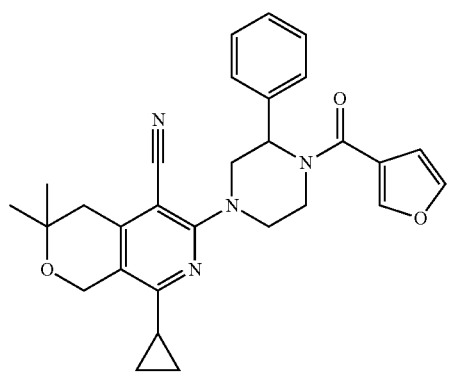 [SMILES: CC1(C)Cc2c(C#N)c(N3CCN(C(=O)c4ccoc4)C(c4ccccc4)C3)nc(C3CC3)c2CO1] |
| 157 | 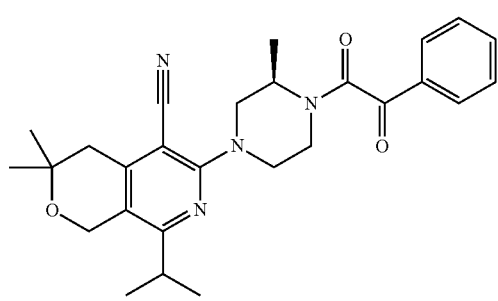 [SMILES: CC(C)c1nc(N2CCN(C(=O)C(=O)c3ccccc3)[C@H](C)C2)c(C#N)c2c1COC(C)(C)C2] |

-continued
| Cmpd No | Structure |
|---|---|
| 158 | 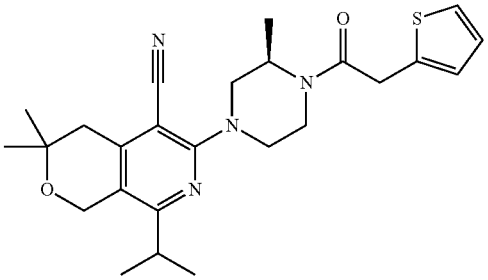 [SMILES: CC(C)c1nc(N2CCN(C(=O)Cc3cccs3)[C@H](C)C2)c(C#N)c2c1COC(C)(C)C2] |
| 159 | 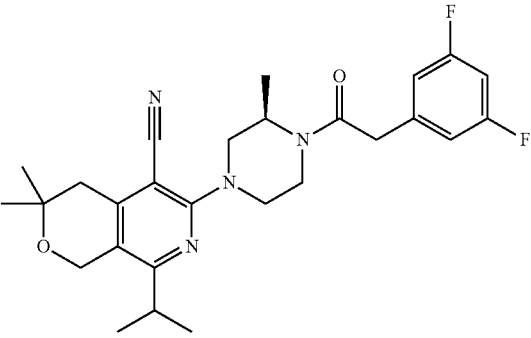 [SMILES: CC(C)c1nc(N2CCN(C(=O)Cc3cc(F)cc(F)c3)[C@H](C)C2)c(C#N)c2c1COC(C)(C)C2] |
| 160 | 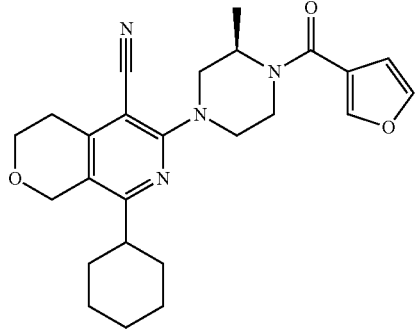 [SMILES: C[C@@H]1CN(c2nc(C3CCCCC3)c3c(c2C#N)CCOC3)CCN1C(=O)c1ccoc1] |
| 161 | 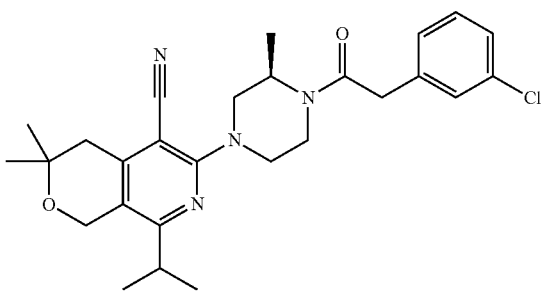 [SMILES: CC(C)c1nc(N2CCN(C(=O)Cc3cccc(Cl)c3)[C@H](C)C2)c(C#N)c2c1COC(C)(C)C2] |
| 162 | 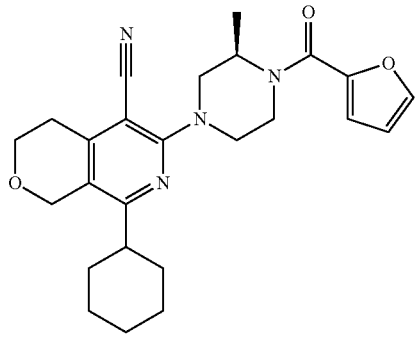 [SMILES: C[C@@H]1CN(c2nc(C3CCCCC3)c3c(c2C#N)CCOC3)CCN1C(=O)c1ccco1] |

-continued

| Cmpd No | Structure |
|---------|-----------|
| 163 | 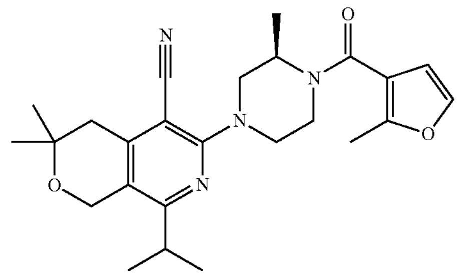 [SMILES: Cc1occc1C(=O)N1CCN(c2nc(C(C)C)c3c(c2C#N)CC(C)(C)OC3)C[C@H]1C] |
| 164 | 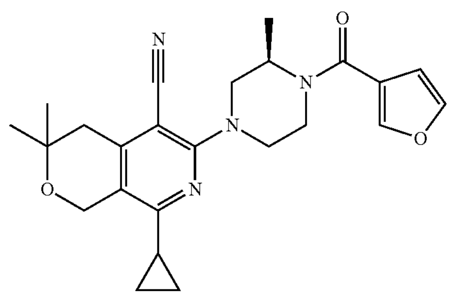 [SMILES: C[C@@H]1CN(c2nc(C3CC3)c3c(c2C#N)CC(C)(C)OC3)CCN1C(=O)c1ccoc1] |
| 165 | 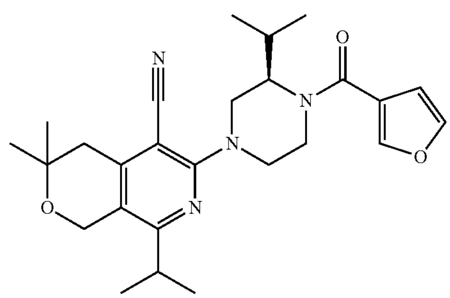 |
| 166 | 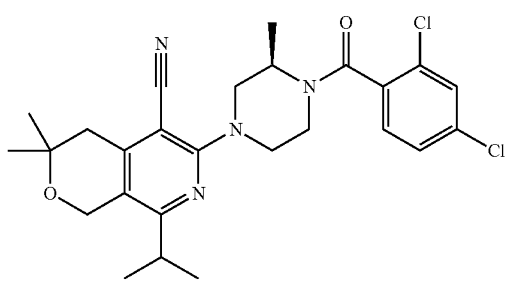 [SMILES: CC(C)c1nc(N2CCN(C(=O)c3ccc(Cl)cc3Cl)[C@H](C)C2)c(C#N)c2c1COC(C)(C)C2] |
| 167 | 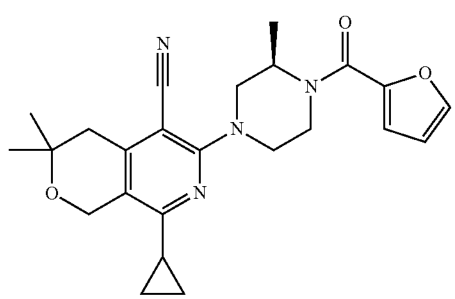 [SMILES: C[C@@H]1CN(c2nc(C3CC3)c3c(c2C#N)CC(C)(C)OC3)CCN1C(=O)c1ccco1] |

-continued

| Cmpd No | Structure |
|---------|-----------|
| 168 | 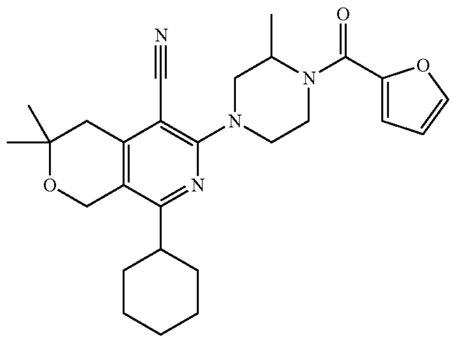 [SMILES: CC1CN(c2nc(C3CCCCC3)c3c(c2C#N)CC(C)(C)OC3)CCN1C(=O)c1ccco1] |
| 169 | 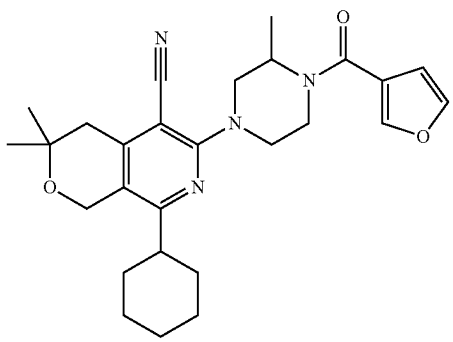 [SMILES: CC1CN(c2nc(C3CCCCC3)c3c(c2C#N)CC(C)(C)OC3)CCN1C(=O)c1ccoc1] |
| 170 | 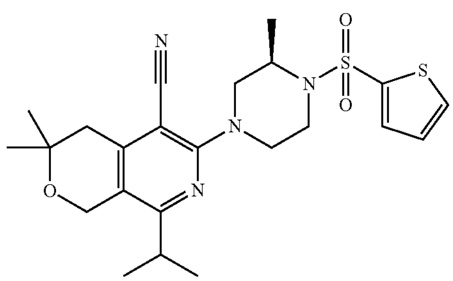 [SMILES: CC(C)c1nc(N2CCN(S(=O)(=O)c3cccs3)[C@H](C)C2)c(C#N)c2c1COC(C)(C)C2] |
| 171 | 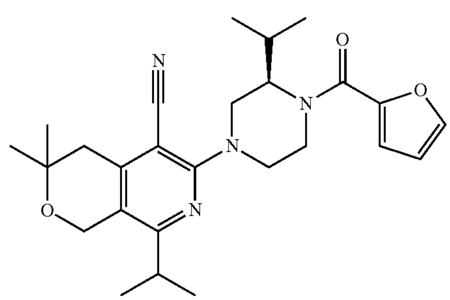 [SMILES: CC(C)c1nc(N2CCN(C(=O)c3ccco3)[C@H](C(C)C)C2)c(C#N)c2c1COC(C)(C)C2] |
| 172 | 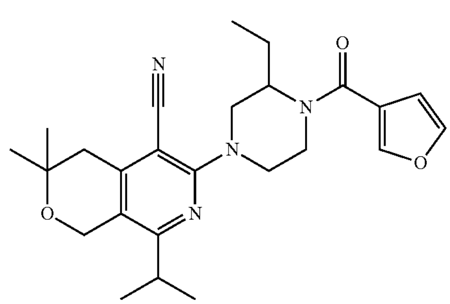 [SMILES: CCC1CN(c2nc(C(C)C)c3c(c2C#N)CC(C)(C)OC3)CCN1C(=O)c1ccoc1] |

-continued

| Cmpd No | Structure |
|---------|-----------|
| 173 | 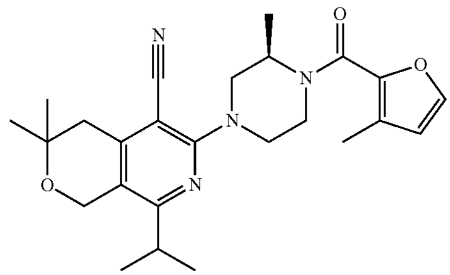 [SMILES: Cc1ccoc1C(=O)N1CCN(c2nc(C(C)C)c3c(c2C#N)CC(C)(C)OC3)C[C@H]1C] |
| 174 | 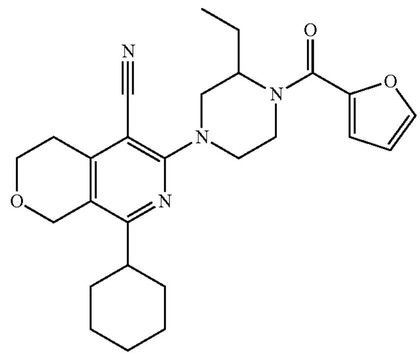 [SMILES: CCC1CN(c2nc(C3CCCCC3)c3c(c2C#N)CCOC3)CCN1C(=O)c1ccco1] |
| 175 | 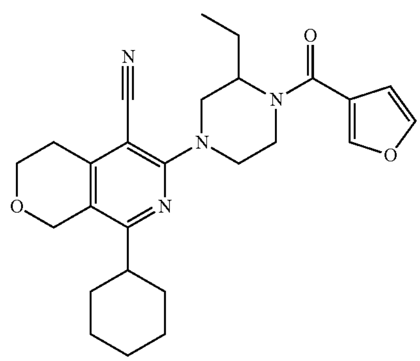 [SMILES: CCC1CN(c2nc(C3CCCCC3)c3c(c2C#N)CCOC3)CCN1C(=O)c1ccoc1] |
| 176 | 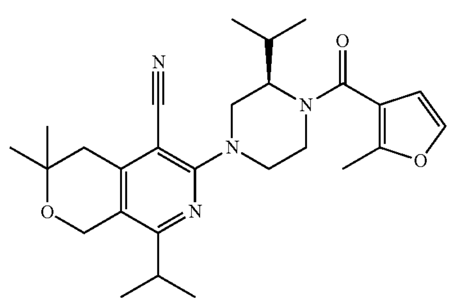 [SMILES: Cc1occc1C(=O)N1CCN(c2nc(C(C)C)c3c(c2C#N)CC(C)(C)OC3)C[C@H]1C(C)C] |
| 177 | 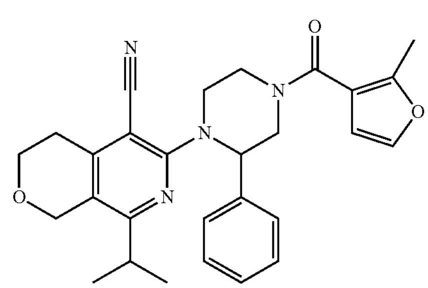 [SMILES: Cc1occc1C(=O)N1CCN(c2nc(C(C)C)c3c(c2C#N)CCOC3)C(c2ccccc2)C1] |

-continued
| Cmpd No | Structure |
|---|---|
| 178 | 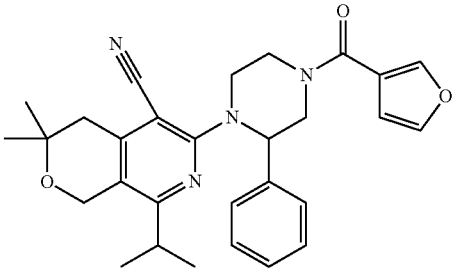 [SMILES: CC(C)c1nc(N2CCN(C(=O)c3ccoc3)CC2c2ccccc2)c(C#N)c2c1COC(C)(C)C2] |
| 179 | 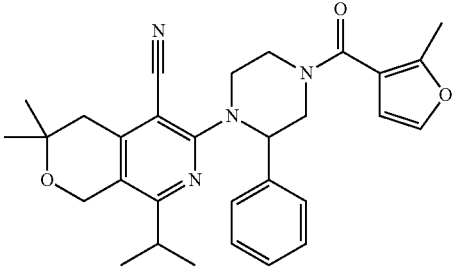 [SMILES: Cc1occc1C(=O)N1CCN(c2nc(C(C)C)c3c(c2C#N)CC(C)(C)OC3)C(c2ccccc2)C1] |
| 180 | 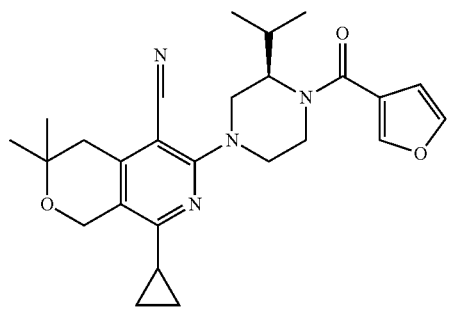 [SMILES: CC(C)[C@@H]1CN(c2nc(C3CC3)c3c(c2C=N)CC(C)(C)OC3)CCN1C(=O)c1ccoc1] |
| 181 | 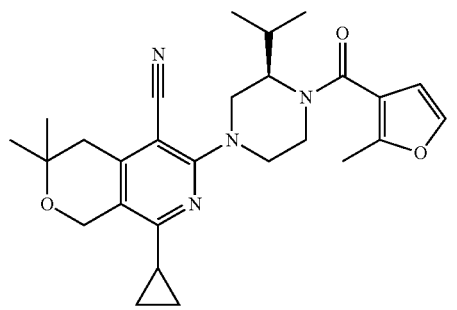 [SMILES: Cc1occc1C(=O)N1CCN(c2nc(C3CC3)c3c(c2C#N)CC(C)(C)OC3)C[C@H]1C(C)C] |
| 182 | 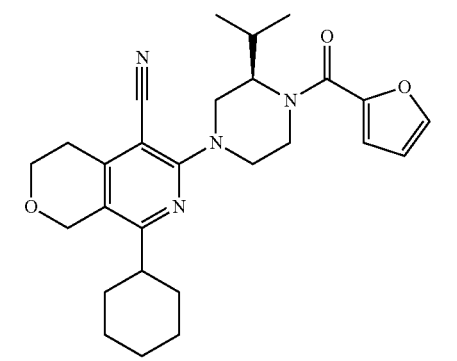 [SMILES: CC(C)[C@@H]1CN(c2nc(C3CCCCC3)c3c(c2C#N)CCOC3)CCN1C(=O)c1ccco1] |

| Cmpd No | Structure |
|---|---|
| 183 | 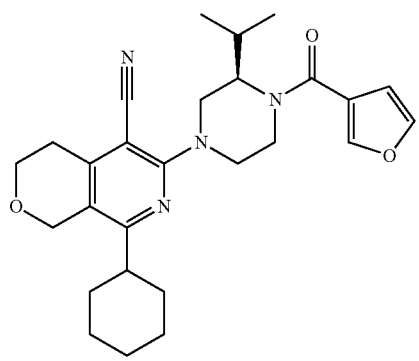 [SMILES: CC(C)[C@@H]1CN(c2nc(C3CCCCC3)c3c(c2C#N)CCOC3)CCN1C(=O)c1ccoc1] |
| 184 | 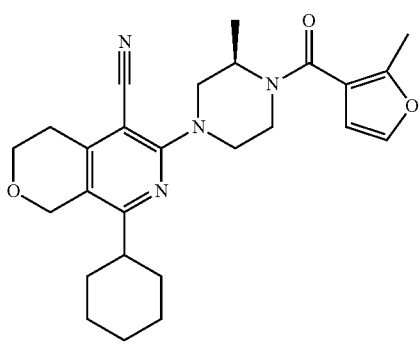 [SMILES: Cc1occc1C(=O)N1CCN(c2nc(C3CCCCC3)c3c(c2C#N)CCOC3)C[C@H]1C] |
| 185 | 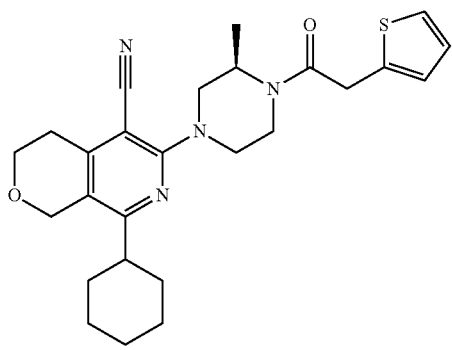 [SMILES: C[C@@H]1CN(c2nc(C3CCCCC3)c3c(c2C#N)CCOC3)CCN1C(=O)Cc1cccs1] |
| 186 | 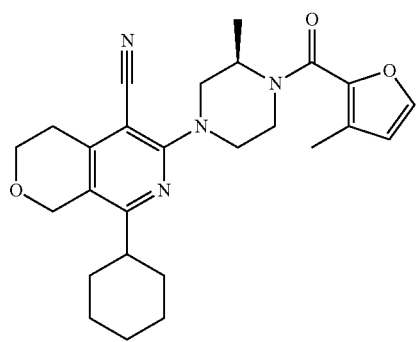 [SMILES: Cc1ccoc1C(=O)N1CCN(c2nc(C3CCCCC3)c3c(c2C#N)CCOC3)C[C@H]1C] |

| Cmpd No | Structure |
|---|---|
| 187 | 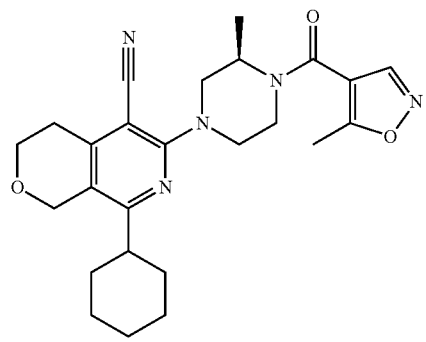 [SMILES: Cc1oncc1C(=O)N1CCN(c2nc(C3CCCCC3)c3c(c2C#N)CCOC3)C[C@H]1C] |
| 188 | 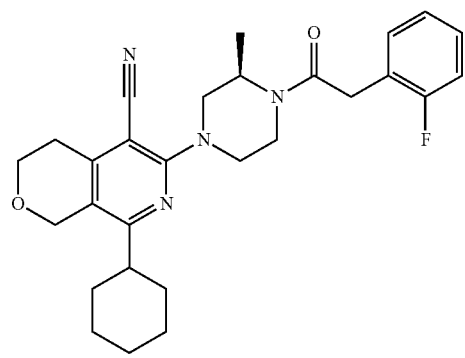 [SMILES: C[C@@H]1CN(c2nc(C3CCCCC3)c3c(c2C#N)CCOC3)CCN1C(=O)Cc1ccccc1F] |
| 189 | 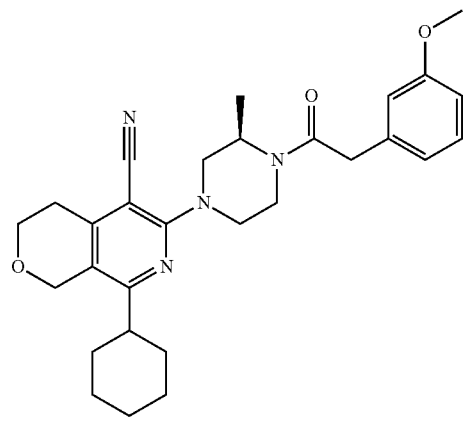 [SMILES: COc1cccc(CC(=O)N2CCN(c3nc(C4CCCCC4)c4c(c3C#N)CCOC4)C[C@H]2C)c1] |
| 190 | 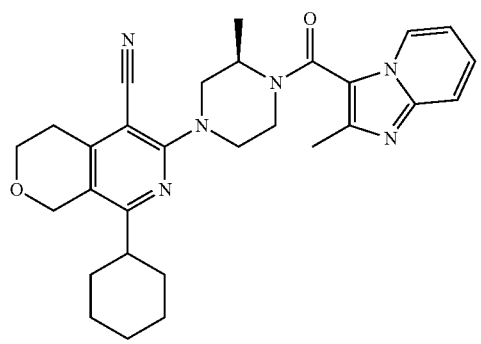 [SMILES: Cc1nc2ccccn2c1C(=O)N1CCN(c2nc(C3CCCCC3)c3c(c2C#N)CCOC3)C[C@H]1C] |

| Cmpd No | Structure |
|---|---|
| 191 | 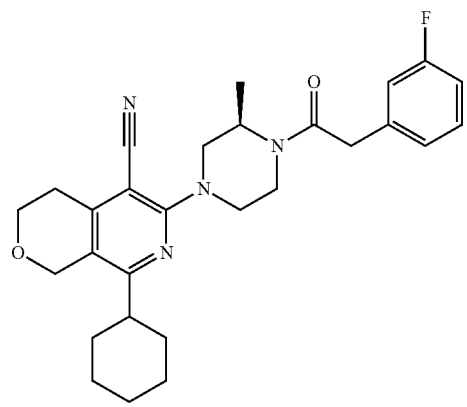 [SMILES: C[C@@H]1CN(c2nc(C3CCCCC3)c3c(c2C#N)CCOC3)CCN1C(=O)Cc1cccc(F)c1] |
| 192 | 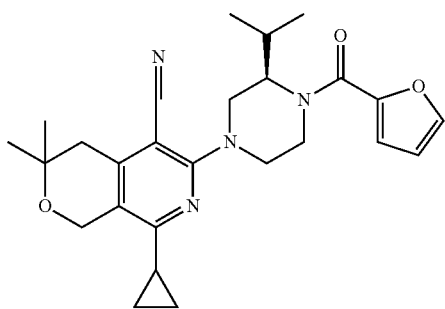 [SMILES: CC(C)[C@@H]1CN(c2nc(C3CC3)c3c(c2C=N)CC(C)(C)OC3)CCN1C(=O)c1ccco1] |
| 193 | 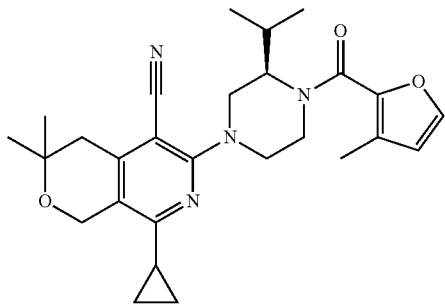 [SMILES: Cc1ccoc1C(=O)N1CCN(c2nc(C3CC3)c3c(c2C#N)CC(C)(C)OC3)C[C@H]1C(C)C] |
| 194 | 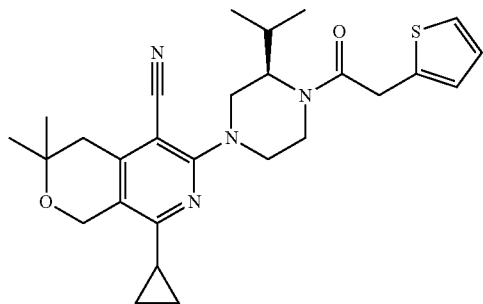 [SMILES: CC(C)[C@@H]1CN(c2nc(C3CC3)c3c(c2C#N)CC(C)(C)OC3)CCN1C(=O)Cc1cccs1] |

| Cmpd No | Structure |
|---|---|
| 195 | 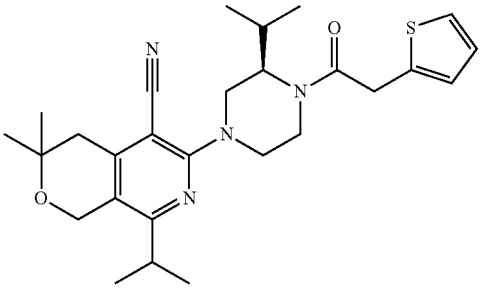 [SMILES: CC(C)c1nc(N2CCN(C(=O)Cc3cccs3)[C@H](C(C)C)C2)c(C#N)c2c1COC(C)(C)C2] |
| 196 | 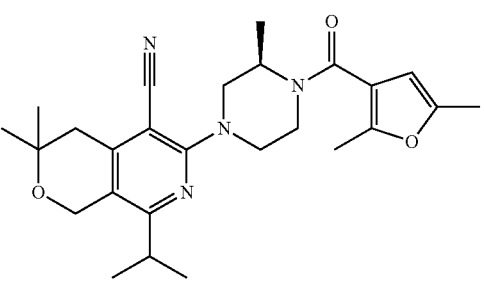 |
| 197 | 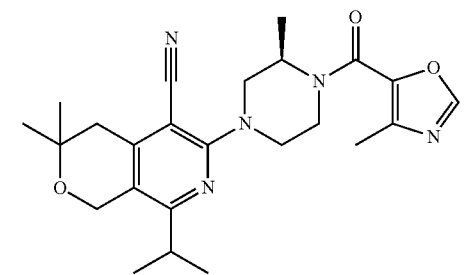 [SMILES: Cc1ncoc1C(=O)N1CCN(c2nc(C(C)C)c3c(c2C#N)CC(C)(C)OC3)C[C@H]1C] |
| 198 | 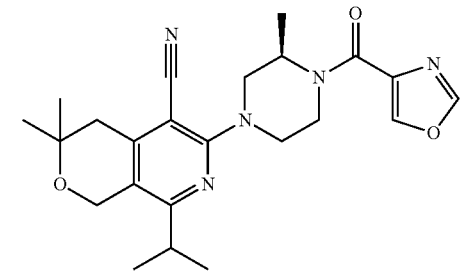 |
| 199 | 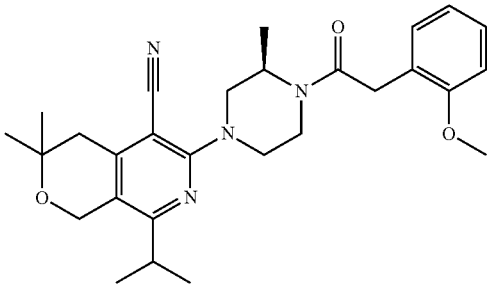 |

| Cmpd No | Structure |
|---|---|
| 200 | 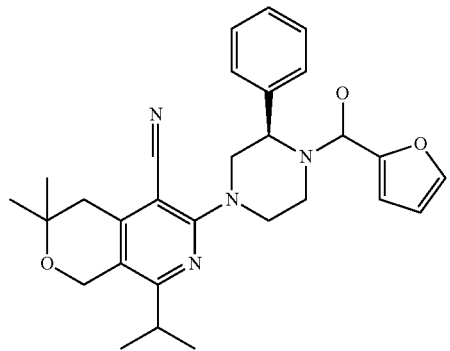 [SMILES: CC(C)c1nc(N2CCN(C(O)c3ccco3)[C@H](c3ccccc3)C2)c(C=N)c2c1COC(C)(C)C2] |
| 201 | 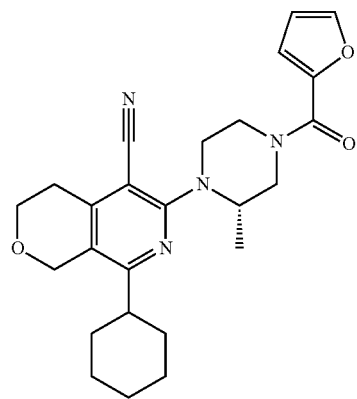 [SMILES: C[C@H]1CN(C(=O)c2ccco2)CCN1c1nc(C2CCCCC2)c2c(c1C#N)CCOC2] |
| 202 | 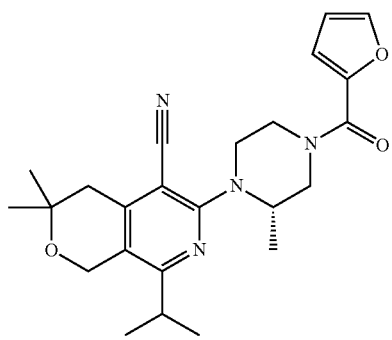 [SMILES: CC(C)c1nc(N2CCN(C(=O)c3ccco3)C[C@@H]2C)c(C#N)c2c1COC(C)(C)C2] |
| 203 | 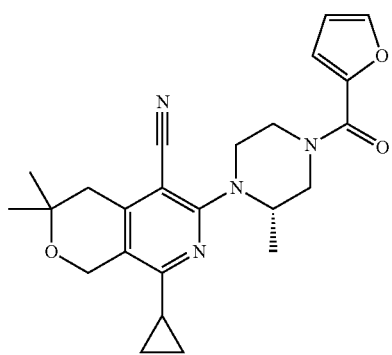 [SMILES: C[C@H]1CN(C(=O)c2ccco2)CCN1c1nc(C2CC2)c2c(c1C#N)CC(C)(C)OC2] |

| Cmpd No | Structure |
|---------|-----------|
| 204 | 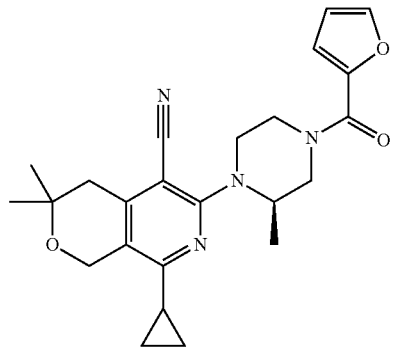 [SMILES: C[C@@H]1CN(C(=O)c2ccco2)CCN1c1nc(C2CC2)c2c(c1C#N)CC(C)(C)OC2] |
| 205 | 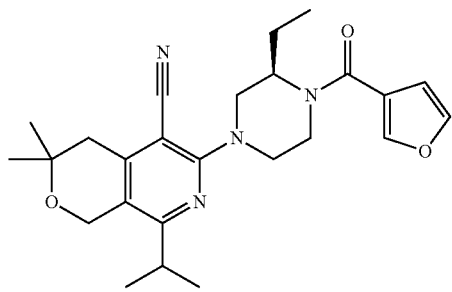 [SMILES: CC[C@@H]1CN(c2nc(C(C)C)c3c(c2C#N)CC(C)(C)OC3)CCN1C(=O)c1ccoc1] |
| 206 | 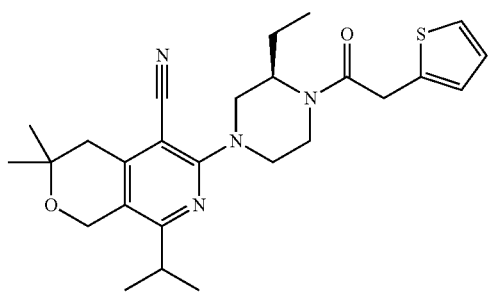 [SMILES: CC[C@@H]1CN(c2nc(C(C)C)c3c(c2C#N)CC(C)(C)OC3)CCN1C(=O)Cc1cccs1] |
| 207 | 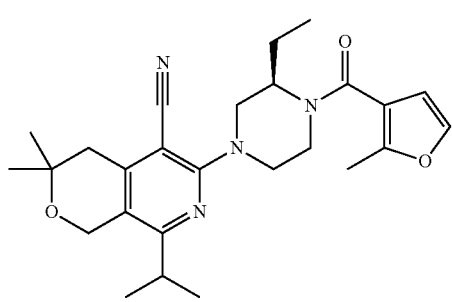 [SMILES: CC[C@@H]1CN(c2nc(C(C)C)c3c(c2C#N)CC(C)(C)OC3)CCN1C(=O)c1ccoc1C] |
| 208 | 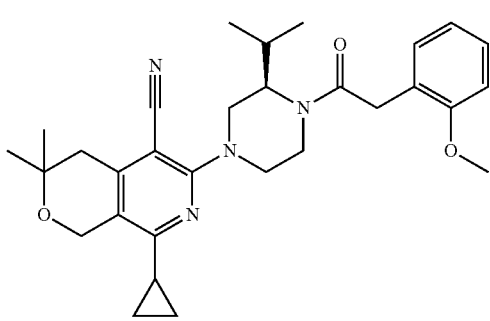 |

-continued
| Cmpd No | Structure |
|---|---|
| 209 | 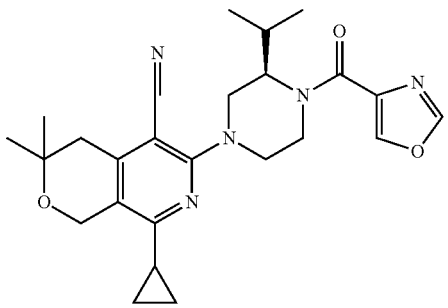 [SMILES: CC(C)[C@@H]1CN(c2nc(C3CC3)c3c(c2C=N)CC(C)(C)OC3)CCN1C(=O)c1cocn1] |
| 210 | 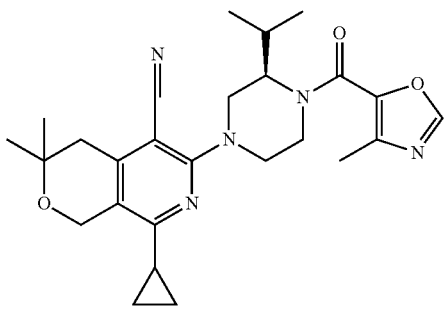 [SMILES: Cc1ncoc1C(=O)N1CCN(c2nc(C3CC3)c3c(c2C=N)CC(C)(C)OC3)C[C@H]1C(C)C] |
| 211 | 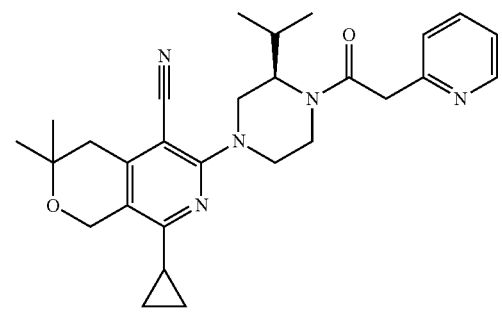 [SMILES: CC(C)[C@@H]1CN(c2nc(C3CC3)c3c(c2C#N)CC(C)(C)OC3)CCN1C(=O)Cc1ccccn1] |
| 212 | 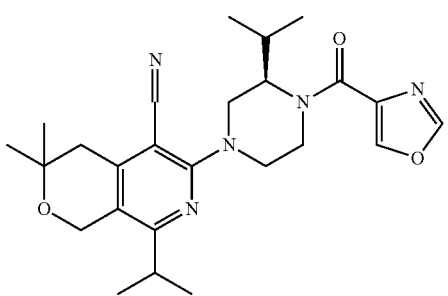 [SMILES: CC(C)c1nc(N2CCN(C(=O)c3cocn3)[C@H](C(C)C)C2)c(C=N)c2c1COC(C)(C)C2] |
| 213 | 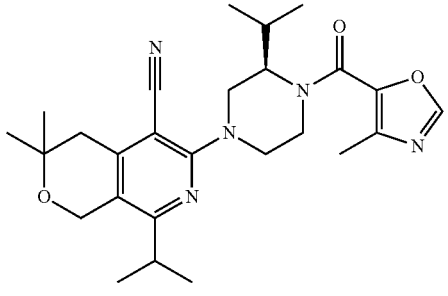 [SMILES: Cc1ncoc1C(=O)N1CCN(c2nc(C(C)C)c3c(c2C#N)CC(C)(C)OC3)C[C@H]1C(C)C] |

| Cmpd No | Structure |
|---|---|
| 214 | 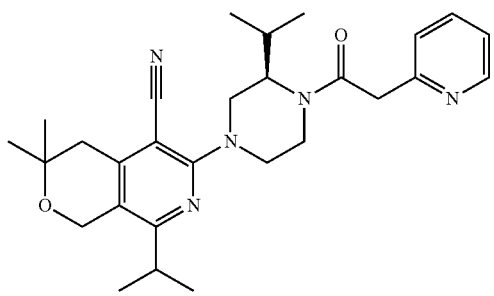 [SMILES: CC(C)c1nc(N2CCN(C(=O)Cc3ccccn3)[C@H](C(C)C)C2)c(C#N)c2c1COC(C)(C)C2] |
| 215 | 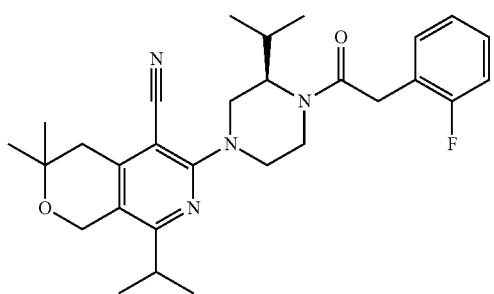 [SMILES: CC(C)c1nc(N2CCN(C(=O)Cc3ccccc3F)[C@H](C(C)C)C2)c(C#N)c2c1COC(C)(C)C2] |
| 216 | 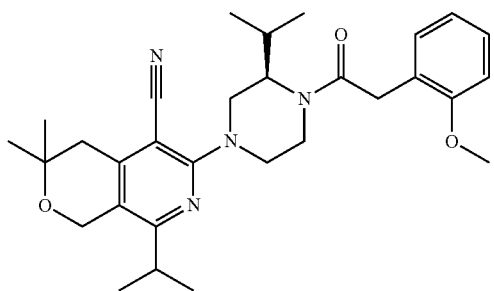 |
| 217 | 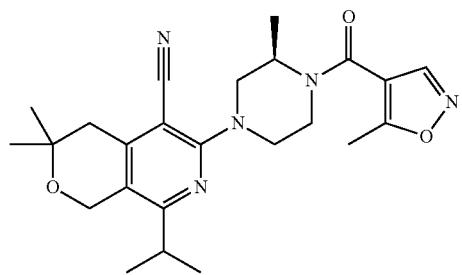 [SMILES: Cc1oncc1C(=O)N1CCN(c2nc(C(C)C)c3c(c2C#N)CC(C)(C)OC3)C[C@H]1C] |
| 218 | 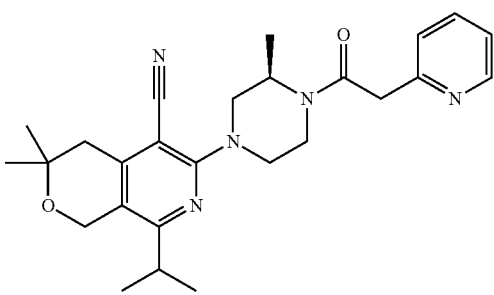 [SMILES: CC(C)c1nc(N2CCN(C(=O)Cc3ccccn3)[C@H](C)C2)c(C#N)c2c1COC(C)(C)C2] |

-continued

| Cmpd No | Structure |
|---|---|
| 219 | 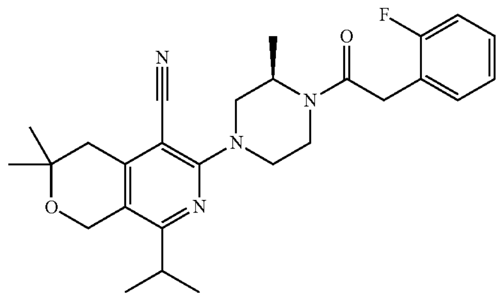 [SMILES: CC(C)c1nc(N2CCN(C(=O)Cc3ccccc3F)[C@H](C)C2)c(C#N)c2c1COC(C)(C)C2] |
| 220 | 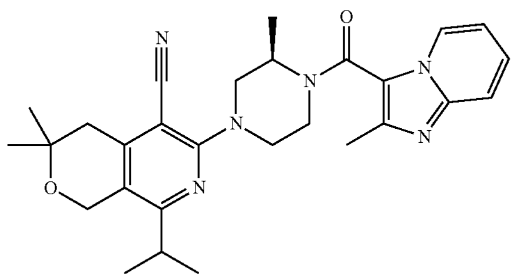 [SMILES: Cc1nc2ccccn2c1C(=O)N1CCN(c2nc(C(C)C)c3c(c2C#N)CC(C)(C)OC3)C[C@H]1C] |
| 221 | 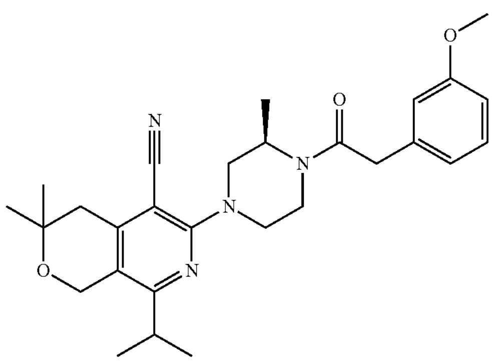 |
| 222 | 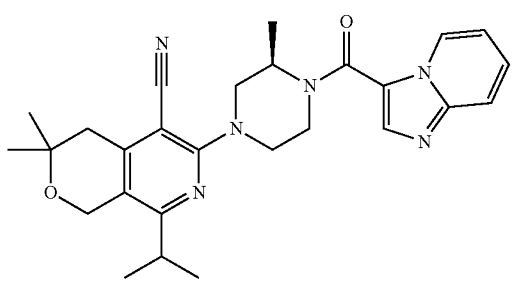 [SMILES: CC(C)c1nc(N2CCN(C(=O)c3cnc4ccccn34)[C@H](C)C2)c(C#N)c2c1COC(C)(C)C2] |
| 223 | 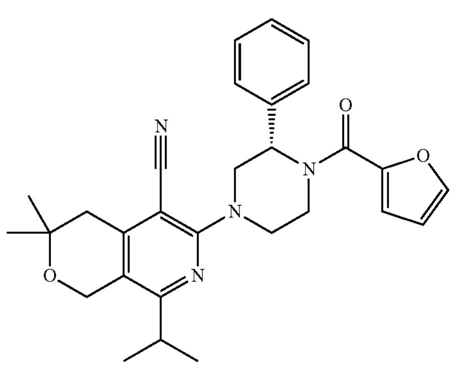 [SMILES: CC(C)c1nc(N2CCN(C(=O)c3ccco3)[C@@H](c3ccccc3)C2)c(C#N)c2c1COC(C)(C)C2] |

| Cmpd No | Structure |
|---|---|
| 224 | 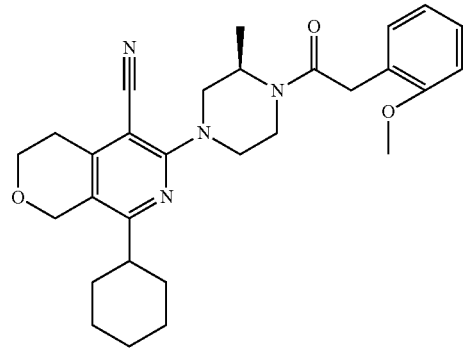 [SMILES: COc1ccccc1CC(=O)N1CCN(c2nc(C3CCCCC3)c3c(c2C#N)CCOC3)C[C@H]1C] |
| 225 | 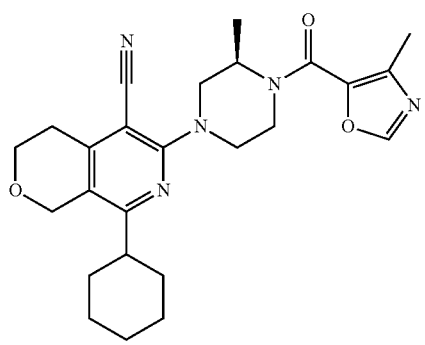 [SMILES: Cc1ncoc1C(=O)N1CCN(c2nc(C3CCCCC3)c3c(c2C#N)CCOC3)C[C@H]1C] |
| 226 | 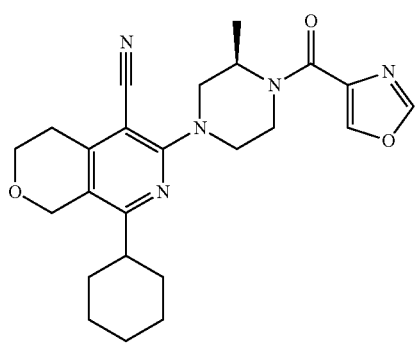 [SMILES: C[C@@H]1CN(c2nc(C3CCCCC3)c3c(c2C#N)CCOC3)CCN1C(=O)c1cocn1] |
| 227 | 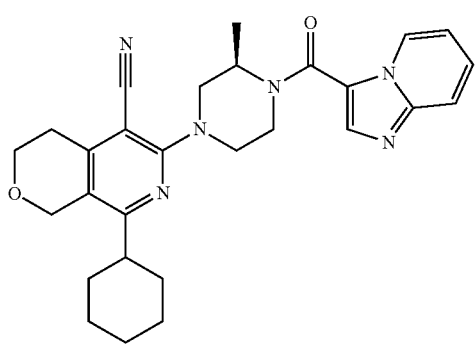 [SMILES: C[C@@H]1CN(c2nc(C3CCCCC3)c3c(c2C#N)CCOC3)CCN1C(=O)c1cnc2ccccn12] |

-continued
| Cmpd No | Structure |
|---------|-----------|
| 228 | 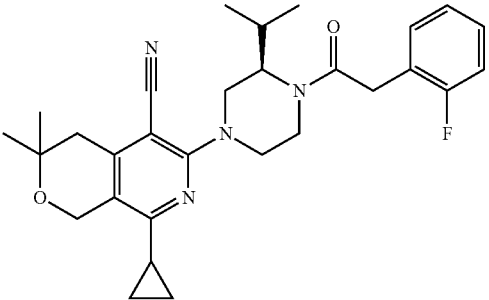 [SMILES: CC(C)[C@@H]1CN(c2nc(C3CC3)c3c(c2C#N)CC(C)(C)OC3)CCN1C(=O)Cc1ccccc1F] |
| 229 | 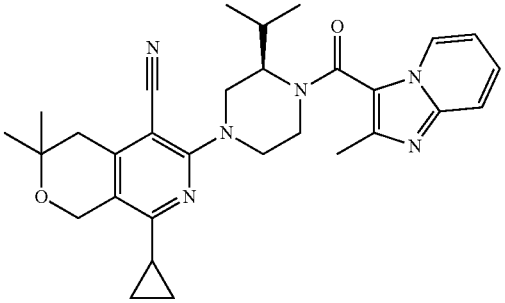 [SMILES: Cc1nc2ccccn2c1C(=O)N1CCN(c2nc(C3CC3)c3c(c2C#N)CC(C)(C)OC3)C[C@H]1C(C)C] |
| 230 | 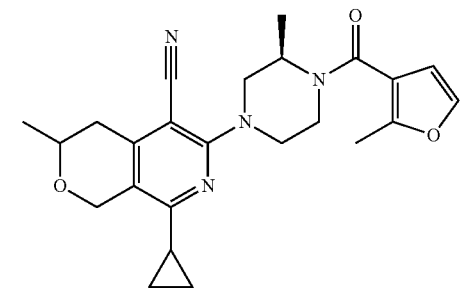 [SMILES: Cc1occc1C(=O)N1CCN(c2nc(C3CC3)c3c(c2C#N)CC(C)OC3)C[C@H]1C] |
| 231 | 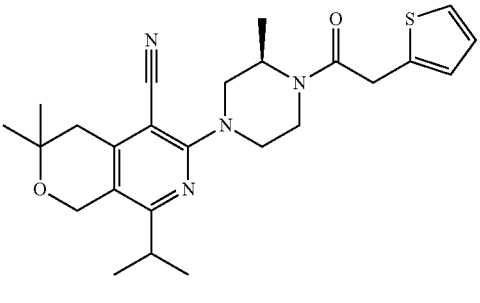 [SMILES: CC(C)c1nc(N2CCN(C(=O)Cc3cccs3)[C@H](C)C2)c(C#N)c2c1COC(C)(C)C2] |
| 232 | 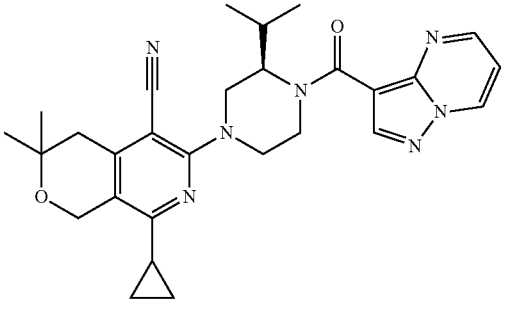 [SMILES: CC(C)[C@@H]1CN(c2nc(C3CC3)c3c(c2C#N)CC(C)(C)OC3)CCN1C(=O)c1cnn2cccnc12] |

| Cmpd No | Structure |
|---|---|
| 233 | 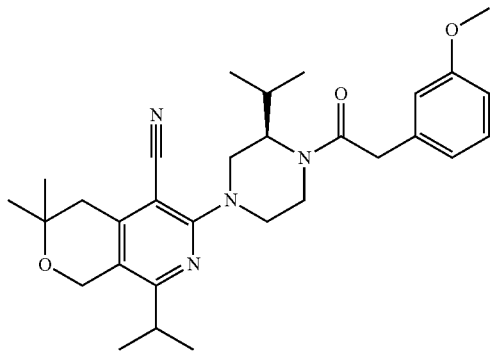 |
| 234 | 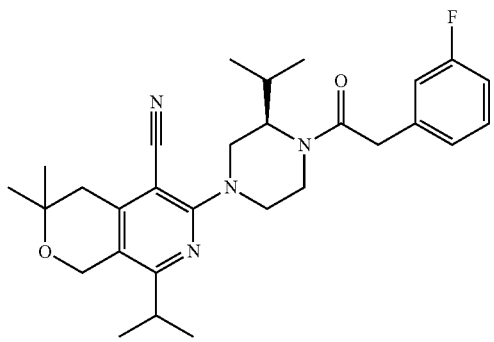 [SMILES: CC(C)c1nc(N2CCN(C(=O)Cc3cccc(F)c3)[C@H](C(C)C)C2)c(C#N)c2c1COC(C)(C)C2] |
| 235 | 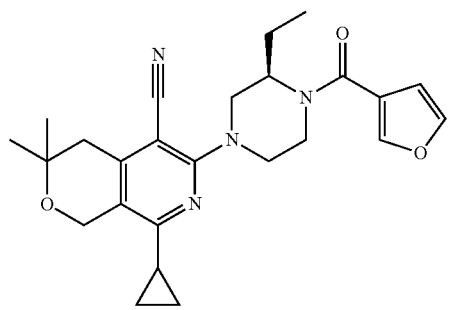 [SMILES: CC[C@@H]1CN(c2nc(C3CC3)c3c(c2C#N)CC(C)(C)OC3)CCN1C(=O)c1ccoc1] |
| 236 | 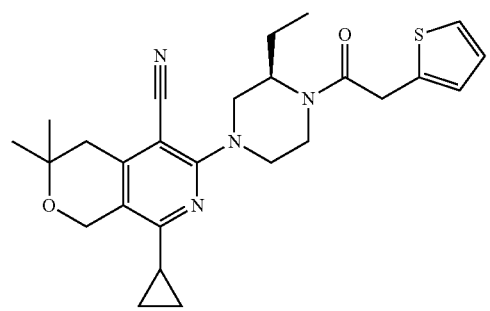 [SMILES: CC[C@@H]1CN(c2nc(C3CC3)c3c(c2C#N)CC(C)(C)OC3)CCN1C(=O)Cc1cccs1] |

| Cmpd No | Structure |
|---|---|
| 237 | 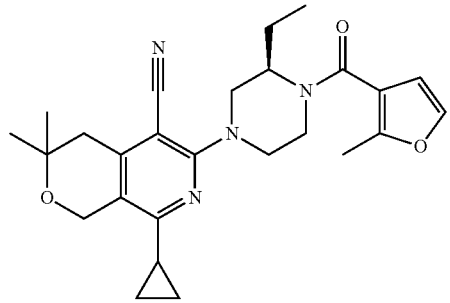 [SMILES: CC[C@@H]1CN(c2nc(C3CC3)c3c(c2C#N)CC(C)(C)OC3)CCN1C(=O)c1ccoc1C] |
| 238 | 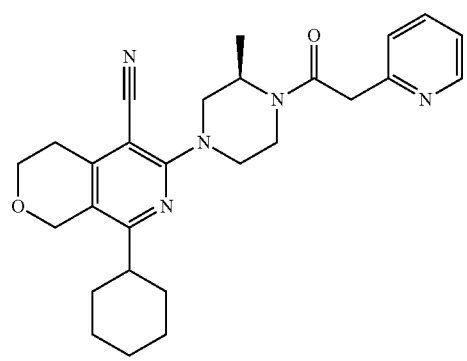 [SMILES: C[C@@H]1CN(c2nc(C3CCCCC3)c3c(c2C#N)CCOC3)CCN1C(=O)Cc1ccccn1] |
| 239 | 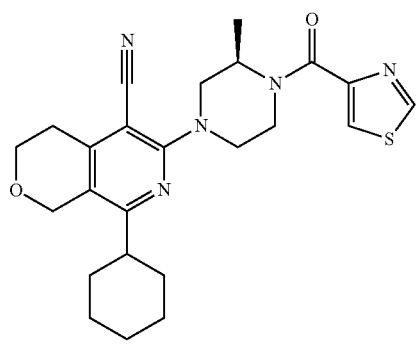 |
| 240 | 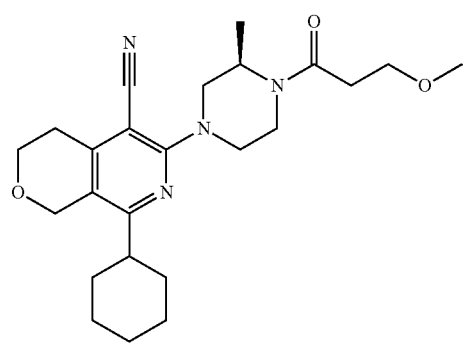 |

-continued
| Cmpd No | Structure |
|---|---|
| 241 | 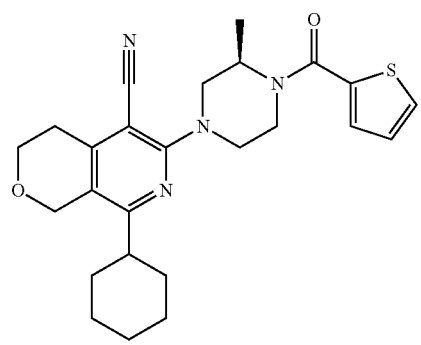 [SMILES: C[C@@H]1CN(c2nc(C3CCCCC3)c3c(c2C#N)CCOC3)CCN1C(=O)c1cccs1] |
| 242 | 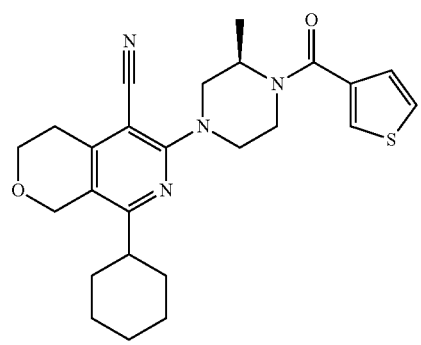 [SMILES: C[C@@H]1CN(c2nc(C3CCCCC3)c3c(c2C#N)CCOC3)CCN1C(=O)c1ccsc1] |
| 243 | 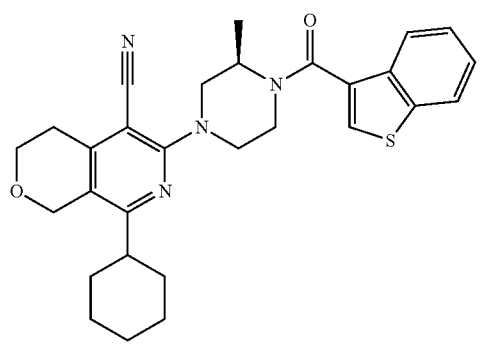 [SMILES: C[C@@H]1CN(c2nc(C3CCCCC3)c3c(c2C#N)CCOC3)CCN1C(=O)c1csc2ccccc12] |
| 244 | 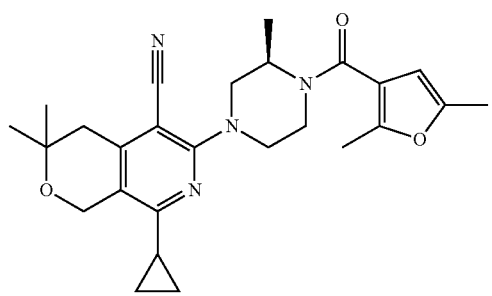 |

-continued
| Cmpd No | Structure |
|---|---|
| 245 | 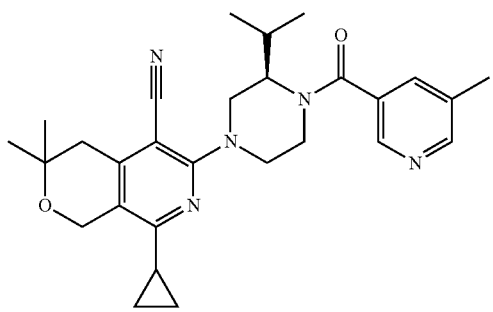 |
| 246 | 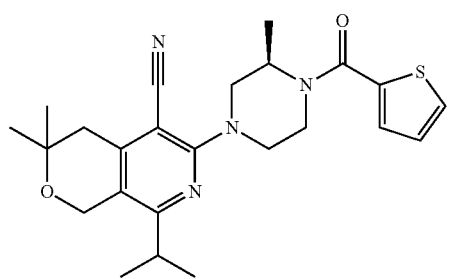 |
| 247 | 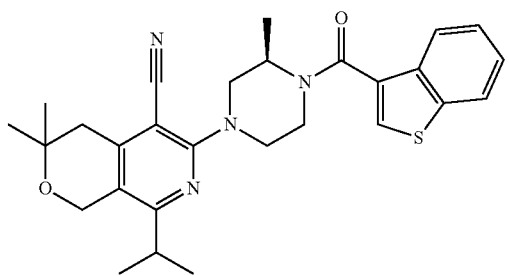 [SMILES: CC(C)c1nc(N2CCN(C(=O)c3csc4ccccc34)[C@H](C)C2)c(C#N)c2c1COC(C)(C)C2] |
| 248 | 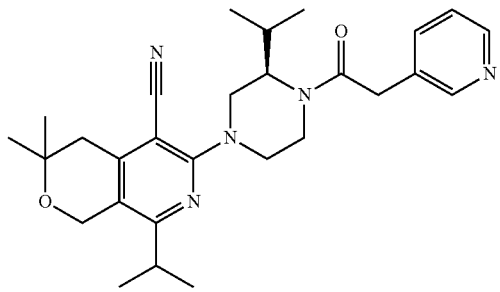 [SMILES: CC(C)c1nc(N2CCN(C(=O)Cc3cccnc3)[C@H](C(C)C)C2)c(C#N)c2c1COC(C)(C)C2] |
| 249 | 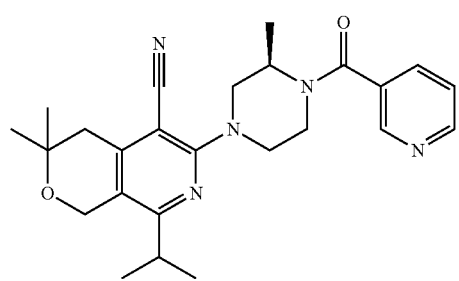 [SMILES: CC(C)c1nc(N2CCN(C(=O)c3cccnc3)[C@H](C)C2)c(C#N)c2c1COC(C)(C)C2] |

-continued
| Cmpd No | Structure |
|---------|-----------|
| 250 | 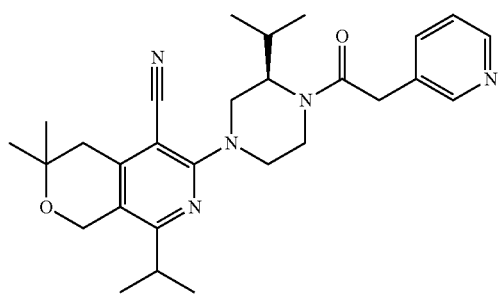 [SMILES: CC(C)c1nc(N2CCN(C(=O)Cc3cccnc3)[C@H](C(C)C)C2)c(C#N)c2c1COC(C)(C)C2] |
| 251 | 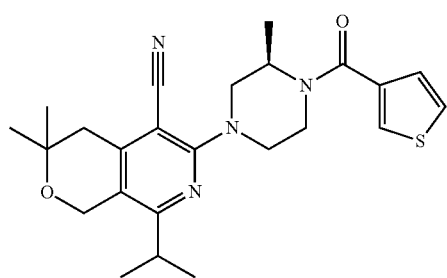 |
| 252 | 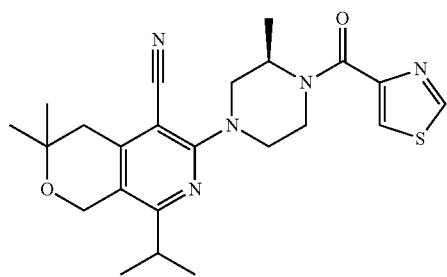 [SMILES: CC(C)c1nc(N2CCN(C(=O)c3cscn3)[C@H](C)C2)c(C#N)c2c1COC(C)(C)C2] |
| 253 | 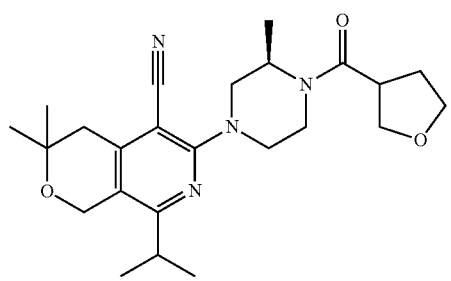 [SMILES: CC(C)c1nc(N2CCN(C(=O)C3CCOC3)[C@H](C)C2)c(C#N)c2c1COC(C)(C)C2] |
| 254 | 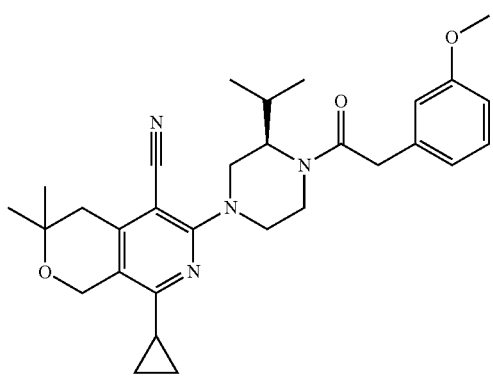 |

| Cmpd No | Structure |
|---|---|
| 255 | 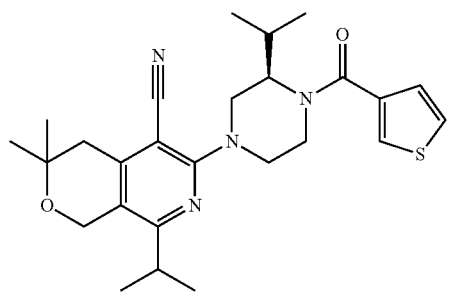 [SMILES: CC(C)c1nc(N2CCN(C(=O)c3ccsc3)[C@H](C(C)C)C2)c(C#N)c2c1COC(C)(C)C2] |
| 256 | 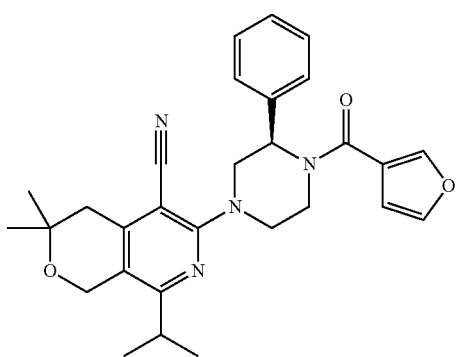 [SMILES: CC(C)c1nc(N2CCN(C(=O)c3ccoc3)[C@H](c3ccccc3)C2)c(C#N)c2c1COC(C)(C)C2] |
| 257 | 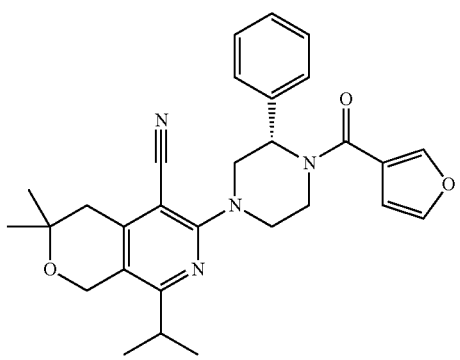 [SMILES: CC(C)c1nc(N2CCN(C(=O)c3ccoc3)[C@@H](c3ccccc3)C2)c(C#N)c2c1COC(C)(C)C2] |
| 258 | 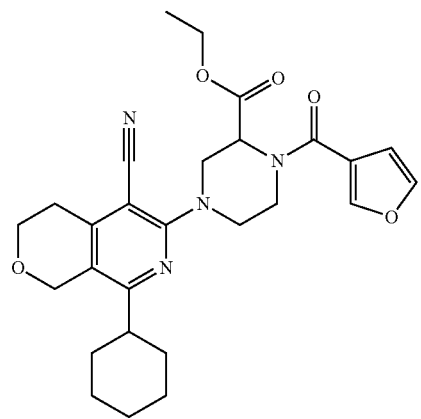 [SMILES: CCOC(=O)C1CN(c2nc(C3CCCCC3)c3c(c2C#N)CCOC3)CCN1C(=O)c1ccoc1] |

| Cmpd No | Structure |
|---|---|
| 259 | 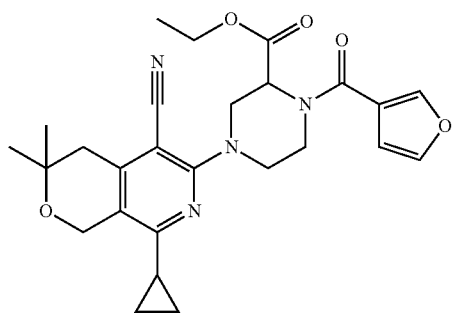 [SMILES: CCOC(=O)C1CN(c2nc(C3CC3)c3c(c2C#N)CC(C)(C)OC3)CCN1C(=O)c1ccoc1] |
| 260 | 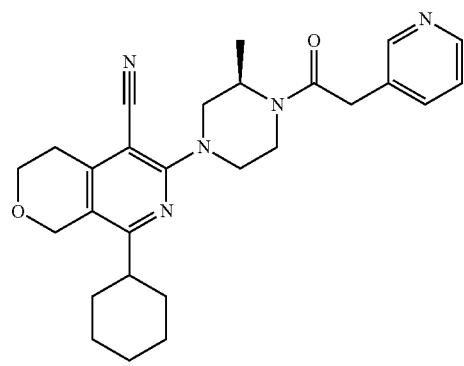 [SMILES: C[C@@H]1CN(c2nc(C3CCCCC3)c3c(c2C#N)CCOC3)CCN1C(=O)Cc1cccnc1] |
| 261 | 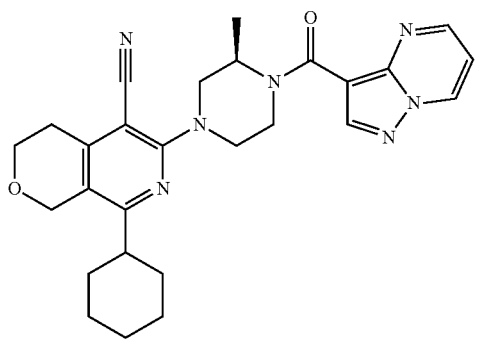 [SMILES: C[C@@H]1CN(c2nc(C3CCCCC3)c3c(c2C#N)CCOC3)CCN1C(=O)c1cnn2cccnc12] |
| 262 | 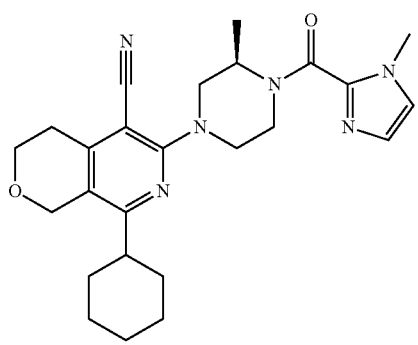 [SMILES: C[C@@H]1CN(c2nc(C3CCCCC3)c3c(c2C#N)CCOC3)CCN1C(=O)c1nccn1C] |

-continued

| Cmpd No | Structure |
|---|---|
| 263 | 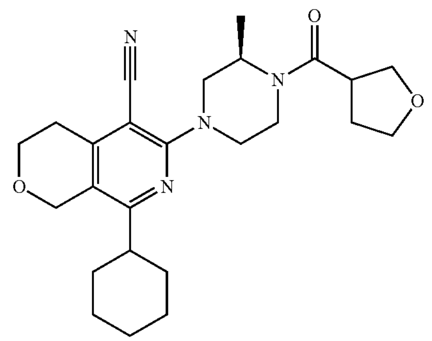 [SMILES: C[C@@H]1CN(c2nc(C3CCCCC3)c3c(c2C#N)CCOC3)CCN1C(=O)C1CCOC1] |
| 264 | 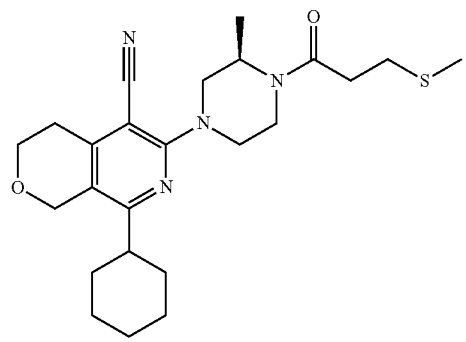 |
| 265 | 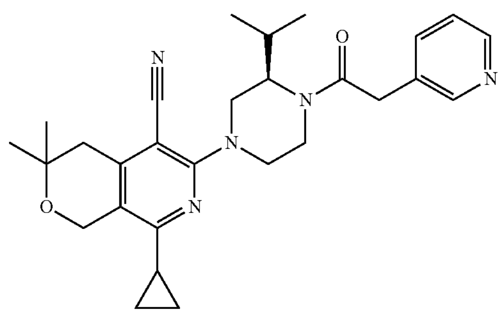 [SMILES: CC(C)[C@@H]1CN(c2nc(C3CC3)c3c(c2C#N)CC(C)(C)OC3)CCN1C(=O)Cc1cccnc1] |
| 266 | 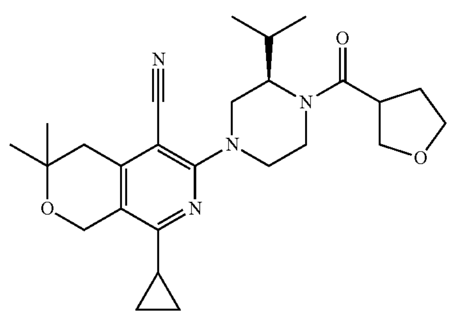 [SMILES: CC(C)[C@@H]1CN(c2nc(C3CC3)c3c(c2C#N)CC(C)(C)OC3)CCN1C(=O)C1CCOC1] |
| 267 | 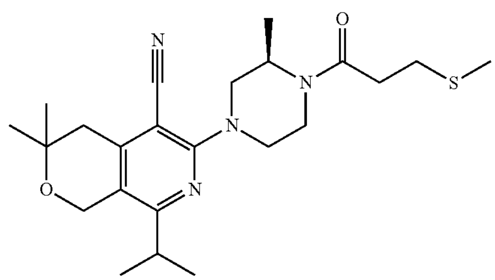 |

-continued

| Cmpd No | Structure |
|---|---|
| 268 | 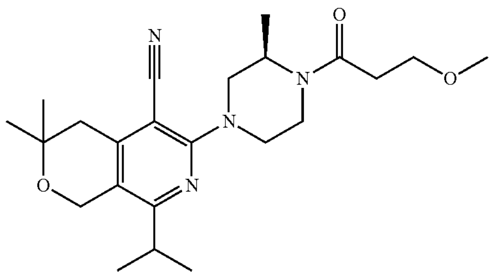 |
| 269 | 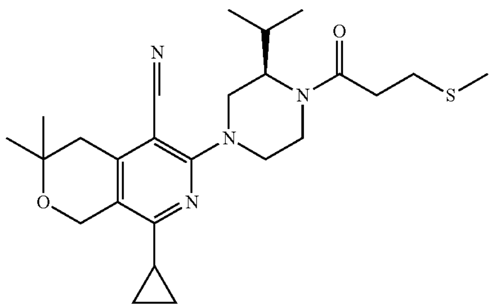 |
| 270 | 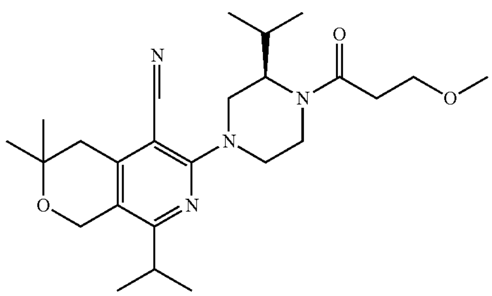 |
| 271 | 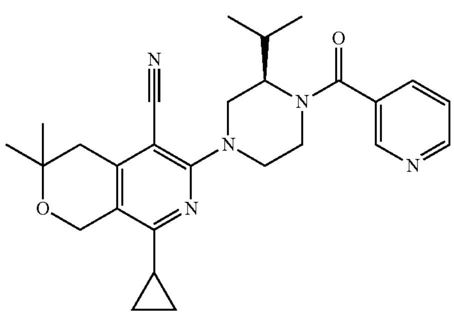 [SMILES: CC(C)[C@@H]1CN(c2nc(C3CC3)c3c(c2C#N)CC(C)(C)OC3)CCN1C(=O)c1cccnc1] |
| 272 | 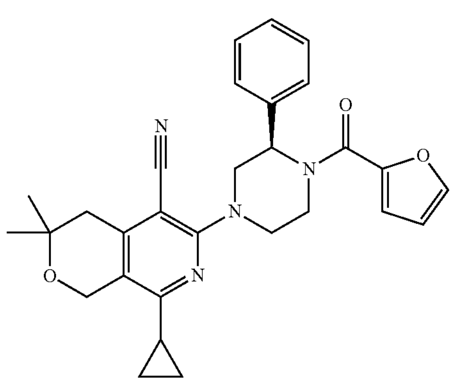 [SMILES: CC1(C)Cc2c(C#N)c(N3CCN(C(=O)c4ccco4)[C@H](c4ccccc4)C3)nc(C3CC3)c2CO1] |

-continued
| Cmpd No | Structure |
|---|---|
| 273 | 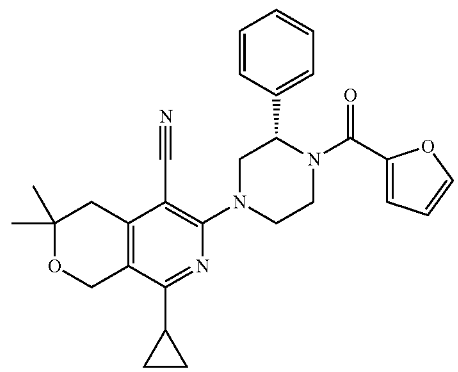 [SMILES: CC1(C)Cc2c(C#N)c(N3CCN(C(=O)c4ccco4)[C@@H](c4ccccc4)C3)nc(C3CC3)c2CO1] |
| 274 | 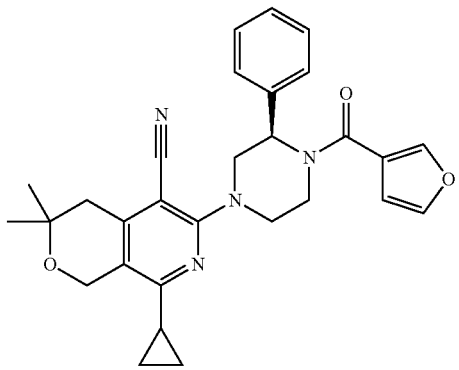 [SMILES: CC1(C)Cc2c(C#N)c(N3CCN(C(=O)c4ccoc4)[C@H](c4ccccc4)C3)nc(C3CC3)c2CO1] |
| 275 | 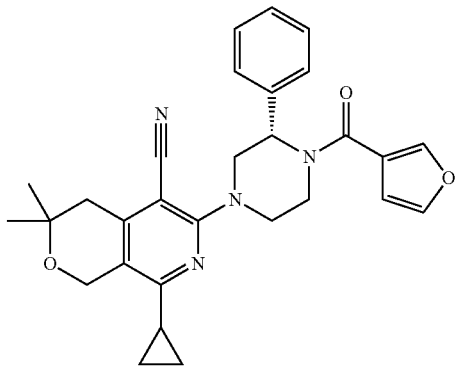 [SMILES: CC1(C)Cc2c(C#N)c(N3CCN(C(=O)c4ccoc4)[C@@H](c4ccccc4)C3)nc(C3CC3)c2CO1] |
| 276 | 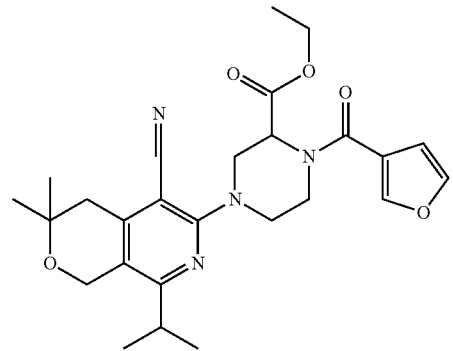 [SMILES: CCOC(=O)C1CN(c2nc(C(C)C)c3c(c2C=N)CC(C)(C)OC3)CCN1C(=O)c1ccoc1] |

| Cmpd No | Structure |
|---|---|
| 277 | 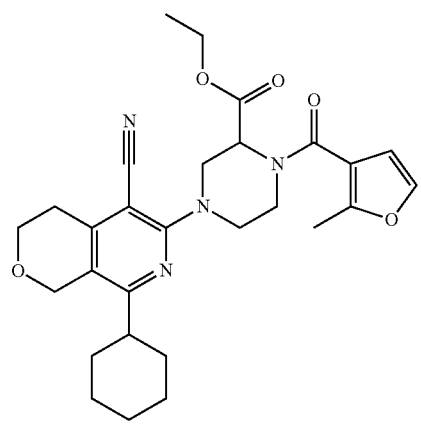 [SMILES: CCOC(=O)C1CN(c2nc(C3CCCCC3)c3c(c2C#N)CCOC3)CCN1C(=O)c1ccoc1C] |
| 278 | 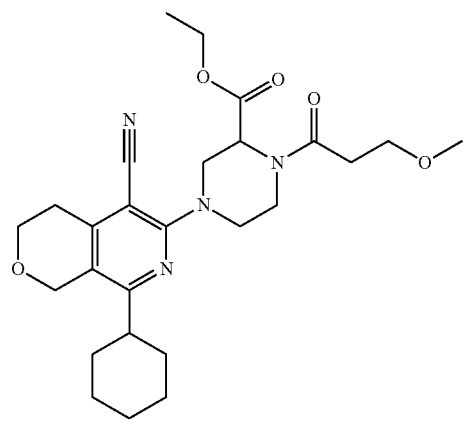 [SMILES: CCOC(=O)C1CN(c2nc(C3CCCCC3)c3c(c2C#N)CCOC3)CCN1C(=O)CCOC] |
| 279 | 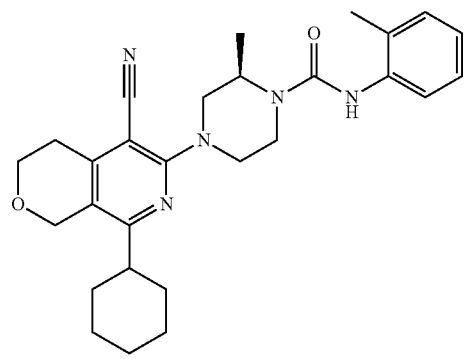 [SMILES: Cc1ccccc1NC(=O)N1CCN(c2nc(C3CCCCC3)c3c(c2C#N)CCOC3)C[C@H]1C] |
| 280 | 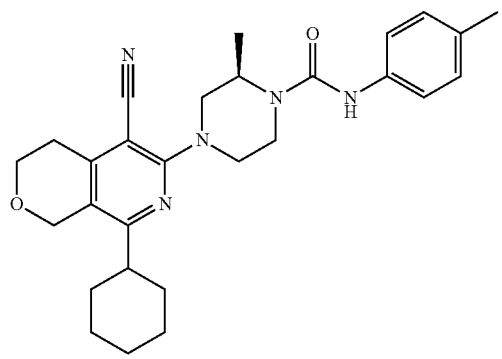 [SMILES: Cc1ccc(NC(=O)N2CCN(c3nc(C4CCCCC4)c4c(c3C#N)CCOC4)C[C@H]2C)cc1] |

-continued
| Cmpd No | Structure |
|---|---|
| 281 | 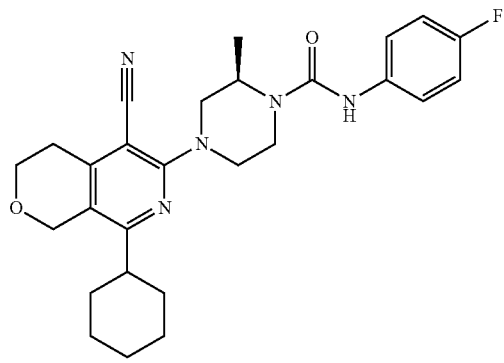 [SMILES: C[C@@H]1CN(c2nc(C3CCCCC3)c3c(c2C#N)CCOC3)CCN1C(=O)Nc1ccc(F)cc1] |
| 282 | 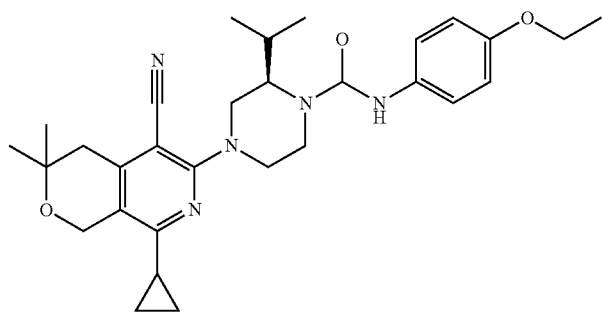 [SMILES: CCOc1ccc(NC(O)N2CCN(c3nc(C4CC4)c4c(c3C#N)CC(C)(C)OC4)C[C@H]2C(C)C)cc1] |
| 283 | 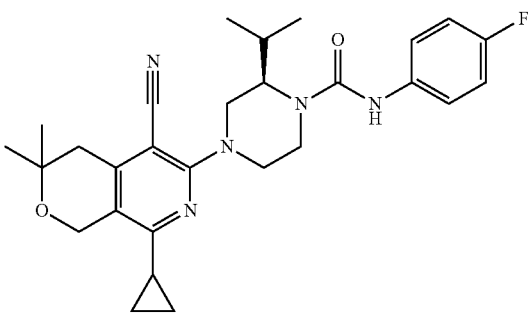 [SMILES: CC(C)[C@@H]1CN(c2nc(C3CC3)c3c(c2C#N)CC(C)(C)OC3)CCN1C(=O)Nc1ccc(F)cc1] |
| 284 | 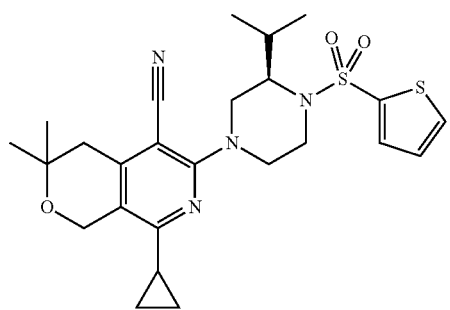 [SMILES: CC(C)[C@@H]1CN(c2nc(C3CC3)c3c(c2C#N)CC(C)(C)OC3)CCN1S(=O)(=O)c1cccs1] |

| Cmpd No | Structure |
|---|---|
| 285 | 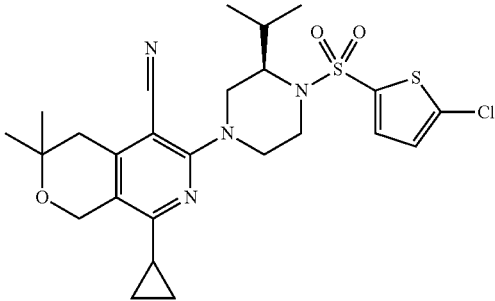 [SMILES: CC(C)[C@@H]1CN(c2nc(C3CC3)c3c(c2C=N)CC(C)(C)OC3)CCN1S(=O)(=O)c1ccc(Cl)s1] |
| 286 | 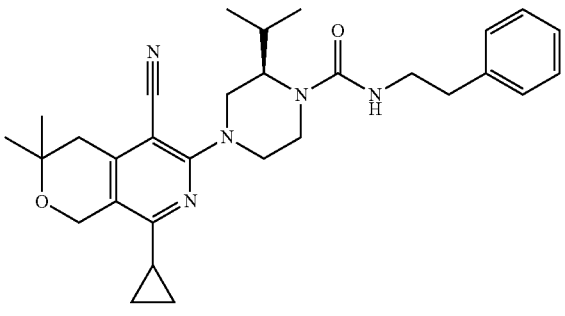 [SMILES: CC(C)[C@@H]1CN(c2nc(C3CC3)c3c(c2C#N)CC(C)(C)OC3)CCN1C(=O)NCCc1ccccc1] |
| 287 | 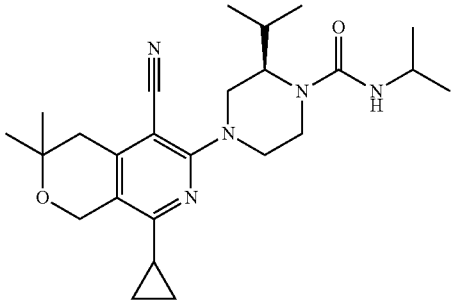 [SMILES: CC(C)NC(=O)N1CCN(c2nc(C3CC3)c3c(c2C#N)CC(C)(C)OC3)C[C@H]1C(C)C] |
| 288 | 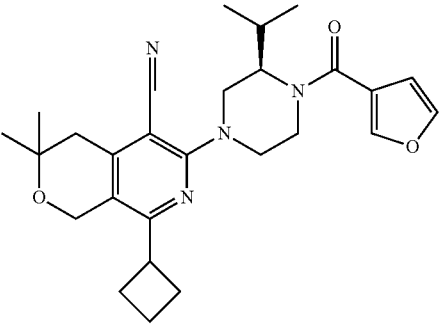 [SMILES: CC(C)[C@@H]1CN(c2nc(C3CCC3)c3c(c2C=N)CC(C)(C)OC3)CCN1C(=O)c1ccoc1] |
| 289 | 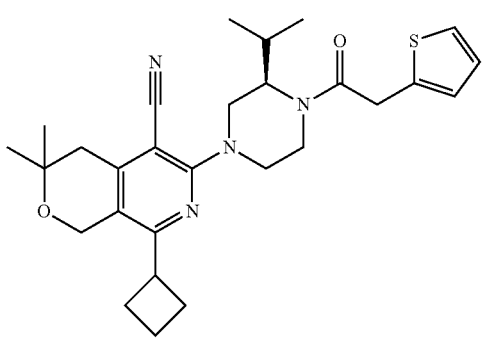 [SMILES: CC(C)[C@@H]1CN(c2nc(C3CCC3)c3c(c2C#N)CC(C)(C)OC3)CCN1C(=O)Cc1cccs1] |

-continued
| Cmpd No | Structure |
|---|---|
| 290 | 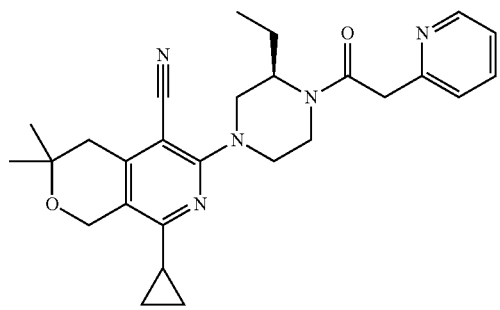 [SMILES: CC[C@@H]1CN(c2nc(C3CC3)c3c(c2C#N)CC(C)(C)OC3)CCN1C(=O)Cc1ccccn1] |
| 291 | 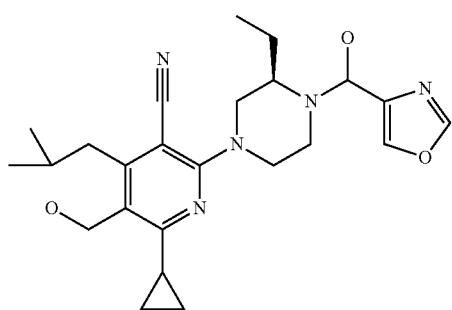 [SMILES: CC[C@@H]1CN(c2nc(C3CC3)c(CO)c(CC(C)C)c2C#N)CCN1C(O)c1cocn1] |
| 292 | 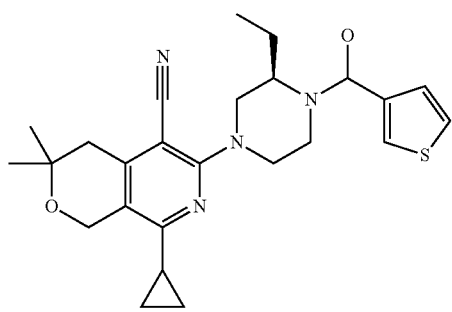 [SMILES: CC[C@@H]1CN(c2nc(C3CC3)c3c(c2C#N)CC(C)(C)OC3)CCN1C(O)c1ccsc1] |
| 293 | 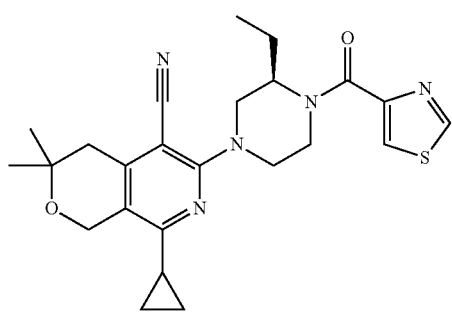 [SMILES: CC[C@@H]1CN(c2nc(C3CC3)c3c(c2C#N)CC(C)(C)OC3)CCN1C(=O)c1cscn1] |
| 294 | 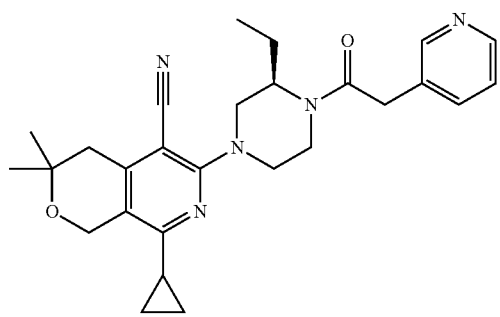 [SMILES: CC[C@@H]1CN(c2nc(C3CC3)c3c(c2C#N)CC(C)(C)OC3)CCN1C(=O)Cc1cccnc1] |

-continued
| Cmpd No | Structure |
|---|---|
| 295 | 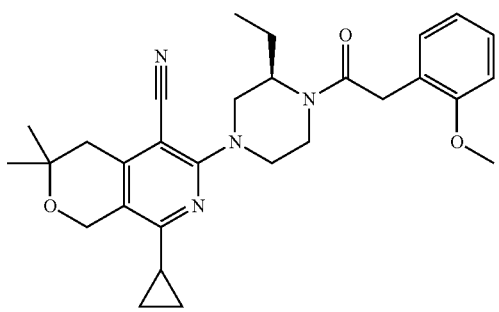 |
| 296 | 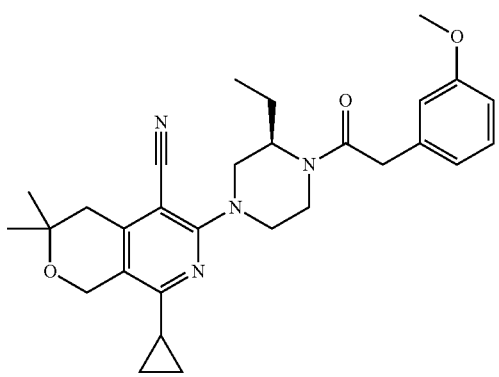 [SMILES: CC[C@@H]1CN(c2nc(C3CC3)c3c(c2C#N)CC(C)(C)OC3)CCN1C(=O)Cc1cccc(OC)c1] |
| 297 | 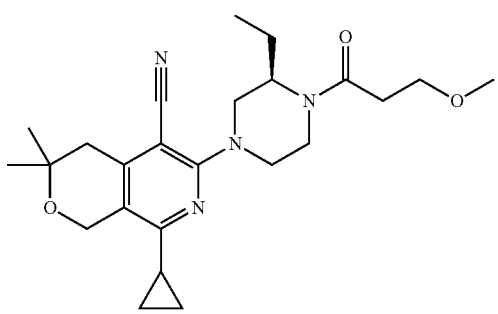 |
| 298 | 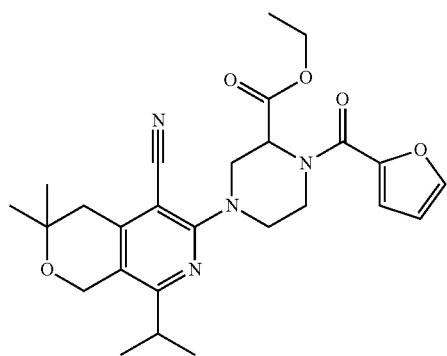 [SMILES: CCOC(=O)C1CN(c2nc(C(C)C)c3c(c2C#N)CC(C)(C)OC3)CCN1C(=O)c1ccco1] |

-continued
| Cmpd No | Structure |
|---|---|
| 299 | 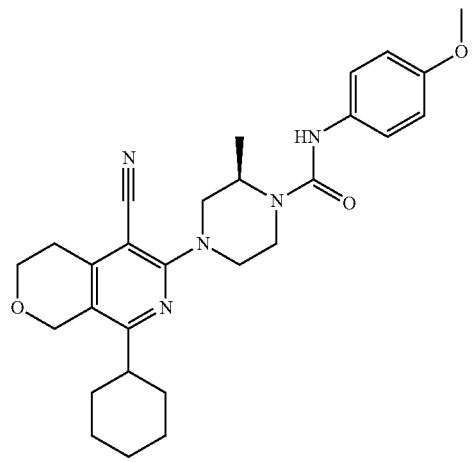 [SMILES: COc1ccc(NC(=O)N2CCN(c3nc(C4CCCCC4)c4c(c3C#N)CCOC4)C[C@H]2C)cc1] |
| 300 | 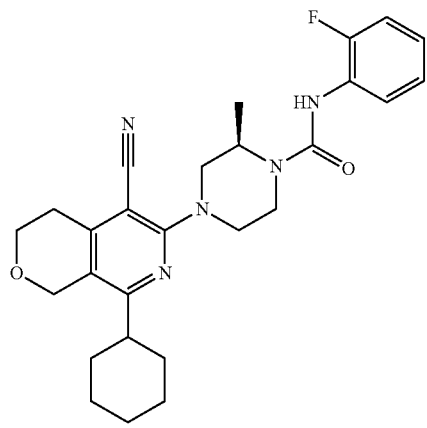 [SMILES: C[C@@H]1CN(c2nc(C3CCCCC3)c3c(c2C#N)CCOC3)CCN1C(=O)Nc1ccccc1F] |
| 301 | 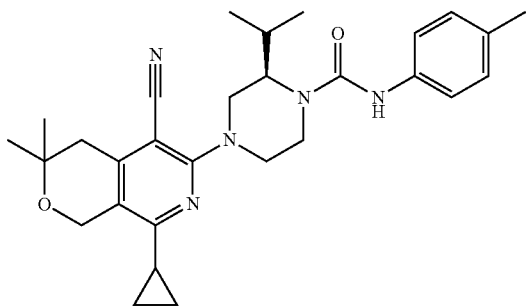 |
| 302 | 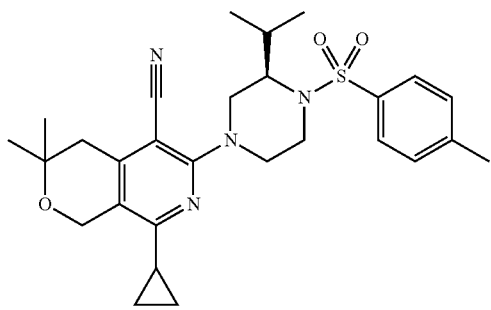 |

-continued

| Cmpd No | Structure |
|---------|-----------|
| 303 | 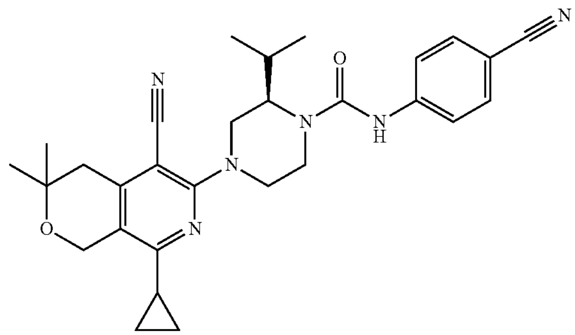 [SMILES: CC(C)[C@@H]1CN(c2nc(C3CC3)c3c(c2C#N)CC(C)(C)OC3)CCN1C(=O)Nc1ccc(C#N)cc1] |
| 304 | 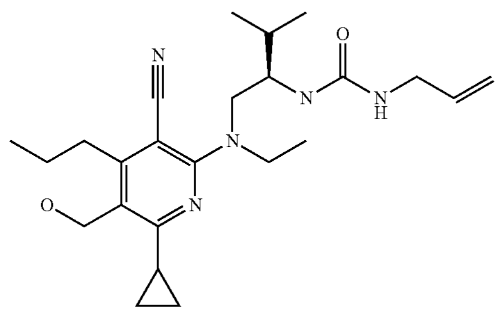 [SMILES: C=CCNC(=O)N[C@@H](CN(CC)c1nc(C2CC2)c(CO)c(CCC)c1C#N)C(C)C] |
| 305 | 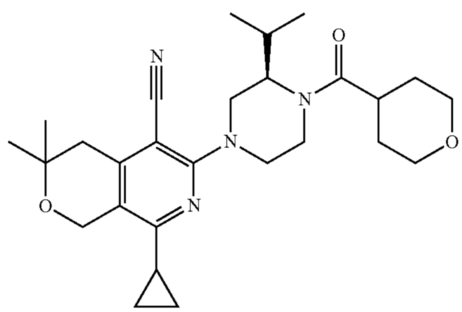 [SMILES: CC(C)[C@@H]1CN(c2nc(C3CC3)c3c(c2C#N)CC(C)(C)OC3)CCN1C(=O)C1CCOCC1] |
| 306 | 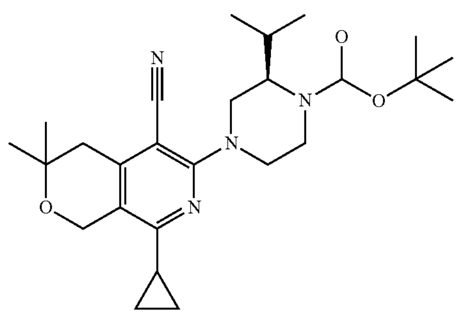 [SMILES: CC(C)[C@@H]1CN(c2nc(C3CC3)c3c(c2C#N)CC(C)(C)OC3)CCN1C(O)OC(C)(C)C] |
| 307 | 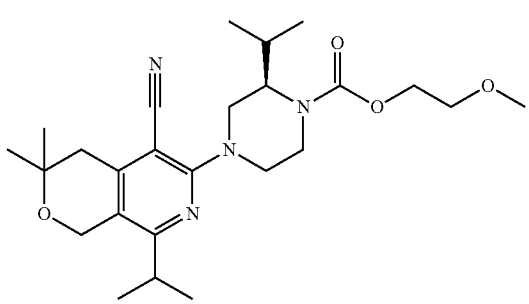 |

-continued
| Cmpd No | Structure |
|---|---|
| 308 | 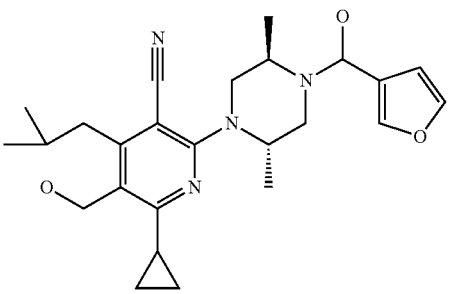 [SMILES: CC(C)Cc1c(C#N)c(N2C[C@@H](C)N(C(O)c3ccoc3)C[C@@H]2C)nc(C2CC2)c1CO] |
| 309 | 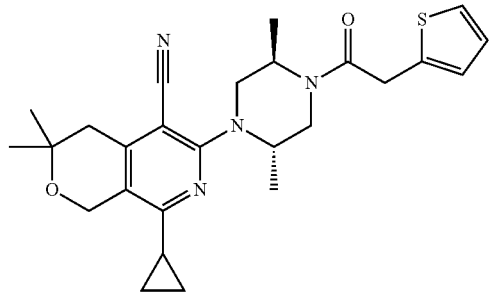 [SMILES: C[C@@H]1CN(c2nc(C3CC3)c3c(c2C#N)CC(C)(C)OC3)[C@@H](C)CN1C(=O)Cc1cccs1] |
| 310 | 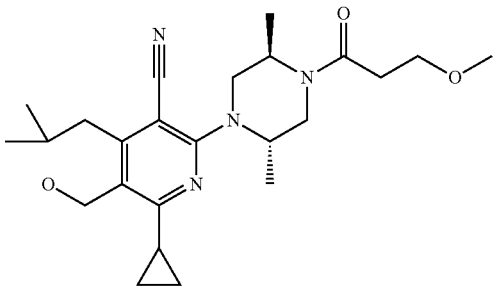 [SMILES: COCCC(=O)N1C[C@H](C)N(c2nc(C3CC3)c(CO)c(CC(C)C)c2C#N)C[C@H]1C] |
| 311 | 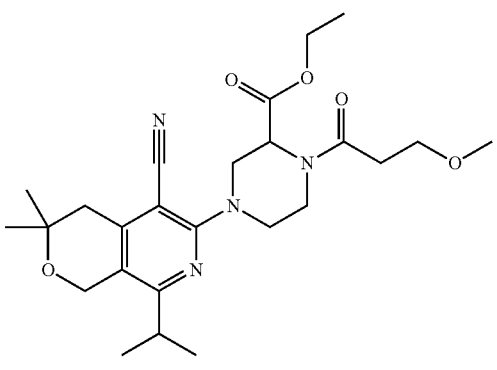 |
| 312 | 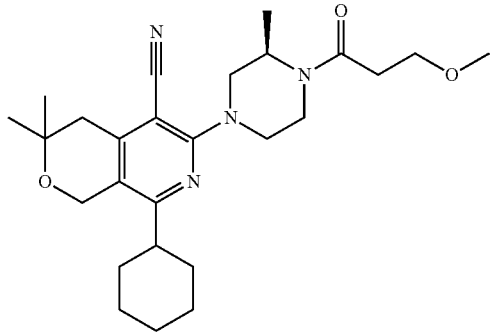 |

-continued
| Cmpd No | Structure |
|---|---|
| 313 | 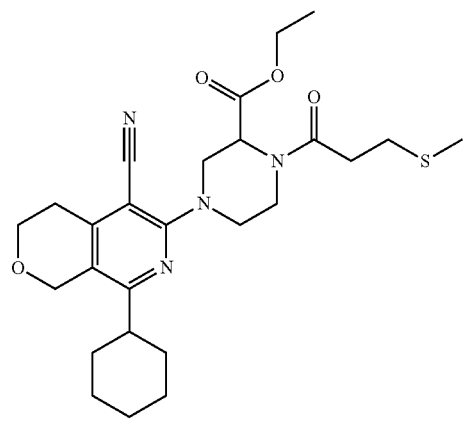 [SMILES: CCOC(=O)C1CN(c2nc(C3CCCCC3)c3c(c2C#N)CCOC3)CCN1C(=O)CCSC] |
| 314 | 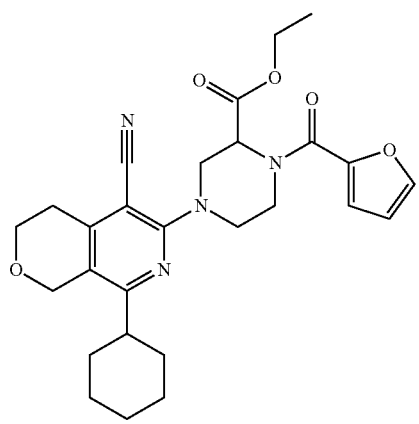 [SMILES: CCOC(=O)C1CN(c2nc(C3CCCCC3)c3c(c2C#N)CCOC3)CCN1C(=O)c1ccco1] |
| 315 | 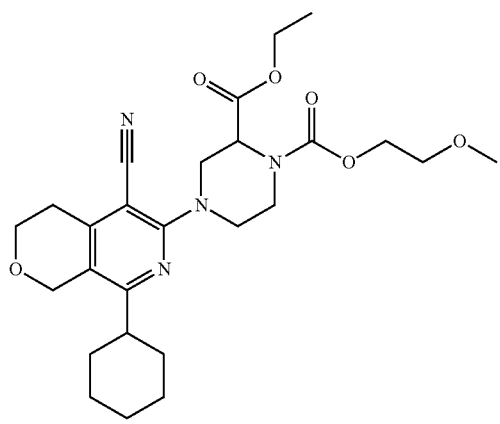 [SMILES: CCOC(=O)C1CN(c2nc(C3CCCCC3)c3c(c2C#N)CCOC3)CCN1C(=O)OCCOC] |
| 316 | 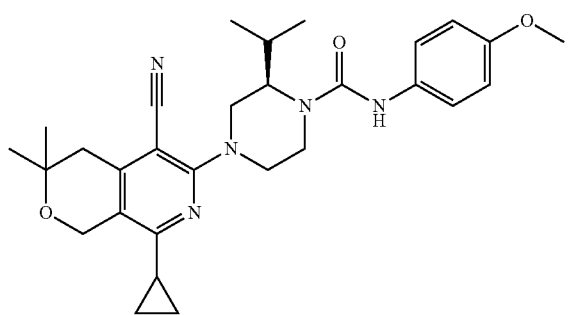 |

-continued
| Cmpd No | Structure |
|---|---|
| 317 | 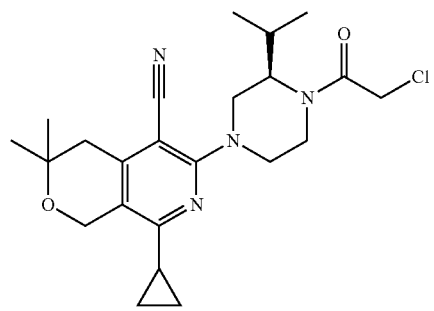 [SMILES: CC(C)[C@@H]1CN(c2nc(C3CC3)c3c(c2C#N)CC(C)(C)OC3)CCN1C(=O)CCl] |
| 318 | 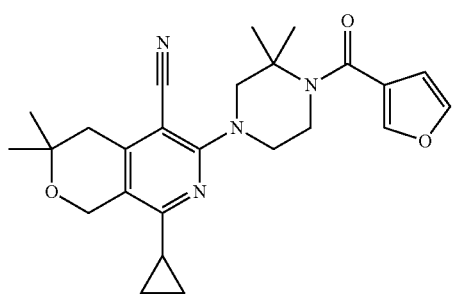 [SMILES: CC1(C)Cc2c(C#N)c(N3CCN(C(=O)c4ccoc4)C(C)(C)C3)nc(C3CC3)c2CO1] |
| 319 | 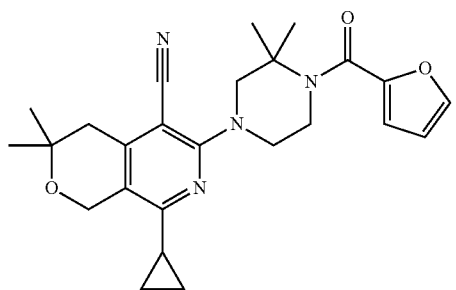 [SMILES: CC1(C)Cc2c(C#N)c(N3CCN(C(=O)c4ccco4)C(C)(C)C3)nc(C3CC3)c2CO1] |
| 320 | 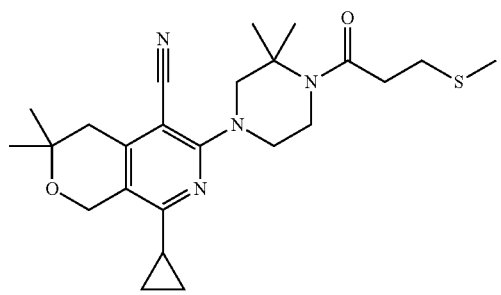 |
| 321 | 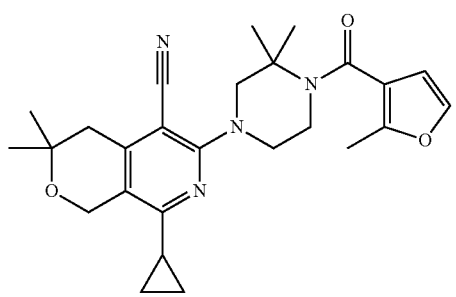 [SMILES: Cc1occc1C(=O)N1CCN(c2nc(C3CC3)c3c(c2C#N)CC(C)(C)OC3)CC1(C)C] |

-continued
| Cmpd No | Structure |
|---|---|
| 322 | 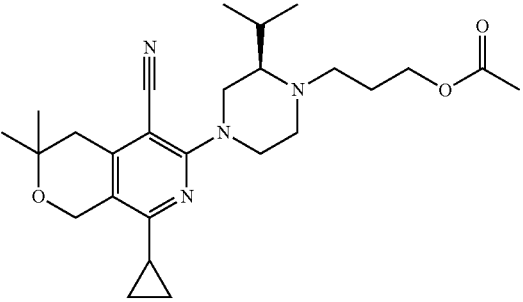 [SMILES: CC(=O)OCCCN1CCN(c2nc(C3CC3)c3c(c2C#N)CC(C)(C)OC3)C[C@H]1C(C)C] |
| 323 | 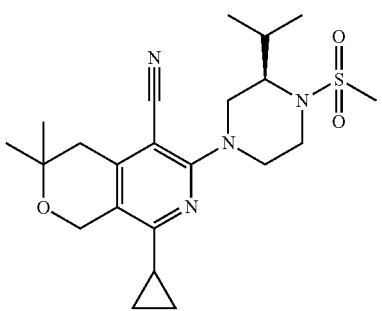 |
| 324 | 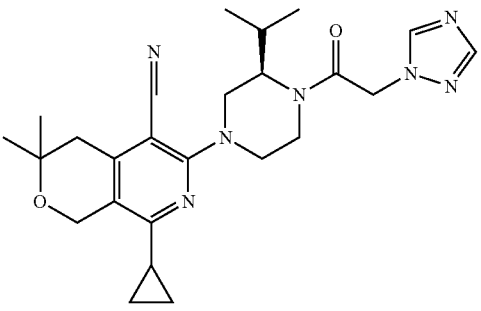 [SMILES: CC(C)[C@@H]1CN(c2nc(C3CC3)c3c(c2C=N)CC(C)(C)OC3)CCN1C(=O)Cn1cncn1] |
| 325 | 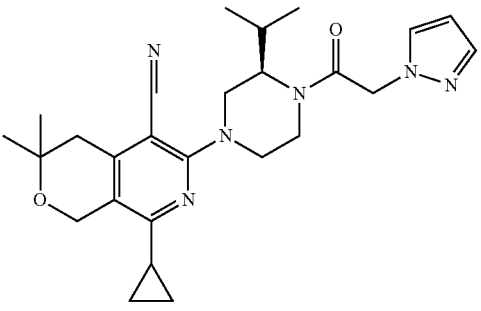 [SMILES: CC(C)[C@@H]1CN(c2nc(C3CC3)c3c(c2C=N)CC(C)(C)OC3)CCN1C(=O)Cn1cccn1] |
| 326 | 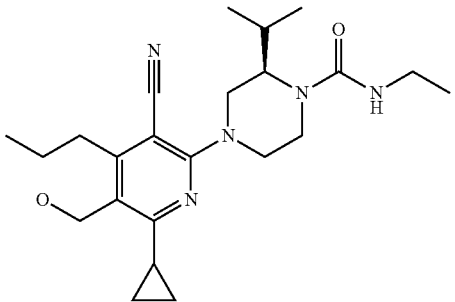 [SMILES: CCCc1c(C#N)c(N2CCN(C(=O)NCC)[C@H](C(C)C)C2)nc(C2CC2)c1CO] |

| Cmpd No | Structure |
|---|---|
| 327 | 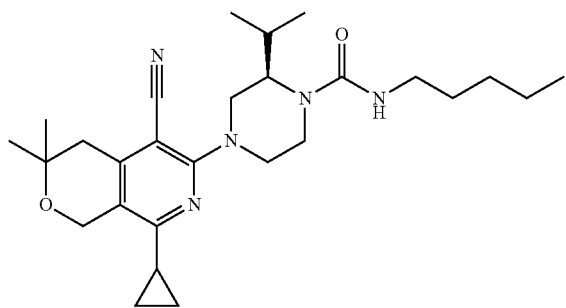 [SMILES: CCCCCNC(=O)N1CCN(c2nc(C3CC3)c3c(c2C#N)CC(C)(C)OC3)C[C@H]1C(C)C] |
| 328 | 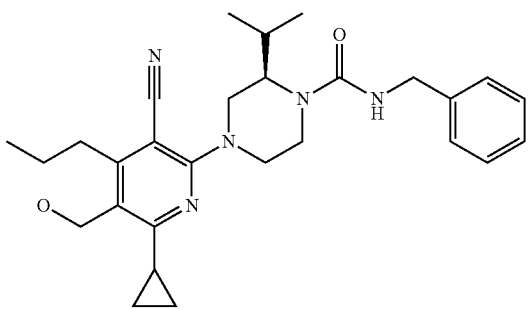 [SMILES: CCCc1c(C#N)c(N2CCN(C(=O)NCc3ccccc3)[C@H](C(C)C)C2)nc(C2CC2)c1CO] |
| 329 | 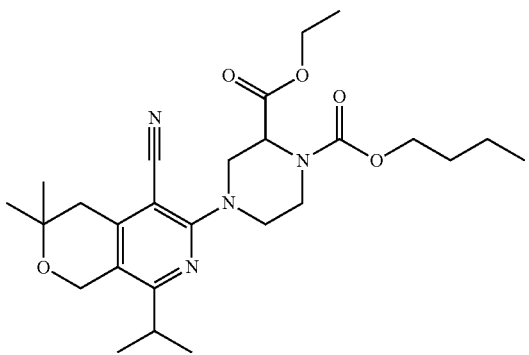 [SMILES: CCCCOC(=O)N1CCN(c2nc(C(C)C)c3c(c2C#N)CC(C)(C)OC3)CC1C(=O)OCC] |
| 330 | 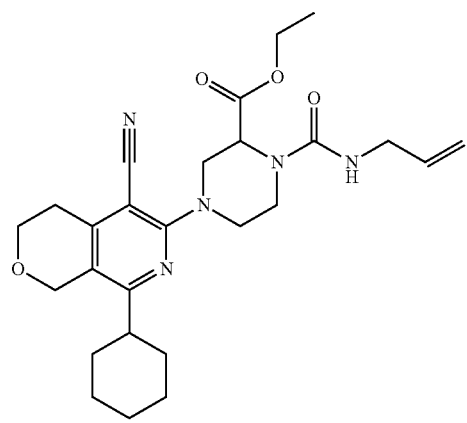 [SMILES: C=CCNC(=O)N1CCN(c2nc(C3CCCCC3)c3c(c2C#N)CCOC3)CC1C(=O)OCC] |

| Cmpd No | Structure |
|---|---|
| 331 | 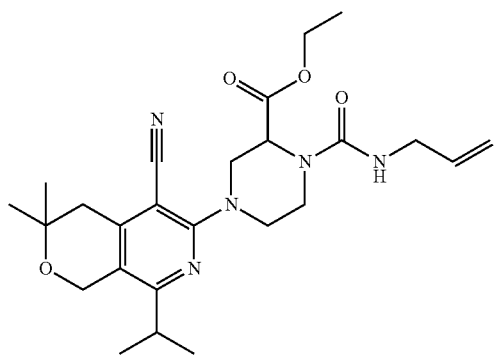 [SMILES: C=CCNC(=O)N1CCN(c2nc(C(C)C)c3c(c2C#N)CC(C)(C)OC3)CC1C(=O)OCC] |
| 332 | 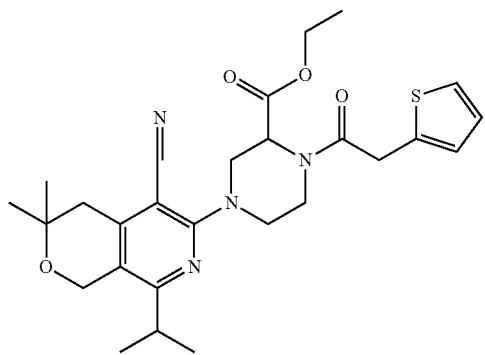 [SMILES: CCOC(=O)C1CN(c2nc(C(C)C)c3c(c2C=N)CC(C)(C)OC3)CCN1C(=O)Cc1cccs1] |
| 333 | 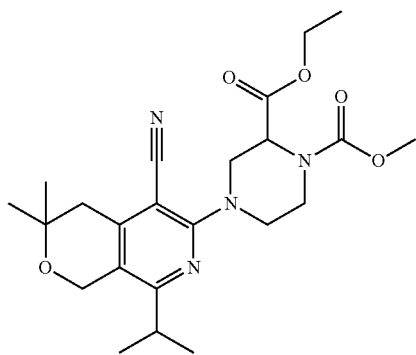 |
| 334 | 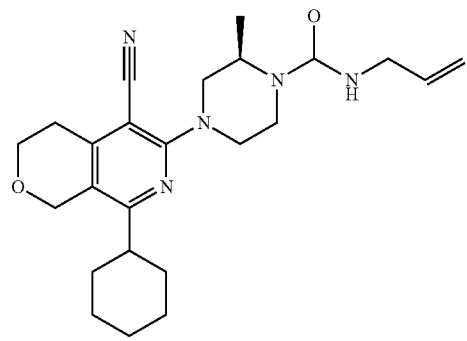 [SMILES: C=CCNC(O)N1CCN(c2nc(C3CCCCC3)c3c(c2C#N)CCOC3)C[C@H]1C] |

| Cmpd No | Structure |
|---|---|
| 335 | 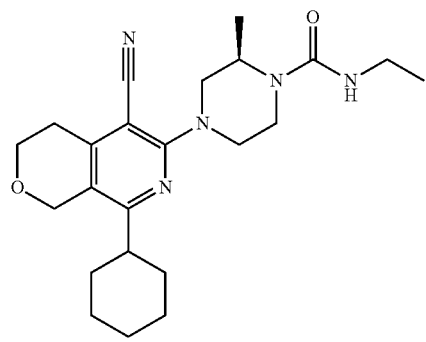 [SMILES: CCNC(=O)N1CCN(c2nc(C3CCCCC3)c3c(c2C#N)CCOC3)C[C@H]1C] |
| 336 | 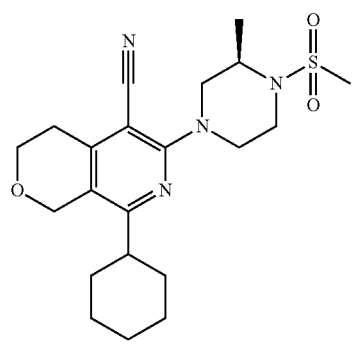 [SMILES: C[C@@H]1CN(c2nc(C3CCCCC3)c3c(c2C#N)CCOC3)CCN1S(C)(=O)=O] |
| 337 | 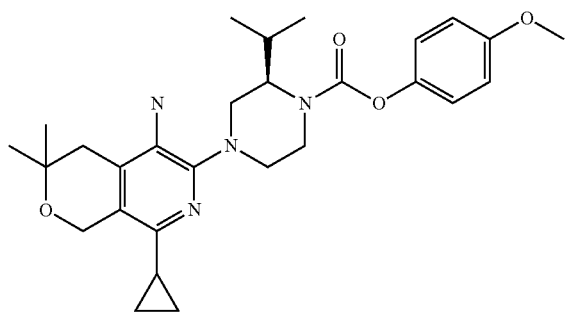 |
| 338 | 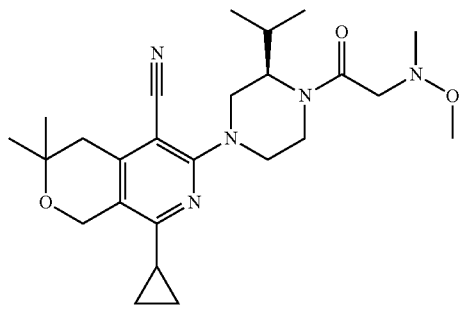 |

| Cmpd No | Structure |
|---|---|
| 339 | 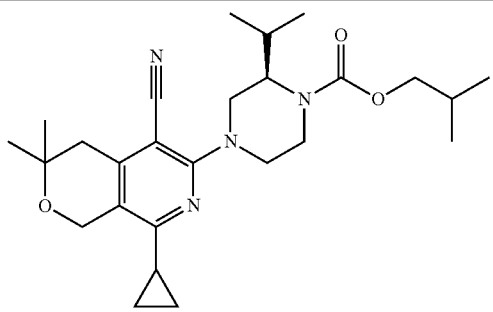 [SMILES: CC(C)COC(=O)N1CCN(c2nc(C3CC3)c3c(c2C#N)CC(C)(C)OC3)C[C@H]1C(C)C] |
| 340 | 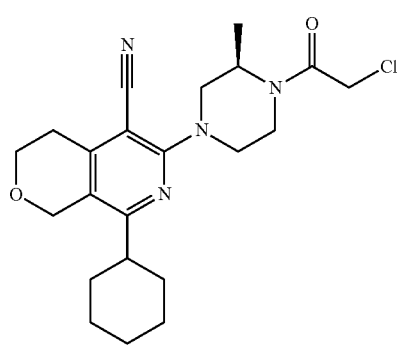 [SMILES: C[C@@H]1CN(c2nc(C3CCCCC3)c3c(c2C#N)CCOC3)CCN1C(=O)CCl] |
| 341 | 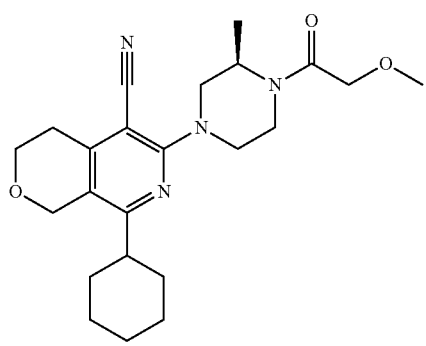 [SMILES: COCC(=O)N1CCN(c2nc(C3CCCCC3)c3c(c2C#N)CCOC3)C[C@H]1C] |
| 342 | 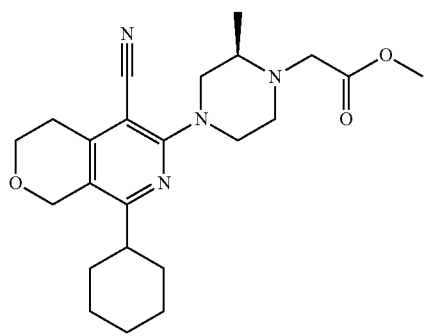 [SMILES: COC(=O)CN1CCN(c2nc(C3CCCCC3)c3c(c2C#N)CCOC3)C[C@H]1C] |

| Cmpd No | Structure |
|---|---|
| 343 | 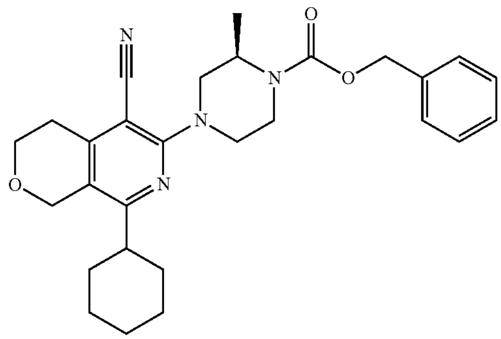 [SMILES: C[C@@H]1CN(c2nc(C3CCCCC3)c3c(c2C#N)CCOC3)CCN1C(=O)OCc1ccccc1] |
| 344 | 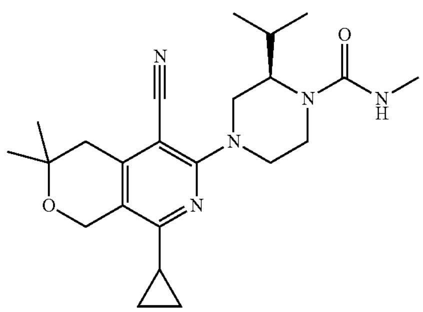 |
| 345 | 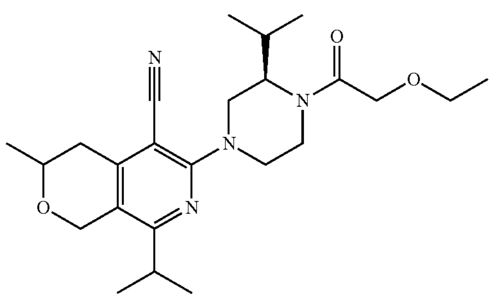 [SMILES: CCOCC(=O)N1CCN(c2nc(C(C)C)c3c(c2C#N)CC(C)OC3)C[C@H]1C(C)C] |
| 346 | 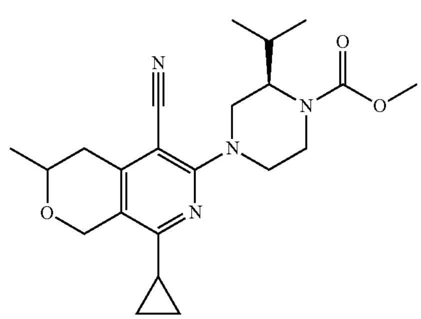 |
| 347 | 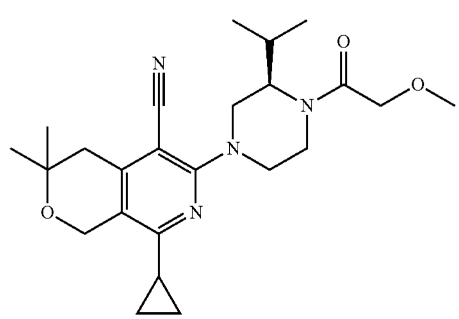 |

| Cmpd No | Structure |
|---|---|
| 348 | 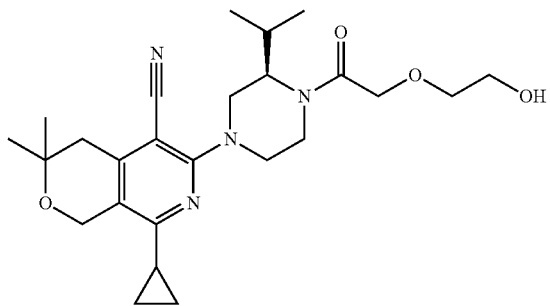 [SMILES: CC(C)[C@@H]1CN(c2nc(C3CC3)c3c(c2C#N)CC(C)(C)OC3)CCN1C(=O)COCCO] |
| 349 | 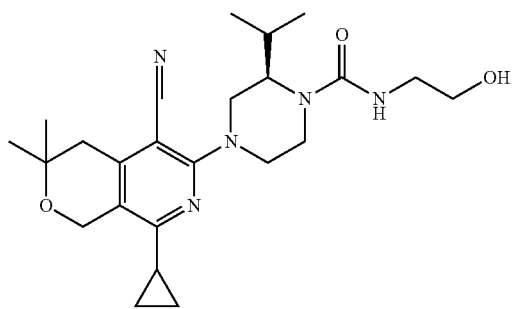 [SMILES: CC(C)[C@@H]1CN(c2nc(C3CC3)c3c(c2C=N)CC(C)(C)OC3)CCN1C(=O)NCCO] |
| 350 | 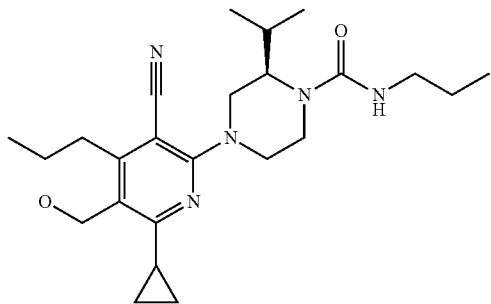 [SMILES: CCCNC(=O)N1CCN(c2nc(C3CC3)c(CO)c(CCC)c2C#N)C[C@H]1C(C)C] |
| 351 | 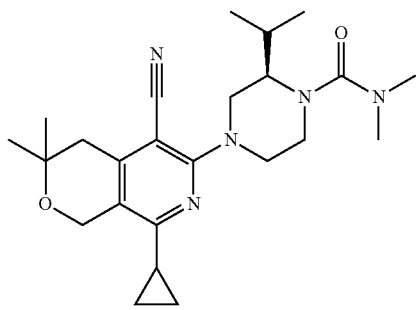 |
| 352 | 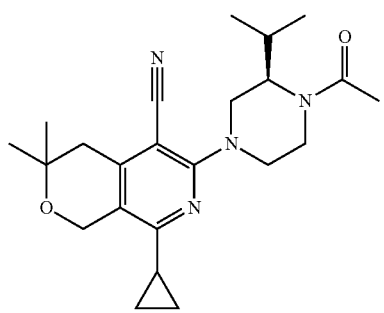 [SMILES: CC(=O)N1CCN(c2nc(C3CC3)c3c(c2C#N)CC(C)(C)OC3)C[C@H]1C(C)C] |

| Cmpd No | Structure |
|---|---|
| 353 | 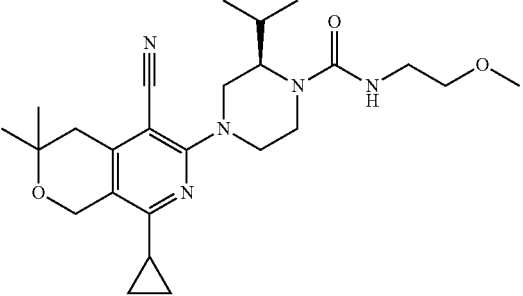 |
| 354 | 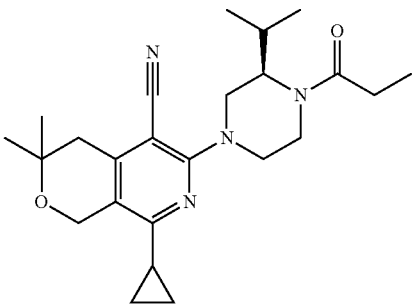 [SMILES: CCC(=O)N1CCN(c2nc(C3CC3)c3c(c2C#N)CC(C)(C)OC3)C[C@H]1C(C)C] |
| 355 | 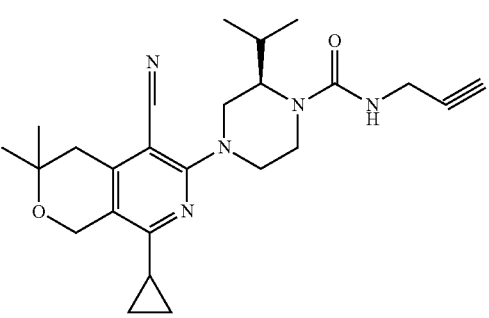 [SMILES: C#CCNC(=O)N1CCN(c2nc(C3CC3)c3c(c2C=N)CC(C)(C)OC3)C[C@H]1C(C)C] |
| 356 | 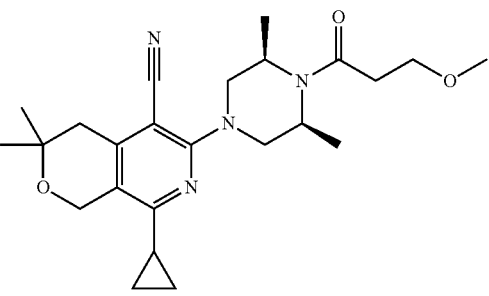 |
| 357 | 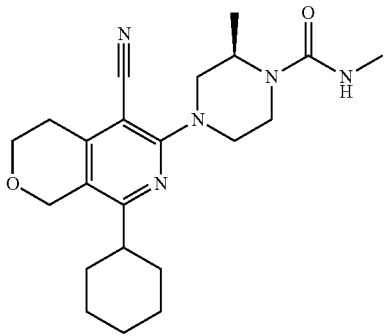 [SMILES: CNC(=O)N1CCN(c2nc(C3CCCCC3)c3c(c2C#N)CCOC3)C[C@H]1C] |

-continued
| Cmpd No | Structure |
|---|---|
| 358 | 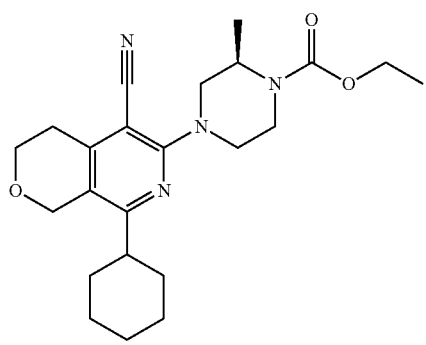 [SMILES: CCOC(=O)N1CCN(c2nc(C3CCCCC3)c3c(c2C#N)CCOC3)C[C@H]1C] |
| 359 | 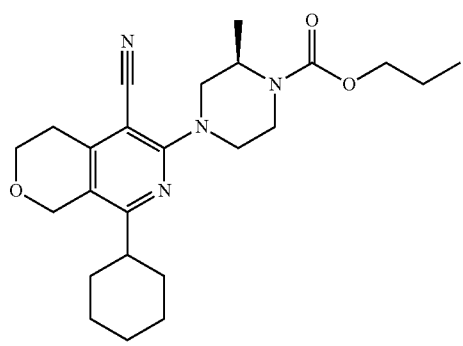 [SMILES: CCCOC(=O)N1CCN(c2nc(C3CCCCC3)c3c(c2C#N)CCOC3)C[C@H]1C] |
| 360 | 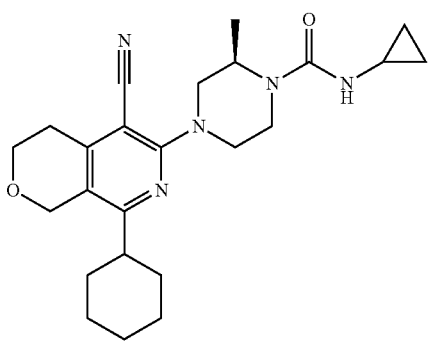 [SMILES: C[C@@H]1CN(c2nc(C3CCCCC3)c3c(c2C#N)CCOC3)CCN1C(=O)NC1CC1] |
| 361 | 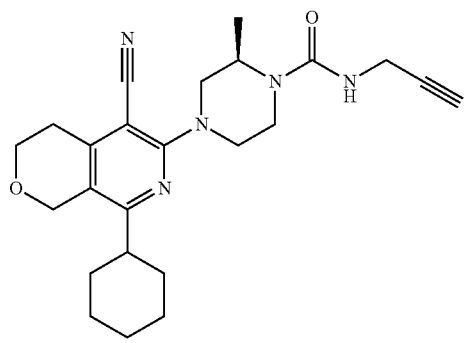 [SMILES: C#CCNC(=O)N1CCN(c2nc(C3CCCCC3)c3c(c2C#N)CCOC3)C[C@H]1C] |

| Cmpd No | Structure |
|---|---|
| 362 | 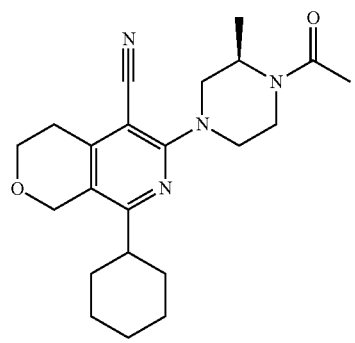 [SMILES: CC(=O)N1CCN(c2nc(C3CCCCC3)c3c(c2C#N)CCOC3)C[C@H]1C] |
| 363 | 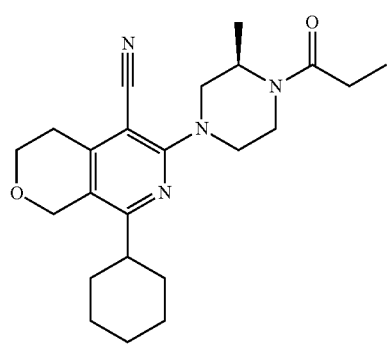 [SMILES: CCC(=O)N1CCN(c2nc(C3CCCCC3)c3c(c2C#N)CCOC3)C[C@H]1C] |
| 364 | 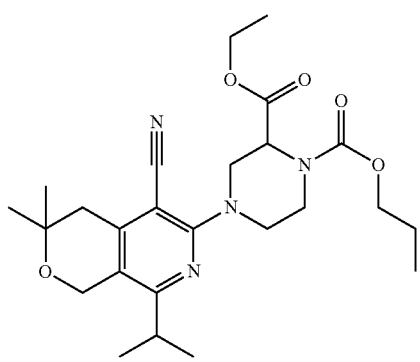 [SMILES: CCCOC(=O)N1CCN(c2nc(C(C)C)c3c(c2C#N)CC(C)(C)OC3)CC1C(=O)OCC] |
| 365 | 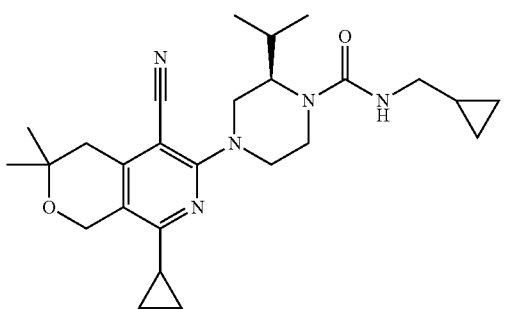 [SMILES: CC(C)[C@@H]1CN(c2nc(C3CC3)c3c(c2C#N)CC(C)(C)OC3)CCN1C(=O)NCC1CC1] |

-continued
| Cmpd No | Structure |
|---------|-----------|
| 366 | 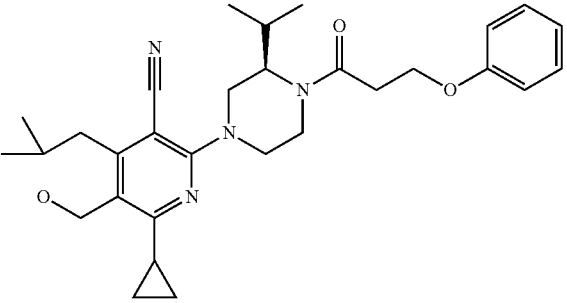 [SMILES: CC(C)Cc1c(C#N)c(N2CCN(C(=O)CCOc3ccccc3)[C@H](C(C)C)C2)nc(C2CC2)c1CO] |
| 367 | 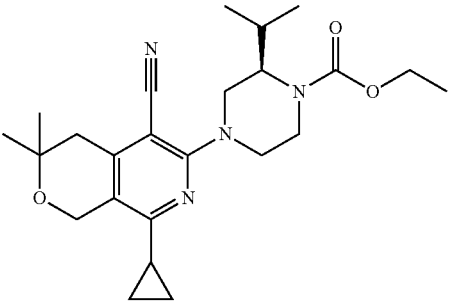 |
| 368 | 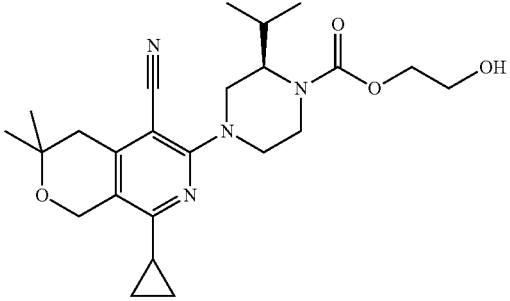 [SMILES: CC(C)[C@@H]1CN(c2nc(C3CC3)c3c(c2C#N)CC(C)(C)OC3)CCN1C(=O)OCCO] |
| 369 | 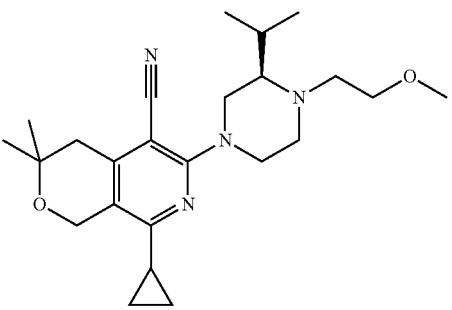 |
| 370 | 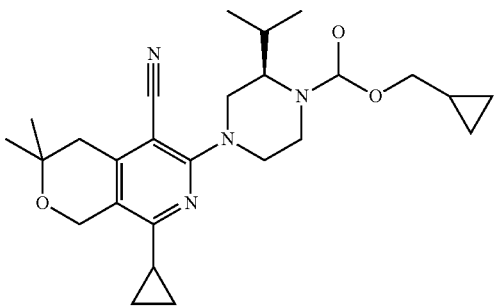 [SMILES: CC(C)[C@@H]1CN(c2nc(C3CC3)c3c(c2C#N)CC(C)(C)OC3)CCN1C(O)OCC1CC1] |

-continued

| Cmpd No | Structure |
|---|---|
| 371 | 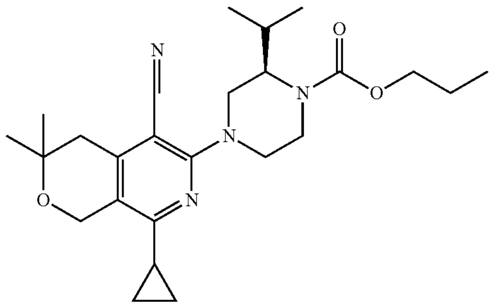 [SMILES: CCCOC(=O)N1CCN(c2nc(C3CC3)c3c(c2C=N)CC(C)(C)OC3)C[C@H]1C(C)C] |
| 372 | 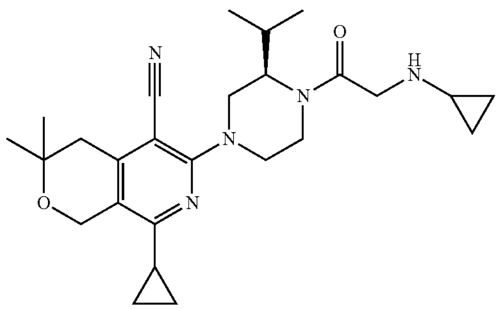 [SMILES: CC(C)[C@@H]1CN(c2nc(C3CC3)c3c(c2C#N)CC(C)(C)OC3)CCN1C(=O)CNC1CC1] |
| 373 | 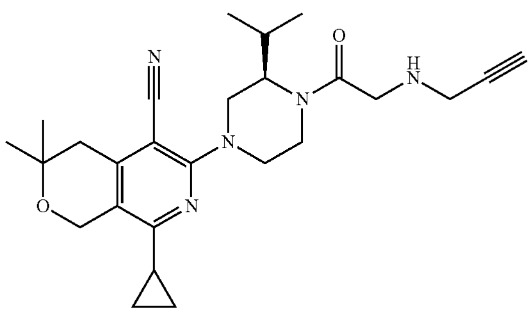 [SMILES: C#CCNCC(=O)N1CCN(c2nc(C3CC3)c3c(c2C#N)CC(C)(C)OC3)C[C@H]1C(C)C] |
| 374 | 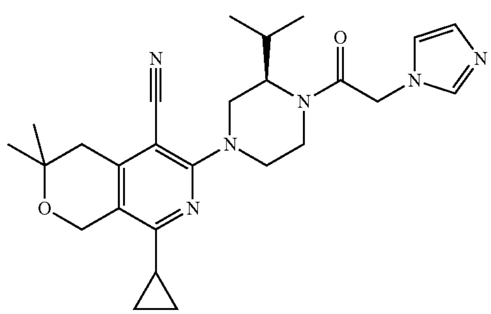 [SMILES: CC(C)[C@@H]1CN(c2nc(C3CC3)c3c(c2C#N)CC(C)(C)OC3)CCN1C(=O)Cn1ccnc1] |
| 375 | 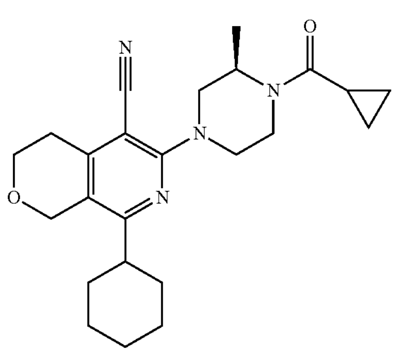 [SMILES: C[C@@H]1CN(c2nc(C3CCCCC3)c3c(c2C#N)CCOC3)CCN1C(=O)C1CC1] |

| Cmpd No | Structure |
|---|---|
| 376 | 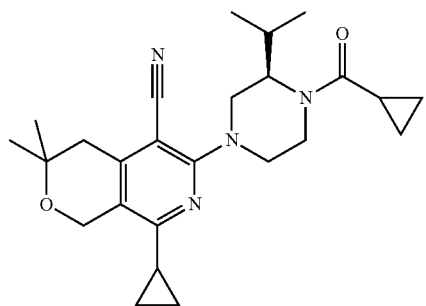 [SMILES: CC(C)[C@@H]1CN(c2nc(C3CC3)c3c(c2C#N)CC(C)(C)OC3)CCN1C(=O)C1CC1] |
| 377 | 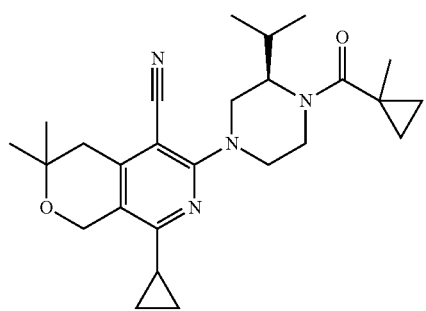 [SMILES: CC(C)[C@@H]1CN(c2nc(C3CC3)c3c(c2C#N)CC(C)(C)OC3)CCN1C(=O)C1(C)CC1] |
| 378 | 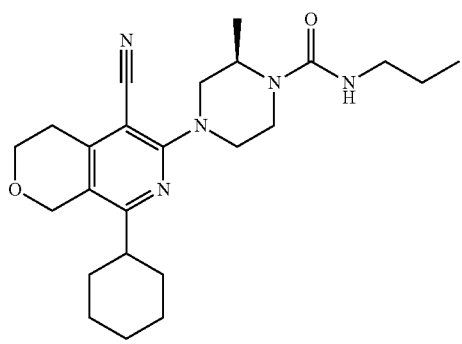 |
| 379 | 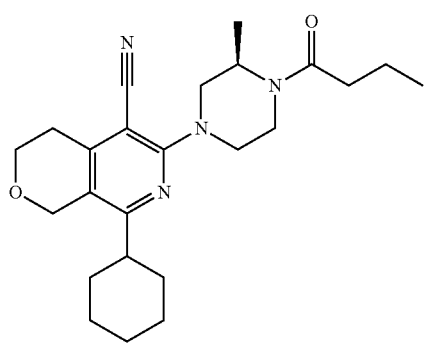 [SMILES: CCCC(=O)N1CCN(c2nc(C3CCCCC3)c3c(c2C#N)CCOC3)C[C@H]1C] |

-continued
| Cmpd No | Structure |
|---|---|
| 380 | 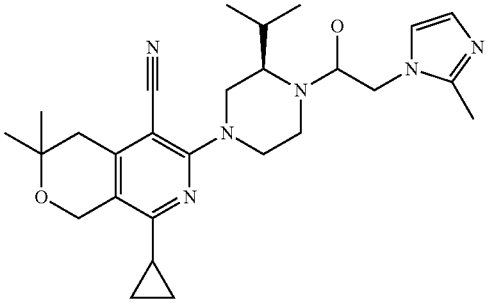 [SMILES: Cc1nccn1CC(O)N1CCN(c2nc(C3CC3)c3c(c2C#N)CC(C)(C)OC3)C[C@H]1C(C)C] |
| 381 | 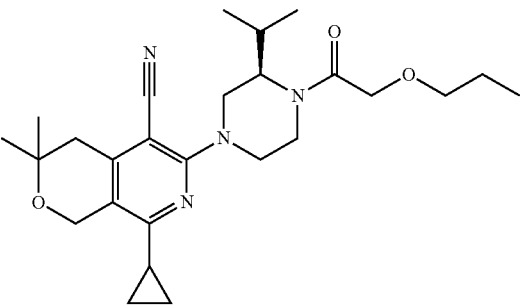 |
| 382 | 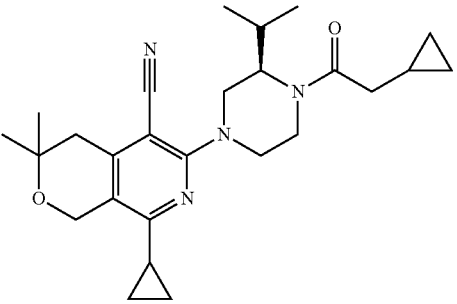 [SMILES: CC(C)[C@@H]1CN(c2nc(C3CC3)c3c(c2C#N)CC(C)(C)OC3)CCN1C(=O)CC1CC1] |
| 383 | 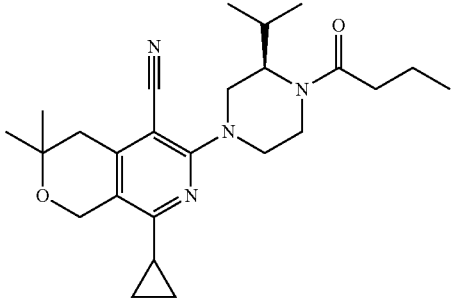 [SMILES: CCCC(=O)N1CCN(c2nc(C3CC3)c3c(c2C#N)CC(C)(C)OC3)C[C@H]1C(C)C] |
| 384 | 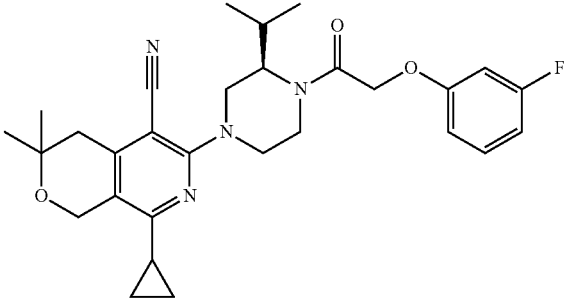 [SMILES: CC(C)[C@@H]1CN(c2nc(C3CC3)c3c(c2C#N)CC(C)(C)OC3)CCN1C(=O)COc1cccc(F)c1] |

| Cmpd No | Structure |
|---|---|
| 385 | 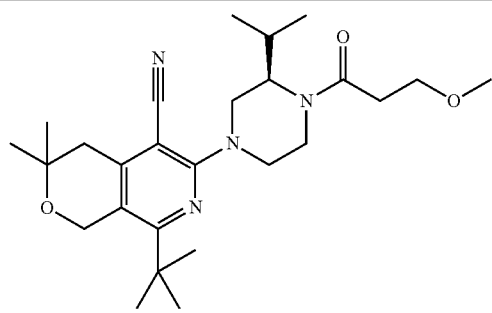 |
| 386 | 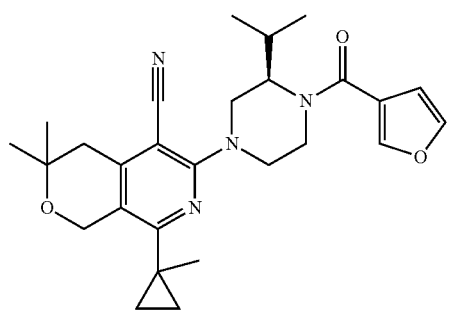 [SMILES: CC(C)[C@@H]1CN(c2nc(C3(C)CC3)c3c(c2C#N)CC(C)(C)OC3)CCN1C(=O)c1ccoc1] |
| 387 | 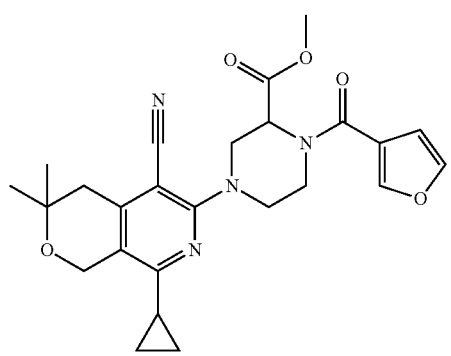 [SMILES: COC(=O)C1CN(c2nc(C3CC3)c3c(c2C#N)CC(C)(C)OC3)CCN1C(=O)c1ccoc1] |
| 388 | 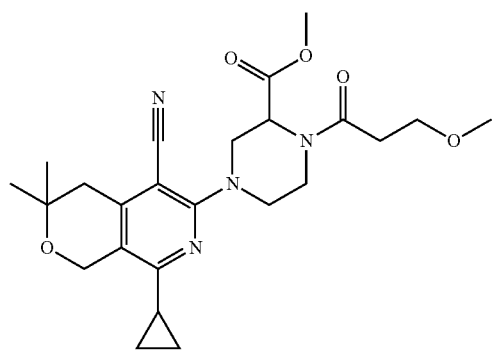 |

| Cmpd No | Structure |
|---|---|
| 389 | 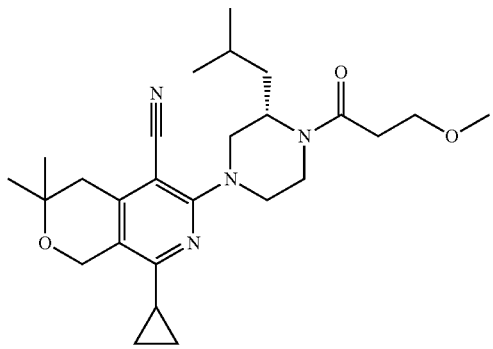 |
| 390 | 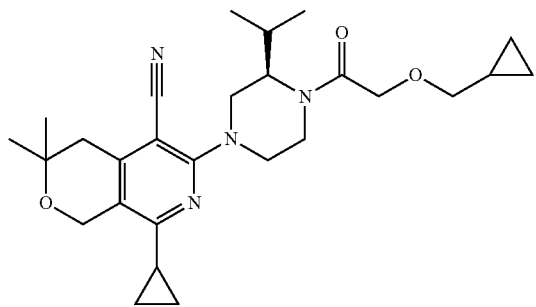 [SMILES: CC(C)[C@@H]1CN(c2nc(C3CC3)c3c(c2C#N)CC(C)(C)OC3)CCN1C(=O)COCC1CC1] |
| 391 | 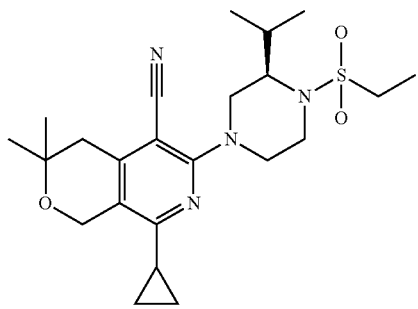 [SMILES: CCS(O)(O)N1CCN(c2nc(C3CC3)c3c(c2C#N)CC(C)(C)OC3)C[C@H]1C(C)C] |
| 392 | 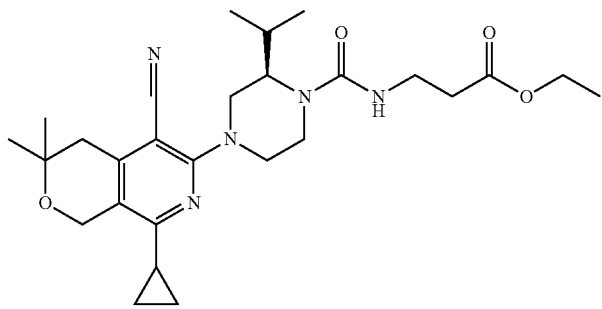 [SMILES: CCOC(=O)CCNC(=O)N1CCN(c2nc(C3CC3)c3c(c2C=N)CC(C)(C)OC3)C[C@H]1C(C)C] |

| Cmpd No | Structure |
|---------|-----------|
| 393 | 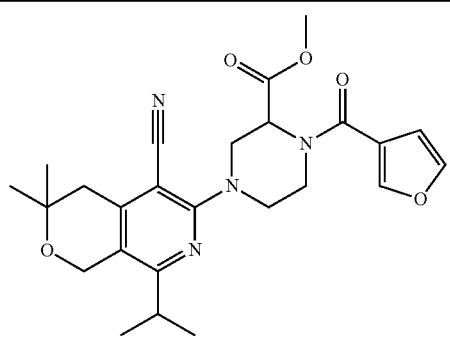 |
| 394 | 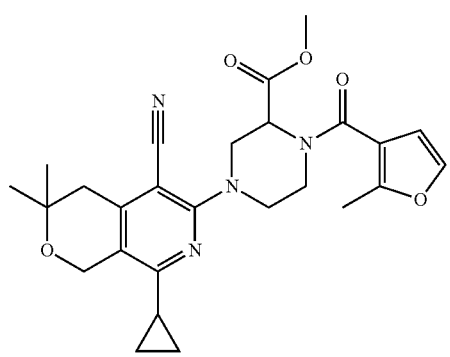 [SMILES: COC(=O)C1CN(c2nc(C3CC3)c3c(c2C#N)CC(C)(C)OC3)CCN1C(=O)c1ccoc1C] |
| 395 | 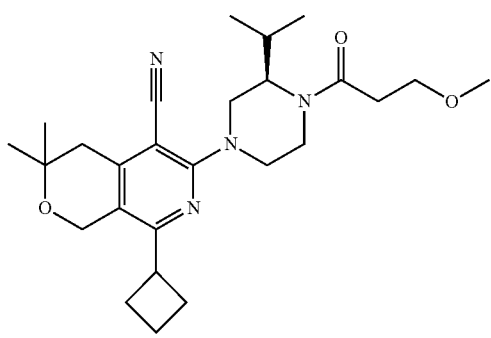 |
| 396 | 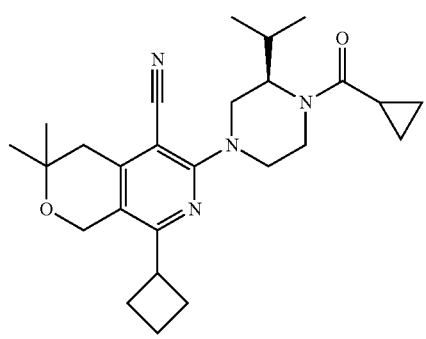 [SMILES: CC(C)[C@@H]1CN(c2nc(C3CCC3)c3c(c2C#N)CC(C)(C)OC3)CCN1C(=O)C1CC1] |

| Cmpd No | Structure |
|---------|-----------|
| 397 | 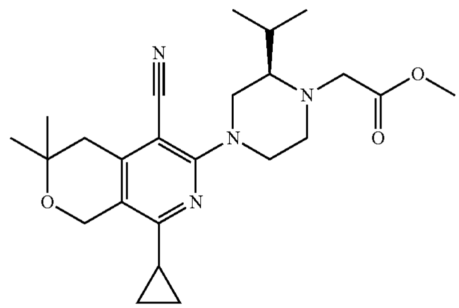 |
| 398 | 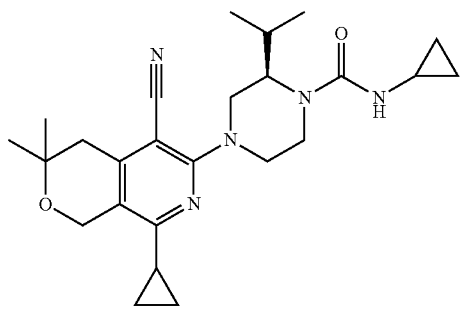 [SMILES: CC(C)[C@@H]1CN(c2nc(C3CC3)c3c(c2C#N)CC(C)(C)OC3)CCN1C(=O)NC1CC1] |
| 399 | 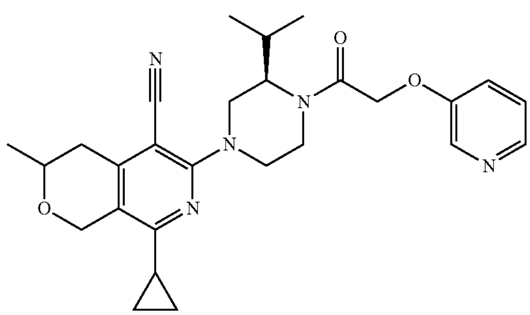 [SMILES: CC1Cc2c(C#N)c(N3CCN(C(=O)COc4cccnc4)[C@H](C(C)C)C3)nc(C3CC3)c2CO1] |
| 400 | 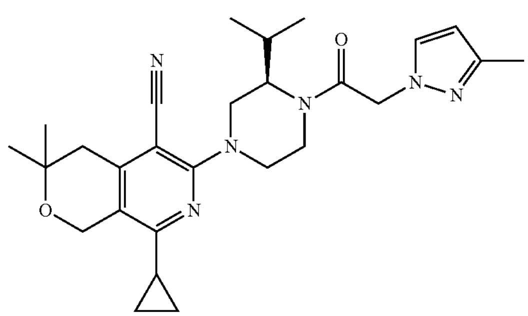 |
| 401 | 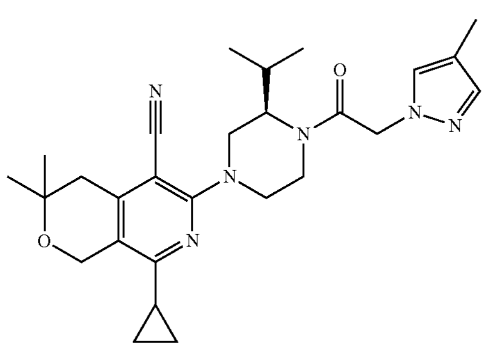 [SMILES: Cc1cnn(CC(=O)N2CCN(c3nc(C4CC4)c4c(c3C#N)CC(C)(C)OC4)C[C@H]2C(C)C)c1] |

-continued
| Cmpd No | Structure |
|---|---|
| 402 | 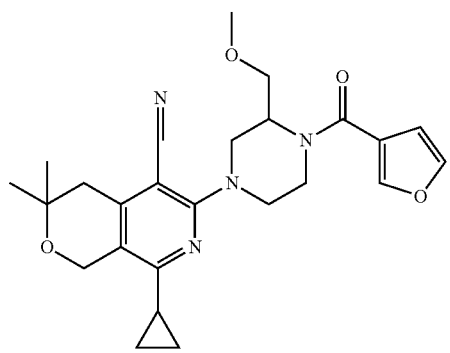 [SMILES: COCC1CN(c2nc(C3CC3)c3c(c2C=N)CC(C)(C)OC3)CCN1C(=O)c1ccoc1] |
| 403 | 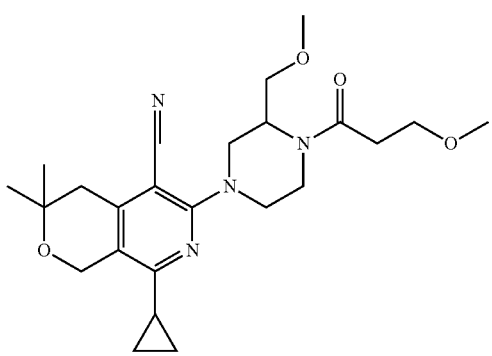 |
| 404 | 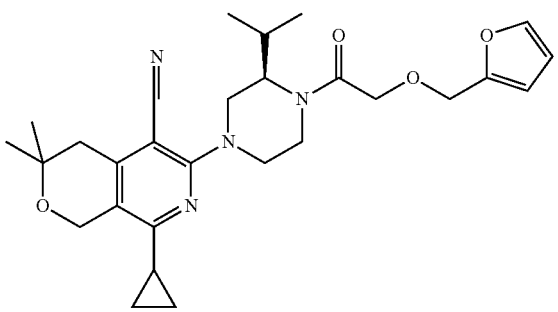 [SMILES: CC(C)[C@@H]1CN(c2nc(C3CC3)c3c(c2C=N)CC(C)(C)OC3)CCN1C(=O)COCc1ccco1] |
| 405 | 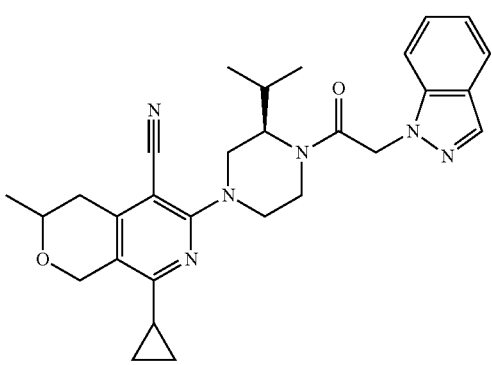 [SMILES: CC1Cc2c(C#N)c(N3CCN(C(=O)Cn4ncc5ccccc54)[C@H](C(C)C)C3)nc(C3CC3)c2CO1] |

| Cmpd No | Structure |
|---|---|
| 406 | 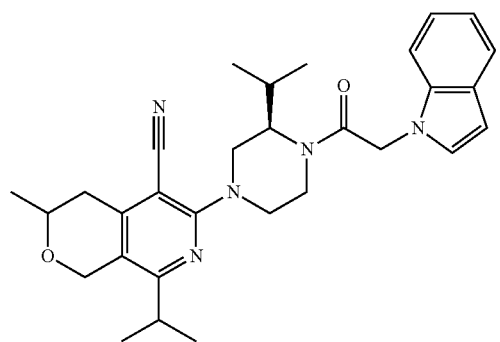 [SMILES: CC1Cc2c(C#N)c(N3CCN(C(=O)Cn4ccc5ccccc54)[C@H](C(C)C)C3)nc(C(C)C)c2CO1] |
| 407 | 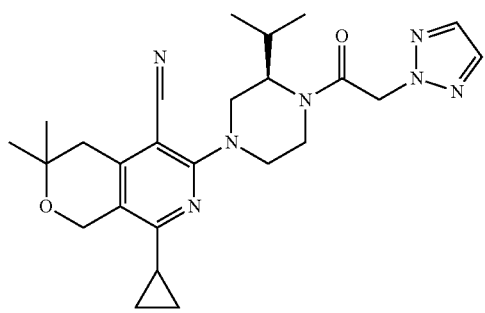 [SMILES: CC(C)[C@@H]1CN(c2nc(C3CC3)c3c(c2C=N)CC(C)(C)OC3)CCN1C(=O)Cn1nccn1] |
| 408 | 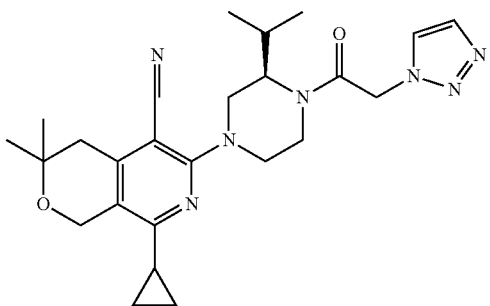 [SMILES: CC(C)[C@@H]1CN(c2nc(C3CC3)c3c(c2C=N)CC(C)(C)OC3)CCN1C(=O)Cn1ccnn1] |
| 409 | 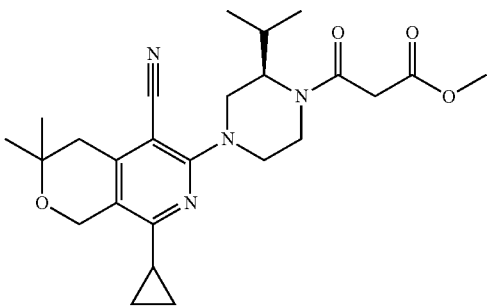 |

-continued
| Cmpd No | Structure |
|---------|-----------|
| 410 | 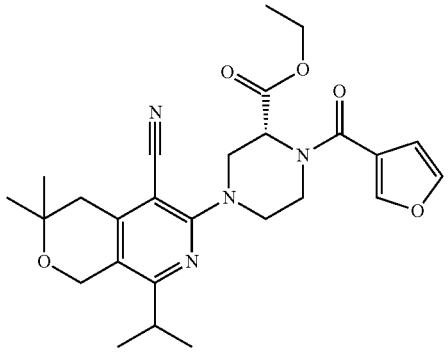 [SMILES: CCOC(=O)[C@H]1CN(c2nc(C(C)C)c3c(c2C#N)CC(C)(C)OC3)CCN1C(=O)c1ccoc1] |
| 411 | 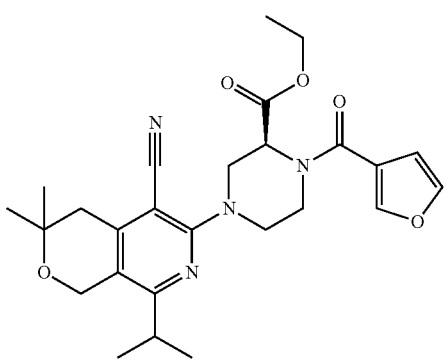 [SMILES: CCOC(=O)[C@@H]1CN(c2nc(C(C)C)c3c(c2C#N)CC(C)(C)OC3)CCN1C(=O)c1ccoc1] |
| 412 | 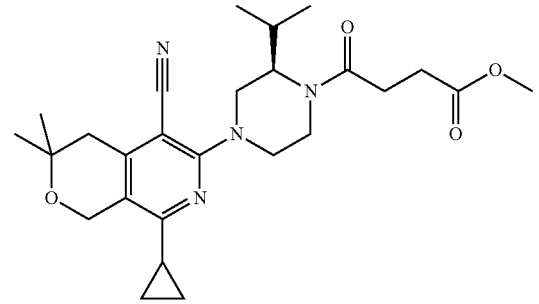 |
| 413 | 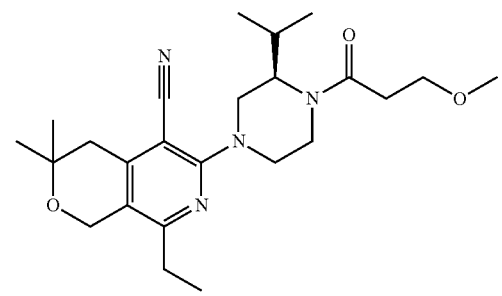 |
| 414 | 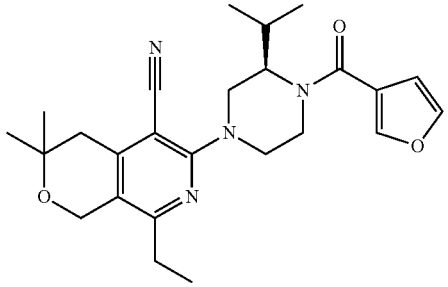 [SMILES: CCc1nc(N2CCN(C(=O)c3ccoc3)[C@H](C(C)C)C2)c(C#N)c2c1COC(C)(C)C2] |

| Cmpd No | Structure |
|---|---|
| 415 | 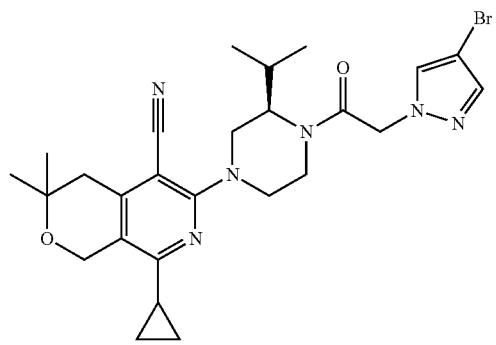 [SMILES: CC(C)[C@@H]1CN(c2nc(C3CC3)c3c(c2C#N)CC(C)(C)OC3)CCN1C(=O)Cn1cc(Br)cn1] |
| 416 | 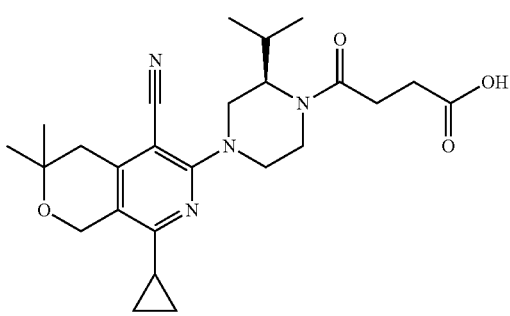 [SMILES: CC(C)[C@@H]1CN(c2nc(C3CC3)c3c(c2C#N)CC(C)(C)OC3)CCN1C(=O)CCC(=O)O] |
| 417 | 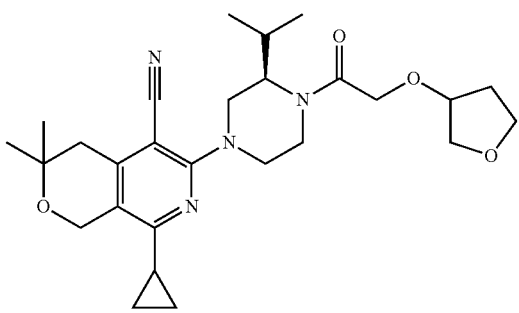 [SMILES: CC(C)[C@@H]1CN(c2nc(C3CC3)c3c(c2C#N)CC(C)(C)OC3)CCN1C(=O)COC1CCOC1] |
| 418 | 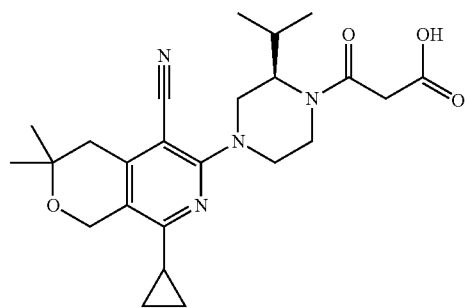 [SMILES: CC(C)[C@@H]1CN(c2nc(C3CC3)c3c(c2C#N)CC(C)(C)OC3)CCN1C(=O)CC(=O)O] |
| 419 | 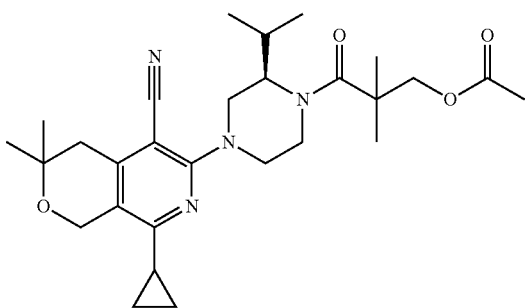 [SMILES: CC(=O)OCC(C)(C)C(=O)N1CCN(c2nc(C3CC3)c3c(c2C#N)CC(C)(C)OC3)C[C@H]1C(C)C] |

| Cmpd No | Structure |
| --- | --- |
| 420 | 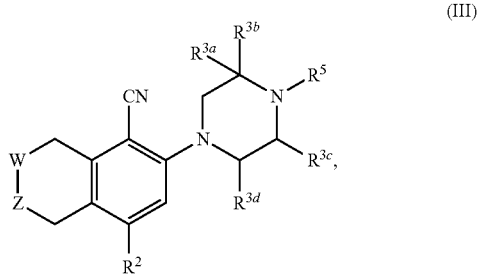 |

In some embodiments, the compound is depicted by Structural Formula III:

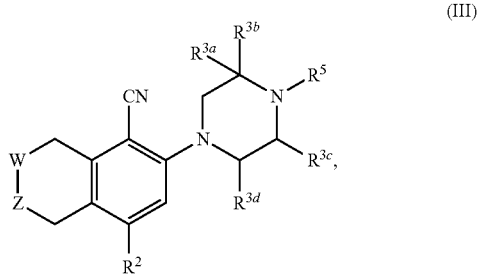

wherein:

one of W or Z is N(R$^7$) and the other of W or Z is C(R$^1$)(R$^1$)

each R$^1$ is the same and is selected from hydrogen and methyl;

R$^2$ is selected from phenyl optionally substituted with a single fluoro or a single methyl, cyclohexyl, cyclopentyl, cyclobutyl, cyclopropyl optionally substituted with a single methyl, isopropyl and methyl;

R$^{3a}$ is selected from hydrogen and methyl;

R$^{3b}$ is selected from hydrogen, methyl, ethyl, isobutyl, isopropyl, phenyl, C$_3$-C$_7$ cycloalkyl, —C(O)—O—CH$_2$CH$_3$, —C(O)—O—CH$_3$, and —CH$_2$—O—CH$_3$;

R$^{3c}$ is selected from hydrogen and methyl;

R$^{3d}$ is selected from hydrogen, phenyl and methyl; and

R$^5$ is selected from: —C(O)—(C$_1$-C$_4$ alkyl), —C(O)—(C$_0$-C$_2$ alkylene)-Q, —C(O)—(C$_1$-C$_4$ alkylene)-O—C(O)—(C$_1$-C$_4$ alkyl), —C(O)—(C$_1$-C$_4$ alkylene)-C(O)—O—(C$_1$-C$_4$ alkyl), —C(O)—(C$_1$-C$_2$ alkylene)-O—(C$_1$-C$_4$ alkyl), —C(O)—O—(C$_1$-C$_4$ alkylene)-O—(C$_1$-C$_4$ alkyl), —(C$_0$-C$_4$ alkylene)-O—C(O)—(C$_1$-C$_4$ alkyl), —(C$_0$-C$_4$ alkylene)-C(O)—O—(C$_1$-C$_4$ alkyl), and —(C$_0$-C$_4$ alkylene)-O—(C$_1$-C$_4$ alkyl), wherein:

any alkylene moiety present in R$^5$ is optionally substituted with OH or F;

any terminal methyl moiety present in R$^5$ is optionally replaced with —CH$_2$OH, CF$_3$, —CH$_2$F, —CH$_2$Cl, C(O)CH$_3$, or C(O)CF$_3$;

Q is selected from aryl, heteroaryl, carbocyclyl and heterocyclyl; and Q is optionally substituted with up to 3 substituents independently selected from C$_1$-C$_4$ alkyl, C$_1$-C$_4$ alkoxy, —CN, fluoro, chloro, and bromo; and R$^7$ is defined as for Structural Formula I.

In some embodiments, each of R$^1$ is H.

In some embodiments, Z is N(R$^7$) and W is CH$_2$. In some embodiments, R$^7$ is such that G-L-M together form C(O) C$_1$-C$_4$ alkyl, for example, C(O)CH$^3$, C(O)C$_2$-C$_4$ alkenyl, for example, C(O)CHCH2, or C(O)C$_2$-C$_4$ alkynyl, for example, C(O)CCH, In some embodiments, R$^7$ is such that G-L-M together form S(O)$_2$C$_1$-C$_4$ alkyl, for example, S(O)$_2$CH$_3$ or S(O)2C$_2$-C$_4$ alkenyl. In some embodiments, R$^7$ is such that G-L-M together form —C$_1$-C$_4$—OH, for example, —CH$_2$CH$_2$OH.

In some embodiments, W is N(R$^7$) and Z is CH$_2$. In some embodiments, R$^7$ is such that G-L-M together form C(O) C$_1$-C$_4$ alkyl, for example, C(O)CH$^3$, C(O)C$_2$-C$_4$ alkenyl, for example, C(O)CHCH2, or C(O)C$_2$-C$_4$ alkynyl, for example, C(O)CCH, In some embodiments, R7 is such that G-L-M together form S(O)$_2$C$_1$-C$_4$ alkyl, for example, S(O)$_2$CH$_3$ or S(O)2C$_2$-C$_4$ alkenyl. In some embodiment, C(O)C2-C4 alkyl is substituted by a fluoro, e.g., forming C(O)CFCH$_2$.

In some embodiments, R$^2$ is selected from cyclohexyl, cyclopentyl, cyclobutyl, or cyclopropyl optionally substituted with a single methyl, isopropyl and methyl. In some embodiments, R$^2$ is selected from cyclopropyl.

In some embodiments, R$^{3a}$ is hydrogen and R$^{3b}$ is selected from methyl, ethyl, isobutyl, isopropyl, and C$_3$-C$_7$ cycloalkyl. In some embodiments, R$^{3b}$ is C$_3$-C$_7$ cycloalkyl, for example, cyclopropyl such as (R) cyclopropyl.

In some embodiments, R$^{3a}$ and R$^{3b}$ have the following stereoconfiguration in the compound of formula (II):

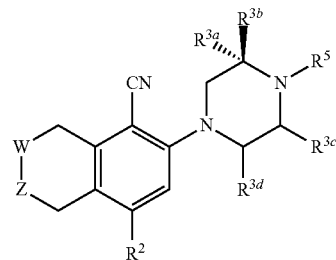

In some embodiments, R$^{3c}$ is hydrogen. In some embodiments R$^{3d}$ is hydrogen. In some embodiments, both R$^{3c}$ and R$^{3d}$ are hydrogen.

In some embodiments, R$^5$ is selected from: —C(O)—(C$_1$-C$_4$ alkyl), —C(O)—(C$_0$-C$_2$ alkylene)-Q, —C(O)—(C$_1$-C$_2$ alkylene)-O—(C$_1$-C$_4$ alkyl), wherein: any alkylene moiety present in R$^5$ is optionally substituted with OH or F; and any terminal methyl moiety present in R$^5$ is optionally replaced with —CH$_2$OH, CF$_3$, —CH$_2$F, —CH$_2$Cl, C(O)CH$_3$, or C(O)CF$_3$. In some embodiments, R$^5$ is: —C(O)—(C$_1$-C$_4$ alkyl), wherein any terminal methyl moiety present in R$^5$ is optionally replaced with —CH$_2$OH, CF$_3$, —CH$_2$F, —CH$_2$Cl, C(O)CH$_3$, or C(O)CF$_3$, for example, CH$_2$CF$_3$. In some embodiments, R$^5$ is C(O)—(C$_0$-C$_2$ alkylene)-Q, wherein Q is carbocyclyl, for example, cyclopropyl. In some embodiments, R$^5$ is —C(O)cyclopropyl. In some embodiments, R$^5$ is —C(O)—(C$_1$-C$_2$ alkylene)-O—(C$_1$-C$_4$ alkyl). In some embodiments, R$^5$ is —C(O)CH$_2$CH$_2$OCH$_3$.

Exemplary compounds are provided in Table 4 below:

TABLE 4

| Compound # | Structure |
| --- | --- |
| 421 | 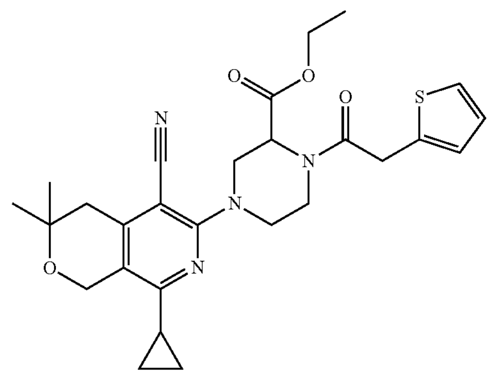 [SMILES: CCOC(=O)C1CN(c2nc(C3CC3)c3c(c2C#N)CC(C)(C)OC3)CCN1C(=O)Cc1cccs1] |
| 422 | 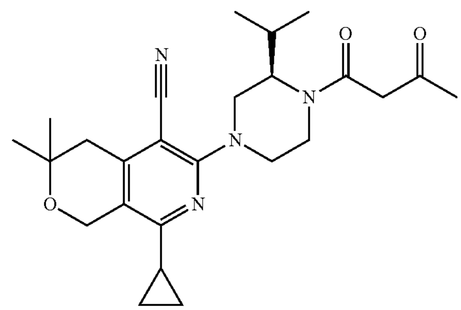 [SMILES: CC(=O)CC(=O)N1CCN(c2nc(C3CC3)c3c(c2C#N)CC(C)(C)OC3)C[C@H]1C(C)C] |
| 423 | 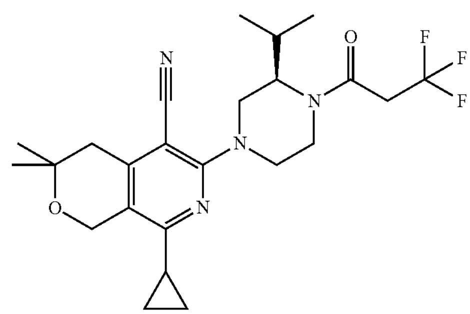 [SMILES: CC(C)[C@@H]1CN(c2nc(C3CC3)c3c(c2C#N)CC(C)(C)OC3)CCN1C(=O)CC(F)(F)F] |
| 424 | 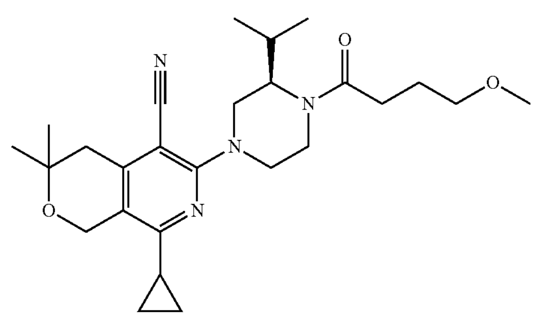 |

TABLE 4-continued
| Compound # | Structure |
|---|---|
| 425 | 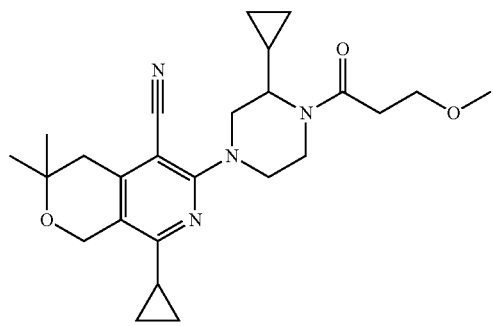 |
| 426 | 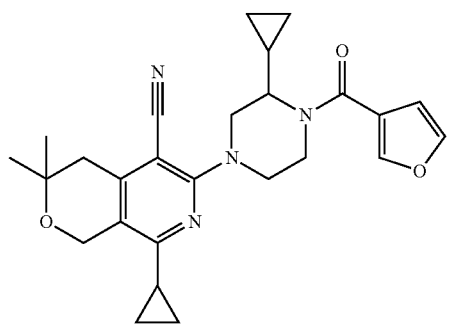 [SMILES: CC1(C)Cc2c(C#N)c(N3CCN(C(=O)c4ccoc4)C(C4CC4)C3)nc(C3CC3)c2CO1] |
| 427 | 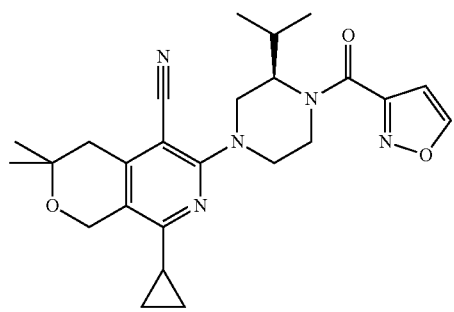 [SMILES: CC(C)[C@@H]1CN(c2nc(C3CC3)c3c(c2C#N)CC(C)(C)OC3)CCN1C(=O)c1ccon1] |
| 428 | 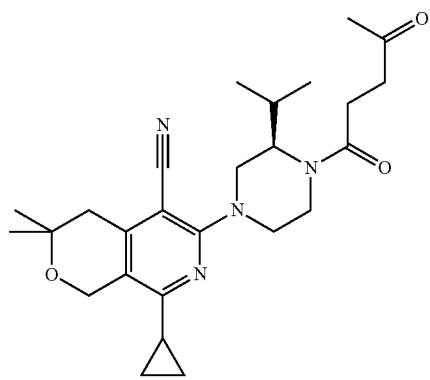 [SMILES: CC(=O)CCC(=O)N1CCN(c2nc(C3CC3)c3c(c2C#N)CC(C)(C)OC3)C[C@H]1C(C)C] |

TABLE 4-continued
| Compound # | Structure |
|---|---|
| 429 | 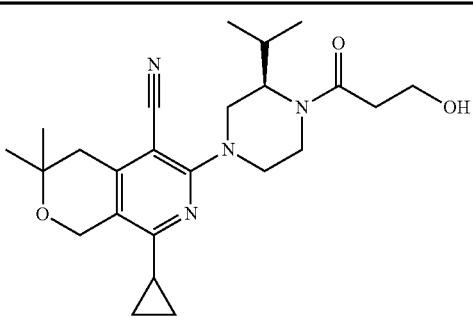 |
| 430 | 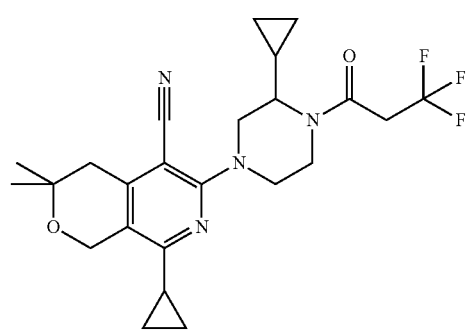 [SMILES: CC1(C)Cc2c(C#N)c(N3CCN(C(=O)CC(F)(F)F)C(C4CC4)C3)nc(C3CC3)c2CO1] |
| 431 | 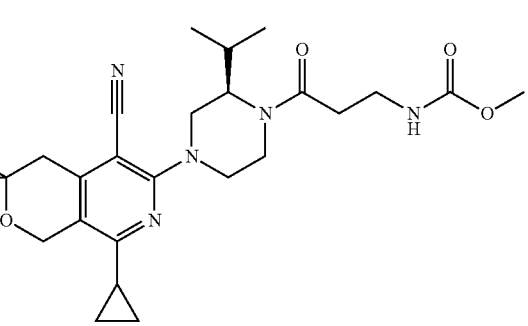 |
| 432 | 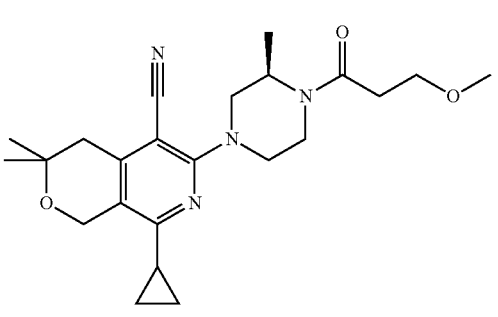 |
| 433 | 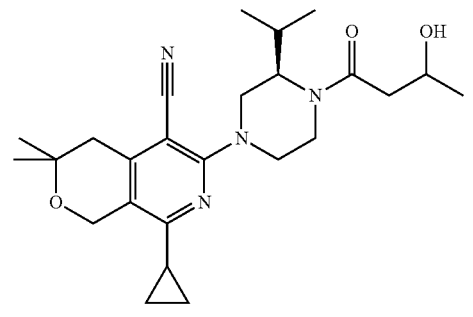 [SMILES: CC(O)CC(=O)N1CCN(c2nc(C3CC3)c3c(c2C#N)CC(C)(C)OC3)C[C@H]1C(C)C] |

TABLE 4-continued
| Compound # | Structure |
|---|---|
| 434 | 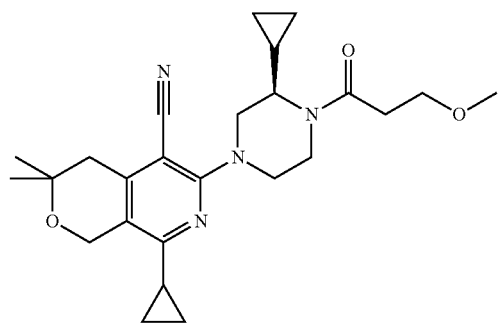 |
| 435 | 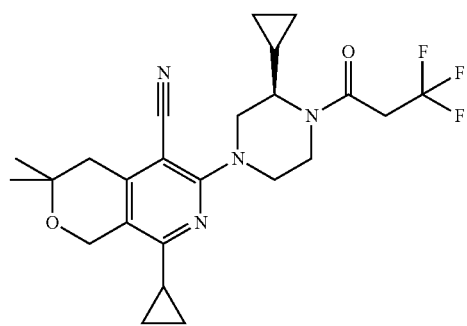 [SMILES: CC1(C)Cc2c(C#N)c(N3CCN(C(=O)CC(F)(F)F)[C@H](C4CC4)C3)nc(C3CC3)c2CO1] |
| 436 | 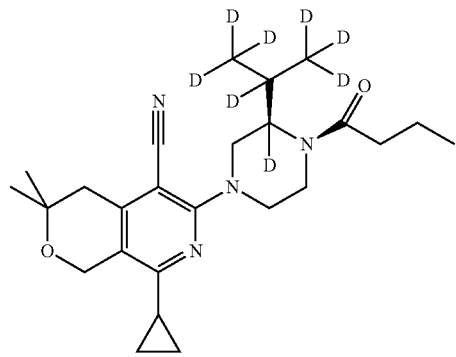 |
| 437 | 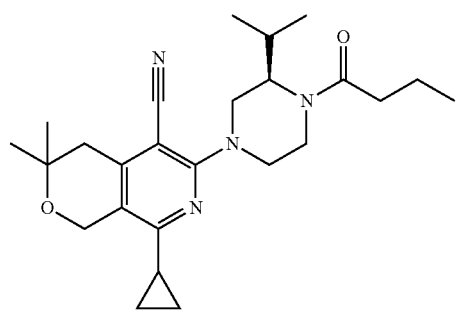 [SMILES: CCCC(=O)N1CCN(c2nc(C3CC3)c3c(c2C#N)CC(C)(C)OC3)C[C@H]1C(C)C] |

TABLE 4-continued

| Compound # | Structure |
|---|---|
| 438 | 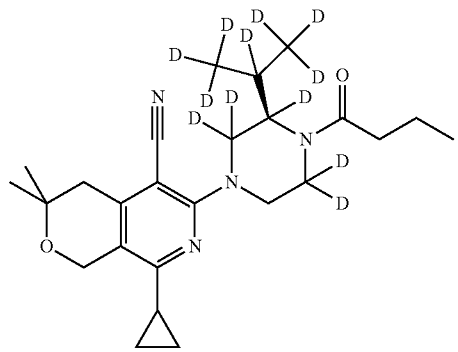 [SMILES: [2H]C1([2H])CN(c2nc(C3CC3)c3c(c2C#N)CC(C)(C)OC3)C([2H])([2H])[C@@]([2H])(C([2H])(C([2H])([2H])[2H])C([2H])([2H])[2H])N1C(=O)CCC] |
| 439 | 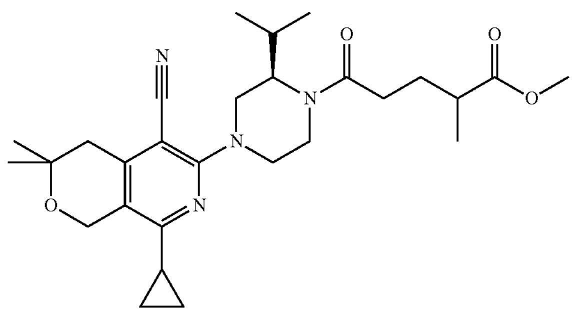 |
| 440 | 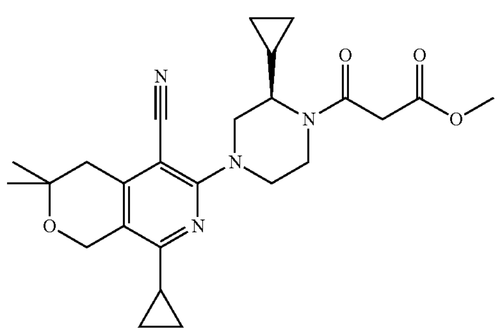 |
| 441 | 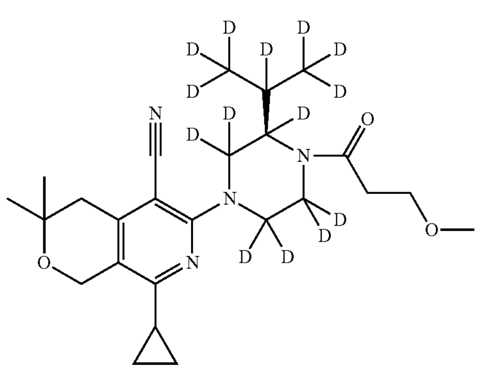 |

TABLE 4-continued

| Compound # | Structure |
|---|---|
| 442 | 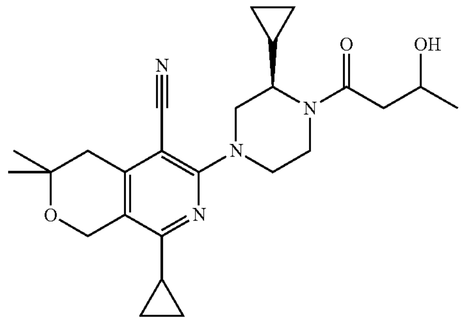 [SMILES: CC(O)CC(=O)N1CCN(c2nc(C3CC3)c3c(c2C#N)CC(C)(C)OC3)C[C@H]1C1CC1] |
| 443 | 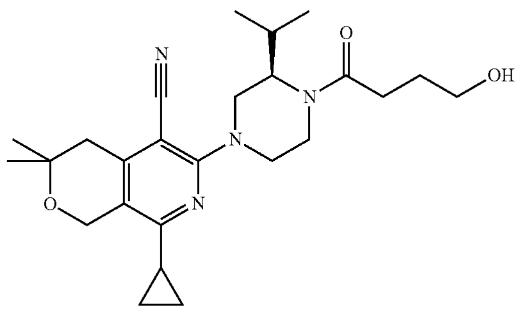 [SMILES: CC(C)[C@@H]1CN(c2nc(C3CC3)c3c(c2C#N)CC(C)(C)OC3)CCN1C(=O)CCCO] |
| 444 | 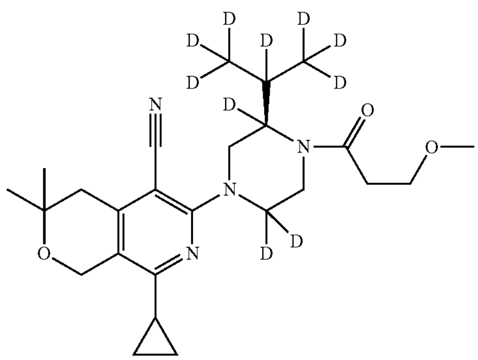 |
| 445 | 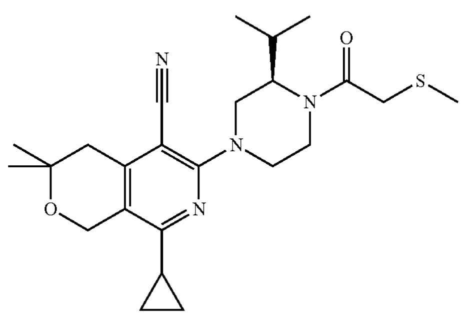 |
| 446 | 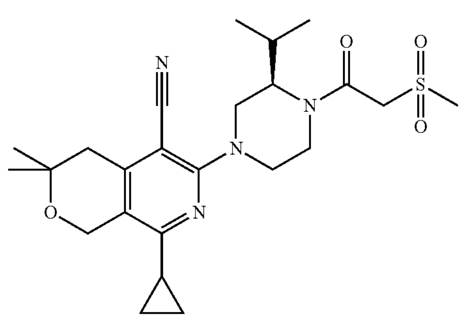 |

TABLE 4-continued
| Compound # | Structure |
|---|---|
| 447 | 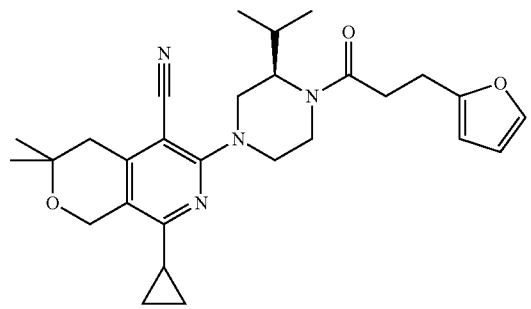 [SMILES: CC(C)[C@@H]1CN(c2nc(C3CC3)c3c(c2C#N)CC(C)(C)OC3)CCN1C(=O)CCc1ccco1] |
| 448 | 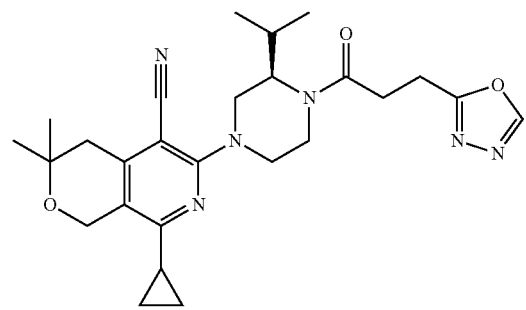 [SMILES: CC(C)[C@@H]1CN(c2nc(C3CC3)c3c(c2C#N)CC(C)(C)OC3)CCN1C(=O)CCc1nnco1] |
| 449 | 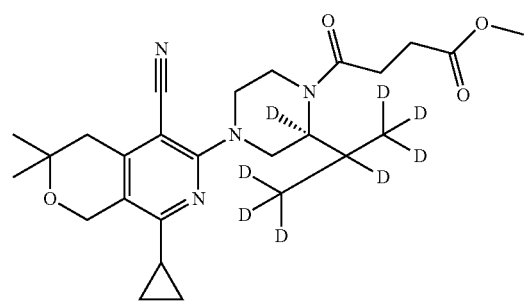 |
| 450 | 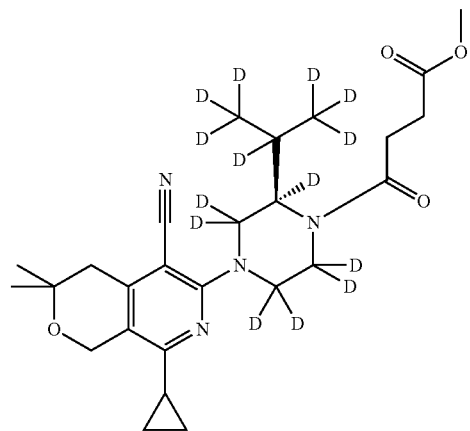 |

TABLE 4-continued
| Compound # | Structure |
|---|---|
| 451 | 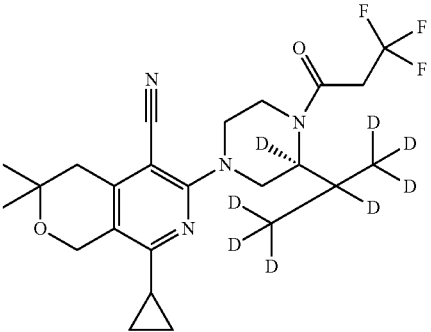 |
| 452 | 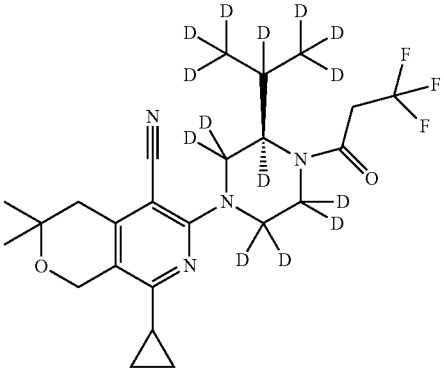 |
| 453 | 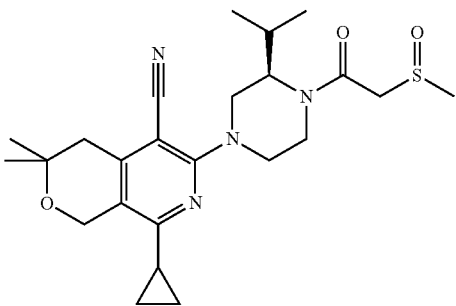 |
| 454 | 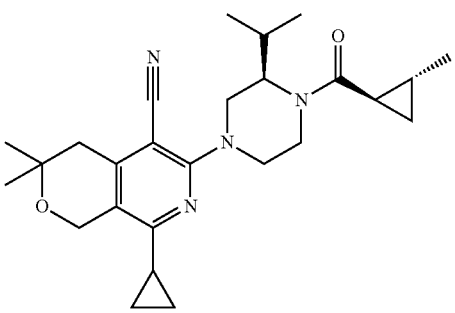 |

TABLE 4-continued

| Compound # | Structure |
|---|---|
| 455 | 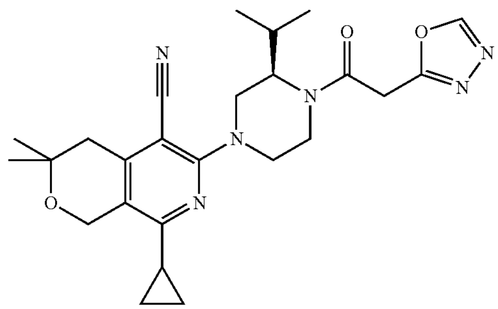 [SMILES: CC(C)[C@@H]1CN(c2nc(C3CC3)c3c(c2C#N)CC(C)(C)OC3)CCN1C(=O)Cc1nnco1] |
| 456 | 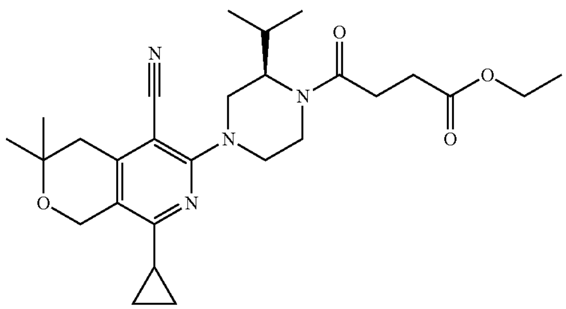 [SMILES: CCOC(=O)CCC(=O)N1CCN(c2nc(C3CC3)c3c(c2C#N)CC(C)(C)OC3)C[C@H]1C(C)C] |
| 457 | 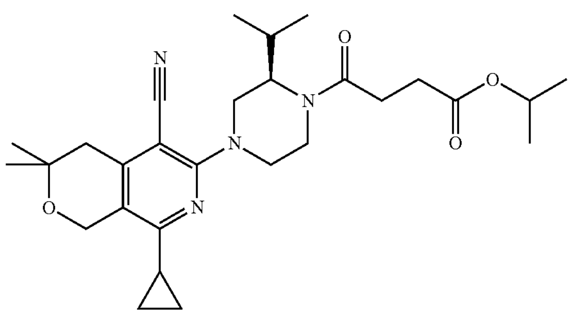 [SMILES: CC(C)OC(=O)CCC(=O)N1CCN(c2nc(C3CC3)c3c(c2C#N)CC(C)(C)OC3)C[C@H]1C(C)C] |
| 458 | 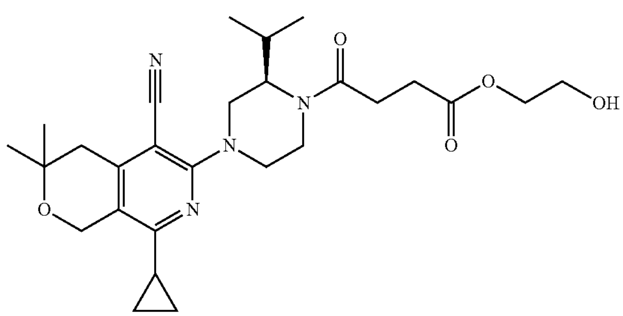 [SMILES: CC(C)[C@@H]1CN(c2nc(C3CC3)c3c(c2C#N)CC(C)(C)OC3)CCN1C(=O)CCC(=O)OCCO] |
| 459 | 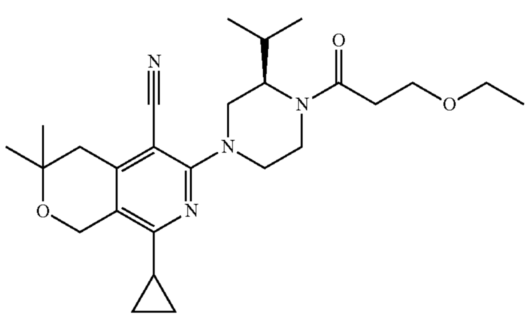 [SMILES: CCOCCC(=O)N1CCN(c2nc(C3CC3)c3c(c2C#N)CC(C)(C)OC3)C[C@H]1C(C)C] |

TABLE 4-continued

| Compound # | Structure |
|---|---|
| 460 | 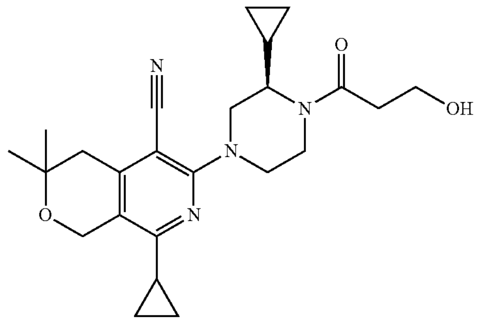 [SMILES: CC1(C)Cc2c(C#N)c(N3CCN(C(=O)CCO)[C@H](C4CC4)C3)nc(C3CC3)c2CO1] |
| 461 | 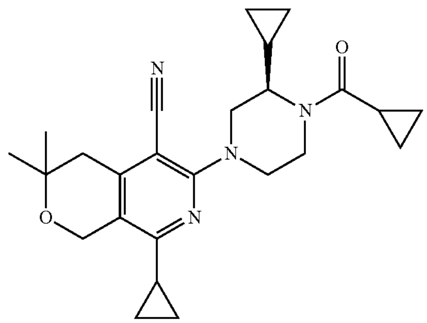 [SMILES: CC1(C)Cc2c(C#N)c(N3CCN(C(=O)C4CC4)[C@H](C4CC4)C3)nc(C3CC3)c2CO1] |
| 462 | 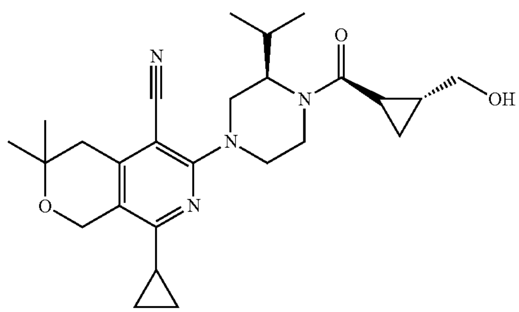 |
| 463 | 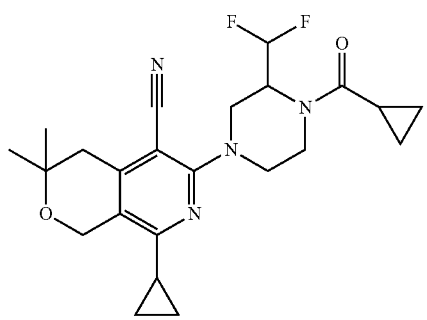 [SMILES: CC1(C)Cc2c(C#N)c(N3CCN(C(=O)C4CC4)C(C(F)F)C3)nc(C3CC3)c2CO1] |
| 464 | 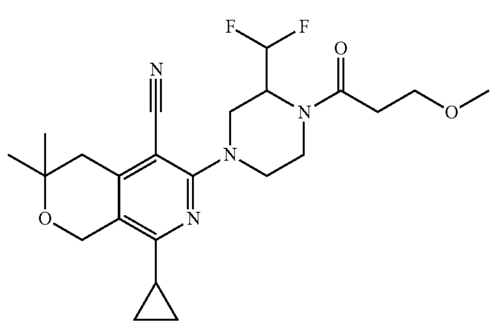 |

TABLE 4-continued
| Compound # | Structure |
|---|---|
| 465 | 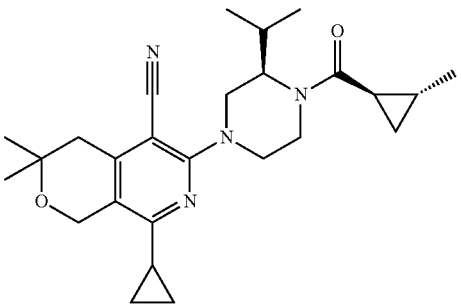 |
| 466 | 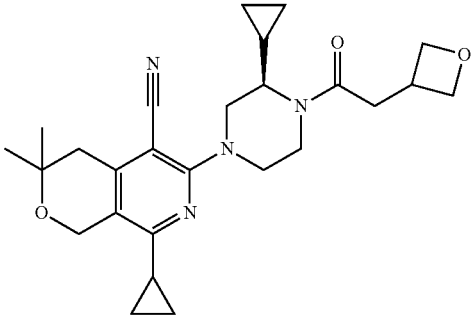 [SMILES: CC1(C)Cc2c(C#N)c(N3CCN(C(=O)CC4COC4)[C@H](C4CC4)C3)nc(C3CC3)c2CO1] |
| 467 | 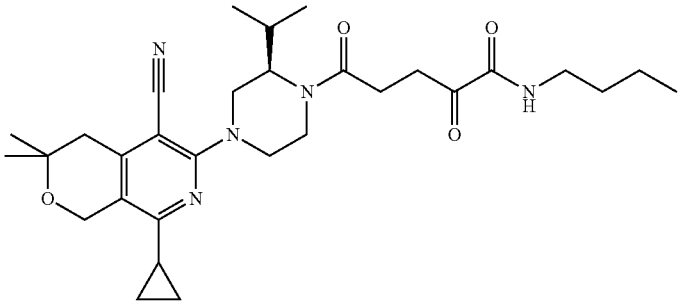 [SMILES: CCCCNC(=O)C(=O)CCC(=O)N1CCN(c2nc(C3CC3)c3c(c2C#N)CC(C)(C)OC3)C[C@H]1C(C)C] |
| 468 | 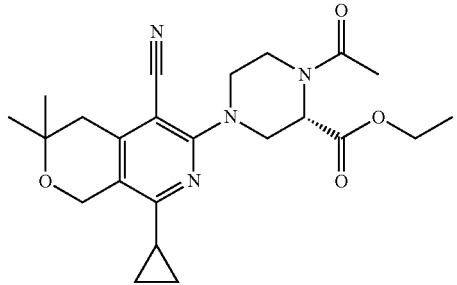 [SMILES: CCOC(=O)[C@@H]1CN(c2nc(C3CC3)c3c(c2C#N)CC(C)(C)OC3)CCN1C(C)=O] |
| 469 | 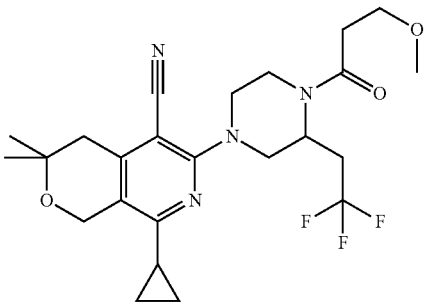 |

TABLE 4-continued
| Compound # | Structure |
|---|---|
| 470 | 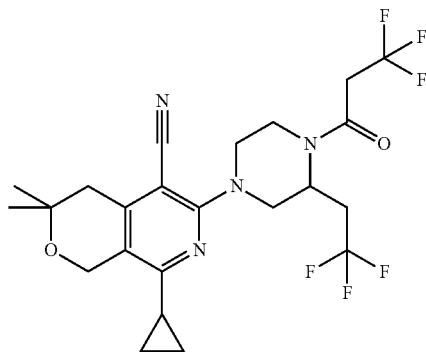 [SMILES: CC1(C)Cc2c(C#N)c(N3CCN(C(=O)CC(F)(F)F)C(CC(F)(F)F)C3)nc(C3CC3)c2CO1] |
| 471 | 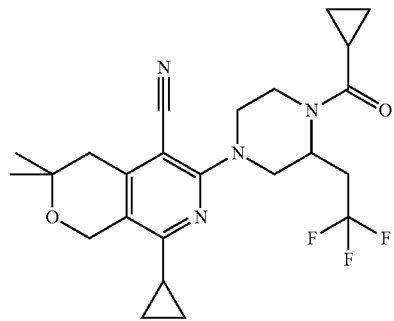 [SMILES: CC1(C)Cc2c(C#N)c(N3CCN(C(=O)C4CC4)C(CC(F)(F)F)C3)nc(C3CC3)c2CO1] |
| 472 | 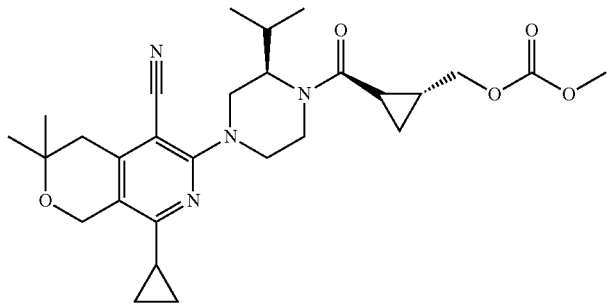 |
| 473 | 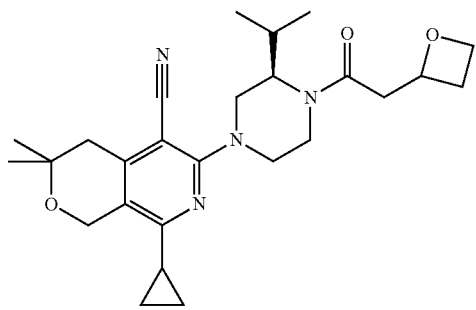 [SMILES: CC(C)[C@@H]1CN(c2nc(C3CC3)c3c(c2C#N)CC(C)(C)OC3)CCN1C(=O)CC1CCO1] |

TABLE 4-continued

| Compound # | Structure |
|---|---|
| 474 | 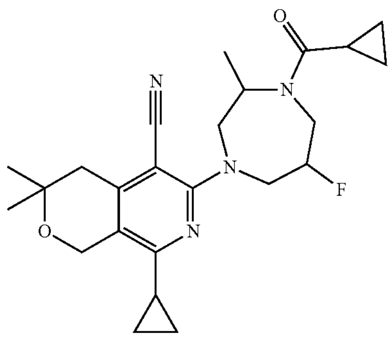 [SMILES: CC1CN(c2nc(C3CC3)c3c(c2C#N)CC(C)(C)OC3)CC(F)CN1C(=O)C1CC1] |
| 475 | 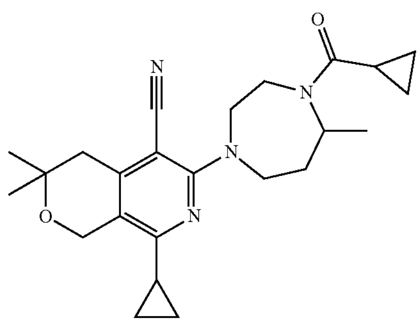 [SMILES: CC1CCN(c2nc(C3CC3)c3c(c2C#N)CC(C)(C)OC3)CCN1C(=O)C1CC1] |
| 476 | 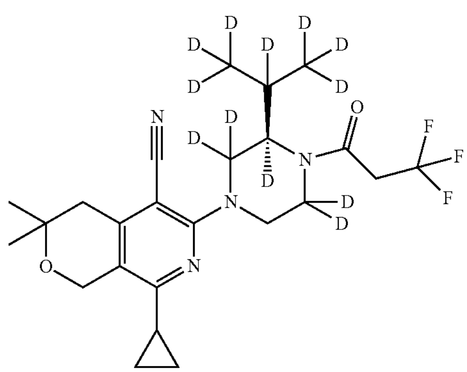 |
| 477 | 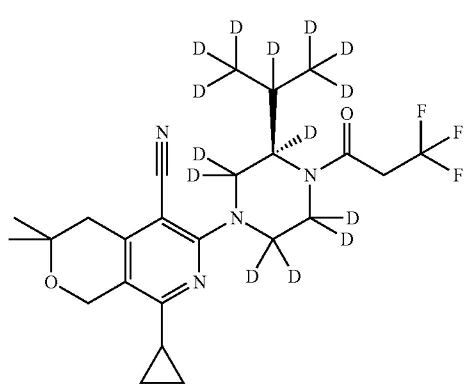 [SMILES: [2H]C([2H])([2H])C([2H])(C([2H])([2H])[2H])[C@@]1([2H])N(C(=O)CC(F)(F)F)C([2H])([2H])C([2H])([2H])N(c2nc(C3CC3)c3c(c2C#N)CC(C)(C)OC3)C1([2H])[2H]] |

TABLE 4-continued
| Compound # | Structure |
|---|---|
| 478 | 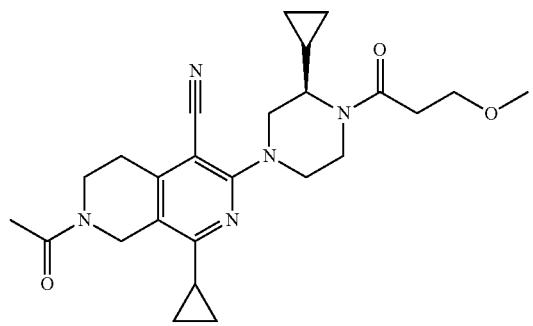 [SMILES: COCCC(=O)N1CCN(c2nc(C3CC3)c3c(c2C#N)CCN(C(C)=O)C3)C[C@H]1C1CC1] |
| 479 | 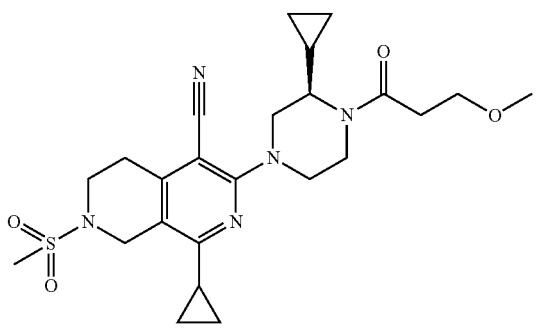 [SMILES: COCCC(=O)N1CCN(c2nc(C3CC3)c3c(c2C#N)CCN(S(C)(=O)=O)C3)C[C@H]1C1CC1] |
| 480 | 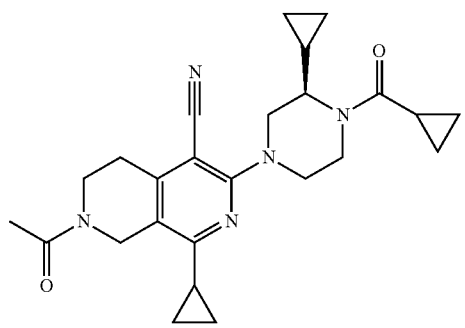 [SMILES: CC(=O)N1CCc2c(C#N)c(N3CCN(C(=O)C4CC4)[C@H](C4CC4)C3)nc(C3CC3)c2C1] |
| 481 | 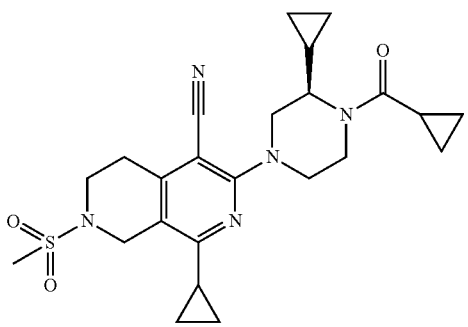 [SMILES: CS(=O)(=O)N1CCc2c(C#N)c(N3CCN(C(=O)C4CC4)[C@H](C4CC4)C3)nc(C3CC3)c2C1] |

TABLE 4-continued
| Compound # | Structure |
|---|---|
| 482 | 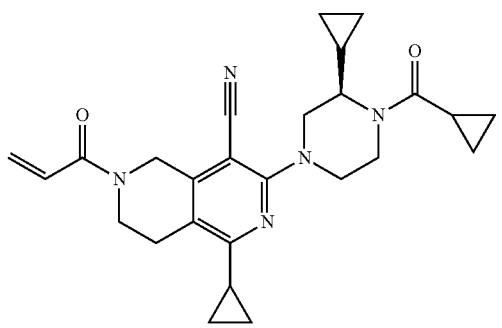 [SMILES: C=CC(=O)N1CCc2c(C3CC3)nc(N3CCN(C(=O)C4CC4)[C@H](C4CC4)C3)c(C#N)c2C1] |
| 483 | 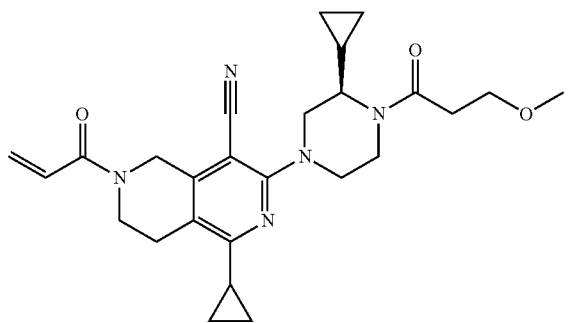 [SMILES: C=CC(=O)N1CCc2c(C3CC3)nc(N3CCN(C(=O)CCOC)[C@H](C4CC4)C3)c(C#N)c2C1] |
| 484 | 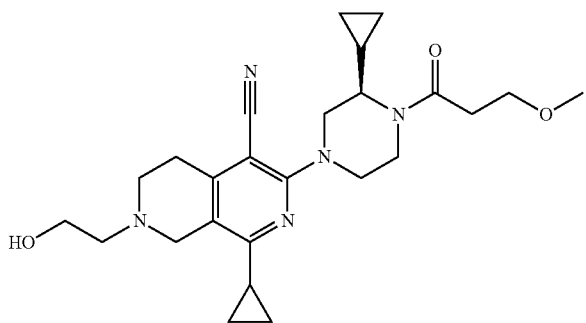 [SMILES: COCCC(=O)N1CCN(c2nc(C3CC3)c3c(c2C#N)CCN(CCO)C3)C[C@H]1C1CC1] |
| 485 | 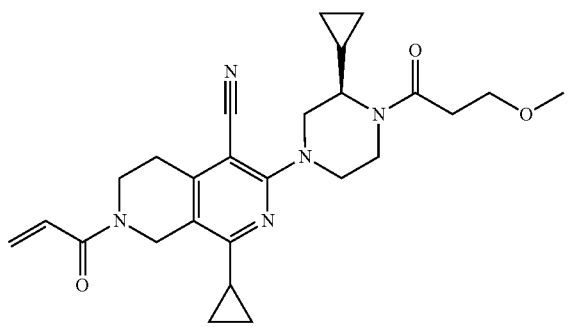 [SMILES: C=CC(=O)N1CCc2c(C#N)c(N3CCN(C(=O)CCOC)[C@H](C4CC4)C3)nc(C3CC3)c2C1] |

TABLE 4-continued

| Compound # | Structure |
|---|---|
| 486 | 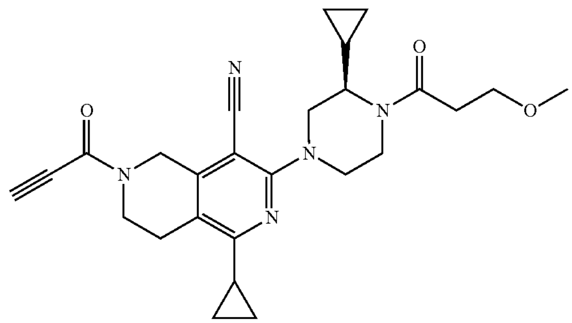 [SMILES: C#CC(=O)N1CCc2c(C3CC3)nc(N3CCN(C(=O)CCOC)[C@H](C4CC4)C3)c(C#N)c2C1] |
| 487 | 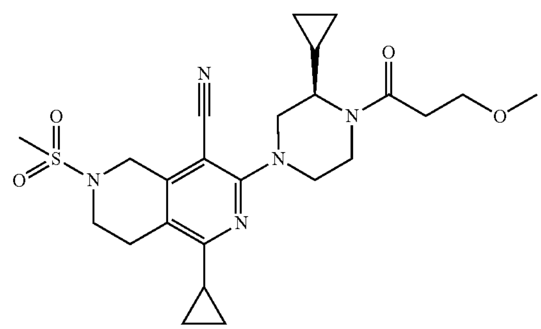 [SMILES: COCCC(=O)N1CCN(c2nc(C3CC3)c3c(c2C#N)CN(S(C)(=O)=O)CC3)C[C@H]1C1CC1] |
| 488 | 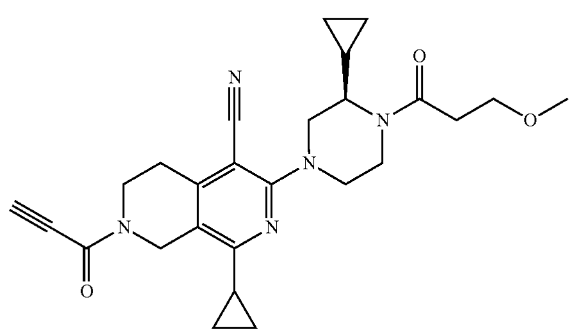 [SMILES: C#CC(=O)N1CCc2c(C#N)c(N3CCN(C(=O)CCOC)[C@H](C4CC4)C3)nc(C3CC3)c2C1] |
| 489 | 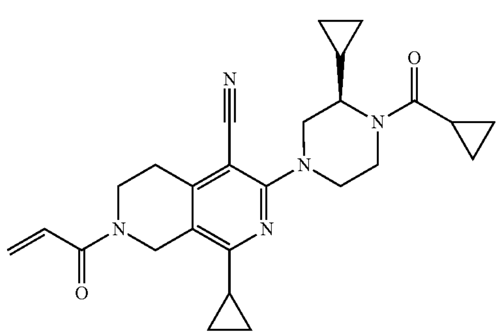 [SMILES: C=CC(=O)N1CCc2c(C#N)c(N3CCN(C(=O)C4CC4)[C@H](C4CC4)C3)nc(C3CC3)c2C1] |

TABLE 4-continued
| Compound # | Structure |
|---|---|
| 490 | 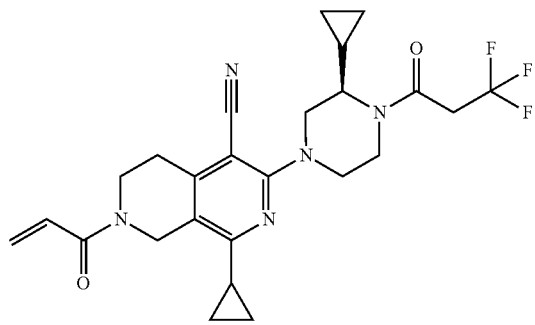 [SMILES: C=CC(=O)N1CCc2c(C#N)c(N3CCN(C(=O)CC(F)(F)F)[C@H](C4CC4)C3)nc(C3CC3)c2C1] |
| 491 | 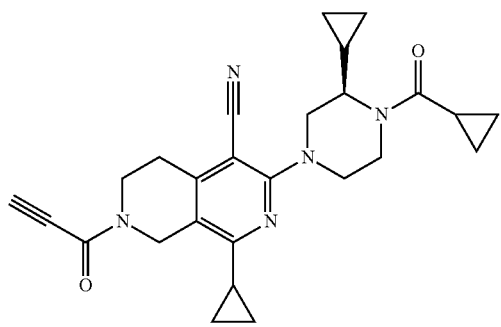 [SMILES: C#CC(=O)N1CCc2c(C#N)c(N3CCN(C(=O)C4CC4)[C@H](C4CC4)C3)nc(C3CC3)c2C1] |
| 492 | 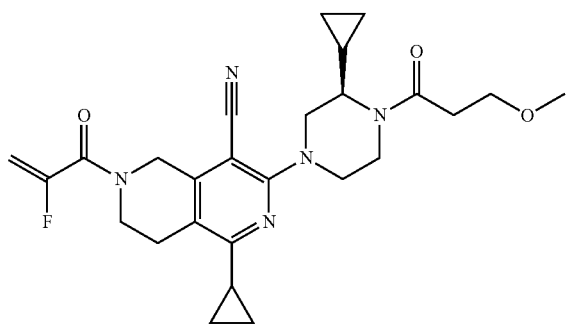 [SMILES: C=C(F)C(=O)N1CCc2c(C3CC3)nc(N3CCN(C(=O)CCOC)[C@H](C4CC4)C3)c(C#N)c2C1] |
| 493 | 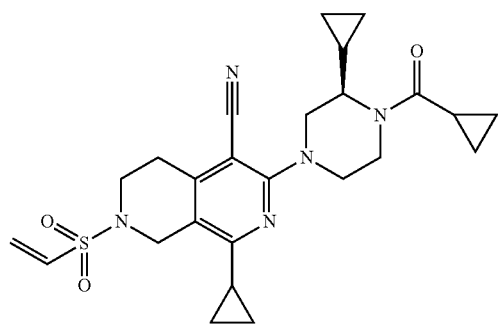 [SMILES: C=CS(=O)(=O)N1CCc2c(C#N)c(N3CCN(C(=O)C4CC4)[C@H](C4CC4)C3)nc(C3CC3)c2C1] |

TABLE 4-continued
| Compound # | Structure |
|---|---|
| 494 | 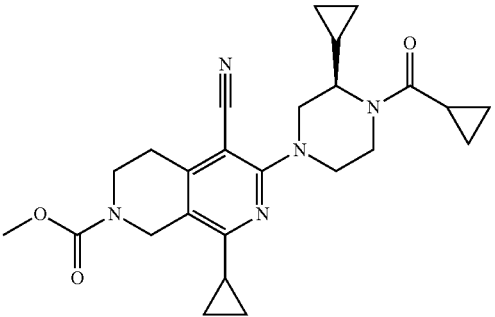 [SMILES: COC(=O)N1CCc2c(C#N)c(N3CCN(C(=O)C4CC4)[C@H](C4CC4)C3)nc(C3CC3)c2C1] |
| 495 | 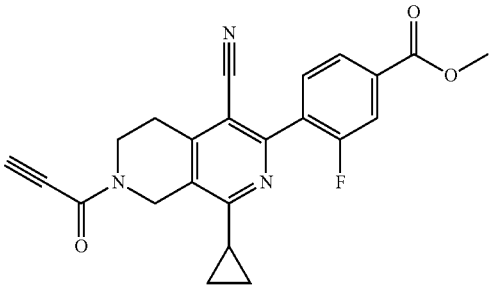 [SMILES: C#CC(=O)N1CCc2c(C#N)c(-c3ccc(C(=O)OC)cc3F)nc(C3CC3)c2C1] |
| 496 | 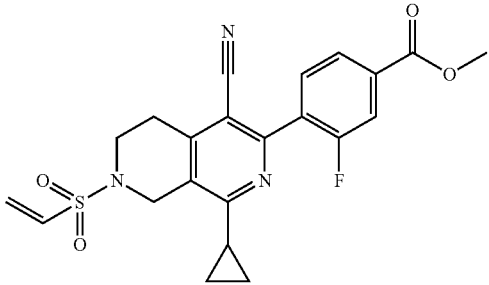 [SMILES: C=CS(=O)(=O)N1CCc2c(C#N)c(-c3ccc(C(=O)OC)cc3F)nc(C3CC3)c2C1] |
| 497 | 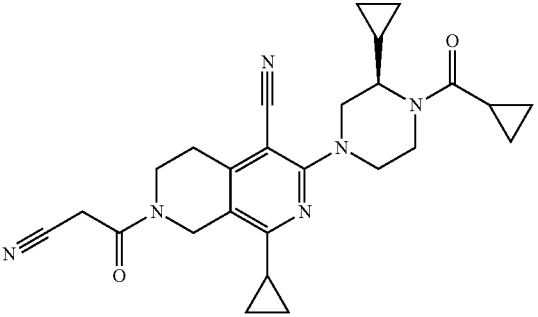 [SMILES: N#CCC(=O)N1CCc2c(C#N)c(N3CCN(C(=O)C4CC4)[C@H](C4CC4)C3)nc(C3CC3)c2C1] |
| 498 | 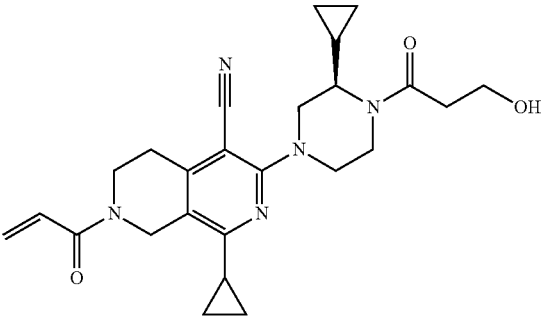 [SMILES: C=CC(=O)N1CCc2c(C#N)c(N3CCN(C(=O)CCO)[C@H](C4CC4)C3)nc(C3CC3)c2C1] |

TABLE 4-continued

| Compound # | Structure |
|---|---|
| 499 | (structure) |
| 500 | (structure) |
| 501 | (structure) |
| 502 | (structure) |
| 503 | (structure) |

The compounds of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In one embodiment, when m is 2 and two different $R^3$ groups are bound to the same carbon, the compound of Formula I is enriched for a structure or structures having a selected stereochemistry at the carbon atom that is bound to two $R^3$ groups. In one embodiment, the selected stereochemistry at that carbon atom is R. In another embodiment the selected stereochemistry at that carbon atom is S. For example, the compound is enriched in the specific stereoisomer by at least about 60%, 65%, 70%, 75%, 80%, 85%, 90%, 95%, 96%, 97%, 98%, or 99%.

The compounds of formula I may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

Unless otherwise indicated when a disclosed compound is named or depicted by a structure without specifying the stereochemistry and has one or more chiral centers, it is understood to represent all possible stereoisomers of the compound.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$^{2+}$, NHR$^{3+}$, NR$^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Structural Formula I or II or a compound described in any one of the embodiments herein, may further comprise another therapeutic agent useful for treating cancer.

Methods of Use

Provided is a method for inhibiting a mutant IDH1 activity comprising contacting a subject in need thereof a compound of Structural Formula I or II, a compound described in any one of the embodiments herein, or a pharmaceutically acceptable salt thereof. In one embodiment, the cancer to be treated is characterized by a mutant allele of IDH1 wherein the IDH1 mutation result in a new ability of the enzyme to catalyze the NAPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

Also provided are methods of treating a cancer characterized by the presence of a mutant allele of IDH1 comprising the step of administering to subject in need thereof (a) a compound of Structural Formula I or II, a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation result in a new ability of the enzyme to catalyze the NAPH-dependent reduction of α-ketoglutarate to R(−)-2-hydroxyglutarate in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132H. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation result in a new ability of the enzyme to catalyze the NAPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such activity and in particular an IDH1 R132H mutation.

In one aspect of this embodiment, the efficacy of cancer treatment is monitored by measuring the levels of 2HG in the subject. Typically levels of 2HG are measured prior to treatment, wherein an elevated level is indicative of the use of the compound of Formula I to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 µm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

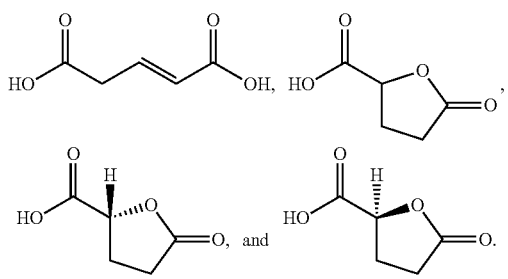

In one embodiment the cancer is a tumor wherein at least 30, 40, 50, 60, 70, 80 or 90% of the tumor cells carry an IDH1 mutation, and in particular an IDH1 R132H mutation, at the time of diagnosis or treatment.

IDH1 R132X mutations are known to occur in certain types of cancers as indicated in Table 2, below.

TABLE 2

IDH mutations associated with certain cancers

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in glioblastoma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (glioblastoma), acute myelogenous leukemia, sarcoma, melanoma, non-small cell lung cancer (NSCLC) or cholangiocarcinomas, chondrosarcoma, myelodysplastic syndromes (MDS), myeloproliferative neoplasm (MPN) or colon cancer in a patient.

Accordingly in one embodiment, the cancer is a cancer selected from any one of the cancer types listed in Table 2, and the IDH R132X mutation is one or more of the IDH1 R132X mutations listed in Table 2 for that particular cancer type.

Treatment methods described herein can additionally comprise various evaluation steps prior to and/or following treatment with a compound of Structural Formula I or II or a compound described in any one of the embodiments described herein.

In one embodiment, prior to and/or after treatment with a compound of Structural Formula I or II or a compound described in any one of the embodiments described herein, the method further comprises the step of evaluating the growth, size, weight, invasiveness, stage and/or other phenotype of the cancer.

In one embodiment, prior to and/or after treatment with a compound of formula I or I-a or a compound described in any one of the embodiments described herein, the method further comprises the step of evaluating the IDH1 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of formula I or I-a or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of this invention as part of a single dosage form (such as a composition of this invention comprising a compound of the invention and an second therapeutic agent as described above) or as separate, multiple dosage forms. Alternatively, the additional cancer therapeutic agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment. The term "co-administering" as used herein with respect to an additional cancer treatment means that the additional cancer treatment may occur prior to, consecutively with, concurrently with or following the administration of a compound of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others) and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR® (tositumomab and iodine I 131 tositumomab).

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

Abbreviations anhy.—anhydrous
aq.—aqueous
min—minute(s)
mL—milliliter
mmol—millimole(s)
mol—mole(s)
MS—mass spectrometry
NMR—nuclear magnetic resonance
TLC—thin layer chromatography
HPLC—high-performance liquid chromatography
Hz—hertz
δ—chemical shift
J—coupling constant
s—singlet
d—doublet
t—triplet
q—quartet
m—multiplet
br—broad
qd—quartet of doublets
dquin—doublet of quintets
dd—doublet of doublets
dt—doublet of triplets CHCl₃—chloroform
DCM—dichloromethane
DMF—dimethylformamide
Et₂O—diethyl ether
EtOH—ethyl alcohol
EtOAc—ethyl acetate
MeOH—methyl alcohol
MeCN—acetonitrile
PE—petroleum ether
THF—tetrahydrofuran
AcOH—acetic acid
HCl—hydrochloric acid
H₂SO₄—sulfuric acid
NH₄Cl—ammonium chloride
KOH—potassium hydroxide
NaOH—sodium hydroxide
K₂CO₃—potassium carbonate
Na₂CO₃—sodium carbonate
TFA—trifluoroacetic acid
Na₂SO₄—sodium sulfate
NaBH₄—sodium borohydride
NaHCO₃—sodium bicarbonate
LiHMDS—lithium hexamethyldisilylamide
NaHMDS—sodium hexamethyldisilylamide
LAH—lithium aluminum hydride
NaBH₄—sodium borohydride
LDA—lithium diisopropylamide
Et₃N—triethylamine
DMAP—4-(dimethylamino)pyridine
DIPEA—N,N-diisopropylethylamine
NH₄OH—ammonium hydroxide
EDCI—1-ethyl-3-(3-dimethylaminopropyl)carbodiimide
HOBt—1-hydroxybenzotriazole
HATU—O-(7-azabenzotriazol-1-yl)-N,N,N',N'-tetra-methyluronium
BINAP—2,2'-bis(diphenylphosphanyl)-1,1'-binaphthyl In the following examples, reagents were purchased from commercial sources (including Alfa, Acros, Sigma Aldrich, TCI and Shanghai Chemical Reagent Company), and used without further purification. Flash chromatography was performed on an Ez Purifier III using a column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were run with electrospray ionization (ESI) from a Waters LCT TOF Mass Spectrometer (Waters, USA). HPLC chromatographs were recorded on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%.

Example 1

Synthesis of Optionally Substituted Dimethyl-Cyclopropyl Pyranopyridine (5)

Optionally Substituted Dimethyl-cyclopropyl pyranopyridine 5 was used as a common synthetic intermediate during the preparation of compounds of Structural Formula I and II and was itself synthesized following Scheme 1, below.

Scheme 1.

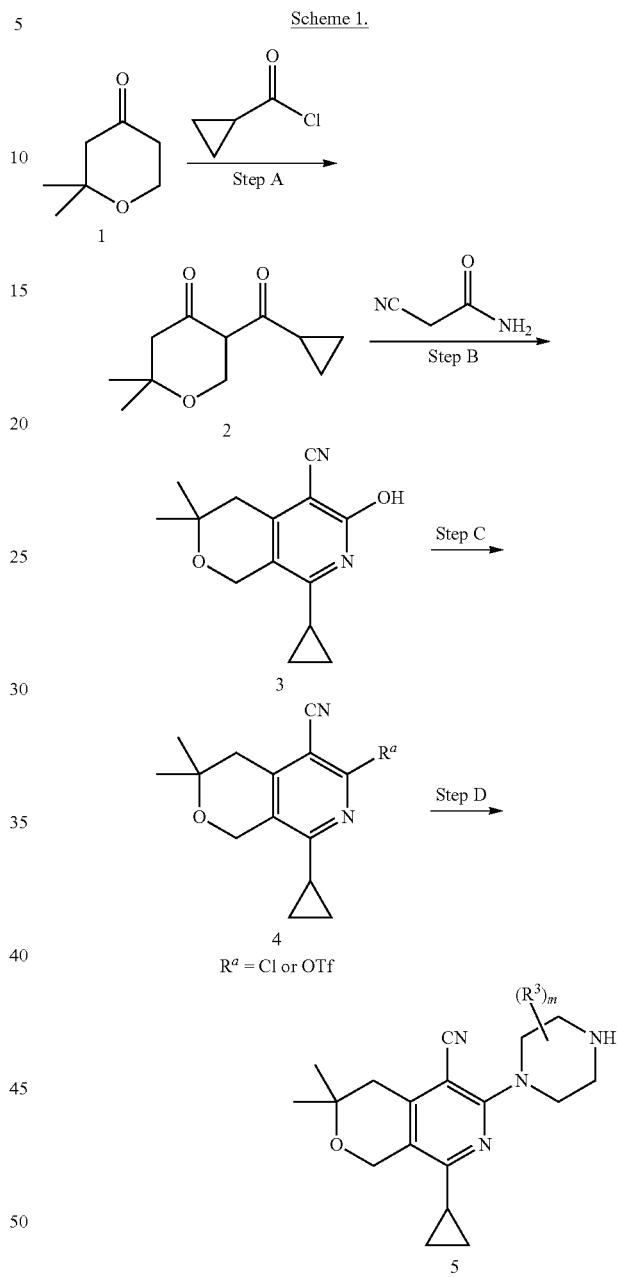

Step A: 5-(cyclopropanecarbonyl)-2,2-dimethyldihydro-2H-pyran-4(3H)-one (2)

A 500 mL three-neck round bottom flask equipped with a stirring bar was charged with 2,2-dimethyldihydro-2H-pyran-4(3H)-one (6 g, 46.8 mmol) and 120 mL of dry toluene. The solution was purged with nitrogen and cooled to 0° C. With stirring, a solution of LDA (2M soln. in THF/n-heptane, 24.5 mL, 15.6 mmol) was added dropwise, and the reaction mixture was allowed to continue to stir for 5 min at 0° C. before cyclopropanecarbonyl chloride (2.8 mL, 31.2 mmol) was added with vigorous stirring. After stirring at 0° C. for additional 20 min, the reaction mixture was quenched with 1N HCl to PH<7. After partition between H₂O and methylene chloride, the combined organic layer was then washed with brine, dried over anhy. Na₂SO₄ and concentrated in vacuo. Flash column chromatography (10% ethyl acetate/petroleum ether) afforded 6 g of crude title compound as yellowish oil. MS (ES) M+H expected 197.1, found 197.3.

Step B: 8-cyclopropyl-6-hydroxy-3,3-dimethyl-3,4-dihydro-1H-pyrano[3,4-c]pyridine-5-carbonitrile (3)

To a solution of 5-(cyclopropanecarbonyl)-2,2-dimethyl-dihydro-2H-pyran-4(3H)-one (2; 6 g, 30.6 mmol) and 2-cyanoacetamide (4.1 g, 49.0 mmol) in 70 mL of EtOH was added diethylamine (2.1 mL, 20.4 mmol). The reaction mixture was stirred at room temperature for 72 hours until LC-MS indicated the complete formation of product. The reaction mixture was then heated to reflux and enough EtOH was added to make a clear solution. After cooling back to room temperature, the product was precipitated out from EtOH solution and 3.3 g of the title compound was obtained as a white solid after vacuum filtration and air-dried. MS (ES) M+H expected 245.1, found 245. ¹H NMR (CHLOROFORM-d) δ 4.74 (s, 2H), 2.82 (s, 2H), 1.68-1.78 (m, 1H), 1.34 (s, 6H), 1.30-1.32 (m, 2H), 1.24-1.26 (m, 2H).

Step C1: 5-cyano-8-cyclopropyl-3,3-dimethyl-3,4-dihydro-1H-pyrano[3,4-c]pyridin-6-yl trifluoromethane-sulfonate (4, R$^a$=OTf)

To a 250 mL round bottom flask was charged with 8-cyclopropyl-6-hydroxy-3,3-dimethyl-3,4-dihydro-1H-pyrano[3,4-c]pyridine-5-carbonitrile (3; 3.7 g, 15.16 mmol), DMAP (185 mg, 1.52 mmol), triethylamine (2.74 mL, 19.7 mmol) and 150 mL of methylene chloride. After the reaction mixture was cooled to 0° C. in a dry ice-acetone bath, trifluoromethanesulfonic anhydride (3.3 mL, 19.7 mmol) was added dropwise via a syringe. The resulting mixture was stirred at 0° C. for 30 min before it was allowed to warm up to room temperature and stirred for additional 2 hours. After TLC indicated the complete conversion of starting material to the product, the reaction mixture was concentrated in vacuo and purified by flash column chromatography (1:10 ethyl acetate/petroleum ether) to give 4.9 g of the title compound as a white solid. ¹H NMR (CHLOROFORM-d) δ 4.91 (s, 2H), 2.88 (s, 2H), 1.73-1.84 (m, 1H), 1.34 (s, 6H), 1.23-1.27 (m, 2H), 1.17-1.22 (m, 2H).

Step C2: 6-chloro-8-cyclopropyl-3,3-dimethyl-3,4-dihydro-1H-pyrano[3,4-c]pyridine-5-carbonitrile (4, R$^a$=Cl)

A mixture of 8-cyclopropyl-6-hydroxy-3,3-dimethyl-3,4-dihydro-1H-pyrano[3,4-c]pyridine-5-carbonitrile (3; 5 g, 20.5 mmol), 20 mL of phosphoryl trichloride and one drop of DMF were heated to reflux overnight until LC-MS indicated the complete conversion to the product. After evaporation of excess of phosphoryl trichloride under reduced pressure, the residue was re-dissolved in methylene chloride and neutralized carefully with 10% aq. KOH and washed subsequently with 1N HCl and brine. The combined organic layer was dried over anhy. Na₂SO₄ and concentrated in vacuo. Flash column chromatography separation (1:10 ethyl acetate/petroleum ether) then afforded 1 g of the title compound as a yellowish solid. MS (ES) M+H expected 263.1, found 263.

Step D: (R)-8-cyclopropyl-6-(3-isopropylpiperazin-1-yl)-3,3-dimethyl-3,4-dihydro-1H-pyrano[3,4-c]pyridine-5-carbonitrile (5; R³=3-(R)-isopropyl; m=1)

To a sealed tube was charged with 4 from Step C1 (600 mg, 1.60 mmol), (R)-2-isopropylpiperazine (170 mg, 1.33 mmol), and triethylamine (0.24 mL, 1.73 mmol) in 2 mL of EtOH. The reaction mixture was heated at refluxing temperature overnight. After concentrated under reduced pressure, the reaction mixture was purified by flash column chromatography (1:10 methanol/methylene chloride) to give 428 mg of the title compound. MS (ES) M+H expected 355.2, found 355.2. ¹H NMR (CHLOROFORM-d) δ 4.84 (s, 2H), 4.33 (d, J=13.1 Hz, 1H), 4.19 (d, J=14.3 Hz, 1H), 3.47-3.55 (m, 1H), 3.35-3.47 (m, 1H), 2.94-3.21 (m, 3H), 2.77 (s, 2H), 1.98-2.14 (m, 1H), 1.64-1.77 (m, 1H), 1.31 (s, 6H), 1.14-1.21 (m, 3H), 1.08-1.14 (m, 5H), 0.98-1.07 (m, 2H).

Alternatively, (R)-8-cyclopropyl-6-(3-isopropylpiperazin-1-yl)-3,3-dimethyl-3,4-dihydro-1H-pyrano[3,4-c]pyridine-5-carbonitrile was formed combining together 4 from Step C1 (200 mg, 0.53 mmol), (R)-2-isopropylpiperazine (135 mg, 1.06 mmol), and triethylamine (0.2 mL, 1.59 mmol) suspended in 0.8 mL of acetonitrile and subjecting the mixture to microwave reaction at 175° C. for 45 min. After the reaction mixture was concentrated in vacuo, the residue was purified by flash column chromatography to give 189 mg of the title compound as yellowish oil.

Example 2

Preparation of Compounds of Formula II

Various compounds of Formula II, wherein each R¹ is methyl and R² is cyclopropyl were prepared from intermediate 5 according to Scheme 2, below.

Scheme 2:

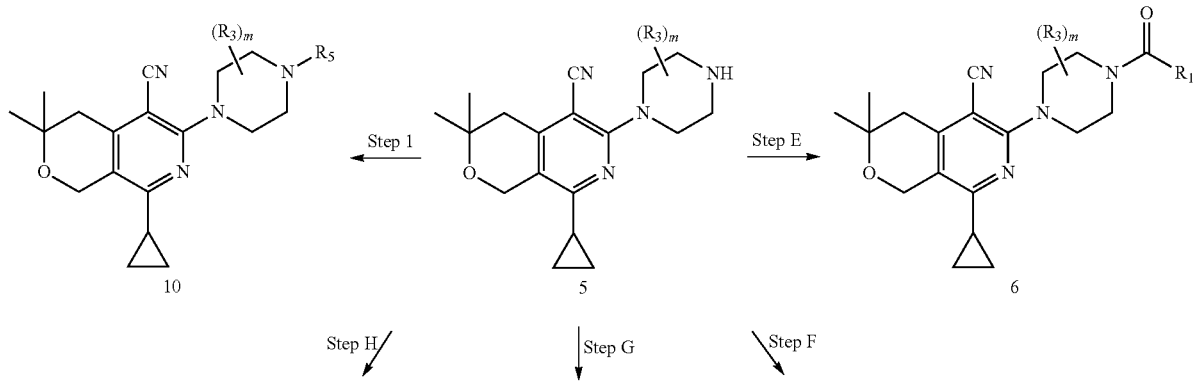

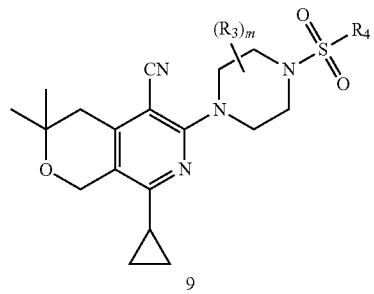 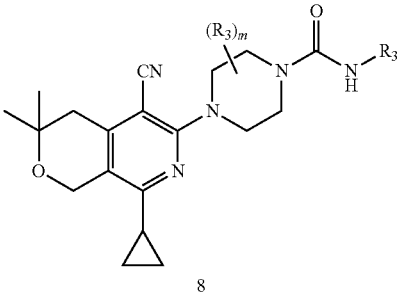 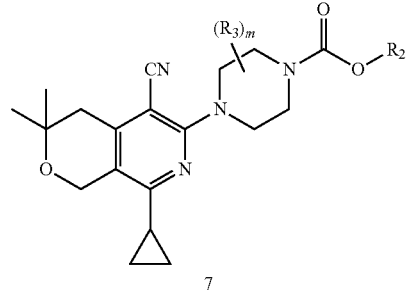

9  8  7

The final step(s) in the synthesis of the compounds of this invention are described in detail below. Step E1: (R)-8-cyclopropyl-6-(4-(furan-3-carbonyl)-3-isopropylpiperazin-1-yl)-3,3-dimethyl-3,4-dihydro-1H-pyrano[3,4-c]pyridine-5-carbonitrile (Compound 180). In a 5-mL of amber glass vial was placed 5 (30 mg, 0.08 mmol), furan-3-carboxylic acid (38 mg, 0.34 mmol), EDCI (68.8 mg, 0.36 mmol), HOBt (48.6 mg, 0.36 mmol), triethylamine (36.8 mg, 0.36 mmol) and 1 mL of methylene chloride. The resulting reaction mixture was stirred at room temperature overnight. The mixture was quenched with 1 N HCl aqueous solution, extracted with EtOAc three times. The combined organic layer was washed with satd. NaHCO$_3$ and brine, dried over anhy. Na$_2$SO$_4$, and concentrated in vacuo. The crude product was purified by preparative TLC (DCM: acetone/70:1) to afford 29 mg of the title compound as a white solid. MS (ES) M+H expected 449.3, found 449.1. $^1$H NMR (CHLOROFORM-d) δ 7.71 (br. s., 1H), 7.45 (t, J=1.8 Hz, 1H), 6.55 (s, 1H), 4.75-4.91 (m, 2H), 3.49-4.48 (m, 5H), 2.93-3.11 (m, 2H), 2.77 (s, 2H), 2.14-2.34 (m, 1H), 1.68-1.77 (m, 1H), 1.32 (d, J=2.0 Hz, 6H), 1.00-1.16 (m, 6H), 0.81-0.94 (m, 4H).

Step E2: (R)-6-(4-(2-chloroacetyl)-3-isopropylpiperazin-1-yl)-8-cyclopropyl-3,3-dimethyl-3,4-dihydro-1H-pyrano[3,4-c]pyridine-5-carbonitrile (Compound 317)

To a solution of 5 (30 mg, 0.08 mmol) in 1.5 mL of methylene chloride and triethylamine (0.02 mL, 0.16 mmol) was added chloroacetyl chloride (2 drops, 0.16 mmol) slowly. The resulting reaction mixture was allowed to stir at room temperature overnight. The reaction mixture was then quenched with brine and separated. The organic layer was dried over anhy. Na$_2$SO$_4$ and concentrated in vacuo. The crude product was purified by preparative TLC (DCM: acetone/70:1) to afford 23 mg of the title compound as yellowish oil. MS (ES) M+H expected 431.2, found 431.0. $^1$H NMR (CHLOROFORM-d) δ 4.77-4.89 (m, 2H), 4.54-4.57 (m, 0.5H), 4.04-4.38 (m, 4.5H), 3.75 (d, J=13.6 Hz, 0.5H), 3.55 (td, J=12.9, 3.1 Hz, 0.5H), 4.42-4.45 (m, 0.5H), 2.95-3.17 (m, 2.5H), 2.77 (s, 2H), 2.10-2.30 (m, 1H), 1.67-1.77 (m, 1H), 1.32 (d, J=2.5 Hz, 6H), 1.07-1.19 (m, 2H), 0.98-1.06 (m, 5H), 0.81-0.93 (m, 3H).

Step E3: (R)-6-(4-(2-(1H-pyrazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 325)

To a solution of 1H-pyrazole (10 mg, 0.14 mmol) and K$_2$CO$_3$ (20 mg, 0.14 mmol, in some cases, Cs$_2$CO$_3$ was used as alternative base) in 1 mL of MeCN was added 5 (30 mg, 0.07 mmol). The resulting reaction mixture was stirred at room temperature overnight. After dilution with methylene chloride, the mixture was washed with brine. The organic layer was dried over anhy. Na$_2$SO$_4$ and concentrated in vacuo. The crude product was purified by preparative TLC separation (DCM: acetone/70:1) to afford 10 mg of the title compound as a white solid. MS (ES) M+H expected 463.3, found 463.1. $^1$H NMR (CHLOROFORM-d) δ 7.45-7.63 (m, 2H), 6.33 (d, J=2.0 Hz, 1H), 4.90-5.20 (m, 2H), 4.74-4.89 (m, 2H), 4.55-4.58 (m, 0.5H), 4.22-4.40 (m, 1.5H), 4.07-4.21 (m, 1H), 3.88 (d, J=13.6 Hz, 0.5H), 3.59-3.61 (m, 0.5H), 3.36-3.49 (m, 0.5H), 2.81-3.10 (m, 2.5H), 2.76 (s, 2H), 2.07-2.36 (m, 1H), 1.64-1.79 (m, 1H), 1.31 (d, J=2.8 Hz, 6H), 0.94-1.19 (m, 7H), 0.86-0.93 (m, 1.5H), 0.74-0.84 (m, 1.5H).

Step E4: (R)-8-cyclopropyl-6-(3-isopropyl-4-(2-methoxyacetyl)piperazin-1-yl)-3,3-dimethyl-3,4-dihydro-1H-pyrano[3,4-c]pyridine-5-carbonitrile (Compound 347)

To a 1.5 mL MeCN solution of 5 (30 mg, 0.07 mmol) was added MeOH (0.3 mL) and DIPEA (0.04 mL, 0.21 mmol). The resulting reaction mixture was heated at 65° C. overnight. After dilution with 5 mL of methylene chloride, the reaction mixture was washed with brine. The organic layer was then dried over anhy. Na$_2$SO$_4$ and concentrated in vacuo. The crude product was purified by preparative TLC (DCM: acetone/60:1) to afford 14 mg of the title compound as colorless oil. MS (ES) M+H expected 427.6, found 427.3. $^1$H NMR (CHLOROFORM-d) δ 4.77-4.90 (m, 2H), 4.56-4.58 (m, 0.5H), 3.99-4.36 (m, 4.5H), 3.79 (d, J=13.6 Hz, 0.5H), 3.37-3.52 (m, 4H), 2.91-3.11 (m, 2.5H), 2.70-2.82 (m, 2H), 2.08-2.33 (m, 1H), 1.64-1.77 (m, 1H), 1.31 (d, J=2.5 Hz, 6H), 0.96-1.19 (m, 7H), 0.80-0.93 (m, 3H).

Step E5: (R)-8-cyclopropyl-6-(4-(2-(cyclopropylamino)acetyl)-3-isopropylpiperazin-1-yl)-3,3-dimethyl-3,4-dihydro-1H-pyrano[3,4-c]pyridine-5-carbonitrile (Compound 372)

To a 1.5 mL MeCN solution of 5 (30 mg, 0.07 mmol) was added cyclopropyl amine (12 mg, 0.21 mmol). The resulting reaction mixture was heated at 65° C. overnight. After dilution with 5 mL of methylene chloride, the reaction mixture was washed with brine. The organic layer was then dried over anhy. Na$_2$SO$_4$ and concentrated in vacuo. The crude product was purified by preparative TLC (DCM: acetone/30:1) to afford 11 mg of the title compound as colorless oil. MS (ES) M+H expected 452.3, found 452.4. $^1$H NMR (CHLOROFORM-d) δ 4.78-4.90 (m, 2H), 4.52-

4.74 (m, 0.5H), 4.28-4.45 (m, 1.5H), 4.11-4.23 (m, 1H), 3.49-3.71 (m, 2.5H), 3.30-3.49 (m, 1H), 2.93-3.11 (m, 3H), 2.72-2.80 (m, 2H), 2.20-2.33 (m, 1.5H), 1.98-2.18 (m, 1H), 1.67-1.75 (m, 1H), 1.31 (d, J=2.5 Hz, 7H), 1.06-1.17 (m, 2H), 0.97-1.05 (m, 5H), 0.86-0.93 (m, 1.5H), 0.82 (d, J=6.8 Hz, 1.5H), 0.43-0.56 (m, 3H).

Step E6: (R)-6-(4-(2-(1H-indazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 405)

In a sealed tube was placed a mixture of 1H-indazole (25 mg, 0.21 mmol) and $Cs_2CO_3$ (68 mg, 0.21 mmol, in some cases, $K_2CO_3$ was used as alternative base), 5 (30 mg, 0.07 mmol), and 1.5 mL of MeCN. The resulting reaction mixture was stirred at 60° C. overnight. After dilution with methylene chloride, the mixture was washed with brine. The organic layer was dried over anhy. $Na_2SO_4$ and concentrated in vacuo. The crude product was purified by preparative TLC (DCM: acetone/70:1) to afford 15 mg of the title compound as colorless oil. MS (ES) M+H expected 513.3, found 513.2. $^1$H NMR (CHLOROFORM-d) δ8.06 (d, J=6.3 Hz, 1H), 7.74 (dd, J=8.2, 4.1 Hz, 1H), 7.34-7.57 (m, 2H), 7.11-7.22 (m, 1H), 5.15-5.45 (m, 2H), 4.81 (br. s., 2H), 4.52-4.56 (m, 0.5H), 4.19-4.38 (m, 1.5H), 3.97-4.18 (m, 1.5H), 3.71-4.73 (m, 0.5H), 3.38-4.45 (m, 0.5H), 2.98-3.06 (m, 0.5H), 2.82-2.95 (m, 1H), 2.63-2.80 (m, 3H), 2.04-2.32 (m, 1H), 1.65-1.74 (m, 1H), 1.29-1.33 (m, 6H), 0.87-1.17 (m, 8.5H), 0.74 (d, J=6.8 Hz, 1.5H).

Step F1: (R)-methyl 4-(5-cyano-8-cyclopropyl-3,3-dimethyl-3,4-dihydro-1H-pyrano[3,4-c]pyridin-6-yl)-2-isopropylpiperazine-1-carboxylate (Compound 346)

To a solution of 5 (30 mg, 0.08 mmol) in 1.5 mL of methylene chloride was added triethylamine (0.02 mL, 0.16 mmol) and methyl chloroformate (15 mg, 0.16 mmol). The resulting reaction mixture was allowed to stir at room temperature overnight. After dilution with DCM, the mixture was washed with brine. The organic layer was dried over anhy. $Na_2SO_4$ and concentrated in vacuo. The crude product was purified by preparative TLC (DCM: acetone/70:1) to afford 12 mg of the title compound as yellowish oil. MS (ES) M+H expected 413.3, found 413.2. $^1$H NMR (CHLOROFORM-d) δ 4.74-4.89 (m, 2H), 4.28 (d, J=13.3 Hz, 1H), 4.13 (d, J=12.3 Hz, 2H), 3.76-3.86 (m, 1H), 3.69-3.74 (m, 3H), 3.18 (t, J=11.8 Hz, 1H), 2.96-3.09 (m, 2H), 2.76 (s, 2H), 2.11 (dquin, J=10.3, 6.6 Hz, 1H), 1.65-1.74 (m, 1H), 1.31 (d, J=2.3 Hz, 6H), 0.93-1.18 (m, 7H), 0.82-0.90 (m, 3H).

Step F2: (R)-2-hydroxyethyl 4-(5-cyano-8-cyclopropyl-3,3-dimethyl-3,4-dihydro-1H-pyrano[3,4-c]pyridin-6-yl)-2-isopropylpiperazine-1-carboxylate (Compound 368)

At 0° C., to a solution of 5 (30 mg, 0.08 mmol) in 2 mL of acetonitrile was added pyridine (12.7 mg, 0.16 mmol) followed by triphosgene (15 mg, 0.16 mmol). The resulting reaction mixture was stirred at 0° C. for 5 min before additional of excess amount of ethane-1,2-diol was added. The resulting reaction mixture was warmed up to room temperature and then heated at 60° C. overnight. After dilution with methylene chloride, the reaction mixture was washed with brine and the organic layer was dried over anhy. $Na_2SO_4$ and concentrated in vacuo. The crude product was purified by preparative TLC (DCM/acetone: 10:1) to afford 16 mg of the title compound as yellowish oil. MS (ES) M+H expected 443.3, found 443.4. $^1$H NMR (CHLOROFORM-d) δ 4.76-4.90 (m, 2H), 4.22-4.39 (m, 3H), 4.00-4.21 (m, 2H), 3.73-3.96 (m, 3H), 3.21 (br. s., 1H), 2.99-3.11 (m, 2H), 2.66-2.84 (m, 2H), 2.09-2.20 (m, 1H), 1.66-1.76 (m, 1H), 1.31 (d, J=2.8 Hz, 6H), 1.06-1.17 (m, 2H), 0.94-1.05 (m, 5H), 0.82-0.92 (m, 3H).

Step F3: (R)-tert-butyl 4-(5-cyano-8-cyclopropyl-3,3-dimethyl-3,4-dihydro-1H-pyrano[3,4-c]pyridin-6-yl)-2-isopropylpiperazine-1-carboxylate (Compound 306)

To a solution of 5 (30 mg, 0.08 mmol) in 1.5 mL of methylene chloride was added triethylamine (0.02 mL, 0.16 mmol) and di-tert-butyl dicarbonate (35 mg, 0.16 mmol). The resulting reaction mixture was allowed to stir at room temperature overnight. The reaction mixture was diluted with DCM, washed with brine. The organic layer was dried over anhy. $Na_2SO_4$ and concentrated in vacuo. The crude product was purified by preparative TLC (DCM/acetone: 70:1) to afford 18 mg of the title compound as colorless oil. MS (ES) M+H expected 455.3, found 399.1. $^1$H NMR (CHLOROFORM-d) δ 4.75-4.88 (m, 2H), 4.29 (d, J=12.8 Hz, 1H), 3.95-4.19 (m, 2H), 3.68-3.88 (m, 1H), 2.94-3.19 (m, 3H), 2.71-2.80 (m, 2H), 2.09 (dq, J=17.1, 6.6 Hz, 1H), 1.66-1.76 (m, 1H), 1.47 (s, 9H), 1.29-1.35 (m, 6H), 1.06-1.20 (m, 2H), 0.92-1.03 (m, 5H), 0.82-0.89 (m, 3H).

Step G1: (R)—N-allyl-4-(5-cyano-8-cyclopropyl-3,3-dimethyl-3,4-dihydro-1H-pyrano[3,4-c]pyridin-6-yl)-2-isopropylpiperazine-1-carboxamide (Compound 304)

To a solution of 5 (100 mg, 0.282 mmol) in 3 mL of methylene chloride was added allyl isocyanate (35.2 mg, 0.424 mmol). The resulting reaction mixture was stirred at room temperature overnight. Ethane-1,2-diamine was added to the reaction mixture to destroy excess of isocyanate by stirring at room temperature for 5 min. The reaction mixture was diluted with DCM and then washed with brine. The organic layer was dried over anhy. $Na_2SO_4$ and concentrated in vacuo. The crude product was purified by preparative TLC (DCM/acetone: 60:1) to afford 41.4 mg of the title compound as a white solid. MS (ES) M+H expected 438.3, found 438.3. $^1$H NMR (CHLOROFORM-d) δ 5.82-5.98 (m, 1H), 5.07-5.24 (m, 2H), 4.74-4.90 (m, 2H), 4.43 (br. s., 1H), 4.24 (d, J=13.1 Hz, 1H), 4.12 (d, J=11.5 Hz, 1H), 3.81-4.02 (m, 3H), 3.68 (br. s., 1H), 3.04-3.34 (m, 3H), 2.71-2.83 (m, 2H), 2.12-2.22 (m, 1H), 1.69 (td, J=8.0, 3.9 Hz, 1H), 1.28-1.37 (m, 6H), 0.94-1.19 (m, 7H), 0.90 (d, J=6.8 Hz, 3H).

Step G2: (R)-4-(5-cyano-8-cyclopropyl-3,3-dimethyl-3,4-dihydro-1H-pyrano[3,4-c]pyridin-6-yl)-2-isopropyl-N-propylpiperazine-1-carboxamide (Compound 350)

At 0° C., to a solution of 5 (30 mg, 0.08 mmol) in 3 mL of methylene chloride was added triethylamine (0.03 mL, 0.16 mmol) followed by triphosgene (47 mg, 0.16 mmol). After stirred for 5 min, 0.5 mL of propyl amine was added into the reaction mixture slowly. After additional stirring at 0° C. for 30 min, the reaction mixture was warmed up to room temperature and stirred overnight. The reaction mixture was diluted with DCM and then washed with brine. The organic layer was dried over anhy. $Na_2SO_4$ and concentrated in vacuo. The crude product was purified by preparative TLC (DCM/acetone: 40:1) to afford 20 mg of the title compound as colorless oil. MS (ES) M+H expected 440.3, found 440.3. $^1$H NMR (CHLOROFORM-d) δ 4.75-4.89 (m, 2H), 4.39 (br. s., 1H), 4.23 (d, J=13.3 Hz, 1H), 4.12 (d, J=11.8 Hz, 1H), 3.92 (d, J=12.8 Hz, 1H), 3.64 (d, J=9.5 Hz, 1H), 3.04-3.30 (m, 5H), 2.70-2.80 (m, 2H), 2.10-2.19 (m, 1H), 1.65-1.74 (m, 1H), 1.53 (sxt, J=7.3 Hz, 2H), 1.31 (d, J=2.5 Hz, 6H), 1.06-1.17 (m, 2H), 0.96-1.03 (m, 5H), 0.86-0.95 (m, 6H).

Step H: (R)-8-cyclopropyl-6-(4-(ethylsulfonyl)-3-isopropylpiperazin-1-yl)-3,3-dimethyl-3,4-dihydro-1H-pyrano[3,4-c]pyridine-5-carbonitrile (Compound 391)

To a solution of 5 (30 mg, 0.08 mmol) in 1.5 mL of methylene chloride was added triethylamine (0.02 mL, 0.16 mmol) and ethanesulfonyl chloride (20 mg, 0.16 mmol). The resulting reaction mixture was stirred at room temperature overnight. The reaction mixture was diluted with DCM and then washed with brine. The organic layer was dried over anhy. $Na_2SO_4$ and concentrated in vacuo. The crude product was purified by preparative TLC (DCM/acetone: 70:1) to afford 11 mg of the title compound as colorless oil. MS (ES) M+H expected 447.2, found 447.1. $^1$H NMR (CHLOROFORM-d) δ 4.75-4.89 (m, 2H), 4.31 (d, J=13.6 Hz, 1H), 4.04-4.18 (m, 1H), 3.73 (dt, J=14.2, 1.5 Hz, 1H), 3.51 (d, J=10.0 Hz, 1H), 3.28-3.43 (m, 1H), 2.95-3.17 (m, 4H), 2.76 (s, 2H), 2.11-2.27 (m, 1H), 1.65-1.75 (m, 1H), 1.39 (t, J=7.4 Hz, 3H), 1.28-1.35 (m, 6H), 1.05-1.17 (m, 2H), 0.92-1.03 (m, 8H).

Step 11-1: (R)-8-cyclopropyl-6-(4-(2-hydroxyethyl)-3-isopropylpiperazin-1-yl)-3,3-dimethyl-3,4-dihydro-1H-pyrano[3,4-c]pyridine-5-carbonitrile (Compound 420)

In a 20 mL sealed tube was placed 5 (200 mg, 0.565 mmol), 3-bromopropan-1-ol (157.1 mg, 1.13 mmol), and $K_2CO_3$ (171.5 mg, 1.243 mmol), and 5 mL of MeCN. The reaction mixture was subjected to microwave reaction at 175° C. for 30 min. After the solvent was evaporated, the residue was dissolved in methylene chloride and washed with brine. The organic layer was dried over anhy. $Na_2SO_4$, and concentrated in vacuo. The crude product was purified by flash column chromatography (DCM/acetone: 4:1) to afford 170 mg of the title compound as colorless oil. MS (ES) M+H expected 412.3, found 413.1. $^1$H NMR (CHLOROFORM-d) δ 4.75-4.89 (m, 2H), 4.21-4.34 (m, 1H), 4.09-4.18 (m, 1H), 3.97-4.05 (m, 1H), 3.79-3.88 (m, 2H), 3.33 (d, J=12.0 Hz, 1H), 3.08-3.25 (m, 2H), 2.84-3.02 (m, 1H), 2.69-2.81 (m, 2H), 2.41 (d, J=12.5 Hz, 1H), 2.20-2.36 (m, 3H), 1.95-2.09 (m, 1H), 1.65-1.73 (m, 1H), 1.31 (s, 6H), 0.94-1.18 (m, 10H).

Step 11-2: (R)-2-(4-(5-cyano-8-cyclopropyl-3,3-dimethyl-3,4-dihydro-1H-pyrano[3,4-c]pyridin-6-yl)-2-isopropylpiperazin-1-yl)ethyl acetate (Compound 322)

To a solution of Compound 420 (30 mg, 0.073 mmol) in 1.5 mL of methylene chloride was added triethylamine (0.02 mL, 0.15 mmol) and acetyl chloride (11.2 mg, 0.15 mmol). The resulting reaction mixture was stirred at room temperature overnight. The reaction mixture was diluted with DCM and then washed with brine. The organic layer was dried over anhy. $Na_2SO_4$ and concentrated in vacuo. The crude product was purified by preparative TLC (DCM/acetone: 10:1) to afford 17 mg of the title compound as colorless oil. MS (ES) M+H expected 455.3, found 455.3. $^1$H NMR (CHLOROFORM-d) δ 4.72-4.89 (m, 2H), 4.07-4.18 (m, 3H), 4.03 (dd, J=12.8, 2.3 Hz, 1H), 3.15 (t, J=10.0 Hz, 1H), 2.94-3.03 (m, 1H), 2.89 (t, J=9.9 Hz, 2H), 2.71-2.78 (m, 2H), 2.35-2.48 (m, 2H), 2.24-2.32 (m, 1H), 2.10-2.20 (m, 1H), 2.06 (s, 3H), 1.81 (d, J=6.0 Hz, 2H), 1.65-1.73 (m, 1H), 1.31 (s, 6H), 1.10-1.19 (m, 2H), 1.03 (d, J=6.8 Hz, 3H), 0.99 (dd, J=7.9, 1.9 Hz, 2H), 0.87-0.94 (m, 3H).

Step 12: (R)-methyl 2-(4-(5-cyano-8-cyclopropyl-3,3-dimethyl-3,4-dihydro-1H-pyrano[3,4-c]pyridin-6-yl)-2-isopropylpiperazin-1-yl)acetate (Compound 397)

To a solution of 5 (30 mg, 0.073 mmol) in 1.5 mL of acetonitrile and $K_2CO_3$ (33 mg, 0.24 mmol) was added methyl 2-bromoacetate (37 mg, 0.24 mmol) and the resulting reaction mixture was stirred at room temperature overnight. The reaction mixture was diluted with DCM and then washed with brine. The organic layer was dried over anhy. $Na_2SO_4$ and concentrated in vacuo. The crude product was purified by preparative TLC (DCM/acetone: 70:1) to afford 15 mg of the title compound as colorless oil. MS (ES) M+H expected 427.3, found 427.4. $^1$H NMR (CHLOROFORM-d) δ 4.75-4.89 (m, 2H), 4.20 (d, J=12.5 Hz, 1H), 4.08 (dd, J=12.9, 2.4 Hz, 1H), 3.71 (s, 3H), 3.34-3.58 (m, 2H), 3.17 (br. s., 1H), 2.82-3.01 (m, 3H), 2.75 (s, 2H), 2.69 (d, J=10.3 Hz, 1H), 2.02-2.15 (m, 1H), 1.65-1.74 (m, 1H), 1.31 (s, 6H), 1.09-1.16 (m, 2H), 1.03-1.08 (m, 3H), 0.96-1.01 (m, 2H), 0.89-0.96 (m, 3H).

Example 3

Preparation of 8-substituted-6-hydroxy-3,4-dihydro-1H-pyrano[3,4-c]pyridine-5-carbonitrile Intermediates Various 8-substituted-6-hydroxy-3,4-dihydro-1H-pyrano[3,4-c]pyridine-5-carbonitrile Intermediates of the general formula

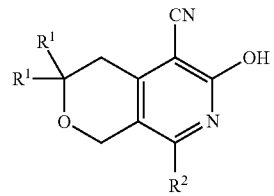

were prepared as described below. These intermediates were used as a substitute for 8-cyclopropyl-6-hydroxy-3,3-dimethyl-3,4-dihydro-1H-pyrano[3,4-c]pyridine-5-carbonitrile (3) in Scheme 1 to produce additional compounds of Formula I and II.

6-hydroxy-8-isopropyl-3,3-dimethyl-3,4-dihydro-1H-pyrano[3,4-c]pyridine-5-carbonitrile

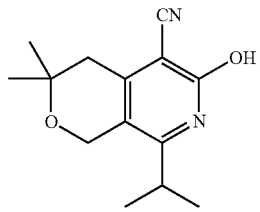 [SMILES: CC(C)c1nc(O)c(C#N)c2c1COC(C)(C)C2]

was prepared from isobutyric acid chloride and 2,2-dimethyldihydro-2H-pyran-4(3H)-one according to the methods described in Example 1, Steps A and B. MS (ES) M+H expected 247.1, found 247.0. $^1$H NMR (CHLOROFORM-d) δ4.64 (s, 2H), 2.89 (quin, J=7.0 Hz, 1H), 2.84 (s, 2H), 1.38-1.45 (m, 6H), 1.33 (s, 6H).

8-ethyl-6-hydroxy-3,3-dimethyl-3,4-dihydro-1H-pyrano[3,4-c]pyridine-5-carbonitrile

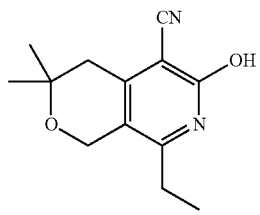 [SMILES: CCc1nc(O)c(C#N)c2c1COC(C)(C)C2]

was prepared from propionyl chloride and 2,2-dimethyldihydro-2H-pyran-4(3H)-one according to the methods described in the experimental procedures of dimethyl-cyclopropyl pyranopyridine (Step A and B). MS (ES) M+H expected 233.1, found 233.1. 6-hydroxy-3,3-dimethyl-8-(1-methylcyclopropyl)-3,4-dihydro-1H-pyrano[3,4-c]pyridine-5-carbonitrile was prepared from 1-methylcyclopropanecarbonyl chloride and 2,2-dimethyldihydro-2H-pyran-4(3H)-one according to the methods described in Example 1, Steps A and B. MS (ES) M+H expected 259.1, found 259.1. $^1$H NMR (CHLOROFORM-d) δ4.73 (s, 2H), 2.81 (s, 2H), 1.34 (s, 3H), 1.31 (s, 6H), 0.83-0.98 (m, 4H).

8-cyclobutyl-6-hydroxy-3,3-dimethyl-3,4-dihydro-1H-pyrano[3,4-c]pyridine-5-carbonitrile

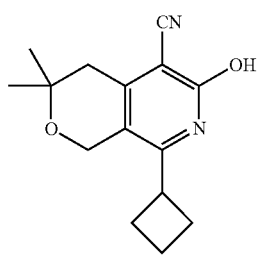 [SMILES: CC1(C)Cc2c(C#N)c(O)nc(C3CCC3)c2CO1]

was prepared from cyclobutanecarbonyl chloride and 2,2-dimethyldihydro-2H-pyran-4(3H)-one according to the methods described in Example 1, Steps A and B. MS (ES) M+H expected 259.1, found 259.2. $^1$H NMR (CHLOROFORM-d) δ 4.54 (s, 2H), 3.43-3.55 (m, 1H), 2.80 (s, 2H), 2.46-2.62 (m, 2H), 2.30-2.42 (m, 2H), 2.03-2.18 (m, 2H), 1.30 (s, 6H).

8-cyclopentyl-6-hydroxy-3,3-dimethyl-3,4-dihydro-1H-pyrano[3,4-c]pyridine-5-carbonitrile

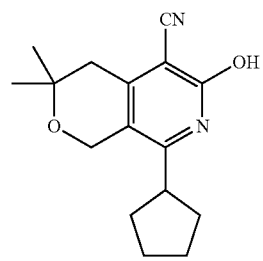 [SMILES: CC1(C)Cc2c(C#N)c(O)nc(C3CCCC3)c2CO1]

was prepared from cyclopentanecarbonyl chloride and 2,2-dimethyldihydro-2H-pyran-4(3H)-one according to the methods described in Example 1, Steps A and B. MS (ES) M+H expected 273.1, found 273.1.

8-cyclohexyl-6-hydroxy-3,3-dimethyl-3,4-dihydro-1H-pyrano[3,4-c]pyridine-5-carbonitrile

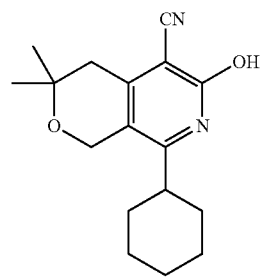 [SMILES: CC1(C)Cc2c(C#N)c(O)nc(C3CCCCC3)c2CO1]

was prepared from cyclohexanecarbonyl chloride and 2,2-dimethyldihydro-2H-pyran-4(3H)-one according to the methods described in Example 1, Steps A and B. MS (ES) M+H expected 287.2, found 287.0. $^1$H NMR (CHLOROFORM-d) δ 4.64 (s, 2H), 2.84 (s, 2H), 2.42-2.57 (m, 1H), 1.86-2.02 (m, 4H), 1.80 (d, J=13.3 Hz, 1H), 1.71 (d, J=12.0 Hz, 2H), 1.54-1.65 (m, 1H), 1.34-1.41 (m, 2H), 1.33 (s, 6H). 8-(3-fluorophenyl)-6-hydroxy-3,3-dimethyl-3,4-dihydro-1H-pyrano[3,4-c]pyridine-5-carbonitrile.

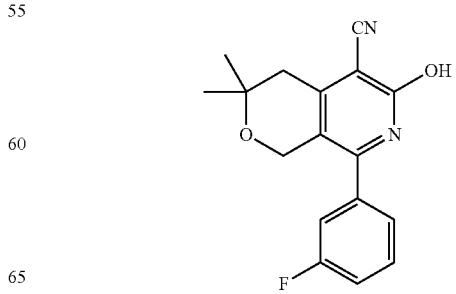

was prepared from 3-fluorobenzoyl chloride and 2,2-dimethyldihydro-2H-pyran-4(3H)-one according to the methods described in Example 1, Steps A and B. MS (ES) M+H expected 299.1, found 299.0.

8-cyclohexyl-6-hydroxy-3,4-dihydro-1H-pyrano[3,4-c]pyridine-5-carbonitrile

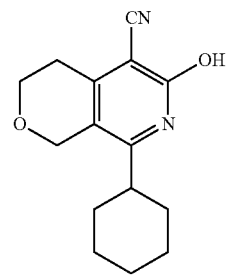 [SMILES: N#Cc1c(O)nc(C2CCCCC2)c2c1CCOC2]

was prepared from cyclohexanecarbonyl chloride and dihydro-2H-pyran-4(3H)-one according to the methods described in Example 1, Steps A and B. MS (ES) M+H expected 259.1, found 258.9. $^1$H NMR (CHLOROFORM-d) δ12.97 (br. s., 1H), 4.63 (s, 2H), 3.94 (t, J=5.8 Hz, 2H), 2.99 (t, J=5.8 Hz, 2H), 2.31-2.54 (m, 1H), 1.87-2.04 (m, 4H), 1.79 (d, J=13.1 Hz, 1H), 1.70 (d, J=11.0 Hz, 2H), 1.54-1.66 (m, 1H), 1.24-1.43 (m, 2H). 8-cyclopentyl-6-hydroxy-3,4-dihydro-1H-pyrano[3,4-c]pyridine-5-carbonitrile.

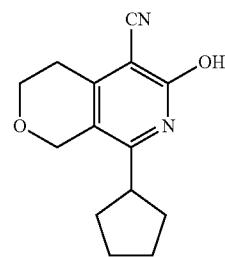 [SMILES: N#Cc1c(O)nc(C2CCCC2)c2c1CCOC2]

was prepared from cyclopentanecarbonyl chloride and dihydro-2H-pyran-4(3H)-one according to the methods described in Example 1, Steps A and B. MS (ES) M+H expected 245.1, found 245.1. $^1$H NMR (CHLOROFORM-d) δ 4.61-4.68 (m, 2H), 3.90-3.98 (m, 2H), 2.98 (t, J=5.8 Hz, 2H), 2.79-2.91 (m, 1H), 2.10-2.19 (m, 2H), 1.96-2.06 (m, 2H), 1.86-1.95 (m, 2H), 1.78-1.85 (m, 2H).

6-hydroxy-8-isopropyl-3,4-dihydro-1H-pyrano[3,4-c]pyridine-5-carbonitrile

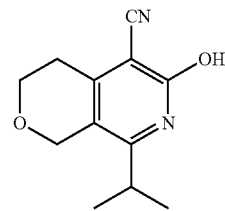 [SMILES: CC(C)c1nc(O)c(C#N)c2c1COCC2]

was prepared from isobutyryl chloride and dihydro-2H-pyran-4(3H)-one according to the methods described in Example 1, Steps A and B. MS (ES) M+H expected 219.1, found 219.1. $^1$H NMR (CHLOROFORM-d) δ 4.62 (s, 2H), 3.90-3.98 (m, 2H), 2.98 (t, J=5.8 Hz, 2H), 2.86 (spt, J=6.9 Hz, 1H), 1.39 (d, J=6.8 Hz, 6H).

6-hydroxy-8-p-tolyl-3,4-dihydro-1H-pyrano[3,4-c]pyridine-5-carbonitrile

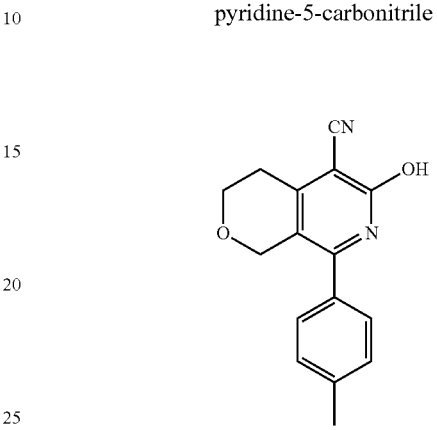

was prepared from 4-methylbenzoyl chloride and dihydro-2H-pyran-4(3H)-one according to the methods described in Example 1, Steps A and B. MS (ES) M+H expected 267.1, found 267.1. $^1$H NMR (DMSO-d$_6$) δ7.34 (s, 4H), 4.31 (s, 2H), 3.87 (t, J=5.9 Hz, 2H), 2.91 (t, J=5.9 Hz, 2H), 2.38 (s, 3H).

Example 4

Preparation of 3-hydroxy-1-isopropyl-5,6,7,8-tetrahydroisoquinoline-4-carbonitrile Intermediates 3-hydroxy-1-isopropyl-5,6,7,8-tetrahydroisoquinoline-4-carbonitrile intermediates were prepared according to Scheme 3. These intermediate were also used as a substitute for 8-cyclopropyl-6-hydroxy-3,3-dimethyl-3,4-dihydro-1H-pyrano[3,4-c]pyridine-5-carbonitrile (3) in Scheme 1 to produce additional compounds of the invention.

Scheme 3:

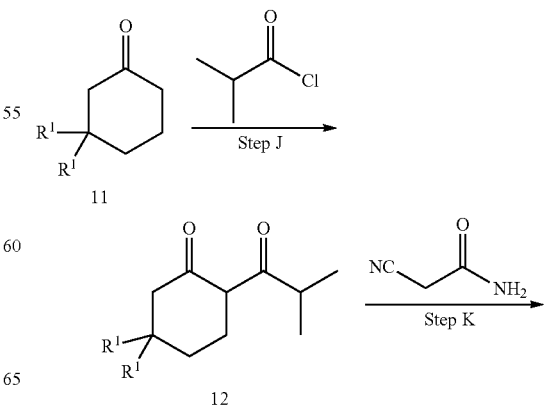

-continued

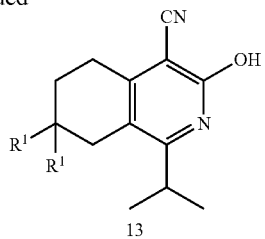

13

Step J: 2-isobutyrylcyclohexanone (12; R=R=H)

A 250 mL three-neck round bottom flask equipped with a stirring bar was charged with cyclohexanone (4.91 g, 50 mmol) and 87 mL of dry toluene. The solution was purged with nitrogen and cooled to 0° C. With stirring, a solution of LiHMDS (1.0M soln. in methyl tert-butyl ether, 52.5 mL, 52.5 mmol) was added dropwise, and the reaction mixture was allowed to stir for 2 min at 0° C. before isobutyryl chloride (2.66 g, 25 mmol) was added with vigorous stirring. After an additional 2 min at 0° C., the cold bath was removed and after 5 min, the reaction mixture was quenched with acetic acid (20 mL, 50% AcOH/H$_2$O). After partitioning between H$_2$O and ether, the organic layer was washed with brine, dried over anhy. Na$_2$SO$_4$ and concentrated in vacuo. Flash column chromatography (30% ethyl acetate/petroleum ether) afforded 4.4 g of title compound as yellowish oil. MS (ES) M+H expected 169.1, found 169.1. $^1$H NMR (DMSO-d$_6$) δ 16.36 (s, 1H), 2.85-2.96 (m, 1H), 2.38 (qd, J=6.4, 1.1 Hz, 4H), 1.69-1.73 (m, 4H), 1.13 (s, 3H), 1.11 (s, 3H).

Step K: 3-hydroxy-1-isopropyl-5,6,7,8-tetrahydroisoquinoline-4-carbonitrile (13; R=R=H)

To a solution of 2-isobutyrylcyclohexanone (12; 4.33 g, 25.76 mmol) and 2-cyanoacetamide (2.17 g, 25.76 mmol) in 26 mL of EtOH was added diethylamine (2.7 mL, 25.76 mmol). The reaction mixture was stirred at room temperature for 72 hours until LC-MS indicated the complete formation of the product. The reaction mixture was then heated to reflux and enough EtOH was added to make a clear solution. After cooling back to room temperature, the desired product and its regioisomer were precipitated out from EtOH solution. After vacuum filtration and air-dry, 4.1 g of the title compound together with its regioisomer were obtained as a mixture of white solid and used without further purification in the next step. MS (ES) M+H expected 217.1, found 217.1.

3-hydroxy-1-isopropyl-7,7-dimethyl-5,6,7,8-tetrahydroisoquinoline-4-carbonitrile (13; R=R=CH$_3$)

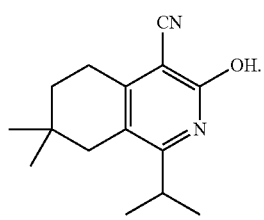 [SMILES: CC(C)c1nc(O)c(C#N)c2c1CC(C)(C)CC2]

The titled compound was prepared from isobutyryl chloride and 4,4-dimethylcyclohexanone according to the methods described in Steps J and K, above as a mixture of two regioisomeric products. MS (ES) M+H expected 245.2, found 245.0.

Example 5

Preparation of Various Substituted Piperazine Intermediates

Various substituted piperazine intermediates useful as a substitute for (R)-2-isopropylpiperazine in Step D of Scheme 1 were used to synthesize other compounds of Formula I and II. One of these substituted piperazine intermediates 23 was prepared according to Scheme 4A.

Scheme 4A:

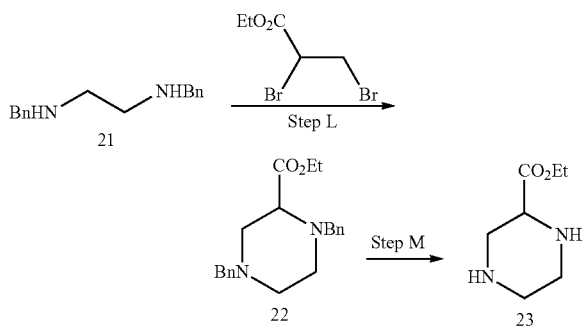

Step L: ethyl 1,4-dibenzylpiperazine-2-carboxylate 22

At 80° C., to a stirred solution of N,N'-dibenzylethane-1,2-diamine (21; 7.2 g, 30 mmol) and Et$_3$N (10 mL) in toluene (30 mL) was added dropwise ethyl 2,3-dibromopropanoate (8 g, 31 mmol) in toluene (30 mL). After the addition, the reaction mixture was stirred at 80° C. for 3 hours until TLC indicated the complete formation of product. The resulting mixture was cooled to room temperature and the solid was filtered. The filtrate was washed with saturated aq. NaHCO$_3$ (20 mL). The organic phase was dried over anhy. Na$_2$SO$_4$ and concentrated in vacuo. Flash column chromatography (5% ethyl acetate/petroleum ether) afforded 7.5 g of the title compound as pale oil. MS (ES) M+H expected 339.2, found 339.

Step M: ethyl piperazine-2-carboxylate 23

At 40° C., a mixture of ethyl 1,4-dibenzylpiperazine-2-carboxylate (22; 4 g, 12 mmol) and 10% Pd/C (60 mg) in EtOH (30 mL) was stirred under H$_2$ atmosphere for 24 hours until TLC indicated the complete consumption of starting material. The resulting mixture was cooled to room temperature and the solid was filtered. The filtrate was concentrated to give 2 g of the title compound as a white solid. $^1$H NMR (DMSO-d6) δ: 4.07 (q, J=7.1 Hz, 2H), 3.31 (dd, J=8.3, 3.0 Hz, 2H), 2.29-2.32 (m, 2H), 2.76-2.92 (m, 2H), 2.63 (d, J=8.0 Hz, 2H), 2.52 (s, 1H), 1.18 (t, J=7.0 Hz, 3H).

Additional substituted piperazines intermediates 29 and 30 were prepared according to Scheme 4B.

Scheme 4B:

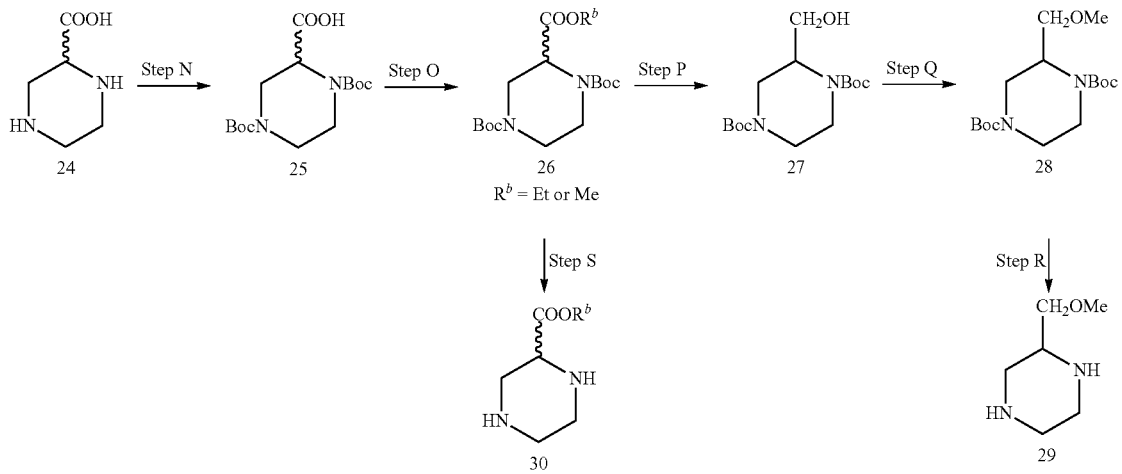

$R^b$ = Et or Me

Step N: 1,4-bis(tert-butoxycarbonyl)piperazine-2-carboxylic acid 25

To an aqueous solution of $Na_2CO_3$ (40 g, 380 mmol, in 200 mL of water) at room temperature was added piperazine-2-carboxylic acid dihydrochloride (either an enantiomeric mixture or a specific stereoisomer) (24; 10 g, 50 mmol), followed by di-tert-butyl dicarbonate (41 g, 183 mmol) in tetrahydrofuran (200 mL). The reaction mixture was stirred at room temperature for 20 hours and then the volatiles were removed under reduced pressure. The resulting mixture was then extracted with diethyl ether (100 mL). The aqueous layer was treated with 3.0 M HCl until it was slightly acidic (pH=4) and then extracted with ethyl acetate (150 mL). The organic layer was washed with brine, dried over anhy. $Na_2SO_4$, filtered, and concentrated to afford 16 g of the title compound as a white solid.

Step O: 1,4-di-tert-butyl 2-methyl piperazine-1,2,4-tricarboxylate (26; $R^b$=Me)

To a mixture of 1,4-bis(tert-butoxycarbonyl)-piperazine-2-carboxylic acid (25; 3.6 g, 11 mmol) in DMF (10 mL) was added $K_2CO_3$ (2 g, 18 mmol). The resulting suspension was cooled to 0° C. and treated with iodomethane (1.5 mL, 12 mmol). The mixture was then allowed to warm to room temperature, stirred for 6 hours. After quenched with water (200 mL), the mixture was extracted with ethyl acetate (100 mL), and the organic layer was washed with brine, dried over anhy. $Na_2SO_4$, filtered, and concentrated in vacuo to afford 3.6 g of the title compound as a white solid.

1,4-di-tert-butyl 2-ethyl piperazine-1,2,4-tricarboxylate (26; $R^b$=ethyl)

To a mixture of 1,4-bis(tert-butoxycarbonyl)piperazine-2-carboxylic acid (either an enantiomeric mixture or a specific stereoisomer) (25; 0.5 g, 1.38 mmol) in 10 mL of DMF was added $K_2CO_3$ (0.6 g, 4.4 mmol). The resulting suspension was cooled to 0° C. and treated with bromoethane (1 mL, 9.34 mmol). The reaction mixture was allowed to warm to room temperature, stirred for 24 hours. After quenching with water (10 mL), the mixture was extracted with ethyl acetate (20 mL), and the organic layer was washed with brine, dried over anhy. $Na_2SO_4$, filtered, and concentrated in vacuo to afford 0.48 g of the title compound as white solid.

Step P: di-tert-butyl 2-(hydroxymethyl)piperazine-1,4-dicarboxylate 27

To a solution of 1,4-di-tert-butyl 2-methyl piperazine-1,2,4-tricarboxylate (26; 2 g, 56 mmol) in ethanol (10 mL) was added $CaCl_2$ (5 g, 45 mmol) at 0° C., followed by $NaBH_4$ (1.1 g, 28 mmol) in two portions. The reaction mixture was warmed to room temperature and stirred for 1.5 h. After cooling to 0° C., the mixture was quenched with aq. citric acid solution (6 g citric acid in 50 mL of water). The resulting mixture was then extracted with ethyl acetate (200 mL), and the organic layer was washed with brine, dried over anhy. $Na_2SO_4$, filtered, and concentrated in vacuo to give 1.8 g of the crude title compound as a white solid.

Step Q: di-tert-butyl 2-(methoxymethyl)piperazine-1,4-dicarboxylate 28

To a solution of di-tert-butyl 2-(hydroxymethyl)piperazine-1,4-dicarboxylate (27; 1.5 g, 4.74 mmol) in anhy. THF was added NaH (210 mg, 60% dispersion in mineral oil) portionwise at −20° C. under nitrogen atmosphere. After stirring for 5 min, iodomethane was then added and the mixture was stirred at room temperature for 3 hours and poured into water (20 mL). The mixture was then extracted with ethyl acetate (2×100 mL), the combined organic extracts were washed with brine, dried over anhy. $Na_2SO_4$, filtered, and concentrated in vacuo to afford 1.6 g of the crude title compound as a white solid.

Step R: 2-(methoxymethyl)piperazine 29

To a solution of di-tert-butyl 2-(methoxymethyl)piperazine-1,4-dicarboxylate (28; 1.5 g, 4.5 mmol) in methanol (5 mL) at room temperature was added HCl solution (10 mL, 4.0 M in EtOAc). The reaction mixture was stirred at room temperature overnight and then concentrated in vacuo to give 1.2 g of 2-(methoxymethyl) piperazine as the hydrochloride salt, which was used in the next step without further purification. Step S: Ethyl piperazine-2-carboxylate 30

($R^b$=ethyl). To a solution of 1,4-di-tert-butyl 2-ethyl piperazine-1,2,4-tricarboxylate (26, $R^b$=ethyl; 1.2 g, 4.5 mmol) in methanol (4 mL) at room temperature was added HCl solution (5 mL, 4.0 M in EtOAc). The reaction mixture was stirred at room temperature overnight and then concentrated to afford 1 g of 2-(methoxymethyl) piperazine as the hydrochloride salt, which was used in the next step without further purification. This reaction was performed separately with both (S)- and (R)-isomers of 26 to produce the corresponding isomers of 29.

Still other substituted piperazines intermediates 35 were prepared according to Scheme 4c.

Scheme 4c:

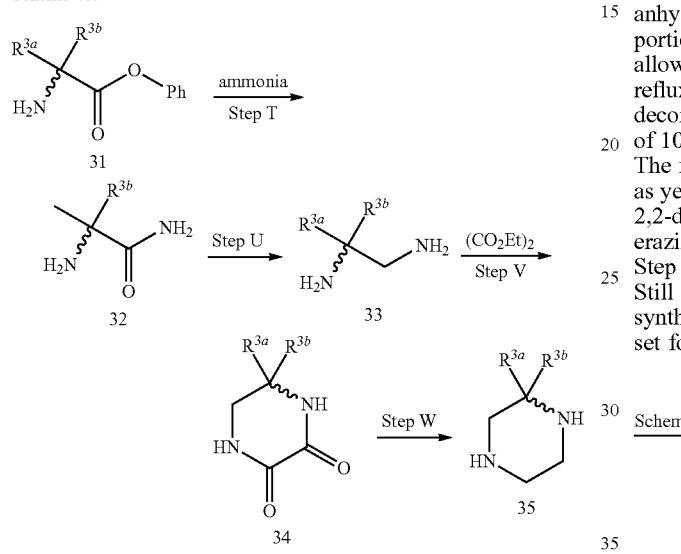

Step T: 2-amino-2-phenylacetamide 32

To methyl 2-amino-2-phenylacetate hydrochloride (enantiomeric or a specific stereoisomer) (31; 5.0 g, 25 mmol) in 5 mL of water was added ammonium hydroxide (25 mL, 28%) and the mixture was stirred at room temperature for 18 hours. After the TLC indicated the completion of the reaction, the mixture was evaporated to dryness. After partitioning between water and methylene chloride, the organic layer was separated, dried with anhy. $MgSO_4$, filtered, and concentrated in vacuo to afford 2.34 g of title compound as a white solid. MS (ES) M+H expected 151.1, found 151.

Step U: 1-phenylethane-1,2-diamine 33

To a suspension of 32 (2.34 g, 15.6 mmol) in 50 mL of anhydrous THF was added $LiAlH_4$ (1.78 g, 46.8 mmol) portionwise in an ice-water bath. The resulting mixture was allowed to warm to room temperature and then heated to reflux temperature for 4 hours. After cooling to 0° C., excess of LAH was decomposed with vigorous stirring by slow addition of 8 mL of 10% KOH solution. The solid was removed by filtration. The filtrate was evaporated to dryness to give 2 g of 33 as yellowish oil. MS (ES) M+H expected 137.1, found 137.

Step V: 5-phenylpiperazine-2,3-dione 34

To a solution of 33 (1.9 g, 14 mmol) in 200 mL of EtOH was added diethyl oxalate (2.04 g, 14 mmol). The resulting mixture was stirred at reflux for 2 hours. After cooling to room temperature, the mixture was quenched with brine, extracted with EtOAc. The organic layer was concentrated in vacuo to afford 2.15 g of 34 as yellowish oil. MS (ES) M+H expected 191.1, found 191.

5,5-dimethylpiperazine-2,3-dione was prepared from 2-methylpropane-1,2-diamine according to the methods described in Step V. MS (ES) M+H expected 143.1, found 143.

Step W: 2-phenylpiperazine 35

To a suspension of 34 (2.15 g, 11 mmol) in 50 mL of anhydrous THF was added $LiAlH_4$ (2.58 g, 68 mmol) portionwise in an ice-water bath. The resulting mixture was allowed to warm to room temperature and then heated to reflux for 4 hours. After cooling to 0° C., excess of LAH was decomposed with vigorous stirring by slow addition of 8 mL of 10% KOH solution. The solid was removed by filtration. The filtrate was evaporated to dryness to give 1.65 g of 35 as yellowish oil. MS (ES) M+H expected 163.1, found 163. 2,2-dimethylpiperazine was prepared from 5,5-dimethylpiperazine-2,3-dione according to the methods described in Step W. MS (ES) M+H expected 115.1, found 115.

Still other substituted piperazine intermediates useful in the synthesis of compounds of Formula I 39 were prepared as set forth in Scheme 4d.

Scheme 4d:

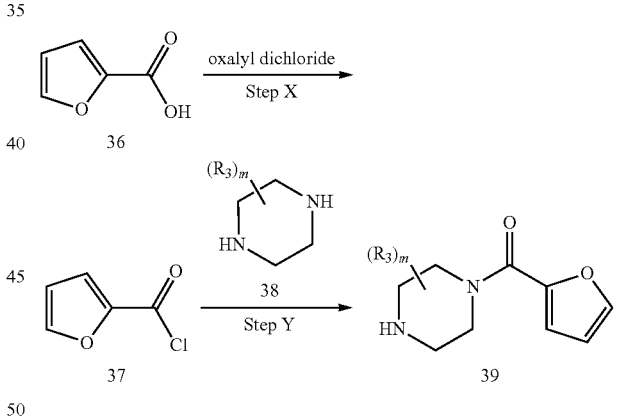

Step X: Furan-2-carbonyl chloride 37

To a solution of furan-2-carboxylic acid (36; 0.5 g, 4.5 mmol) in 5 mL of DCM was slowly added oxalyl dichloride (0.5 mL) at 0° C. in ice-water bath followed by addition of a drop of DMF. The resulting mixture was stirred at room temperature for 30 min and then slowly warmed up to reflux temperature for 1 hour. After the mixture was cooled to room temperature, it was concentrated in vacuo to afford 0.59 g of the crude title compound.

Step Y: Furan-2-yl(3-methylpiperazin-1-yl)methanone 39

To a mixture of 2-methylpiperazine (enantiomeric mixture or a specific stereoisomer) (38; 0.41 g, 4.1 mmol) and NaHCO$_3$ (1.56 g, 18.5 mmol) in 5 mL of H$_2$O and 2.5 mL of acetone at 0° C. was slowly added furan-2-carbonyl chloride (37; 0.59 g, 4.5 mmol) in 1.5 mL of acetone. The resulting mixture was allowed to warm to room temperature and stirred for 2 hours. The mixture was quenched with brine, extracted with EtOAc. The organic layer was dried and concentrated in vacuo. The residue was purified by flash column chromatography (25% petroleum ether/ethyl acetate) to give 0.32 g of the title compound. MS (ES) M+H expected 195.1, found 195.

Furan-2-yl(3-phenylpiperazin-1-yl)methanone was prepared from 2-phenylpiperazine (enantiomeric mixture or a specific stereoisomer) according to the method described in Step Y. MS (ES) M+H expected 257.1, found 257.

Example 6

Additional Compounds of Formula I Produced According to Scheme 2, Step E1

Using the appropriate pyraonpyridine and substituted piperazine intermediates, the following compounds of the invention were made in an equivalent manner to compounds made using Step E1 of Scheme 2.

3-(4-(furan-2-carbonyl)-3-methylpiperazin-1-yl)-1-isopropyl-5,6,7,8-tetrahydroisoquinoline-4-carbonitrile (Compound 125)

$^1$H NMR (CHLOROFORM-d) δ 7.45-7.59 (m, 1H), 7.03 (d, J=3.5 Hz, 1H), 6.51 (dd, J=3.5, 1.8 Hz, 1H), 4.86 (br. s., 1H), 4.48 (d, J=13.6 Hz, 1H), 4.15-4.24 (m, 1H), 4.11 (dt, J=13.1, 2.0 Hz, 1H), 3.55 (br. s., 1H), 3.28 (dd, J=13.1, 3.8 Hz, 1H), 3.06-3.23 (m, 2H), 2.84-2.96 (m, 2H), 2.58-2.74 (m, 2H), 1.78-1.87 (m, 4H), 1.44-1.53 (m, 3H), 1.15-1.23 (m, 6H). LC-MS: m/z 393.0 (M+H)$^+$.

3-(4-(furan-2-carbonyl)piperazin-1-yl)-1-isopropyl-7,7-dimethyl-5,6,7,8-tetrahydroisoquinoline-4-carbonitrile (Compound 116)

$^1$H NMR (CHLOROFORM-d) δ 7.53 (dd, J=1.8, 0.8 Hz, 1H), 7.06 (dd, J=3.4, 0.9 Hz, 1H), 6.52 (dd, J=3.5, 1.8 Hz, 1H), 3.98 (br. s., 4H), 3.61-3.78 (m, 4H), 3.08-3.23 (m, 1H), 2.92 (t, J=6.8 Hz, 2H), 2.42 (s, 2H), 1.56-1.62 (m, 2H), 1.16-1.22 (m, 6H), 0.98-1.05 (m, 6H). LC-MS: m/z 406.9 (M+H)$^+$.

(R)-8-cyclohexyl-6-(3-methyl-4-(5-methylisoxazole-4-carbonyl)piperazin-1-yl)-3,4-dihydro-1H-pyrano[3,4-c]pyridine-5-carbonitrile (Compound 187)

$^1$H NMR (CHLOROFORM-d) δ 8.23 (s, 1H), 4.71 (s, 2H), 4.13-4.25 (m, 2H), 3.94 (t, J=5.8 Hz, 2H), 3.51 (br. s., 1H), 3.22 (dd, J=13.1, 3.5 Hz, 1H), 3.05 (td, J=12.5, 3.3 Hz, 1H), 2.94 (t, J=5.8 Hz, 2H), 2.57 (s, 3H), 2.42 (tt, J=11.2, 3.6 Hz, 1H), 1.81-1.88 (m, 2H), 1.75 (d, J=11.0 Hz, 1H), 1.62-1.71 (m, 3H), 1.43 (d, J=6.8 Hz, 3H), 1.26-1.40 (m, 4H). LC-MS: m/z 450.1 (M+H)$^+$.

(R)-8-cyclohexyl-6-(4-(furan-3-carbonyl)-3-methyl-piperazin-1-yl)-3,4-dihydro-1H-pyrano[3,4-c]pyridine-5-carbonitrile (Compound 160)

$^1$H NMR (CHLOROFORM-d) δ 7.75 (s, 1H), 7.47 (s, 1H), 6.55-6.64 (m, 1H), 4.72 (s, 3H), 4.14-4.41 (m, 3H), 3.95 (t, J=5.6 Hz, 2H), 3.49 (br. s., 1H), 3.26 (dd, J=13.1, 3.3 Hz, 1H), 3.09 (td, J=12.5, 3.3 Hz, 1H), 2.95 (t, J=5.5 Hz, 2H), 2.33-2.51 (m, 1H), 1.85 (d, J=12.5 Hz, 2H), 1.77 (d, J=10.8 Hz, 1H), 1.65-1.72 (m, 2H), 1.60 (d, J=12.0 Hz, 2H), 1.44 (d, J=6.8 Hz, 3H), 1.30-1.39 (m, 3H). LC-MS: m/z 435.1 (M+H)$^+$.

(R)-8-cyclohexyl-6-(4-(3-methoxypropanoyl)-3-methylpiperazin-1-yl)-3,4-dihydro-1H-pyrano[3,4-c]pyridine-5-carbonitrile (Compound 240)

$^1$H NMR (CHLOROFORM-d) δ 4.89 (br. s., 1H), 4.69 (s, 2H), 4.12-4.26 (m, 2H), 3.90-3.97 (m, 2H), 3.66-3.83 (m, 3H), 3.47-3.66 (m, 1H), 3.33-3.41 (m, 3H), 2.99-3.28 (m, 2H), 2.92 (t, J=5.6 Hz, 2H), 2.63-2.80 (m, 1H), 2.52-2.63 (m, 1H), 2.41 (tt, J=11.1, 3.7 Hz, 1H), 1.84 (d, J=12.8 Hz, 2H), 1.75 (d, J=10.5 Hz, 1H), 1.62-1.71 (m, 3H), 1.26-1.41 (m, 7H). LC-MS: m/z 427.2 (M+H)$^+$.

(R)-8-cyclohexyl-6-(4-(furan-3-carbonyl)-3-isopropylpiperazin-1-yl)-3,4-dihydro-1H-pyrano[3,4-c]pyridine-5-carbonitrile (Compound 183)

$^1$H NMR (CHLOROFORM-d) δ 7.72 (br. s., 1H), 7.40-7.49 (m, 1H), 6.51-6.66 (m, 1H), 4.70 (s, 2H), 4.45-4.64 (m, 2H), 4.27 (br. s., 1H), 3.87-4.16 (m, 3H), 3.54-3.75 (m, 1H), 3.11 (dd, J=13.3, 3.0 Hz, 2H), 2.92 (t, J=5.6 Hz, 2H), 2.41 (tt, J=11.1, 3.5 Hz, 1H), 2.17-2.34 (m, 1H), 1.84 (d, J=12.5 Hz, 2H), 1.70-1.77 (m, 2H), 1.54-1.65 (m, 3H), 1.29-1.39 (m, 3H), 0.84-1.07 (m, 4H). LC-MS: m/z 463.2 (M+H)$^+$.

8-cyclohexyl-6-(4-(furan-3-carbonyl)-3-methylpiperazin-1-yl)-3,4-dihydro-1H-pyrano[3,4-c]pyridine-5-carbonitrile (Compound 133)

$^1$H NMR (CHLOROFORM-d) δ 7.70-7.80 (m, 1H), 7.39-7.54 (m, 1H), 6.60 (s, 1H), 4.72 (s, 3H), 4.13-4.42 (m, 3H), 3.95 (t, J=5.6 Hz, 2H), 3.50 (br. s., 1H), 3.26 (d, J=12.5 Hz, 1H), 3.04-3.17 (m, 1H), 2.95 (t, J=5.5 Hz, 2H), 2.43 (t, J=11.2 Hz, 1H), 1.85 (d, J=12.3 Hz, 2H), 1.56-1.80 (m, 5H), 1.44 (d, J=6.8 Hz, 3H), 1.25-1.37 (m, 3H). LC-MS: m/z 435.1 (M+H)$^+$.

ethyl 4-(5-cyano-8-cyclohexyl-3,4-dihydro-1H-pyrano[3,4-c]pyridin-6-yl)-1-(3-(methylthio)-propanoyl)piperazine-2-carboxylate (Compound 313)

$^1$H NMR (CHLOROFORM-d) δ 5.21-5.32 (m, 1H), 4.72-4.84 (m, 1H), 4.69 (s, 2H), 4.11-4.28 (m, 2H), 4.02-4.09 (m, 1H), 3.78-4.01 (m, 4H), 3.32 (dd, J=13.6, 4.5 Hz, 1H), 3.02-3.18 (m, 1H), 2.82-2.97 (m, 4H), 2.69-2.79 (m, 2H), 2.36-2.46 (m, 1H), 2.13-2.20 (m, 3H), 1.85 (d, J=11.8 Hz, 2H), 1.76 (d, J=9.5 Hz, 1H), 1.66 (br. s., 1H), 1.60 (d, J=11.8 Hz, 2H), 1.27-1.41 (m, 4H), 1.14-1.22 (m, 3H). LC-MS: m/z 501.0 (M+H)$^+$.

(R)-8-cyclohexyl-6-(3-methyl-4-(2-(thiophen-2-yl)acetyl)piperazin-1-yl)-3,4-dihydro-1H-pyrano[3,4-c]pyridine-5-carbonitrile (Compound 185)

$^1$H NMR (CHLOROFORM-d) δ 7.21 (dd, J=5.1, 1.1 Hz, 1H), 6.87-6.99 (m, 2H), 4.91 (br. s., 1H), 4.69 (s, 2H), 4.22 (d, J=13.6 Hz, 1H), 4.13 (d, J=13.3 Hz, 1H), 3.86-3.98 (m, 4H), 3.77 (d, J=13.3 Hz, 1H), 3.50-3.67 (m, 1H), 3.11-3.23 (m, 1H), 2.88-3.05 (m, 3H), 2.33-2.48 (m, 1H), 1.84 (d, J=12.3 Hz, 2H), 1.75 (d, J=10.3 Hz, 1H), 1.62-1.69 (m, 3H), 1.26-1.38 (m, 7H). LC-MS: m/z 465.1 (M+H)$^+$.

ethyl 4-(5-cyano-8-cyclohexyl-3,4-dihydro-1H-pyrano[3,4-c]pyridin-6-yl)-1-(furan-3-carbonyl) piperazine-2-carboxylate (Compound 258)

$^1$H NMR (CHLOROFORM-d) δ 7.79 (br. s., 1H), 7.40-7.52 (m, 1H), 6.49-6.70 (m, 1H), 5.39 (br. s., 0.5H), 4.79 (br. s., 0.5H), 4.65-4.74 (m, 2H), 4.21 (dq, J=10.7, 7.1 Hz, 2H), 4.03-4.16 (m, 2H), 3.81-4.03 (m, 3H), 3.39 (d, J=11.5 Hz, 1H), 3.03-3.17 (m, 1H), 2.92 (t, J=5.6 Hz, 2H), 2.34-2.47 (m, 1H), 1.50-1.84 (m, 10H), 1.09-1.39 (m, 3H). LC-MS: m/z 493.2 (M+H)$^+$.

8-cyclohexyl-6-(4-(furan-3-carbonyl)piperazin-1-yl)-3,4-dihydro-1H-pyrano[3,4-c]pyridine-5-carbonitrile (Compound 120)

$^1$H NMR (CHLOROFORM-d) δ 7.77 (s, 1H), 7.47 (s, 1H), 6.60 (s, 1H), 4.72 (s, 2H), 3.96 (t, J=5.6 Hz, 2H), 3.87 (br. s., 4H), 3.69 (br. s., 4H), 2.95 (t, J=5.4 Hz, 2H), 2.44 (t, J=10.9 Hz, 1H), 1.86 (d, J=12.5 Hz, 2H), 1.57-1.81 (m, 5H), 1.31-1.42 (m, 3H). LC-MS: m/z 420.9 (M+H)$^+$.

8-cyclohexyl-6-(3-ethyl-4-(furan-3-carbonyl)piperazin-1-yl)-3,4-dihydro-1H-pyrano[3,4-c]pyridine-5-carbonitrile (Compound 175)

$^1$H NMR (CHLOROFORM-d) δ 7.74 (s, 1H), 7.45-7.54 (m, 1H), 6.54-6.64 (m, 1H), 4.53-5.02 (m, 2H), 4.11-4.41 (m, 3H), 3.89-4.08 (m, 2H), 3.51 (m, 1H), 3.21 (dd, J=13.1, 3.5 Hz, 1H), 3.01-3.15 (m, 1H), 2.94 (t, J=5.8 Hz, 2H), 2.43 (tt, J=11.1, 3.5 Hz, 1H), 1.73-1.96 (m, 6H), 1.53-1.65 (m, 2H), 1.29-1.43 (m, 4H), 0.85-1.03 (m, 3H). LC-MS: m/z 449.2 (M+H)$^+$.

ethyl 4-(5-cyano-8-cyclohexyl-3,4-dihydro-1H-pyrano[3,4-c]pyridin-6-yl)-1-(furan-2-carbonyl) piperazine-2-carboxylate (Compound 314)

$^1$H NMR (CHLOROFORM-d) δ 7.52 (br. s., 1H), 7.11 (d, J=3.5 Hz, 1H), 6.51 (br. s., 1H), 5.34 (br. s., 1H), 4.70 (s, 3H), 4.53 (d, J=13.6 Hz, 1H), 4.16-4.31 (m, 2H), 4.12 (d, J=7.0 Hz, 1H), 3.86-4.05 (m, 3H), 3.50 (d, J=10.0 Hz, 1H), 3.23 (br. s., 1H), 2.93 (t, J=5.5 Hz, 2H), 2.41 (br. s., 1H), 1.84 (d, J=11.5 Hz, 2H), 1.75 (d, J=9.5 Hz, 1H), 1.65 (br. s., 3H), 1.29-1.38 (m, 4H), 1.20 (t, J=7.2 Hz, 3H). LC-MS: m/z 495.2 (M+H)$^+$.

ethyl 4-(5-cyano-8-cyclohexyl-3,4-dihydro-1H-pyrano[3,4-c]pyridin-6-yl)-1-(2-methylfuran-3-carbonyl)piperazine-2-carboxylate (Compound 277)

$^1$H NMR (CHLOROFORM-d) δ 7.69 (br. s., 1H), 7.46-7.51 (m, 1H), 5.39 (br. s., 0.5H), 4.80 (br. s., 0.5H), 4.72 (d, J=3.5 Hz, 2H), 4.25 (dq, J=9.7, 7.3 Hz, 2H), 4.01-4.15 (m, 2H), 3.93 (br. s., 1H), 3.40 (d, J=11.8 Hz, 1H), 3.03-3.18 (m, 1H), 2.92 (t, J=5.6 Hz, 2H), 2.54-2.57 (s, 3H), 2.34-2.47 (m, 1H), 1.50-1.84 (m, 10H), 1.09-1.39 (m, 3H). LC-MS: m/z 507.2 (M+H)$^+$.

(R)-8-cyclohexyl-6-(3-methyl-4-(thiophene-3-carbonyl)piperazin-1-yl)-3,4-dihydro-1H-pyrano[3,4-c]pyridine-5-carbonitrile (Compound 242)

$^1$H NMR (CHLOROFORM-d) δ 7.53 (d, J=2.8 Hz, 1H), 7.36 (dd, J=4.9, 2.9 Hz, 1H), 7.20 (d, J=5.0 Hz, 1H), 4.59-4.83 (m, 3H), 4.08-4.38 (m, 3H), 3.88-3.99 (m, 2H), 3.46 (br. s., 1H), 3.23 (d, J=10.8 Hz, 1H), 3.07 (td, J=12.5, 3.4 Hz, 1H), 2.87-2.97 (m, 2H), 2.41 (tt, J=11.0, 3.5 Hz, 1H), 1.83 (d, J=12.8 Hz, 2H), 1.74 (d, J=11.0 Hz, 1H), 1.68 (br. s., 1H), 1.53-1.61 (m, 2H), 1.41 (d, J=6.8 Hz, 3H), 1.27-1.39 (m, 4H). LC-MS: m/z 451.0 (M+H)$^+$.

8-cyclohexyl-6-(3-ethyl-4-(furan-2-carbonyl)piperazin-1-yl)-3,4-dihydro-1H-pyrano[3,4-c]pyridine-5-carbonitrile (Compound 174)

$^1$H NMR (CHLOROFORM-d) δ 7.44-7.59 (m, 1H), 7.05 (d, J=3.3 Hz, 1H), 6.52 (dd, J=3.3, 1.8 Hz, 1H), 4.72 (s, 3H), 4.48 (br. s., 1H), 4.23-4.38 (m, 2H), 3.87-4.04 (m, 2H), 3.47 (br. s., 1H), 3.30 (dd, J=13.2, 3.6 Hz, 1H), 3.16 (td, J=12.4, 3.3 Hz, 1H), 2.95 (t, J=5.6 Hz, 2H), 2.43 (tt, J=10.9, 3.6 Hz, 1H), 1.89-2.08 (m, 1H), 1.74-1.88 (m, 4H), 1.52-1.64 (m, 2H), 1.21-1.44 (m, 5H), 0.83-1.04 (m, 3H). LC-MS: m/z 449.1 (M+H)$^+$.

(R)-8-cyclohexyl-6-(3-methyl-4-(2-(pyridin-2-yl)acetyl)piperazin-1-yl)-3,4-dihydro-1H-pyrano[3,4-c]pyridine-5-carbonitrile (Compound 238)

$^1$H NMR (CHLOROFORM-d) δ 8.57 (dd, J=5.0, 0.8 Hz, 1H), 7.70 (t, J=7.2 Hz, 1H), 7.39 (dd, J=14.1, 7.8 Hz, 1H), 7.22 (d, J=6.8 Hz, 1H), 4.89 (br. s., 0.5H), 4.69 (s, 2H), 4.53 (d, J=13.8 Hz, 0.5H), 4.09-4.24 (m, 2.5H), 3.89-4.07 (m, 3H), 3.54 (t, J=11.0 Hz, 1H), 3.09-3.23 (m, 1H), 2.78-3.05 (m, 2.5H), 2.29-2.47 (m, 1H), 1.83 (d, J=12.5 Hz, 4H), 1.75 (d, J=10.0 Hz, 2H), 1.62-1.70 (m, 2H), 1.46-1.62 (m, 2H), 1.12-1.40 (m, 3H). LC-MS: m/z 460.1 (M+H)$^+$.

(R)-8-cyclohexyl-6-(3-methyl-4-(4-methyloxazole-5-carbonyl)piperazin-1-yl)-3,4-dihydro-1H-pyrano[3,4-c]pyridine-5-carbonitrile (Compound 225)

$^1$H NMR (CHLOROFORM-d) δ 7.83 (s, 1H), 4.70 (s, 3H), 4.12-4.32 (m, 3H), 3.85-3.99 (m, 2H), 3.53 (br. s., 1H), 3.30 (dd, J=13.1, 3.5 Hz, 1H), 3.14 (td, J=12.5, 3.5 Hz, 1H), 2.93 (t, J=5.6 Hz, 2H), 2.36-2.47 (m, 4H), 1.80-1.89 (m, 2H), 1.75 (d, J=11.3 Hz, 1H), 1.53-1.63 (m, 2H), 1.45 (d, J=6.8 Hz, 3H), 1.26-1.41 (m, 5H). LC-MS: m/z 450.2 (M+H)$^+$.

(R)-8-cyclohexyl-6-(3-methyl-4-(2-methylfuran-3-carbonyl)piperazin-1-yl)-3,4-dihydro-1H-pyrano[3,4-c]pyridine-5-carbonitrile (Compound 184)

$^1$H NMR (CHLOROFORM-d) δ 7.28 (d, J=1.8 Hz, 1H), 6.36 (d, J=1.8 Hz, 1H), 4.70 (s, 2H), 4.14-4.25 (m, 2H), 3.93 (t, J=5.8 Hz, 2H), 3.44 (br. s., 1H), 3.22 (d, J=10.8 Hz, 1H), 3.00-3.09 (m, 1H), 2.93 (t, J=5.6 Hz, 2H), 2.35-2.47 (m, 4H), 1.84 (d, J=12.8 Hz, 2H), 1.75 (d, J=11.3 Hz, 1H), 1.63-1.70 (m, 3H), 1.39 (d, J=6.8 Hz, 3H), 1.27-1.35 (m, 4H). LC-MS: m/z 449.1 (M+H)$^+$.

8-cyclohexyl-6-((3R)-3-methyl-4-(tetrahydrofuran-3-carbonyl)piperazin-1-yl)-3,4-dihydro-1H-pyrano[3,4-c]pyridine-5-carbonitrile (Compound 263)

$^1$H NMR (CHLOROFORM-d) δ 4.89 (br. s., 1H), 4.70 (s, 2H), 4.13-4.27 (m, 2H), 3.80-4.08 (m, 7H), 3.42-3.67 (m, 1H), 3.12-3.42 (m, 2H), 2.99-3.10 (m, 1H), 2.93 (t, J=5.6 Hz, 2H), 2.42 (tt, J=11.0, 3.6 Hz, 1H), 1.98-2.24 (m, 1H), 1.84 (d, J=12.5 Hz, 2H), 1.75 (d, J=10.5 Hz, 1H), 1.63-1.70 (m, 3H), 1.28-1.43 (m, 7H). LC-MS: m/z 439.1 (M+H)$^+$.

(R)-8-cyclohexyl-6-(4-(2-(2-methoxyphenyl)acetyl)-3-methylpiperazin-1-yl)-3,4-dihydro-1H-pyrano[3,4-c]pyridine-5-carbonitrile (Compound 224)

$^1$H NMR (CHLOROFORM-d) δ 7.19-7.26 (m, 2H), 6.86-6.95 (m, 2H), 4.92 (br. s., 1H), 4.69 (s, 2H), 4.22 (d, J=10.8 Hz, 1H), 4.11 (d, J=12.8 Hz, 1H), 3.81-4.03 (m, 4H), 3.71-3.81 (m, 2H), 3.34-3.51 (m, 1H), 3.09-3.34 (m, 1H), 2.87-3.04 (m, 3H), 2.40 (tt, J=11.0, 3.6 Hz, 1H), 1.83 (d, J=12.5 Hz, 2H), 1.74 (d, J=14.6 Hz, 2H), 1.59-1.68 (m, 3H), 1.26-1.37 (m, 5H). LC-MS: m/z 489.1 (M+H)$^+$.

(R)-8-cyclohexyl-6-(4-(2-(3-methoxyphenyl)acetyl)-3-methylpiperazin-1-yl)-3,4-dihydro-1H-pyrano[3,4-c]pyridine-5-carbonitrile (Compound 189)

$^1$H NMR (CHLOROFORM-d) δ 7.24 (t, J=8.0 Hz, 1H), 6.73-6.89 (m, 3H), 4.91 (br. s., 1H), 4.68 (s, 2H), 4.21 (d, J=13.8 Hz, 1H), 4.10 (d, J=12.3 Hz, 2H), 3.92 (t, J=5.0 Hz, 2H), 3.72-3.83 (m, 4H), 3.44 (t, J=11.2 Hz, 1H), 3.07-3.23 (m, 1H), 2.96-3.07 (m, 1H), 2.90 (t, J=5.5 Hz, 2H), 2.39 (tt, J=11.0, 3.5 Hz, 1H), 1.72-1.86 (m, 4H), 1.61-1.67 (m, 2H), 1.51-1.61 (m, 2H), 1.25-1.34 (m, 5H). LC-MS: m/z 489.1 (M+H)$^+$.

(R)-8-cyclohexyl-6-(4-(furan-2-carbonyl)-3-methylpiperazin-1-yl)-3,4-dihydro-1H-pyrano[3,4-c]pyridine-5-carbonitrile (Compound 162)

$^1$H NMR (CHLOROFORM-d) δ 7.52 (dd, J=1.8, 0.8 Hz, 1H), 7.05 (dd, J=3.5, 0.8 Hz, 1H), 6.51 (dd, J=3.5, 1.8 Hz, 1H), 4.88 (br. s., 1H), 4.71 (s, 2H), 4.49 (d, J=13.1 Hz, 1H), 4.27 (d, J=12.0 Hz, 1H), 4.18 (dt, J=13.1, 2.1 Hz, 1H), 3.87-4.05 (m, 2H), 3.55 (br. s., 1H), 3.34 (d, J=13.1, 3.8 Hz, 1H), 3.17 (td, J=12.5, 3.4 Hz, 1H), 2.94 (t, J=5.6 Hz, 2H), 2.43 (tt, J=11.1, 3.7 Hz, 1H), 1.85 (d, J=12.8 Hz, 2H), 1.54-1.79 (m, 5H), 1.46 (d, J=6.8 Hz, 3H), 1.31-1.42 (m, 3H). LC-MS: m/z 435.2 (M+H)$^+$.

(R)-8-cyclohexyl-6-(3-methyl-4-(3-(methylthio)propanoyl)piperazin-1-yl)-3,4-dihydro-1H-pyrano[3,4-c]pyridine-5-carbonitrile (Compound 264)

$^1$H NMR (CHLOROFORM-d) δ 4.88 (br. s., 1H), 4.70 (s, 2H), 4.52 (d, J=13.6 Hz, 1H), 4.23 (d, J=13.1 Hz, 1H), 3.90-3.97 (m, 2H), 3.52-3.82 (m, 1H), 3.00-3.30 (m, 3H), 2.80-2.97 (m, 4H), 2.56-2.78 (m, 2H), 2.37-2.46 (m, 1H), 2.11-2.21 (m, 3H), 1.84 (d, J=12.8 Hz, 2H), 1.75 (d, J=14.6 Hz, 2H), 1.52-1.63 (m, 2H), 1.26-1.42 (m, 7H). LC-MS: m/z 443.2 (M+H)$^+$.

(R)-8-cyclohexyl-6-(3-methyl-4-(thiophene-2-carbonyl)piperazin-1-yl)-3,4-dihydro-1H-pyrano[3,4-c]pyridine-5-carbonitrile (Compound 241)

$^1$H NMR (CHLOROFORM-d) δ 7.46 (dd, J=5.0, 1.0 Hz, 1H), 7.32 (dd, J=3.6, 1.1 Hz, 1H), 7.06 (dd, J=5.0, 3.8 Hz, 1H), 4.77 (br. s., 1H), 4.70 (s, 2H), 4.37 (d, J=13.6 Hz, 1H), 4.12-4.28 (m, 2H), 3.91-3.98 (m, 2H), 3.53 (t, J=11.4 Hz, 1H), 3.28 (dd, J=13.1, 3.5 Hz, 1H), 3.12 (td, J=12.5, 3.3 Hz, 1H), 2.93 (t, J=5.6 Hz, 2H), 2.41 (tt, J=11.1, 3.6 Hz, 1H), 1.83 (d, J=12.8 Hz, 2H), 1.75 (d, J=10.8 Hz, 1H), 1.68 (br. s., 1H), 1.55-1.59 (m, 1H), 1.45 (d, J=6.8 Hz, 3H), 1.27-1.40 (m, 5H). LC-MS: m/z 451.0 (M+H)$^+$.

(R)-8-cyclohexyl-6-(3-methyl-4-(2-methylimidazo[1,2-a]pyridine-3-carbonyl)piperazin-1-yl)-3,4-dihydro-1H-pyrano[3,4-c]pyridine-5-carbonitrile (Compound 190)

$^1$H NMR (CHLOROFORM-d) δ 8.47 (d, J=6.8 Hz, 1H), 7.60 (d, J=8.5 Hz, 1H), 7.31 (t, J=7.4 Hz, 1H), 6.89 (t, J=6.0 Hz, 1H), 4.60-4.87 (m, 3H), 4.23 (d, J=12.8 Hz, 2H), 3.88-4.08 (m, 3H), 3.55-3.76 (m, 1H), 3.32 (d, J=11.3 Hz, 1H), 3.08 (br. s., 1H), 2.94 (t, J=5.6 Hz, 2H), 2.54 (s, 3H), 2.42 (tt, J=11.0, 3.6 Hz, 1H), 1.83 (d, J=12.8 Hz, 2H), 1.57-1.79 (m, 5H), 1.45 (d, J=5.3 Hz, 3H), 1.27-1.38 (m, 3H). LC-MS: m/z 499.1 (M+H)$^+$.

8-cyclohexyl-6-((3S,5R)-4-(furan-2-carbonyl)-3,5-dimethylpiperazin-1-yl)-3,4-dihydro-1H-pyrano[3,4-c]pyridine-5-carbonitrile (Compound 128)

$^1$H NMR (CHLOROFORM-d) δ 7.47-7.56 (m, 1H), 7.07 (d, J=3.3 Hz, 1H), 6.52 (dd, J=3.3, 1.8 Hz, 1H), 4.87 (br. s., 2H), 4.73 (s, 2H), 4.31 (d, J=13.1 Hz, 2H), 3.96 (t, J=5.8 Hz, 2H), 3.23 (dd, J=12.9, 4.1 Hz, 2H), 2.96 (t, J=5.6 Hz, 2H), 2.39-2.52 (m, 1H), 1.86 (d, J=12.8 Hz, 2H), 1.60-1.80 (m, 5H), 1.57 (d, J=6.8 Hz, 6H), 1.30-1.43 (m, 3H). LC-MS: m/z 449.2 (M+H)$^+$.

(R)-8-cyclohexyl-6-(3-methyl-4-(1-methyl-1H-imidazole-2-carbonyl)piperazin-1-yl)-3,4-dihydro-1H-pyrano[3,4-c]pyridine-5-carbonitrile (Compound 262)

$^1$H NMR (CHLOROFORM-d) δ 7.79 (br. s., 1H), 7.32 (br. s., 1H), 4.79 (br. s., 1H), 4.71 (s, 2H), 4.35 (d, J=6.5 Hz, 1H), 4.11-4.27 (m, 2H), 3.91-3.99 (m, 2H), 3.86 (s, 3H), 3.55 (br. s., 1H), 3.21-3.28 (m, 1H), 3.03-3.14 (m, 1H), 2.94 (t, J=5.6 Hz, 2H), 2.42 (tt, J=11.0, 3.6 Hz, 1H), 1.75 (d, J=10.3 Hz, 2H), 1.69 (br. s., 1H), 1.54-1.62 (m, 2H), 1.45 (d, J=6.5 Hz, 3H), 1.27-1.41 (m, 5H). LC-MS: m/z 449.1 (M+H)$^+$.

8-cyclohexyl-6-(4-(furan-2-carbonyl)piperazin-1-yl)-3,4-dihydro-1H-pyrano[3,4-c]pyridine-5-carbonitrile (Compound 110)

$^1$H NMR (CHLOROFORM-d) δ 7.47-7.57 (m, 1H), 7.05 (d, J=3.5 Hz, 1H), 6.50 (dd, J=3.5, 1.8 Hz, 1H), 4.70 (s, 2H), 3.87-4.11 (m, 6H), 3.66-3.78 (m, 4H), 2.93 (t, J=5.8 Hz, 2H), 2.42 (tt, J=11.0, 3.6 Hz, 1H), 1.80-1.89 (m, 2H), 1.53-1.78 (m, 5H), 1.27-1.41 (m, 3H). LC-MS: m/z 421.0 (M+H)$^+$.

(R)-8-cyclohexyl-6-(3-methyl-4-(2-(pyridin-3-yl)acetyl)piperazin-1-yl)-3,4-dihydro-1H-pyrano[3,4-c]pyridine-5-carbonitrile (Compound 260)

$^1$H NMR (CHLOROFORM-d) δ 8.54 (br. s., 2H), 7.72 (br. s., 1H), 7.34 (dd, J=7.7, 4.9 Hz, 1H), 4.89 (br. s., 1H), 4.69 (s, 3H), 4.53 (d, J=14.3 Hz, 1H), 4.02-4.31 (m, 3H), 3.89-3.97 (m, 2H), 3.72-3.80 (m, 3H), 3.37-3.63 (m, 1H), 3.17 (t, J=13.7 Hz, 2H), 2.89-3.05 (m, 3H), 2.41 (tt, J=11.1, 3.5 Hz, 1H), 1.28-1.37 (m, 7H). LC-MS: m/z 480.1 (M+H)$^+$.

(R)-8-cyclohexyl-6-(4-(furan-2-carbonyl)-3-isopropylpiperazin-1-yl)-3,4-dihydro-1H-pyrano[3,4-c]pyridine-5-carbonitrile (Compound 182)

$^1$H NMR (CHLOROFORM-d) δ 7.44-7.59 (m, 1H), 7.03 (br. s., 1H), 6.50 (dd, J=3.3, 1.8 Hz, 1H), 4.70 (s, 2H), 4.21-4.58 (m, 4H), 3.85-4.04 (m, 2H), 3.60 (br. s., 1H), 3.08-3.28 (m, 2H), 2.92 (t, J=5.6 Hz, 2H), 2.41 (tt, J=11.0, 3.7 Hz, 1H), 2.18-2.32 (m, 1H), 1.84 (d, J=12.5 Hz, 2H), 1.54-1.75 (m, 5H), 1.06 (br. s., 3H), 0.80-0.95 (m, 3H). LC-MS: m/z 463.1 (M+H)$^+$.

8-cyclohexyl-6-(4-(furan-2-carbonyl)-3-methylpiperazin-1-yl)-3,4-dihydro-1H-pyrano[3,4-c]pyridine-5-carbonitrile (Compound 132)

$^1$H NMR (CHLOROFORM-d) δ 7.52 (s, 1H), 7.05 (d, J=3.5 Hz, 1H), 6.46-6.58 (m, 1H), 4.88 (br. s., 1H), 4.72 (s, 2H), 4.50 (d, J=13.1 Hz, 1H), 4.28 (d, J=12.5 Hz, 1H), 4.19 (d, J=12.8 Hz, 1H), 3.95 (t, J=5.6 Hz, 2H), 3.56 (br. s., 1H), 3.34 (dd, J=13.2, 3.6 Hz, 1H), 3.10-3.26 (m, 1H), 2.95 (t, J=5.6 Hz, 2H), 2.43 (t, J=11.3 Hz, 1H), 1.85 (d, J=12.3 Hz, 2H), 1.55-1.77 (m, 5H), 1.47 (d, J=6.8 Hz, 3H), 1.31-1.42 (m, 3H). LC-MS: m/z 435.1 (M+H)$^+$.

6-(4-(1H-indole-5-carbonyl)-3-methylpiperazin-1-yl)-8-cyclohexyl-3,4-dihydro-1H-pyrano[3,4-c]pyridine-5-carbonitrile (Compound 134)

$^1$H NMR (CHLOROFORM-d) δ 8.88 (br. s., 1H), 7.74 (s, 1H), 7.36 (d, J=8.5 Hz, 1H), 7.22-7.28 (m, 2H), 6.59 (br. s., 1H), 4.72 (s, 3H), 4.08-4.37 (m, 3H), 3.95 (t, J=5.6 Hz, 2H), 3.50 (t, J=11.4 Hz, 1H), 3.29 (d, J=11.5 Hz, 1H), 3.04-3.18 (m, 1H), 2.94 (t, J=5.6 Hz, 2H), 2.42 (tt, J=11.0, 3.5 Hz, 1H), 1.85 (d, J=12.5 Hz, 2H), 1.55-1.79 (m, 5H), 1.43 (d, J=6.5 Hz, 3H), 1.30-1.39 (m, 3H). LC-MS: m/z 484.1 (M+H)$^+$.

8-cyclohexyl-6-(4-(2,5-dimethylfuran-3-carbonyl)piperazin-1-yl)-3,4-dihydro-1H-pyrano[3,4-c]pyridine-5-carbonitrile (Compound 121)

$^1$H NMR (CHLOROFORM-d) δ 5.97 (s, 1H), 4.72 (s, 2H), 3.95 (t, J=5.8 Hz, 2H), 3.80 (br. s., 4H), 3.67 (br. s., 4H), 2.95 (t, J=5.6 Hz, 2H), 2.40-2.48 (m, 1H), 2.37 (s, 3H), 2.27 (s, 3H), 1.85 (d, J=12.5 Hz, 2H), 1.61-1.76 (m, 5H), 1.30-1.42 (m, 3H). LC-MS: m/z 448.9 (M+H)$^+$.

6-(4-(1H-indole-4-carbonyl)piperazin-1-yl)-8-cyclohexyl-3,4-dihydro-1H-pyrano[3,4-c]pyridine-5-carbonitrile (Compound 119)

$^1$H NMR (CHLOROFORM-d) δ 8.87 (br. s., 1H), 7.42 (d, J=7.3 Hz, 1H), 7.14-7.27 (m, 3H), 6.55 (br. s., 1H), 4.72 (s, 2H), 4.06 (br. s., 2H), 3.94 (t, J=5.6 Hz, 2H), 3.80 (br. s., 2H), 3.56 (br. s., 4H), 2.93 (t, J=5.6 Hz, 2H), 2.36-2.48 (m, 1H), 1.80-1.89 (m, 2H), 1.53-1.79 (m, 5H), 1.29-1.41 (m, 3H). LC-MS: m/z 469.9 (M+H)$^+$.

(R)-cyclohexyl-6-(3-methyl-4-(thiazole-4-carbonyl)piperazin-1-yl)-3,4-dihydro-1H-pyrano[3,4-c]pyridine-5-carbonitrile (Compound 239)

$^1$H NMR (CHLOROFORM-d) δ 8.81 (d, J=1.8 Hz, 1H), 8.01 (d, J=2.0 Hz, 1H), 4.88-5.04 (m, 1H), 4.70 (s, 2H), 4.57 (br. s., 1H), 4.13-4.41 (m, 2H), 3.89-3.97 (m, 2H), 3.55-3.77 (m, 1H), 3.36 (br. s., 1H), 3.18 (br. s., 1H), 2.93 (t, J=5.8 Hz, 2H), 2.41 (tt, J=11.1, 3.7 Hz, 1H), 1.80-1.91 (m, 2H), 1.74 (d, J=10.8 Hz, 1H), 1.63-1.68 (m, 2H), 1.41-1.45 (m, 3H), 1.26-1.40 (m, 5H). LC-MS: m/z 452.1 (M+H)$^+$.

(S)-8-cyclohexyl-6-(4-(furan-2-carbonyl)-2-methylpiperazin-1-yl)-3,4-dihydro-1H-pyrano[3,4-c]pyridine-5-carbonitrile (Compound 201)

$^1$H NMR (CHLOROFORM-d) δ 7.47-7.54 (m, 1H), 7.04-7.09 (m, 1H), 6.51 (dd, J=3.5, 1.8 Hz, 1H), 4.66-4.76 (m, 2H), 4.58 (br. s., 1H), 4.46 (d, J=12.0 Hz, 1H), 4.27 (dd, J=13.3, 1.5 Hz, 1H), 4.05 (d, J=13.3 Hz, 1H), 3.94 (t, J=5.6 Hz, 2H), 3.36-3.59 (m, 3H), 2.93 (t, J=5.6 Hz, 2H), 2.41 (tt, J=11.2, 3.5 Hz, 1H), 1.84 (d, J=12.5 Hz, 2H), 1.52-1.79 (m, 5H), 1.29 (d, J=6.5 Hz, 6H). LC-MS: m/z 435.2 (M+H)$^+$.

(R)-6-(4-(benzo[b]thiophene-3-carbonyl)-3-methylpiperazin-1-yl)-8-cyclohexyl-3,4-dihydro-1H-pyrano[3,4-c]pyridine-5-carbonitrile (Compound 243)

$^1$H NMR (CHLOROFORM-d) δ 7.87-7.94 (m, 1H), 7.77-7.84 (m, 1H), 7.53-7.60 (m, 1H), 7.37-7.46 (m, 2H), 5.26-5.38 (m, 1H), 4.69 (s, 2H), 4.17 (d, J=14.1 Hz, 3H), 3.90-3.96 (m, 2H), 3.49 (t, J=11.7 Hz, 1H), 3.28 (d, J=11.8 Hz, 1H), 3.08 (t, J=11.5 Hz, 1H), 2.88-2.96 (m, 2H), 2.40 (tt, J=11.0, 3.6 Hz, 1H), 1.82 (d, J=12.8 Hz, 2H), 1.73 (d, J=11.3 Hz, 1H), 1.60-1.69 (m, 3H), 1.56 (br. s., 1H), 1.43 (dd, J=3.9, 1.9 Hz, 3H), 1.28-1.36 (m, 3H). LC-MS: m/z 501.1 (M+H)$^+$.

ethyl 4-(5-cyano-8-cyclohexyl-3,4-dihydro-1H-pyrano[3,4-c]pyridin-6-yl)-1-(3-methoxypropanoyl)piperazine-2-carboxylate (Compound 278)

$^1$H NMR (CHLOROFORM-d) δ 5.29 (d, J=2.0 Hz, 0.5H), 4.76 (s, 0.5H), 4.71 (s, 2H), 4.15 (d, J=7.0 Hz, 2H), 4.06 (d, J=7.0 Hz, 1H), 3.83-4.00 (m, 2H), 3.72-3.83 (m, 2H), 3.63-3.71 (m, 4H), 3.36-3.41 (m, 3H), 3.25-3.36 (m, 2H), 2.92 (t, J=5.6 Hz, 2H), 2.58-2.74 (m, 3H), 1.85 (d, J=11.8 Hz, 3H), 1.47-1.75 (m, 4H), 1.27-1.42 (m, 3H), 1.18 (t, J=7.2 Hz, 3H). LC-MS: m/z 485.1 (M+H)$^+$.

(R)-8-cyclohexyl-6-(4-(2-(3-fluorophenyl)acetyl)-3-methylpiperazin-1-yl)-3,4-dihydro-1H-pyrano[3,4-c]pyridine-5-carbonitrile (Compound 191)

$^1$H NMR (CHLOROFORM-d) δ 7.27-7.35 (m, 1H), 6.93-7.08 (m, 3H), 4.69 (s, 2H), 4.55 (d, J=13.6 Hz, 1H), 4.22 (d, J=12.8 Hz, 1H), 4.02-4.17 (m, 2H), 3.93 (t, J=5.8 Hz, 2H), 3.75 (br. s., 2H), 3.12-3.35 (m, 1H), 3.02-3.12 (m, 1H), 2.91 (t, J=5.6 Hz, 3H), 2.33-2.47 (m, 1H), 1.83 (d, J=12.8 Hz, 2H), 1.75 (d, J=10.5 Hz, 1H), 1.67 (br. s., 1H), 1.50-1.61 (m, 2H), 1.26-1.40 (m, 7H). LC-MS: m/z 477.1 (M+H)$^+$.

(R)-8-cyclohexyl-6-(4-(imidazo[1,2-a]pyridine-3-carbonyl)-3-methylpiperazin-1-yl)-3,4-dihydro-1H-pyrano[3,4-c]pyridine-5-carbonitrile (Compound 227)

$^1$H NMR (CHLOROFORM-d) δ 9.02 (d, J=6.8 Hz, 1H), 7.94 (s, 1H), 7.77 (d, J=8.0 Hz, 1H), 7.40 (t, J=7.7 Hz, 1H), 7.00 (t, J=6.9 Hz, 1H), 4.93 (br. s., 1H), 4.71 (s, 2H), 4.49 (d, J=13.1 Hz, 1H), 4.14-4.32 (m, 2H), 3.87-4.00 (m, 2H), 3.65 (br. s., 1H), 3.32 (dd, J=13.1, 3.5 Hz, 1H), 3.17 (td, J=12.5, 3.4 Hz, 1H), 2.94 (t, J=5.6 Hz, 2H), 2.42 (tt, J=11.0, 3.7 Hz, 1H), 1.84 (d, J=12.3 Hz, 2H), 1.75 (d, J=9.8 Hz, 1H), 1.56-1.62 (m, 2H), 1.53 (d, J=6.8 Hz, 3H), 1.28-1.42 (m, 5H). LC-MS: m/z 385.1 (M+H)$^+$.

(R)-8-cyclohexyl-6-(3-methyl-4-(3-methylfuran-2-carbonyl)piperazin-1-yl)-3,4-dihydro-1H-pyrano[3,4-c]pyridine-5-carbonitrile (Compound 186)

$^1$H NMR (CHLOROFORM-d) δ 7.34 (d, J=1.5 Hz, 1H), 6.34 (d, J=1.5 Hz, 1H), 4.62-4.85 (m, 3H), 4.13-4.42 (m, 3H), 3.94 (t, J=5.8 Hz, 2H), 3.51 (br. s., 1H), 3.32 (d, J=10.0 Hz, 1H), 3.06-3.21 (m, 1H), 2.93 (t, J=5.6 Hz, 2H), 2.42 (t,

J=11.3 Hz, 1H), 2.29 (s, 3H), 1.84 (d, J=12.5 Hz, 2H), 1.75 (d, J=10.5 Hz, 3H), 1.43 (d, J=6.5 Hz, 3H), 1.27-1.38 (m, 5H). LC-MS: m/z 449.0 (M+H)+.

6-(4-(1H-indole-5-carbonyl)piperazin-1-yl)-8-cyclohexyl-3,4-dihydro-1H-pyrano[3,4-c]pyridine-5-carbonitrile (Compound 122)

¹H NMR (CHLOROFORM-d) δ 8.74 (br. s., 1H), 7.78 (s, 1H), 7.36-7.43 (m, 1H), 7.25-7.32 (m, 2H), 6.51-6.67 (m, 1H), 4.72 (s, 2H), 3.95 (t, J=5.8 Hz, 3H), 3.84 (br. s., 2H), 3.70 (br. s., 5H), 2.94 (t, J=5.6 Hz, 2H), 2.43 (tt, J=11.0, 3.6 Hz, 1H), 1.81-1.89 (m, 2H), 1.55-1.81 (m, 5H), 1.30-1.41 (m, 3H). LC-MS: m/z 470.2 (M+H)+.

6-(4-(1H-indole-3-carbonyl)piperazin-1-yl)-8-cyclohexyl-3,4-dihydro-1H-pyrano[3,4-c]pyridine-5-carbonitrile (Compound 118)

¹H NMR (CHLOROFORM-d) δ 8.78 (br. s., 1H), 7.72 (d, J=7.3 Hz, 1H), 7.58 (d, J=2.3 Hz, 1H), 7.39-7.47 (m, 1H), 7.20-7.26 (m, 2H), 4.71 (s, 2H), 3.94 (t, J=5.8 Hz, 2H), 3.88 (br. s., 4H), 3.69 (br. s., 4H), 2.93 (t, J=5.6 Hz, 2H), 2.34-2.48 (m, 1H), 1.83 (d, J=12.8 Hz, 2H), 1.74 (d, J=10.8 Hz, 1H), 1.67 (br. s., 2H), 1.53-1.60 (m, 2H), 1.28-1.38 (m, 3H). LC-MS: m/z 469.9 (M+H)+.

8-cyclohexyl-6-(4-(3-methylfuran-2-carbonyl)piperazin-1-yl)-3,4-dihydro-1H-pyrano[3,4-c]pyridine-5-carbonitrile (Compound 129)

¹H NMR (CHLOROFORM-d) δ 7.38 (d, J=1.5 Hz, 1H), 6.36 (d, J=1.5 Hz, 1H), 4.72 (s, 2H), 3.96 (t, J=5.8 Hz, 2H), 3.85-3.93 (m, 4H), 3.68-3.81 (m, 4H), 2.95 (t, J=5.6 Hz, 2H), 2.38-2.50 (m, 1H), 2.32 (s, 3H), 1.86 (d, J=12.3 Hz, 2H), 1.56-1.81 (m, 5H), 1.29-1.44 (m, 3H). LC-MS: m/z 435.1 (M+H)+.

(R)-8-cyclohexyl-6-(4-(2-(2-fluorophenyl)acetyl)-3-methylpiperazin-1-yl)-3,4-dihydro-1H-pyrano[3,4-c]pyridine-5-carbonitrile (Compound 188)

¹H NMR (CHLOROFORM-d) δ 7.27-7.37 (m, 1H), 7.21-7.26 (m, 1H), 7.03-7.15 (m, 2H), 4.91 (br. s., 1H), 4.69 (s, 2H), 4.18-4.27 (m, 1H), 4.14 (d, J=13.3 Hz, 1H), 3.86-4.04 (m, 2H), 3.71-3.86 (m, 3H), 3.53 (t, J=11.2 Hz, 1H), 3.17 (t, J=14.7 Hz, 1H), 2.87-3.04 (m, 3H), 2.40 (tt, J=11.1, 3.7 Hz, 1H), 1.84 (d, J=12.5 Hz, 2H), 1.75 (d, J=10.0 Hz, 1H), 1.65 (br. s., 4H), 1.27-1.37 (m, 6H). LC-MS: m/z 477.1 (M+H)+.

6-(4-(1H-indole-6-carbonyl)piperazin-1-yl)-8-cyclohexyl-3,4-dihydro-1H-pyrano[3,4-c]pyridine-5-carbonitrile (Compound 123)

¹H NMR (CHLOROFORM-d) δ 8.54 (br. s., 1H), 7.68 (d, J=8.0 Hz, 1H), 7.60 (br. s., 1H), 7.34 (d, J=2.5 Hz, 1H), 7.21 (d, J=8.0 Hz, 1H), 6.61 (d, J=2.8 Hz, 1H), 4.72 (s, 2H), 3.70-3.97 (m, 10H), 2.95 (t, J=5.6 Hz, 2H), 2.38-2.52 (m, 1H), 1.85 (d, J=12.5 Hz, 2H), 1.55-1.80 (m, 5H), 1.30-1.41 (m, 3H). LC-MS: m/z 469.9 (M+H)+.

(R)-8-cyclohexyl-6-(3-methyl-4-(pyrazolo[1,5-a]pyrimidine-3-carbonyl)piperazin-1-yl)-3,4-dihydro-1H-pyrano[3,4-c]pyridine-5-carbonitrile (Compound 261)

¹H NMR (CHLOROFORM-d) δ 8.71-8.79 (m, 1H), 8.64 (dd, J=4.0, 1.8 Hz, 1H), 8.43 (s, 1H), 6.96 (dd, J=6.9, 4.1 Hz, 1H), 4.70 (s, 3H), 4.11-4.41 (m, 3H), 3.88-3.98 (m, 2H), 3.57 (br. s., 1H), 3.43 (dd, J=13.1, 3.5 Hz, 1H), 3.26 (t, J=11.5 Hz, 1H), 2.86-2.98 (m, 2H), 2.41 (tt, J=11.0, 3.7 Hz, 1H), 1.83 (d, J=12.8 Hz, 2H), 1.74 (d, J=11.3 Hz, 1H), 1.69 (br. s., 1H), 1.54-1.63 (m, 2H), 1.43 (d, J=6.8 Hz, 3H), 1.26-1.38 (m, 4H). LC-MS: m/z 486.2 (M+H)+.

(R)-8-cyclohexyl-6-(3-methyl-4-(oxazole-4-carbonyl)piperazin-1-yl)-3,4-dihydro-1H-pyrano[3,4-c]pyridine-5-carbonitrile (Compound 226)

¹H NMR (CHLOROFORM-d) δ 8.20-8.26 (m, 1H), 7.86-7.93 (m, 1H), 4.81-5.04 (m, 1H), 4.70 (s, 3H), 4.15-4.34 (m, 2H), 3.87-3.97 (m, 2H), 3.55-3.76 (m, 1H), 3.30-3.37 (m, 1H), 3.09-3.24 (m, 1H), 2.93 (t, J=5.6 Hz, 2H), 2.41 (tt, J=11.0, 3.7 Hz, 1H), 1.81-1.87 (m, 2H), 1.75 (d, J=10.8 Hz, 2H), 1.54-1.63 (m, 2H), 1.43 (d, J=6.5 Hz, 3H), 1.27-1.38 (m, 4H). LC-MS: m/z 436.1 (M+H)+.

8-cyclopentyl-6-(4-(furan-2-carbonyl)piperazin-1-yl)-3,4-dihydro-1H-pyrano[3,4-c]pyridine-5-carbonitrile (Compound 124)

¹H NMR (CHLOROFORM-d) δ 7.48-7.60 (m, 1H), 7.07 (d, J=3.5 Hz, 1H), 6.52 (dd, J=3.3, 1.8 Hz, 1H), 4.74 (s, 2H), 3.85-4.14 (m, 6H), 3.67-3.83 (m, 4H), 2.87-3.06 (m, 3H), 1.76-1.99 (m, 5H), 1.62-1.75 (m, 3H). LC-MS: m/z 406.9 (M+H)+.

8-cyclopentyl-6-((3S,5R)-4-(furan-2-carbonyl)-3,5-dimethylpiperazin-1-yl)-3,4-dihydro-1H-pyrano[3,4-c]pyridine-5-carbonitrile (Compound 126)

¹H NMR (CHLOROFORM-d) δ 7.52 (d, J=1.0 Hz, 1H), 7.07 (d, J=3.3 Hz, 1H), 6.52 (dd, J=3.5, 1.8 Hz, 1H), 4.87 (br. s., 2H), 4.74 (s, 2H), 4.28 (d, J=12.8 Hz, 2H), 3.97 (t, J=5.8 Hz, 2H), 3.22 (dd, J=12.9, 4.4 Hz, 2H), 2.91-3.03 (m, 3H), 1.80-1.96 (m, 5H), 1.56 (d, J=6.8 Hz, 6H), 1.33 (br. s., 3H). LC-MS: m/z 435.1 (M+H)+.

(R)-6-(4-(furan-3-carbonyl)-3-methylpiperazin-1-yl)-8-isopropyl-3,4-dihydro-1H-pyrano[3,4-c]pyridine-5-carbonitrile (Compound 140)

¹H NMR (CHLOROFORM-d) δ 7.71-7.80 (m, 1H), 7.47 (t, J=1.6 Hz, 1H), 6.54-6.67 (m, 1H), 4.72 (s, 3H), 4.14-4.42 (m, 3H), 3.89-4.01 (m, 2H), 3.50 (br. s., 1H), 3.27 (dd, J=12.9, 3.4 Hz, 1H), 3.10 (td, J=12.5, 3.5 Hz, 1H), 2.95 (t, J=5.6 Hz, 2H), 2.83 (dt, J=13.3, 6.7 Hz, 1H), 1.44 (d, J=6.8 Hz, 3H), 1.15-1.24 (m, 6H). LC-MS: m/z 395.0 (M+H)+.

8-isopropyl-6-(4-(2-methylfuran-3-carbonyl)-2-phenylpiperazin-1-yl)-3,4-dihydro-1H-pyrano[3,4-c]pyridine-5-carbonitrile (Compound 177)

¹H NMR (CHLOROFORM-d) δ 7.38 (br. s., 1H), 7.22-7.33 (m, 5H), 7.18 (d, J=6.5 Hz, 1H), 5.26 (br. s., 1H), 4.58-4.76 (m, 2H), 4.15 (br. s., 1H), 3.86-4.05 (m, 3H), 3.78 (br. s., 3H), 3.47-3.61 (m, 1H), 2.88-3.03 (m, 2H), 2.62-2.77 (m, 1H), 2.30-2.43 (m, 3H), 1.16 (d, J=6.5 Hz, 3H), 0.85 (br. s., 3H). LC-MS: m/z 471.1 (M+H)+.

6-(4-(1H-indole-3-carbonyl)piperazin-1-yl)-8-isopropyl-3,4-dihydro-1H-pyrano[3,4-c]pyridine-5-carbonitrile (Compound 104)

¹H NMR (CHLOROFORM-d) δ 9.18 (br. s., 1H), 7.76 (d, J=7.5 Hz, 1H), 7.36-7.50 (m, 2H), 7.14-7.34 (m, 2H), 4.74

(s, 2H), 3.83-4.01 (m, 6H), 3.73 (br. s., 4H), 2.96 (br. s., 2H), 2.75-2.89 (m, 1H), 1.21 (d, J=6.5 Hz, 6H). LC-MS: m/z 430.4 (M+H)+.

6-(4-(furan-2-carbonyl)-2-phenylpiperazin-1-yl)-8-isopropyl-3,4-dihydro-1H-pyrano[3,4-c]pyridine-5-carbonitrile (Compound 111)

$^1$H NMR (CHLOROFORM-d) δ 7.51 (dd, J=1.8, 0.8 Hz, 1H), 7.37 (br. s., 2H), 7.25 (t, J=7.4 Hz, 2H), 7.13-7.20 (m, 1H), 7.06 (d, J=3.5 Hz, 1H), 6.51 (dd, J=3.5, 1.8 Hz, 1H), 5.20 (br. s., 1H), 4.55-4.74 (m, 2H), 4.31 (br. s., 2H), 3.78-4.08 (m, 5H), 3.61 (br. s., 1H), 2.89-3.01 (m, 2H), 2.57-2.77 (m, 1H), 1.09-1.19 (m, 3H), 0.81 (d, J=6.3 Hz, 3H). LC-MS: m/z 456.9 (M+H)+.

6-(4-(3,4-dichlorobenzoyl)piperazin-1-yl)-8-isopropyl-3,4-dihydro-1H-pyrano[3,4-c]pyridine-5-carbonitrile (Compound 105)

$^1$H NMR (CHLOROFORM-d) δ 7.48-7.63 (m, 2H), 7.29-7.33 (m, 1H), 4.73 (s, 2H), 3.96 (t, J=5.8 Hz, 4H), 3.62-3.74 (m, 6H), 2.96 (t, J=5.8 Hz, 2H), 2.83 (dt, J=13.4, 6.5 Hz, 1H), 1.21 (d, J=6.5 Hz, 6H). LC-MS: m/z 459.1 (M+H)+.

6-(4-(2,4-dichlorobenzoyl)piperazin-1-yl)-8-isopropyl-3,4-dihydro-1H-pyrano[3,4-c]pyridine-5-carbonitrile (Compound 106)

$^1$H NMR (CHLOROFORM-d) δ 7.47 (d, J=1.8 Hz, 1H), 7.33-7.38 (m, 1H), 7.26-7.31 (m, 1H), 4.72 (s, 2H), 3.99-4.09 (m, 1H), 3.86-3.98 (m, 3H), 3.70-3.81 (m, 2H), 3.56-3.70 (m, 2H), 3.43-3.52 (m, 1H), 3.33-3.42 (m, 1H), 2.95 (t, J=5.6 Hz, 2H), 2.83 (dt, J=13.3, 6.7 Hz, 1H), 1.20 (d, J=6.8 Hz, 6H). LC-MS: m/z 459.1 (M+H)+.

6-(4-(furan-2-carbonyl)-2,5-dimethylpiperazin-1-yl)-8-isopropyl-3,4-dihydro-1H-pyrano[3,4-c]pyridine-5-carbonitrile (Compound 114)

$^1$H NMR (CHLOROFORM-d) δ 7.50 (s, 1H), 7.05 (d, J=3.0 Hz, 1H), 6.50 (br. s., 1H), 4.65-4.95 (m, 4H), 4.29 (br. s., 1H), 4.17 (d, J=13.6 Hz, 1H), 3.94 (t, J=5.6 Hz, 2H), 3.59 (dd, J=13.6, 3.3 Hz, 2H), 2.92 (t, J=5.5 Hz, 2H), 2.81 (dt, J=13.4, 6.6 Hz, 1H), 1.43 (br. s., 3H), 1.31 (d, J=6.5 Hz, 3H), 1.18 (d, J=6.5 Hz, 3H), 1.19 (d, J=6.5 Hz, 3H). LC-MS: m/z 408.9 (M+H)+.

(R)-6-(4-(furan-2-carbonyl)-3-methylpiperazin-1-yl)-8-isopropyl-3,4-dihydro-1H-pyrano[3,4-c]pyridine-5-carbonitrile (Compound 139)

$^1$H NMR (CHLOROFORM-d) δ 7.52 (dd, J=1.8, 0.8 Hz, 1H), 7.05 (d, J=3.5 Hz, 1H), 6.51 (dd, J=3.5, 1.8 Hz, 1H), 4.88 (br. s., 1H), 4.72 (s, 2H), 4.49 (d, J=13.3 Hz, 1H), 4.29 (d, J=12.0 Hz, 1H), 4.14-4.24 (m, 1H), 3.92-4.03 (m, 2H), 3.55 (br. s., 1H), 3.35 (dd, J=13.1, 3.8 Hz, 1H), 3.19 (td, J=12.4, 3.5 Hz, 1H), 2.95 (t, J=5.6 Hz, 2H), 2.72-2.88 (m, 1H), 1.46 (d, J=6.8 Hz, 3H), 1.15-1.25 (m, 6H). LC-MS: m/z 395.0 (M+H)+.

8-isopropyl-6-(4-(2-methylfuran-3-carbonyl)piperazin-1-yl)-3,4-dihydro-1H-pyrano[3,4-c]pyridine-5-carbonitrile (Compound 113)

$^1$H NMR (CHLOROFORM-d) δ 7.25-7.34 (m, 1H), 6.39 (d, J=1.8 Hz, 1H), 4.72 (s, 2H), 3.95 (t, J=5.8 Hz, 2H), 3.80 (br. s., 4H), 3.68 (br. s., 4H), 2.95 (t, J=5.6 Hz, 2H), 2.82 (dt, J=13.4, 6.7 Hz, 1H), 2.42 (s, 3H), 1.16-1.25 (m, 6H). LC-MS: m/z 394.9 (M+H)+.

6-(4-(furan-2-carbonyl)-3,5-dimethylpiperazin-1-yl)-8-p-tolylisochroman-5-carbonitrile (Compound 112)

$^1$H NMR (CHLOROFORM-d) δ 7.52-7.58 (m, 1H), 7.37-7.44 (m, 2H), 7.24-7.35 (m, 2H), 7.07 (dd, J=3.5, 0.8 Hz, 1H), 6.52 (dd, J=3.5, 1.8 Hz, 1H), 4.88 (br. s., 2H), 4.70 (s, 2H), 4.31 (d, J=13.1 Hz, 2H), 4.05 (t, J=5.9 Hz, 2H), 3.25 (dd, J=12.9, 4.1 Hz, 2H), 3.07 (t, J=5.9 Hz, 2H), 2.44 (s, 3H), 1.59 (d, J=7.0 Hz, 6H). LC-MS: m/z 456.9 (M+H)+.

(R)-8-cyclopropyl-6-(3-isopropyl-4-(3-methoxypropanoyl)piperazin-1-yl)-3,3-dimethyl-3,4-dihydro-1H-pyrano[3,4-c]pyridine-5-carbonitrile (Compound 270)

$^1$H NMR (CHLOROFORM-d) δ 4.77-4.89 (m, 2H), 4.65 (d, J=10.3 Hz, 0.5H), 4.40 (d, J=10.3 Hz, 0.5H), 4.27-4.36 (m, 1H), 4.07-4.26 (m, 1H), 3.64-3.87 (m, 2.5H), 3.39-3.58 (m, 1H), 3.36 (d, J=3.8 Hz, 3H), 2.90-3.09 (m, 2.5H), 2.76 (s, 2H), 2.52-2.74 (m, 2H), 2.19-2.30 (m, 0.5H), 2.10 (dt, J=10.4, 6.7 Hz, 0.5H), 1.67-1.74 (m, 1H), 1.31 (d, J=2.5 Hz, 6H), 1.05-1.17 (m, 2H), 0.97-1.04 (m, 5H), 0.84-0.92 (d, J=6.8 Hz, 1.5H), 0.82 (d, J=6.8 Hz, 1.5H). LC-MS: m/z 441.2 (M+H)+.

(R)-8-cyclopropyl-6-(3-ethyl-4-(3-methoxypropanoyl)piperazin-1-yl)-3,3-dimethyl-3,4-dihydro-1H-pyrano[3,4-c]pyridine-5-carbonitrile (Compound 297)

$^1$H NMR (CHLOROFORM-d) δ 4.83 (s, 2H), 4.69 (br. s., 0.5H), 4.58 (d, J=12.8 Hz, 0.5H), 4.05-4.22 (m, 2H), 3.90 (br. s., 0.5H), 3.67-3.81 (m, 2.5H), 3.42-3.54 (m, 0.5H), 3.36 (s, 3H), 2.88-3.18 (m, 2.5H), 2.76 (s, 2H), 2.51-2.74 (m, 2H), 1.66-1.80 (m, 3H), 1.31 (d, J=1.5 Hz, 6H), 1.09-1.17 (m, 2H), 0.99-1.04 (m, 2H), 0.90 (dt, J=18.1, 7.5 Hz, 3H). LC-MS: m/z 427.0 (M+H)+.

(R)-8-cyclopropyl-6-(3-isopropyl-4-(3-(methylthio)propanoyl)piperazin-1-yl)-3,3-dimethyl-3,4-dihydro-1H-pyrano[3,4-c]pyridine-5-carbonitrile (Compound 269)

$^1$H NMR (CHLOROFORM-d) δ 4.76-4.89 (m, 2H), 4.64 (d, J=9.2 Hz, 0.5H), 4.39 (d, J=10.3 Hz, 0.5H), 4.32 (d, J=13.6 Hz, 1H), 4.10-4.24 (m, 1H), 3.74 (d, J=13.6 Hz, 0.5H), 3.39-3.54 (m, 1H), 2.90-3.08 (m, 2.5H), 2.80-2.89 (m, 2H), 2.76 (s, 2H), 2.59-2.72 (m, 2H), 2.20-2.33 (m, 0.5H), 2.04-2.13 (m, 0.5H), 1.67-1.75 (m, 1H), 1.31 (d, J=2.3 Hz, 6H), 1.05-1.19 (m, 2H), 0.96-1.05 (m, 5H), 0.88 (d, J=6.8 Hz, 1.5H), 0.82 (d, J=6.8 Hz, 1.5H). LC-MS: m/z 457.2 (M+H)+.

(R)-8-cyclopropyl-6-(4-(2-cyclopropylacetyl)-3-isopropylpiperazin-1-yl)-3,3-dimethyl-3,4-dihydro-1H-pyrano[3,4-c]pyridine-5-carbonitrile (Compound 382)

$^1$H NMR (CHLOROFORM-d) δ 4.76-4.89 (m, 2H), 4.66-4.68 (m, 0.5H), 4.32-4.43 (m, 1.5H), 4.18 (t, J=9.0 Hz, 1H), 3.73 (d, J=13.3 Hz, 0.5H), 3.38-3.51 (m, 1H), 2.89-3.12 (m, 2.5H), 2.76 (s, 2H), 2.10-2.43 (m, 3H), 1.64-1.75 (m, 1H), 1.31 (d, J=2.3 Hz, 6H), 1.06-1.18 (m, 3H), 0.96-1.05 (m,

5H), 0.79-0.91 (m, 3H), 0.59 (d, J=7.5 Hz, 2H), 0.13-0.29 (m, 2H). LC-MS: m/z 437.3 (M+H)⁺.

(R)-8-cyclopropyl-6-(3-ethyl-4-(2-methylfuran-3-carbonyl)piperazin-1-yl)-3,3-dimethyl-3,4-dihydro-1H-pyrano[3,4-c]pyridine-5-carbonitrile (Compound 237)

¹H NMR (CHLOROFORM-d) δ 7.28 (d, J=2.0 Hz, 1H), 6.32-6.40 (m, 1H), 4.83 (s, 2H), 3.85-4.82 (m, 4H), 3.34 (br. s., 1H), 3.13 (dd, J=13.2, 3.6 Hz, 1H), 2.90-3.04 (m, 1H), 2.77 (s, 2H), 2.37-2.40 (m, 3H), 1.83-1.96 (m, 1H), 1.66-1.79 (m, 2H), 1.29-1.35 (m, 6H), 1.08-1.15 (m, 2H), 0.98-1.04 (m, 2H), 0.84-0.94 (m, 3H). LC-MS: m/z 449.1 (M+H)⁺.

(R)-8-cyclopropyl-6-(3-ethyl-4-(2-(thiophen-2-yl)acetyl)piperazin-1-yl)-3,3-dimethylisochroman-5-carbonitrile (Compound 236)

¹H NMR (CHLOROFORM-d) δ7.20 (dd, J=5.1, 1.1 Hz, 1H), 6.87-6.99 (m, 2H), 4.82 (s, 2H), 4.69 (br. s., 0.5H), 4.46-4.64 (m, 0.5H), 4.01-4.17 (m, 2H), 3.87-3.94 (m, 1H), 3.77 (d, J=13.1 Hz, 1H), 3.39-3.56 (m, 1H), 3.01-3.14 (m, 1H), 2.81-3.01 (m, 2H), 2.72-2.79 (m, 2H), 1.66-1.84 (m, 3H), 1.30 (d, J=2.5 Hz, 6H), 1.10 (d, J=4.0 Hz, 2H), 0.98-1.05 (m, 2H), 0.82-0.94 (m, 3H). LC-MS: m/z 465.1 (M+H)⁺.

(R)-8-cyclopropyl-6-(3-isopropyl-4-(2-(thiophen-2-yl)acetyl)piperazin-1-yl)-3,3-dimethylisochroman-5-carbonitrile (Compound 194)

¹H NMR (CHLOROFORM-d) δ7.16-7.26 (m, 1H), 6.85-6.99 (m, 2H), 4.75-4.88 (m, 2H), 4.64-4.65 (m, 0.5H), 4.40 (d, J=10.5 Hz, 0.51H), 4.24-4.33 (m, 1H), 4.08-4.18 (m, 1H), 3.79-4.05 (m, 3H), 3.32-3.50 (m, 1H), 2.92-3.04 (m, 1H), 2.78-2.90 (m, 1H), 2.75 (s, 2H), 2.06-2.275 (m, 1H), 1.62-1.71 (m, 1H), 1.31 (d, J=3.0 Hz, 6H), 0.93-1.19 (m, 7H), 0.76-0.90 (m, 3H). LC-MS: m/z 479.1 (M+H)⁺.

(R)-8-cyclopropyl-6-(3-isopropyl-4-(2-methylfuran-3-carbonyl)piperazin-1-yl)-3,3-dimethylisochroman-5-carbonitrile (Compound 181)

¹H NMR (CHLOROFORM-d) δ7.24-7.34 (m, 1H), 6.35 (br. s., 1H), 4.78-4.92 (m, 2H), 4.13-4.56 (m, 3H), 3.87 (d, J=12.3 Hz, 0.5H), 3.46-3.54 (m, 1H), 2.92-3.16 (m, 2.5H), 2.78 (s, 2H), 2.35-2.48 (m, 3H), 2.18-2.32 (m, 1H), 1.69-1.77 (m, 1H), 1.33 (d, J=2.3 Hz, 6H), 1.00-1.21 (m, 6H), 0.79-0.98 (m, 4H). LC-MS: m/z 463.1 (M+H)⁺.

(R)-8-cyclopropyl-6-(3-ethyl-4-(furan-3-carbonyl)piperazin-1-yl)-3,3-dimethylisochroman-5-carbonitrile (Compound 235)

¹H NMR (CHLOROFORM-d) δ 7.65-7.76 (m, 1H), 7.40-7.48 (m, 1H), 6.46-6.60 (m, 1H), 4.83 (s, 2H), 3.98-4.52 (m, 4H), 3.98 (br. s., 1H), 3.40 (br. s., 1H), 3.13 (dd, J=13.1, 3.8 Hz, 1H), 2.92-3.05 (m, 1H), 2.77 (s, 2H), 1.66-1.96 (m, 3H), 1.29-1.38 (m, 6H), 1.08-1.15 (m, 2H), 0.98-1.04 (m, 2H), 0.85-0.96 (m, 3H). LC-MS: m/z 435.2 (M+H)⁺.

(R)-8-cyclopropyl-6-(3-isopropyl-4-(2-(pyridin-3-yl)acetyl)piperazin-1-yl)-3,3-dimethylisochroman-5-carbonitrile (Compound 265)

¹H NMR (CHLOROFORM-d) δ8.46-8.57 (m, 2H), 7.67 (d, J=7.5 Hz, 1H), 7.27-7.32 (m, 1H), 4.82 (s, 2H), 4.63-4.65 (m, 0.5H), 4.40 (d, J=10.3 Hz, 0.5H), 4.23-4.34 (m, 1H), 4.09-4.19 (m, 1H), 3.72-3.80 (m, 2.5H), 3.39-3.55 (m, 1H), 2.92-3.04 (m, 1H), 2.79-2.91 (m, 1.5H), 2.75 (s, 2H), 2.07-2.30 (m, 1H), 1.66-1.73 (m, 1H), 1.29-1.33 (m, 6H), 0.96-1.16 (m, 7H), 0.88 (d, J=6.8 Hz, 1.5H), 0.79 (d, J=6.8 Hz, 1.5H). LC-MS: m/z 474.2 (M+H)⁺.

(R)-8-cyclopropyl-3,3-dimethyl-6-(3-methyl-4-(2-methylfuran-3-carbonyl)piperazin-1-yl)isochroman-5-carbonitrile (Compound 230)

¹H NMR (CHLOROFORM-d) δ7.27 (d, J=2.5 Hz, 1H), 6.35 (d, J=2.0 Hz, 1H), 4.52-5.22 (m, 3H), 3.98-4.28 (m, 3H), 3.41 (br. s., 1H), 3.15 (dd, J=12.9, 3.4 Hz, 1H), 2.97 (td, J=12.5, 3.5 Hz, 1H), 2.77 (s, 2H), 2.35-2.45 (m, 3H), 1.66-1.75 (m, 1H), 1.38 (d, J=6.8 Hz, 3H), 1.31 (s, 6H), 1.09-1.15 (m, 2H), 0.98-1.04 (m, 2H). LC-MS: m/z 435.1 (M+H)⁺.

(R)-8-cyclopropyl-3,3-dimethyl-6-(3-methyl-4-(2-(thiophen-2-yl)acetyl)piperazin-1-yl)isochroman-5-carbonitrile (Compound 231)

¹H NMR (CHLOROFORM-d) δ7.16-7.24 (m, 1H), 6.85-6.99 (m, 2H), 4.89 (br. s., 0.5H), 4.82 (s, 2H), 4.51-4.54 (m, 0.5H), 4.10-4.22 (m, 0.5H), 3.97-4.12 (m, 2H), 3.88-3.97 (m, 2H), 3.74 (d, J=13.3 Hz, 0.5H), 3.52 (t, J=11.9 Hz, 0.5H), 2.99-3.22 (m, 1.5H), 2.82-2.96 (m, 1H), 2.76 (s, 2H), 1.68-1.75 (m, 1H), 1.26-1.36 (m, 9H), 1.07-1.15 (m, 2H), 0.95-1.04 (m, 2H). LC-MS: m/z 451.1 (M+H)⁺.

(R)-8-cyclopropyl-6-(3-isopropyl-4-(3-phenoxypropanoyl)piperazin-1-yl)-3,3-dimethylisochroman-5-carbonitrile (Compound 366)

¹H NMR (CHLOROFORM-d) δ7.25-7.32 (m, 2H), 6.84-7.02 (m, 3H), 4.76-4.89 (m, 2H), 4.67 (d, J=10.5 Hz, 0.5H), 4.42 (d, J=10.5 Hz, 0.5H), 4.29-4.38 (m, 3H), 4.10-4.25 (m, 1H), 3.87 (d, J=13.6 Hz, 0.5H), 3.59 (d, J=10.3 Hz, 0.5H), 3.48 (td, J=12.8, 3.0 Hz, 0.5H), 2.84-3.10 (m, 4.5H), 2.71-2.79 (m, 2H), 2.29 (dt, J=10.3, 6.7 Hz, 0.5H), 2.05-2.18 (m, 0.5H), 1.67-1.76 (m, 1H), 1.32 (d, J=2.3 Hz, 6H), 1.07-1.18 (m, 2H), 0.96-1.05 (m, 5H), 0.89-0.96 (m, 1.5H), 0.83 (d, J=6.8 Hz, 1.5H). LC-MS: m/z 503.2 (M+H)⁺.

(R)-8-cyclopropyl-6-(3-isopropyl-4-(2-(pyridin-2-yl)acetyl)piperazin-1-yl)-3,3-dimethylisochroman-5-carbonitrile (Compound 211)

¹H NMR (CHLOROFORM-d) δ8.46-8.62 (m, 1H), 7.66 (t, J=7.7 Hz, 1H), 7.39 (t, J=7.4 Hz, 1H), 7.19 (dd, J=6.9, 4.4 Hz, 1H), 4.76-4.92 (m, 2H), 4.61-4.64 (m, 0.5H), 4.37 (d, J=10.5 Hz, 0.5H), 4.24-4.34 (m, 1H), 4.02-4.19 (m, 2H), 3.99 (d, J=5.3 Hz, 1H), 3.79-3.95 (m, 1H), 3.31-3.43 (m, 0.5H), 2.87-3.02 (m, 1.5H), 2.82 (dd, J=12.9, 3.4 Hz, 1H), 2.72-2.78 (m, 2H), 1.99-2.27 (m, 2H), 1.64-1.75 (m, 1H), 1.31 (d, J=3.0 Hz, 6H), 0.95-1.18 (m, 7H), 0.79 (dd, J=12.8, 6.8 Hz, 3H). LC-MS: m/z 474.3 (M+H)⁺.

(R)-8-cyclopropyl-6-(3-isopropyl-4-(oxazole-4-carbonyl)piperazin-1-yl)-3,3-dimethylisochroman-5-carbonitrile (Compound 209)

¹H NMR (CHLOROFORM-d) δ8.23 (d, J=9.0 Hz, 1H), 7.89 (s, 1H), 4.76-4.96 (m, 3H), 4.61-4.64 (m, 0.5H), 4.36-4.51 (m, 1.5H), 4.15-4.32 (m, 1H), 3.44-3.60 (m, 0.5H), 3.02-3.20 (m, 2.5H), 2.77 (s, 2H), 2.19-2.34 (m, 1H), 1.66-1.74 (m, 1H), 1.29-1.35 (m, 6H), 0.82-1.18 (m, 10H). LC-MS: m/z 450.2 (M+H)+.

(S)-8-cyclopropyl-6-(4-(furan-2-carbonyl)-3-phenylpiperazin-1-yl)-3,3-dimethylisochroman-5-carbonitrile (Compound 273)

$^1$H NMR (CHLOROFORM-d) δ7.48 (s, 1H), 7.37-7.44 (m, 2H), 7.30-7.36 (m, 2H), 7.27 (br. s., 1H), 7.23-7.26 (m, 1H), 6.99 (br. s., 1H), 6.41-6.49 (m, 1H), 5.87 (t, J=4.1 Hz, 1H), 4.76-4.88 (m, 2H), 4.59 (d, J=13.1 Hz, 1H), 4.47 (d, J=11.0 Hz, 1H), 4.20 (d, J=12.0 Hz, 1H), 3.85 (dd, J=13.8, 4.5 Hz, 1H), 3.60 (br. s., 1H), 3.42-3.52 (m, 1H), 2.75 (s, 2H), 1.67-1.75 (m, 1H), 1.31 (d, J=1.8 Hz, 6H), 1.06-1.20 (m, 2H), 1.02 (dd, J=8.0, 3.5 Hz, 2H). LC-MS: m/z 483.1 (M+H)+.

8-cyclopropyl-6-((3R)-3-isopropyl-4-(tetrahydrofuran-3-carbonyl)piperazin-1-yl)-3,3-dimethylisochroman-5-carbonitrile (Compound 266)

$^1$H NMR (CHLOROFORM-d) δ4.78-4.90 (m, 2H), 4.28-4.46 (m, 1.5H), 4.12-4.24 (m, 1H), 3.81-4.09 (m, 4.5H), 3.40-3.60 (m, 1H), 3.24-3.36 (m, 1H), 2.92-3.07 (m, 2H), 2.76 (s, 2H), 2.22-2.34 (m, 1H), 1.98-2.21 (m, 3H), 1.69-1.76 (m, 1H), 1.31 (d, J=2.3 Hz, 6H), 0.95-1.19 (m, 6H), 0.77-0.92 (m, 4H). LC-MS: m/z 453.3 (M+H)+.

(R)-8-cyclopropyl-6-(3-isopropyl-4-(thiophene-3-carbonyl)piperazin-1-yl)-3,3-dimethylisochroman-5-carbonitrile (Compound 255)

$^1$H NMR (CHLOROFORM-d) δ7.45-7.60 (m, 1H), 7.37 (dd, J=5.0, 3.0 Hz, 1H), 7.11-7.22 (m, 1H), 4.77-4.90 (m, 2H), 4.10-4.55 (m, 3H), 3.85 (d, J=10.8 Hz, 0.5H), 3.50 (br. s., 1H), 3.07 (d, J=11.0 Hz, 2H), 2.87-3.03 (m, 0.5H), 2.76 (s, 2H), 2.20-2.33 (m, 1H), 1.65-1.77 (m, 1H), 1.31 (d, J=2.0 Hz, 6H), 0.93-1.18 (m, 8H), 0.78-0.93 (m, 2H). LC-MS: m/z 465.2 (M+H)+.

(R)-8-cyclopropyl-6-(3-ethyl-4-(thiophene-3-carbonyl)piperazin-1-yl)-3,3-dimethylisochroman-5-carbonitrile (Compound 292)

$^1$H NMR (CHLOROFORM-d) δ7.47-7.53 (m, 1H), 7.36 (dd, J=4.9, 2.9 Hz, 1H), 7.18 (dd, J=5.0, 1.0 Hz, 1H), 4.83 (s, 2H), 4.16 (d, J=12.5 Hz, 3H), 3.42 (br. s., 1H), 3.14 (d, J=11.0 Hz, 1H), 2.92-3.05 (m, 1H), 2.77 (s, 2H), 1.64-2.02 (m, 4H), 1.29-1.35 (m, 6H), 1.07-1.15 (m, 2H), 0.98-1.05 (m, 2H), 0.77-0.98 (m, 3H). LC-MS: m/z 451.1 (M+H)+.

methyl 4-(5-cyano-8-cyclopropyl-3,3-dimethylisochroman-6-yl)-1-(furan-3-carbonyl)piperazine-2-carboxylate (Compound 387)

$^1$H NMR (CHLOROFORM-d) δ7.79 (br. s., 1H), 7.46 (s, 1H), 6.63 (br. s., 1H), 5.39 (br. s., 1H), 4.83 (s, 2H), 4.66 (d, J=11.5 Hz, 1H), 4.01-4.21 (m, 3H), 3.73 (s, 3H), 3.28 (d, J=11.0 Hz, 1H), 3.03 (td, J=12.3, 3.5 Hz, 1H), 2.77 (s, 2H), 1.63-1.80 (m, 1H), 1.29-1.39 (m, 6H), 1.14 (dd, J=8.0, 4.0 Hz, 2H), 1.03 (dt, J=5.1, 2.7 Hz, 2H). LC-MS: m/z 465.2 (M+H)+.

(R)-8-cyclopropyl-6-(3-isopropyl-4-(2-(2-methoxyphenyl)acetyl)piperazin-1-yl)-3,3-dimethylisochroman-5-carbonitrile (Compound 208)

$^1$H NMR (CHLOROFORM-d) δ7.18-7.27 (m, 2H), 6.79-6.96 (m, 2H), 4.76-4.88 (m, 2H), 4.64-4.66 (m, 0.5H), 4.41 (d, J=10.5 Hz, 0.5H), 4.20-4.34 (m, 1H), 4.03-4.17 (m, 1H), 3.81-3.91 (m, 3.5H), 3.71-3.81 (m, 1.5H), 3.51-3.71 (m, 1H), 3.29-3.42 (m, 0.5H), 2.89-3.01 (m, 1.5H), 2.71-2.84 (m, 3H), 2.06-2.25 (m, 1H), 1.66-1.71 (m, 1H), 1.30 (d, J=2.8 Hz, 6H), 0.95-1.18 (m, 7H), 0.84 (dd, J=16.6, 6.8 Hz, 3H). LC-MS: m/z 503.2 (M+H)+.

(R)-8-cyclopropyl-6-(4-(furan-2-carbonyl)-3-phenylpiperazin-1-yl)-3,3-dimethylisochroman-5-carbonitrile (Compound 272)

$^1$H NMR (CHLOROFORM-d) δ7.45-7.51 (m, 1H), 7.37-7.44 (m, 2H), 7.33 (t, J=7.5 Hz, 2H), 7.20-7.27 (m, 2H), 6.99 (br. s., 1H), 6.46 (br. s., 1H), 5.87 (br. s., 1H), 4.75-4.89 (m, 2H), 4.60 (d, J=13.1 Hz, 1H), 4.47 (d, J=11.5 Hz, 1H), 4.20 (d, J=11.8 Hz, 1H), 3.85 (dd, J=13.8, 4.3 Hz, 1H), 3.60 (br. s., 1H), 3.38-3.52 (m, 1H), 2.70-2.81 (m, 2H), 1.68-1.73 (m, 1H), 1.29-1.33 (m, 6H), 1.07-1.19 (m, 2H), 1.02 (dd, J=7.9, 3.4 Hz, 2H). LC-MS: m/z 483.1 (M+H)+.

(R)-8-cyclopropyl-6-(3-ethyl-4-(2-(pyridin-3-yl)acetyl)piperazin-1-yl)-3,3-dimethylisochroman-5-carbonitrile (Compound 294)

$^1$H NMR (CHLOROFORM-d) δ8.46-8.61 (m, 2H), 7.62-7.73 (m, 1H), 7.28-7.33 (m, 1H), 4.82 (s, 2H), 4.70 (d, J=11.8 Hz, 0.5H), 4.58 (d, J=13.3 Hz, 0.5H), 4.01-4.21 (m, 2H), 3.68-3.88 (m, 3H), 3.38-3.59 (m, 0.5H), 2.81-3.11 (m, 2.5H), 2.76 (s, 2H), 1.66-1.92 (m, 3H), 1.29-1.35 (m, 6H), 1.06-1.16 (m, 2H), 0.97-1.05 (m, 2H), 0.80-0.97 (m, 3H). LC-MS: m/z 460.1 (M+H)+.

(R)-8-cyclopropyl-6-(3-ethyl-4-(oxazole-4-carbonyl)piperazin-1-yl)-3,3-dimethylisochroman-5-carbonitrile (Compound 291)

$^1$H NMR (CHLOROFORM-d) δ8.24 (s, 1H), 7.89 (s, 1H), 5.13 (br. s., 0.5H), 4.80-4.98 (m, 3H), 4.49-4.69 (m, 0.5H), 4.20 (d, J=13.1 Hz, 2H), 3.49-3.56 (m, 0.5H), 3.22 (dd, J=13.3, 3.8 Hz, 1.5H), 2.99-3.12 (m, 1H), 2.77 (s, 2H), 1.60-1.87 (m, 3H), 1.32 (s, 6H), 1.10-1.17 (m, 2H), 0.99-1.05 (m, 2H), 0.80-0.98 (m, 3H). LC-MS: m/z 436.1 (M+H)+.

(R)-8-cyclopropyl-6-(3-ethyl-4-(2-(3-methoxyphenyl)acetyl)piperazin-1-yl)-3,3-dimethylisochroman-5-carbonitrile (Compound 296)

$^1$H NMR (CHLOROFORM-d) δ7.22-7.28 (m, 1H), 6.78-6.89 (m, 3H), 4.83 (s, 2H), 4.73 (br. s., 0.5H), 4.60-4.63 (m, 0.5H), 3.96-4.16 (m, 2H), 3.87 (br. s., 0.5H), 3.81 (d, J=2.3 Hz, 3H), 3.77 (s, 2H), 3.68-3.75 (m, 1H), 3.31-3.46 (m, 0.5H), 2.97-3.15 (m, 1H), 2.79-2.95 (m, 1H), 2.76 (s, 2H), 1.66-1.81 (m, 3H), 1.28-1.36 (m, 6H), 1.11 (d, J=2.5 Hz, 2H), 0.96-1.04 (m, 2H), 0.88 (td, J=7.3, 3.1 Hz, 3H). LC-MS: m/z 489.2 (M+H)+.

(R)-8-cyclopropyl-6-(3-isopropyl-4-(2-(3-methoxyphenyl)acetyl)piperazin-1-yl)-3,3-dimethylisochroman-5-carbonitrile (Compound 254)

$^1$H NMR (CHLOROFORM-d) δ7.18-7.28 (m, 1H), 6.71-6.88 (m, 3H), 4.73-4.89 (m, 2H), 4.41 (d, J=10.3 Hz, 0.5H), 4.40-4.42 (m, 0.5H), 4.02-4.30 (m, 2H), 3.69-3.87 (m, 6H), 3.48-3.51 (m, 0.5H), 3.33 (t, J=11.7 Hz, 0.5H), 2.88-3.00 (m, 1H), 2.64-2.81 (m, 3H), 2.04-2.22 (m, 1H), 1.64-1.75 (m,

1H), 1.30 (d, J=3.5 Hz, 6H), 0.94-1.16 (m, 7H), 0.75-0.88 (m, 3H). LC-MS: m/z 503.2 (M+H)⁺.

(R)-8-cyclopropyl-6-(3-ethyl-4-(2-(2-methoxyphenyl)acetyl)piperazin-1-yl)-3,3-dimethylisochroman-5-carbonitrile (Compound 295)

¹H NMR (CHLOROFORM-d) δ7.20-7.26 (m, 2H), 6.81-6.96 (m, 2H), 4.82 (s, 2H), 4.71 (br. s., 0.5H), 4.60 (d, J=13.1 Hz, 0.5H), 3.97-4.18 (m, 2H), 3.81-3.92 (m, 4H), 3.69-3.79 (m, 2H), 3.33-3.47 (m, 0.5H), 2.97-3.12 (m, 1H), 2.79-2.96 (m, 1.5H), 2.71-2.78 (m, 2H), 1.63-1.81 (m, 3H), 1.30 (d, J=2.8 Hz, 6H), 1.06-1.14 (m, 2H), 0.96-1.03 (m, 2H), 0.83-0.92 (m, 3H). LC-MS: m/z 489.2 (M+H)⁺.

(R)-8-cyclopropyl-6-(3-isopropyl-4-(4-methyloxazole-5-carbonyl)piperazin-1-yl)-3,3-dimethylisochroman-5-carbonitrile (Compound 210)

¹H NMR (CHLOROFORM-d) δ7.84 (s, 1H), 4.77-4.89 (m, 2H), 4.14-4.45 (m, 3H), 3.99 (d, J=12.5 Hz, 0.5H), 3.43-3.77 (m, 1H), 2.99-3.22 (m, 2.5H), 2.77 (s, 2H), 2.37-2.47 (m, 3H), 2.20-2.31 (m, 1H), 1.66-1.75 (m, 1H), 1.32 (d, J=2.3 Hz, 6H), 0.96-1.18 (m, 7H), 0.77-0.96 (m, 3H). LC-MS: m/z 464.1 (M+H)⁺.

methyl 4-(5-cyano-8-cyclopropyl-3,3-dimethylisochroman-6-yl)-1-(3-methoxypropanoyl)-piperazine-2-carboxylate (Compound 388)

¹H NMR (CHLOROFORM-d) δ5.16-5.35 (m, 1H), 4.83 (s, 2H), 4.62 (dt, J=13.6, 2.0 Hz, 1H), 4.11 (dd, J=12.7, 2.1 Hz, 1H), 3.71-3.91 (m, 3H), 3.61-3.70 (m, 2H), 3.34-3.41 (m, 3H), 3.27 (br. s., 1H), 3.21 (dd, J=13.4, 4.4 Hz, 1H), 3.04 (td, J=12.0, 3.5 Hz, 1H), 2.72-2.79 (m, 3H), 2.60-2.71 (m, 1H), 1.57-1.78 (m, 1H), 1.27-1.39 (m, 6H), 1.10-1.18 (m, 2H), 0.96-1.10 (m, 2H). LC-MS: m/z 457.3 (M+H)⁺.

(R)-8-cyclopropyl-6-(4-(furan-3-carbonyl)-3-methylpiperazin-1-yl)-3,3-dimethylisochroman-5-carbonitrile (Compound 164)

¹H NMR (CHLOROFORM-d) δ7.71-7.80 (m, 1H), 7.41-7.52 (m, 1H), 6.59 (dd, J=1.9, 0.9 Hz, 1H), 4.85 (s, 2H), 4.69 (br. s., 1H), 4.30 (br. s., 1H), 4.00-4.17 (m, 2H), 3.47 (br. s., 1H), 3.18 (dd, J=13.1, 3.5 Hz, 1H), 3.01 (td, J=12.5, 3.4 Hz, 1H), 2.79 (s, 2H), 1.69-1.77 (m, 1H), 1.40-1.50 (m, 3H), 1.33 (s, 6H), 1.08-1.19 (m, 2H), 0.98-1.07 (m, 2H). LC-MS: m/z 421.2 (M+H)⁺.

(R)-8-cyclopropyl-6-(3-ethyl-4-(2-(pyridin-2-yl)acetyl)piperazin-1-yl)-3,3-dimethylisochroman-5-carbonitrile (Compound 290)

¹H NMR (CHLOROFORM-d) δ8.44-8.63 (m, 1H), 7.67 (td, J=7.7, 1.5 Hz, 1H), 7.39 (t, J=8.4 Hz, 1H), 7.16-7.25 (m, 1H), 4.82 (s, 2H), 4.68 (br. s., 0.5H), 4.57 (d, J=13.3 Hz, 0.5H), 3.85-4.18 (m, 5H), 3.32-3.52 (m, 0.5H), 2.95-3.09 (m, 1H), 2.78-2.93 (m, 1.5H), 2.75 (s, 2H), 1.62-1.82 (m, 3H), 1.28-1.34 (m, 6H), 1.05-1.13 (m, 2H), 0.94-1.03 (m, 2H), 0.81-0.92 (m, 3H). LC-MS: m/z 460.1 (M+H)⁺.

(R)-8-cyclopropyl-6-(3-isopropyl-4-(1-methylcyclopropanecarbonyl)piperazin-1-yl)-3,3-dimethylisochroman-5-carbonitrile (Compound 377)

¹H NMR (CHLOROFORM-d) δ4.83 (s, 2H), 4.17-4.41 (m, 4H), 3.38-3.51 (m, 1H), 2.87-3.06 (m, 2H), 2.77 (s, 2H), 2.13 (dt, J=10.5, 6.5 Hz, 1H), 1.65-1.74 (m, 1H), 1.28-1.39 (m, 9H), 1.06-1.19 (m, 2H), 0.96-1.06 (m, 6H), 0.84-0.94 (m, 2H), 0.79 (d, J=6.8 Hz, 4H), 0.54-0.68 (m, 2H). LC-MS: m/z 481.2 (M+H)⁺.

(R)-8-cyclopropyl-6-(3-isopropyl-4-nicotinoylpiperazin-1-yl)-3,3-dimethylisochroman-5-carbonitrile (Compound 271)

¹H NMR (CHLOROFORM-d) δ8.71 (br. s., 2H), 7.80 (d, J=7.5 Hz, 1H), 7.38-7.51 (m, 1H), 4.77-4.92 (m, 2H), 4.07-4.65 (m, 3H), 3.55-3.67 (m, 1H), 2.95-3.34 (m, 3H), 2.77 (s, 2H), 2.21-2.38 (m, 1H), 1.65-1.76 (m, 1H), 1.31 (s, 6H), 0.95-1.16 (m, 8H), 0.80 (br. s., 2H). LC-MS: m/z 460.2 (M+H)⁺.

8-cyclopropyl-6-(4-(furan-3-carbonyl)-3-phenylpiperazin-1-yl)-3,3-dimethylisochroman-5-carbonitrile (Compound 156)

¹H NMR (CHLOROFORM-d) δ7.63 (br. s., 1H), 7.34-7.45 (m, 5H), 7.29-7.32 (m, 1H), 6.53 (br. s., 1H), 4.74-4.90 (m, 2H), 4.46 (br. s., 2H), 4.18 (d, J=11.3 Hz, 1H), 3.83 (d, J=13.1 Hz, 1H), 3.58 (br. s., 1H), 3.43 (br. s., 1H), 2.76 (s, 2H), 1.70-1.72 (m, 1H), 1.33 (d, J=3.5 Hz, 6H), 1.15 (dd, J=7.8, 4.5 Hz, 1H), 1.03 (d, J=7.8 Hz, 3H). LC-MS: m/z 483.3 (M+H)⁺.

8-cyclopropyl-6-((3S,5R)-4-(3-methoxypropanoyl)-3,5-dimethylpiperazin-1-yl)-3,3-dimethylisochroman-5-carbonitrile (Compound 356)

¹H NMR (CHLOROFORM-d) δ4.84 (s, 2H), 4.78 (br. s., 1H), 4.13 (d, J=12.5 Hz, 3H), 3.75 (t, J=6.4 Hz, 2H), 3.33-3.43 (m, 3H), 3.01 (br. s., 2H), 2.78 (s, 2H), 2.49-2.74 (m, 2H), 1.67-1.82 (m, 1H), 1.36-1.52 (m, 6H), 1.32 (s, 6H), 1.09-1.18 (m, 2H), 0.99-1.05 (m, 2H). LC-MS: m/z 427.2 (M+H)⁺.

(R)-8-cyclopropyl-6-(4-(2-(2-fluorophenyl)acetyl)-3-isopropylpiperazin-1-yl)-3,3-dimethylisochroman-5-carbonitrile (Compound 228)

¹H NMR (CHLOROFORM-d) δ7.30-7.37 (m, 1H), 7.19-7.26 (m, 1H), 6.99-7.15 (m, 2H), 4.75-4.88 (m, 2H), 4.64 (d, J=10.5 Hz, 0.5H), 4.40 (d, J=10.3 Hz, 0.5H), 4.22-4.34 (m, 1H), 4.06-4.21 (m, 1H), 3.71-3.80 (m, 2H), 3.50-3.54 (m, 0.5H), 3.32-3.46 (m, 1.5H), 2.93-3.01 (m, 1H), 2.81-2.89 (m, 1H), 2.75 (s, 2H), 2.24 (dt, J=9.7, 6.6 Hz, 0.5H), 2.10 (dt, J=10.4, 6.7 Hz, 0.5H), 1.66-1.72 (m, 1H), 1.31 (d, J=3.0 Hz, 6H), 1.06-1.19 (m, 2H), 0.94-1.05 (m, 5H), 0.87 (d, J=6.8 Hz, 1.5H), 0.80 (d, J=6.8 Hz, 1.5H). LC-MS: m/z 491.3 (M+H)⁺.

8-cyclopropyl-6-(4-(furan-3-carbonyl)-3-methylpiperazin-1-yl)-3,3-dimethylisochroman-5-carbonitrile (Compound 136)

¹H NMR (CHLOROFORM-d) δ7.75 (s, 1H), 7.42-7.53 (m, 1H), 6.59 (dd, J=1.8, 0.8 Hz, 1H), 4.85 (s, 2H), 4.68 (br. s., 1H), 4.28 (br. s., 1H), 4.01-4.16 (m, 2H), 3.46 (br. s., 1H), 3.18 (dd, J=12.9, 3.4 Hz, 1H), 3.01 (td, J=12.5, 3.4 Hz, 1H), 2.79 (s, 2H), 1.68-1.80 (m, 1H), 1.39-1.49 (m, 3H), 1.33 (s, 6H), 1.09-1.18 (m, 2H), 0.99-1.07 (m, 2H). LC-MS: m/z 421.1 (M+H)⁺.

(R)-6-(4-(furan-3-carbonyl)-3-isopropylpiperazin-1-yl)-3,3-dimethyl-8-(1-methylcyclopropyl)isochroman-5-carbonitrile (Compound 386)

¹H NMR (CHLOROFORM-d) δ7.71 (br. s., 1H), 7.45 (t, J=1.6 Hz, 1H), 6.40-6.64 (m, 1H), 4.86 (s, 2H), 4.53-4.56 (m, 2H), 4.27 (s, 1H), 3.48 (s, 1H), 3.00-3.24 (m, 3H), 2.78 (s, 2H), 2.24 (m, 1H), 1.26-1.36 (m, 9H), 1.04-1.16 (m, 2H), 0.79-0.98 (m, 6H), 0.63-0.79 (m, 2H). LC-MS: m/z 463.2 (M+H)⁺.

(R)-8-cyclopropyl-6-(4-(furan-2-carbonyl)-3-isopropylpiperazin-1-yl)-3,3-dimethylisochroman-5-carbonitrile (Compound 192)

¹H NMR (CHLOROFORM-d) δ7.50 (d, J=1.3 Hz, 1H), 7.02 (br. s., 1H), 6.50 (dd, J=3.3, 1.8 Hz, 1H), 4.77-4.89 (m, 2H), 4.20-4.54 (m, 4H), 3.58 (br. s., 1H), 3.00-3.21 (m, 2H), 2.77 (s, 2H), 2.18-2.34 (m, 1H), 1.65-1.76 (m, 1H), 1.32 (d, J=1.8 Hz, 6H), 0.92-1.19 (m, 8H), 0.79-0.92 (m, 2H). LC-MS: m/z 449.2 (M+H)⁺.

(R)-6-(3-isopropyl-4-(3-methoxypropanoyl)piperazin-1-yl)-3,3-dimethyl-8-(1-methylcyclopropyl)isochroman-5-carbonitrile (Compound 385)

¹H NMR (CHLOROFORM-d) δ4.87 (s, 2H), 4.55 (d, J=13.6 Hz, 2H), 4.28 (dd, J=12.9, 1.9 Hz, 1H), 3.64-3.91 (m, 3H), 3.39 (d, J=4.3 Hz, 3H), 2.88-3.18 (m, 3H), 2.79 (s, 2H), 2.47-2.76 (m, 1H), 1.28-1.37 (m, 6H), 1.07 (d, J=6.5 Hz, 3H), 0.86-0.92 (m, 3H), 0.78-0.86 (m, 2H), 0.65-0.76 (m, 2H). LC-MS: m/z 455.2 (M+H)⁺.

8-cyclopropyl-6-((2S,5R)-2,5-dimethyl-4-(2-(thiophen-2-yl)acetyl)piperazin-1-yl)-3,3-dimethylisochroman-5-carbonitrile (Compound 309)

¹H NMR (CHLOROFORM-d) δ7.21 (br. s., 1H), 6.90-6.96 (m, 2H), 4.90 (br. s., 0.5H), 4.81 (br. s., 2H), 4.59 (br. s., 1H), 4.34 (d, J=13.3 Hz, 0.5H), 4.20 (br. s., 0.5H), 3.81-4.07 (m, 3H), 3.64 (d, J=11.5 Hz, 1H), 3.33-3.58 (m, 1H), 3.21 (d, J=11.3 Hz, 0.5H), 2.75 (br. s., 2H), 1.69 (br. s., 1H), 1.25-1.43 (m, 8H), 0.99-1.17 (m, 8H). LC-MS: m/z 465.0 (M+H)⁺.

(S)-8-cyclopropyl-6-(3-isobutyl-4-(3-methoxypropanoyl)piperazin-1-yl)-3,3-dimethylisochroman-5-carbonitrile (Compound 389)

¹H NMR (CHLOROFORM-d) δ4.87 (br. s., 0.5H), 4.83 (s, 2H), 4.55-4.58 (m, 0.5H), 3.98-4.18 (m, 2.5H), 3.65-3.81 (m, 2.5H), 3.42-3.57 (m, 1H), 3.36 (s, 3H), 2.90-3.20 (m, 2.5H), 2.73-2.81 (m, 2H), 2.49-2.73 (m, 2H), 1.47-1.74 (m, 4H), 1.31 (s, 6H), 1.07-1.16 (m, 2H), 0.99-1.04 (m, 2H), 0.89-0.97 (m, 6H). LC-MS: m/z 455.4 (M+H)⁺.

(R)-8-cyclopropyl-6-(3-isopropyl-4-(tetrahydro-2H-pyran-4-carbonyl)piperazin-1-yl)-3,3-dimethylisochroman-5-carbonitrile (Compound 305)

¹H NMR (CHLOROFORM-d) δ4.78-4.88 (m, 2H), 4.62-4.64 (m, 0.5H), 4.30-4.47 (m, 1.5H), 4.13-4.26 (m, 1H), 3.96-4.09 (m, 2H), 3.79 (d, J=13.3 Hz, 0.5H), 3.39-3.55 (m, 3H), 2.88-3.08 (m, 2.5H), 2.71-2.82 (m, 3H), 2.08-2.34 (m, 2H), 1.77-2.06 (m, 2H), 1.67-1.74 (m, 1H), 1.63 (m, 1H), 1.31 (d, J=2.0 Hz, 6H), 1.07-1.18 (m, 2H), 0.97-1.05 (m, 5H), 0.84-0.90 (m, 1.5H), 0.79 (d, J=6.8 Hz, 1.5H). LC-MS: m/z 467.1 (M+H)⁺.

(R)-8-cyclopropyl-6-(3-ethyl-4-(thiazole-4-carbonyl)piperazin-1-yl)-3,3-dimethylisochroman-5-carbonitrile (Compound 293)

¹H NMR (CHLOROFORM-d) δ8.81 (d, J=2.3 Hz, 1H), 8.00 (d, J=2.0 Hz, 1H), 4.44-4.83 (m, 4H), 4.09-4.24 (m, 2H), 3.54-3.56 (m, 0.5H), 3.25 (dd, J=13.2, 3.6 Hz, 1.5H), 3.09 (td, J=12.4, 3.3 Hz, 1H), 2.77 (s, 2H), 1.89-2.05 (m, 1H), 1.65-1.75 (m, 2H), 1.31 (s, 6H), 1.08-1.18 (m, 2H), 0.95-1.04 (m, 4H), 0.79 (br. s., 1H). LC-MS: m/z 452.1 (M+H)⁺.

(R)-8-cyclopropyl-6-(4-(2,5-dimethylfuran-3-carbonyl)-3-methylpiperazin-1-yl)-3,3-dimethylisochroman-5-carbonitrile (Compound 244)

¹H NMR (CHLOROFORM-d) δ5.88-5.96 (m, 1H), 4.83 (s, 2H), 4.65 (br. s., 1H), 3.99-4.29 (m, 3H), 3.39 (br. s., 1H), 3.14 (dd, J=12.9, 3.4 Hz, 1H), 2.96 (td, J=12.5, 3.4 Hz, 1H), 2.77 (s, 2H), 2.31-2.37 (m, 3H), 2.22-2.28 (m, 3H), 1.64-1.75 (m, 1H), 1.37 (d, J=6.8 Hz, 3H), 1.31 (s, 6H), 1.09-1.16 (m, 2H), 0.97-1.04 (m, 2H). LC-MS: m/z 449.1 (M+H)⁺.

(R)-8-cyclopropyl-6-(3-isopropyl-4-(3-methylfuran-2-carbonyl)piperazin-1-yl)-3,3-dimethylisochroman-5-carbonitrile (Compound 193)

¹H NMR (CHLOROFORM-d) δ7.34 (d, J=1.5 Hz, 1H), 6.30-6.37 (m, 1H), 4.75-4.92 (m, 2H), 3.40-4.42 (m, 5H), 3.00-3.21 (m, 2H), 2.69-2.82 (m, 2H), 2.17-2.33 (m, 4H), 1.67-1.76 (m, 1H), 1.32 (d, J=1.8 Hz, 6H), 0.72-1.19 (m, 10H). LC-MS: m/z 463.2 (M+H)⁺.

(S)-8-cyclopropyl-6-(4-(furan-3-carbonyl)-3-phenylpiperazin-1-yl)-3,3-dimethylisochroman-5-carbonitrile (Compound 275)

¹H NMR (CHLOROFORM-d) δ7.57-7.69 (m, 1H), 7.32-7.42 (m, 5H), 7.27-7.31 (m, 1H), 6.51 (br. s., 1H), 5.67 (br. s., 1H), 4.73-4.88 (m, 2H), 4.43 (br. s., 2H), 4.16 (d, J=11.8 Hz, 1H), 3.80 (d, J=11.3 Hz, 1H), 3.50-3.63 (m, 1H), 3.40 (br. s., 1H), 2.68-2.81 (m, 2H), 1.66-1.74 (m, 1H), 1.30 (d, J=3.8 Hz, 6H), 1.03-1.17 (m, 2H), 1.01 (m, 2H). LC-MS: m/z 483.1 (M+H)⁺.

8-cyclopropyl-6-(3,3-dimethyl-4-(2-methylfuran-3-carbonyl)piperazin-1-yl)-3,3-dimethylisochroman-5-carbonitrile (Compound 321)

¹H NMR (CHLOROFORM-d) δ7.24 (d, J=1.8 Hz, 1H), 6.33 (d, J=2.0 Hz, 1H), 4.82 (s, 2H), 3.79-3.84 (m, 2H), 3.74-3.79 (m, 4H), 2.70-2.82 (m, 2H), 2.40 (s, 3H), 1.70 (td, J=8.2, 4.0 Hz, 1H), 1.60 (s, 6H), 1.31 (s, 6H), 1.12 (dt, J=7.3, 3.7 Hz, 2H), 0.97-1.03 (m, 2H). LC-MS: m/z 449.0 (M+H)⁺.

(R)-8-cyclopropyl-6-(4-(furan-2-carbonyl)-3-methylpiperazin-1-yl)-3,3-dimethylisochroman-5-carbonitrile (Compound 167)

¹H NMR (CHLOROFORM-d) δ7.51 (d, J=1.0 Hz, 1H), 7.03 (d, J=3.5 Hz, 1H), 6.50 (dd, J=3.4, 1.9 Hz, 1H), 4.84 (s, 3H), 4.46 (d, J=12.8 Hz, 1H), 4.00-4.22 (m, 2H), 3.50 (d, J=10.8 Hz, 1H), 3.25 (dd, J=13.1, 3.5 Hz, 1H), 3.09 (td,

J=12.4, 3.5 Hz, 1H), 2.78 (s, 2H), 1.67-1.77 (m, 1H), 1.41-1.50 (m, 3H), 1.26-1.38 (m, 6H), 1.13 (dd, J=6.3, 4.3 Hz, 2H), 0.97-1.06 (m, 2H). LC-MS: m/z 421.3 (M+H)+.

8-cyclopropyl-6-(4-(furan-2-carbonyl)-3,3-dimethylpiperazin-1-yl)-3,3-dimethylisochroman-5-carbonitrile (Compound 319)

$^1$H NMR (CHLOROFORM-d) δ7.45-7.53 (m, 1H), 6.95 (dd, J=3.4, 0.6 Hz, 1H), 6.47 (dd, J=3.5, 1.8 Hz, 1H), 4.82 (s, 2H), 3.95-4.04 (m, 2H), 3.87-3.95 (m, 2H), 3.82 (s, 2H), 2.76 (s, 2H), 1.68-1.76 (m, 1H), 1.59 (s, 6H), 1.32 (s, 6H), 1.09-1.15 (m, 2H), 0.97-1.03 (m, 2H). LC-MS: m/z 435.0 (M+H)+.

8-cyclopropyl-6-(4-(furan-2-carbonyl)-3-methylpiperazin-1-yl)-3,3-dimethyl-3,4-dihydro-1H-pyrano[3,4-c]pyridine-5-carbonitrile (Compound 135)

$^1$H NMR (CHLOROFORM-d) δ7.52 (d, J=1.3 Hz, 1H), 7.05 (d, J=3.3 Hz, 1H), 6.52 (dd, J=3.5, 1.8 Hz, 1H), 4.85 (s, 3H), 4.48 (d, J=13.8 Hz, 1H), 4.15 (d, J=12.8 Hz, 1H), 4.08 (dt, J=13.1, 2.0 Hz, 1H), 3.53 (br. s., 1H), 3.26 (dd, J=12.9, 3.6 Hz, 1H), 3.10 (td, J=12.4, 3.5 Hz, 1H), 2.79 (s, 2H), 1.70-1.77 (m, 1H), 1.47 (d, J=6.8 Hz, 3H), 1.34 (s, 6H), 1.11-1.18 (m, 2H), 0.97-1.07 (m, 2H). LC-MS: m/z 421.1 (M+H)+.

ethyl 4-(5-cyano-8-cyclopropyl-3,3-dimethyl-3,4-dihydro-1H-pyrano[3,4-c]pyridin-6-yl)-1-(furan-3-carbonyl)piperazine-2-carboxylate (Compound 259)

$^1$H NMR (CHLOROFORM-d) δ7.80 (br. s., 1H), 7.37-7.51 (m, 1H), 6.64 (br. s., 1H), 5.38 (br. s., 1H), 4.78-4.89 (m, 2H), 4.69 (br. s., 1H), 4.00-4.27 (m, 4H), 3.29 (br. s., 1H), 3.03 (td, J=12.2, 3.4 Hz, 1H), 2.68-2.86 (m, 2H), 1.64-1.79 (m, 1H), 1.18-1.35 (m, 9H), 1.14 (br. s., 2H), 0.94-1.08 (m, 2H). LC-MS: m/z 479.1 (M+H)+.

(R)-8-cyclopropyl-6-(4-(furan-3-carbonyl)-3-phenylpiperazin-1-yl)-3,3-dimethyl-3,4-dihydro-1H-pyrano[3,4-c]pyridine-5-carbonitrile (Compound 274)

$^1$H NMR (CHLOROFORM-d) δ7.54-7.72 (m, 1H), 7.33-7.44 (m, 5H), 7.27-7.29 (m, 1H), 6.51 (br. s., 1H), 5.67 (br. s., 1H), 4.74-4.87 (m, 2H), 4.43 (br. s., 2H), 4.16 (d, J=12.0 Hz, 1H), 3.72-3.87 (m, 1H), 3.50-3.64 (m, 1H), 3.33-3.46 (m, 1H), 2.68-2.79 (m, 2H), 1.68-1.75 (m, 1H), 1.30 (d, J=3.5 Hz, 6H), 1.03-1.17 (m, 2H), 0.98-1.02 (m, 2H). LC-MS: m/z 483.1 (M+H)+.

(R)-8-cyclopropyl-6-(3-isopropyl-4-(2-methylindolizine-3-carbonyl)piperazin-1-yl)-3,3-dimethyl-3,4-dihydro-1H-pyrano[3,4-c]pyridine-5-carbonitrile (Compound 229)

$^1$H NMR (CHLOROFORM-d) δ8.39 (br. s., 1H), 7.58 (br. s., 1H), 7.27-7.40 (m, 1H), 6.88 (br. s., 1H), 4.77-4.89 (m, 2H), 4.10-4.55 (m, 3H), 3.52-3.85 (m, 3H), 3.21 (br. s., 2H), 2.77 (s, 2H), 2.54 (s, 3H), 2.21-2.35 (m, 2H), 1.67-1.78 (m, 1H), 1.29-1.38 (m, 6H), 0.67-1.20 (m, 10H). LC-MS: m/z 513.3 (M+H)+.

8-cyclopropyl-6-(4-(furan-2-carbonyl)piperazin-1-yl)-3,3-dimethyl-3,4-dihydro-1H-pyrano[3,4-c]pyridine-5-carbonitrile (Compound 142)

$^1$H NMR (CHLOROFORM-d) δ7.45-7.55 (m, 1H), 7.05 (d, J=3.5 Hz, 1H), 6.51 (dd, J=3.5, 1.8 Hz, 1H), 4.84 (s, 2H), 3.95 (br. s., 4H), 3.60-3.70 (m, 4H), 2.79 (s, 2H), 1.68-1.77 (m, 1H), 1.32 (s, 6H), 1.14 (quin, J=3.7 Hz, 2H), 0.98-1.06 (m, 2H). LC-MS: m/z 407.2 (M+H)+.

8-cyclopropyl-6-((2S,5R)-4-(3-methoxypropanoyl)-2,5-dimethylpiperazin-1-yl)-3,3-dimethyl-3,4-dihydro-1H-pyrano[3,4-c]pyridine-5-carbonitrile (Compound 310)

$^1$H NMR (CHLOROFORM-d) δ4.85-4.96 (m, 0.5H), 4.82 (s, 2H), 4.53-4.65 (m, 1H), 4.32 (d, J=13.6 Hz, 0.5H), 4.18 (br. s., 0.5H), 3.88-4.07 (m, 1H), 3.69-3.77 (m, 2H), 3.65 (dd, J=13.4, 3.6 Hz, 0.5H), 3.40-3.55 (m, 1.5H), 3.34-3.39 (m, 3H), 3.20 (dd, J=13.4, 3.6 Hz, 0.5H), 2.72-2.85 (m, 2.5H), 2.53-2.64 (m, 1.5H), 1.66-1.74 (m, 1H), 1.51-1.58 (m, 1H), 1.41-1.48 (m, 1H), 1.31 (d, J=2.8 Hz, 6H), 1.19-1.27 (m, 3H), 1.16 (d, J=6.5 Hz, 1H), 1.10 (dd, J=9.5, 5.0 Hz, 2H), 0.97-1.03 (m, 2H). LC-MS: m/z 427.0 (M+H)+.

(R)-8-cyclopropyl-6-(3-isopropyl-4-(5-methylnicotinoyl)piperazin-1-yl)-3,3-dimethyl-3,4-dihydro-1H-pyrano[3,4-c]pyridine-5-carbonitrile (Compound 245)

$^1$H NMR (CHLOROFORM-d) δ8.47 (s, 1H), 8.52 (s, 1H), 7.57 (s, 1H), 4.76-4.92 (m, 2H), 4.28-4.54 (m, 2H), 4.02-4.16 (m, 1H), 3.50-3.61 (m, 1H), 2.90-3.15 (m, 2H), 2.76 (s, 2H), 2.41 (s, 3H), 2.19-2.33 (m, 1H), 1.92-2.06 (m, 1H), 1.67-1.78 (m, 1H), 1.29-1.38 (m, 6H), 0.96-1.18 (m, 8H), 0.81-0.91 (m, 2H). LC-MS: m/z 474.2 (M+H)+.

8-cyclopropyl-6-(3,3-dimethyl-4-(3-(methylthio)propanoyl)piperazin-1-yl)-3,3-dimethyl-3,4-dihydro-1H-pyrano[3,4-c]pyridine-5-carbonitrile (Compound 320)

$^1$H NMR (CHLOROFORM-d) δ4.82 (s, 2H), 3.85-3.94 (m, 2H), 3.76 (s, 2H), 3.69-3.75 (m, 2H), 2.77-2.85 (m, 2H), 2.76 (s, 2H), 2.56-2.67 (m, 2H), 2.15 (s, 3H), 1.68-1.74 (m, 1H), 1.51 (s, 6H), 1.31 (s, 6H), 1.08-1.14 (m, 2H), 0.96-1.03 (m, 2H). LC-MS: m/z 443.0 (M+H)+.

(S)-8-cyclopropyl-6-(4-(furan-2-carbonyl)-2-methylpiperazin-1-yl)-3,3-dimethyl-3,4-dihydro-1H-pyrano[3,4-c]pyridine-5-carbonitrile (Compound 203)

$^1$H NMR (CHLOROFORM-d) δ7.50 (s, 1H), 7.03-7.10 (m, 1H), 6.50 (dd, J=3.5, 1.8 Hz, 1H), 4.84 (s, 2H), 4.38-4.56 (m, 2H), 4.23-4.32 (m, 1H), 3.89-3.98 (m, 1H), 3.54 (d, J=8.8 Hz, 1H), 3.33-3.50 (m, 2H), 2.78 (s, 2H), 1.92-2.10 (m, 1H), 1.32 (s, 6H), 1.25 (s, 3H), 1.09-1.17 (m, 2H), 0.99-1.03 (m, 2H). LC-MS: m/z 422.9 (M+H)+.

8-cyclopropyl-6-((2S,5R)-4-(furan-3-carbonyl)-2,5-dimethylpiperazin-1-yl)-3,3-dimethyl-3,4-dihydro-1H-pyrano[3,4-c]pyridine-5-carbonitrile (Compound 308)

$^1$H NMR (CHLOROFORM-d) δ7.62-7.82 (m, 1H), 7.38-7.50 (m, 1H), 6.56 (s, 1H), 4.76-5.04 (m, 2.5H), 4.31-4.60 (m, 2H), 3.97 (d, J=13.6 Hz, 1H), 3.37-3.51 (m, 2.5H), 2.76 (s, 2H), 1.65-1.79 (m, 1H), 1.31 (d, J=3.5 Hz, 6H), 1.20-1.28 (m, 6H), 1.05-1.15 (m, 2H), 0.96-1.04 (m, 2H). LC-MS: m/z 435.0 (M+H)+.

8-cyclopropyl-6-(4-(furan-3-carbonyl)-3,3-dimethyl-piperazin-1-yl)-3,3-dimethyl-3,4-dihydro-1H-pyrano[3,4-c]pyridine-5-carbonitrile (Compound 318)

$^1$H NMR (CHLOROFORM-d) δ7.69-7.74 (m, 1H), 7.43 (t, J=1.6 Hz, 1H), 6.52-6.56 (m, 1H), 4.82 (s, 2H), 3.87-3.92 (m, 2H), 3.83-3.87 (m, 2H), 3.80 (s, 2H), 2.76 (s, 2H), 2.22 (t, J=7.7 Hz, 1H), 1.59 (s, 6H), 1.32 (s, 6H), 1.12 (quin, J=3.7 Hz, 2H), 0.98-1.05 (m, 2H). LC-MS: m/z 435.1 (M+H)$^+$.

(R)-8-cyclopropyl-6-(4-(furan-2-carbonyl)-2-methyl-piperazin-1-yl)-3,3-dimethyl-3,4-dihydro-1H-pyrano[3,4-c]pyridine-5-carbonitrile (Compound 204)

$^1$H NMR (CHLOROFORM-d) δ7.47-7.53 (m, 1H), 7.02-7.09 (m, 1H), 6.50 (dd, J=3.4, 1.9 Hz, 1H), 4.83 (s, 2H), 4.38-4.56 (m, 2H), 4.22-4.31 (m, 1H), 3.88-3.98 (m, 1H), 3.34-3.61 (m, 3H), 2.77 (s, 2H), 1.67-1.76 (m, 1H), 1.32 (s, 6H), 1.25 (s, 3H), 1.08-1.14 (m, 2H), 0.98-1.04 (m, 2H). LC-MS: m/z 421.2 (M+H)$^+$.

(R)-8-cyclopropyl-6-(3-isopropyl-4-(pyrazolo[1,5-a]pyrimidine-3-carbonyl)piperazin-1-yl)-3,3-dimethyl-3,4-dihydro-1H-pyrano[3,4-c]pyridine-5-carbonitrile (Compound 232)

$^1$H NMR (CHLOROFORM-d) δ8.73 (d, J=6.8 Hz, 1H), 8.64 (br. s., 1H), 8.43 (s, 1H), 6.87-7.04 (m, 1H), 4.78-4.90 (m, 2H), 4.35-4.62 (m, 2.5H), 4.16 (d, J=12.5 Hz, 0.5H), 3.55-3.97 (m, 2H), 3.06-3.29 (m, 2H), 2.76 (s, 2H), 2.21-2.38 (m, 1H), 1.64-1.75 (m, 1H), 1.28-1.36 (m, 6H), 0.96-1.21 (m, 8H), 0.69-0.84 (m, 2H). LC-MS: m/z 500.1 (M+H)$^+$.

(R)-6-(4-(furan-2-carbonyl)-3-isopropylpiperazin-1-yl)-8-isopropyl-3,3-dimethyl-3,4-dihydro-1H-pyrano[3,4-c]pyridine-5-carbonitrile (Compound 171)

$^1$H NMR (CHLOROFORM-d) δ7.52 (s, 1H), 7.04 (br. s., 1H), 6.52 (dd, J=3.4, 1.6 Hz, 1H), 4.68-4.81 (m, 2H), 4.37-4.68 (m, 4H), 3.63 (br. s., 1H), 3.10-3.32 (m, 2H), 2.83-2.91 (m, 1H), 2.80 (s, 2H), 1.72 (br. s., 1H), 1.30-1.36 (m, 6H), 1.16-1.25 (m, 6H), 1.06 (br. s., 3H), 0.91 (br. s., 3H). LC-MS: m/z 451.2 (M+H)$^+$.

(R)-6-(3-ethyl-4-(2-methylfuran-3-carbonyl)piper-azin-1-yl)-8-isopropyl-3,3-dimethyl-3,4-dihydro-1H-pyrano[3,4-c]pyridine-5-carbonitrile (Compound 207)

$^1$H NMR (CHLOROFORM-d) δ7.28 (d, J=2.0 Hz, 1H), 6.28-6.42 (m, 1H), 4.72 (s, 3H), 3.93-4.37 (m, 3H), 3.43 (br. s., 1H), 3.20 (dd, J=13.1, 3.5 Hz, 1H), 2.96-3.10 (m, 1H), 2.80-2.89 (m, 1H), 2.78 (s, 2H), 2.40 (s, 3H), 1.84-1.98 (m, 1H), 1.76 (dt, J=14.2, 7.0 Hz, 1H), 1.30 (s, 6H), 1.15-1.23 (m, 6H), 0.85-0.95 (m, 3H). LC-MS: m/z 451.2 (M+H)$^+$.

(R)-6-(4-(furan-3-carbonyl)-3-isopropylpiperazin-1-yl)-8-isopropyl-3,3-dimethyl-3,4-dihydro-1H-pyrano[3,4-c]pyridine-5-carbonitrile (Compound 165)

$^1$H NMR (CHLOROFORM-d) δ7.74 (br. s., 1H), 7.47 (t, J=1.8 Hz, 1H), 6.47-6.68 (m, 1H), 4.69-4.79 (m, 2H), 4.30-4.58 (m, 3H), 3.50-4.03 (m, 2H), 3.14 (dd, J=13.3, 3.3 Hz, 2H), 2.83-2.90 (m, 1H), 2.80 (s, 2H), 2.26 (br. s., 1H), 1.28-1.34 (m, 6H), 1.17-1.25 (m, 6H), 1.07 (br. s., 2H), 0.91 (br. s., 4H). LC-MS: m/z 451.2 (M+H)$^+$.

(R)-6-(3-ethyl-4-(2-(thiophen-2-yl)acetyl)piperazin-1-yl)-8-isopropyl-3,3-dimethyl-3,4-dihydro-1H-pyrano[3,4-c]pyridine-5-carbonitrile (Compound 206)

$^1$H NMR (CHLOROFORM-d) δ7.21 (dd, J=5.0, 1.3 Hz, 1H), 6.89-6.99 (m, 2H), 4.70 (s, 2.5H), 4.61 (d, J=12.5 Hz, 0.5H), 4.13-4.34 (m, 2H), 3.78-4.07 (m, 3H), 3.39-3.60 (m, 0.5H), 2.88-3.18 (m, 2.5H), 2.74-2.87 (m, 3H), 1.77-1.86 (m, 1H), 1.72 (dd, J=14.9, 7.7 Hz, 1H), 1.29 (d, J=2.5 Hz, 6H), 1.16-1.21 (m, 6H), 0.83-0.96 (m, 3H). LC-MS: m/z 467.1 (M+H)$^+$.

(R)-6-(3-ethyl-4-(furan-3-carbonyl)piperazin-1-yl)-8-isopropyl-3,3-dimethyl-3,4-dihydro-1H-pyrano[3,4-c]pyridine-5-carbonitrile (Compound 205)

$^1$H NMR (CHLOROFORM-d) δ7.72 (s, 1H), 7.46 (t, J=1.8 Hz, 1H), 6.57 (d, J=1.0 Hz, 1H), 4.72 (s, 3H), 4.10-4.39 (m, 3H), 3.29-3.58 (m, 1H), 3.20 (dd, J=13.2, 3.4 Hz, 1H), 3.07 (td, J=12.4, 3.0 Hz, 1H), 2.74-2.88 (m, 3H), 1.75-1.97 (m, 2H), 1.30 (s, 6H), 1.16-1.23 (m, 6H), 0.86-0.99 (m, 3H). LC-MS: m/z 437.2 (M+H)$^+$.

(R)-8-isopropyl-6-(3-isopropyl-4-(2-(thiophen-2-yl)acetyl)piperazin-1-yl)-3,3-dimethyl-3,4-dihydro-1H-pyrano[3,4-c]pyridine-5-carbonitrile (Compound 195)

$^1$H NMR (CHLOROFORM-d) δ7.17-7.24 (m, 1H), 6.83-7.04 (m, 2H), 4.67-4.75 (m, 2H), 4.38-4.57 (m, 1.5H), 4.17-4.32 (m, 1H), 3.81-4.10 (m, 3H), 3.46-3.47 (m, 1H), 2.79-3.53 (m, 3.5H), 2.76 (s, 2H), 2.10-2.30 (m, 1H), 1.29 (d, J=2.3 Hz, 6H), 1.13-1.22 (m, 6H), 0.97-1.08 (m, 3H), 0.79-0.91 (m, 3H). LC-MS: m/z 481.2 (M+H)$^+$.

(R)-8-isopropyl-6-(3-isopropyl-4-(2-methylfuran-3-carbonyl)piperazin-1-yl)-3,3-dimethyl-3,4-dihydro-1H-pyrano[3,4-c]pyridine-5-carbonitrile (Compound 176)

$^1$H NMR (CHLOROFORM-d) δ7.30 (d, J=2.0 Hz, 1H), 6.37 (br. s., 1H), 4.69-4.79 (m, 2H), 4.26-4.67 (m, 3H), 3.90 (d, J=9.8 Hz, 0.5H), 3.52 (br. s., 1H), 2.99-3.22 (m, 2.5H), 2.86 (quin, J=6.7 Hz, 1H), 2.80 (s, 2H), 2.42 (s, 3H), 2.20-2.33 (m, 1H), 1.31-1.36 (m, 6H), 1.15-1.26 (m, 6H), 1.09 (br. s., 2H), 0.84-1.02 (m, 4H). LC-MS: m/z 465.2 (M+H)$^+$.

ethyl 4-(5-cyano-8-isopropyl-3,3-dimethyl-3,4-di-hydro-1H-pyrano[3,4-c]pyridin-6-yl)-1-(2-(thio-phen-2-yl)acetyl)piperazine-2-carboxylate (Compound 332)

$^1$H NMR (CHLOROFORM-d) δ7.19-7.25 (m, 1H), 6.89-7.01 (m, 2H), 5.24-5.40 (m, 1H), 4.63-4.82 (m, 3H), 3.98-4.24 (m, 5H), 3.77-3.93 (m, 2H), 3.25-3.36 (m, 1H), 2.94-3.10 (m, 1H), 2.74-2.89 (m, 3H), 1.29 (d, J=4.8 Hz, 6H), 1.14-1.22 (m, 9H). LC-MS: m/z 511.4 (M+H)$^+$.

ethyl 4-(5-cyano-8-isopropyl-3,3-dimethyl-3,4-di-hydro-1H-pyrano[3,4-c]pyridin-6-yl)-1-(furan-3-carbonyl)piperazine-2-carboxylate (Compound 276)

$^1$H NMR (CHLOROFORM-d) δ7.79 (br. s., 1H), 7.46 (s, 1H), 6.63 (br. s., 1H), 5.39 (br. s., 0.5H), 4.80 (br. s., 0.5H), 4.72 (d, J=3.5 Hz, 2H), 4.21 (dq, J=10.7, 7.1 Hz, 2H), 4.01-4.15 (m, 2H), 3.93 (br. s., 1H), 3.40 (d, J=11.8 Hz, 1H), 3.03-3.18 (m, 1H), 2.76-2.89 (m, 3H), 1.11-1.34 (m, 15H). LC-MS: m/z 481.2 (M+H)+.

(R)-8-isopropyl-3,3-dimethyl-6-(3-methyl-4-(2-methylfuran-3-carbonyl)piperazin-1-yl)-3,4-dihydro-1H-pyrano[3,4-c]pyridine-5-carbonitrile (Compound 163)

1H NMR (CHLOROFORM-d) δ7.30 (d, J=2.0 Hz, 1H), 6.38 (d, J=2.0 Hz, 1H), 4.56-4.83 (m, 3H), 4.03-4.32 (m, 3H), 3.47 (br. s., 1H), 3.18-3.31 (m, 1H), 3.07 (td, J=12.6, 3.1 Hz, 1H), 2.83-2.92 (m, 1H), 2.81 (s, 2H), 2.36-2.46 (m, 3H), 1.38-1.46 (m, 3H), 1.30-1.37 (m, 6H), 1.21 (d, J=6.5 Hz, 6H). LC-MS: m/z 437.2 (M+H)+.

(R)-8-isopropyl-3,3-dimethyl-6-(3-methyl-4-(5-methylisoxazole-4-carbonyl)piperazin-1-yl)-3,4-dihydro-1H-pyrano[3,4-c]pyridine-5-carbonitrile (Compound 217)

1H NMR (CHLOROFORM-d) δ8.24 (s, 1H), 4.73 (s, 2H), 4.12-4.29 (m, 2H), 3.49 (s, 1H), 3.23 (dd, J=13.1, 3.5 Hz, 1H), 3.01-3.14 (m, 1H), 2.77-2.91 (m, 3H), 2.57 (s, 3H), 1.44 (d, J=6.8 Hz, 3H), 1.31 (s, 6H), 1.16-1.23 (m, 6H). LC-MS: m/z 438.1 (M+H)+.

(R)-8-isopropyl-6-(3-isopropyl-4-(oxazole-4-carbonyl)piperazin-1-yl)-3,3-dimethyl-3,4-dihydro-1H-pyrano[3,4-c]pyridine-5-carbonitrile (Compound 212)

1H NMR (CHLOROFORM-d) δ8.25 (d, J=7.0 Hz, 1H), 7.93 (d, J=10.8 Hz, 1H), 4.84 (d, J=12.0 Hz, 1H), 4.71 (s, 2H), 4.66 (d, J=9.8 Hz, 0.5H), 4.60 (d, J=14.1 Hz, 1H), 4.49 (d, J=10.3 Hz, 0.5H), 4.33 (d, J=12.8 Hz, 1H), 3.57 (t, J=11.7 Hz, 1H), 3.12-3.32 (m, 2H), 2.81-2.89 (m, 1H), 2.74-2.81 (m, 2H), 2.19-2.34 (m, 1H), 1.30 (s, 6H), 1.18 (d, J=6.8 Hz, 3H), 1.21 (d, J=6.8 Hz, 3H), 1.00-1.09 (m, 3H), 0.80-0.94 (m, 3H). LC-MS: m/z 452.2 (M+H)+.

(R)-8-isopropyl-3,3-dimethyl-6-(3-methyl-4-(3-(methylthio)propanoyl)piperazin-1-yl)-3,4-dihydro-1H-pyrano[3,4-c]pyridine-5-carbonitrile (Compound 267)

1H NMR (CHLOROFORM-d) δ4.89 (br. s., 0.5H), 4.72 (s, 2H), 4.52 (d, J=12.0 Hz, 0.5H), 4.02-4.32 (m, 2.5H), 3.74 (d, J=13.1 Hz, 0.5H), 3.59 (t, J=11.3 Hz, 0.5H), 3.01-3.30 (m, 2.5H), 2.84 (quin, J=6.6 Hz, 3H), 2.79 (s, 2H), 2.56-2.73 (m, 2H), 2.16 (s, 3H), 1.30-1.44 (m, 9H), 1.20 (d, J=6.3 Hz, 6H). LC-MS: m/z 431.2 (M+H)+.

(R)-8-isopropyl-6-(3-isopropyl-4-(2-(pyridin-3-yl)acetyl)piperazin-1-yl)-3,3-dimethyl-3,4-dihydro-1H-pyrano[3,4-c]pyridine-5-carbonitrile (Compound 250)

1H NMR (CHLOROFORM-d) δ8.55 (d, J=5.0 Hz, 2H), 7.73 (d, J=6.5 Hz, 1H), 7.33 (dd, J=7.5, 5.0 Hz, 1H), 4.62-4.75 (m, 2.5H), 4.37-4.57 (m, 1.5H), 4.16-4.33 (m, 1H), 3.72-3.87 (m, 2.5H), 3.42-3.61 (m, 1H), 2.91-3.12 (m, 2.5H), 2.83 (dt, J=13.3, 6.7 Hz, 1H), 2.77 (s, 2H), 2.08-2.37 (m, 1H), 1.30 (s, 2.3 Hz, 6H), 1.15-1.24 (m, 6H), 1.03 (dd, J=13.4, 6.4 Hz, 3H), 0.89 (dd, J=10.3, 6.8 Hz, 1.5H), 0.80 (d, J=6.8 Hz, 1.5H). LC-MS: m/z 476.2 (M+H)+.

(R)-8-isopropyl-6-(3-isopropyl-4-(2-(pyridin-2-yl)acetyl)piperazin-1-yl)-3,3-dimethyl-3,4-dihydro-1H-pyrano[3,4-c]pyridine-5-carbonitrile (Compound 214)

1H NMR (CHLOROFORM-d) δ8.54 (d, J=2.8 Hz, 1H), 7.61-7.77 (m, 1H), 7.41 (t, J=8.4 Hz, 1H), 7.15-7.24 (m, 1H), 4.58-4.74 (m, 2.5H), 4.49 (dt, J=13.6, 2.0 Hz, 1H), 4.40 (d, J=10.3 Hz, 0.5H), 4.18-4.34 (m, 1H), 3.87-4.15 (m, 3H), 3.33-3.51 (m, 0.5H), 2.96-3.06 (m, 1.5H), 2.85-2.94 (m, 1H), 2.82 (quin, J=6.7 Hz, 1H), 2.76 (s, 2H), 2.09-2.30 (m, 1H), 1.29 (d, J=2.3 Hz, 6H), 1.17 (dd, J=10.4, 6.7 Hz, 6H), 1.01 (dd, J=9.9, 6.7 Hz, 3H), 0.80 (dd, J=12.7, 6.9 Hz, 3H). LC-MS: m/z 476.2 (M+H)+.

(R)-8-isopropyl-6-(4-(3-methoxypropanoyl)-3-methylpiperazin-1-yl)-3,3-dimethyl-3,4-dihydro-1H-pyrano[3,4-c]pyridine-5-carbonitrile (Compound 268)

1H NMR (CHLOROFORM-d) δ4.89 (br. s., 0.5H), 4.71 (s, 2H), 4.53 (d, J=12.8 Hz, 0.5H), 4.09-4.31 (m, 2.5H), 3.66-3.82 (m, 2.5H), 3.50-3.63 (m, 0.5H), 3.37 (s, 3H), 3.01-3.29 (m, 2.5H), 2.81-2.88 (m, 1H), 2.76-2.81 (m, 2H), 2.53-2.74 (m, 2H), 1.30-1.44 (m, 9H), 1.19 (d, J=6.5 Hz, 6H). LC-MS: m/z 415.2 (M+H)+.

(R)-8-isopropyl-3,3-dimethyl-6-(3-methyl-4-(2-(thiophen-2-yl)acetyl)piperazin-1-yl)-3,4-dihydro-1H-pyrano[3,4-c]pyridine-5-carbonitrile (Compound 158)

1H NMR (CHLOROFORM-d) δ7.23 (dd, J=5.0, 1.3 Hz, 1H), 6.86-7.07 (m, 2H), 4.93 (br. s., 0.5H), 4.73 (s, 2H), 4.57 (d, J=13.3 Hz, 0.5H), 4.09-4.35 (m, 2.5H), 3.90-4.05 (m, 2H), 3.79 (d, J=12.8 Hz, 0.5H), 3.57 (t, J=12.0 Hz, 0.5H), 3.13-3.32 (m, 1.5H), 3.00 (q, J=11.7 Hz, 1H), 2.82-2.88 (m, 1H), 2.75-2.82 (m, 2H), 1.28-1.39 (m, 9H), 1.14-1.24 (m, 6H). LC-MS: m/z 453.0 (M+H)+.

ethyl 4-(5-cyano-8-isopropyl-3,3-dimethyl-3,4-dihydro-1H-pyrano[3,4-c]pyridin-6-yl)-1-(3-methoxypropanoyl)piperazine-2-carboxylate (Compound 311)

1H NMR (CHLOROFORM-d) δ5.29 (dd, J=4.3, 2.0 Hz, 1H), 4.74-4.86 (m, 1H), 4.63-4.74 (m, 2H), 4.25 (dd, J=12.8, 2.0 Hz, 3H), 3.97-4.21 (m, 2H), 3.62-3.89 (m, 3H), 3.37-3.40 (m, 2H), 3.33-3.37 (m, 1H), 3.11 (ddd, J=12.9, 10.7, 4.5 Hz, 1H), 2.76-2.87 (m, 3H), 2.60-2.71 (m, 1H), 1.29 (d, J=3.5 Hz, 6H), 1.09-1.23 (m, 9H). LC-MS: m/z 473.3 (M+H)+.

(S)-6-(4-(furan-2-carbonyl)-3-phenylpiperazin-1-yl)-8-isopropyl-3,3-dimethyl-3,4-dihydro-1H-pyrano[3,4-c]pyridine-5-carbonitrile (Compound 223)

1H NMR (CHLOROFORM-d) δ7.46 (s, 1H), 7.43 (d, J=7.5 Hz, 2H), 7.29-7.35 (m, 2H), 7.22-7.25 (m, 1H), 6.95-7.02 (m, 1H), 6.45 (br. s., 1H), 5.91 (t, J=4.4 Hz, 1H), 4.68-4.75 (m, 2H), 4.57-4.67 (m, 2H), 4.27 (d, J=10.5 Hz, 1H), 3.96 (dd, J=13.8, 4.5 Hz, 1H), 3.56-3.67 (m, 1H), 3.50-3.56 (m, 1H), 2.83 (dt, J=13.2, 6.6 Hz, 1H), 2.76 (s, 2H), 1.29 (s, 6H), 1.21 (d, J=6.5 Hz, 3H), 1.13-1.19 (m, 3H). LC-MS: m/z 485.1 (M+H)⁺.

6-(4-(furan-2-carbonyl)-3-phenylpiperazin-1-yl)-8-isopropyl-3,3-dimethyl-3,4-dihydro-1H-pyrano[3,4-c]pyridine-5-carbonitrile (Compound 154)

¹H NMR (CHLOROFORM-d) δ7.42-7.51 (m, 3H), 7.31-7.38 (m, 2H), 7.24-7.28 (m, 1H), 7.00 (br. s., 1H), 6.47 (br. s., 1H), 5.94 (t, J=4.4 Hz, 1H), 4.72 (d, J=6.3 Hz, 2H), 4.58-4.69 (m, 2H), 4.30 (d, J=10.3 Hz, 1H), 3.98 (dd, J=13.9, 4.1 Hz, 1H), 3.46-3.73 (m, 2H), 2.81-2.90 (m, 1H), 2.78 (s, 2H), 1.32 (s, 6H), 1.23 (d, J=6.8 Hz, 3H), 1.19 (d, J=6.5 Hz, 3H). LC-MS: m/z 485.3 (M+H)⁺.

ethyl 4-(5-cyano-8-isopropyl-3,3-dimethyl-3,4-dihydro-1H-pyrano[3,4-c]pyridin-6-yl)-1-(furan-2-carbonyl)piperazine-2-carboxylate (Compound 298)

¹H NMR (CHLOROFORM-d) δ7.52 (br. s., 1H), 7.12 (d, J=3.5 Hz, 1H), 6.52 (br. s., 1H), 5.34 (t, J=3.1 Hz, 1H), 4.76 (s, 1H), 4.72 (d, J=3.8 Hz, 2H), 4.53 (d, J=13.3 Hz, 1H), 4.15-4.34 (m, 2H), 3.42-3.57 (m, 1H), 3.23 (br. s., 1H), 2.75-2.91 (m, 3H), 1.30 (d, J=4.5 Hz, 6H), 1.10-1.23 (m, 6H).

(R)-6-(4-(furan-3-carbonyl)-3-methylpiperazin-1-yl)-8-isopropyl-3,3-dimethyl-3,4-dihydro-1H-pyrano[3,4-c]pyridine-5-carbonitrile (Compound 149)

¹H NMR (CHLOROFORM-d) δ7.75 (s, 1H), 7.47 (t, J=1.8 Hz, 1H), 6.55-6.64 (m, 1H), 4.74 (s, 3H), 4.12-4.42 (m, 3H), 3.49 (br. s., 1H), 3.26 (dd, J=12.9, 3.9 Hz, 1H), 3.10 (td, J=12.5, 3.4 Hz, 1H), 2.86 (quin, J=6.7 Hz, 1H), 2.81 (s, 2H), 1.45 (d, J=6.8 Hz, 3H), 1.32 (s, 6H), 1.21 (d, J=6.5 Hz, 6H). LC-MS: m/z 423.1 (M+H)⁺.

(R)-8-isopropyl-6-(3-isopropyl-4-(4-methyloxazole-5-carbonyl)piperazin-1-yl)-3,3-dimethyl-3,4-dihydro-1H-pyrano[3,4-c]pyridine-5-carbonitrile (Compound 213)

¹H NMR (CHLOROFORM-d) δ7.97 (s, 1H), 4.72 (s, 2H), 4.51-4.66 (m, 1.5H), 4.29-4.49 (m, 2H), 3.99 (d, J=14.1 Hz, 0.5H), 3.62-3.77 (m, 1H), 3.08-3.28 (m, 2H), 2.81-2.93 (m, 1H), 2.79 (s, 2H), 2.41-2.49 (m, 3H), 2.20-2.32 (m, 1H), 1.28-1.36 (m, 6H), 1.18-1.22 (m, 6H), 0.83-1.08 (m, 6H). LC-MS: m/z 466.2 (M+H)⁺.

(R)-8-isopropyl-6-(4-(2-(3-methoxyphenyl)acetyl)-3-methylpiperazin-1-yl)-3,3-dimethyl-3,4-dihydro-1H-pyrano[3,4-c]pyridine-5-carbonitrile (Compound 221)

¹H NMR (CHLOROFORM-d) δ7.24 (dd, J=8.5, 7.8 Hz, 1H), 6.77-6.88 (m, 3H), 4.92 (br. s., 1H), 4.70 (s, 2H), 4.16-4.24 (m, 1H), 4.09 (t, J=11.9 Hz, 1H), 3.80 (s, 3H), 3.56-3.76 (m, 2H), 3.44 (br. s., 1H), 3.19 (dd, J=13.3, 3.3 Hz, 1H), 2.92-3.10 (m, 1H), 2.70-2.92 (m, 4H), 1.29 (d, J=1.8 Hz, 9H), 1.17 (d, J=6.8 Hz, 6H). LC-MS: m/z 477.1 (M+H)⁺.

(R)-8-isopropyl-3,3-dimethyl-6-(3-methyl-4-(2-methylimidazo[1,2-a]pyridine-3-carbonyl)piperazin-1-yl)-3,4-dihydro-1H-pyrano[3,4-c]pyridine-5-carbonitrile (Compound 220)

¹H NMR (CHLOROFORM-d) δ8.47 (d, J=6.5 Hz, 1H), 7.58 (br. s., 1H), 7.30 (br. s., 1H), 6.89 (br. s., 1H), 4.62-4.92 (m, 3H), 4.23 (d, J=12.8 Hz, 2H), 3.99 (br. s., 1H), 3.65 (br. s., 1H), 3.32 (d, J=11.8 Hz, 1H), 3.08 (br. s., 1H), 2.75-2.91 (m, 3H), 2.53 (br. s., 3H), 1.41-1.51 (m, 3H), 1.31 (s, 6H), 1.19 (dd, J=6.7, 1.6 Hz, 6H). LC-MS: m/z 487.1 (M+H)⁺.

(R)-8-isopropyl-6-(3-isopropyl-4-(2-(2-methoxyphenyl)acetyl)piperazin-1-yl)-3,3-dimethyl-3,4-dihydro-1H-pyrano[3,4-c]pyridine-5-carbonitrile (Compound 216)

¹H NMR (CHLOROFORM-d) δ7.27-7.30 (m, 1H), 7.20-7.25 (m, 1H), 6.85-6.96 (m, 2H), 4.60-4.79 (m, 2.5H), 4.37-4.57 (m, 1.5H), 4.17-4.28 (m, 1H), 3.57-3.92 (m, 6H), 3.38 (t, J=11.4 Hz, 0.5H), 2.77-3.07 (m, 3.5H), 2.76 (d, J=2.5 Hz, 2H), 2.09-2.27 (m, 1H), 1.29 (d, J=1.8 Hz, 6H), 1.13-1.22 (m, 6H), 1.01 (dd, J=6.4, 1.6 Hz, 3H), 0.85 (dd, J=17.1, 6.8 Hz, 3H). LC-MS: m/z 505.2 (M+H)⁺.

(R)-8-isopropyl-3,3-dimethyl-6-(3-methyl-4-(thiophene-2-carbonyl)piperazin-1-yl)-3,4-dihydro-1H-pyrano[3,4-c]pyridine-5-carbonitrile (Compound 246)

¹H NMR (CHLOROFORM-d) δ7.46 (dd, J=5.0, 1.0 Hz, 1H), 7.33 (dd, J=3.8, 1.0 Hz, 1H), 7.07 (dd, J=5.0, 3.8 Hz, 1H), 4.78 (br. s., 1H), 4.72 (s, 2H), 4.38 (d, J=13.1 Hz, 1H), 4.07-4.28 (m, 2H), 3.43-3.63 (m, 1H), 3.28 (dd, J=13.1, 3.5 Hz, 1H), 3.12 (td, J=12.5, 3.5 Hz, 1H), 2.84 (dt, J=13.3, 6.7 Hz, 1H), 2.79 (s, 2H), 1.42-1.51 (m, 3H), 1.30 (s, 6H), 1.15-1.22 (m, 6H). LC-MS: m/z 439.1 (M+H)⁺.

(S)-6-(4-(furan-3-carbonyl)-3-phenylpiperazin-1-yl)-8-isopropyl-3,3-dimethyl-3,4-dihydro-1H-pyrano[3,4-c]pyridine-5-carbonitrile (Compound 257)

¹H NMR (CHLOROFORM-d) δ7.61 (br. s., 1H), 7.39 (br. s., 3H), 7.34 (t, J=7.5 Hz, 3H), 6.51 (br. s., 1H), 5.71 (br. s., 1H), 4.52-4.74 (m, 4H), 4.24 (d, J=10.8 Hz, 1H), 3.92 (d, J=11.3 Hz, 1H), 3.56 (d, J=11.8 Hz, 1H), 3.50 (d, J=10.0 Hz, 1H), 2.81 (dt, J=13.3, 6.7 Hz, 1H), 2.75 (s, 2H), 1.27-1.31 (m, 6H), 1.19 (d, J=6.5 Hz, 3H), 1.13 (d, J=6.0 Hz, 3H). LC-MS: m/z 485.1 (M+H)⁺.

6-(4-(furan-3-carbonyl)-3-phenylpiperazin-1-yl)-8-isopropyl-3,3-dimethyl-3,4-dihydro-1H-pyrano[3,4-c]pyridine-5-carbonitrile (Compound 155)

¹H NMR (CHLOROFORM-d) δ7.63 (br. s., 1H), 7.32-7.46 (m, 5H), 7.25-7.31 (m, 1H), 6.53 (br. s., 1H), 5.73 (br. s., 1H), 4.60-4.81 (m, 4H), 4.26 (d, J=11.0 Hz, 1H), 3.94 (d, J=12.0 Hz, 1H), 3.41-3.70 (m, 2H), 2.83 (dt, J=13.3, 6.7 Hz, 1H), 2.77 (s, 2H), 1.31 (d, J=2.0 Hz, 6H), 1.19-1.24 (m, 3H), 1.16 (d, J=6.5 Hz, 3H). LC-MS: m/z 485.4 (M+H)⁺.

(R)-8-isopropyl-3,3-dimethyl-6-(3-methyl-4-(thiophene-3-carbonyl)piperazin-1-yl)-3,4-dihydro-1H-pyrano[3,4-c]pyridine-5-carbonitrile (Compound 251)

¹H NMR (CHLOROFORM-d) δ7.51-7.58 (m, 1H), 7.37 (dd, J=4.9, 2.9 Hz, 1H), 7.18-7.23 (m, 1H), 4.59-4.87 (m, 3H), 4.09-4.39 (m, 3H), 3.48 (br. s., 1H), 3.24 (d, J=12.0 Hz, 1H), 3.07 (td, J=12.5, 3.3 Hz, 1H), 2.84 (dt, J=13.3, 6.7 Hz, 1H), 2.79 (s, 2H), 1.43 (d, J=6.8 Hz, 3H), 1.30 (s, 6H), 1.19 (d, J=6.8 Hz, 6H). LC-MS: m/z 439.1 (M+H)⁺.

(R)-6-(4-(2-(2-fluorophenyl)acetyl)-3-isopropylpiperazin-1-yl)-8-isopropyl-3,3-dimethyl-3,4-dihydro-1H-pyrano[3,4-c]pyridine-5-carbonitrile (Compound 215)

¹H NMR (CHLOROFORM-d) δ7.30-7.38 (m, 1H), 7.20-7.30 (m, 1H), 7.03-7.14 (m, 2H), 4.62-4.78 (m, 2H), 4.40-4.56 (m, 1.5H), 4.20-4.32 (m, 1H), 3.55-3.92 (m, 3H), 3.32-3.47 (m, 1H), 2.88-3.10 (m, 2H), 2.83 (dt, J=13.3, 6.7 Hz, 1H), 2.76 (s, 2H), 2.10-2.32 (m, 1.5H), 1.30 (d, J=2.5 Hz, 6H), 1.14-1.23 (m, 6H), 1.02 (dd, J=9.0, 6.5 Hz, 3H), 0.88 (dd, J=6.9, 4.9 Hz, 1.5H), 0.81 (d, J=6.8 Hz, 1.5H). LC-MS: m/z 493.2 (M+H)⁺.

6-(4-(furan-3-carbonyl)-3-methylpiperazin-1-yl)-8-isopropyl-3,3-dimethyl-3,4-dihydro-1H-pyrano[3,4-c]pyridine-5-carbonitrile (Compound 138)

¹H NMR (CHLOROFORM-d) δ7.76 (s, 1H), 7.47 (s, 1H), 6.60 (d, J=1.0 Hz, 1H), 4.74 (s, 3H), 4.13-4.42 (m, 3H), 3.50 (br. s., 1H), 3.26 (dd, J=13.1, 3.0 Hz, 1H), 3.10 (td, J=12.4, 3.3 Hz, 1H), 2.86 (quin, J=6.7 Hz, 1H), 2.81 (s, 2H), 1.45 (d, J=6.8 Hz, 3H), 1.32 (s, 6H), 1.21 (d, J=6.5 Hz, 6H). LC-MS: m/z 423.0 (M+H)⁺.

(R)-6-(4-(2-(3-fluorophenyl)acetyl)-3-isopropylpiperazin-1-yl)-8-isopropyl-3,3-dimethyl-3,4-dihydro-1H-pyrano[3,4-c]pyridine-5-carbonitrile (Compound 234)

¹H NMR (CHLOROFORM-d) δ7.28-7.33 (m, 1H), 6.91-7.09 (m, 3H), 4.62-4.79 (m, 2.5H), 4.37-4.55 (m, 1.5H), 4.12-4.32 (m, 1H), 3.66-3.84 (m, 3H), 3.33-3.47 (m, 1H), 2.96-3.11 (m, 1H), 2.78-2.91 (m, 2H), 2.76 (d, J=3.3 Hz, 2H), 2.06-2.28 (m, 1H), 1.29 (d, J=2.3 Hz, 6H), 1.15-1.22 (m, 6H), 1.01 (dd, J=6.4, 2.1 Hz, 3H), 0.85 (d, J=7.0 Hz, 1.5H), 0.80 (d, J=6.8 Hz, 1.5H). LC-MS: m/z 493.3 (M+H)⁺.

(R)-8-isopropyl-3,3-dimethyl-6-(3-methyl-4-(3-methylfuran-2-carbonyl)piperazin-1-yl)-3,4-dihydro-1H-pyrano[3,4-c]pyridine-5-carbonitrile (Compound 173)

¹H NMR (CHLOROFORM-d) δ7.36 (s, 1H), 6.35 (s, 1H), 4.73 (s, 3H), 4.14-4.44 (m, 3H), 3.43-3.63 (m, 1H), 3.33 (dd, J=13.1, 3.5 Hz, 1H), 3.17 (td, J=12.3, 3.3 Hz, 1H), 2.76-2.92 (m, 3H), 2.30 (s, 3H), 1.45 (d, J=6.8 Hz, 3H), 1.32 (s, 7H), 1.21 (d, J=6.8 Hz, 6H). LC-MS: m/z 437.1 (M+H)⁺.

(R)-6-(4-(2-(2-fluorophenyl)acetyl)-3-methylpiperazin-1-yl)-8-isopropyl-3,3-dimethyl-3,4-dihydro-1H-pyrano[3,4-c]pyridine-5-carbonitrile (Compound 219)

¹H NMR (CHLOROFORM-d) δ7.28-7.36 (m, 1H), 7.21-7.26 (m, 1H), 7.03-7.14 (m, 2H), 4.71 (s, 3H), 4.01-4.26 (m, 2H), 3.70-3.95 (m, 3H), 3.10-3.37 (m, 2H), 2.98 (d, J=13.6 Hz, 1H), 2.75-2.88 (m, 3H), 1.27-1.33 (m, 9H), 1.18 (d, J=6.8 Hz, 6H). LC-MS: m/z 465.1 (M+H)⁺.

(R)-8-isopropyl-6-(3-isopropyl-4-(2-(3-methoxyphenyl)acetyl)piperazin-1-yl)-3,3-dimethyl-3,4-dihydro-1H-pyrano[3,4-c]pyridine-5-carbonitrile (Compound 233)

¹H NMR (CHLOROFORM-d) δ7.24 (t, J=7.8 Hz, 1H), 6.82-6.88 (m, 2H), 6.76-6.82 (m, 1H), 4.61-4.78 (m, 2.5H), 4.35-4.54 (m, 1.5H), 4.14-4.28 (m, 1H), 3.72-3.86 (m, 5.5H), 3.31-3.54 (m, 1H), 2.95-3.08 (m, 1.5H), 2.71-2.86 (m, 4H), 2.07-2.30 (m, 1H), 1.29 (d, J=2.5 Hz, 6H), 1.14-1.22 (m, 6H), 1.00 (dd, J=6.5, 2.0 Hz, 3H), 0.75-0.87 (m, 3H). LC-MS: m/z 505.3 (M+H)⁺.

(R)-6-(4-(2-(3,5-difluorophenyl)acetyl)-3-methylpiperazin-1-yl)-8-isopropyl-3,3-dimethyl-3,4-dihydro-1H-pyrano[3,4-c]pyridine-5-carbonitrile (Compound 159)

¹H NMR (CHLOROFORM-d) δ6.79-6.89 (m, 2H), 6.69-6.78 (m, 1H), 4.92 (br. s., 0.5H), 4.73 (s, 2H), 4.57 (d, J=13.8 Hz, 0.5H), 4.05-4.30 (m, 2.5H), 3.63-3.86 (m, 2.5H), 3.46-3.62 (m, 0.5H), 3.11-3.26 (m, 1.5H), 2.92-3.08 (m, 1H), 2.85 (quin, J=6.7 Hz, 1H), 2.80 (s, 2H), 1.29-1.38 (m, 9H), 1.20 (d, J=6.8 Hz, 6H). LC-MS: m/z 483.0 (M+H)⁺.

6-(4-(furan-2-carbonyl)-3-methylpiperazin-1-yl)-8-isopropyl-3,3-dimethyl-3,4-dihydro-1H-pyrano[3,4-c]pyridine-5-carbonitrile (Compound 137)

¹H NMR (CHLOROFORM-d) δ7.52 (d, J=1.0 Hz, 1H), 7.05 (d, J=3.0 Hz, 1H), 6.52 (dd, J=3.5, 1.8 Hz, 1H), 4.88 (br. s., 1H), 4.74 (s, 2H), 4.50 (d, J=13.6 Hz, 1H), 4.27 (d, J=13.1 Hz, 1H), 4.19 (dd, J=13.1, 2.0 Hz, 1H), 3.56 (br. s., 1H), 3.35 (dd, J=13.1, 3.8 Hz, 1H), 3.18 (td, J=12.4, 3.5 Hz, 1H), 2.79-2.90 (m, 3H), 1.48 (d, J=6.8 Hz, 3H), 1.32 (s, 6H), 1.18-1.23 (m, 6H). LC-MS: m/z 423.0 (M+H)⁺.

(R)-8-isopropyl-3,3-dimethyl-6-(3-methyl-4-(2-oxo-2-phenylacetyl)piperazin-1-yl)-3,4-dihydro-1H-pyrano[3,4-c]pyridine-5-carbonitrile (Compound 157)

¹H NMR (CHLOROFORM-d) δ7.95-8.03 (m, 2H), 7.65-7.73 (m, 1H), 7.51-7.59 (m, 2H), 4.95-5.08 (m, 0.5H), 4.74 (s, 2H), 4.64 (d, J=13.6 Hz, 0.5H), 4.35 (d, J=13.1 Hz, 0.5H), 4.25 (d, J=13.3 Hz, 0.5H), 4.08-4.19 (m, 1H), 3.92 (br. s., 0.5H), 3.64 (td, J=12.8, 3.3 Hz, 0.5H), 3.49 (d, J=13.3 Hz, 0.5H), 3.30-3.43 (m, 1H), 3.03-3.27 (m, 1.5H), 2.76-2.92 (m, 3H), 1.51 (d, J=6.8 Hz, 1.5H), 1.43 (d, J=6.8 Hz, 1.5H), 1.32 (s, 6H), 1.16-1.24 (m, 6H). LC-MS: m/z 461.1 (M+H)⁺.

(R)-8-isopropyl-6-(4-(2-(2-methoxyphenyl)acetyl)-3-methylpiperazin-1-yl)-3,3-dimethyl-3,4-dihydro-1H-pyrano[3,4-c]pyridine-5-carbonitrile (Compound 199)

¹H NMR (CHLOROFORM-d) δ7.17-7.29 (m, 2H), 6.83-7.00 (m, 2H), 4.93 (br. s., 0.5H), 4.71 (s, 2H), 4.57 (d, J=13.3 Hz, 0.5H), 4.22 (d, J=10.3 Hz, 1H), 4.11 (d, J=12.8 Hz, 1.5H), 3.81-3.89 (m, 3H), 3.67-3.78 (m, 2.5H), 3.46 (t, J=11.7 Hz, 0.5H), 3.07-3.26 (m, 1.5H), 2.88-3.05 (m, 1H), 2.73-2.87 (m, 3H), 1.30 (s, 9H), 1.18 (d, J=6.8 Hz, 6H). LC-MS: m/z 477.3 (M+H)⁺.

6-(3-ethyl-4-(furan-3-carbonyl)piperazin-1-yl)-8-isopropyl-3,3-dimethyl-3,4-dihydro-1H-pyrano[3,4-c]pyridine-5-carbonitrile (Compound 172)

¹H NMR (CHLOROFORM-d) δ7.73 (s, 1H), 7.41-7.54 (m, 1H), 6.58 (s, 1H), 4.73 (s, 3H), 4.12-4.41 (m, 3H), 3.50 (br. s., 1H), 3.22 (dd, J=13.2, 3.4 Hz, 1H), 3.04-3.15 (m, 1H), 2.75-2.93 (m, 3H), 1.78-2.02 (m, 2H), 1.32 (s, 6H), 1.15-1.24 (m, 6H), 0.87-1.03 (m, 3H). LC-MS: m/z 437.3 (M+H)⁺.

(R)-6-(4-(benzo[b]thiophene-3-carbonyl)-3-methyl-piperazin-1-yl)-8-isopropyl-3,3-dimethyl-3,4-dihydro-1H-pyrano[3,4-c]pyridine-5-carbonitrile (Compound 247)

¹H NMR (CHLOROFORM-d) δ7.86-7.95 (m, 1H), 7.82 (dd, J=6.5, 2.3 Hz, 1H), 7.57 (s, 1H), 7.36-7.48 (m, 2H), 4.71 (s, 3H), 4.15-4.20 (m, 3H), 3.49 (t, J=11.7 Hz, 1H), 3.29 (d, J=12.0 Hz, 1H), 3.09 (t, J=11.3 Hz, 1H), 2.73-2.91 (m, 3H), 1.44 (d, J=6.0 Hz, 3H), 1.28-1.35 (m, 6H), 1.16-1.19 (m, 6H). LC-MS: m/z 489.1 (M+H)⁺.

(R)-8-isopropyl-3,3-dimethyl-6-(3-methyl-4-nicotinoylpiperazin-1-yl)-3,4-dihydro-1H-pyrano[3,4-c]pyridine-5-carbonitrile (Compound 249)

¹H NMR (CHLOROFORM-d) δ8.70 (br. s., 2H), 7.79 (d, J=7.8 Hz, 1H), 7.41 (dd, J=7.4, 4.9 Hz, 1H), 4.72 (s, 3H), 4.03-4.33 (m, 3H), 3.50 (br. s., 1H), 3.25 (d, J=10.3 Hz, 1H), 3.09 (t, J=12.2 Hz, 1H), 2.73-2.93 (m, 3H), 1.45 (d, J=6.5 Hz, 3H), 1.30 (s, 6H), 1.19 (d, J=6.5 Hz, 6H). LC-MS: m/z 434.2 (M+H)⁺.

(R)-6-(4-(2-(3-chlorophenyl)acetyl)-3-methylpiperazin-1-yl)-8-isopropyl-3,3-dimethyl-3,4-dihydro-1H-pyrano[3,4-c]pyridine-5-carbonitrile (Compound 161)

¹H NMR (CHLOROFORM-d) δ7.21-7.35 (m, 3H), 7.12-7.21 (m, 1H), 4.93 (br. s., 0.5H), 4.73 (s, 2H), 4.57 (d, J=12.8 Hz, 0.5H), 4.11-4.25 (m, 2.5H), 3.67-3.84 (m, 3H), 3.51 (t, J=11.3 Hz, 0.5H), 3.09-3.25 (m, 1.5H), 2.89-3.06 (m, 1H), 2.75-2.88 (m, 3H), 1.30-1.34 (m, 9H), 1.20 (d, J=6.8 Hz, 6H). LC-MS: m/z 481.2 (M+H)⁺.

(R)-8-isopropyl-3,3-dimethyl-6-(3-methyl-4-(oxazole-4-carbonyl)piperazin-1-yl)-3,4-dihydro-1H-pyrano[3,4-c]pyridine-5-carbonitrile (Compound 198)

¹H NMR (CHLOROFORM-d) δ8.24 (s, 1H), 7.93 (s, 1H), 4.62-5.21 (m, 4H), 4.27 (br. s., 1H), 4.19 (d, J=13.1 Hz, 1H), 3.34-3.66 (m, 2H), 3.18 (br. s., 1H), 2.73-2.92 (m, 3H), 1.39-1.50 (m, 3H), 1.31 (s, 6H), 1.19 (d, J=6.8 Hz, 6H). LC-MS: m/z 424.2 (M+H)⁺.

(R)-6-(4-(imidazo[1,2-a]pyridine-3-carbonyl)-3-methylpiperazin-1-yl)-8-isopropyl-3,3-dimethyl-3,4-dihydro-1H-pyrano[3,4-c]pyridine-5-carbonitrile (Compound 222)

¹H NMR (CHLOROFORM-d) δ9.03 (d, J=7.0 Hz, 1H), 7.98 (br. s., 1H), 7.84 (br. s., 1H), 7.44 (t, J=7.8 Hz, 1H), 6.98-7.08 (m, 1H), 4.94 (br. s., 1H), 4.73 (s, 2H), 4.49 (d, J=11.5 Hz, 1H), 4.16-4.32 (m, 2H), 3.66 (br. s., 1H), 3.32 (dd, J=13.1, 3.3 Hz, 1H), 3.17 (td, J=12.4, 3.3 Hz, 1H), 2.71-2.93 (m, 3H), 1.54 (d, J=6.8 Hz, 3H), 1.31 (s, 6H), 1.17-1.21 (m, 6H). LC-MS: m/z 473.0 (M+H)⁺.

(R)-6-(4-(furan-2-carbonyl)-3-methylpiperazin-1-yl)-8-isopropyl-3,3-dimethyl-3,4-dihydro-1H-pyrano[3,4-c]pyridine-5-carbonitrile (Compound 148)

¹H NMR (CHLOROFORM-d) δ7.47-7.57 (m, 1H), 7.05 (d, J=3.5 Hz, 1H), 6.47-6.59 (m, 1H), 4.88 (br. s., 1H), 4.73 (s, 2H), 4.50 (d, J=13.1 Hz, 1H), 4.27 (d, J=13.8 Hz, 1H), 4.19 (d, J=13.3 Hz, 1H), 3.56 (br. s., 1H), 3.35 (dd, J=13.2, 3.6 Hz, 1H), 3.18 (td, J=12.5, 3.4 Hz, 1H), 2.74-2.94 (m, 3H), 1.42-1.54 (m, 3H), 1.30-1.37 (m, 6H), 1.17-1.24 (m, 6H). LC-MS: m/z 423.1 (M+H)⁺.

(R)-8-isopropyl-3,3-dimethyl-6-(3-methyl-4-(4-methyloxazole-5-carbonyl)piperazin-1-yl)-3,4-dihydro-1H-pyrano[3,4-c]pyridine-5-carbonitrile (Compound 197)

¹H NMR (CHLOROFORM-d) δ7.94 (s, 1H), 4.72 (s, 3H), 4.12-4.41 (m, 3H), 3.50 (br. s., 1H), 3.31 (dd, J=12.9, 3.1 Hz, 1H), 3.15 (td, J=12.4, 3.0 Hz, 1H), 2.71-2.93 (m, 3H), 2.45 (s, 3H), 1.47 (d, J=6.8 Hz, 3H), 1.28-1.38 (m, 6H), 1.20 (d, J=6.5 Hz, 6H). LC-MS: m/z 438.1 (M+H)⁺.

(R)-8-isopropyl-3,3-dimethyl-6-(3-methyl-4-(thiazole-4-carbonyl)piperazin-1-yl)-3,4-dihydro-1H-pyrano[3,4-c]pyridine-5-carbonitrile (Compound 252)

¹H NMR (CHLOROFORM-d) δ8.82 (s, 1H), 8.01 (s, 1H), 4.96 (br. s., 1H), 4.72 (s, 2H), 4.56 (br. s., 1H), 4.19 (d, J=13.1 Hz, 2H), 3.64 (br. s., 1H), 3.38 (br. s., 1H), 3.19 (br. s., 1H), 2.71-2.91 (m, 3H), 1.45 (d, J=6.8 Hz, 3H), 1.30 (s, 6H), 1.19 (d, J=6.5 Hz, 6H). LC-MS: m/z 440.1 (M+H)⁺.

(R)-6-(4-(2,5-dimethylfuran-3-carbonyl)-3-methyl-piperazin-1-yl)-8-isopropyl-3,3-dimethyl-3,4-dihydro-1H-pyrano[3,4-c]pyridine-5-carbonitrile (Compound 196)

¹H NMR (CHLOROFORM-d) δ5.94 (s, 1H), 4.55-4.84 (m, 3H), 4.12-4.31 (m, 3H), 3.42 (br. s., 1H), 3.17-3.29 (m, 1H), 2.98-3.11 (m, 1H), 2.73-2.89 (m, 3H), 2.31-2.39 (m, 3H), 2.22-2.30 (m, 3H), 1.35-1.42 (m, 3H), 1.30 (s, 6H), 1.19 (d, J=6.8 Hz, 6H). LC-MS: m/z 451.2 (M+H)⁺.

(R)-6-(4-(furan-2-carbonyl)-3-phenylpiperazin-1-yl)-8-isopropyl-3,3-dimethyl-3,4-dihydro-1H-pyrano[3,4-c]pyridine-5-carbonitrile (Compound 200)

¹H NMR (CHLOROFORM-d) δ7.47 (s, 1H), 7.43 (d, J=7.5 Hz, 2H), 7.28-7.36 (m, 2H), 7.21-7.26 (m, 1H), 6.98 (br. s., 1H), 6.46 (br. s., 1H), 5.92 (t, J=4.4 Hz, 1H), 4.70 (d, J=6.3 Hz, 2H), 4.55-4.67 (m, 2H), 4.27 (d, J=10.0 Hz, 1H), 3.96 (dd, J=13.8, 4.0 Hz, 1H), 3.48-3.74 (m, 2H), 2.83 (dt, J=13.3, 6.7 Hz, 1H), 2.76 (s, 2H), 1.30 (s, 6H), 1.21 (d, J=6.8 Hz, 3H), 1.17 (d, J=6.5 Hz, 3H). LC-MS: m/z 485.1 (M+H)⁺.

(R)-6-(4-(2,4-dichlorobenzoyl)-3-methylpiperazin-1-yl)-8-isopropyl-3,3-dimethyl-3,4-dihydro-1H-pyrano[3,4-c]pyridine-5-carbonitrile (Compound 166)

¹H NMR (CHLOROFORM-d) δ7.46 (dd, J=8.8, 1.8 Hz, 1H), 7.32-7.38 (m, 1H), 7.20-7.30 (m, 1H), 5.07 (d, J=4.0 Hz, 0.5H), 4.65-4.80 (m, 2.5H), 4.21-4.38 (m, 1H), 4.06-4.21 (m, 1H), 3.68 (td, J=12.8, 3.3 Hz, 1H), 3.23-3.41 (m, 2H), 3.07-3.23 (m, 1H), 2.75-2.91 (m, 3H), 1.44-1.50 (m, 1.5H), 1.32 (s, 7.5H), 1.21 (dt, J=6.7, 3.2 Hz, 6H). LC-MS: m/z 501.2 (M+H)⁺.

(R)-8-isopropyl-3,3-dimethyl-6-(3-methyl-4-(2-(pyridin-3-yl)acetyl)piperazin-1-yl)-3,4-dihydro-1H-pyrano[3,4-c]pyridine-5-carbonitrile (Compound 248)

¹H NMR (CHLOROFORM-d) δ8.48-8.61 (m, 2H), 7.70 (br. s., 1H), 7.32 (dd, J=7.8, 5.0 Hz, 1H), 4.89 (br. s., 0.5H), 4.71 (s, 2H), 4.53 (d, J=13.1 Hz, 0.5H), 4.05-4.31 (m, 2.5H), 3.68-3.87 (m, 2.5H), 3.57 (t, J=11.3 Hz, 0.5H), 3.17 (t, J=13.2 Hz, 1.5H), 2.92-3.09 (m, 1H), 2.71-2.89 (m, 3H), 1.37 (d, J=6.0 Hz, 1.5H), 1.30 (s, 7.5H), 1.19 (d, J=6.8 Hz, 6H). LC-MS: m/z 448.1 (M+H)$^+$.

8-isopropyl-3,3-dimethyl-6-(4-(2-methylfuran-3-carbonyl)-2-phenylpiperazin-1-yl)-3,4-dihydro-1H-pyrano[3,4-c]pyridine-5-carbonitrile (Compound 179)

$^1$H NMR (CHLOROFORM-d) δ7.71 (br. s., 1H), 7.39-7.49 (m, 2H), 7.36 (d, J=9.3 Hz, 1H), 7.25 (br. s., 2H), 7.19 (d, J=7.5 Hz, 1H), 6.52-6.62 (m, 1H), 5.37 (br. s., 1H), 4.91-5.16 (m, 1H), 4.59-4.73 (m, 2H), 4.21 (br. s., 2H), 3.82 (br. s., 2H), 3.57 (br. s., 1H), 2.77-2.87 (m, 2H), 2.67-2.77 (m, 1H), 1.29-1.30 (m, 6H), 1.16 (d, J=6.5 Hz, 3H), 0.83 (br. s., 3H). LC-MS: m/z 499.1 (M+H)$^+$.

(R)-6-(4-(furan-3-carbonyl)-3-phenylpiperazin-1-yl)-8-isopropyl-3,3-dimethyl-3,4-dihydro-1H-pyrano[3,4-c]pyridine-5-carbonitrile (Compound 256)

$^1$H NMR (CHLOROFORM-d) δ7.61 (br. s., 1H), 7.44 (br. s., 1H), 7.39 (br. s., 2H), 7.27-7.36 (m, 3H), 6.51 (br. s., 1H), 5.71-5.79 (br. s., 1H), 4.45-4.74 (m, 4H), 4.24 (d, J=10.8 Hz, 1H), 3.91 (d, J=10.3 Hz, 1H), 3.56 (d, J=11.8 Hz, 1H), 3.50 (d, J=9.8 Hz, 1H), 2.81 (dt, J=13.2, 6.6 Hz, 1H), 2.75 (s, 2H), 1.29 (s, 6H), 1.19 (d, J=6.5 Hz, 3H), 1.13 (d, J=5.8 Hz, 3H). LC-MS: m/z 485.1 (M+H)$^+$.

6-(4-(furan-3-carbonyl)-2-phenylpiperazin-1-yl)-8-isopropyl-3,3-dimethyl-3,4-dihydro-1H-pyrano[3,4-c]pyridine-5-carbonitrile (Compound 178)

$^1$H NMR (CHLOROFORM-d) δ7.38-7.54 (m, 2H), 7.22-7.28 (m, 3H), 7.18 (d, J=6.5 Hz, 1H), 6.36 (d, J=1.5 Hz, 1H), 5.37 (br. s., 1H), 4.91-5.14 (m, 1H), 4.60-4.73 (m, 2H), 4.05 (br. s., 2H), 3.79 (br. s., 2H), 3.58 (br. s., 1H), 2.77-2.86 (m, 2H), 2.68-2.77 (m, 1H), 2.37 (s, 3H), 1.29-1.31 (m, 6H), 1.17 (d, J=6.5 Hz, 3H), 0.89-0.92 (m, 3H). LC-MS: m/z 485.1 (M+H)$^+$.

(R)-8-isopropyl-3,3-dimethyl-6-(3-methyl-4-(2-(pyridin-2-yl)acetyl)piperazin-1-yl)-3,4-dihydro-1H-pyrano[3,4-c]pyridine-5-carbonitrile (Compound 218)

$^1$H NMR (CHLOROFORM-d) δ8.57 (d, J=4.8 Hz, 1H), 7.65-7.76 (m, 1H), 7.40 (dd, J=14.4, 7.9 Hz, 1H), 7.23 (dd, J=6.8, 5.3 Hz, 1H), 4.71 (s, 2H), 4.52 (br. s., 1H), 3.94-4.24 (m, 5H), 3.06-3.27 (m, 2H), 2.95 (dd, J=13.1, 3.0 Hz, 1H), 2.73-2.90 (m, 3H), 1.29 (s, 9H), 1.18 (d, J=6.5 Hz, 6H). LC-MS: m/z 448.1 (M+H)$^+$.

8-isopropyl-3,3-dimethyl-6-((3R)-3-methyl-4-(tetrahydrofuran-3-carbonyl)piperazin-1-yl)-3,4-dihydro-1H-pyrano[3,4-c]pyridine-5-carbonitrile (Compound 253)

$^1$H NMR (CHLOROFORM-d) δ4.90 (br. s., 0.5H), 4.72 (s, 2H), 4.54 (d, J=13.1 Hz, 0.5H), 4.12-4.37 (m, 2.5H), 3.81-4.08 (m, 4.5H), 3.59 (q, J=11.5 Hz, 0.5H), 3.12-3.35 (m, 2.5H), 2.95-3.10 (m, 1H), 2.76-2.90 (m, 3H), 2.04-2.25 (m, 2H), 1.39-1.48 (m, 1.5H), 1.30 (s, 7.5H), 1.20 (d, J=6.8 Hz, 6H). LC-MS: m/z 427.2 (M+H)$^+$.

8-isopropyl-3,3-dimethyl-6-(4-(2-(thiophen-2-yl)acetyl)piperazin-1-yl)-3,4-dihydro-1H-pyrano[3,4-c]pyridine-5-carbonitrile (Compound 145)

$^1$H NMR (CHLOROFORM-d) δ7.24 (d, J=5.0 Hz, 1H), 6.99 (dd, J=5.3, 3.5 Hz, 1H), 6.95 (br. s., 1H), 4.73 (s, 2H), 3.98 (s, 2H), 3.83 (br. s., 2H), 3.68 (d, J=18.3 Hz, 4H), 3.60 (d, J=4.8 Hz, 2H), 2.75-2.90 (m, 3H), 1.32 (s, 6H), 1.21 (d, J=6.5 Hz, 6H). LC-MS: m/z 439.2 (M+H)$^+$.

6-(4-(furan-2-carbonyl)piperazin-1-yl)-8-isopropyl-3,3-dimethyl-3,4-dihydro-1H-pyrano[3,4-c]pyridine-5-carbonitrile (Compound 145)

$^1$H NMR (CHLOROFORM-d) δ7.48-7.57 (m, 1H), 7.07 (d, J=3.5 Hz, 1H), 6.52 (dd, J=3.5, 1.8 Hz, 1H), 4.74 (s, 2H), 3.99 (br. s., 4H), 3.69-3.85 (m, 4H), 2.77-2.96 (m, 3H), 1.32 (s, 6H), 1.22 (d, J=6.5 Hz, 6H). LC-MS: m/z 409.1 (M+H)$^+$.

(S)-6-(4-(furan-2-carbonyl)-2-methylpiperazin-1-yl)-8-isopropyl-3,3-dimethyl-3,4-dihydro-1H-pyrano[3,4-c]pyridine-5-carbonitrile (Compound 202)

$^1$H NMR (CHLOROFORM-d) δ7.51 (s, 1H), 7.07 (dd, J=3.4, 0.6 Hz, 1H), 6.51 (dd, J=3.5, 1.8 Hz, 1H), 4.72 (s, 2H), 4.60 (br. s., 1H), 4.47 (d, J=11.3 Hz, 1H), 4.29 (dt, J=13.2, 1.4 Hz, 1H), 4.07 (d, J=13.1 Hz, 1H), 3.51 (t, J=10.8 Hz, 2H), 2.84 (dt, J=13.3, 6.7 Hz, 1H), 2.79 (s, 2H), 2.20-2.25 (m, 1H), 1.31 (s, 6H), 1.20 (d, J=2.5 Hz, 3H), 1.18 (d, J=2.5 Hz, 3H). LC-MS: m/z 423.2 (M+H)$^+$.

(R)-8-cyclohexyl-6-(4-(furan-3-carbonyl)-3-methylpiperazin-1-yl)-3,3-dimethyl-3,4-dihydro-1H-pyrano[3,4-c]pyridine-5-carbonitrile (Compound 151)

$^1$H NMR (CHLOROFORM-d) δ7.69-7.83 (m, 1H), 7.39-7.52 (m, 1H), 6.59 (dd, J=1.8, 0.8 Hz, 1H), 4.73 (s, 3H), 4.13-4.42 (m, 3H), 3.50 (d, J=6.8 Hz, 1H), 3.25 (dd, J=13.2, 3.4 Hz, 1H), 3.08 (td, J=12.5, 3.5 Hz, 1H), 2.80 (s, 2H), 2.46 (tt, J=11.2, 3.6 Hz, 1H), 1.82-1.90 (m, 2H), 1.56-1.79 (m, 6H), 1.43-1.48 (m, 3H), 1.29-1.39 (m, 8H). LC-MS: m/z 463.1 (M+H)$^+$.

8-cyclohexyl-6-(4-(furan-3-carbonyl)-3-methylpiperazin-1-yl)-3,3-dimethyl-3,4-dihydro-1H-pyrano[3,4-c]pyridine-5-carbonitrile (Compound 169)

$^1$H NMR (CHLOROFORM-d) δ7.76 (s, 1H), 7.41-7.52 (m, 1H), 6.60 (d, J=1.3 Hz, 1H), 4.73 (s, 3H), 4.13-4.43 (m, 3H), 3.51 (br. s., 1H), 3.25 (dd, J=12.8, 3.0 Hz, 1H), 3.09 (td, J=12.5, 3.4 Hz, 1H), 2.75-2.85 (m, 2H), 2.46 (tt, J=11.1, 3.7 Hz, 1H), 1.86 (d, J=12.8 Hz, 2H), 1.59-1.73 (m, 6H), 1.45 (d, J=6.8 Hz, 3H), 1.29-1.40 (m, 8H). LC-MS: m/z 463.2 (M+H)$^+$.

(R)-8-cyclohexyl-6-(4-(3-methoxypropanoyl)-3-methylpiperazin-1-yl)-3,3-dimethyl-3,4-dihydro-1H-pyrano[3,4-c]pyridine-5-carbonitrile (Compound 312)

$^1$H NMR (CHLOROFORM-d) δ4.90 (br. s., 0.5H), 4.71 (s, 2H), 4.53 (d, J=12.5 Hz, 0.5H), 4.04-4.33 (m, 2.5H), 3.68-3.84 (m, 2.5H), 3.49-3.64 (m, 0.5H), 3.38 (s, 3H), 2.99-3.27 (m, 2.5H), 2.64-2.84 (m, 3H), 2.52-2.62 (m, 1H), 2.44 (tt, J=11.0, 3.5 Hz, 1H), 1.84 (d, J=12.8 Hz, 2H), 1.75

(R)-8-cyclohexyl-3,3-dimethyl-6-(3-methyl-4-(2-(thiophen-2-yl)acetyl)piperazin-1-yl)-3,4-dihydro-1H-pyrano[3,4-c]pyridine-5-carbonitrile (Compound 153)

$^1$H NMR (CHLOROFORM-d) δ7.19-7.26 (m, 1H), 6.87-7.04 (m, 2H), 4.94 (br. s., 0.5H), 4.72 (s, 2H), 4.57 (d, J=12.8 Hz, 0.5H), 4.09-4.34 (m, 2.5H), 3.88-3.99 (m, 2H), 3.79 (d, J=12.0 Hz, 0.5H), 3.51-3.67 (m, 0.5H), 3.11-3.31 (m, 1.5H), 2.91-3.08 (m, 1H), 2.79 (s, 2H), 2.45 (tt, J=11.1, 3.6 Hz, 1H), 1.86 (d, J=12.8 Hz, 2H), 1.77 (d, J=10.3 Hz, 1H), 1.54-1.72 (m, 6H), 1.30-1.36 (m, 10H). LC-MS: m/z 493.1 (M+H)$^+$.

8-cyclohexyl-6-(4-(furan-3-carbonyl)-3-phenylpiperazin-1-yl)-3,3-dimethyl-3,4-dihydro-1H-pyrano[3,4-c]pyridine-5-carbonitrile (Compound 143)

$^1$H NMR (CHLOROFORM-d) δ7.64 (br. s., 1H), 7.39-7.47 (m, 3H), 7.36 (t, J=7.7 Hz, 2H), 7.25-7.32 (m, 1H), 6.53 (br. s., 1H), 5.76 (br. s., 1H), 4.45-4.75 (m, 4H), 4.25 (d, J=11.3 Hz, 1H), 3.90 (d, J=13.8 Hz, 1H), 3.39-3.66 (m, 2H), 2.71-2.81 (m, 2H), 2.44 (t, J=11.0 Hz, 1H), 1.74-1.91 (m, 3H), 1.67 (d, J=8.5 Hz, 2H), 1.29-1.43 (m, 11H). LC-MS: m/z 525.0 (M+H)$^+$.

(R)-8-cyclohexyl-6-(4-(furan-2-carbonyl)-3-methylpiperazin-1-yl)-3,3-dimethyl-3,4-dihydro-1H-pyrano[3,4-c]pyridine-5-carbonitrile (Compound 150)

$^1$H NMR (CHLOROFORM-d) δ7.52 (s, 1H), 7.05 (d, J=3.3 Hz, 1H), 6.46-6.63 (m, 1H), 4.89 (br. s., 1H), 4.73 (s, 2H), 4.50 (d, J=13.1 Hz, 1H), 4.26 (d, J=13.3 Hz, 1H), 4.18 (d, J=13.1 Hz, 1H), 3.56 (br. s., 1H), 3.34 (dd, J=12.8, 3.0 Hz, 1H), 3.12-3.24 (m, 1H), 2.80 (s, 2H), 2.37-2.55 (m, 1H), 1.86 (d, J=11.8 Hz, 2H), 1.56-1.77 (m, 6H), 1.48 (d, J=6.5 Hz, 3H), 1.34-1.42 (m, 2H), 1.32 (s, 6H). LC-MS: m/z 463.1 (M+H)$^+$.

8-cyclohexyl-6-(4-(furan-2-carbonyl)-3-methylpiperazin-1-yl)-3,3-dimethyl-3,4-dihydro-1H-pyrano[3,4-c]pyridine-5-carbonitrile (Compound 168)

$^1$H NMR (CHLOROFORM-d) δ7.45-7.58 (m, 1H), 7.04 (d, J=3.5 Hz, 1H), 6.50 (dd, J=3.3, 1.8 Hz, 1H), 4.87 (br. s., 1H), 4.71 (s, 2H), 4.49 (d, J=13.8 Hz, 1H), 4.25 (d, J=13.8 Hz, 1H), 4.17 (dd, J=13.1, 2.0 Hz, 1H), 3.54 (br. s., 1H), 3.32 (dd, J=13.1, 3.8 Hz, 1H), 3.16 (td, J=12.4, 3.5 Hz, 1H), 2.79 (s, 2H), 2.45 (tt, J=11.0, 3.8 Hz, 1H), 1.79-1.91 (m, 3H), 1.54-1.79 (m, 5H), 1.43-1.52 (m, 3H), 1.27-1.36 (m, 8H). LC-MS: m/z 463.2 (M+H)$^+$.

8-cyclohexyl-6-(4-(furan-2-carbonyl)piperazin-1-yl)-3,3-dimethyl-3,4-dihydro-1H-pyrano[3,4-c]pyridine-5-carbonitrile (Compound 117)

$^1$H NMR (CHLOROFORM-d) δ7.53 (dd, J=1.6, 0.9 Hz, 1H), 7.07 (dd, J=3.4, 0.6 Hz, 1H), 6.52 (dd, J=3.5, 1.8 Hz, 1H), 4.73 (s, 2H), 3.99 (br. s., 4H), 3.61-3.80 (m, 4H), 2.81 (s, 2H), 2.39-2.53 (m, 1H), 1.82-1.90 (m, 2H), 1.55-1.80 (m, 6H), 1.34-1.45 (m, 2H), 1.30-1.33 (m, 6H). LC-MS: m/z 448.9 (M+H)$^+$.

8-(3-fluorophenyl)-6-(4-(furan-3-carbonyl)-3-methylpiperazin-1-yl)-3,3-dimethyl-3,4-dihydro-1H-pyrano[3,4-c]pyridine-5-carbonitrile (Compound 130)

$^1$H NMR (CHLOROFORM-d) δ7.73-7.84 (m, 1H), 7.39-7.54 (m, 2H), 7.13-7.26 (m, 3H), 6.53-6.66 (m, 1H), 4.75 (br. s., 1H), 4.68 (s, 2H), 4.18-4.41 (m, 3H), 3.52 (br. s., 1H), 3.30 (dd, J=12.9, 3.6 Hz, 1H), 3.12 (td, J=12.5, 3.4 Hz, 1H), 2.90 (s, 2H), 1.44-1.53 (m, 3H), 1.37 (s, 6H). LC-MS: m/z 475.1 (M+H)$^+$.

(R)-8-cyclobutyl-6-(4-(furan-3-carbonyl)-3-isopropylpiperazin-1-yl)-3,3-dimethyl-3,4-dihydro-1H-pyrano[3,4-c]pyridine-5-carbonitrile (Compound 288)

$^1$H NMR (CHLOROFORM-d) δ7.72 (br. s., 1H), 7.44-7.51 (m, 1H), 6.52-6.61 (m, 1H), 4.46-4.70 (m, 4H), 4.31 (br. s., 1H), 4.04 (br. s., 0.5H), 3.81 (br. s., 0.5H), 3.57 (br. s., 0.5H), 3.46 (quin, J=8.2 Hz, 1H), 3.03-3.26 (m, 2H), 2.71-2.83 (m, 2H), 2.32-2.46 (m, 2H), 2.21-2.31 (m, 3H), 1.98-2.12 (m, 1H), 1.84-1.95 (m, 1H), 1.29 (d, J=2.0 Hz, 6H), 0.99-1.14 (m, 2H), 0.85-0.99 (m, 4H). LC-MS: m/z 463.2 (M+H)$^+$.

(R)-8-cyclobutyl-6-(3-isopropyl-4-(2-(thiophen-2-yl)acetyl)piperazin-1-yl)-3,3-dimethyl-3,4-dihydro-1H-pyrano[3,4-c]pyridine-5-carbonitrile (Compound 289)

$^1$H NMR (CHLOROFORM-d) δ7.20 (d, J=5.0 Hz, 1H), 6.88-7.01 (m, 2H), 4.41-4.65 (m, 4H), 4.19-4.35 (m, 1H), 3.83-4.07 (m, 2.5H), 3.38-3.61 (m, 2H), 2.87-3.17 (m, 2.5H), 2.68-2.83 (m, 2H), 2.30-2.48 (m, 2H), 2.19-2.29 (m, 2H), 1.98-2.16 (m, 1H), 1.23-1.30 (m, 6H), 0.99-1.11 (m, 3H), 0.85 (dd, J=19.6, 6.8 Hz, 3H). LC-MS: m/z 493.2 (M+H)$^+$.

8-cyclopentyl-6-((3S,5R)-4-(furan-3-carbonyl)-3,5-dimethylpiperazin-1-yl)-3,3-dimethyl-3,4-dihydro-1H-pyrano[3,4-c]pyridine-5-carbonitrile (Compound 146)

$^1$H NMR (CHLOROFORM-d) δ7.70-7.80 (m, 1H), 7.47 (t, J=1.6 Hz, 1H), 6.64 (dd, J=1.8, 0.8 Hz, 1H), 4.75 (s, 4H), 4.22 (d, J=13.1 Hz, 2H), 3.16 (dd, J=13.1, 4.3 Hz, 2H), 2.93-3.08 (m, 1H), 2.81 (s, 2H), 1.89-1.98 (m, 2H), 1.80-1.87 (m, 3H), 1.54 (d, J=7.0 Hz, 6H), 1.33 (s, 6H), 1.26-1.31 (m, 3H). LC-MS: m/z 463.1 (M+H)$^+$.

8-cyclopentyl-6-(4-(furan-2-carbonyl)-3-methylpiperazin-1-yl)-3,3-dimethyl-3,4-dihydro-1H-pyrano[3,4-c]pyridine-5-carbonitrile (Compound 147)

$^1$H NMR (CHLOROFORM-d) δ7.47-7.58 (m, 1H), 7.01-7.10 (m, 1H), 6.51 (dd, J=3.3, 1.8 Hz, 1H), 4.88 (br. s., 1H), 4.74 (s, 2H), 4.49 (d, J=13.3 Hz, 1H), 4.24 (d, J=13.8 Hz, 1H), 4.11-4.18 (m, 1H), 3.55 (br. s., 1H), 3.32 (dd, J=13.1, 3.8 Hz, 1H), 3.16 (td, J=12.4, 3.5 Hz, 1H), 2.95-3.05 (m, 1H), 2.80 (s, 2H), 1.87-1.96 (m, 2H), 1.77-1.86 (m, 4H), 1.63-1.74 (m, 2H), 1.44-1.51 (m, 3H), 1.30-1.36 (m, 6H). LC-MS: m/z 449.1 (M+H)$^+$.

(R)-8-ethyl-6-(4-(furan-3-carbonyl)-3-isopropylpiperazin-1-yl)-3,3-dimethyl-3,4-dihydro-1H-pyrano[3,4-c]pyridine-5-carbonitrile (Compound 414)

$^1$H NMR (DMSO-d$_6$) δ7.72 (br. s., 1H), 7.39-7.55 (m, 1H), 6.55 (s, 1H), 4.45-4.74 (m, 4H), 4.27 (br. s., 1H), 4.02

(d, J=12.0 Hz, 0.5H), 3.55 (br. s., 1H), 3.12 (dd, J=13.4, 3.4 Hz, 2.5H), 2.71-2.82 (m, 2H), 2.55 (q, J=7.5 Hz, 2H), 2.11-2.39 (m, 1H), 1.27-1.32 (m, 6H), 1.23 (t, J=7.4 Hz, 3H), 1.06 (br. s., 2H), 0.82-0.98 (m, 4H). LC-MS: m/z 437.3 (M+H)+.

(R)-8-ethyl-6-(3-isopropyl-4-(3-methoxypropanoyl)piperazin-1-yl)-3,3-dimethyl-3,4-dihydro-1H-pyrano[3,4-c]pyridine-5-carbonitrile (Compound 413)

$^1$H NMR (CHLOROFORM-d) δ4.61-4.75 (m, 2.5H), 4.52 (d, J=13.3 Hz, 1H), 4.44 (d, J=10.3 Hz, 0.5H), 4.25-4.36 (m, 1H), 3.79-3.89 (m, 0.5H), 3.69-3.78 (m, 2H), 3.56 (d, J=9.8 Hz, 0.5H), 3.41-3.52 (m, 0.5H), 3.34-3.40 (m, 3H), 2.92-3.18 (m, 2.5H), 2.51-2.81 (m, 6H), 2.03-2.32 (m, 1H), 1.31 (d, J=2.0 Hz, 6H), 1.25 (t, J=7.4 Hz, 3H), 1.04 (d, J=6.5 Hz, 3H), 0.90 (d, J=6.8 Hz, 1.5H), 0.84 (d, J=6.8 Hz, 1.5H).

(S)-ethyl 4-(5-cyano-8-cyclopropyl-3,3-dimethyl-3,4-dihydro-1H-pyrano[3,4-c]pyridin-6-yl)-1-(furan-3-carbonyl)piperazine-2-carboxylate (Compound 411)

$^1$H NMR (CHLOROFORM-d) δ7.79 (br. s., 1H), 7.46 (s, 1H), 6.63 (br. s., 1H), 5.39 (br. s., 0.5H), 4.80 (br. s., 0.5H), 4.72 (d, J=3.5 Hz, 2H), 4.21 (dq, J=10.7, 7.1 Hz, 2H), 4.01-4.15 (m, 2H), 3.93 (br. s., 1H), 3.40 (d, J=11.8 Hz, 1H), 3.03-3.18 (m, 1H), 2.76-2.89 (m, 3H), 1.11-1.34 (m, 15H). LC-MS: m/z 481.4 (M+H)+.

(R)-ethyl 4-(5-cyano-8-cyclopropyl-3,3-dimethyl-3,4-dihydro-1H-pyrano[3,4-c]pyridin-6-yl)-1-(furan-3-carbonyl)piperazine-2-carboxylate (Compound 410)

$^1$H NMR (CHLOROFORM-d) δ7.79 (br. s., 1H), 7.46 (s, 1H), 6.63 (br. s., 1H), 5.39 (br. s., 0.5H), 4.80 (br. s., 0.5H), 4.72 (d, J=3.5 Hz, 2H), 4.21 (dq, J=10.7, 7.1 Hz, 2H), 4.01-4.15 (m, 2H), 3.93 (br. s., 1H), 3.40 (d, J=11.8 Hz, 1H), 3.03-3.18 (m, 1H), 2.76-2.89 (m, 3H), 1.11-1.34 (m, 15H). LC-MS: m/z 481.2 (M+H)+.

8-cyclopropyl-6-(3-(methoxymethyl)-4-(3-methoxypropanoyl)piperazin-1-yl)-3,3-dimethyl-3,4-dihydro-1H-pyrano[3,4-c]pyridine-5-carbonitrile (Compound 403)

$^1$H NMR (CHLOROFORM-d) δ4.91 (s, 0.5H), 4.83 (s, 2H), 4.56 (d, J=13.6 Hz, 0.5H), 4.18 (d, J=13.3 Hz, 2H), 4.07 (d, J=11.0 Hz, 1H), 3.58-3.84 (m, 5H), 3.54 (d, J=6.5 Hz, 1H), 3.33-3.41 (m, 4H), 3.30 (s, 3H), 2.99-3.20 (m, 2H), 2.94 (d, J=11.0 Hz, 1H), 1.62-1.76 (m, 1H), 1.31 (s, 6H), 1.13 (br. s., 2H), 0.94-1.08 (m, 2H). LC-MS: m/z 443.2 (M+H)+.

8-cyclopropyl-6-(4-(furan-3-carbonyl)-3-(methoxymethyl)piperazin-1-yl)-3,3-dimethyl-3,4-dihydro-1H-pyrano[3,4-c]pyridine-5-carbonitrile (Compound 402)

$^1$H NMR (CHLOROFORM-d) δ7.82 (br. s., 1H), 7.43 (t, J=1.5 Hz, 1H), 6.65 (br. s., 1H), 4.84 (s, 2H), 4.07 (d, J=12.5 Hz, 3H), 3.77 (br. s., 1H), 3.59-3.73 (m, 1H), 3.35 (s, 4H), 3.01 (td, J=12.5, 3.3 Hz, 2H), 2.68-2.84 (m, 3H), 1.70 (td, J=8.2, 3.9 Hz, 1H), 1.27-1.37 (m, 6H), 1.08-1.17 (m, 2H), 0.95-1.08 (m, 2H). LC-MS: m/z 451.1 (M+H)+.

(R)-8-cyclobutyl-6-(3-isopropyl-4-(3-methoxypropanoyl)piperazin-1-yl)-3,3-dimethyl-3,4-dihydro-1H-pyrano[3,4-c]pyridine-5-carbonitrile (Compound 395)

$^1$H NMR (CHLOROFORM-d) δ4.50-4.75 (m, 3.5H), 4.39-4.50 (m, 0.5H), 4.24-4.37 (m, 1H), 3.84 (d, J=13.6 Hz, 0.5H), 3.68-3.79 (m, 2H), 3.53-3.62 (m, 0.5H), 3.40-3.52 (m, 1.5H), 3.37 (d, J=3.3 Hz, 3H), 2.95-3.22 (m, 2.5H), 2.53-2.83 (m, 4H), 2.32-2.48 (m, 2H), 2.19-2.31 (m, 2H), 1.99-2.19 (m, 2H), 1.85-1.96 (m, 1H), 1.29 (d, J=2.5 Hz, 6H), 1.00-1.11 (m, 3H), 0.87-0.94 (m, 1.5H), 0.80-0.87 (m, 1.5H). LC-MS: m/z 455.4 (M+H)+.

methyl 4-(5-cyano-8-cyclopropyl-3,3-dimethyl-3,4-dihydro-1H-pyrano[3,4-c]pyridin-6-yl)-1-(2-methylfuran-3-carbonyl)piperazine-2-carboxylate (Compound 394)

$^1$H NMR (CHLOROFORM-d) δ7.17-7.37 (m, 2H), 6.43 (br. s., 0.5H), 5.40 (br. s., 0.5H), 4.83 (s, 2H), 4.67 (d, J=13.1 Hz, 1H), 4.05 (d, J=11.0 Hz, 1H), 3.84-3.98 (m, 1H), 3.81 (d, J=13.8 Hz, 1H), 3.72 (s, 3H), 3.27 (d, J=11.5 Hz, 1H), 2.90-3.07 (m, 1H), 2.77 (s, 2H), 2.43 (br. s., 3H), 1.64-1.79 (m, 1H), 1.31 (d, J=2.8 Hz, 6H), 1.14 (dd, J=8.0, 3.8 Hz, 2H), 0.92-1.08 (m, 2H). LC-MS: m/z 479.4 (M+H)+.

methyl 4-(5-cyano-8-isopropyl-3,3-dimethyl-3,4-dihydro-1H-pyrano[3,4-c]pyridin-6-yl)-1-(furan-3-carbonyl)piperazine-2-carboxylate (Compound 393)

$^1$H NMR (CHLOROFORM-d) δ7.80 (br. s., 1H), 7.46 (s, 1H), 6.64 (br. s., 1H), 5.42 (br. s., 1H), 4.64-4.86 (m, 3H), 4.19 (d, J=10.3 Hz, 2H), 3.73 (s, 3H), 3.38 (d, J=11.3 Hz, 1H), 3.06-3.22 (m, 2H), 2.70-2.92 (m, 3H), 1.24-1.34 (m, 6H), 1.20 (d, J=6.5 Hz, 6H). LC-MS: m/z 467.4 (M+H)+.

Example 7

Additional Compounds of Formula I Produced According to Scheme 2, Step E2

Using the appropriate pyraonpyridine and substituted piperazine intermediates, the following compounds of the invention were made in an equivalent manner to compounds made using Step E2 of Scheme 2.

(R)-6-(4-(2-chloroacetyl)-3-methylpiperazin-1-yl)-8-cyclohexyl-3,4-dihydro-1H-pyrano[3,4-c]pyridine-5-carbonitrile (Compound 340)

$^1$H NMR (CHLOROFORM-d) δ 4.82 (br. s., 1H), 4.70 (s, 2H), 4.23 (d, J=19.3 Hz, 2H), 3.99-4.18 (m, 3H), 3.90-3.97 (m, 2H), 3.59-3.80 (m, 1H), 3.08-3.30 (m, 2H), 2.93 (t, J=5.6 Hz, 2H), 2.37-2.48 (m, 1H), 1.84 (d, J=12.5 Hz, 2H), 1.75 (d, J=10.5 Hz, 1H), 1.69 (br. s., 1H), 1.55-1.64 (m, 3H), 1.46 (d, J=6.0 Hz, 1H), 1.35-1.41 (m, 1H), 1.32 (d, J=7.8 Hz, 3H), 1.27-1.29 (m, 1H). LC-MS: m/z 417.0 (M+H)+.

(R)-8-cyclohexyl-6-(3-methyl-4-propionylpiperazin-1-yl)-3,4-dihydro-1H-pyrano[3,4-c]pyridine-5-carbonitrile (Compound 363)

$^1$H NMR (CHLOROFORM-d) δ4.88 (br. s., 0.5H), 4.65-4.75 (m, 2H), 4.50 (d, J=13.1 Hz, 0.5H), 4.06-4.29 (m, 2.5H), 3.88-3.99 (m, 2H), 3.52-3.78 (m, 1H), 3.00-3.29 (m, 2.5H), 2.93 (t, J=5.8 Hz, 2H), 2.33-2.48 (m, 1H), 2.10-2.18

(m, 3H), 1.79-1.89 (m, 2H), 1.55-1.76 (m, 5H), 1.35-1.41 (m, 2H), 1.24-1.34 (m, 6H). LC-MS: m/z 397.2 (M+H)+.

(R)-8-cyclohexyl-6-(4-(cyclopropanecarbonyl)-3-methylpiperazin-1-yl)-3,4-dihydro-1H-pyrano[3,4-c]pyridine-5-carbonitrile (Compound 375)

$^1$H NMR (CHLOROFORM-d) δ4.70 (s, 2H), 4.45 (d, J=11.8 Hz, 1H), 4.24 (br. s., 1H), 4.05-4.21 (m, 2H), 3.89-3.98 (m, 2H), 3.56-3.81 (m, 1H), 3.39 (d, J=10.5 Hz, 1H), 3.21 (br. s., 1H), 3.00-3.16 (m, 1H), 2.86-2.97 (m, 2H), 2.41 (tt, J=11.1, 3.6 Hz, 1H), 1.80-1.89 (m, 2H), 1.54-1.79 (m, 6H), 1.40-1.45 (m, 1H), 1.27-1.38 (m, 4H), 0.95-1.08 (m, 2H), 0.73-0.85 (m, 2H). LC-MS: m/z 409.2 (M+H)+.

8-cyclohexyl-6-(4-(2-phenylacetyl)piperazin-1-yl)-3,4-dihydro-1H-pyrano[3,4-c]pyridine-5-carbonitrile (Compound 131)

$^1$H NMR (CHLOROFORM-d) δ7.32-7.39 (m, 2H), 7.24-7.32 (m, 3H), 4.71 (s, 2H), 3.94 (t, J=5.8 Hz, 2H), 3.77-3.86 (m, 4H), 3.57-3.67 (m, 4H), 3.46-3.53 (m, 2H), 2.92 (t, J=5.6 Hz, 2H), 2.42 (tt, J=11.1, 3.5 Hz, 1H), 1.85 (d, J=12.5 Hz, 2H), 1.76 (d, J=14.8 Hz, 2H), 1.61-1.69 (m, 2H), 1.58 (d, J=12.0 Hz, 1H), 1.24-1.42 (m, 3H). LC-MS: m/z 445.1 (M+H)+.

(R)-8-cyclohexyl-6-(4-(3-methoxypropanoyl)-3-methylpiperazin-1-yl)-3,4-dihydro-1H-pyrano[3,4-c]pyridine-5-carbonitrile (Compound 341)

$^1$H NMR (CHLOROFORM-d) δ5.27-5.53 (m, 1H), 4.70 (s, 3H), 4.23 (br. s., 4H), 4.16 (br. s., 2H), 3.93 (t, J=5.4 Hz, 1H), 3.48 (br. s., 3H), 3.24 (br. s., 1H), 3.08 (br. s., 1H), 2.93 (t, J=5.4 Hz, 2H), 2.42 (br. s., 1H), 1.84 (d, J=11.0 Hz, 2H), 1.75 (d, J=10.0 Hz, 1H), 1.66 (br. s., 4H), 1.30-1.39 (m, 6H). LC-MS: m/z 413.2 (M+H)+.

(R)-6-(4-acetyl-3-methylpiperazin-1-yl)-8-cyclohexyl-3,4-dihydro-1H-pyrano[3,4-c]pyridine-5-carbonitrile (Compound 362)

$^1$H NMR (CHLOROFORM-d) δ4.81-4.96 (m, 0.5H), 4.66-4.75 (m, 2H), 4.50 (d, J=13.6 Hz, 0.5H), 4.06-4.33 (m, 2.5H), 3.87-4.03 (m, 2H), 3.51-3.79 (m, 1H), 2.96-3.23 (m, 2.5H), 2.86-2.95 (m, 2H), 2.41 (tt, J=11.1, 3.6 Hz, 1H), 2.14 (d, J=9.5 Hz, 3H), 1.80-1.89 (m, 2H), 1.54-1.75 (m, 5H), 1.32-1.41 (m, 3H), 1.25-1.31 (m, 3H). LC-MS: m/z 383.2 (M+H)+.

8-cyclohexyl-6-(4-(cyclopropanecarbonyl)piperazin-1-yl)-3,4-dihydro-1H-pyrano[3,4-c]pyridine-5-carbonitrile (Compound 141)

$^1$H NMR (CHLOROFORM-d) δ4.71 (s, 2H), 3.95 (t, J=5.8 Hz, 2H), 3.85 (br. s., 2H), 3.80 (br. s., 2H), 3.73 (br. s., 2H), 3.66 (br. s., 2H), 2.94 (t, J=5.6 Hz, 2H), 2.43 (tt, J=11.1, 3.7 Hz, 1H), 1.73-1.90 (m, 3H), 1.55-1.72 (m, 4H), 1.23-1.43 (m, 4H), 1.00-1.07 (m, 2H), 0.76-0.84 (m, 2H). LC-MS: m/z 395.2 (M+H)+.

(R)-6-(4-butyryl-3-methylpiperazin-1-yl)-8-cyclohexyl-3,4-dihydro-1H-pyrano[3,4-c]pyridine-5-carbonitrile (Compound 379)

$^1$H NMR (CHLOROFORM-d) δ4.89 (br. s., 1H), 4.70 (s, 2H), 4.12-4.25 (m, 2H), 3.89-3.98 (m, 2H), 3.74 (d, J=12.8 Hz, 1H), 2.98-3.28 (m, 2H), 2.88-2.97 (m, 2H), 2.20-2.48 (m, 3H), 1.80-1.88 (m, 2H), 1.60-1.77 (m, 6H), 1.26-1.42 (m, 6H), 0.99 (t, J=7.4 Hz, 3H). LC-MS: m/z 411.2 (M+H)+.

(R)-6-(4-(cyclopropanecarbonyl)-3-isopropylpiperazin-1-yl)-8-cyclopropyl-3,3-dimethyl-3,4-dihydro-1H-pyrano[3,4-c]pyridine-5-carbonitrile (Compound 376)

$^1$H NMR (CHLOROFORM-d) δ4.83 (s, 2H), 4.60 (d, J=9.8 Hz, 1H), 4.28-4.49 (m, 1H), 4.04-4.28 (m, 1H), 3.84 (d, J=9.8 Hz, 1H), 3.12 (td, J=13.2, 3.0 Hz, 1H), 2.91-3.05 (m, 2H), 2.77 (s, 2H), 2.12-2.29 (m, 1H), 1.64-1.82 (m, 2H), 1.32 (d, J=2.3 Hz, 6H), 1.06-1.19 (m, 2H), 0.96-1.05 (m, 8H), 0.87-0.94 (m, 2H), 0.71-0.84 (m, 2H). LC-MS: m/z 423.2 (M+H)+.

(R)-8-cyclopropyl-6-(3-isopropyl-4-propionylpiperazin-1-yl)-3,3-dimethyl-3,4-dihydro-1H-pyrano[3,4-c]pyridine-5-carbonitrile (Compound 354)

$^1$H NMR (CHLOROFORM-d) δ4.83 (s, 2H), 4.40 (d, J=10.3 Hz, 1H), 4.33 (d, J=13.1 Hz, 1H), 4.10-4.24 (m, 1H), 3.73 (d, J=13.3 Hz, 1H), 3.28-3.58 (m, 1H), 2.84-3.10 (m, 2H), 2.76 (s, 2H), 2.40 (d, J=7.3 Hz, 1H), 1.70 (td, J=7.9, 4.0 Hz, 2H), 1.31 (d, J=2.3 Hz, 6H), 1.18 (t, J=7.3 Hz, 3H), 0.93-1.06 (m, 6H), 0.64-0.92 (m, 4H). LC-MS: m/z 411.2 (M+H)+.

(R)-6-(4-butyryl-3-isopropylpiperazin-1-yl)-8-cyclopropyl-3,3-dimethylisochroman-5-carbonitrile (Compound 383)

$^1$H NMR (CHLOROFORM-d) δ4.76-4.89 (m, 2H), 4.64-4.67 (m, 0.5H), 4.41 (d, J=10.5 Hz, 0.5H), 4.33 (dd, J=13.3, 1.8 Hz, 1H), 4.14-4.24 (m, 1H), 3.74 (d, J=13.6 Hz, 0.5H), 3.36-3.55 (m, 1H), 2.90-3.07 (m, 2.5H), 2.76 (s, 2H), 2.29-2.43 (m, 2.5H), 2.08-2.20 (m, 0.5H), 1.64-1.76 (m, 3H), 1.31 (d, J=2.5 Hz, 6H), 0.95-1.18 (m, 10H), 0.87 (d, J=6.8 Hz, 1.5H), 0.81 (d, J=6.8 Hz, 1.5H). LC-MS: m/z 425.3 (M+H)+.

(R)-6-(4-acetyl-3-isopropylpiperazin-1-yl)-8-cyclopropyl-3,3-dimethylisochroman-5-carbonitrile (Compound 352)

$^1$H NMR (CHLOROFORM-d) δ4.83 (s, 2H), 4.38 (d, J=10.3 Hz, 1H), 4.32 (d, J=13.3 Hz, 1H), 4.03-4.25 (m, 1H), 3.69 (d, J=13.3 Hz, 1H), 3.35-3.58 (m, 1H), 2.86-3.12 (m, 2H), 2.76 (s, 2H), 2.24 (d, J=7.3 Hz, 1H), 2.09-2.18 (m, 3H), 1.67-1.76 (m, 1H), 1.31 (d, J=2.5 Hz, 6H), 0.94-1.06 (m, 6H), 0.86-0.94 (m, 2H), 0.83 (d, J=6.8 Hz, 2H). LC-MS: m/z 397.2 (M+H)+.

8-isopropyl-3,3-dimethyl-6-(4-(2-phenylacetyl)piperazin-1-yl)-3,4-dihydro-1H-pyrano[3,4-c]pyridine-5-carbonitrile (Compound 144)

$^1$H NMR (CHLOROFORM-d) δ7.33-7.39 (m, 2H), 7.26-7.31 (m, 3H), 4.72 (s, 2H), 3.77-3.86 (m, 4H), 3.57-3.68 (m, 4H), 3.43-3.54 (m, 2H), 2.74-2.92 (m, 3H), 1.31 (s, 6H), 1.19 (d, J=6.8 Hz, 6H). LC-MS: m/z 433.2 (M+H)+.

(R)-8-cyclohexyl-3,3-dimethyl-6-(3-methyl-4-(2-phenylacetyl)piperazin-1-yl)-3,4-dihydro-1H-pyrano[3,4-c]pyridine-5-carbonitrile (Compound 152)

$^1$H NMR (CHLOROFORM-d) δ7.23-7.42 (m, 5H), 4.95 (br. s., 0.5H), 4.71 (s, 2H), 4.59 (d, J=13.3 Hz, 0.5H), 4.20-4.23 (m, 1H), 4.08-4.23 (m, 1.5H), 3.80 (br. s., 2H), 3.72 (d, J=13.6 Hz, 0.5H), 3.48 (t, J=10.9 Hz, 0.5H), 3.13-3.21 (m, 1H), 2.92-3.08 (m, 1H), 2.86 (t, J=11.2 Hz, 0.5H), 2.77 (s, 2H), 2.39-2.53 (m, 1H), 1.85 (d, J=12.3 Hz, 2H), 1.54-1.63 (m, 6H), 1.29-1.43 (m, 11H). LC-MS: m/z 487.1 (M+H)$^+$.

(R)-3-(4-(5-cyano-8-cyclopropyl-3,3-dimethyl-3,4-dihydro-1H-pyrano[3,4-c]pyridin-6-yl)-2-isopropylpiperazin-1-yl)-2,2-dimethyl-3-oxopropyl acetate (Compound 419)

$^1$H NMR (CHLOROFORM-d) δ4.83 (s, 2H), 4.31-4.45 (m, 2H), 4.16-4.27 (m, 3H), 4.09 (d, J=8.5 Hz, 1H), 3.40 (br. s., 1H), 2.90-3.08 (m, 2H), 2.76 (s, 2H), 2.12-2.28 (m, 1H), 2.03-2.10 (m, 3H), 1.67-1.76 (m, 1H), 1.33 (dd, J=11.7, 1.4 Hz, 12H), 1.07-1.18 (m, 2H), 0.97-1.06 (m, 5H), 0.82 (d, J=6.8 Hz, 3H). LC-MS: m/z 497.5 (M+H)$^+$.

(R)-methyl 4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate (Compound 412)

$^1$H NMR (CHLOROFORM-d) δ4.78-4.91 (m, 2H), 4.62-4.65 (m, 0.5H), 4.29-4.44 (m, 1.5H), 4.10-4.26 (m, 1H), 3.79 (d, J=13.8 Hz, 0.5H), 3.68-3.74 (m, 3H), 3.40-3.58 (m, 1H), 2.91-3.15 (m, 2.5H), 2.78 (s, 2H), 2.64-2.74 (m, 4H), 2.07-2.34 (m, 1H), 1.69-1.76 (m, 1H), 1.33 (d, J=2.5 Hz, 6H), 1.07-1.20 (m, 2H), 0.99-1.06 (m, 5H), 0.89-0.95 (m, 1.5H), 0.82 (d, J=7.0 Hz, 1.5H). LC-MS: m/z 469.4 (M+H)$^+$.

(R)-4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoic acid (Compound 416)

The titled compound was prepared from LiOH/methanol-H$_2$O hydrolysis of Compound 412. $^1$H NMR (METHANOL-d$_4$) δ4.80-4.92 (m, 2H), 4.50-4.53 (m, 0.5H), 4.23-4.45 (m, 1.5H), 4.10-4.22 (m, 1H), 3.97 (d, J=14.1 Hz, 0.5H), 3.42-3.55 (m, 0.5H), 2.91-3.20 (m, 2.5H), 2.58-2.87 (m, 6H), 2.07-2.32 (m, 1H), 1.81-1.92 (m, 1H), 1.26-1.38 (m, 6H), 1.09-1.17 (m, 2H), 1.02-1.09 (m, 3H), 1.00 (d, J=6.5 Hz, 2H), 0.92 (d, J=6.8 Hz, 1H), 0.82 (d, J=6.8 Hz, 2H). LC-MS: m/z 455.4 (M+H)$^+$.

(R)-methyl 3-(4-(5-cyano-8-cyclopropyl-3,3-dimethyl-3,4-dihydro-1H-pyrano[3,4-c]pyridin-6-yl)-2-isopropylpiperazin-1-yl)-3-oxopropanoate (Compound 409)

$^1$H NMR (CHLOROFORM-d) δ4.75-4.90 (m, 2H), 4.63-4.68 (m, 0.5H), 4.29-4.44 (m, 1.5H), 4.11-4.27 (m, 1H), 3.71-3.83 (m, 3H), 3.42-3.67 (m, 4H), 2.93-3.15 (m, 2H), 2.71-2.84 (m, 2H), 2.06-2.33 (m, 1H), 1.66-1.78 (m, 1H), 1.32 (d, J=2.5 Hz, 6H), 1.06-1.18 (m, 2H), 0.97-1.05 (m, 5H), 0.81-0.94 (m, 3H). LC-MS: m/z 455.3 (M+H)$^+$.

(R)-3-(4-(5-cyano-8-cyclopropyl-3,3-dimethyl-3,4-dihydro-1H-pyrano[3,4-c]pyridin-6-yl)-2-isopropylpiperazin-1-yl)-3-oxopropanoic acid (Compound 418)

The titled compound was prepared from LiOH/methanol-H$_2$O hydrolysis of Compound 409. $^1$H NMR (METHANOL-d$_4$) δ4.82-4.90 (m, 2H), 4.25-4.46 (m, 2H), 4.10-4.25 (m, 1H), 3.85 (d, J=14.1 Hz, 1H), 3.39-3.65 (m, 2H), 2.93-3.22 (m, 3H), 2.78 (s, 2H), 2.09-2.21 (m, 1H), 1.82-1.90 (m, 1H), 1.32 (s, 6H), 0.97-1.17 (m, 7H), 0.84-0.94 (m, 3H). LC-MS: m/z 441.5 (M+H)$^+$.

(R)-8-cyclobutyl-6-(4-(cyclopropanecarbonyl)-3-isopropylpiperazin-1-yl)-3,3-dimethyl-3,4-dihydro-1H-pyrano[3,4-c]pyridine-5-carbonitrile (Compound 396)

$^1$H NMR (CHLOROFORM-d) δ4.52-4.69 (m, 3.5H), 4.26-4.49 (m, 1.5H), 4.16 (d, J=12.5 Hz, 0.5H), 3.90 (d, J=10.0 Hz, 0.5H), 3.37-3.66 (m, 2H), 2.99-3.29 (m, 2.5H), 2.70-2.83 (m, 2H), 2.37 (dt, J=19.6, 10.1 Hz, 2H), 2.20-2.31 (m, 2.5H), 1.98-2.11 (m, 1H), 1.84-1.96 (m, 1H), 1.73-1.83 (m, 1H), 1.29 (d, J=2.3 Hz, 6H), 0.89-1.11 (m, 7H), 0.77-0.87 (m, 3H). LC-MS: m/z 437.3 (M+H)$^+$.

Example 8

Additional Compounds of Formula I Produced According to Scheme 2, Step E3

Using the appropriate pyraonpyridine and substituted piperazine intermediates, the following compounds of the invention were made in an equivalent manner to compounds made using Step E3 of Scheme 2.

(R)-8-cyclopropyl-6-(3-isopropyl-4-(2-(methoxy (methyl)amino)acetyl)piperazin-1-yl)-3,3-dimethylisochroman-5-carbonitrile (Compound 338)

$^1$H NMR (CHLOROFORM-d) δ4.77-4.89 (m, 2H), 4.51-4.68 (m, 0.5H), 4.28-4.43 (m, 1.5H), 4.21 (d, J=11.0 Hz, 1H), 4.00 (d, J=13.6 Hz, 0.5H), 3.66-3.83 (m, 1H), 3.52-3.64 (m, 3.5H), 3.38-3.50 (m, 1H), 2.91-3.21 (m, 2.5H), 2.73-2.80 (m, 2H), 2.64-2.71 (m, 2H), 1.97-2.29 (m, 2H), 1.67-1.75 (m, 1H), 1.31 (d, J=2.0 Hz, 6H), 0.98-1.20 (m, 7H), 0.81-0.91 (m, 3H). LC-MS: m/z 456.1 (M+H)$^+$.

(R)-6-(4-(2-(1H-imidazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 374)

$^1$H NMR (CHLOROFORM-d) δ7.83 (d, J=10.0 Hz, 1H), 7.12 (s, 1H), 7.04 (s, 1H), 5.06 (dd, J=16.3, 7.8 Hz, 1H), 4.86-4.97 (m, 1H), 4.79-4.85 (m, 2H), 4.53-4.56 (m, 0.5H), 4.26-4.41 (m, 1.5H), 4.12-4.24 (m, 1H), 3.70 (d, J=13.3 Hz, 0.5H), 3.40-3.58 (m, 1H), 2.95-3.16 (m, 2.5H), 2.76 (s, 2H), 2.09-2.27 (m, 1H), 1.67-1.75 (m, 1H), 1.31 (d, J=2.8 Hz, 6H), 0.90-1.19 (m, 8.5H), 0.82 (d, J=6.8 Hz, 1.5H). LC-MS: m/z 463.2 (M+H)$^+$.

(R)-8-cyclopropyl-6-(3-isopropyl-4-(2-(2-methyl-1H-imidazol-1-yl)acetyl)piperazin-1-yl)-3,3-dimethyl-3,4-dihydro-1H-pyrano[3,4-c]pyridine-5-carbonitrile (Compound 380)

$^1$H NMR (CHLOROFORM-d) δ6.93-7.16 (m, 1H), 6.86 (s, 1H), 4.73-5.03 (m, 4H), 4.12-4.42 (m, 3H), 3.82 (br. s., 0.5H), 3.50-3.65 (m, 1H), 2.95-3.19 (m, 2.5H), 2.68-2.82 (m, 2H), 2.32-2.43 (m, 3H), 2.12-2.25 (m, 1H), 1.67-1.78 (m, 1H), 1.32 (d, J=2.8 Hz, 6H), 1.07-1.19 (m, 3.5H), 0.92-1.05 (m, 5H), 0.82 (d, J=6.8 Hz, 1.5H). LC-MS: m/z 477.3 (M+H)$^+$.

(R)-6-(4-(2-(1H-1,2,4-triazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 324)

$^1$H NMR (CHLOROFORM-d) δ8.28 (br. s., 1H), 7.98 (br. s., 1H), 4.99-5.22 (m, 2H), 4.75-4.92 (m, 2H), 4.57 (d, J=12.8 Hz, 0.5H), 4.26-4.44 (m, 1.5H), 4.19 (dd, J=19.1, 13.3 Hz, 1H), 3.79 (d, J=13.3 Hz, 0.5H), 3.45-3.65 (m, 1H), 2.92-3.16 (m, 2.5H), 2.70-2.85 (m, 2H), 2.11-2.41 (m, 1H), 1.67-1.80 (m, 1H), 1.32 (d, J=2.8 Hz, 6H), 0.90-1.19 (m, 8.5H), 0.82 (d, J=6.5 Hz, 1.5H). LC-MS: m/z 464.0 (M+H)$^+$.

Example 9

Additional Compound of Formula I Produced According to Scheme 2, Step E4

Using the appropriate pyraonpyridine and substituted piperazine intermediates, the following compound of the invention was made in an equivalent manner to compounds made using Step E4 of Scheme 2.

(R)-8-cyclopropyl-6-(4-(2-(2-hydroxyethoxy)acetyl)-3-isopropylpiperazin-1-yl)-3,3-dimethylisochroman-5-carbonitrile (Compound 348)

$^1$H NMR (CHLOROFORM-d) δ4.78-4.90 (m, 2H), 4.58-4.60 (m, 0.5H), 4.11-4.41 (m, 4.5H), 3.73 (dd, J=18.6, 4.3 Hz, 4H), 3.60 (d, J=13.6 Hz, 1H), 3.35-3.52 (m, 0.5H), 3.27-3.29 (m, 0.5H), 2.92-3.10 (m, 2H), 2.76 (s, 2H), 2.22-2.35 (m, 0.5H), 2.13 (dt, J=10.8, 6.5 Hz, 0.5H), 1.66-1.75 (m, 1H), 1.32 (d, J=2.8 Hz, 6H), 0.97-1.18 (m, 7H), 0.88-0.92 (m, 1.5H), 0.84 (d, J=6.8 Hz, 1.5H). LC-MS: m/z 457.3 (M+H)$^+$.

Example 10

Additional Compound of Formula I Produced According to Scheme 2, Step E5

Using the appropriate pyraonpyridine and substituted piperazine intermediates, the following compound of the invention was made in an equivalent manner to compounds made using Step E5 of Scheme 2.

(R)-8-cyclopropyl-6-(3-isopropyl-4-(2-(prop-2-ynylamino)acetyl)piperazin-1-yl)-3,3-dimethyl-3,4-dihydro-1H-pyrano[3,4-c]pyridine-5-carbonitrile (Compound 373)

$^1$H NMR (CHLOROFORM-d) δ4.76-4.90 (m, 2H), 4.61 (d, J=10.3 Hz, 0.5H), 4.27-4.42 (m, 1.5H), 4.09-4.23 (m, 1H), 3.34-3.70 (m, 6H), 2.93-3.11 (m, 3H), 2.76 (s, 2H), 2.20-2.33 (m, 2H), 1.67-1.75 (m, 1H), 1.31 (d, J=2.3 Hz, 6H), 1.07-1.17 (m, 2H), 0.98-1.05 (m, 5H), 0.88-0.92 (m, 1.5H), 0.83 (d, J=6.8 Hz, 1.5H). LC-MS: m/z 450.4 (M+H)$^+$.

Example 11

Additional Compounds of Formula I Produced According to Scheme 2, Step E6

Using the appropriate pyraonpyridine and substituted piperazine intermediates, the following compounds of the invention were made in an equivalent manner to compounds made using Step E6 of Scheme 2.

(R)-8-cyclopropyl-6-(4-(2-ethoxyacetyl)-3-isopropylpiperazin-1-yl)-3,3-dimethylisochroman-5-carbonitrile (Compound 345)

$^1$H NMR (CHLOROFORM-d) δ4.75-4.90 (m, 2H), 4.54-4.57 (m, 0.5H), 4.25-4.41 (m, 2H), 4.05-4.23 (m, 2.5H), 3.87 (d, J=13.6 Hz, 0.5H), 3.58 (q, J=6.9 Hz, 2H), 3.42 (t, J=11.7 Hz, 1H), 2.90-3.11 (m, 2.5H), 2.76 (s, 2H), 2.07-2.33 (m, 1H), 1.66-1.75 (m, 1H), 1.31 (d, J=2.0 Hz, 6H), 1.20-1.28 (m, 3H), 0.97-1.19 (m, 7H), 0.79-0.93 (m, 3H). LC-MS: m/z 441.3 (M+H)$^+$.

(R)-8-cyclopropyl-6-(4-(2-(cyclopropylmethoxy)acetyl)-3-isopropylpiperazin-1-yl)-3,3-dimethylisochroman-5-carbonitrile (Compound 390)

$^1$H NMR (CHLOROFORM-d) δ4.77-4.89 (m, 2H), 4.53-4.56 (m, 0.5H), 4.28-4.41 (m, 2H), 4.10-4.28 (m, 2.5H), 3.89 (d, J=13.6 Hz, 0.5H), 3.58-3.60 (m, 0.5H), 3.31-3.49 (m, 2.5H), 2.92-3.12 (m, 2.5H), 2.70-2.84 (m, 2H), 2.10-2.31 (m, 1H), 1.65-1.77 (m, 1H), 1.31 (d, J=2.0 Hz, 6H), 0.95-1.17 (m, 8H), 0.79-0.92 (m, 3H), 0.50-0.64 (m, 2H), 0.18-0.31 (m, 2H). LC-MS: m/z 467.4 (M+H)$^+$.

(R)-8-cyclopropyl-6-(3-isopropyl-4-(2-propoxyacetyl)piperazin-1-yl)-3,3-dimethylisochroman-5-carbonitrile (Compound 381)

$^1$H NMR (CHLOROFORM-d) δ4.76-4.89 (m, 2H), 4.54-4.56 (m, 0.5H), 4.25-4.40 (m, 2H), 4.04-4.24 (m, 2.5H), 3.89 (d, J=13.6 Hz, 0.5H), 3.36-3.62 (m, 3H), 2.89-3.10 (m, 2.5H), 2.72-2.81 (m, 2H), 2.08-2.30 (m, 1H), 1.60-1.70 (m, 3H), 1.31 (d, J=2.5 Hz, 6H), 1.05-1.18 (m, 2H), 0.98-1.04 (m, 5H), 0.91-0.97 (m, 3H), 0.82-0.90 (m, 3H). LC-MS: m/z 455.4 (M+H)$^+$.

8-cyclopropyl-6-((3R)-3-isopropyl-4-(2-(tetrahydrofuran-3-yloxy)acetyl)piperazin-1-yl)-3,3-dimethyl-3,4-dihydro-1H-pyrano[3,4-c]pyridine-5-carbonitrile (Compound 417)

$^1$H NMR (CHLOROFORM-d) δ4.79-4.91 (m, 2H), 4.55-4.57 (m, 0.5H), 4.11-4.40 (m, 5.5H), 3.76-3.97 (m, 4.5H), 3.44 (t, J=12.5 Hz, 1H), 2.92-3.14 (m, 2.5H), 2.73-2.82 (m, 2H), 2.13-2.31 (m, 1H), 2.00-2.11 (m, 2H), 1.68-1.78 (m, 1H), 1.33 (d, J=2.5 Hz, 6H), 1.08-1.19 (m, 2H), 0.98-1.07 (m, 5H), 0.83-0.95 (m, 3H). LC-MS: m/z 483.5 (M+H)$^+$.

(R)-8-cyclopropyl-6-(4-(2-(furan-2-ylmethoxy)acetyl)-3-isopropylpiperazin-1-yl)-3,3-dimethyl-3,4-dihydro-1H-pyrano[3,4-c]pyridine-5-carbonitrile (Compound 404)

$^1$H NMR (CHLOROFORM-d) δ7.43 (s, 1H), 6.30-6.49 (m, 2H), 4.76-4.91 (m, 2H), 4.48-4.67 (m, 2.5H), 4.08-4.38 (m, 4.5H), 3.76 (d, J=13.3 Hz, 0.5H), 3.30-3.58 (m, 1H), 2.87-3.16 (m, 2.5H), 2.67-2.84 (m, 2H), 2.07-2.33 (m, 1H), 1.62-1.79 (m, 1H), 1.31 (d, J=1.5 Hz, 6H), 1.06-1.18 (m, 2H), 0.93-1.06 (m, 5H), 0.80-0.90 (m, 3H). LC-MS: m/z 493.4 (M+H)$^+$.

(R)-8-cyclopropyl-6-(4-(2-(3-fluorophenoxy)acetyl)-3-isopropylpiperazin-1-yl)-3,3-dimethylisochroman-5-carbonitrile (Compound 384)

$^1$H NMR (CHLOROFORM-d) δ7.11-7.26 (m, 1H), 6.66-6.77 (m, 2.5H), 6.56-6.65 (m, 0.5H), 4.83 (s, 2H), 4.67-4.78

(m, 2H), 4.53-4.57 (m, 0.5H), 4.26-4.40 (m, 1.5H), 4.07-4.25 (m, 1H), 3.89 (d, J=13.6 Hz, 0.5H), 3.51-3.60 (m, 0.5H), 3.42-3.49 (m, 0.5H), 2.86-3.14 (m, 2.5H), 2.76 (s, 2H), 2.05-2.23 (m, 1H), 1.64-1.78 (m, 1H), 1.31 (d, J=3.5 Hz, 6H), 0.95-1.18 (m, 7H), 0.83-0.95 (m, 1.5H), 0.76 (d, J=6.8 Hz, 1.5H). LC-MS: m/z 507.4 (M+H)$^+$.

(R)-8-cyclopropyl-6-(3-isopropyl-4-(2-(pyridin-3-yloxy)acetyl)piperazin-1-yl)-3,3-dimethyl-3,4-dihydro-1H-pyrano[3,4-c]pyridine-5-carbonitrile (Compound 399)

$^1$H NMR (CHLOROFORM-d) δ8.38 (br. s., 1H), 8.28 (br. s., 1H), 7.19-7.46 (m, 2H), 4.72-4.98 (m, 4H), 4.54-4.57 (m, 0.5H), 4.26-4.42 (m, 1.5H), 4.12-4.25 (m, 1H), 3.85 (d, J=13.3 Hz, 0.5H), 3.45-3.62 (m, 1H), 2.90-3.17 (m, 2.5H), 2.72-2.82 (m, 2H), 2.09-2.35 (m, 1H), 1.66-1.76 (m, 1H), 1.32 (d, J=3.8 Hz, 6H), 0.91-1.19 (m, 8.5H), 0.76 (d, J=6.8 Hz, 1.5H). LC-MS: m/z 490.4 (M+H)$^+$.

(R)-6-(4-(2-(4-bromo-1H-pyrazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 415)

$^1$H NMR (CHLOROFORM-d) δ7.60 (d, J=7.8 Hz, 1H), 7.51 (s, 1H), 4.90-5.13 (m, 2H), 4.80-4.90 (m, 2H), 4.56-4.59 (m, 0.5H), 4.27-4.40 (m, 1.5H), 4.18 (d, J=12.8 Hz, 1H), 3.82 (d, J=13.3 Hz, 0.5H), 3.41-3.63 (m, 1H), 2.89-3.12 (m, 2.5H), 2.78 (s, 2H), 2.08-2.34 (m, 1H), 1.65-1.81 (m, 1H), 1.33 (d, J=3.0 Hz, 6H), 0.96-1.19 (m, 7H), 0.88-0.95 (m, 1.5H), 0.82 (d, J=6.8 Hz, 1.5H). LC-MS: m/z 541.2 (M+H)$^+$.

(R)-6-(4-(2-(1H-1,2,3-triazol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 408)

$^1$H NMR (CHLOROFORM-d) δ7.70-7.87 (m, 2H), 5.19-5.47 (m, 2H), 4.76-4.91 (m, 2H), 4.55-4.58 (m, 0.5H), 4.26-4.43 (m, 1.5H), 4.18 (t, J=13.1 Hz, 1H), 3.84 (d, J=13.6 Hz, 0.5H), 3.43-3.67 (m, 1H), 2.90-3.16 (m, 2.5H), 2.77 (s, 2H), 2.16 (td, J=6.8, 3.5 Hz, 1H), 1.67-1.78 (m, 1H), 1.32 (d, J=2.5 Hz, 6H), 0.97-1.19 (m, 7H), 0.89-0.96 (m, 1.5H), 0.80 (d, J=6.8 Hz, 1.5H). LC-MS: m/z 464.4 (M+H)$^+$.

(R)-6-(4-(2-(2H-1,2,3-triazol-2-yl)acetyl)-3-isopropylpiperazin-1-yl)-8-cyclopropyl-3,3-dimethyl-3,4-dihydro-1H-pyrano[3,4-c]pyridine-5-carbonitrile (Compound 407)

$^1$H NMR (CHLOROFORM-d) δ7.62-7.74 (m, 2H), 5.32-5.50 (m, 2H), 4.75-4.91 (m, 2H), 4.56-4.59 (m, 0.5H), 4.32 (t, J=11.3 Hz, 1.5H), 4.17 (d, J=10.8 Hz, 1H), 3.69 (d, J=13.8 Hz, 0.5H), 3.35-3.58 (m, 1H), 2.92-3.14 (m, 2.5H), 2.70-2.83 (m, 2H), 2.08-2.26 (m, 1H), 1.71 (dd, J=7.5, 4.5 Hz, 1H), 1.31 (d, J=2.8 Hz, 6H), 0.94-1.18 (m, 8.5H), 0.78-0.91 (m, 1.5H). LC-MS: m/z 464.4 (M+H)$^+$.

(R)-6-(4-(2-(1H-indol-1-yl)acetyl)-3-isopropylpiperazin-1-yl)-8-cyclopropyl-3,3-dimethyl-3,4-dihydro-1H-pyrano[3,4-c]pyridine-5-carbonitrile (Compound 406)

$^1$H NMR (CHLOROFORM-d) δ7.62 (d, J=7.8 Hz, 1H), 7.17-7.30 (m, 2H), 7.05-7.14 (m, 2H), 6.57 (br. s., 1H), 4.85-5.00 (m, 2H), 4.81 (br. s., 2H), 4.57 (d, J=10.0 Hz, 0.5H), 4.34 (d, J=10.0 Hz, 0.5H), 4.23 (dd, J=18.9, 13.7 Hz, 1H), 4.13 (d, J=12.5 Hz, 0.5H), 4.03 (d, J=12.5 Hz, 0.5H), 3.63 (d, J=13.6 Hz, 0.5H), 3.31-3.52 (m, 1H), 2.89-3.08 (m, 1.5H), 2.62-2.86 (m, 3H), 2.06-2.32 (m, 1H), 1.66-1.75 (m, 1H), 1.30 (d, J=3.5 Hz, 6H), 0.91-1.16 (m, 8.5H), 0.82 (d, J=6.8 Hz, 1.5H). LC-MS: m/z 512.4 (M+H)$^+$.

(R)-8-cyclopropyl-6-(3-isopropyl-4-(2-(4-methyl-1H-pyrazol-1-yl)acetyl)piperazin-1-yl)-3,3-dimethyl-3,4-dihydro-1H-pyrano[3,4-c]pyridine-5-carbonitrile (Compound 401)

$^1$H NMR (CHLOROFORM-d) δ7.30-7.38 (m, 2H), 4.79-5.11 (m, 4H), 4.55-4.58 (m, 0.5H), 4.23-4.39 (m, 1.5H), 4.15 (dd, J=9.9, 7.7 Hz, 1H), 3.87 (d, J=13.6 Hz, 0.5H), 3.58-4.61 (m, 0.5H), 3.35-3.52 (m, 0.5H), 2.83-3.12 (m, 2.5H), 2.71-2.82 (m, 2H), 2.04-2.15 (m, 4H), 1.66-1.75 (m, 1H), 1.31 (d, J=2.8 Hz, 6H), 0.96-1.16 (m, 7H), 0.85-0.93 (m, 1.5H), 0.80 (d, J=6.8 Hz, 1.5H). LC-MS: m/z 477.5 (M+H)$^+$.

(R)-8-cyclopropyl-6-(3-isopropyl-4-(2-(3-methyl-1H-pyrazol-1-yl)acetyl)piperazin-1-yl)-3,3-dimethyl-3,4-dihydro-1H-pyrano[3,4-c]pyridine-5-carbonitrile (Compound 400)

$^1$H NMR (CHLOROFORM-d) δ7.42 (dd, J=7.0, 2.3 Hz, 1H), 6.10 (t, J=2.5 Hz, 1H), 4.76-5.15 (m, 3H), 4.55-4.58 (m, 0.5H), 4.29 (t, J=14.3 Hz, 1.5H), 4.14 (t, J=10.3 Hz, 1H), 3.85 (d, J=13.6 Hz, 0.5H), 3.56-3.58 (m, 0.5H), 3.33-3.50 (m, 0.5H), 2.83-3.12 (m, 2.5H), 2.69-2.81 (m, 2H), 2.26-2.35 (m, 3H), 2.08-2.25 (m, 1H), 1.65-1.75 (m, 1H), 1.31 (d, J=2.8 Hz, 6H), 0.94-1.20 (m, 7H), 0.88 (d, J=6.8 Hz, 1.5H), 0.81 (d, J=6.8 Hz, 1.5H). LC-MS: m/z 477.5 (M+H)$^+$.

Example 11

Additional Compounds of Formula I Produced According to Scheme 2, Step F1

Using the appropriate pyraonpyridine and substituted piperazine intermediates, the following compounds of the invention were made in an equivalent manner to compounds made using Step F1 of Scheme 2.

2-ethyl-1-(2-methoxyethyl) 4-(5-cyano-8-cyclohexyl-3,4-dihydro-1H-pyrano[3,4-c]pyridin-6-yl)-piperazine-1,2-dicarboxylate (Compound 315)

$^1$H NMR (CHLOROFORM-d) δ4.68-4.91 (m, 4H), 4.06-4.34 (m, 6H), 3.87-4.00 (m, 2H), 3.58-3.69 (m, 3H), 3.37-3.45 (m, 4H), 3.09 (t, J=12.5 Hz, 1H), 2.93 (t, J=5.6 Hz, 2H), 2.38-2.48 (m, 1H), 1.86 (d, J=11.5 Hz, 2H), 1.77 (d, J=9.0 Hz, 1H), 1.63-1.70 (m, 3H), 1.29-1.44 (m, 4H), 1.20 (t, J=7.2 Hz, 3H). LC-MS: m/z 501.0 (M+H)$^+$.

(R)-ethyl 4-(5-cyano-8-cyclohexyl-3,4-dihydro-1H-pyrano[3,4-c]pyridin-6-yl)-2-methylpiperazine-1-carboxylate (Compound 358)

$^1$H NMR (CHLOROFORM-d) δ4.69 (s, 2H), 4.41 (br. s., 1H), 4.08-4.25 (m, 4H), 4.01 (d, J=13.3 Hz, 1H), 3.93 (td, J=5.8, 1.0 Hz, 2H), 3.18-3.40 (m, 2H), 3.05 (td, J=12.4, 3.5 Hz, 1H), 2.92 (t, J=5.6 Hz, 2H), 2.35-2.46 (m, 1H), 1.79-1.89 (m, 2H), 1.75 (d, J=10.3 Hz, 1H), 1.54-1.70 (m, 4H), 1.31-1.41 (m, 2H), 1.30 (d, J=3.0 Hz, 3H), 1.27-1.29 (m, 3H), 1.23-1.26 (m, 1H). LC-MS: m/z 413.3 (M+H)+.

(R)-propyl 4-(5-cyano-8-cyclohexyl-3,4-dihydro-1H-pyrano[3,4-c]pyridin-6-yl)-2-methylpiperazine-1-carboxylate (Compound 359)

$^1$H NMR (CHLOROFORM-d) δ4.69 (s, 2H), 4.41 (br. s., 1H), 3.97-4.25 (m, 5H), 3.88-3.96 (m, 2H), 3.20-3.41 (m, 2H), 3.06 (td, J=12.4, 3.8 Hz, 1H), 2.92 (t, J=5.6 Hz, 2H), 2.41 (tt, J=10.9, 3.9 Hz, 1H), 1.84 (d, J=12.8 Hz, 2H), 1.71-1.77 (m, 1H), 1.53-1.71 (m, 6H), 1.26-1.41 (m, 6H), 0.97 (t, J=7.4 Hz, 3H). LC-MS: m/z 427.3 (M+H)+.

(R)-benzyl 4-(5-cyano-8-cyclohexyl-3,4-dihydro-1H-pyrano[3,4-c]pyridin-6-yl)-2-methylpiperazine-1-carboxylate (Compound 343)

$^1$H NMR (CHLOROFORM-d) δ7.30-7.43 (m, 6H), 5.11-5.22 (m, 2H), 4.63-4.73 (m, 2H), 4.45 (br. s., 1H), 4.09-4.27 (m, 2H), 4.04 (d, J=13.3 Hz, 1H), 3.93 (td, J=5.8, 1.0 Hz, 2H), 3.36 (td, J=12.7, 3.3 Hz, 1H), 3.25 (dd, J=13.1, 3.8 Hz, 1H), 3.05 (td, J=12.4, 3.5 Hz, 1H), 2.91 (t, J=5.8 Hz, 2H), 2.33-2.49 (m, 1H), 1.78-1.88 (m, 2H), 1.74 (d, J=10.5 Hz, 1H), 1.48-1.70 (m, 6H), 1.25-1.40 (m, 7H). LC-MS: m/z 475.3 (M+H)+.

4-methoxyphenyl 4-(5-cyano-8-isopropyl-3,4-dihydro-1H-pyrano[3,4-c]pyridin-6-yl)piperazine-1-carboxylate (Compound 103)

$^1$H NMR (CHLOROFORM-d) δ7.04-7.16 (m, 2H), 6.86-6.98 (m, 2H), 4.74 (s, 2H), 3.92-4.03 (m, 2H), 3.82 (s, 5H), 3.69-3.79 (m, 6H), 2.97 (t, J=5.6 Hz, 2H), 2.84 (dt, J=13.3, 6.7 Hz, 1H), 1.22 (d, J=6.5 Hz, 6H). LC-MS: m/z 437.3 (M+H)+.

(R)-2-methoxyethyl 4-(5-cyano-8-cyclopropyl-3,3-dimethylisochroman-6-yl)-2-isopropyl-piperazine-1-carboxylate (Compound 307)

$^1$H NMR (CHLOROFORM-d) δ4.74-4.90 (m, 2H), 4.20-4.33 (m, 3H), 4.14 (d, J=12.0 Hz, 2H), 3.85 (br. s., 1H), 3.55-3.65 (m, 2H), 3.39 (s, 3H), 3.20 (d, J=6.3 Hz, 1H), 2.97-3.11 (m, 2H), 2.76 (s, 2H), 2.12 (dt, J=10.4, 6.6 Hz, 1H), 1.68-1.74 (m, 1H), 1.31 (d, J=2.3 Hz, 6H), 0.94-1.17 (m, 7H), 0.86 (d, J=6.8 Hz, 3H). LC-MS: m/z 457.0 (M+H)+.

(R)-ethyl 4-(5-cyano-8-cyclopropyl-3,3-dimethylisochroman-6-yl)-2-isopropyl-piperazine-1-carboxylate (Compound 367)

$^1$H NMR (CHLOROFORM-d) δ4.77-4.88 (m, 2H), 4.29 (d, J=13.3 Hz, 1H), 4.14 (d, J=13.3 Hz, 4H), 3.83 (br. s., 1H), 3.11-3.24 (m, 1H), 2.95-3.10 (m, 2H), 2.72-2.81 (m, 2H), 2.11 (dq, J=17.1, 6.7 Hz, 1H), 1.65-1.73 (m, 1H), 1.31 (d, J=2.5 Hz, 6H), 1.27 (t, J=7.0 Hz, 3H), 1.05-1.17 (m, 2H), 0.94-1.04 (m, 5H), 0.83-0.88 (m, 3H). LC-MS: m/z 427.2 (M+H)+.

(R)-propyl 4-(5-cyano-8-cyclopropyl-3,3-dimethylisochroman-6-yl)-2-isopropylpiperazine-1-carboxylate (Compound 371)

$^1$H NMR (CHLOROFORM-d) δ4.77-4.89 (m, 2H), 4.29 (d, J=13.1 Hz, 1H), 4.01-4.16 (m, 4H), 3.82 (br. s., 1H), 3.10-3.26 (m, 1H), 2.93-3.10 (m, 2H), 2.73-2.81 (m, 2H), 2.07-2.18 (m, 1H), 1.62-1.74 (m, 3H), 1.31 (d, J=2.5 Hz, 6H), 1.05-1.19 (m, 2H), 0.93-1.03 (m, 8H), 0.82-0.89 (m, 3H). LC-MS: m/z 441.3 (M+H)+.

(R)-4-methoxyphenyl 4-(5-cyano-8-cyclopropyl-3,3-dimethyl-3,4-dihydro-1H-pyrano[3,4-c]pyridine-6-yl)-2-isopropylpiperazine-1-carboxylate (Compound 337)

$^1$H NMR (CHLOROFORM-d) δ6.98-7.05 (m, 2H), 6.84-6.91 (m, 2H), 4.78-4.89 (m, 2H), 4.35 (d, J=13.6 Hz, 1H), 4.20 (d, J=11.8 Hz, 2H), 3.91-4.03 (m, 1H), 3.80 (s, 3H), 3.40 (dt, J=12.9, 6.7 Hz, 1H), 3.15 (d, J=12.8 Hz, 2H), 2.77 (s, 2H), 2.18-2.27 (m, 1H), 1.68-1.77 (m, 1H), 1.32 (d, J=2.5 Hz, 6H), 1.09-1.22 (m, 2H), 0.92-1.06 (m, 8H). LC-MS: m/z 505.0 (M+H)+.

(R)-isobutyl 4-(5-cyano-8-cyclopropyl-3,3-dimethyl-3,4-dihydro-1H-pyrano[3,4-c]pyridin-6-yl)-2-isopropyl-piperazine-1-carboxylate (Compound 339)

$^1$H NMR (CHLOROFORM-d) δ4.76-4.90 (m, 2H), 4.30 (d, J=13.3 Hz, 1H), 4.15 (d, J=12.5 Hz, 2H), 3.78-3.97 (m, 3H), 3.17 (d, J=11.5 Hz, 1H), 2.97-3.10 (m, 2H), 2.76 (s, 2H), 2.12 (dt, J=10.3, 6.7 Hz, 1H), 1.95 (dt, J=13.3, 6.7 Hz, 1H), 1.66-1.74 (m, 1H), 1.31 (d, J=2.3 Hz, 6H), 1.07-1.18 (m, 2H), 0.92-1.03 (m, 11H), 0.86 (d, J=6.8 Hz, 3H). LC-MS: m/z 455.0 (M+H)+.

2-ethyl 1-methyl 4-(5-cyano-8-isopropyl-3,3-dimethyl-3,4-dihydro-1H-pyrano[3,4-c]pyridine-6-yl)piperazine-1,2-dicarboxylate (Compound 333)

$^1$H NMR (CHLOROFORM-d) δ4.87 (br. s., 1H), 4.68-4.84 (m, 3H), 4.12-4.29 (m, 2H), 3.92-4.12 (m, 2H), 3.69-3.82 (m, 3H), 3.48-3.68 (m, 1H), 3.35 (td, J=13.6, 4.3 Hz, 1H), 3.00-3.14 (m, 1H), 2.75-2.88 (m, 3H), 1.29 (d, J=3.5 Hz, 6H), 1.19 (td, J=7.0, 4.0 Hz, 9H). LC-MS: m/z 477.1 (M+H)+.

2-ethyl 1-(2-methoxyethyl) 4-(5-cyano-8-isopropyl-3,3-dimethyl-3,4-dihydro-1H-pyrano[3, 4-c]pyridin-6-yl)piperazine-1,2-dicarboxylate (Compound 329)

$^1$H NMR (CHLOROFORM-d) δ4.73-4.88 (m, 2H), 4.71 (d, J=3.8 Hz, 2H), 4.14-4.39 (m, 4H), 3.97-4.13 (m, 2H), 3.50-3.69 (m, 3H), 3.42 (s, 1.5H), 3.31-3.37 (m, 1.5H), 3.08 (t, J=12.2 Hz, 1H), 2.75-2.91 (m, 3H), 1.24-1.36 (m, 9H), 1.13-1.23 (m, 6H). LC-MS: m/z 489.0 (M+H)+.

2-ethyl 1-propyl 4-(5-cyano-8-isopropyl-3,3-dimethyl-3,4-dihydro-1H-pyrano[3,4-c]pyridin-6-yl) piperazine-1,2-dicarboxylate (Compound 364)

$^1$H NMR (CHLOROFORM-d) δ4.72-4.92 (m, 2H), 4.71 (d, J=3.5 Hz, 2H), 4.00-4.27 (m, 6H), 3.60 (d, J=13.1 Hz, 1H), 3.28-3.47 (m, 1H), 3.08 (d, J=11.5 Hz, 1H), 2.80-2.88 (m, 1H), 2.75-2.80 (m, 2H), 1.62-1.75 (m, 2H), 1.29 (d, J=4.0 Hz, 7H), 1.14-1.22 (m, 10H). LC-MS: m/z 473.3 (M+H)+.

Example 12

Additional Compound of Formula I Produced According to Scheme 2, Step F2

Using the appropriate pyraonpyridine and substituted piperazine intermediates, the following compound of the invention was made in an equivalent manner to compounds made using Step F2 of Scheme 2.

(R)-cyclopropylmethyl 4-(5-cyano-8-cyclopropyl-3,3-dimethyl-3,4-dihydro-1H-pyrano[3,4-c]pyridine-6-yl)-2-isopropylpiperazine-1-carboxylate (Compound 370)

$^1$H NMR (CHLOROFORM-d) δ4.75-4.91 (m, 2H), 4.30 (d, J=12.5 Hz, 1H), 4.07-4.21 (m, 2H), 3.80-3.98 (m, 3H), 3.18 (br. s., 1H), 2.96-3.10 (m, 2H), 2.76 (s, 2H), 2.11 (dt, J=10.4, 6.5 Hz, 1H), 1.67-1.73 (m, 1H), 1.31 (d, J=2.5 Hz, 6H), 1.07-1.20 (m, 3H), 0.94-1.05 (m, 5H), 0.87 (d, J=6.8 Hz, 3H), 0.50-0.63 (m, 2H), 0.28 (q, J=4.7 Hz, 2H). LC-MS: m/z 453.4 (M+H)$^+$.

Example 13

Additional Compounds of Formula I Produced According to Scheme 2, Step G1

Using the appropriate pyaronpyridine and substituted piperazine intermediates, the following compounds of the invention were made in an equivalent manner to compounds made using Step G1 of Scheme 2.

4-(4-cyano-1-isopropyl-5,6,7,8-tetrahydroisoquinolin-3-yl)-N-cyclohexylpiperazine-1-carboxamide (Compound 115)

$^1$H NMR (CHLOROFORM-d) δ4.32 (d, J=7.5 Hz, 1H), 3.67-3.75 (m, 1H), 3.61-3.67 (m, 4H), 3.49-3.55 (m, 4H), 3.17 (quin, J=6.7 Hz, 1H), 2.89 (d, J=6.3 Hz, 2H), 2.64 (d, J=6.0 Hz, 2H), 1.93-2.04 (m, 2H), 1.79-1.85 (m, 4H), 1.61-1.76 (m, 4H), 1.33-1.47 (m, 2H), 1.19 (d, J=6.8 Hz, 6H), 1.08-1.17 (m, 2H). LC-MS: m/z 410.0 (M+H)$^+$.

(2S,6R)-4-(4-cyano-1-isopropyl-5,6,7,8-tetrahydroisoquinolin-3-yl)-N-cyclohexyl-2,6-dimethylpiperazine-1-carboxamide (Compound 109)

$^1$H NMR (CHLOROFORM-d) δ4.29 (d, J=6.8 Hz, 1H), 4.17 (d, J=12.5 Hz, 4H), 3.74 (br. s., 1H), 3.07-3.27 (m, 3H), 2.89 (br. s., 2H), 2.66 (br. s., 2H), 2.00 (d, J=10.5 Hz, 2H), 1.71 (br. s., 7H), 1.34-1.49 (m, 8H), 1.08-1.26 (m, 9H). LC-MS: m/z 438.0 (M+H)$^+$.

(R)-4-(5-cyano-8-cyclohexyl-3,4-dihydro-1H-pyrano[3,4-c]pyridin-6-yl)-N-(4-fluorophenyl)-2-methylpiperazine-1-carboxamide (Compound 281)

$^1$H NMR (CHLOROFORM-d) δ7.30-7.36 (m, 2H), 6.97-7.02 (m, 2H), 6.40 (s, 1H), 4.70 (s, 2H), 4.36 (dt, J=6.5, 3.2 Hz, 1H), 4.13-4.31 (m, 2H), 3.85-4.01 (m, 3H), 3.31-3.51 (m, 2H), 3.17 (td, J=12.3, 3.5 Hz, 1H), 2.93 (t, J=5.6 Hz, 2H), 2.42 (tt, J=11.1, 3.7 Hz, 1H), 1.80-1.88 (m, 2H), 1.76 (d, J=10.8 Hz, 1H), 1.65-1.71 (m, 2H), 1.53-1.62 (m, 2H), 1.37 (d, J=6.5 Hz, 3H), 1.26-1.35 (m, 3H). LC-MS: m/z 478.2 (M+H)$^+$.

ethyl 1-(allylcarbamoyl)-4-(5-cyano-8-cyclohexyl-3,4-dihydro-1H-pyrano[3,4-c]pyridin-6-yl)-piperazine-2-carboxylate (Compound 330)

$^1$H NMR (CHLOROFORM-d) δ5.90 (ddt, J=17.1, 10.5, 5.4 Hz, 1H), 5.23 (dq, J=17.1, 1.6 Hz, 1H), 5.14 (dd, J=10.3, 1.3 Hz, 1H), 4.99 (dd, J=4.0, 2.3 Hz, 1H), 4.79 (dt, J=13.6, 2.0 Hz, 1H), 4.65-4.74 (m, 3H), 4.22-4.30 (m, 1H), 3.86-4.19 (m, 6H), 3.64-3.75 (m, 1H), 3.50-3.60 (m, 1H), 3.37 (dd, J=13.4, 4.4 Hz, 1H), 3.09-3.20 (m, 1H), 2.91 (t, J=5.8 Hz, 2H), 2.35-2.45 (m, 1H), 1.84 (d, J=12.0 Hz, 2H), 1.75 (d, J=9.5 Hz, 1H), 1.64-1.72 (m, 2H), 1.54-1.60 (m, 1H), 1.28-1.41 (m, 4H), 1.17 (t, J=7.2 Hz, 3H). LC-MS: m/z 482.4 (M+H)$^+$.

(R)-4-(5-cyano-8-cyclohexyl-3,4-dihydro-1H-pyrano[3,4-c]pyridin-6-yl)-N-ethyl-2-methylpiperazine-1-carboxamide (Compound 335)

$^1$H NMR (CHLOROFORM-d) δ4.69 (s, 2H), 4.16-4.27 (m, 2H), 4.12 (d, J=12.8 Hz, 1H), 3.88-3.97 (m, 2H), 3.81 (d, J=12.5 Hz, 1H), 3.28-3.41 (m, 4H), 3.15 (br. s., 1H), 2.92 (t, J=5.6 Hz, 2H), 2.40 (tt, J=11.1, 3.5 Hz, 1H), 1.84 (d, J=12.5 Hz, 2H), 1.75 (d, J=10.3 Hz, 1H), 1.68 (br. s., 1H), 1.53-1.62 (m, 2H), 1.27-1.37 (m, 7H), 1.15-1.19 (m, 3H). LC-MS: m/z 412.2 (M+H)$^+$.

(R)—N-allyl-4-(5-cyano-8-cyclohexyl-3,4-dihydro-1H-pyrano[3,4-c]pyridin-6-yl)-2-methylpiperazine-1-carboxamide (Compound 334)

$^1$H NMR (CHLOROFORM-d) δ5.91 (ddt, J=17.1, 10.4, 5.6 Hz, 1H), 5.09-5.25 (m, 2H), 4.69 (s, 2H), 4.51 (br. s., 1H), 4.17-4.26 (m, 2H), 4.13 (d, J=13.1 Hz, 1H), 3.89-3.98 (m, 4H), 3.78-3.89 (m, 1H), 3.28-3.39 (m, 2H), 3.04-3.22 (m, 1H), 2.92 (t, J=5.8 Hz, 2H), 2.40 (tt, J=11.1, 3.7 Hz, 1H), 1.84 (d, J=12.5 Hz, 2H), 1.75 (d, J=10.3 Hz, 1H), 1.63-1.70 (m, 3H), 1.52-1.63 (m, 2H), 1.32-1.42 (m, 2H), 1.30 (d, J=6.8 Hz, 3H). LC-MS: m/z 424.3 (M+H)$^+$.

(R)-4-(5-cyano-8-cyclohexyl-3,4-dihydro-1H-pyrano[3,4-c]pyridin-6-yl)-N-(2-fluorophenyl)-2-methylpiperazine-1-carboxamide (Compound 300)

$^1$H NMR (CHLOROFORM-d) δ8.07-8.16 (m, 1H), 6.93-7.16 (m, 3H), 6.63 (d, J=3.8 Hz, 1H), 4.70 (s, 2H), 4.33-4.44 (m, 1H), 4.27 (d, J=13.3 Hz, 1H), 4.17 (d, J=13.1 Hz, 1H), 3.88-4.03 (m, 3H), 3.35-3.54 (m, 2H), 3.13-3.27 (m, 1H), 2.93 (t, J=5.6 Hz, 2H), 2.34-2.49 (m, 1H), 1.85 (d, J=12.5 Hz, 2H), 1.76 (d, J=10.0 Hz, 1H), 1.54-1.64 (m, 3H), 1.40 (d, J=6.5 Hz, 3H), 1.27-1.38 (m, 4H). LC-MS: m/z 477.9 (M+H)$^+$.

(R)-4-(5-cyano-8-cyclohexyl-3,4-dihydro-1H-pyrano[3,4-c]pyridin-6-yl)-2-methyl-N-p-tolylpiperazine-1-carboxamide (Compound 280)

$^1$H NMR (CHLOROFORM-d) δ7.25 (s, 1H), 7.10 (d, J=8.3 Hz, 2H), 6.34 (br. s., 1H), 4.70 (s, 2H), 4.36 (dd, J=6.4, 3.1 Hz, 1H), 4.11-4.31 (m, 2H), 3.87-4.02 (m, 3H), 3.31-3.51 (m, 2H), 3.17 (td, J=12.2, 3.5 Hz, 1H), 2.93 (t, J=5.8 Hz, 2H), 2.41 (tt, J=11.1, 3.6 Hz, 1H), 2.30 (s, 3H), 1.84 (d, J=12.8 Hz, 2H), 1.75 (d, J=10.3 Hz, 1H), 1.64-1.71 (m, 3H), 1.54-1.60 (m, 1H), 1.36 (d, J=6.5 Hz, 3H), 1.26-1.34 (m, 3H). LC-MS: m/z 474.2 (M+H)$^+$.

(R)-4-(5-cyano-8-cyclohexyl-3,4-dihydro-1H-pyrano[3,4-c]pyridin-6-yl)-2-methyl-N-o-tolylpiperazine-1-carboxamide (Compound 279)

$^1$H NMR (CHLOROFORM-d) δ7.09-7.22 (m, 2H), 6.87 (d, J=7.3 Hz, 1H), 6.32 (s, 1H), 4.70 (s, 2H), 4.37 (dt, J=6.5, 3.2 Hz, 1H), 4.14-4.31 (m, 2H), 3.93 (td, J=5.8, 1.3 Hz, 3H), 3.33-3.51 (m, 2H), 3.18 (td, J=12.3, 3.8 Hz, 1H), 2.93 (t,

J=5.8 Hz, 2H), 2.37-2.47 (m, 1H), 2.33 (s, 3H), 1.85 (d, J=12.5 Hz, 2H), 1.76 (d, J=10.3 Hz, 1H), 1.60-1.72 (m, 4H), 1.37 (d, J=6.8 Hz, 3H), 1.26-1.35 (m, 3H). LC-MS: m/z 474.2 (M+H)$^+$.

(R)-4-(5-cyano-8-cyclohexyl-3,4-dihydro-1H-pyrano[3,4-c]pyridin-6-yl)-N-(4-methoxyphenyl)-2-methylpiperazine-1-carboxamide (Compound 299)

$^1$H NMR (CHLOROFORM-d) δ7.27 (br. s., 1H), 7.25 (br. s., 1H), 6.85 (d, J=8.8 Hz, 2H), 6.35 (br. s., 1H), 4.70 (s, 2H), 4.35 (br. s., 1H), 4.10-4.31 (m, 2H), 3.87-4.00 (m, 3H), 3.79 (s, 3H), 3.31-3.50 (m, 2H), 3.18 (br. s., 1H), 2.93 (t, J=5.6 Hz, 2H), 2.37-2.46 (m, 1H), 1.84 (d, J=12.5 Hz, 2H), 1.75 (d, J=10.3 Hz, 1H), 1.69 (br. s., 1H), 1.54-1.63 (m, 2H), 1.36 (d, J=6.5 Hz, 3H), 1.26-1.35 (m, 4H). LC-MS: m/z 490.0 (M+H)$^+$.

(2S,6R)-4-(5-cyano-8-cyclopentyl-3,4-dihydro-1H-pyrano[3,4-c]pyridin-6-yl)-N-cyclohexyl-2,6-dimethylpiperazine-1-carboxamide (Compound 127)

$^1$H NMR (CHLOROFORM-d) δ4.72 (s, 2H), 4.31 (d, J=7.8 Hz, 1H), 4.14-4.28 (m, 4H), 3.95 (t, J=5.6 Hz, 2H), 3.72 (dtd, J=10.7, 7.1, 3.6 Hz, 1H), 3.15 (dd, J=12.7, 4.1 Hz, 2H), 2.89-3.02 (m, 3H), 1.94-2.04 (m, 2H), 1.77-1.93 (m, 7H), 1.60-1.76 (m, 5H), 1.40 (d, J=6.8 Hz, 7H), 1.09-1.23 (m, 3H). LC-MS: m/z 466.2 (M+H)$^+$.

4-(5-cyano-8-isopropyl-3,4-dihydro-1H-pyrano[3,4-c]pyridin-6-yl)-N-cyclohexyl-2,6-dimethylpiperazine-1-carboxamide (Compound 108)

$^1$H NMR (CHLOROFORM-d) δ4.67-4.75 (m, 2H), 4.28 (d, J=12.8 Hz, 3H), 4.13-4.23 (m, 2H), 3.94 (t, J=5.6 Hz, 2H), 3.63-3.84 (m, 1H), 3.17 (dd, J=12.7, 4.1 Hz, 2H), 2.93 (t, J=5.5 Hz, 2H), 2.81 (dt, J=13.4, 6.7 Hz, 1H), 1.90-2.05 (m, 3H), 1.67-1.76 (m, 3H), 1.34-1.43 (m, 8H), 1.15-1.23 (m, 8H). LC-MS: m/z 439.9 (M+H)$^+$.

4-(5-cyano-8-isopropyl-3,4-dihydro-1H-pyrano[3,4-c]pyridin-6-yl)-N-cyclohexylpiperazine-1-carboxamide (Compound 107)

$^1$H NMR (CHLOROFORM-d) δ4.72 (s, 2H), 4.34 (d, J=7.3 Hz, 1H), 3.95 (t, J=5.6 Hz, 2H), 3.64-3.85 (m, 5H), 3.54 (d, J=5.0 Hz, 4H), 2.95 (t, J=5.4 Hz, 2H), 2.82 (dt, J=13.1, 6.4 Hz, 1H), 1.99 (d, J=9.8 Hz, 2H), 1.70-1.77 (m, 2H), 1.31-1.50 (m, 3H), 1.27 (br. s., 1H), 1.08-1.24 (m, 8H). LC-MS: m/z 412.2 (M+H)$^+$.

4-(5-cyano-8-isopropyl-3,4-dihydro-1H-pyrano[3,4-c]pyridin-6-yl)-N-(4-fluorophenyl)piperazine-1-carboxamide (Compound 102)

$^1$H NMR (CHLOROFORM-d) δ7.32-7.41 (m, 2H), 6.97-7.10 (m, 2H), 6.43 (s, 1H), 4.73 (s, 2H), 3.97 (t, J=5.8 Hz, 2H), 3.74-3.81 (m, 4H), 3.64-3.73 (m, 4H), 2.96 (t, J=5.6 Hz, 2H), 2.84 (dt, J=13.3, 6.7 Hz, 1H), 1.22 (d, J=6.8 Hz, 6H). LC-MS: m/z 424.3 (M+H)$^+$.

(R)-ethyl 3-(4-(5-cyano-8-cyclopropyl-3,3-dimethylisochroman-6-yl)-2-isopropylpiperazine-1-carboxamido)propanoate (Compound 392)

$^1$H NMR (CHLOROFORM-d) δ5.17 (br. s., 1H), 4.75-4.89 (m, 2H), 4.24 (d, J=13.3 Hz, 1H), 4.08-4.20 (m, 3H), 3.94 (d, J=11.0 Hz, 1H), 3.59 (br. s., 1H), 3.52 (br. s., 2H), 3.01-3.30 (m, 3H), 2.71-2.80 (m, 2H), 2.55 (br. s., 2H), 2.14 (m, 1H), 1.65-1.74 (m, 1H), 1.31 (d, J=2.5 Hz, 6H), 1.27 (t, J=7.2 Hz, 3H), 0.94-1.18 (m, 7H), 0.81-0.91 (m, 3H). LC-MS: m/z 498.3 (M+H)$^+$.

(R)-4-(5-cyano-8-cyclopropyl-3,3-dimethylisochroman-6-yl)-N-ethyl-2-isopropylpiperazine-1-carboxamide (Compound 326)

$^1$H NMR (CHLOROFORM-d) δ4.76-4.89 (m, 2H), 4.36 (br. s., 1H), 4.24 (d, J=13.1 Hz, 1H), 4.12 (d, J=11.5 Hz, 1H), 3.92 (d, J=11.0 Hz, 1H), 3.58-3.76 (m, 1H), 3.30 (br. s., 2H), 3.22 (br. s., 1H), 3.03-3.19 (m, 2H), 2.70-2.82 (m, 2H), 2.09-2.19 (m, 1H), 1.66-1.74 (m, 1H), 1.31 (d, J=2.3 Hz, 6H), 1.07-1.20 (m, 5H), 0.95-1.04 (m, 5H), 0.89 (d, J=6.5 Hz, 3H). LC-MS: m/z 426.2 (M+H)$^+$.

(R)-4-(5-cyano-8-cyclopropyl-3,3-dimethylisochroman-6-yl)-2-isopropyl-N-pentylpiperazine-1-carboxamide (Compound 327)

$^1$H NMR (CHLOROFORM-d) δ4.76-4.89 (m, 2H), 4.38 (br. s., 1H), 4.24 (d, J=13.3 Hz, 1H), 4.12 (d, J=11.8 Hz, 1H), 3.91 (d, J=12.5 Hz, 1H), 3.64 (d, J=9.5 Hz, 1H), 3.04-3.32 (m, 5H), 2.75 (s, 2H), 2.08-2.20 (m, 1H), 1.66-1.73 (m, 1H), 1.48-1.56 (m, 2H), 1.28-1.37 (m, 10H), 1.05-1.17 (m, 2H), 0.95-1.02 (m, 5H), 0.85-0.93 (m, 6H). LC-MS: m/z 468.5 (M+H)$^+$.

(R)—N-benzyl-4-(5-cyano-8-cyclopropyl-3,3-dimethylisochroman-6-yl)-2-isopropylpiperazine-1-carboxamide (Compound 328)

$^1$H NMR (CHLOROFORM-d) δ7.22-7.40 (m, 5H), 4.76-4.91 (m, 2H), 4.69 (br. s., 1H), 4.45 (br. s., 2H), 4.24 (d, J=13.1 Hz, 1H), 4.11 (d, J=12.0 Hz, 1H), 3.94 (d, J=11.8 Hz, 1H), 3.58-3.77 (m, 1H), 3.04-3.33 (m, 3H), 2.69-2.82 (m, 2H), 2.10-2.17 (m, 1H), 1.65-1.76 (m, 1H), 1.31 (d, J=3.3 Hz, 6H), 1.05-1.17 (m, 2H), 0.93-1.02 (m, 5H), 0.83-0.93 (m, 3H). LC-MS: m/z 488.5 (M+H)$^+$.

(R)-4-(5-cyano-8-cyclopropyl-3,3-dimethylisochroman-6-yl)-N-(4-fluorophenyl)-2-isopropylpiperazine-1-carboxamide (Compound 283)

$^1$H NMR (CHLOROFORM-d) δ7.22-7.36 (m, 2H), 6.91-7.07 (m, 2H), 6.44 (s, 1H), 4.73-4.92 (m, 2H), 4.29 (d, J=13.3 Hz, 1H), 4.16 (d, J=12.5 Hz, 1H), 4.00 (d, J=12.5 Hz, 1H), 3.80 (d, J=9.0 Hz, 1H), 3.31 (td, J=12.5, 3.1 Hz, 1H), 3.07-3.24 (m, 2H), 2.76 (s, 2H), 2.18-2.29 (m, 1H), 1.67-1.74 (m, 1H), 1.32 (d, J=2.3 Hz, 6H), 1.05-1.18 (m, 2H), 0.98-1.04 (m, 5H), 0.94 (d, J=6.8 Hz, 3H). LC-MS: m/z 492.2 (M+H)$^+$.

(R)-4-(5-cyano-8-cyclopropyl-3,3-dimethylisochroman-6-yl)-N,2-diisopropylpiperazine-1-carboxamide (Compound 287)

$^1$H NMR (CHLOROFORM-d) δ4.74-4.89 (m, 2H), 4.24 (d, J=13.3 Hz, 1H), 4.07-4.19 (m, 2H), 3.94-4.06 (m, 1H), 3.88 (d, J=12.5 Hz, 1H), 3.58-3.72 (m, 1H), 3.03-3.28 (m, 3H), 2.70-2.80 (m, 2H), 2.09-2.18 (m, 1H), 1.65-1.73 (m, 1H), 1.31 (d, J=1.8 Hz, 6H), 1.15 (dd, J=6.4, 3.1 Hz, 6H), 1.07-1.13 (m, 2H), 0.94-1.03 (m, 5H), 0.83-0.92 (m, 3H). LC-MS: m/z 440.2 (M+H)$^+$.

(R)-4-(5-cyano-8-cyclopropyl-3,3-dimethylisochroman-6-yl)-2-isopropyl-N-phenethylpiperazine-1-carboxamide (Compound 286)

$^1$H NMR (CHLOROFORM-d) δ7.28-7.34 (m, 2H), 7.17-7.25 (m, 3H), 4.73-4.88 (m, 2H), 4.36 (br. s., 1H), 4.19 (d, J=13.3 Hz, 1H), 4.08 (d, J=11.5 Hz, 1H), 3.85 (d, J=12.3 Hz, 1H), 3.44-3.59 (m, 3H), 3.01-3.21 (m, 3H), 2.84 (t, J=6.8 Hz, 2H), 2.75 (s, 2H), 2.04-2.12 (m, 1H), 1.65-1.73 (m, 1H), 1.31 (d, J=2.5 Hz, 6H), 1.04-1.17 (m, 2H), 0.97-1.02 (m, 2H), 0.90-0.95 (m, 3H), 0.74-0.82 (m, 3H). LC-MS: m/z 502.2 (M+H)$^+$.

(R)-4-(5-cyano-8-cyclopropyl-3,3-dimethyl-3,4-dihydro-1H-pyrano[3,4-c]pyridin-6-yl)-N-(4-cyanophenyl)-2-isopropylpiperazine-1-carboxamide (Compound 303)

$^1$H NMR (CHLOROFORM-d) δ7.44-7.63 (m, 4H), 6.78 (br. s., 1H), 4.74-4.91 (m, 2H), 4.30 (d, J=13.3 Hz, 1H), 4.17 (d, J=12.0 Hz, 1H), 4.01 (d, J=12.0 Hz, 1H), 3.84 (d, J=8.3 Hz, 1H), 3.35 (t, J=11.5 Hz, 1H), 3.05-3.24 (m, 2H), 2.76 (s, 2H), 2.20-2.32 (m, 1H), 1.63-1.76 (m, 1H), 1.32 (d, J=2.3 Hz, 6H), 1.07-1.15 (m, 2H), 0.99-1.05 (m, 5H), 0.93 (d, J=6.8 Hz, 3H). LC-MS: m/z 499.1 (M+H)$^+$.

(R)-4-(5-cyano-8-cyclopropyl-3,3-dimethyl-3,4-dihydro-1H-pyrano[3,4-c]pyridin-6-yl)-N-(4-ethoxyphenyl)-2-isopropylpiperazine-1-carboxamide (Compound 282)

$^1$H NMR (CHLOROFORM-d) δ7.20-7.26 (m, 2H), 6.80-6.86 (m, 2H), 6.29 (s, 1H), 4.75-4.90 (m, 2H), 4.28 (d, J=13.3 Hz, 1H), 4.16 (d, J=12.3 Hz, 1H), 3.99 (q, J=6.9 Hz, 3H), 3.78 (d, J=9.3 Hz, 1H), 3.29 (td, J=12.5, 3.1 Hz, 1H), 3.09-3.23 (m, 2H), 2.73-2.80 (m, 2H), 2.16-2.23 (m, 1H), 1.67-1.73 (m, 1H), 1.37-1.43 (m, 3H), 1.31 (d, J=2.5 Hz, 6H), 1.06-1.18 (m, 2H), 0.98-1.04 (m, 5H), 0.95 (d, J=6.8 Hz, 3H). LC-MS: m/z 518.2 (M+H)$^+$.

(R)-4-(5-cyano-8-cyclopropyl-3,3-dimethyl-3,4-dihydro-1H-pyrano[3,4-c]pyridin-6-yl)-2-isopropyl-N-p-tolylpiperazine-1-carboxamide (Compound 301)

$^1$H NMR (CHLOROFORM-d) δ7.21-7.26 (m, J=8.5 Hz, 2H), 7.03-7.15 (m, J=8.0 Hz, 2H), 6.29-6.46 (m, 1H), 4.74-4.91 (m, 2H), 4.28 (d, J=13.3 Hz, 1H), 4.11-4.20 (m, 1H), 4.01 (d, J=12.8 Hz, 1H), 3.80 (d, J=9.5 Hz, 1H), 3.29 (td, J=12.5, 3.1 Hz, 1H), 3.08-3.22 (m, 2H), 2.76 (s, 2H), 2.29 (s, 3H), 2.16-2.23 (m, 1H), 1.66-1.72 (m, 1H), 1.31 (d, J=2.3 Hz, 6H), 1.07-1.18 (m, 2H), 0.98-1.03 (m, 5H), 0.94 (d, J=6.8 Hz, 3H). LC-MS: m/z 488.0 (M+H)$^+$.

(R)-4-(5-cyano-8-cyclopropyl-3,3-dimethyl-3,4-dihydro-1H-pyrano[3,4-c]pyridin-6-yl)-2-isopropyl-N-(4-methoxyphenyl)piperazine-1-carboxamide (Compound 316)

$^1$H NMR (CHLOROFORM-d) δ7.25 (d, J=8.8 Hz, 2H), 6.84 (d, J=8.5 Hz, 2H), 6.30 (br. s., 1H), 4.75-4.89 (m, 2H), 4.28 (d, J=13.1 Hz, 1H), 4.16 (d, J=12.0 Hz, 1H), 4.01 (d, J=12.5 Hz, 1H), 3.78 (s, 4H), 3.25-3.35 (m, 1H), 3.09-3.24 (m, 2H), 2.72-2.81 (m, 2H), 2.18-2.26 (m, 1H), 1.67-1.76 (m, 1H), 1.31 (d, J=2.0 Hz, 6H), 1.07-1.19 (m, 2H), 1.01 (d, J=6.3 Hz, 5H), 0.95 (d, J=6.8 Hz, 3H). LC-MS: m/z 503.9 (M+H)$^+$.

ethyl 1-(allylcarbamoyl)-4-(5-cyano-8-isopropyl-3,3-dimethyl-3,4-dihydro-1H-pyrano[3,4-c]pyridin-6-yl)piperazine-2-carboxylate (Compound 331)

$^1$H NMR (CHLOROFORM-d) δ5.81-5.98 (m, 1H), 5.23 (dd, J=17.1, 1.3 Hz, 1H), 5.14 (dd, J=10.3, 1.3 Hz, 1H), 4.99 (br. s., 1H), 4.65-4.84 (m, 4H), 4.22-4.30 (m, 1H), 4.01-4.18 (m, 2H), 3.92 (t, J=5.3 Hz, 2H), 3.63-3.77 (m, 1H), 3.56 (d, J=11.3 Hz, 1H), 3.39 (dd, J=13.4, 4.1 Hz, 1H), 3.09-3.22 (m, 1H), 2.75-2.87 (m, 3H), 1.29 (d, J=2.8 Hz, 6H), 1.15-1.22 (m, 9H). LC-MS: m/z 470.4 (M+H)$^+$.

Example 14

Additional Compounds of Formula I Produced According to Scheme 2, Step G2

Using the appropriate pyraonpyridine and substituted piperazine intermediates, the following compounds of the invention were made in an equivalent manner to compounds made using Step G2 of Scheme 2.

(R)-4-(5-cyano-8-cyclohexyl-3,4-dihydro-1H-pyrano[3,4-c]pyridin-6-yl)-N,2-dimethylpiperazine-1-carboxamide (Compound 357)

$^1$H NMR (CHLOROFORM-d) δ4.69 (s, 2H), 4.38-4.61 (m, 1H), 4.17-4.29 (m, 2H), 4.13 (d, J=13.1 Hz, 1H), 3.89-4.00 (m, 2H), 3.77-3.87 (m, 1H), 3.20-3.40 (m, 2H), 3.04-3.19 (m, 1H), 2.92 (t, J=5.6 Hz, 2H), 2.81-2.88 (m, 3H), 2.40 (tt, J=11.0, 3.6 Hz, 1H), 1.84 (d, J=12.8 Hz, 2H), 1.52-1.75 (m, 5H), 1.24-1.41 (m, 6H). LC-MS: m/z 398.3 (M+H)$^+$.

(R)-4-(5-cyano-8-cyclohexyl-3,4-dihydro-1H-pyrano[3,4-c]pyridin-6-yl)-2-methyl-N-(prop-2-ynyl)piperazine-1-carboxamide (Compound 361)

$^1$H NMR (CHLOROFORM-d) δ4.70 (s, 3H), 4.10-4.28 (m, 3H), 4.07 (br. s., 2H), 3.89-3.97 (m, 2H), 3.84 (dt, J=12.8, 2.9 Hz, 1H), 3.27-3.40 (m, 2H), 3.11 (td, J=12.2, 3.6 Hz, 1H), 2.88-2.95 (m, 2H), 2.41 (tt, J=11.1, 3.7 Hz, 1H), 2.25 (t, J=2.5 Hz, 1H), 1.81-1.88 (m, 2H), 1.75 (d, J=10.3 Hz, 1H), 1.63-1.71 (m, 2H), 1.52-1.63 (m, 2H), 1.27-1.44 (m, 6H). LC-MS: m/z 422.4 (M+H)$^+$.

(R)-4-(5-cyano-8-cyclohexyl-3,4-dihydro-1H-pyrano[3,4-c]pyridin-6-yl)-N-cyclopropyl-2-methylpiperazine-1-carboxamide (Compound 360)

$^1$H NMR (CHLOROFORM-d) δ4.69 (s, 3H), 4.05-4.29 (m, 3H), 3.93 (td, J=5.8, 1.3 Hz, 2H), 3.69-3.86 (m, 1H), 3.31 (td, J=12.1, 3.4 Hz, 2H), 3.11 (br. s., 1H), 2.85-2.95 (m, 2H), 2.68 (dt, J=7.0, 3.4 Hz, 1H), 2.33-2.46 (m, 1H), 1.80-1.87 (m, 2H), 1.75 (d, J=10.5 Hz, 1H), 1.63-1.70 (m, 2H), 1.58 (d, J=12.0 Hz, 2H), 1.29-1.41 (m, 3H), 1.28 (d, J=6.5 Hz, 3H), 0.69-0.80 (m, 2H), 0.42-0.57 (m, 2H). LC-MS: m/z 424.4 (M+H)$^+$.

(R)-4-(5-cyano-8-cyclohexyl-3,4-dihydro-1H-pyrano[3,4-c]pyridin-6-yl)-2-methyl-N-propylpiperazine-1-carboxamide (Compound 378)

$^1$H NMR (CHLOROFORM-d) δ4.70 (s, 2H), 4.53 (br. s., 1H), 4.07-4.27 (m, 3H), 3.88-3.98 (m, 2H), 3.78-3.86 (m, 1H), 3.17-3.38 (m, 4H), 3.12 (t, J=10.9 Hz, 1H), 2.92 (t, J=5.6 Hz, 2H), 2.40 (tt, J=11.0, 3.6 Hz, 1H), 1.80-1.88 (m,

2H), 1.75 (d, J=10.5 Hz, 1H), 1.45-1.70 (m, 6H), 1.26-1.41 (m, 6H), 0.91-0.96 (m, 3H). LC-MS: m/z 426.2 (M+H)$^+$.

(R)-4-(5-cyano-8-cyclopropyl-3,3-dimethylisochroman-6-yl)-2-isopropyl-N-methylpiperazine-1-carboxamide (Compound 344)

$^1$H NMR (CHLOROFORM-d) δ4.75-4.90 (m, 2H), 4.45 (br. s., 1H), 4.23 (d, J=13.3 Hz, 1H), 4.11 (d, J=11.5 Hz, 1H), 3.92 (d, J=12.8 Hz, 1H), 3.65 (d, J=9.8 Hz, 1H), 3.03-3.31 (m, 3H), 2.83 (s, 3H), 2.75 (s, 2H), 2.09-2.22 (m, 1H), 1.66-1.74 (m, 1H), 1.31 (d, J=2.8 Hz, 6H), 0.95-1.18 (m, 7H), 0.88 (d, J=6.8 Hz, 3H). LC-MS: m/z 412.3 (M+H)$^+$.

(R)-4-(5-cyano-8-cyclopropyl-3,3-dimethylisochroman-6-yl)-2-isopropyl-N-(prop-2-ynyl)piperazine-1-carboxamide (Compound 355)

$^1$H NMR (CHLOROFORM-d) δ4.72-4.90 (m, 2H), 4.55 (br. s., 1H), 4.25 (d, J=13.3 Hz, 1H), 4.13 (d, J=12.3 Hz, 1H), 4.05 (br. s., 2H), 3.93 (d, J=12.8 Hz, 1H), 3.64 (d, J=8.5 Hz, 1H), 3.18-3.33 (m, 1H), 3.02-3.18 (m, 2H), 2.76 (s, 2H), 2.20-2.28 (m, 1H), 2.15 (dt, J=10.0, 6.7 Hz, 1H), 1.31 (d, J=3.0 Hz, 6H), 0.97-1.06 (m, 6H), 0.84-0.96 (m, 4H). LC-MS: m/z 436.2 (M+H)$^+$.

(R)-4-(5-cyano-8-cyclopropyl-3,3-dimethylisochroman-6-yl)-2-isopropyl-N-(2-methoxyethyl)piperazine-1-carboxamide (Compound 353)

$^1$H NMR (CHLOROFORM-d) δ4.74-4.86 (m, 3H), 4.26 (d, J=13.3 Hz, 1H), 4.13 (d, J=12.3 Hz, 1H), 3.93 (d, J=12.3 Hz, 1H), 3.65 (d, J=8.8 Hz, 1H), 3.41-3.50 (m, 2H), 3.33-3.40 (m, 3H), 3.01-3.29 (m, 4H), 2.76 (s, 2H), 2.08-2.19 (m, 1H), 1.64-1.74 (m, 1H), 1.28-1.36 (m, 6H), 0.95-1.03 (m, 6H), 0.88 (d, J=7.0 Hz, 4H). LC-MS: m/z 456.2 (M+H)$^+$.

(R)-4-(5-cyano-8-cyclopropyl-3,3-dimethylisochroman-6-yl)-N-(2-hydroxyethyl)-2-isopropylpiperazine-1-carboxamide (Compound 349)

$^1$H NMR (CHLOROFORM-d) δ4.96 (br. s., 1H), 4.76-4.88 (m, 2H), 4.25 (d, J=13.3 Hz, 1H), 4.12 (d, J=12.0 Hz, 1H), 3.91 (d, J=12.0 Hz, 1H), 3.61-3.79 (m, 3H), 3.43 (br. s., 2H), 3.18-3.31 (m, 1H), 3.03-3.18 (m, 2H), 2.70-2.81 (m, 2H), 2.12-2.23 (m, 1H), 1.66-1.74 (m, 1H), 1.31 (d, J=2.8 Hz, 6H), 1.07-1.18 (m, 2H), 0.95-1.05 (m, 5H), 0.89 (d, J=6.8 Hz, 3H). LC-MS: m/z 442.3 (M+H)$^+$.

(R)-4-(5-cyano-8-cyclopropyl-3,3-dimethylisochroman-6-yl)-2-isopropyl-N,N-dimethylpiperazine-1-carboxamide (Compound 351)

$^1$H NMR (CHLOROFORM-d) δ4.76-4.88 (m, 2H), 4.29 (d, J=13.3 Hz, 1H), 4.11 (d, J=12.8 Hz, 1H), 3.49-3.71 (m, 2H), 3.37 (td, J=12.6, 3.1 Hz, 1H), 3.16 (dd, J=13.3, 3.5 Hz, 1H), 3.02 (td, J=12.2, 3.4 Hz, 1H), 2.82 (s, 6H), 2.76 (s, 2H), 2.08-2.24 (m, 1H), 1.63-1.73 (m, 1H), 1.31 (s, 6H), 1.06-1.19 (m, 2H), 0.97-1.04 (m, 5H), 0.93 (d, J=6.5 Hz, 3H), 0.87 (d, J=6.8 Hz, 3H). LC-MS: m/z 426.3 (M+H)$^+$.

(R)-4-(5-cyano-8-cyclopropyl-3,3-dimethylisochroman-6-yl)-N-(cyclopropylmethyl)-2-isopropylpiperazine-1-carboxamide (Compound 365)

$^1$H NMR (CHLOROFORM-d) δ4.74-4.92 (m, 2H), 4.47 (br. s., 1H), 4.25 (d, J=13.3 Hz, 1H), 4.13 (d, J=11.8 Hz, 1H), 3.93 (d, J=12.8 Hz, 1H), 3.67 (d, J=9.5 Hz, 1H), 3.03-3.28 (m, 5H), 2.69-2.80 (m, 2H), 2.08-2.18 (m, 1H), 1.82 (br. s., 1H), 1.66-1.74 (m, 1H), 1.31 (d, J=2.5 Hz, 6H), 1.06-1.19 (m, 2H), 0.94-1.02 (m, 5H), 0.85-0.93 (m, 3H), 0.43-0.55 (m, 2H), 0.19 (q, J=4.8 Hz, 2H). LC-MS: m/z 452.2 (M+H)$^+$.

(R)-4-(5-cyano-8-cyclopropyl-3,3-dimethyl-3,4-dihydro-1H-pyrano[3,4-c]pyridin-6-yl)-N-cyclopropyl-2-isopropylpiperazine-1-carboxamide (Compound 398)

$^1$H NMR (CHLOROFORM-d) δ4.76-4.88 (m, 2H), 4.66 (br. s., 1H), 4.23 (d, J=13.3 Hz, 1H), 4.11 (d, J=11.5 Hz, 1H), 3.88 (d, J=12.0 Hz, 1H), 3.54-3.75 (m, 1H), 2.97-3.25 (m, 3H), 2.75 (s, 2H), 2.66 (tt, J=7.0, 3.6 Hz, 1H), 2.09-2.18 (m, 1H), 1.66-1.75 (m, 1H), 1.31 (d, J=2.8 Hz, 6H), 1.00-1.18 (m, 4H), 0.97 (d, J=6.5 Hz, 3H), 0.82-0.90 (m, 3H), 0.69-0.78 (m, 2H), 0.42-0.54 (m, 2H). LC-MS: m/z 438.4 (M+H)$^+$.

Example 15

Additional Compounds of Formula I Produced According to Scheme 2, Step H

Using the appropriate pyraonpyridine and substituted piperazine intermediates, the following compounds of the invention were made in an equivalent manner to compounds made using Step H of Scheme 2.

(R)-8-cyclohexyl-6-(3-methyl-4-(methylsulfonyl)piperazin-1-yl)-3,4-dihydro-1H-pyrano[3,4-c]pyridine-5-carbonitrile (Compound 336)

$^1$H NMR (CHLOROFORM-d) δ4.70 (s, 2H), 4.09-4.25 (m, 3H), 3.94 (t, J=5.9 Hz, 2H), 3.70 (d, J=12.8 Hz, 1H), 3.43 (t, J=12.0 Hz, 1H), 3.28 (d, J=12.0 Hz, 1H), 3.14 (t, J=10.8 Hz, 1H), 2.89-2.95 (m, 5H), 2.42 (t, J=10.7 Hz, 1H), 1.84 (d, J=12.3 Hz, 2H), 1.75 (d, J=10.0 Hz, 1H), 1.68 (br. s., 1H), 1.59 (d, J=12.3 Hz, 2H), 1.41 (d, J=6.8 Hz, 3H), 1.28-1.37 (m, 4H). LC-MS: m/z 419.2 (M+H)$^+$.

(R)-8-isopropyl-6-(3-methyl-4-(thiophen-2-ylsulfonyl)piperazin-1-yl)-3,4-dihydro-1H-pyrano[3,4-c]pyridine-5-carbonitrile (Compound 101)

$^1$H NMR (CHLOROFORM-d) δ7.66 (d, J=5.0 Hz, 1H), 7.59 (d, J=3.0 Hz, 1H), 7.18 (t, J=4.3 Hz, 1H), 4.71 (s, 2H), 3.94 (t, J=5.6 Hz, 2H), 3.73-3.83 (m, 4H), 3.18-3.33 (m, 4H), 2.92 (t, J=5.5 Hz, 2H), 2.81 (dt, J=13.2, 6.6 Hz, 1H), 1.18 (d, J=6.5 Hz, 6H). LC-MS: m/z 433.1 (M+H)$^+$.

(R)-8-cyclopropyl-6-(3-isopropyl-4-(thiophen-2-ylsulfonyl)piperazin-1-yl)-3,3-dimethyl-3,4-dihydro-1H-pyrano[3,4-c]pyridine-5-carbonitrile (Compound 284)

$^1$H NMR (CHLOROFORM-d) δ7.58 (dd, J=3.8, 1.3 Hz, 1H), 7.53 (dd, J=5.0, 1.3 Hz, 1H), 7.04 (dd, J=5.0, 3.8 Hz, 1H), 4.73-4.88 (m, 2H), 4.15 (d, J=13.6 Hz, 1H), 3.86-4.03 (m, 2H), 3.61-3.73 (m, 1H), 3.37-3.50 (m, 1H), 2.99 (dd, J=13.8, 4.0 Hz, 1H), 2.89 (td, J=12.5, 3.8 Hz, 1H), 2.64-2.78 (m, 2H), 2.04-2.15 (m, 1H), 1.64-1.72 (m, 1H), 1.30 (d, J=6.3 Hz, 6H), 0.92-1.12 (m, 10H). LC-MS: m/z 501.2 (M+H)$^+$.

(R)-8-cyclopropyl-6-(3-isopropyl-4-tosylpiperazin-1-yl)-3,3-dimethyl-3,4-dihydro-1H-pyrano[3,4-c]pyridine-5-carbonitrile (Compound 302)

$^1$H NMR (CHLOROFORM-d) δ7.72 (d, J=8.3 Hz, 2H), 7.19-7.31 (m, 2H), 4.71-4.87 (m, 2H), 4.05-4.18 (m, 1H), 3.79-3.95 (m, 2H), 3.63 (dt, J=9.7, 3.0 Hz, 1H), 3.29-3.45 (m, 1H), 2.96 (dd, J=13.7, 3.9 Hz, 1H), 2.73-2.85 (m, 1H), 2.70 (d, J=3.3 Hz, 2H), 2.40 (s, 3H), 2.07 (dq, J=9.8, 6.7 Hz, 1H), 1.65-1.71 (m, 1H), 1.29 (d, J=7.8 Hz, 6H), 1.05-1.13 (m, 1H), 0.97-1.04 (m, 3H), 0.94 (d, J=6.5 Hz, 6H). LC-MS: m/z 509.0 (M+H)$^+$.

(R)-6-(4-(5-chlorothiophen-2-ylsulfonyl)-3-isopropylpiperazin-1-yl)-8-cyclopropyl-3,3-dimethyl-3,4-dihydro-1H-pyrano[3,4-c]pyridine-5-carbonitrile (Compound 285)

$^1$H NMR (CHLOROFORM-d) δ7.35 (d, J=4.0 Hz, 1H), 6.86 (d, J=4.0 Hz, 1H), 4.74-4.89 (m, 2H), 4.05-4.16 (m, 1H), 3.97 (dt, J=12.8, 1.6 Hz, 1H), 3.79-3.91 (m, 1H), 3.64 (dt, J=9.3, 3.5 Hz, 1H), 3.37-3.49 (m, 1H), 3.12 (dd, J=13.8, 4.0 Hz, 1H), 3.00 (td, J=12.5, 4.0 Hz, 1H), 2.66-2.81 (m, 2H), 2.06-2.15 (m, 1H), 1.64-1.72 (m, 1H), 1.30 (d, J=8.5 Hz, 6H), 1.08-1.16 (m, 1H), 1.00-1.07 (m, 3H), 0.97 (d, J=3.0 Hz, 3H), 0.97 (d, J=10.5 Hz, 3H). LC-MS: m/z 535.0 (M+H)$^+$.

(R)-8-cyclopropyl-6-(3-isopropyl-4-(methylsulfonyl)piperazin-1-yl)-3,3-dimethyl-3,4-dihydro-1H-pyrano[3,4-c]pyridine-5-carbonitrile (Compound 323)

$^1$H NMR (CHLOROFORM-d) δ4.77-4.90 (m, 2H), 4.22-4.33 (m, 1H), 4.04-4.14 (m, 1H), 3.80 (dt, J=14.3, 1.6 Hz, 1H), 3.56 (d, J=10.3 Hz, 1H), 3.32-3.44 (m, 1H), 3.09-3.19 (m, 2H), 2.90-2.98 (m, 3H), 2.76 (s, 2H), 2.14-2.20 (m, 1H), 1.68-1.76 (m, 1H), 1.32 (d, J=3.8 Hz, 6H), 1.01-1.17 (m, 4H), 0.97 (d, J=3.8 Hz, 3H), 0.99 (d, J=4.0 Hz, 3H). LC-MS: m/z 433.4 (M+H)$^+$.

(R)-8-isopropyl-3,3-dimethyl-6-(3-methyl-4-(thiophen-2-ylsulfonyl)piperazin-1-yl)-3,4-dihydro-1H-pyrano[3,4-c]pyridine-5-carbonitrile (Compound 170)

$^1$H NMR (CHLOROFORM-d) δ7.60 (ddd, J=9.3, 4.3, 1.4 Hz, 2H), 7.10 (dd, J=5.0, 3.8 Hz, 1H), 4.72 (s, 2H), 4.27-4.41 (m, 1H), 4.16 (d, J=12.8 Hz, 1H), 4.06 (dd, J=13.2, 2.1 Hz, 1H), 3.77-3.89 (m, 1H), 3.45 (td, J=12.3, 3.3 Hz, 1H), 3.28 (dd, J=13.1, 3.5 Hz, 1H), 3.14 (td, J=12.3, 3.5 Hz, 1H), 2.85 (quin, J=6.7 Hz, 1H), 2.78 (s, 2H), 1.31 (d, J=3.0 Hz, 6H), 1.26 (d, J=6.8 Hz, 3H), 1.19 (d, J=4.0 Hz, 3H), 1.21 (d, J=4.0 Hz, 3H). LC-MS: m/z 475.2 (M+H)$^+$.

Example 16

Additional Compound of Formula I Produced According to Scheme 2, Step I1-1

Using the appropriate pyraonpyridine and substituted piperazine intermediates, the following compound of the invention was made in an equivalent manner to compounds made using Step I1-1 of Scheme 2.

(R)-8-cyclopropyl-6-(3-isopropyl-4-(2-methoxyethyl)piperazin-1-yl)-3,3-dimethyl-3,4-dihydro-1H-pyrano[3,4-c]pyridine-5-carbonitrile (Compound 369)

$^1$H NMR (CHLOROFORM-d) δ4.76-4.88 (m, 2H), 4.13 (dd, J=12.8, 2.3 Hz, 1H), 3.97-4.07 (m, 1H), 3.45-3.62 (m, 2H), 3.36 (s, 3H), 3.12-3.24 (m, 1H), 2.98-3.10 (m, 2H), 2.89 (t, J=11.3 Hz, 1H), 2.75 (s, 2H), 2.51 (dd, J=11.5, 8.0 Hz, 2H), 2.28-2.37 (m, 1H), 2.12-2.25 (m, 1H), 1.64-1.72 (m, 1H), 1.30 (s, 6H), 1.09-1.17 (m, 2H), 1.01-1.06 (m, 3H), 0.96-1.00 (m, 2H), 0.93 (d, J=7.0 Hz, 3H). LC-MS: m/z 413.3 (M+H)$^+$.

Example 17

Additional Compound of Formula I Produced According to Scheme 2, Step 12

Using the appropriate pyranopyridine and substituted piperazine intermediates, the following compound of the invention were made in an equivalent manner to compounds made using Step 12 of Scheme 2.

(R)-methyl 2-(4-(5-cyano-8-cyclohexyl-3,4-dihydro-1H-pyrano[3,4-c]pyridin-6-yl)-2-methylpiperazin-1-yl)acetate (Compound 342)

$^1$H NMR (CHLOROFORM-d) δ4.70 (s, 2H), 4.09-4.24 (m, 2H), 3.94 (t, J=5.8 Hz, 2H), 3.68-3.83 (m, 3H), 3.45-3.59 (m, 1H), 3.39 (br. s., 2H), 3.07 (br. s., 1H), 2.73-3.02 (m, 5H), 2.41 (tt, J=11.1, 3.6 Hz, 1H), 1.86 (d, J=12.5 Hz, 2H), 1.76 (d, J=10.0 Hz, 1H), 1.70 (br. s., 1H), 1.54-1.64 (m, 2H), 1.29-1.42 (m, 4H), 1.10-1.24 (m, 3H). LC-MS: m/z 412.6 (M+H)$^+$.

Example 18

Assays for IDH1 R132H Inhibitors

Assays were conducted in a volume of 76 μl assay buffer (150 mM NaCl, 10 mM MgCl$_2$, 20 mM Tris pH 7.5, 0.03% bovine serum albumin) as follows in a standard 384-well plate: To 25 ul of substrate mix (8 uM NADPH, 2 mM aKG), 1 μl of test compound was added in DMSO. The plate was centrifuged briefly, and then 25 μl of enzyme mix was added (0.2 μg/ml IDH1 R132H) followed by a brief centrifugation and shake at 100 RPM. The reaction was incubated for 50 minutes at room temperature, then 25 μl of detection mix (30 μM resazurin, 36 μg/ml) was added and the mixture further incubated for 5 minutes at room temperature. The conversion of resazurin to resorufin was detected by fluorescent spectroscopy at Ex544 Em590 c/o 590.

The compounds of Formula I set forth in Table 1 were tested in this assay and the results set forth below in Table 2. As used in Table 2, "A" refers to an inhibitory activity against IDH1 R132H with an IC$_{50}$≤0.5 μM; "B" refers to an inhibitory activity against IDH1 R132H with an IC$_{50}$ greater than 0.5 μM and ≤1 μM; "C" refers to an inhibitory activity against IDH1 R132H with an IC$_{50}$ greater than 1 μM and ≤10 μM; "D" refers to an inhibitory activity against IDH1 R132H with an IC$_{50}$ greater than 10 μM. As used in Table 3, "A" refers to an inhibitory activity against IDH1 R132H with an IC$_{50}$≤0.5 μM or an IC$_{50}$ for inhibition of 2-HG production ≤0.5 μM; "B" refers to an inhibitory activity against IDH1 R132H with an IC$_{50}$ greater than 0.5 μM and ≤1 μM or an IC$_{50}$ for inhibition of 2-HG production greater than 0.5 μM and ≤1 μM; "C" refers to an inhibitory activity against IDH1 R132H with an IC$_{50}$ greater than 1 μM and ≤10 μM or an IC$_{50}$ for inhibition of 2-HG production greater than 1 μM and ≤10 μM; and "D" refers to an inhibitory activity against IDH1 R132H with an IC$_{50}$ greater than 10 μM or an IC$_{50}$ for inhibition of 2-HG production greater than 10 μM.

TABLE 2

IDH1 R132H Inhibition by Compounds of formula I

| Cmpd No | IDHR132H Activity |
| --- | --- |
| 101 | C |
| 102 | C |
| 103 | C |
| 104 | C |
| 105 | C |
| 106 | C |
| 107 | C |
| 108 | C |
| 109 | C |
| 110 | C |
| 111 | C |
| 112 | C |
| 113 | C |
| 114 | C |
| 115 | C |
| 116 | C |
| 117 | C |
| 118 | C |
| 119 | C |
| 120 | C |
| 121 | C |
| 122 | C |
| 123 | C |
| 124 | C |
| 125 | C |
| 126 | C |
| 127 | C |
| 128 | C |
| 129 | C |
| 130 | C |
| 131 | C |
| 132 | C |
| 133 | C |
| 134 | C |
| 135 | C |
| 136 | C |
| 137 | C |
| 138 | C |
| 139 | C |
| 140 | C |
| 141 | C |
| 142 | C |
| 143 | C |
| 144 | C |
| 145 | C |
| 146 | C |
| 147 | C |
| 148 | C |
| 149 | C |
| 150 | C |
| 151 | C |
| 152 | C |
| 153 | C |
| 154 | B |
| 155 | C |
| 156 | C |
| 157 | C |
| 158 | B |
| 159 | C |
| 160 | C |
| 161 | C |
| 162 | C |
| 163 | B |
| 164 | B |
| 165 | A |
| 166 | C |
| 167 | C |
| 168 | C |
| 169 | C |
| 170 | C |
| 171 | A |
| 172 | C |
| 173 | C |
| 174 | C |
| 175 | C |
| 176 | A |
| 177 | C |
| 178 | C |
| 179 | C |
| 180 | A |
| 181 | A |
| 182 | C |
| 183 | C |
| 184 | C |
| 185 | C |
| 186 | C |
| 187 | B |
| 188 | C |
| 189 | C |
| 190 | C |
| 191 | C |
| 192 | C |
| 193 | C |
| 194 | A |
| 195 | A |
| 196 | C |
| 197 | C |
| 198 | C |
| 199 | C |
| 200 | C |
| 201 | C |
| 202 | C |
| 203 | C |
| 204 | C |
| 205 | A |
| 206 | A |
| 207 | A |
| 208 | B |
| 209 | B |
| 210 | B |
| 211 | A |
| 212 | B |
| 213 | C |
| 214 | B |
| 215 | C |
| 216 | C |
| 217 | B |
| 218 | C |
| 219 | C |
| 220 | C |
| 221 | C |
| 222 | C |
| 223 | B |
| 224 | C |
| 225 | C |
| 226 | C |
| 227 | C |
| 228 | C |
| 229 | C |
| 230 | A |
| 231 | A |
| 232 | C |
| 233 | C |
| 234 | C |
| 235 | A |
| 236 | A |
| 237 | A |
| 238 | C |
| 239 | C |
| 240 | C |
| 241 | C |
| 242 | C |

TABLE 2-continued

IDH1 R132H Inhibition by Compounds of formula I

| Cmpd No | IDHR132H Activity |
|---|---|
| 243 | C |
| 244 | C |
| 245 | C |
| 246 | C |
| 247 | C |
| 248 | C |
| 249 | C |
| 250 | B |
| 251 | C |
| 252 | C |
| 253 | C |
| 254 | B |
| 255 | B |
| 256 | C |
| 257 | C |
| 258 | C |
| 259 | C |
| 260 | C |
| 261 | C |
| 262 | C |
| 263 | C |
| 264 | C |
| 265 | A |
| 266 | B |
| 267 | B |
| 268 | B |
| 269 | A |
| 270 | A |
| 271 | C |
| 272 | B |
| 273 | B |
| 274 | C |
| 275 | C |
| 276 | B |
| 277 | C |
| 278 | C |
| 279 | C |
| 280 | C |
| 281 | C |
| 282 | C |
| 283 | C |
| 284 | C |
| 285 | C |
| 286 | C |
| 287 | C |
| 288 | A |
| 289 | A |
| 290 | C |
| 291 | B |
| 292 | B |
| 293 | C |
| 294 | B |
| 295 | B |
| 296 | B |
| 297 | A |
| 298 | C |
| 299 | C |
| 300 | C |
| 301 | C |
| 302 | C |
| 303 | C |
| 304 | A |
| 305 | C |
| 306 | C |
| 307 | A |
| 308 | C |
| 309 | C |
| 310 | C |
| 311 | B |
| 312 | C |
| 313 | C |
| 314 | C |
| 315 | C |
| 316 | C |
| 317 | A |
| 318 | C |
| 319 | C |
| 320 | C |
| 321 | C |
| 322 | C |
| 323 | C |
| 324 | C |
| 325 | B |
| 326 | B |
| 327 | C |
| 328 | C |
| 329 | C |
| 330 | C |
| 331 | C |
| 332 | B |
| 333 | C |
| 334 | C |
| 335 | C |
| 336 | C |
| 337 | C |
| 338 | C |
| 339 | C |
| 340 | A |
| 341 | C |
| 342 | C |
| 343 | C |
| 344 | A |
| 345 | A |
| 346 | A |
| 347 | A |
| 348 | C |
| 349 | C |
| 350 | C |
| 351 | C |
| 352 | B |
| 353 | B |
| 354 | A |
| 355 | B |
| 356 | C |
| 357 | C |
| 358 | C |
| 359 | C |
| 360 | C |
| 361 | C |
| 362 | C |
| 363 | C |
| 364 | C |
| 365 | C |
| 366 | A |
| 367 | C |
| 368 | B |
| 369 | C |
| 370 | C |
| 371 | C |
| 372 | C |
| 373 | C |
| 374 | C |
| 375 | C |
| 376 | A |
| 377 | C |
| 378 | C |
| 379 | C |
| 380 | C |
| 381 | B |
| 382 | A |
| 383 | A |
| 384 | C |
| 385 | C |
| 386 | C |
| 387 | B |
| 388 | B |
| 389 | C |
| 390 | B |
| 391 | C |
| 392 | A |
| 393 | B |
| 394 | B |

TABLE 2-continued

IDH1 R132H Inhibition by Compounds of formula I

| Cmpd No | IDHR132H Activity |
|---|---|
| 395 | A |
| 396 | B |
| 397 | C |
| 398 | C |
| 399 | C |
| 400 | C |
| 401 | A |
| 402 | C |
| 403 | C |
| 404 | C |
| 405 | C |
| 406 | C |
| 407 | B |
| 408 | C |
| 409 | A |
| 410 | B |
| 411 | B |
| 412 | A |
| 413 | A |
| 414 | C |
| 415 | B |
| 416 | C |
| 417 | C |
| 418 | C |
| 419 | C |

TABLE 3

| Cmpd No | R132H IC50 (uM) | HT1080 IC50 (uM) | U87R132H IC50 (uM) |
|---|---|---|---|
| 421 | B | C | C |
| 422 | B | C | C |
| 423 | A | C | B |
| 424 | A | B | B |
| 425 | A | A | A |
| 426 | A | A | B |
| 427 | B | C | C |
| 428 | A | C | A |
| 429 | A | A | A |
| 430 | A | B | A |
| 431 | B | C | C |
| 432 | B | C | C |
| 433 | A | B | B |
| 434 | A | A | A |
| 435 | A | A | A |
| 436 | A | A | A |
| 437 | A | C | C |
| 438 | A | A | A |
| 439 | B | | |
| 440 | A | A | A |
| 441 | A | A | A |
| 442 | A | B | B |
| 443 | A | C | C |
| 444 | A | A | A |
| 445 | A | A | A |
| 446 | B | | |
| 447 | B | | |
| 448 | B | | |
| 449 | A | A | A |
| 450 | A | A | A |
| 451 | A | C | C |
| 452 | A | C | B |
| 453 | B | | |
| 454 | A | B | B |
| 455 | B | A | A |
| 456 | A | B | A |
| 457 | A | B | B |
| 458 | A | B | A |
| 459 | A | | |
| 460 | A | A | A |
| 461 | A | B | A |
| 462 | A | B | B |
| 463 | B | C | C |
| 464 | B | | |
| 465 | A | B | A |
| 466 | B | | |
| 467 | B | | |
| 468 | B | | |
| 469 | A | C | C |
| 470 | B | | |
| 471 | B | | |
| 472 | A | | |
| 473 | A | A | B |
| 474 | B | | |
| 475 | B | | |
| 476 | A | C | C |
| 477 | A | C | C |
| 478 | A | | |
| 479 | A | B | A |
| 480 | B | | |
| 481 | A | C | B |
| 482 | A | A | A |
| 483 | A | A | A |
| 484 | B | | |
| 485 | A | A | A |
| 486 | A | A | A |
| 487 | A | C | C |
| 488 | A | A | A |
| 489 | A | B | |
| 490 | A | B | |
| 491 | A | A | |
| 492 | B | C | |
| 493 | A | A | A |
| 494 | B | A | A |
| 495 | B | A | |
| 496 | A | A | A |
| 497 | B | C | |
| 498 | A | A | A |
| 499 | B | | |
| 500 | B | B | |
| 501 | B | | |
| 502 | B | B | |
| 503 | B | | |

In some embodiments, the invention provides a compound selected from any one of compound numbers 165, 171, 176, 180, 181, 194, 195, 205, 206, 207, 211, 230, 231, 235, 236, 237, 265, 269, 270, 288, 289, 297, 304, 307, 317, 340, 344, 345, 346, 347, 354, 366, 376, 382, 383, 392, 395, 401, 409, 412, and 413.

Example 19

Cellular Assays for IDH1m (R132H or R132C) Inhibitors

Cells (e.g., HT1080 or U87MG) are grown in T125 flasks in DMEM containing 10% FBS, 1× penicillin/streptomycin and 500 ug/mL G418. They are harvested by trypsin and seeded into 96 well white bottom plates at a density of 5000 cell/well in 100 ul/well in DMEM with 10% FBS. No cells are plates in columns 1 and 12. Cells are incubated overnight at 37 C in 5% CO2. The next day compounds are made up at 2× concentration and 100 ul are added to each cell well. The final concentration of DMSO is 0.2% and the DMSO control wells are plated in row G. The plates are then placed in the incubator for 48 hours. At 48 hours, 100 ul of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of reagent is added to each well of media. The cell plate is then placed on an orbital shaker for 10 minutes and then allowed to sit at room temperature for 20 minutes. The plate is then read for luminescence with an integration time of 500 ms.

The $IC_{50}$ for inhibition of 2-HG production (concentration of test compound to reduce 2HG production by 50% compared to control) in these two cell lines for various compounds of formula I is set forth in Table 3 above.

Example 20

Procedures (Dimethyl-Cyclopropyl Pyranopyridine)

Core 1 Synthesis, Exemplified Below for 5:

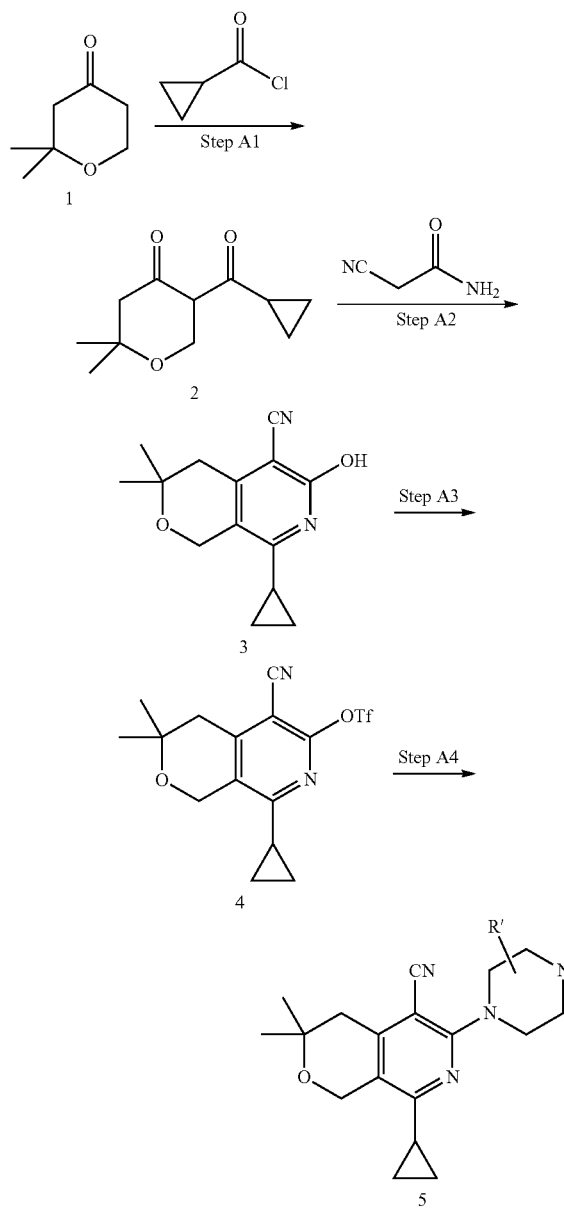

Step A1: 5-(cyclopropanecarbonyl)-2,2-dimethyldihydro-2H-pyran-4(3H)-one (2)

A 500 mL three-neck round bottom flask equipped with a stirring bar was charged with 2,2-dimethyldihydro-2H-pyran-4(3H)-one (6 g, 46.8 mmol) and 120 mL of dry toluene. The solution was purged with nitrogen and cooled to 0° C. With stirring, a solution of LDA (2M soln. in THF/n-heptane, 24.5 mL, 15.6 mmol) was added dropwise, and the reaction mixture was allowed to continue to stir for 5 min at 0° C. before cyclopropanecarbonyl chloride (2.8 mL, 31.2 mmol) was added. After stirring at 0° C. for an additional 20 min, the reaction mixture was quenched with 1N HCl until pH was above 7. After partitioning between $H_2O$ and methylene chloride, the organic layer was then washed with brine, dried over anhy. $Na_2SO_4$ and concentrated under vacuum. Flash column chromatography (10% ethyl acetate/petroleum ether) afforded 6 g of crude title compound as yellowish oil, which was used directly for the next step without further purification. MS (ES) M+H expected 197.1, found 197.3.

Step A2: 8-cyclopropyl-6-hydroxy-3,3-dimethyl-3,4-dihydro-1H-pyrano[3,4-c]pyridine-5-carbonitrile (3)

To a solution of 5-(cyclopropanecarbonyl)-2,2-dimethyl-dihydro-2H-pyran-4(3H)-one (2) (6 g, 30.6 mmol) and 2-cyanoacetamide (4.1 g, 49.0 mmol) in 70 mL of EtOH was added diethylamine (2.1 mL, 20.4 mmol). The reaction mixture was stirred at room temperature for 72 hours until LC-MS indicated the complete formation of product. The reaction mixture was then heated to reflux temperature, during this period enough EtOH was added to make a clear solution. After cooling back to room temperature, the product was precipitated out from EtOH solution and 3.3 g of the title compound was obtained as a white solid after vacuum filtration and air-drying. MS (ES) M+H expected 245.1, found 245. $^1$H NMR (CHLOROFORM-d) δ 4.74 (s, 2H), 2.82 (s, 2H), 1.68-1.78 (m, 1H), 1.34 (s, 6H), 1.30-1.32 (m, 2H), 1.24-1.26 (m, 2H)

Step A3: 5-cyano-8-cyclopropyl-3,3-dimethyl-3,4-dihydro-1H-pyrano[3,4-c]pyridin-6-yl trifluoromethane-sulfonate (4)

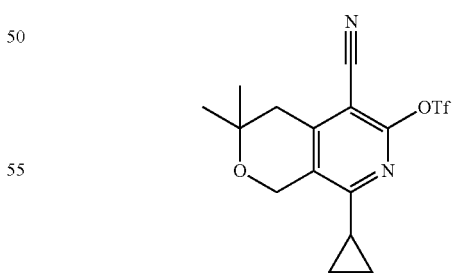

To a 250 mL round bottom flask was charged with 8-cyclopropyl-6-hydroxy-3,3-dimethyl-3,4-dihydro-1H-pyrano[3,4-c]pyridine-5-carbonitrile (3) (3.7 g, 15.16 mmol), DMAP (185 mg, 1.52 mmol), triethylamine (2.74 mL, 19.7 mmol) and 150 mL of methylene chloride. After the reaction mixture was cooled to 0° C. in a dry ice-acetone bath, trifluoromethanesulfonic anhydride (3.3 mL, 19.7 mmol) was added dropwise via a syringe. The resulting mixture was stirred at 0° C. for 30 min before allowed to warm up to room temperature and stirred for additional 2 hours.

After TLC indicated the complete conversion of starting material to the product, the reaction mixture was concentrated under vacuum and purified by flash column chromatography (1:10 ethyl acetate/petroleum ether) to give 4.9 g of the title compound as a white solid. ¹H NMR (CHLOROFORM-d) δ 4.91 (s, 2H), 2.88 (s, 2H), 1.73-1.84 (m, 1H), 1.34 (s, 6H), 1.23-1.27 (m, 2H), 1.17-1.22 (m, 2H)

Step A4: (R)-8-cyclopropyl-6-(3-isopropylpiperazin-1-yl)-3,3-dimethyl-3,4-dihydro-1H-pyrano[3,4-c]pyridine-5-carbonitrile (compound A2)

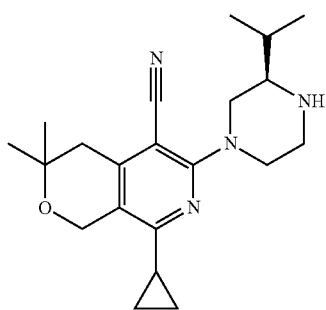 [SMILES: CC(C)[C@@H]1CN(c2nc(C3CC3)c3c(c2C#N)CC(C)(C)OC3)CCN1]

To a sealed tube was charged with 5-cyano-8-cyclopropyl-3,3-dimethyl-3,4-dihydro-1H-pyrano[3,4-c]pyridin-6-yl trifluoromethane-sulfonate (600 mg, 1.60 mmol), (R)-2-isopropylpiperazine (170 mg, 1.33 mmol), and triethylamine (0.24 mL, 1.73 mmol) in 2 mL of EtOH. The reaction mixture was heated at refluxing temperature overnight. After it was concentrated under reduced pressure, the reaction mixture was purified by flash column chromatography (1:10 methanol/methylene chloride) to give 428 mg of the title compound. MS (ES) M+H expected 355.2, found 355.2. ¹H NMR (CHLOROFORM-d) δ 4.84 (s, 2H), 4.33 (d, J=13.1 Hz, 1H), 4.19 (d, J=14.3 Hz, 1H), 3.47-3.55 (m, 1H), 3.35-3.47 (m, 1H), 2.94-3.21 (m, 3H), 2.77 (s, 2H), 1.98-2.14 (m, 1H), 1.64-1.77 (m, 1H), 1.31 (s, 6H), 1.14-1.21 (m, 3H), 1.08-1.14 (m, 5H), 0.98-1.07 (m, 2H)

Alternatively, it can be prepared by the following method.

A mixture of 4 (200 mg, 0.53 mmol), (R)-2-isopropylpiperazine (135 mg, 1.06 mmol), and triethylamine (0.2 mL, 1.59 mmol) suspended in 0.8 mL of acetonitrile was subjected to microwave reaction at 175° C. for 45 min. After the reaction mixture was concentrated under vacuum, the residue was purified by flash column chromatography to give 189 mg of the title compound as yellowish oil.

AMIDE COUPLING EXAMPLES

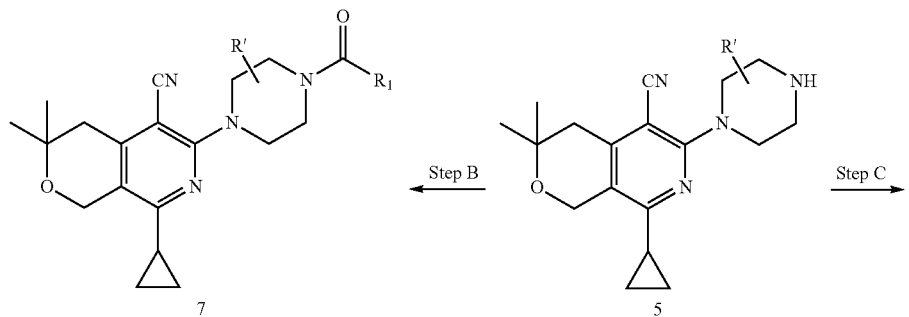

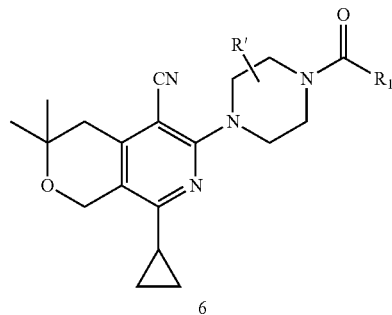

Step B: ethyl 4-(5-cyano-8-cyclopropyl-3,3-dimethyl-3,4-dihydro-1H-pyrano[3,4-c]pyridin-6-yl)-1-(2-(thiophen-2-yl)acetyl)piperazine-2-carboxylate Compound #421

In a 5-mL of amber glass vial was added ethyl 4-(5-cyano-8-cyclopropyl-3,3-dimethyl-3,4-dihydro-1H-pyrano[3,4-c]pyridin-6-yl)piperazine-2-carboxylate (31 mg, 0.08 mmol), 2-(thiophen-2-yl)acetic acid (48 mg, 0.34 mmol), EDCI (68.8 mg, 0.36 mmol), HOBt (48.6 mg, 0.36 mmol), triethylamine (36.8 mg, 0.36 mmol) and 1 mL of methylene chloride. The resulting reaction mixture was stirred at room temperature overnight. The mixture was quenched with 1 N HCl aqueous solution, extracted with EtOAc three times. The combined organic layer was washed with satd. NaHCO$_3$ and brine, dried over anhy. Na$_2$SO$_4$, and concentrated under vacuum. The crude product was purified by preparative TLC separation (DCM: acetone/70:1) to afford 21 mg of the title compound as a white solid. MS (ES) M+H expected 509.2, found 509.3. $^1$H NMR (CHLOROFORM-d) δ: 7.22-7.26 (m, 1H), 6.89-7.01 (m, 2H), 5.24-5.38 (m, 0.5H), 4.79-4.89 (m, 2H), 4.61-4.73 (m, 1H), 4.00-4.28 (m, 4.5H), 3.74-3.93 (m, 2H), 3.19-3.29 (m, 1H), 2.92-3.05 (m, 1H), 2.72-2.85 (m, 2H), 1.68-1.78 (m, 1H), 1.29-1.36 (m, 6H), 1.12-1.23 (m, 5H), 0.99-1.08 (m, 2H)

Step C: (R)-methyl 3-(4-(5-cyano-8-cyclopropyl-3,3-dimethyl-3,4-dihydro-1H-pyrano[3,4-c]pyridin-6-yl)-2-cyclopropylpiperazin-1-yl)-3-oxopropanoate Compound #440

To a solution of (R)-8-cyclopropyl-6-(3-cyclopropylpiperazin-1-yl)-3,3-dimethyl-3,4-dihydro-1H-pyrano[3,4-c]pyridine-5-carbonitrile (250 mg, 0.7 mmol) in 15 mL of methylene chloride was added triethylamine (0.2 mL, 1.4 mmol) and methyl 3-chloro-3-oxopropanoate (191 mg, 1.4 mmol). The resulting reaction mixture was allowed to stir at room temperature overnight. The reaction mixture was diluted with DCM and then washed with brine. The organic layer was dried over anhy. Na$_2$SO$_4$ and concentrated under vacuum. The crude product was purified by preparative TLC separation (DCM/acetone: 70:1) to afford 200 mg of the title compound as yellow oil. $^1$H NMR (CHLOROFORM-d) δ 4.83 (s, 2H), 4.62-4.65 (m, 0.5H), 4.26 (d, J=13.1 Hz, 1H), 4.16 (d, J=12.5 Hz, 1H), 4.03 (d, J=9.3 Hz, 0.5H), 3.71-3.85 (m, 3.5H), 3.60-3.70 (m, 0.5H), 2.93-3.58 (m, 5H), 2.78 (s, 2H), 1.66-1.75 (m, 1H), 1.36-1.44 (m, 1H), 1.32 (d, J=3.0 Hz, 6H), 1.13 (t, J=3.6 Hz, 2H), 0.97-1.07 (m, 2H), 0.31-0.64 (m, 4H) LC-MS: m/z 453.2 (M+H)$^+$ Building Block Syntheses Synthesis of Building Block 1:
(R)-2-Isopropylpiperazine

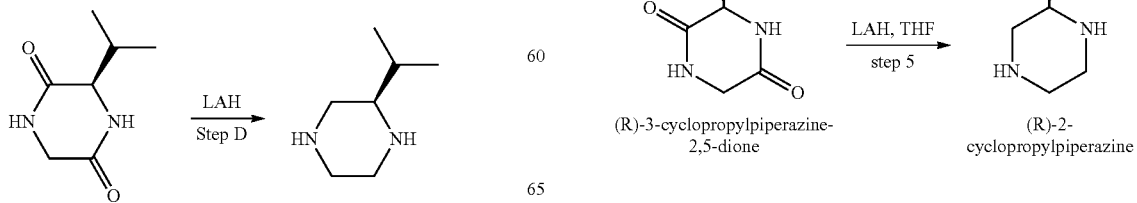

Step D: (R)-2-isopropylpiperazine

To a flask was added (R)-3-isopropylpiperazine-2,5-dione (154 mg, 1 mmol) in THF (5 mL), and LAH (2.5 M solution in THF) (2.5 mL, 6 mmol) was added dropwise under N$_2$ at 0° C. The resulting mixture was heated to 65° C. and allowed to stir overnight. The reaction mixture was then cooled to RT followed by addition of 0.23 mL H$_2$O, 0.23 mL 10% NaOH and 0.46 mL H$_2$O. The reaction mixture was filtered and the cake washed with EtOAc. The organic phase was concentrated to give the crude product as solid (86 mg): $^1$H NMR (CHLOROFORM-d) δ ☐0.91 (d, 3H, J=6.8 Hz), 0.93 (d, 3H, J=6.6 Hz), 1.48-1.57 (m, 1H), 1.75 (br, 2H), 2.31-2.45 (m, 2H), 2.67-2.83 (m, 2H), 2.90 (d, 1H, J=11.5 Hz), 2.99-3.02 (m, 2H)

Synthesis of Building Block 2:
(R)-2-Cyclopropylpiperazine

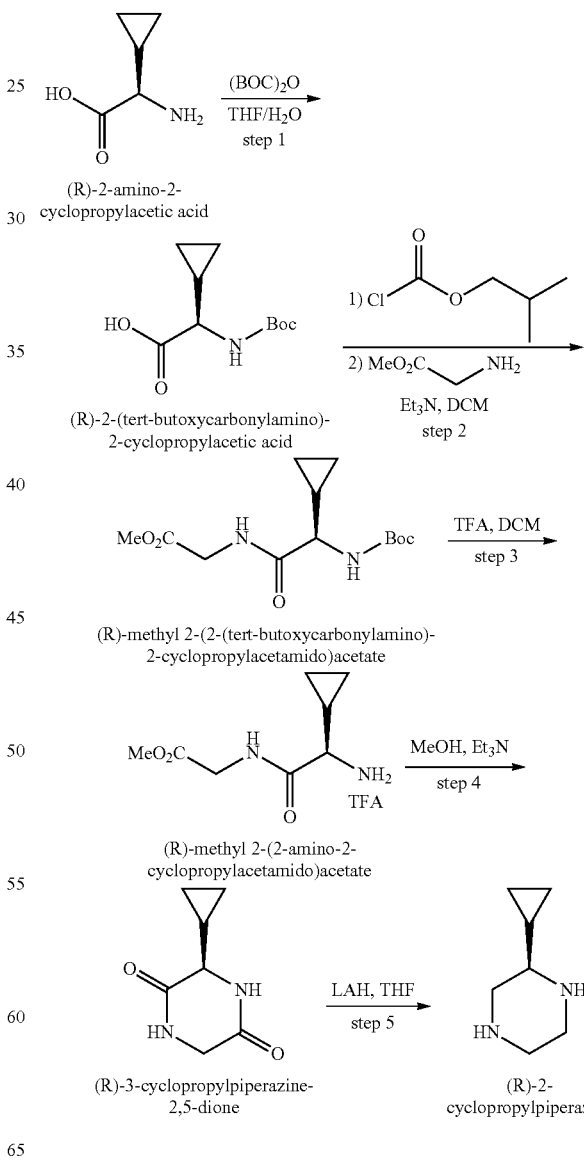

Step 1: To a solution of (R)-6-cyclopropyl-2-(4-(3-methoxypropanoyl)-3-methylpiperazin-1-yl)-5-(2-vinylquinazolin-5-yl)nicotinonitrile (100 g, 0.87 mol) in water (1250 ml), NaHCO₃ (175 g, 2.08 mol) was added at room temperature followed by a solution of (Boc)₂O in THF (1250 mL). The resulting reaction mixture was heated to reflux overnight. After stirring overnight the reaction mixture was concentrated to remove THF under reduced pressure. EtOAc (1250 mL) was added to the residue and the resulting mixture was cooled to 5° C. and then adjusted to pH 3 with saturated aqueous NaHSO₄. The layers were separated and the aqueous was extracted with EtOAc (1000 mL×3). The combined EtOAc layers were washed with water and brine, dried over Na₂SO₄ and concentrated under reduced pressure to give (R)-2-(tert-butoxycarbonylamino)-2-cyclopropylacetic acid (165 g, yield 88%, ee>99%). ¹H NMR (MeOD 400 MHz) □ δ 3.16-3.14 (d, J=8.8, 1H), 1.11 (s, 9H), 0.73-0.78 (m, 1H), 0.28-0.2 (m, 3H), 0.18-0.15 (m, 1H)

Step 2: Isobutyl chloroformate (81.6 g, 0.6 moL) was added over 1 hr to a stirred mixture of (R)-2-(tert-butoxycarbonylamino)-2-cyclopropylacetic acid (129 g, 0.6 moL) and Et₃N (67 g, 0.66 moL) in DCM (1000 mL) at 0° C.-5° C. and the reaction mixture was stirred 1 hr at 0° C.-5° C. In a separate flask, a mixture of glycine methyl ester hydrochloride (82.8 g, 0.66 moL), Et₃N (73 g, 0.72 moL) and DCM (1000 mL) was stirred for 1 hr and the mixture was then added to the flask over 2 hrs. After the addition was complete, the mixture was stirred overnight at room temperature for 40 hrs and then washed with water and brine, dried with Na₂SO₄, concentrated under reduced pressure and the residue was purified by column chromatography to give (R)-methyl 2-(2-(tert-butoxycarbonylamino)-2-cyclopropyl acetamido)acetate (100 g, yield 58%, ee>99%) as white solid. ¹H NMR (DMSO 400 MHz) □ δ 8.2-8.16 (t, J=5.6, 1H), 6.66-6.86 (d, J=8.8, 9H), 3.71-3.92 (m, 2H), 3.62 (s, 3H), 3.46-3.51 (t, J=8.4, 1H), 1.36 (s, 9H), 0.97-1.01 (m, 1H), 0.38-0.44 (m, 3H), 0.25-0.28 (m, 1H)

Step 3: To a solution of (R)-methyl 2-(2-(tert-butoxycarbonylamino)-2-cyclopropylacetamido) acetate (290 g, 1.014 mol) in DCM (1740 mL), TFA (870 mL) was added dropwise at 0° C. The reaction solution was stirred overnight at room temperature. The resulting solution was concentrated under reduced pressure to give (R)-methyl 2-(2-amino-2-cyclopropylacetamido) acetate (511 g crude).

Step 4: To a solution (R)-methyl 2-(2-amino-2-cyclopropylacetamido)acetate (255.5 g crude, 0.507 mol) in MeOH (1250 ml), Et₃N (750 ml, 10.78 mol) was added was added dropwise at 0° C. Then the reaction mixture was stirred two days at room temperature. The resulting mixture was filtered and the precipitate was washed with MTBE and dried by high vacuum to give (R)-3-cyclopropylpiperazine-2,5-dione (60 g, yield 76.9%). ¹H NMR TH03840-082-1 (DMSO 400 MHz) 7.98 (s, 1H), 7.74 (s, 1H), 3.68-6.64 (d, J=17.6, 1H), 3.30-3.36 (m, 1H), 2.9-2.93 (dd, J=3.2, 1H), 0.87-0.92 (m, 1H), 0.21-0.27 (m, 3H), 0.18-0.21 (m, 1H)

Step 5: To a suspension mixture of (R)-3-cyclopropylpiperazine-2,5-dione (30 g, 0.195 mmol) in THF (1000 mL), AlLiH₄ (45 g, 1.184 mol) was added in portions over 1.5 hrs at 0° C. Then the reaction mixture was heated to 70° C. overnight. After cooling, water (45 mL) was added dropwise at 0° C. and then a solution of KOH (45 mL, 1%) was added dropwise at 0° C. The resulting mixture was filtered and the residue was washed with EtOAc and MeOH (3:1) and the filtrate was concentrated under reduced pressure to give crude product. Then the crude product was washed with DCM and the filtrate was concentrated under reduced pressure to give (R)-2-cyclopropylpiperazine (18.5 g, yield 75.5%, ee>99%). ¹H NMR (MeOD 400 MHz) 2.9-2.96 (m, 1H), 2.8-2.88 (m, 1H), 2.7-2.8 (m, 1H), 2.55-2.68 (m, 2H), 2.4-2.5 (q, J=10.4, 1H), 1.65-1.73 (m, 1H), 0.55-0.67 (m, 1H), 0.35-0.45 (m, 2H), 0.05-0.25 (m, 2H)

Synthesis of Building Block 3:
2-Cyclopropylpiperazine

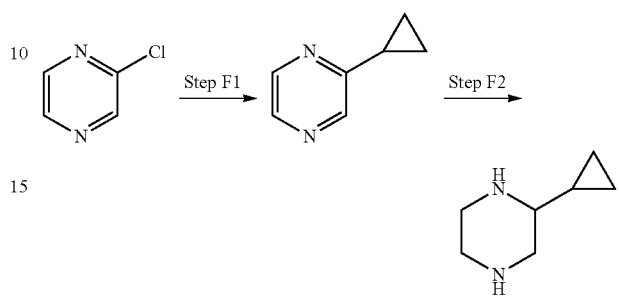

Step F1: 2-cyclopropylpyrazine

To a solution of 2-chloropyrazine (1.14 g, 10 mmol) and 50 mg Fe(acac)₃ in 20 mL anhydrous THF was added cyclopropylmagnesium chloride (10 mL, 1M) at −40° C. over 1 min. Then the solution was stirred at −40° C. for 0.5 h and warmed to 0° C. THF was removed by reduced pressure and 100 mL water and 100 mL EA was added. The EA layer was washed with water (twice) and brine to give product (0.8 g) after purification by flash column chromatography (EA:PE=1:10). ¹H NMR (CHLOROFORM-d) δ 8.48 (d, J=2.5 Hz, 1H), 8.37 (br. s., 1H), 8.29 (t, J=3.0 Hz, 1H), 2.05 (dt, J=6.2, 3.0 Hz, 1H), 0.95-1.19 (m, 4H). Step F2: 2-cyclopropylpiperazine To a solution of 2-cyclopropylpyrazine (0.8 g) in 50 mL methanol was added 5 mL AcOH and 50 mg Pd/C. The reaction mixture was stirred under H₂ (60 psi) at RT overnight. The mixture was filtered and the filtrate was concentrated to dryness to get product (0.85 g) which was used without further purification. ¹H NMR (DMSO) δ: 3.53 (dd, J=13.9, 3.1 Hz, 1H), 3.32-3.48 (m, 2H), 2.99-3.18 (m, 3H), 2.38-2.62 (m, 1H), 0.73-0.89 (m, 1H), 0.50-0.63 (m, 2H), 0.23-0.42 (m, 2H)

Synthesis of Building Block 4:
2-(2,2,2-trifluoroethyl)piperazine

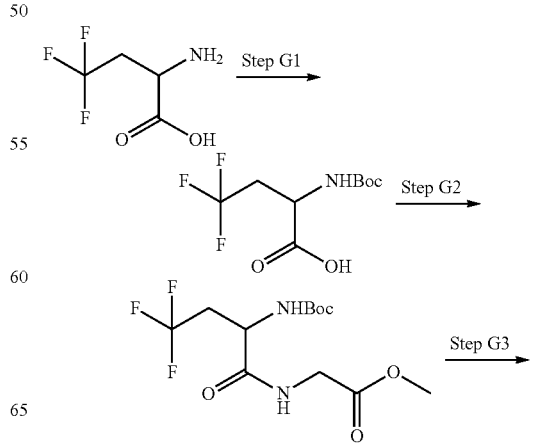

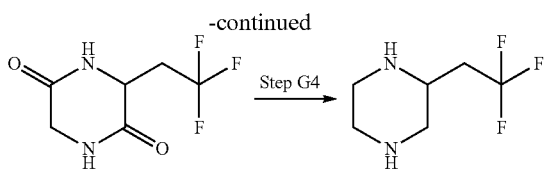

Step G1: 2-(tert-butoxycarbonylamino)-4,4,4-trifluorobutanoic acid

To a solution of 2-amino-4,4,4-trifluorobutanoic acid (450 mg, 3 mmol) in 5 mL H$_2$O and 5 mL THF was added NaHCO$_3$ (504 mg, mmol), followed by a solution of di-tert-butyl dicarbonate (650 mg, 3 mmol) in THF (3 mL). The resulting mixture was stirred at 80° C. overnight. After removal of THF, the mixture poured into water and extracted with methylene chloride. The combined organic layer was dried over anhy. Na$_2$SO$_4$ and concentrated under vacuum. 723 mg of title compound was obtained as a crude product and used in subsequent reaction without further purification. MS (ES) M+H expected 201.1, found 201.3. $^1$H NMR (CHLOROFORM-d) δ □5.25 (d, J=7.8 Hz, 1H), 4.40-4.67 (m, 1H), 2.60-2.90 (m, 2H), 1.46 (s, 9H). Step G2: methyl 2-(2-(tert-butoxycarbonylamino)-4,4,4-trifluorobutanamido)acetate To a 25 mL of round-bottom flask was added 2-(tert-butoxycarbonylamino)-4,4,4-trifluorobutanoic acid (723 mg, 2.8 mmol), Et$_3$N (560 mg, 5.6 mmol), isobutyl carbonochloridate (380 mg, 2.8 mmol) in 5 mL methylene chloride. The resulting reaction mixture was stirred at 0° C. for 0.5 hours. Then methyl 2-aminoacetate (352 mg, 2.8 mmol) was added, and the resulting mixture was stirred at room temperature overnight. After washing with satd. NaHCO$_3$, brine, the combined organic layer was dried over anhy. Na$_2$SO$_4$ and concentrated under vacuum. 900 mg of title compound was obtained as a crude product and used in subsequent reaction without further purification. MS (ES) M+H expected 272.1, found 272.0. $^1$H NMR (CHLOROFORM-d) δ 7.11 (br. s., 1H), 5.28 (br. s., 1H), 4.44-4.67 (m, 1H), 3.84-4.07 (m, 2H), 3.69-3.83 (s, 3H), 2.72-2.95 (m, 1H), 2.42-2.64 (m, 1H), 1.38-1.50 (m, 9H)

Step G3: 3-(2,2,2-trifluoroethyl)piperazine-2,5-dione

A mixture of methyl 2-(2-(tert-butoxycarbonylamino)-4,4,4-trifluorobutanamido)acetate (900 mg, 2.7 mmol) in 5 mL 1,2-dichlorobenzene was heated to 180° C. overnight. The mixture was cooled down and MTBE (5 mL) was added. A brown yellowish precipitate was formed. The filter cake was washed with MTBE and air-dried to give 200 mg of title compound. $^1$H NMR (DMSO-d6) δ 8.28 (d, J=9.3 Hz, 2H), 4.00-4.26 (m, 1H), 3.68-3.87 (m, 2H), 2.66-2.88 (m, 2H).

Step G4: 2-(2,2,2-trifluoroethyl)piperazine

To a flask was added 3-(2,2,2-trifluoroethyl)piperazine-2,5-dione (200 mg, 1 mmol) in THF (5 mL), and LAH (2.5 mL, 6 mmol, (2.5 M solution in THF)) was added dropwise under N$_2$ at 0° C., and then the mixture was heated to 65° C. overnight. After reaction was complete, the mixture was cooled down, and 0.23 mL H$_2$O was added followed by 0.23 mL 10% NaOH and 0.46 mL H$_2$O. The mixture was filtered and the cake washed with EtOAc. The organic phase was concentrated to give the crude product (140 mg solid). $^1$H NMR (CHLOROFORM-d) δ 2.75-3.02 (m, 7H), 2.52 (dd, J=11.7, 9.9 Hz, 1H), 2.10-2.17 (m, 2H).

Synthesis of Building Block 5: 2-methyl-1,4-diazepane

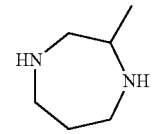

According to the procedure described in: Hidaka, Hiroyoshi; EP1074545; (2001); (A1)

Synthesis of Building Block 6: Ethyl piperazine-2-carboxylate

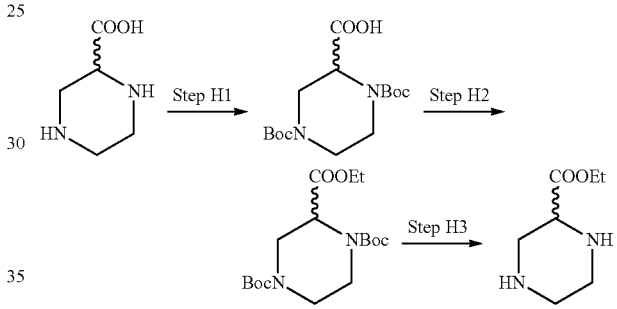

Step H1: 1,4-bis(tert-butoxycarbonyl)piperazine-2-carboxylic acid

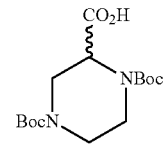

To an aqueous solution of Na$_2$CO$_3$ (40 g, 380 mmol, in 200 mL of water) at room temperature was added piperazine-2-carboxylic acid dihydrochloride (10 g, 50 mmol), followed by di-tert-butyl dicarbonate (41 g, 183 mmol) in tetrahydrofuran (200 mL). The reaction mixture was stirred at room temperature for 20 hours and then the volatiles were removed under reduced pressure. The resulting mixture was then extracted with diethyl ether (100 mL). The aqueous layer was treated with 3.0 M HCl until it was slightly acidic (pH=4) and then extracted with ethyl acetate (150 mL). The organic layer was washed with brine, dried over anhy. Na$_2$SO$_4$, filtered, and concentrated to afford 16 g of the title compound as a white solid. $^1$H NMR (CHLOROFORM-d) δ 12.9 (1H, s), 2.70-4.50 (m, 7H), 1.33 (m, 18H).

301

(S)-1,4-bis(tert-butoxycarbonyl)piperazine-2-carboxylic acid

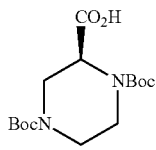

The title compound was prepared from (S)-piperazine-2-carboxylic acid dihydrochloride according to the method described in Step H1.

Step H2: (S)-1,4-di-tert-butyl 2-ethyl piperazine-1,2,4-tricarboxylate

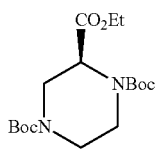

To a mixture of (S)-1,4-bis(tert-butoxycarbonyl)piperazine-2-carboxylic acid (0.5 g, 1.38 mmol) in 10 mL of DMF was added $K_2CO_3$ (0.6 g, 4.4 mmol). The resulting suspension was cooled to 0° C. and treated with bromoethane (1 mL, 9.34 mmol). The reaction mixture was allowed to warm to room temperature, stirred for 24 hours. After quenching with water (10 mL), the mixture was extracted with ethyl acetate (20 mL), and the organic layer was washed with brine, dried over anhy. $Na_2SO_4$, filtered, and concentrated under vacuum to afford 0.48 g of the title compound as white solid, which was used directly for the next step without further purification.

Step H3: (S)-ethyl piperazine-2-carboxylate

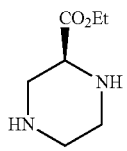

To a solution of (S)-1,4-di-tert-butyl 2-ethyl piperazine-1,2,4-tricarboxylate (1.2 g, 4.5 mmol) in methanol (4 mL) at room temperature was added HCl solution (5 mL, 4.0 M in EtOAc). The reaction mixture was stirred at room temperature overnight and then concentrated to afford 1 g of 2-(methoxymethyl) piperazine as the hydrochloride salt, which was used in the next step without further purification. $^1$H NMR (CHLOROFORM-d) δ 4.18 (m, 2H), 3.43 (dd, 1H), 3.13 (dd, 1H), 2.96 (m, 1H), 2.70 (m, 4H), 1.27 (t, 3H).

302

Synthesis of Building Block 7: 2-(difluoromethyl)piperazine

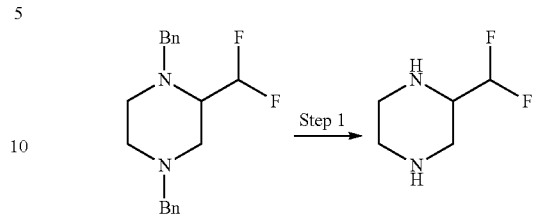

Step I: 2-(difluoromethyl)piperazine

To a solution of 1,4-dibenzyl-2-(difluoromethyl)piperazine (synthesized according to a procedure described in Synthetic Communications, 2011, vol. 41, #14 p. 2031-2035)(80 mg, 0.253 mmol) in 40 mL of EtOH was added Pd(OH)$_2$/C (15 mg). The resulting mixture was hydrogenated under 50 Psi at r.t. for two days. The reaction mixture was filtered, and the filtrate was concentrated to afford the title compound (which was used directly without further purification). $^1$H NMR (CHLOROFORM-d) δ 5.67 (td, 1H), 2.62-3.13 (m, 7H).

Synthesis of Building Block 8: (6-fluoro-2-methyl-1,4-diazepane)

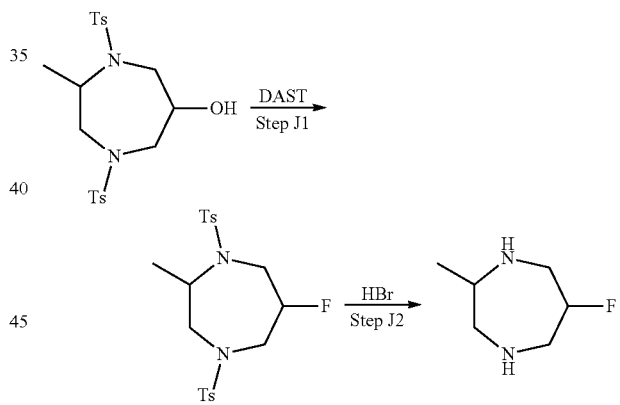

Step J1: 6-fluoro-2-methyl-1,4-ditosyl-1,4-diazepane 2-methyl-1,4-ditosyl-1,4-diazepan-6-ol, and 6-fluoro-2-methyl-1,4-ditosyl-1,4-diazepane were prepared following procedures described in Synthesis 2003, 2, p. 223-226. $^1$H NMR (CHLOROFORM-d) δ □ 7.62-7.75 (m, 4H), 7.30-7.37 (m, 4H), 5.00-4.84 (m, 1H), 4.09-4.37 (m, 2H), 3.73-3.95 (m, 1H), 3.37-3.62 (m, 2H), 3.12-3.32 (m, 1H), 3.05 (ddd, J=13.6, 7.2, 4.0 Hz, 1H), 2.43-2.46 (m, 6H), 1.05-1.14 (m, 3H)

Step J2: 6-fluoro-2-methyl-1,4-diazepane

A suspension of 6-fluoro-2-methyl-1,4-ditosyl-1,4-diazepane (84 mg, 0.19 mmol) in HOAc-HBr (3 mL, 30 wt %) was heated to 100° C. for 3 mins in a pressure tube using microwave irradiation. The solvent was removed in vacuum and the residue triturated with Et2O, washed with Et2O to give the title compound, which was used directly without further purification.

Synthesis of Building Block 9: (R)-2-deuterio-2-(perdeuteriopropan-2-yl)piperazine

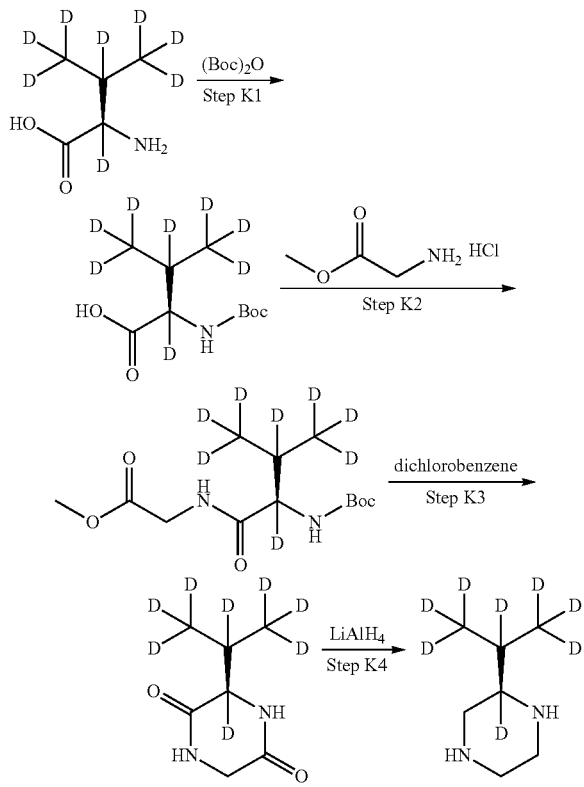

Step K1: (R)-2-(tert-butoxycarbonylamino)-2,3,4,4,4-pentadeuterio-3-(trideuteriomethyl)butanoic acid

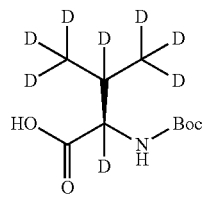

To a solution of D-valine (d8) (500 mg, 4.27 mmol) in water (6.4 mL) was added NaHCO3 (717 mg, 8.53 mmol) followed by a solution of di-tert-butyl dicarbonate (932 mg) in THF (6.4 mL). The mixture was stirred and heated under reflux for 16 h and then concentrated under vacuum to remove THF. Then EtOAc (4.5 mL) was added, and the mixture was cooled to 10° C. and then adjusted to pH 3 with saturated aqueous NaHSO4 (3.3 mL). The layers were separated, and the aqueous layer was extracted with EtOAc (4 mL×3). The combined EtOAc layers were washed with water (2 mL×1) and brine, dried over MgSO4, and concentrated under vacuum to give the desired compound (924 mg, 99%).

$^1$H NMR (CHLOROFORM-d) δ: 5.00 (br. s., 1H), 1.45 (s, 9H)

Step K2: (R)-methyl 2-(2-(tert-butoxycarbonylamino)-2,3,4,4,4-pentadeuterio-3 (trideuteriomethyl)butan-amino)acetate

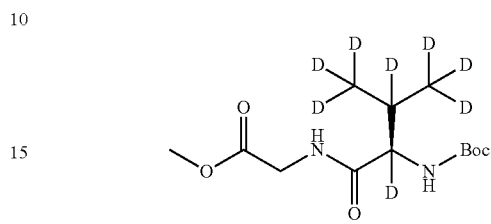

To a stirred mixture of (R)-2-(tert-butoxycarbonylamino)-2,3,4,4,4-pentadeuterio-3-(trideuteriomethyl)butanoic acid (924 g, 4.25 mol) and Et3N (430 mg, 4.25 mmol) in CH2Cl2 (12.3 mL) at 5° C. was added Isobutyl chloroformate (580 mg, 4.25 mmol) over 30 min. When the addition was complete, the mixture was stirred at 0-5° C. for 30 min. In a separate flask, a mixture of glycine methyl ester hydrochloride (534 mg, 4.25 mmol), Et3N (430 mg, 4.25 mmol), and CH2Cl2 (12.3 mL) was stirred for 30 min and this mixture was then added to the mixture above over 0.5 h. After the addition was complete, the mixture was stirred at room temperature for 16 h and then washed with water (3×15 mL) and brine, dried, and concentrated under vacuum to give the product (1.12 g, 91%).

Step K3: (R)-3-deuterio-3-(perdeuteriopropan-2-yl)piperazine-2,5-dione

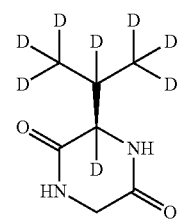

A solution of (R)-methyl 2-(2-(tert-butoxycarbonylamino)-2,3,4,4,4-pentadeuterio-3-(trideuteriomethyl) butan-amino)acetate (999 mg, 3.46 mmol) in 1,2-dichlorobenzene (9 mL) was heated at 175-180° C. for 18 h, allowing any MeOH formed to be removed by distillation. After removal of 6 mL of the solvent by distillation at atmospheric pressure with the aid of a stream of nitrogen, the mixture was cooled to 50° C. and MTBE (5 mL) was added cautiously. The mixture was cooled to room temperature and filtered. The resulting solid was washed with MTBE (0.2 mL) and dried under vacuum at 100° C. to give the product (320 mg, 59%). $^1$H NMR (DMSO-d6) δ: 8.18 (br. s., 1H), 8.01 (br. s., 1H), 3.81 (d, J=17.8 Hz, 1H), 3.61 (dd, J=17.8, 3.0 Hz, 1H)

Step K4: (R)-2-deuterio-2-(perdeuteriopropan-2-yl)piperazine

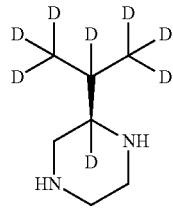

To a solution of (R)-3-deuterio-3-(perdeuteriopropan-2-yl)piperazine-2,5-dione (160 mg, 1 mmol) in dry THF (5 mL) was added LiAlH$_4$ (228 mg, 6 mmol). The mixture was stirred at reflux for 12 h. After cooling to 0° C., water (0.5 mL) was carefully added, and the mixture was stirred at r.t. for 30 min. The solid was filtered out and the filtrate was concentrated under vacuum to give the product. (120 mg, 88%), which was used directly for the next step without further purification.

(R)-2,2,3,5,5-pentadeuterio-3-(perdeuteriopropan-2-yl)piperazine

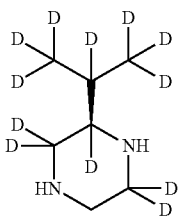

The title compound was prepared from (R)-3-deuterio-3-(perdeuteriopropan-2-yl)piperazine-2,5-dione with LiAlD$_4$ according to the method described in Step K4.

(R)-methyl-2-(2-(tert-butoxycarbonylamino)-2,3,4,4,4-pentadeuterio-3-(trideuteriomethyl)butan-amido)-2,2-dideuterioacetate

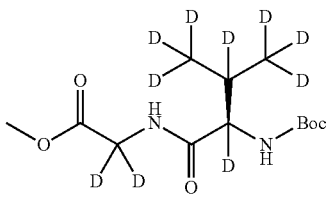 [SMILES: [2H]C([2H])(NC(=O)[C@@]([2H])(NC(=O)OC(C)(C)C)C([2H])(C([2H])([2H])[2H])C([2H])([2H])[2H])C(=O)OC]

The title compound was prepared from (R)-2-(tert-butoxycarbonylamino)-2,3,4,4,4-pentadeuterio-3-(trideuteriomethyl)butanoic acid with glycine methyl ester hydrochloride (d$_2$) according to the method described in Step K2.

(R)-3,3,6-trideuterio-6-(perdeuteriopropan-2-yl)piperazine-2,5-dione

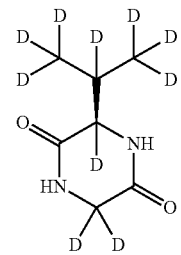

The title compound was prepared from (R)-methyl 2-(2-(tert-butoxycarbonylamino)-2,3,4,4,4-pentadeuterio-3-(trideuteriomethyl)butan-amido)-2,2-dideuterioacetate according to the method described in Step K3.

(R)-2,2,5-trideuterio-5-(perdeuteriopropan-2-yl)piperazine

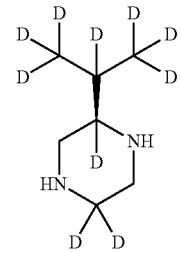

The title compound was prepared from (R)-3,3,6-trideuterio-6-(perdeuteriopropan-2-yl)piperazine-2,5-dione according to the method described in Step K4.

(R)-2,2,3,3,5,5,6-heptadeuterio-6-(perdeuteriopropan-2-yl)piperazine

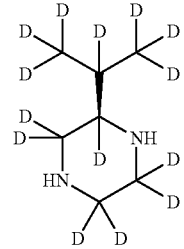

The title compound was prepared from (R)-3,3,6-trideuterio-6-(perdeuteriopropan-2-yl)piperazine-2,5-dione with LiAlD$_4$ according to the method described in Step K4.

Synthesis of Building Block 10: lithium 2-(oxetan-3-yl)acetate

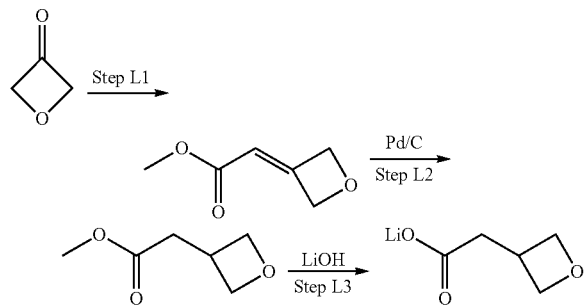

Step L1: Methyl 2-(oxetan-3-ylidene)acetate

The title compound was synthesized according to the procedure described in US20100075983. $^1$H NMR (400 MHz, CDCl$_3$) δ=5.66 (dd, J=4.7, 2.3 Hz, 1H), 5.51 (dd, J=6.5, 2.9 Hz, 2H), 5.31 (dt, J=5.2, 2.7 Hz, 2H), 3.72 (s, 3H).

Step L2: Methyl 2-(oxetan-3-yl)acetate

To a solution of methyl 2-(oxetan-3-ylidene)acetate (641.0 mg, 5 mmol) in methanol (25 mL) was added 25 mg of Pd/C (10%) at rt and the resulting mixture was stirred under H2 atmosphere overnight. After removal of Pd/C via a pad of celite, the residue was dried under a reduced pressure and was then subjected to column chromatography on silica gel using ethyl acetate/petroleum ether (1:1, V/V) as eluent to give a light yellow liquid. Yield: 586.1 mg (90.1%). $^1$H NMR (400 MHz, CDCl$_3$) δ=4.94-4.78 (m, 2H), 4.42 (t, J=6.3 Hz, 2H), 3.67 (s, 3H), 3.44-3.29 (m, 1H), 2.74 (d, J=7.9 Hz, 2H).

Step L3: Lithium 2-(oxetan-3-yl)acetate

To a solution of methyl 2-(oxetan-3-yl)acetate (130.1 mg, 1.00 mmol) in a mixture of tetrahydrofuran (10 mL) and water (3 mL) was added lithium hydroxide monohydrate (44.1 mg, 1.05 mmol) at −10° C. using a dry ice-acetone bath. The resulting solution was allowed to warm to rt and stirred over night. After removal of tetrahydrofuran and water, the obtained white solid was directly used in the next reaction step without any further purification. Yield: 121.4 mg (99.5%). $^1$H NMR (400 MHz, D$_2$O) δ 4.83-4.73 (m, 1H), 4.33 (t, J=6.4 Hz, 1H), 4.33 (t, J=6.4 Hz, 1H), 3.18 (dt, J=14.7, 7.3 Hz, 1H), 2.48 (d, J=8.0 Hz, 1H).

Synthesis of Building Block 11: 2-(oxetan-2-yl)acetic acid

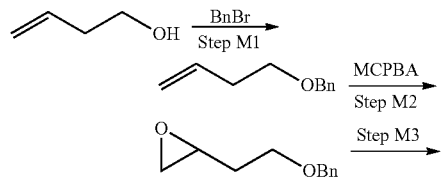

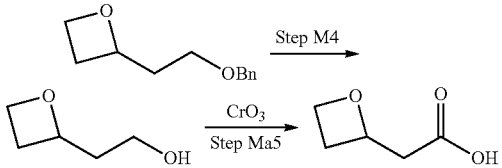

Step M1: ((but-3-en-1-yloxy) methyl)benzene

A mixture of 3-buten-1-ol (5.00 g), triethylamine (0.46 g), sodium hydroxide (4.10 g) and hexane (50 mL) was stirred at 50° C. for 0.5 h and then benzyl bromide (12.9 g) was added to the mixture dropwise below 60° C. The mixture was allowed to warm to reflux and refluxed for 3 h. The mixture was poured into ice cooled water and the mixture was extracted with hexane. The organic layer was washed with water, brine, dried over Na2SO4 and concentrated under vacuum. The residue was purified by chromatography on silica gel (petroleum ether to petroleum ether:ethyl acetate=10:1) to give the title compound as an oil (6 g). $^1$H NMR (CHLOROFORM-6) d: 7.30-7.43 (m, 5H), 5.78-5.95 (m, 1H), 5.03-5.19 (m, 2H), 4.56 (s, 2H), 3.57 (t, J=6.8 Hz, 2H), 2.42 (qt, J=6.7, 1.3 Hz, 2H)

Step M2: 2-(2-(benzyloxy)ethyl)oxirane

To a solution of [(but-3-en-1-yloxy)methyl]benzene (10.6 g) in toluene (200 mL) was added m-chloroperbenzoic acid with water (69-75%, 20.0 g) under ice-cooling and then the mixture was allowed to warm to room temperature. After stirring for 18 h at room temperature, the mixture was filtered. The filtrate was diluted with hexane, washed with a solution of sodium thiosulfate pentahydrate (8.1 g) in 5% aqueous sodium bicarbonate solution (200 mL), 3% aqueous sodium bicarbonate solution (200 mL), water (200 mL), brine, dried over Na2SO4 and concentrated under vacuum. The residue was purified by chromatography on silica gel (hexane:ethyl acetate=20:1 to 4:1) to give the title compound as an oil (10.2 g). $^1$H NMR (CHLOROFORM-d) δ: 7.31-7.42 (m, 5H), 4.56 (s, 2H), 3.60-3.69 (m, 2H), 3.10 (td, J=4.5, 1.9 Hz, 1H), 2.77-2.85 (m, 1H), 2.56 (dd, J=5.0, 2.8 Hz, 1H), 1.88-2.00 (m, 1H), 1.74-1.86 (m, 1H) Refer to US2010/94000.

Step M3: 2-(2-(benzyloxy)ethyl)oxetane

A mixture of KOBu-t (1.12 g, 10 mmol) and trimethyloxosulfonium iodide (2.2 g, 10 mmol) in dry t-BuOH (13 mL) was stirred magnetically at 50° C. for 1 h. A solution of 2-(2-(benzyloxy)ethyl)oxirane (0.9 g, 5 mmol) in dry t-BuOH (10 mL) was then added dropwise and stirred for 3 days. The solvent was carefully evaporated under reduced pressure, and water (30 mL) was added to the residual suspension. The mixture was extracted with n-hexane, dried over anhydrous MgSO4, and concentrated to give the crude product, which was purified by column chromatography to afford product as colorless oil (0.4 g). $^1$H NMR (CHLOROFORM-d) δ: 7.29-7.45 (m, 5H), 5.03 (dd, J=7.2, 5.6 Hz, 1H), 4.70 (td, J=8.0, 5.8 Hz, 1H), 4.47-4.61 (m, 3H), 3.48-3.63 (m, 2H), 2.64-2.77 (m, 1H), 2.35-2.49 (m, 1H), 2.09-2.22 (m, 1H), 1.93-2.09 (m, 1H)

Refer to *Journal of Organic Chemistry*, 2000, 67 (26), 9488-9491

Step M4: 2-(oxetan-2-yl) ethanol

To a solution of 2-(2-(benzyloxy)ethyl)oxetane (0.3 g, 14.2 mmol) in MeOH (15 mL) was added 10% Pd/C (20 mg). The reaction mixture was purged with hydrogen and stirred under a hydrogen atmosphere for 2 d. The black suspension was passed through a plug of celite eluting with MeOH, the organic was then concentrated to yield the desired product as colorless oil (0.10 g, 62%). $^1$H NMR (CHLOROFORM-d) δ: 5.12 (qd, J=7.3, 4.6 Hz, 1H), 4.72 (td, J=8.0, 6.0 Hz, 1H), 4.60 (dt, J=9.1, 6.0 Hz, 1H), 3.88 (ddd, J=11.0, 7.0, 4.5 Hz, 1H), 3.79 (ddd, J=11.0, 6.7, 4.6 Hz, 1H), 2.66-2.80 (m, 1H), 2.56 (br. s., 1H), 2.40-2.52 (m, 1H), 2.07 (dtd, J=14.4, 7.2, 4.5 Hz, 1H), 1.93 (ddt, J=14.4, 7.2, 4.5 Hz, 1H).

Step M5: 2-(oxetan-2-yl)acetic acid

Sulfuric acid (1 mL) and water (3 mL) were successively added to a solution of chromium(VI) oxide in water (3 mL) while ice-cooling. This solution was added dropwise to a solution of 2-hydroxymethyloxetane (40 mg) in acetone (10 mL) while ice-cooling with the inside temperature was kept below 20° C., and the mixture was stirred for 2 hours at room temperature. Then 2-propanol was added to quench the reaction, and this solution was diluted with ethyl acetate and filtered through celite. The filtrate was washed with brine and the aqueous layer was extracted twice with ethyl acetate. After the organic layers were combined together and dried over anhydrous magnesium sulfate, the solvent was evaporated to give the product which was used for the next step without further purification (30 mg). $^1$H NMR (400 MHz, methanol-d4) δ 5.26-5.15 (m, 1H), 4.69 (ddd, J=8.3, 7.8, 5.9 Hz, 1H), 4.58 (dt, J=9.2, 5.9 Hz, 1H), 2.88-2.70 (m, 3H), 2.51 (ddt, J=11.2, 9.1, 7.3 Hz, 1H).

Synthesis of Building Block 12: 2-(methoxycarbonylamino)acetic acid

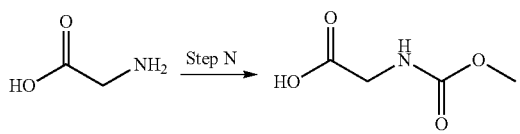

Step N: 2-(methoxycarbonylamino)acetic acid

To a solution of 2-aminoacetic acid (2.0 g, 26.2 mmol) in H$_2$O (1 mL) was added methyl carbonochloridate (1.6 g, 16.6 mmol) and NaOH (2.6 mL, 10 N portionwise. After 15 min, Na$_2$CO$_3$ (1.3 g) was added with continuous stirring. Then, the solution was acidified with 4 mL of concentrated hydrochloric acid and extracted with ethyl acetate, dried over Na$_2$SO$_4$ and concentrated. The residue was diluted with ethyl acetate and stirred at room temperature overnight. The mixture was filtered to get 331 mg white solid, which was used directly for the next step without further purification.

EXAMPLES

Compound#422

(R)-3-(4-(5-cyano-8-cyclopropyl-3,3-dimethyl-3,4-dihydro-1H-pyrano[3,4-c]pyridin-6-yl)-2-isopropylpiperazin-1-yl)-N-methyl-3-oxopropanamide

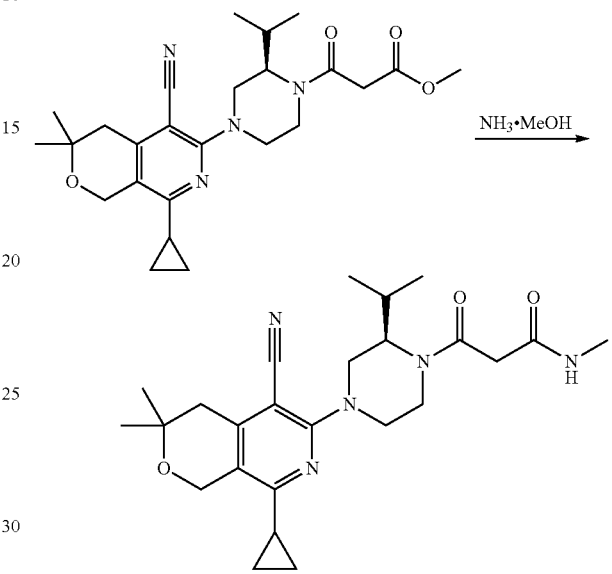

The solution of (R)-methyl 3-(4-(5-cyano-8-cyclopropyl-3,3-dimethyl-3,4-dihydro-1H-pyrano[3,4-c]pyridin-6-yl)-2-cyclopropylpiperazin-1-yl)-3-oxopropanoate (40 mg, 0.09 mmol) in NH$_3$/MeOH (1.5 mL, 1M) was stirred at 30° C. overnight. Then, the reaction mixture was concentrated and purified by preparative TLC separation (DCM/methanol: 20:1) to afford 33 mg of the title compound as colorless oil. $^1$H NMR (CHLOROFORM-d) δ 7.68 (br. s., 0.5H), 7.50 (br. s., 0.5H), 4.76-4.91 (m, 2H), 4.53-4.71 (m, 0.5H), 4.26-4.46 (m, 1.5H), 4.17 (d, J=11.5 Hz, 1H), 3.88 (d, J=13.8 Hz, 0.5H), 3.61 (d, J=10.5 Hz, 0.5H), 3.27-3.53 (m, 2.5H), 2.90-3.15 (m, 2.5H), 2.80-2.87 (m, 3H), 2.77 (s, 2H), 2.05-2.35 (m, 1H), 1.66-1.78 (m, 1H), 1.32 (d, J=3.0 Hz, 6H), 0.95-1.16 (m, 7H), 0.75-0.92 (m, 3H)

LC-MS: m/z 454.4 (M+H)$^+$

Compound #429

(R)-8-cyclopropyl-6-(4-(3-hydroxypropanoyl)-3-isopropylpiperazin-1-yl)-3,3-dimethyl-3,4-dihydro-1H-pyrano[3,4-c]pyridine-5-carbonitrile To a solution of (R)-methyl 3-(4-(5-cyano-8-cyclopropyl-3,3-dimethyl-3,4-dihydro-1H-pyrano[3,4-c]pyridin-6-yl)-2-cyclopropylpiperazin-1-yl)-3-oxopropanoate (43 mg, 0.09 mmol) and NaBH$_4$ (7 mg, 0.18 mmol) in 10 mL of tetrahydrofuran was added BF3.OEt$_2$ (0.02 mL, 0.18 mmol) dropwise. Then, the mixture was stirred at room temperature overnight. The solution was washed with water and brine. The organic layer was dried over anhy. Na$_2$SO$_4$ and concentrated under vacuum. The crude product was purified by preparative TLC (DCM/acetone: 70:1) to afford 14 mg of the title compound as colorless oil. $^1$H NMR (CHLOROFORM-d) δ 4.77-4.91 (m, 2H), 4.64 (d, J=10.0 Hz, 0.5H), 4.28-4.46 (m, 1.5H), 4.10-4.26 (m, 1H), 3.90 (br. s., 2H), 3.63-3.83 (m, 1H), 3.37-3.54 (m, 1H), 2.91-3.11 (m, 2H), 2.72-2.88 (m, 2H), 2.56-2.66 (m, 2H), 2.11-2.36 (m, 1H), 1.67-1.77 (m, 1H), 1.32 (d, J=2.3 Hz, 6H), 0.95-1.18 (m, 7H), 0.78-0.93 (m, 3H)

LC-MS: m/z 427.1 (M+H)+
Compound #437

(R)-8-cyclopropyl-6-(4-(3-fluoropropanoyl)-3-isopropylpiperazin-1-yl)-3,3-dimethyl-3,4-dihydro-1H-pyrano[3,4-c]pyridine-5-carbonitrile To a solution of (R)-8-cyclopropyl-6-(4-(3-hydroxypropanoyl)-3-isopropylpiperazin-1-yl)-3,3-dimethyl-3,4-dihydro-1H-pyrano[3,4-c]pyridine-5-carbonitrile (106 mg, 0.4 mmol) in dry DCM (10 mL) was added DAST at −78° C. The mixture was stirred at this temperature for 2 h, and then quenched with water (0.5 mL). The organic phase was washed with 1N HCl (2×5 mL), brine, dried over anhy. $Na_2SO_4$ and concentrated under vacuum. The crude product was purified by preparative TLC (PE/EA: 5:1) to afford 75 mg of the title compound as colorless oil. 1H NMR (CHLOROFORM-d) □ δ 4.80-4.93 (m, 3H), 4.71-4.80 (m, 1H), 4.66 (d, J=10.3 Hz, 0.5H), 4.41 (d, J=10.3 Hz, 0.5H), 4.33 (d, J=13.6 Hz, 1H), 4.12-4.25 (m, 1H), 3.75 (d, J=13.6 Hz, 0.5H), 3.39-3.52 (m, 1H), 2.96-3.08 (m, 2H), 2.95 (s, 0.5H), 2.81-2.87 (m, 1H), 2.62-2.81 (m, 3H), 2.20-2.35 (m, 0.5H), 2.05-2.20 (m, 0.5H), 1.66-1.76 (m, 1H), 1.32 (d, J=2.5 Hz, 6H), 1.08-1.18 (m, 2H), 0.95-1.06 (m, 5H), 0.89 (d, J=6.8 Hz, 2H), 0.82 (d, J=6.8 Hz, 2H)

LC-MS: m/z 429.5 (M+H)
Compound #456

(R)-ethyl-4-(4-(5-cyano-8-cyclopropyl-3,3-dimethyl-3,4-dihydro-1H-pyrano[3,4-c]pyridin-6-yl)-2-isopropyl piperazin-1-yl)-4-oxobutanoate To a solution of (R)-8-cyclopropyl-6-(3-isopropylpiperazin-1-yl)-3,3-dimethyl-3,4-dihydro-1H-pyrano[3,4-c]pyridine-5-carbonitrile (500 mg, 1.4 mmol) in 20 mL of methylene chloride was added triethylamine (0.4 mL, 2.8 mmol) and methyl 4-chloro-4-oxobutanoate (0.35 mL, 2.8 mmol). The resulting reaction mixture was stirred at room temperature overnight. The reaction mixture was diluted with DCM and then washed with brine. The organic layer was dried over anhy. $Na_2SO_4$ and concentrated under vacuum. The crude product was purified by flash column chromatography (DCM/acetone: 70:1) to afford 368 mg of (R)-methyl 4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate as light yellow oil. H NMR (CHLOROFORM-d) δ 4.83 (s, 2H), 4.28-4.50 (m, 2H), 4.02-4.28 (m, 1H), 3.70-3.84 (m, 3H), 3.40-3.70 (m, 4H), 2.91-3.18 (m, 2H), 2.76 (s, 2H), 2.05-2.32 (m, 1H), 1.61-1.81 (m, 1H), 1.32 (d, J=2.5 Hz, 6H), 0.95-1.18 (m, 7H), 0.78-0.95 (m, 3H)

(R)-methyl-4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate in 10 mL MeOH/$H_2O$ (9:1) was cooled to 0° C. and LiOH (84 mg, 2.0 mmol) was added, then the solution was stirred at room temperature for 24 h. To the mixture water was added, and then the pH was adjusted to ~3 with 1 N HCl. Then, it was extracted with DCM, dried over $N_2SO_4$, concentrated and purified by flash column chromatography to get 331 mg of (R)-4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoic acid as yellow solid. LC-MS: m/z 455.2 (M+H)+

To a solution of (R)-4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoic acid (50 mg, 0.1 mmol) in 2 mL of DMF was added $Cs_2CO_3$ (72 mg, 0.2 mmol) and bromoethane (0.02 mL, 0.3 mmol). The resulting reaction mixture was stirred in a sealed tube at 55° C. overnight. The reaction mixture was diluted with water, extracted with DCM and then washed with brine. The organic layer was dried over anhy. $Na_2SO_4$ and concentrated under vacuum. The crude product was purified by preparative TLC (DCM/acetone: 70:1) to afford 18 mg of the title compound. 1H NMR (CHLOROFORM-d) δ 4.74-4.91 (m, 2H), 4.43-4.72 (m, 0.5H), 4.29-4.40 (m, 1.5H), 4.09-4.23 (m, 3H), 3.79 (d, J=13.6 Hz, 0.5H), 3.36-3.57 (m, 1H), 2.90-3.14 (m, 2.5H), 2.76 (s, 2H), 2.60-2.72 (m, 4H), 2.07-2.33 (m, 1H), 1.67-1.74 (m, 1H), 1.31 (d, J=2.3 Hz, 6H), 1.27 (td, J=7.1, 2.1 Hz, 3H), 0.96-1.19 (m, 7H), 0.77-0.94 (m, 3H). LC-MS: m/z 483.5 (M+H)+
Compound#448

(R)-6-(4-(3-(1,3,4-oxadiazol-2-yl)propanoyl)-3-isopropylpiperazin-1-yl)-8-cyclopropyl-3,3-dimethyl-3,4-dihydro-1H-pyrano[3,4-c]pyridine-5-carbonitrile To a solution of (R)-methyl 4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate (40 mg, 0.1 mmol) in 5 mL of anhydrous ethanol was added Hydrazine hydrate (10 mg, 0.2 mmol). The resulting mixture was heated to reflux for 4 hours. After TLC showed the completion of reaction, the mixture was evaporated under reduced pressure. A mixture of the obtained residue, trimethyl orthoformate (11 mg), 4-methylbenzenesulfonic acid (5 mg) and MeOH (5 mL) was heated under reflux overnight. After LC-MS showed the completion of reaction, the mixture was evaporated. The residue was purified by preparative TLC separation (DCM/acetone: 70:1) to afford the title compound. 1H NMR (400 MHz, CHLOROFORM-d) δ □ 8.34 (d, J=4.2 Hz, 1H), 4.83 (s, 2H), 4.62 (d, J=10.2 Hz, 0.5H), 4.27-4.39 (m, 1.5H), 4.11-4.23 (m, 1H), 3.78 (d, J=14.6 Hz, 0.5H), 3.43-3.55 (m, 1H), 3.27 (t, J=7.2 Hz, 2H), 2.98-3.07 (m, 2H), 2.89-2.98 (m, 2.5H), 2.77 (s, 2H), 2.12 (m, 1H), 1.65-1.75 (m, 1H), 1.32 (d, J=2.6 Hz, 6H), 0.96-1.04 (m, 6H), 0.87-0.93 (m, 2H), 0.79 (d, J=6.8 Hz, 2H)

LC-MS: m/z 479.3 (M+H)+
Compound #462

8-Cyclopropyl-6-((R)-4-((1R,2R)-2-(hydroxymethyl)cyclopropanecarbonyl)-3-isopropylpiperazin-1-yl)-3,3-dimethyl-3,4-dihydro-1H-pyrano[3,4-c]pyridine-5-carbonitrile To a solution of trans-methyl 2-((R)-4-(5-cyano-8-cyclopropyl-3,3-dimethyl-3,4-dihydro-1H-pyrano[3,4-c]pyridin-6-yl)-2-isopropylpiperazine-1-carbonyl)cyclopropanecarboxylate (120 mg, 0.4 mmol) in MeOH/THF (5 mL/5 mL) was added $LiBH_4$ (53 mg, 2.4 mmol) in several portions. The mixture was stirred at r.t. for 2 h. Water (0.5 mL) was added to quench the reaction, and then EA (20 mL) was added. The organic phase was washed with water, brine, dried over anhy. $Na_2SO_4$ and concentrated under vacuum. The crude product was purified by preparative TLC (PE/EA: 2:1) to afford 66 mg of the title compound as colorless oil. 1H NMR (CHLOROFORM-d) □ δ 4.69-4.97 (m, 2H), 4.58 (d, J=10.0 Hz, 0.5H), 4.27-4.47 (m, 1.5H), 4.00-4.27 (m, 1.5H), 3.61-3.91 (m, 1.5H), 3.35-3.61 (m, 1.5H), 2.89-3.18 (m, 2.5H), 2.78 (d, J=17.3 Hz, 2H), 2.27 (ddd, J=13.2, 6.7, 3.4 Hz, 0.5H), 2.12 (dt, J=6.7, 3.3 Hz, 0.5H), 1.62-1.92 (m, 2H), 1.19-1.38 (m, 6H), 0.96-1.17 (m, 7H), 0.69-0.96 (m, 4H)

LC-MS: m/z 453.6 (M+H)$^+$

Compound#472

((1R,2R)-2-((R)-4-(5-cyano-8-cyclopropyl-3,3-dimethyl-3,4-dihydro-1H-pyrano[3,4-c]pyridin-6-yl)-2-isopropylpiperazine-1-carbonyl)cyclopropyl)methyl methyl carbonate To a solution of 8-cyclopropyl-6-((R)-4-((1R,2R)-2-(hydroxymethyl)cyclopropanecarbonyl)-3-isopropylpiperazin-1-yl)-3,3-dimethyl-3,4-dihydro-1H-pyrano[3,4-c]pyridine-5-carbonitrile (100 mg, 0.22 mmol) in DMF (4 mL) was added NaH (16.3 mg, 65%, 0.44 mmol) at 0° C. The mixture was stirred at 0° C. for 30 min. Dimethyl carbonate (30 mg, 0.33 mmol) was added. The resulting mixture was stirred at r.t. for 2 h. Water (20 mL) was carefully added to quench the reaction. The aqueous phase was extracted with DCM (3×10 mL). The combined organic phase was washed with water, brine, dried over anhy. Na$_2$SO$_4$ and concentrated under vacuum. The crude product was purified by preparative TLC (PE/EA: 3:1) to afford 30 mg of the title compound as colorless oil. 1H NMR (CHLOROFORM-d) □ δ 4.74-4.94 (m, 2H), 4.57 (dd, J=10.2, 4.4 Hz, 0.5H), 4.13-4.42 (m, 4H), 3.84-4.01 (m, 1H), 3.74-3.84 (m, 3.5H), 3.38-3.61 (m, 0.5H), 2.92-3.13 (m, 2.5H), 2.77 (s, 2H), 2.27 (dt, J=10.7, 5.5 Hz, 0.5H), 2.13 (dt, J=10.5, 6.5 Hz, 0.5H), 1.65-1.93 (m, 4H), 1.32 (d, J=2.5 Hz, 6H), 0.97-1.19 (m, 7H), 0.76-0.94 (m, 4H)

LC-MS: m/z 511.6 (M+H)

Compound#421

Ethyl 4-(5-cyano-8-cyclopropyl-3,3-dimethyl-3,4-dihydro-1H-pyrano[3,4-c]pyridin-6-yl)-1-(2-(thiophen-2-yl)acetyl)piperazine-2-carboxylate $^1$H NMR (CHLOROFORM-d) δ: 7.22-7.26 (m, 1H), 6.89-7.01 (m, 2H), 5.24-5.38 (m, 0.5H), 4.79-4.89 (m, 2H), 4.61-4.73 (m, 1H), 4.00-4.28 (m, 4.5H), 3.74-3.93 (m, 2H), 3.19-3.29 (m, 1H), 2.92-3.05 (m, 1H), 2.72-2.85 (m, 2H), 1.68-1.78 (m, 1H), 1.29-1.36 (m, 6H), 1.12-1.23 (m, 5H), 0.99-1.08 (m, 2H)

Compound #423

(R)-8-cyclopropyl-6-(3-isopropyl-4-(3,3,3-trifluoropropanoyl)piperazin-1-yl)-3,3-dimethyl-3,4-dihydro-1H-pyrano[3,4-c]pyridine-5-carbonitrile (Step B)

$^1$H NMR (CHLOROFORM-d) δ 4.76-4.91 (m, 2H), 4.65-4.68 (m, 0.5H), 4.42 (d, J=10.5 Hz, 0.5H), 4.34 (d, J=13.6 Hz, 1H), 4.12-4.27 (m, 1H), 3.61-3.75 (m, 0.5H), 3.44-3.60 (m, 0.5H), 3.14-3.43 (m, 2.5H), 2.94-3.10 (m, 2.5H), 2.77 (s, 2H), 2.14 (dq, J=17.2, 6.7 Hz, 1H), 1.67-1.75 (m, 1H), 1.32 (d, J=2.8 Hz, 6H), 0.96-1.18 (m, 7H), 0.77-0.92 (m, 3H)

LC-MS: m/z 465.2 (M+H)$^+$

Compound #424

(R)-8-cyclopropyl-6-(3-isopropyl-4-(4-methoxybutanoyl)piperazin-1-yl)-3,3-dimethyl-3,4-dihydro-1H-pyrano[3,4-c]pyridine-5-carbonitrile (Step B)

$^1$H NMR (CHLOROFORM-d) δ 4.75-4.90 (m, 2H), 4.64-4.66 (m, 0.5H), 4.40 (d, J=10.3 Hz, 0.5H), 4.33 (d, J=13.6 Hz, 1H), 4.07-4.25 (m, 1H), 3.78 (d, J=13.6 Hz, 0.5H), 3.38-3.57 (m, 3H), 3.34 (s, 3H), 2.89-3.07 (m, 2.5H), 2.69-2.82 (m, 2H), 2.35-2.54 (m, 2H), 2.10-2.31 (m, 1H), 1.87-2.04 (m, 2H), 1.66-1.75 (m, 1H), 1.31 (d, J=2.5 Hz, 6H), 0.96-1.16 (m, 7H), 0.75-0.92 (m, 3H)

LC-MS: m/z 455.2 (M+H)$^+$

Compound#425

8-cyclopropyl-6-(3-cyclopropyl-4-(3-methoxypropanoyl)piperazin-1-yl)-3,3-dimethyl-3,4-dihydro-1H-pyrano[3,4-c]pyridine-5-carbonitrile (building block 3, step B)

$^1$H NMR (CHLOROFORM-d) δ 4.78-4.91 (m, 2H), 4.25 (d, J=12.8 Hz, 1H), 4.15 (d, J=12.5 Hz, 1H), 3.69-4.10 (m, 4H), 3.61-3.75 (m, 3H), 2.50-3.24 (m, 7H), 1.67-1.76 (m, 1H), 1.31 (d, J=2.8 Hz, 6H), 1.20 (d, J=6.8 Hz, 1H), 1.09-1.17 (m, 2H), 0.96-1.05 (m, 2H), 0.29-0.64 (m, 4H)

LC-MS: m/z 439.2 (M+H)$^+$

Compound #426

8-cyclopropyl-6-(3-cyclopropyl-4-(furan-3-carbonyl)piperazin-1-yl)-3,3-dimethyl-3,4-dihydro-1H-pyrano[3,4-c]pyridine-5-carbonitrile (building block 3, step B)

$^1$H NMR (CHLOROFORM-d) δ 7.64-7.77 (m, 1H), 7.37-7.50 (m, 1H), 6.55 (s, 1H), 4.84 (s, 2H), 4.14-4.30 (m, 3H), 3.67-4.00 (m, 21H), 3.15 (dd, J=12.8, 3.5 Hz, 1H), 2.98 (td, J=12.5, 3.3 Hz, 1H), 2.78 (s, 2H), 1.67-1.79 (m, 1H), 1.41-1.57 (m, 1H), 1.32 (d, J=2.3 Hz, 6H), 1.10-1.19 (m, 2H), 0.95-1.06 (m, 2H), 0.60 (td, J=8.5, 3.8 Hz, 1H), 0.42-0.54 (m, 1H), 0.38 (br. s., 1H)

LC-MS: m/z 447.2 (M+H)$^+$

Compound#427

(R)-8-cyclopropyl-6-(3-isopropyl-4-(isoxazole-3-carbonyl)piperazin-1-yl)-3,3-dimethyl-3,4-dihydro-1H-pyrano[3,4-c]pyridine-5-carbonitrile (step B)

1H NMR (400 MHz, CHLOROFORM-d) δ 8.48 (d, J=1.5 Hz, 1H), 6.69 (d, J=1.5 Hz, 1H), 4.83 (s, 2H), 4.68 (d, J=13.0 Hz, 0.5H), 4.33-4.53 (m, 2H), 4.12-4.32 (m, 1.5H), 3.53 (td, J=12.9, 3.2 Hz, 0.5H), 3.01-3.22 (m, 2.5H), 2.77 (d, J=3.0 Hz, 2H), 2.16-2.36 (m, 1H), 1.64-1.77 (m, 1H), 1.32 (s, 6H), 1.04-1.15 (m, 3H), 1.02 (dd, J=7.9, 2.6 Hz, 2H), 0.93 (t, J=6.4 Hz, 3H), 0.81 (d, J=6.7 Hz, 2H)

LC-MS: m/z 450.2 (M+H)$^+$

Compound#428

(R)-8-cyclopropyl-6-(3-isopropyl-4-(4-oxopentanoyl)piperazin-1-yl)-3,3-dimethyl-3,4-dihydro-1H-pyrano[3,4-c]pyridine-5-carbonitrile (step B)

1H NMR (400 MHz, CHLOROFORM-d) δ 4.75-4.89 (m, 2H), 4.46-4.69 (m, 0.5H), 4.24-4.40 (m, 2H), 4.06-4.23 (m, 1H), 3.81 (d, J=13.8 Hz, 0.5H), 3.52-3.60 (m, 0.5H), 3.37-3.51 (m, 1H), 2.89-3.12 (m, 2.5H), 2.79-2.84 (m, 2H), 2.76 (s, 2H), 2.55-2.71 (m, 2H), 2.23 (s, 3H), 1.64-1.77 (m, 1H), 1.27-1.37 (s, 6H), 1.06-1.19 (m, 2H), 0.94-1.05 (m, 4H), 0.85-0.94 (m, 2H), 0.80 (d, J=6.8 Hz, 2H)

LC-MS: m/z 453.0 (M+H)$^+$

Compound #430

8-cyclopropyl-6-(3-cyclopropyl-4-(3,3,3-trifluoropropanoyl)piperazin-1-yl)-3,3-dimethyl-3,4-dihydro-1H-pyrano[3,4-c]pyridine-5-carbonitrile (building block 3, step B)

$^1$H NMR (CHLOROFORM-d) δ 4.78-4.90 (m, 2H), 4.66 (br. s., 0.5H), 4.26 (d, J=12.8 Hz, 1H), 4.17 (d, J=12.5 Hz,

1H), 4.07 (d, J=8.5 Hz, 0.5H), 3.67-3.84 (m, 1.5H), 3.30 (q, J=9.8 Hz, 2H), 3.03-3.15 (m, 1.5H), 2.90-3.03 (m, 1H), 2.71-2.84 (m, 2H), 1.68-1.78 (m, 1H), 1.37-1.47 (m, 1H), 1.32 (d, J=3.0 Hz, 6H), 1.10-1.19 (m, 2H), 0.98-1.07 (m, 2H), 0.28-0.71 (m, 4H)

LC-MS: m/z 463.1 (M+H)$^+$

Compound#431

(R)-methyl 3-(4-(5-cyano-8-cyclopropyl-3,3-dimethyl-3,4-dihydro-1H-pyrano[3,4-c]pyridin-6-yl)-2-isopropylpiperazin-1-yl)-3-oxopropylcarbamate (building block 12, step B)

$^1$H NMR (CHLOROFORM-d) δ 5.50 (br. s., 1H), 4.75-4.91 (m, 2H), 4.60-4.65 (m, 0.5H), 4.24-4.41 (m, 1.5H), 4.08-4.22 (m, 1H), 3.60-3.80 (m, 3.5H), 3.33-3.50 (m, 3H), 2.91-3.04 (m, 2.5H), 2.70-2.82 (m, 2H), 2.50-2.63 (m, 2H), 2.05-2.34 (m, 1H), 1.65-1.78 (m, 1H), 1.31 (d, J=2.8 Hz, 6H), 0.95-1.19 (m, 7H), 0.70-0.91 (m, 3H)

LC-MS: m/z 484.1 (M+H)$^+$

Compound#432

(R)-8-cyclopropyl-6-(4-(3-methoxypropanoyl)-3-methylpiperazin-1-yl)-3,3-dimethyl-3,4-dihydro-1H-pyrano[3,4-c]pyridine-5-carbonitrile (step B)

$^1$H NMR (CHLOROFORM-d) δ 4.76-4.96 (m, 2.5H), 4.51 (d, J=13.6 Hz, 0.5H), 4.20 (br. s., 0.5H), 3.93-4.14 (m, 2H), 3.65-3.83 (m, 2.5H), 3.46-3.65 (m, 0.5H), 3.37 (s, 3H), 3.06-3.24 (m, 1.5H), 2.88-3.06 (m, 1H), 2.55-2.80 (m, 4H), 1.66-1.76 (m, 1H), 1.24-1.39 (m, 9H), 1.09-1.19 (m, 2H), 0.97-1.05 (m, 2H)

LC-MS: m/z 413.2 (M+H)$^+$

Compound #433

8-cyclopropyl-6-((3R)-4-(3-hydroxybutanoyl)-3-isopropylpiperazin-1-yl)-3,3-dimethyl-3,4-dihydro-1H-pyrano[3,4-c]pyridine-5-carbonitrile (step B)

1H NMR (400 MHz, CHLOROFORM-d) δ □4.83 (s, 2H) 4.63 (m, 0.5H), 4.28-4.47 (m, 2H), 4.04-4.28 (m, 2H), 3.63-3.78 (m, 0.5H), 3.43 (td, J=8.2, 3.4 Hz, 1H), 2.90-3.08 (m, 2.5H), 2.76 (s, 2H), 2.44-2.62 (m, 1H), 2.21-2.43 (m, 1.5H), 1.58-1.78 (m, 1H), 1.28-1.38 (m, 6H), 1.18-1.28 (m, 5H), 0.94-1.07 (m, 4H), 0.88 (t, J=6.2 Hz, 2H), 0.74-0.84 (m, 2H)

LC-MS: m/z 441.2 (M+H)$^+$

Compound#434

(R)-8-cyclopropyl-6-(3-cyclopropyl-4-(3-methoxypropanoyl)piperazin-1-yl)-3,3-dimethyl-3,4-dihydro-1H-pyrano[3,4-c]pyridine-5-carbonitrile (building block 2, step B)

$^1$H NMR (CHLOROFORM-d) δ 4.83 (s, 2H), 4.63-4.65 (m, 0.5H), 4.24 (d, J=12.5 Hz, 1H), 4.15 (d, J=12.5 Hz, 1H), 4.05 (d, J=8.8 Hz, 0.5H), 3.69-3.88 (m, 3H), 3.36 (s, 3H), 2.94-3.24 (m, 3H), 2.75-2.82 (m, 2H), 2.50-2.67 (m, 2H), 1.66-1.76 (m, 1H), 1.31 (d, J=3.0 Hz, 7H), 1.10-1.18 (m, 2H), 0.98-1.06 (m, 2H), 0.33-0.63 (m, 4H)

LC-MS: m/z 439.1 (M+H)$^+$

Compound #435

(R)-8-cyclopropyl-6-(3-cyclopropyl-4-(3,3,3-trifluoropropanoyl)piperazin-1-yl)-3,3-dimethyl-3,4-dihydro-1H-pyrano[3,4-c]pyridine-5-carbonitrile (building block 2, step B)

$^1$H NMR (CHLOROFORM-d) δ 4.84 (s, 2H), 4.66 (br. s., 0.5H), 4.26 (d, J=12.8 Hz, 1H), 4.17 (d, J=12.8 Hz, 1H), 4.07 (d, J=8.5 Hz, 0.5H), 3.67-3.92 (m, 1.5H), 3.21-3.38 (m, 2H), 3.06-3.18 (m, 1.5H), 2.94-3.01 (m, 1H), 2.78 (s, 2H), 1.68-1.80 (m, 1H), 1.38-1.49 (m, 1H), 1.32 (d, J=3.3 Hz, 6H), 1.10-1.20 (m, 2H), 0.99-1.08 (m, 2H), 0.27-0.79 (m, 4H)

LC-MS: m/z 463.0 (M+H)$^+$

Compound#436

((R)-8-cyclopropyl-6-(3-deuterio-4-(3-methoxypropanoyl)-3-(perdeuteriopropan-2-yl)piperazin-1-yl)-3,3-dimethyl-3,4-dihydro-1H-pyrano[3,4-c]pyridine-5-carbonitrile (building block 9, step B)

$^1$H NMR (CHLOROFORM-d) □ δ 4.75-4.91 (m, 2H), 4.65 (d, J=11.3 Hz, 0.5H), 4.32 (ddd, J=13.3, 5.3, 1.5 Hz, 1H), 4.18 (d, J=14.1 Hz, 1H), 3.62-3.85 (m, 3H), 3.27-3.48 (m, 4.5H), 2.90-3.04 (m, 2H), 2.73-2.79 (m, 2H), 2.52-2.70 (m, 2H), 1.64-1.76 (m, 1H), 1.31 (d, J=2.3 Hz, 6H), 1.08-1.16 (m, 2H), 0.95-1.05 (m, 2H)

LC-MS: m/z 449.6 (M+H)$^+$

Compound#438

(R)-8-cyclopropyl-3,3-dimethyl-6-(2,2,3,5,5-pentadeuterio-4-(3-methoxypropanoyl)-3-(perdeuteriopropan-2-yl)piperazin-1-yl)-3,4-dihydro-1H-pyrano[3,4-c]pyridine-5-carbonitrile (building block 9, step B)

$^1$H NMR (CHLOROFORM-d) □ δ 4.76-4.89 (m, 2H), 4.16 (dd, J=12.7, 7.4 Hz, 1H), 3.64-3.80 (m, 2H), 3.36 (d, J=3.5 Hz, 3H), 2.88-3.05 (m, 1H), 2.76 (s, 2H), 2.49-2.74 (m, 2H), 1.64-1.76 (m, 1H), 1.31 (d, J=2.5 Hz, 6H), 0.96-1.18 ppm (m, 4H)

LC-MS: m/z 453.6 (M+H)$^+$

Compound#439

Methyl 5-((R)-4-(5-cyano-8-cyclopropyl-3,3-dimethyl-3,4-dihydro-1H-pyrano[3,4-c]pyridin-6-yl)-2-isopropylpiperazin-1-yl)-2-methyl-5-oxopentanoate $^1$H NMR (CHLOROFORM-d) δ 4.77-4.91 (m, 2H), 4.62-4.70 (m, 0.5H), 4.28-4.49 (m, 1.5H), 4.07-4.25 (m, 1H), 3.63-3.79 (m, 3.5H), 3.34-3.54 (m, 1H), 2.88-3.11 (m, 2.5H), 2.72-2.83 (m, 2H), 2.49-2.62 (m, 1H), 2.33-2.46 (m, 1H), 2.19-2.30 (m, 1H), 1.81-1.98 (m, 2H), 1.64-1.78 (m, 1H), 1.29-1.37 (m, 6H), 1.21 (d, J=7.0 Hz, 3H), 0.95-1.17 (m, 7H), 0.76-0.89 (m, 3H)

LC-MS: m/z 497.2 (M+H)$^+$

Compound#441

(R)-8-cyclopropyl-6-(2,2,3,3,5,6,6-heptadeuterio-4-(3-methoxypropanoyl)-5-(perdeuteriopropan-2-yl)piperazin-1-yl)-3,3-dimethyl-3,4-dihydro-1H-pyrano[3,4-c]pyridine-5-carbonitrile (building block 9, step B)

$^1$H NMR (CHLOROFORM-d) □ δ 4.82 (s, 2H), 3.65-3.80 (m, 2H), 3.36 (d, J=3.5 Hz, 3H), 2.74-2.80 (m, 2H), 2.49-2.74 (m, 2H), 1.63-1.74 (m, 1H), 1.31 (d, J=2.5 Hz, 6H), 0.96-1.20 (m, 4H)

LC-MS: m/z 454.6 (M+H)$^+$

Compound#444

(R)-8-cyclopropyl-3,3-dimethyl-6-(2,2,5-trideuterio-4-(3-methoxypropanoyl)-5-(perdeuteriopropan-2-yl)piperazin-1-yl)-3,4-dihydro-1H-pyrano[3,4-c]pyridine-5-carbonitrile (building block 9, step B)

$^1$H NMR (CHLOROFORM-d) □ δ 4.83 (s, 2H), 4.64 (d, J=13.8 Hz, 0.5H), 4.25-4.38 (m, 1H), 3.66-3.84 (m, 2.5H), 3.31-3.40 (m, 3H), 2.86-3.08 (m, 2H), 2.73-2.80 (m, 2H), 2.49-2.73 (m, 2H), 1.64-1.75 (m, 1H), 1.31 (d, J=2.3 Hz, 6H), 0.96-1.19 (m, 4H)
LC-MS: m/z 451.6 (M+H)+
Compound#451

(R)-8-cyclopropyl-6-(3-deuterio-3-(perdeuteriopropan-2-yl)-4-(3,3,3-trifluoropropanoyl)piperazin-1-yl)-3,3-dimethyl-3,4-dihydro-1H-pyrano[3,4-c]pyridine-5-carbonitrile (building block 9, step B)

1H NMR (CHLOROFORM-d) □ δ 4.83 (s, 2H), 4.32 (d, J=13.1 Hz, 0.5H), 4.19 (br. s., 2H), 3.64 (br. s., 1.5H), 3.32 (d, J=9.8 Hz, 2H), 2.94-3.05 (m, 2H), 2.77 (s, 2H), 1.66-1.77 (m, 1H), 1.32 (d, J=2.8 Hz, 6H), 0.97-1.19 (m, 4H)
LC-MS: m/z 473.6 (M+H)+
Compound#449

(R)-methyl 4-(4-(5-cyano-8-cyclopropyl-3,3-dimethyl-3,4-dihydro-1H-pyrano[3,4-c]pyridin-6-yl)-2-deuterio-2-(perdeuteriopropan-2-yl)piperazin-1-yl)-4-oxobutanoate (building block 9, step B)

1H NMR (CHLOROFORM-d) □ δ 4.83 (s, 2H), 4.62 (d, J=10.8 Hz, 0.5H), 4.31 (dd, J=12.7, 6.7 Hz, 1H), 4.11-4.24 (m, 1H), 3.78 (d, J=13.6 Hz, 0.5H), 3.70 (d, J=3.8 Hz, 3H), 3.45 (m., 0.5H), 2.88-3.11 (m, 2.5H), 2.76 (s, 2H), 2.60-2.74 (m, 4H), 1.65-1.76 (m, 1H), 1.32 (d, J=2.5 Hz, 6H), 0.99-1.17 (m, 4H)
LC-MS: m/z 477.6 (M+H)+
Compound#449

(R)-methyl 4-(4-(5-cyano-8-cyclopropyl-3,3-dimethyl-3,4-dihydro-1H-pyrano[3,4-c]pyridin-6-yl)-2,2,3,3,5,5,6-heptadeuterio-6-(perdeuteriopropan-2-yl)piperazin-1-yl)-4-oxobutanoate (building block 9, step B)

1H NMR (CHLOROFORM-d) □ δ 4.82 (s, 2H), 3.70 (d, J=3.5 Hz, 3H), 2.76 (s, 2H), 2.57-2.74 (m, 4H), 1.66-1.76 (m, 1H), 1.31 (d, J=2.5 Hz, 6H), 0.96-1.18 (m, 4H)
LC-MS: m/z 483.7 (M+H)+
Compound#452

(R)-8-cyclopropyl-6-(2,2,3,3,5,6,6-hepta deuterio-5-(perdeuteriopropan-2-yl)-4-(3,3,3-trifluoropropanoyl)piperazin-1-yl)-3,3-dimethyl-3,4-dihydro-1H-pyrano[3,4-c]pyridine-5-carbonitrile (building block 9, step B)

1H NMR (CHLOROFORM-d) □ δ 4.83 (s, 2H), 3.14-3.42 (m, 2H), 2.77 (s, 2H), 1.68-1.76 (m, 1H), 1.32 (d, J=2.8 Hz, 6H), 0.97-1.18 (m, 4H)
LC-MS: m/z 479.7 (M+H)+
Compound#476

(R)-8-cyclopropyl-3,3-dimethyl-6-(2,2,3,5,5-pentadeuterio-3-(1,1,1,3,3,3-hexadeuteriopropan-2-yl)-4-(3,3,3-trifluoropropanoyl)piperazin-1-yl)-3,4-dihydro-1H-pyrano[3,4-c]pyridine-5-carbonitrile (building block 11, step B)

1H NMR (CHLOROFORM-d) □ δ 4.75-4.93 (m, 2H), 4.10-4.27 (m, 1H), 3.22-3.47 (m, 2H), 2.90-3.07 (m, 1H), 2.77 (s, 2H), 1.72 (dt, J=8.0, 3.9 Hz, 1H), 1.32 (d, J=2.8 Hz, 6H), 0.98-1.20 (m, 4H)
LC-MS: m/z 477.6 (M+H)+
Compound#477

(R)-8-cyclopropyl-3,3-dimethyl-6-(2,2,3,5,5-pentadeuterio-3-(1,1,1,3,3,3-hexadeuteriopropan-2-yl)-4-(3,3,3-trifluoropropanoyl)piperazin-1-yl)-3,4-dihydro-1H-pyrano[3,4-c]pyridine-5-carbonitrile (building block 9, step B)

1H NMR (CHLOROFORM-d) □ δ 4.74-4.94 (m, 2H), 3.15-3.43 (m, 2H), 2.78 (s, 2H), 1.69-1.76 (m, 1H), 1.33 (d, J=2.8 Hz, 6H), 0.99-1.20 (m, 4H)
LC-MS: m/z 479.6 (M+H)+
Compound#442

8-cyclopropyl-6-((3R)-3-cyclopropyl-4-(3-hydroxybutanoyl)piperazin-1-yl)-3,3-dimethyl-3,4-dihydro-1H-pyrano[3,4-c]pyridine-5-carbonitrile (building block 2, step B)

$^1$H NMR (CHLOROFORM-d) δ 4.84 (s, 2H), 4.62-4.65 (m, 0.5H), 4.13-4.35 (m, 3H), 4.03 (d, J=8.3 Hz, 0.5H), 3.61-3.83 (m, 1H), 2.91-3.19 (m, 3H), 2.78 (s, 2H), 2.30-2.58 (m, 2H), 1.67-1.77 (m, 1H), 1.29-1.35 (m, 7H), 1.19-1.27 (m, 3H), 1.13 (m, 2H), 0.98-1.07 (m, 2H), 0.38-0.68 (m, 4H)
LC-MS: m/z 439.0 (M+H)+
Compound#445

(R)-8-cyclopropyl-6-(3-isopropyl-4-(2-(methylthio)acetyl)piperazin-1-yl)-3,3-dimethyl-3,4-dihydro-1H-pyrano[3,4-c]pyridine-5-carbonitrile (step B)

$^1$H NMR (CHLOROFORM-d) δ 4.76-4.90 (m, 2H), 4.58-4.61 (m, 0.5H), 4.28-4.43 (m, 1.5H), 4.20 (d, J=11.5 Hz, 1H), 3.73 (d, J=13.6 Hz, 0.5H), 3.27-3.53 (m, 3H), 3.07-3.13 (m, 1H), 2.89-3.04 (m, 1H), 2.69-2.84 (m, 2H), 2.05-2.33 (m, 4H), 1.65-1.73 (m, 1H), 1.32 (d, J=2.5 Hz, 6H), 0.95-1.19 (m, 7H), 0.77-0.93 (m, 3H)
LC-MS: m/z 443.5 (M+H)+
Compound#446

(R)-8-cyclopropyl-6-(3-isopropyl-4-(2-(methylsulfonyl)acetyl)piperazin-1-yl)-3,3-dimethyl-3,4-dihydro-1H-pyrano[3,4-c]pyridine-5-carbonitrile (step B)

$^1$H NMR (CHLOROFORM-d) δ 4.76-4.90 (m, 2H), 4.62-4.65 (m, 0.5H), 4.27-4.45 (m, 2H), 4.12-4.26 (m, 2H), 3.81-4.10 (m, 1H), 3.51-3.66 (m, 1H), 3.11-3.20 (m, 4H), 2.99-3.11 (m, 1.5H), 2.68-2.86 (m, 2H), 2.10-2.37 (m, 1H), 1.71 (dddd, J=10.0, 7.6, 5.1, 2.4 Hz, 1H), 1.32 (d, J=3.0 Hz, 6H), 0.97-1.18 (m, 7H), 0.87 (dd, J=6.7, 3.6 Hz, 3H)
LC-MS: m/z 475.6 (M+H)+
Compound#447

(R)-8-cyclopropyl-6-(4-(3-(furan-2-yl)propanoyl)-3-isopropylpiperazin-1-yl)-3,3-dimethyl-3,4-dihydro-1H-pyrano[3,4-c]pyridine-5-carbonitrile (step B)

1H NMR (400 MHz, CHLOROFORM-d) δ □ 7.31 (s, 1H), 6.28 (d, J=3.01 Hz, 1H), 6.04 (d, J=3.0 Hz, 1H), 4.82 (s, 2H), 4.64 (m, 0.5H), 4.40 (d, J=10.3 Hz, 0.5H), 4.30 (t, J=13.9 Hz, 1H) 4.09-4.19 (m, 1H), 3.73 (d, J=13.5 Hz, 0.5H), 3.35-3.51 (m, 1H), 2.97-3.07 (m, 2.5H), 2.88-2.97 (m, 1H), 2.76 (S, 2H), 2.68-2.74 (m, 1H), 2.09 (m, 1H), 1.70 (tt, J=7.9, 4.1 Hz, 2H), 1.31 (d, J=2.2 Hz, 6H), 0.95-1.18 (m, 6H), 0.86 (d, J=6.8 Hz, 2H), 0.79 (d, J=6.8 Hz, 2H)
LC-MS: m/z 477.3 (M+H)+

Compound#453

8-Cyclopropyl-6-((3R)-3-isopropyl-4-(2-(methylsulfinyl)acetyl)piperazin-1-yl)-3,3-dimethyl-3,4-dihydro-1H-pyrano[3,4-c]pyridine-5-carbonitrile (step B)

1H NMR (400 MHz, CHLOROFORM-d) δ ☐ 4.72-4.90 (m, 2H), 4.50-4.67 (m, 0.5H), 4.26-4.45 (m, 1.5H), 4.04-4.25 (m, 1.5H), 3.71-3.85 (m, 0.5H), 3.58-3.71 (m, 0.5H), 3.40-3.58 (m, 0.5H), 2.92-3.17 (m, 3H), 2.71-2.85 (m, 5H), 2.22-2.37 (m, 1H), 2.13 (dd, J=10.8, 5.2 Hz, 1H), 1.61-1.77 (m, 1H), 1.27-1.41 (m, 6H), 1.05-1.16 (m, 3H), 0.95-1.05 (m, 4H), 0.75-0.94 (m, 3H)
LC-MS: m/z 459.3 (M+H)+

Compound#454

(1R,2R)-Methyl 2-((R)-4-(5-cyano-8-cyclopropyl-3,3-dimethyl-3,4-dihydro-1H-pyrano[3,4-c]pyridin-6-yl)-2-isopropylpiperazin-1-carbonyl)cyclopropanecarboxylate) (step B)

1H NMR (CHLOROFORM-d) ☐ δ 4.83 (s, 2H), 4.57 (d, J=10.0 Hz, 0.5H), 4.27-4.40 (m, 1.5H), 4.13-4.25 (m, 1.5H), 3.76-3.84 (m, 0.5H), 3.67-3.76 (m, 3H), 3.52 (d, J=1.8 Hz, 0.5H), 2.93-3.18 (m, 2.5H), 2.77 (s, 2H), 2.31-2.40 (m, 1H), 2.17-2.27 (m, 1H), 1.65-1.76 (m, 1H), 1.43-1.50 (m, 1H), 1.27-1.37 (m, 6H), 1.08-1.19 (m, 2H), 0.97-1.06 (m, 5H), 0.84-0.94 (m, 2H), 0.80 (dd, J=6.7, 4.6 Hz, 1H)
LC-MS: m/z 481.6 (M+H)

Compound#455

(R)-6-(4-(2-(1,3,4-oxadiazol-2-yl)acetyl)-3-isopropylpiperazin-1-yl)-8-cyclopropyl-3,3-dimethyl-3,4-dihydro-1H-pyrano[3,4-c]pyridine-5-carbonitrile (step B)

1H NMR (400 MHz, CHLOROFORM-d) δ ☐ 8.44 (s, 1H), 4.73-4.93 (m, 2H), 4.60 (d, J=11.8 Hz, 0.5H), 4.26-4.41 (m, 1.5H), 3.96-4.25 (m, 3H), 3.78 (d, J=13.5 Hz, 0.5H), 3.43-3.61 (m, 1H), 2.89-3.17 (m, 2.5H), 2.77 (s, 2H), 2.06-2.25 (m, 1H), 1.63-1.77 (m, 1H), 1.32 (d, J=3.0 Hz, 6H), 0.95-1.11 (m, 6H), 0.72-0.95 (m, 4H)
LC-MS: m/z 465.5 (M+H)+

Compound#459

(R)-8-cyclopropyl-6-(4-(3-ethoxypropanoyl)-3-isopropylpiperazin-1-yl)-3,3-dimethyl-3,4-dihydro-1H-pyrano[3,4-c]pyridine-5-carbonitrile (step B)

1H NMR (CHLOROFORM-d) ☐ δ 4.84 (s, 2H), 4.66 (d, J=9.8 Hz, 0.5H), 4.41 (d, J=10.5 Hz, 0.5H), 4.34 (d, J=13.3 Hz, 1H), 4.11-4.23 (m, 1H), 3.70-3.89 (m, 3H), 3.48-3.63 (m, 3H), 3.28-3.48 (m, 1H), 2.92-3.13 (m, 2H), 2.82 (s, 3H), 2.74-2.80 (m, 2H), 2.56-2.73 (m, 2H), 2.19 (dt, 2H), 1.71 (dt, J=7.8, 3.6 Hz, 1H), 1.33 (d, J=2.0 Hz, 6H), 1.24-1.30 (m, 3H), 0.97-1.08 (m, 4H), 0.79-0.92 (m, 4H)
LC-MS: m/z 455.6 (M+H)+

Compound#464

6-(4-(cyclopropanecarbonyl)-3-(difluoromethyl)piperazin-1-yl)-8-cyclopropyl-3,3-dimethyl-3,4-dihydro-1H-pyrano[3,4-c]pyridine-5-carbonitrile (building block 7, step B)

1H NMR (CHLOROFORM-d) δ ☐5.91-6.31 (m, 1H), 4.90-5.04 (m, 0.5H), 4.76-4.90 (m, 2H), 4.68 (d, J=13.3 Hz, 0.5H), 4.16-4.34 (m, 1.5H), 4.04-4.16 (m, 1H), 3.91 (d, J=13.3 Hz, 0.5H), 3.55-3.82 (m, 2.5H), 3.28-3.45 (m, 3.5H), 3.01-3.22 (m, 1.5H), 2.89-3.01 (m, 0.5H), 2.68-2.89 (m, 3H), 2.56-2.68 (m, 1H), 1.67-1.76 (m, 1H), 1.32 (d, J=4.3 Hz, 6H), 1.09-1.18 (m, 2H), 0.96-1.09 (m, 2H)
LC-MS: m/z 449.2 (M+H)+

Compound#465

(1R,2R)-ethyl 2-((R)-4-(5-cyano-8-cyclopropyl-3,3-dimethyl-3,4-dihydro-1H-pyrano[3,4-c]pyridin-6-yl)-2-isopropylpiperazin-1-carbonyl)cyclopropanecarboxylate (step B)

1H NMR (CHLOROFORM-d) ☐ δ 4.77-4.89 (m, 2H), 4.57 (d, J=10.3 Hz, 0.5H), 4.28-4.41 (m, 1.5H), 4.14-4.22 (m, 3H), 3.95-4.12 (m, 0.5H), 3.77 (t, J=10.2 Hz, 0.5H), 3.44-3.60 (m, 1H), 3.05-3.14 (m, 1H), 2.96-3.05 (m, 0.5H), 2.77 (s, 2H), 2.08-2.38 (m, 3H), 1.67-1.77 (m, 1H), 1.46 (ddd, J=8.9, 5.9, 3.3 Hz, 1H), 1.35-1.43 (m, 1H), 1.27-1.34 (m, 9H), 1.09-1.18 (m, 2H), 0.95-1.06 (m, 5H), 0.76-0.93 (m, 4H)
LC-MS: m/z 495.6 (M+H)+

Compound#466

(R)-8-cyclopropyl-6-(3-cyclopropyl-4-(2-(oxetan-3-yl)acetyl)piperazin-1-yl)-3,3-dimethyl-3,4-dihydro-1H-pyrano[3,4-c]pyridine-5-carbonitrile (building block 10, step B)

1H NMR (400 MHz, CDCl3) δ=4.91 (ddd, J=8.0, 6.3, 1.9 Hz, 2H), 4.83 (s, 2H), 4.40 (dd, J=7.9, 4.5 Hz, 2H), 4.24 (d, J=12.8 Hz, 1H), 4.16 (d, J=7.2 Hz, 1H), 3.97 (s, 1H), 3.71 (t, J=10.0 Hz, 2H), 3.41 (dt, J=14.0, 6.3 Hz, 1H), 3.32-2.87 (m, 3H), 2.79 (d, J=11.3 Hz, 4H), 1.77-1.57 (m, 2H), 1.38-1.28 (m, 6H), 1.14 (dd, J=7.1, 3.8 Hz, 2H), 1.02 (ddd, J=9.4, 6.6, 2.8 Hz, 2H), 0.58 (s, 1H), 0.40 (d, J=4.9 Hz, 2H).
LC-MS: m/z 451.6 (M+H)+

Compound#467

(R)—N-butyl-5-(4-(5-cyano-8-cyclopropyl-3,3-dimethyl-3,4-dihydro-1H-pyrano[3,4-c]pyridin-6-yl)-2-isopropylpiperazin-1-yl)-2,5-dioxopentanamide (step B)

1H NMR (400 MHz, CHLOROFORM-d) δ 6.81-6.95 (m, 1H), 4.83 (s, 2H), 4.56 (m, 0.5H), 4.24-4.38 (m, 1.5H), 4.07-4.24 (m, 1H), 3.77 (d, J=13.3 Hz, 0.5H), 3.39-3.56 (m, 1H), 3.30 (qd, J=6.8, 3.6 Hz, 2H), 3.15-3.26 (m, 2H), 2.98-3.10 (m, 1.5H), 2.91-2.98 (m, 1H), 2.70-2.80 (m, 4H), 2.00-2.15 (m, 1H), 1.65-1.76 (m, 1H), 1.48-1.57 (m, 2H), 1.31-1.42 (m, 6H), 1.25-1.31 (m, 3H), 0.88-1.05 (m, 10H), 0.80 (d, J=6.8 Hz, 2H)
LC-MS: m/z 538.5 (M+H)+

Compound#469

8-cyclopropyl-6-(4-(3-methoxypropanoyl)-3-(2,2,2-trifluoroethyl)piperazin-1-yl)-3,3-dimethyl-3,4-dihydro-1H-pyrano[3,4-c]pyridine-5-carbonitrile (building block 4, step B)

1H NMR (CHLOROFORM-d) δ 5.24 (br. s., 0.5H), 4.69-4.73 (m, 0.5H), 4.51 (br, 0.5H), 3.96-4.15 (m, 2H), 3.88 (d, J=13.8 Hz, 0.5H), 3.64-3.83 (m, 2H), 3.46-3.58 (m, 0.5H), 2.88-3.17 (m, 2.5H), 2.56-2.80 (m, 5H), 1.73 (br. s., 1H), 1.33 (s, 6H), 1.02-1.16 (m, 4H)
LC-MS: m/z 481.6 (M+H)+

Compound#470

8-cyclopropyl-3,3-dimethyl-6-(3-(2,2,2-trifluoroethyl)-4-(3,3,3-trifluoropropanoyl)piperazin-1-yl)-3,4-dihydro-1H-pyrano[3,4-c]pyridine-5-carbonitrile (building block 4, step B)

1H NMR (CHLOROFORM-d) δ 5.28 (br. s., 0.5H), 4.71-4.75 (m, 0.5H), 4.32 (br, 0.5H), 3.95-4.16 (m, 2H), 3.75 (d, J=13.3 Hz, 0.5H), 3.55-3.70 (m, 0.5H), 3.16-3.35 (m, 2H), 2.88-3.16 (m, 3H), 2.66-2.86 (m, 3H), 1.73 (dd, J=8.4, 3.9 Hz, 1H), 1.32-1.39 (m, 6H), 1.03-1.17 (m, 4H)
LC-MS: m/z 505.5 (M+H)+

Compound#473

8-cyclopropyl-6-((3R)-3-isopropyl-4-(2-(oxetan-2-yl)acetyl)piperazin-1-yl)-3,3-dimethyl-3,4-dihydro-1H-pyrano[3,4-c]pyridine-5-carbonitrile (building block 11, step B)

1H NMR (400 MHz, CHLOROFORM-d) δ □ 5.20-5.31 (m, 1H), 4.78-4.90 (m, 2H), 4.67-4.78 (m, 1H), 4.48-4.62 (m, 0.5H), 4.29-4.47 (m, 1.5H), 4.08-4.26 (m, 1H), 3.84 (d, J=15.6 Hz, 0.5H), 3.39-3.61 (m, 1H), 2.91-3.10 (m, 3.5H), 2.81-2.91 (m, 1.5H), 2.72-2.81 (m, 2.5H), 2.40-2.64 (m, 1H), 1.91-2.15 (m, 2H), 1.72 (m, 1H), 1.33 (m, 6H), 0.96-1.17 (m, 6H), 0.76-0.96 (m, 4H)
LC-MS: m/z 453.3 (M+H)+

Compound#461

(R)-6-(4-(cyclopropanecarbonyl)-3-cyclopropylpiperazin-1-yl)-8-cyclopropyl-3,3-dimethyl-3,4-dihydro-1H-pyrano[3,4-c]pyridine-5-carbonitrile (building block 2, step C)

1H NMR (CHLOROFORM-d) δ 4.84 (s, 2H), 3.49-4.54 (m, 5H), 2.99-3.17 (m, 2H), 2.78 (s, 2H), 1.66-1.78 (m, 2H), 1.32 (d, J=2.5 Hz, 6H), 1.11-1.19 (m, 2H), 0.89-1.09 (m, 6H), 0.72-0.82 (m, 2H), 0.61 (br. s., 1H), 0.34-0.54 (m, 3H)
LC-MS: m/z 421.4 (M+H)+

Compound#463

6-(4-(cyclopropanecarbonyl)-3-(difluoromethyl)piperazin-1-yl)-8-cyclopropyl-3,3-dimethyl-3,4-dihydro-1H-pyrano[3,4-c]pyridine-5-carbonitrile (building block 7, step C)

1H NMR (CHLOROFORM-d) □ δ □ 5.91-6.34 (m, 1H), 4.94 (d, J=15.6 Hz, 0.5H), 4.76-4.88 (m, 2H), 4.63 (d, J=13.6 Hz, 0.5H), 4.51 (br, 0.5H), 4.13-4.33 (m, 2H), 4.01-4.13 (m, 0.5H), 3.73 (t, J=11.0 Hz, 0.5H), 3.35 (d, J=13.8 Hz, 0.5H), 3.06-3.30 (m, 1.5H), 2.99 (t, J=12.0 Hz, 0.5H), 2.78 (s, 2H), 1.74-1.83 (m, 1H), 1.67-1.74 (m, 1H), 1.32 (d, J=4.3 Hz, 6H), 1.11-1.18 (m, 2H), 0.94-1.11 (m, 4H), 0.82-0.90 (m, 2H)
LC-MS: m/z 431.2 (M+H)+

Compound#468

(S)-ethyl 1-acetyl-4-(5-cyano-8-cyclopropyl-3,3-dimethyl-3,4-dihydro-1H-pyrano[3,4-c]pyridin-6-yl)piperazine-2-carboxylate (building block 6, step C)

1H NMR (CHLOROFORM-d) δ 5.24 (dd, J=4.1, 1.9 Hz, 0.5H), 4.77-4.91 (m, 2H), 4.67 (dt, J=13.4, 2.0 Hz, 1H), 4.42-4.50 (m, 0.5H), 4.11-4.27 (m, 2H), 4.01-4.10 (m, 0.5H), 3.69-3.90 (m, 1.5H), 3.19-3.45 (m, 1.5H), 2.95-3.11 (m, 1H), 2.68-2.84 (m, 2H), 2.05-2.32 (m, 3.5H), 1.66-1.75 (m, 1H), 1.31 (d, J=3.3 Hz, 6H), 1.12-1.23 (m, 5H), 0.97-1.07 (m, 2H)
LC-MS: m/z 427.5 (M+H)+

Compound#471

6-(4-(cyclopropanecarbonyl)-3-(2,2,2-trifluoroethyl)piperazin-1-yl)-8-cyclopropyl-3,3-dimethyl-3,4-dihydro-1H-pyrano[3,4-c]pyridine-5-carbonitrile (building block 4, step C)

1H NMR (CHLOROFORM-d) δ 5.20 (br. s., 0.5H), 4.85 (s, 2H), 4.64 (d, J=13.3 Hz, 1H), 4.19 (d, J=13.3 Hz, 0.5H), 3.94-4.14 (m, 2H), 3.32-3.64 (m, 2H), 2.92-3.22 (m, 3H), 2.68-2.88 (m, 3H), 2.54-2.68 (m, 0.5H), 1.69-1.74 (m, 1H), 1.33 (s, 6H), 1.11-1.15 (m, 2H), 1.01-1.08 (m, 4H), 0.84 (br. s., 2H)
LC-MS: m/z 463.3 (M+H)+

Compound#474

6-(4-(cyclopropanecarbonyl)-6-fluoro-3-methyl-1,4-diazepan-1-yl)-8-cyclopropyl-3,3-dimethyl-3,4-dihydro-1H-pyrano[3,4-c]pyridine-5-carbonitrile (building block 8, step C)

1H NMR (CHLOROFORM-d) δ 4.87 (s, 2H), 4.42-4.83 (m, 4H), 4.29 (m, 1H), 4.11 (br. s., 1H), 3.04-3.15 (m, 2H), 2.80 (s, 2H), 1.71-1.76 (m, 1H), 1.65-1.63 (m, 1H), 1.34 (s, 6H), 1.27 (m, 1.5H), 1.17-1.20 (m, 1.5H), 1.03-1.09 (m, 4H), 0.80-0.98 (m, 4H)
LC-MS: m/z 427.3 (M+H)+

Compound#475

6-(4-(cyclopropanecarbonyl)-5-methyl-1,4-diazepan-1-yl)-8-cyclopropyl-3,3-dimethyl-3,4-dihydro-1H-pyrano[3,4-c]pyridine-5-carbonitrile (building block 5, step C)

1H NMR (CHLOROFORM-d) δ 4.76-4.91 (m, 2H), 4.67 (dt, J=10.1, 6.5 Hz, 0.5H), 4.16-4.42 (m, 3.5H), 3.35-3.52 (m, 1H), 3.05-3.30 (m, 1.5H), 2.90-3.05 (m, 0.5H), 2.71-2.84 (m, 2H), 2.19-2.49 (m, 1H), 1.62-1.92 (m, 4H), 1.21-1.42 (m, 8H), 1.06-1.21 (m, 4H), 0.88-1.06 (m, 3H), 0.73-0.88 (m, 2H)
LC-MS: m/z 409.2 (M+H)+

Compound#443

(R)-8-cyclopropyl-6-(4-(4-hydroxybutanoyl)-3-isopropylpiperazin-1-yl)-3,3-dimethyl-3,4-dihydro-1H-pyrano[3,4-c]pyridine-5-carbonitrile (step B)

1H NMR (CHLOROFORM-d) δ 4.77-4.91 (m, 2H), 4.65 (d, J=10.8 Hz, 0.5H), 4.36-4.48 (m, 0.5H), 4.32 (dd, J=13.3, 1.8 Hz, 1H), 4.10-4.24 (m, 1H), 3.65-3.84 (m, 2.5H), 3.36-3.58 (m, 1H), 2.89-3.11 (m, 2.5H), 2.69-2.83 (m, 2H), 2.47-2.63 (m, 2H), 2.21-2.34 (m, 1H), 1.90-1.98 (m, 1H), 1.66-1.76 (m, 1H), 1.32 (d, J=2.8 Hz, 6H), 0.95-1.17 (m, 7H), 0.75-0.93 (m, 3H)
LC-MS: m/z 441.2 (M+H)+

Compound#460

(R)-8-cyclopropyl-6-(3-cyclopropyl-4-(3-hydroxypropanoyl)piperazin-1-yl)-3,3-dimethyl-3,4-dihydro-1H-pyrano[3,4-c]pyridine-5-carbonitrile 1H NMR (CHLOROFORM-d) δ 4.85 (s, 2H), 4.63-4.67 (m, 0.5H), 4.26 (d, J=12.8 Hz, 1H), 4.17 (dd, J=12.7, 2.1 Hz, 1H), 4.05 (d, J=9.0 Hz, 0.5H), 3.91 (br. s., 2H), 3.74 (br. s., 1H), 2.90-3.38 (m, 3H), 2.79 (s, 2H), 2.47-2.66 (m, 2H), 1.69-1.78 (m, 1H), 1.33-1.41 (m, 7H), 1.10-1.19 (m, 2H), 0.98-1.09 (m, 2H), 0.44-0.69 (m, 4H)

LC-MS: m/z 425.4 (M+H)⁺

Compound#457

(R)-isopropyl 4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate (step B)

¹H NMR (CHLOROFORM-d) δ 5.02 (dq, J=12.4, 6.2 Hz, 1H), 4.75-4.91 (m, 2H), 4.62 (d, J=11.3 Hz, 0.5H), 4.26-4.43 (m, 1.5H), 4.07-4.26 (m, 1H), 3.79 (d, J=13.6 Hz, 0.5H), 3.38-3.60 (m, 1H), 2.91-3.13 (m, 2.5H), 2.71-2.81 (m, 2H), 2.56-2.71 (m, 4H), 2.07-2.39 (m, 1H), 1.66-1.77 (m, 1H), 1.31 (d, J=2.5 Hz, 6H), 1.21-1.27 (m, 6H), 0.97-1.18 (m, 7H), 0.74-0.94 (m, 3H)

LC-MS: m/z 497.3 (M+H)⁺

Compound#458

(R)-2-hydroxyethyl 4-(4-(5-cyano-8-cyclopropyl-3,3-dimethyl-3,4-dihydro-1H-pyrano[3,4-c]pyridin-6-yl)-2-isopropylpiperazin-1-yl)-4-oxobutanoate (step B)

¹H NMR (CHLOROFORM-d) δ 4.76-4.90 (m, 2H), 4.59 (d, J=10.8 Hz, 0.5H), 4.09-4.38 (m, 4.5H), 3.68-3.90 (m, 2.5H), 3.36-3.60 (m, 1H), 2.89-3.15 (m, 2.5H), 2.63-2.83 (m, 6H), 2.07-2.36 (m, 1H), 1.67-1.74 (m, 1H), 1.31 (d, J=2.5 Hz, 6H), 0.95-1.16 (m, 7H), 0.86-0.94 (m, 1.5H), 0.80 (d, J=6.8 Hz, 1.5H)

LC-MS: m/z 449.7 (M+H)⁺

Compound#440

(R)-methyl 3-(4-(5-cyano-8-cyclopropyl-3,3-dimethyl-3,4-dihydro-1H-pyrano[3,4-c]pyridin-6-yl)-2-cyclopropylpiperazin-1-yl)-3-oxopropanoate (building block 2, step C)

¹H NMR (CHLOROFORM-d) δ 4.83 (s, 2H), 4.62-4.65 (m, 0.5H), 4.26 (d, J=13.1 Hz, 1H), 4.16 (d, J=12.5 Hz, 1H), 4.03 (d, J=9.3 Hz, 0.5H), 3.71-3.85 (m, 3.5H), 3.60-3.70 (m, 0.5H), 2.93-3.58 (m, 5H), 2.78 (s, 2H), 1.66-1.75 (m, 1H), 1.36-1.44 (m, 1H), 1.32 (d, J=3.0 Hz, 6H), 1.13 (t, J=3.6 Hz, 2H), 0.97-1.07 (m, 2H), 0.31-0.64 (m, 4H)

LC-MS: m/z 453.2 (M+H)⁺

Example 21

Procedures for 6 and 7-Piperidinopyridine Core

Core Synthesis 1:

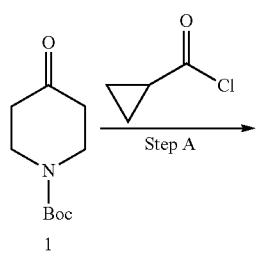

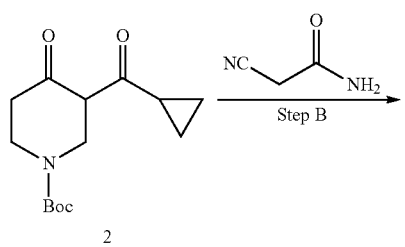

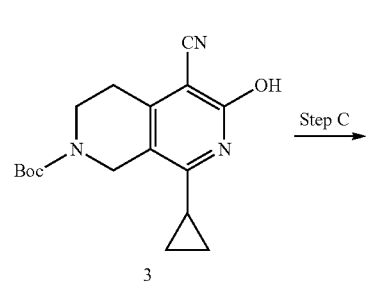

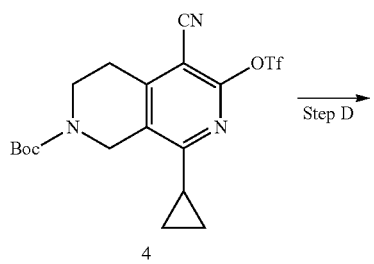

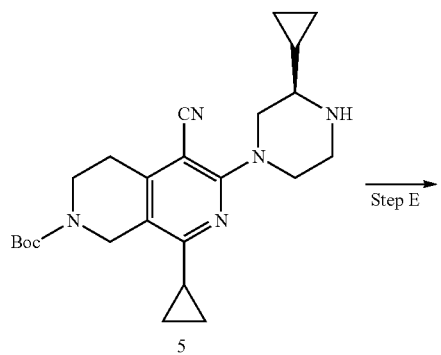

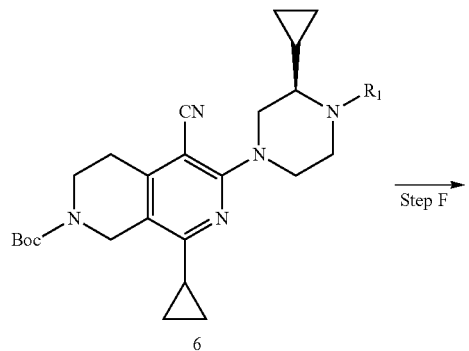

-continued

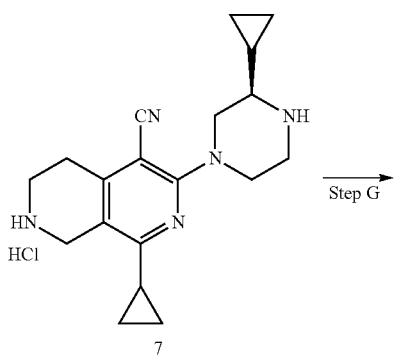

7

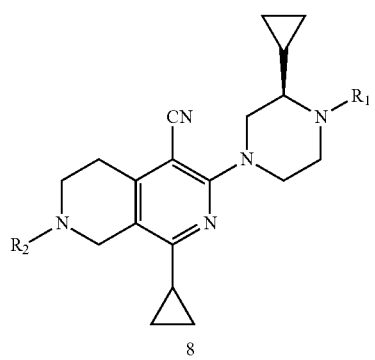

8

Step A: tert-butyl 3-(cyclopropanecarbonyl)-4-oxopiperidine-1-carboxylate

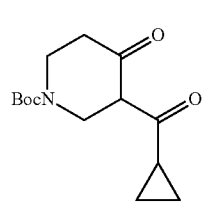 [SMILES: CC(C)(C)OC(=O)N1CCC(=O)C(C(=O)C2CC2)C1]

A 500 mL three-neck round bottom flask equipped with a stirring bar was charged with tert-butyl 4-oxopiperidine-1-carboxylate (9.3 g, 46.8 mmol) and 120 mL of dry toluene. The solution was purged with nitrogen and cooled to 0° C. With stirring, a solution of LDA (2M soln. in THF/n-heptane, 24.5 mL, 15.6 mmol) was added dropwise, and the reaction mixture was allowed to continue stir for 5 min at 0° C. before cyclopropanecarbonyl chloride (2.8 mL, 31.2 mmol) was added with vigorous stirring. After stirring at 0° C. for additional 20 min, the reaction mixture was quenched with 1N HCl until PH<7. After partitioning between H$_2$O and methylene chloride, the combined organic layer was then washed with brine, dried over anhy. Na$_2$SO$_4$ and concentrated in vacuo. Flash column chromatography (10% ethyl acetate/petroleum ether) afforded 9 g of title compound as yellowish oil, which was directly used for the next step without further purification. LC-MS: m/z 268.3 (M+H).

Step B: tert-butyl 5-cyano-8-cyclopropyl-6-hydroxy-3,4-dihydro-2,7-naphthyridine-2(1H)-carboxylate

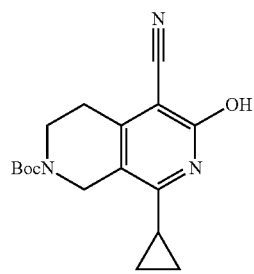 [SMILES: CC(C)(C)OC(=O)N1CCc2c(C#N)c(O)nc(C3CC3)c2C1]

To a solution of tert-butyl 3-(cyclopropanecarbonyl)-4-oxopiperidine-1-carboxylate (8.2 g, 30.6 mmol) and 2-cyanoacetamide (4.1 g, 49.0 mmol) in 70 mL of EtOH was added diethylamine (2.1 mL, 20.4 mmol). The reaction mixture was stirred at room temperature for 72 hours until LC-MS indicated the complete formation of product. The reaction mixture was then heated to reflux temperature, during this period; enough EtOH was added to make a clear solution. After cooling back to room temperature, the product was precipitated out from EtOH solution and 5.3 g of the title compound was obtained as a white solid after vacuum filtration and air-dried, which was directly used for the next step without further purification. LC-MS: m/z 316.5 (M+H).

Step C: tert-butyl 5-cyano-8-cyclopropyl-6-hydroxy-3,4-dihydro-2,7-naphthyridine-2(1H)-carboxylate

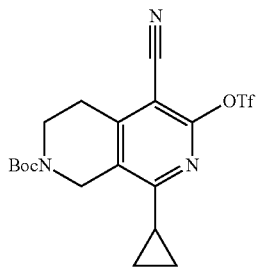 [SMILES: CC(C)(C)OC(=O)N1CCc2c(C#N)c(OS(=O)(=O)C(F)(F)F)nc(C3CC3)c2C1]

A 250 mL round bottom flask was charged with 8-cyclopropyl-6-hydroxy-3,3-dimethyl-3,4-dihydro-1H-pyrano[3,4-c]pyridine-5-carbonitrile (4.8 g, 15.2 mmol), DMAP (185 mg, 1.52 mmol), triethylamine (2.74 mL, 19.7 mmol) and 150 mL of methylene chloride. After the reaction mixture was cooled to 0° C. in a dry ice-acetone bath, trifluoromethanesulfonic anhydride (3.3 mL, 19.7 mmol) was added dropwise via a syringe. The resulting mixture was stirred at 0° C. for 30 min before it was allowed to warm up to room temperature and stirred for additional 2 hours. After TLC indicated the complete conversion of starting material to the product, the reaction mixture was concentrated in vacuo and purified by flash column chromatography (1:10 ethyl acetate/petroleum ether) to give 6.5 g of the title compound as an off-white solid. 1H NMR (CHLOROFORM-d) δ 4.74 (br. s., 2H), 3.72 (t, J=5.9 Hz, 2H), 3.04 (t, J=5.8 Hz, 2H), 1.96 (br. s., 1H), 1.51 (s, 9H), 1.16-1.28 (m, 4H)

Step D: (R)-tert-butyl 5-cyano-8-cyclopropyl-6-(3-cyclopropylpiperazin-1-yl)-3,4-dihydro-2,7-naphthyridine-2(1H)-carboxylate

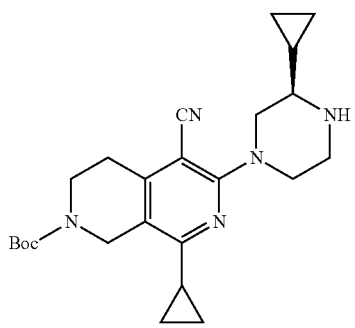 [SMILES: CC(C)(C)OC(=O)N1CCc2c(C#N)c(N3CCN[C@H](C4CC4)C3)nc(C3CC3)c2C1]

A sealed tube was charged with above tert-butyl 5-cyano-8-cyclopropyl-6-hydroxy-3,4-dihydro-2,7-naphthyridine-2(1H)-carboxylate (715 mg, 1.60 mmol), (R)-2-cyclopropylpiperazine (202 mg, 1.60 mmol), and diethylamine (0.24 mL, 1.73 mmol) in 2 mL of CH3CN. The reaction mixture was heated at reflux overnight. After it was concentrated under reduced pressure, the reaction mixture was purified by flash column chromatography (1:10 methanol/methylene chloride) to give 610 mg of the title compound. MS (ES) M+H expected 424.5, found 424.5. 1H NMR (CHLOROFORM-d) δ 4.62 (br. s., 2H), 4.25 (d, J=13.1 Hz, 1H), 4.05-4.15 (m, 1H), 3.58-3.72 (m, 2H), 3.24-3.38 (m, 2H), 3.16 (dd, J=13.3, 10.5 Hz, 1H), 3.00 (td, J=12.0, 3.1 Hz, 1H), 2.91 (t, J=5.5 Hz, 2H), 2.26 (td, J=9.8, 2.8 Hz, 1H), 1.88 (br. s., 1H), 1.50 (s, 9H), 1.08-1.16 (m, 2H), 1.04 (d, J=6.5 Hz, 2H), 0.60-0.67 (m, 2H), 0.47-0.57 (m, 1H), 0.36-0.46 (m, 1H)

Step E1: (R)-tert-butyl 5-cyano-8-cyclopropyl-6-(3-cyclopropyl-4-(3-methoxypropanoyl)piperazin-1-yl)-3,4-dihydro-2,7-naphthyridine-2(1H)-carboxylate

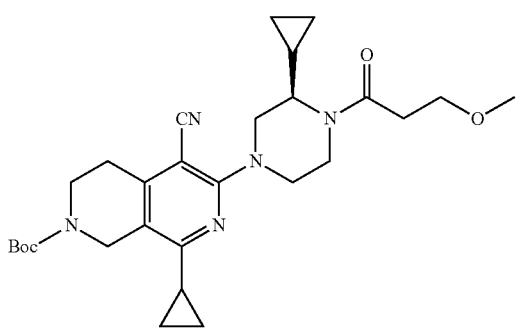 [SMILES: COCCC(=O)N1CCN(c2nc(C3CC3)c3c(c2C#N)CCN(C(=O)OC(C)(C)C)C3)C[C@H]1C1CC1]

To a solution of (R)-tert-butyl 5-cyano-8-cyclopropyl-6-(3-cyclopropylpiperazin-1-yl)-3,4-dihydro-2,7-naphthyridine-2(1H)-carboxylate (30 mg, 0.08 mmol), 3-methoxypropanoic acid (4.23 g, 10 mmol) and DIPEA (2.6 g, 20 mmol) in methylene chloride (30 mL) was added HATU (4.18 g, 11 mmol). The reaction mixture was stirred at room temperature for 2 h. The organic phase was washed with 1N HCl aqueous solution (1×20 mL), satd. NaHCO3 and brine, dried over anhy. Na2SO4, and concentrated in vacuum. The crude product was purified by preparative HPLC (PE:EA/80:20) to afford 4.5 g of the title compound as a white solid. MS (ES) M+H expected 510.6, found 510.5, 1H NMR (CHLOROFORM-d) δ 4.55-4.73 (m, 2H), 4.27 (d, J=12.8 Hz, 1H), 4.17 (d, J=12.5 Hz, 1H), 4.06 (d, J=7.5 Hz, 0.5H), 3.83 (d, J=12.3 Hz, 0.5H), 3.57-3.77 (m, 5H), 3.38 (s, 3H), 3.20-3.33 (m, 1H), 3.08 (d, J=12.8 Hz, 1H), 2.89-3.04 (m, 3H), 2.69 (br. s., 1H), 2.64 (br. s., 1H), 1.90 (br. s., 1H), 1.71 (br. s., 1H), 1.47-1.57 (m, 9H), 1.10-1.19 (m, 2H), 1.05 (d, J=7.0 Hz, 2H), 0.58 (br. s., 1H), 0.51 (br. s., 1H), 0.34-0.47 (m, 2H)

Step E2: (R)-tert-butyl 5-cyano-6-(4-(cyclopropanecarbonyl)-3-cyclopropylpiperazin-1-yl)-8-cyclopropyl-3,4-dihydro-2,7-naphthyridine-2(1H)-carboxylate

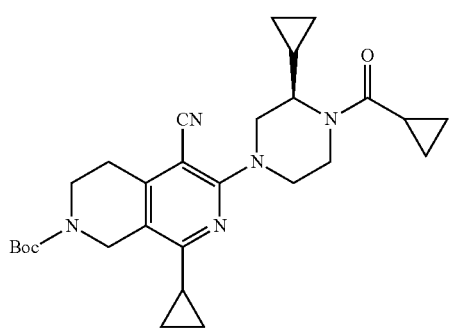 [SMILES: CC(C)(C)OC(=O)N1CCc2c(C#N)c(N3CCN(C(=O)C4CC4)[C@H](C4CC4)C3)nc(C3CC3)c2C1]

To a solution of (R)-tert-butyl 5-cyano-8-cyclopropyl-6-(3-cyclopropylpiperazin-1-yl)-3,4-dihydro-2,7-naphthyridine-2(1H)-carboxylate (4.23 g, 10 mmol) and DIPEA (2.6 g, 20 mmol) in methylene chloride (30 mL) was added cyclopropanecarbonyl chloride (1.76 g, 15 mmol). The reaction mixture was stirred at room temperature for 0.5 h. The organic phase was washed with 1N HCl aqueous solution (1×20 mL), satd. NaHCO3 and brine, dried over anhy. Na2SO4, and concentrated in vacuo. The crude product was purified by preparative HPLC (PE:EA/80:20) to afford 4.1 g of the title compound as a white solid. MS (ES) M+H expected 492.6, found 492.5.1H NMR (CHLOROFORM-d) δ 4.55-4.73 (m, 2H), 4.28 (d, J=12.5 Hz, 1H), 4.18 (d, J=12.3 Hz, 1H), 4.02 (br. s., 1H), 3.59-3.72 (m, 3H), 3.36-3.58 (m, 0.5H), 3.16 (br. s., 1.5H), 3.00 (br. s., 1H), 2.93 (t, J=5.6 Hz, 2H), 1.89 (br. s., 1H), 1.65-1.77 (m, 1H), 1.44-1.55 (m, 9H), 1.14 (br. s., 2H), 0.95-1.09 (m, 4H), 0.85-0.95 (m, 1H), 0.70-0.83 (m, 2H), 0.60 (br. s., 1H), 0.31-0.54 (m, 3H)

(R)-tert-butyl 5-cyano-8-cyclopropyl-6-(3-cyclopropyl-4-(3,3,3-trifluoropropanoyl)piperazin-1-yl)-3,4-dihydro-2,7-naphthyridine-2(1H)-carboxylate

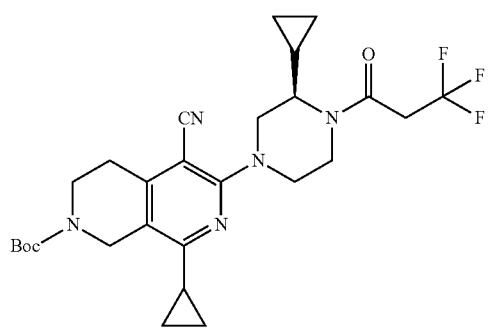 [SMILES: CC(C)(C)OC(=O)N1CCc2c(C#N)c(N3CCN(C(=O)CC(F)(F)F)[C@H](C4CC4)C3)nc(C3CC3)c2C1]

The title compound was prepared from 3,3,3-trifluoropropanoic acid using method E1. MS (ES) M+H expected 534.6, found 534.6.1H NMR (CHLOROFORM-d) δ 4.54-4.73 (m, 2H), 4.26 (d, J=12.8 Hz, 1H), 4.17 (d, J=12.5 Hz, 1H), 4.06 (d, J=8.0 Hz, 1H), 3.75-3.87 (m, 1H), 3.57-3.75 (m, 2.5H), 3.29 (q, J=9.3 Hz, 2H), 3.07 (d, J=11.8 Hz, 1.5H), 2.86-3.02 (m, 3H), 1.89 (br. s., 1H), 1.46-1.56 (m, 9H), 1.36-1.44 (m, 1H), 1.13 (br. s., 2H), 1.05 (d, J=6.8 Hz, 2H), 0.60 (br. s., 1H), 0.52 (br. s., 1H), 0.36-0.48 (m, 2H)

(R)-tert-butyl 5-cyano-8-cyclopropyl-6-(3-cyclopropyl-4-(3-hydroxypropanoyl)piperazin-1-yl)-3,4-dihydro-2,7-naphthyridine-2(1H)-carboxylate

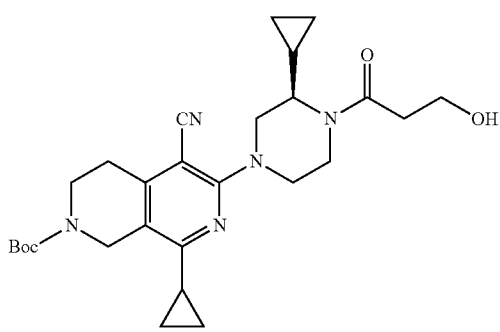 [SMILES: CC(C)(C)OC(=O)N1CCc2c(C#N)c(N3CCN(C(=O)CCO)[C@H](C4CC4)C3)nc(C3CC3)c2C1]

The title compound was prepared from sodium 3-hydroxypropanoate using method E1. LC-MS: m/z 496.6 (M+H).

Step F1: (R)-1-cyclopropyl-3-(3-cyclopropyl-4-(3-methoxypropanoyl)piperazin-1-yl)-5,6,7,8-tetrahydro-2,7-naphthyridine-4-carbonitrile (HCl salt)

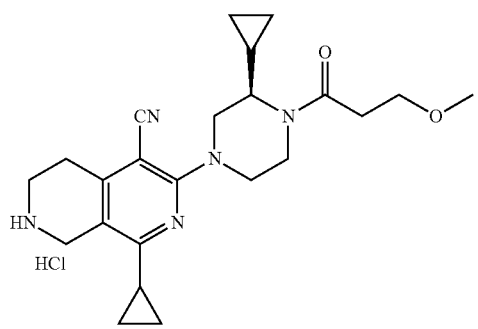 [SMILES: COCCC(=O)N1CCN(c2nc(C3CC3)c3c(c2C#N)CCNC3)C[C@H]1C1CC1 ; Cl]

To a solution of (R)-tert-butyl 5-cyano-8-cyclopropyl-6-(3-cyclopropyl-4-(3-methoxypropanoyl)piperazin-1-yl)-3,4-dihydro-2,7-naphthyridine-2(1H)-carboxylate (2.55 g 5 mmol) in MeOH (10 mL) was added 1N HCl/MeOH solution (50 mL). The mixture was stirred at room temperature until the reaction was complete. Solvent was removed in vacuo to give the crude product as a light-yellow oil (2.3 g), which was used in the next step without further purification. LC-MS: m/z 410.6 (M+H).

(R)-3-(4-(cyclopropanecarbonyl)-3-cyclopropylpiperazin-1-yl)-1-cyclopropyl-5,6,7,8-tetrahydro-2,7-naphthyridine-4-carbonitrile (HCl salt)

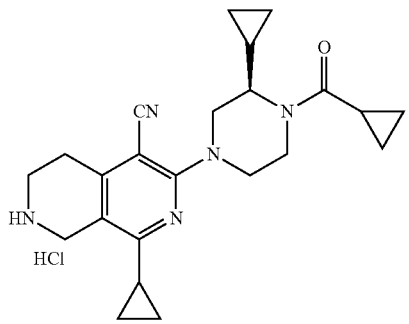 [SMILES: N#Cc1c(N2CCN(C(=O)C3CC3)[C@H](C3CC3)C2)nc(C2CC2)c2c1CCNC2 ; Cl]

The title compound was prepared from (R)-tert-butyl 5-cyano-6-(4-(cyclopropanecarbonyl)-3-cyclopropylpiperazin-1-yl)-8-cyclopropyl-3,4-dihydro-2,7-naphthyridine-2(1H)-carboxylate using method F1. LC-MS: m/z 392.6 (M+H).

(R)-1-cyclopropyl-3-(3-cyclopropyl-4-(3,3,3-trifluoropropanoyl)piperazin-1-yl)-5,6,7,8-tetrahydro-2,7-naphthyridine-4-carbonitrile (HCl salt)

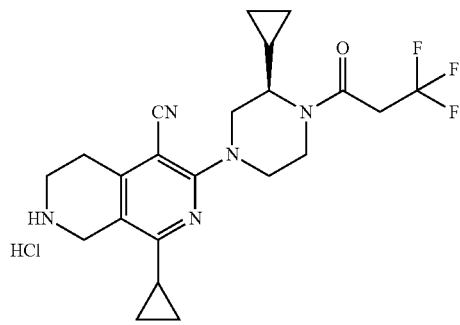 [SMILES: Cl ; N#Cc1c(N2CCN(C(=O)CC(F)(F)F)[C@H](C3CC3)C2)nc(C2CC2)c2c1CCNC2]

The title compound was prepared from (R)-tert-butyl 5-cyano-8-cyclopropyl-6-(3-cyclopropyl-4-(3,3,3-trifluoropropanoyl)piperazin-1-yl)-3,4-dihydro-2,7-naphthyridine-2 (1H)-carboxylate using method F1. LC-MS: m/z 434.5 (M+H).

(R)-1-cyclopropyl-3-(3-cyclopropyl-4-(3-hydroxypropanoyl)piperazin-1-yl)-5,6,7,8-tetrahydro-2,7-naphthyridine-4-carbonitrile (HCl salt)

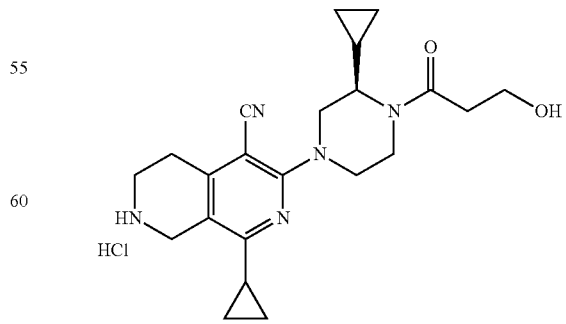

The title compound was prepared from (R)-tert-butyl 5-cyano-8-cyclopropyl-6-(3-cyclopropyl-4-(3-hydroxypropanoyl)piperazin-1-yl)-3,4-dihydro-2,7-naphthyridine-2 (1H)-carboxylate using method F1. LC-MS: m/z 396.6 (M+H).

Step G1: (R)-7-acetyl-1-cyclopropyl-3-(3-cyclopropyl-4-(3-methoxypropanoyl)piperazin-1-yl)-5,6,7,8-tetrahydro-2,7-naphthyridine-4-carbonitrile Compound #478
To a solution of (R)-1-cyclopropyl-3-(3-cyclopropyl-4-(3-methoxypropanoyl)piperazin-1-yl)-5,6,7,8-tetrahydro-2,7-naphthyridine-4-carbonitrile (111 mg, 0.25 mmol) and Et$_3$N (0.1 mL, 0.75 mmol) in methylene chloride (10 mL) was added acetyl chloride (30 mg, 0.375 mmol). The mixture was stirred at room temperature for 1 h. After TLC indicated the complete conversion of starting material to product, the reaction mixture was washed with 1 N HCl aqueous solution (1×20 mL), satd. NaHCO$_3$ and brine, dried over anhy. Na$_2$SO$_4$, and concentrated in vacuo. The crude was purified by preparative HPLC (PE:EA/80:20) to give 78 mg of the title compound as a off-white oil.
1H NMR (CHLOROFORM-d) □ δ 4.70-4.89 (m, 4H), 4.29 (d, J=13.1 Hz, 1H), 4.18 (d, J=12.5 Hz, 1H), 3.78-3.93 (m, 1H), 3.59-3.77 (m, 4H), 3.36 (s, 3H), 3.19-3.31 (m, 1H), 3.09 (d, J=12.8 Hz, 1H), 2.86-3.04 (m, 3H), 2.56-2.74 (m, 2H), 2.17-2.27 (m, 3H), 1.89-2.07 (m, 2H), 1.43 (d, J=3.5 Hz, 0.5H), 1.32 (br. s., 0.5H), 0.99-1.23 (m, 4H), 0.56 (br. s., 1H), 0.50 (br. s., 1H), 0.28-0.46 (m, 2H); LC-MS: m/z 452.6 (M+H)

Step G2: (R)-1-cyclopropyl-3-(3-cyclopropyl-4-(3-methoxypropanoyl)piperazin-1-yl)-'7-propioloyl-5,6,7,8-tetrahydro-2,7-naphthyridine-4-carbonitrile Compound#488
To a solution of (R)-1-cyclopropyl-3-(3-cyclopropyl-4-(3-methoxypropanoyl)piperazin-1-yl)-5,6,7,8-tetrahydro-2,7-naphthyridine-4-carbonitrile (111 mg, 0.25 mmol), propiolic acid (26 mg, 0.375 mmol) and DIPEA (97 mg, 0.75 mmol) in methylene chloride (10 mL) was added HATU (142 mg, 0.375 mmol). The reaction mixture was stirred at room temperature for 2 h. The organic phase was washed with 1 N HCl aqueous solution (1×20 mL), satd. NaHCO$_3$ and brine, dried over anhy. Na$_2$SO$_4$, and concentrated in vacuo. The crude product was purified by preparative HPLC (PE:EA/80:20) to afford 55 mg of the title compound as a white oil.
1H NMR (CHLOROFORM-d) □ δ 4.98 (s, 1H), 4.73-4.93 (m, 1H), 4.32 (d, J=12.8 Hz, 1H), 4.22 (d, J=12.8 Hz, 1H), 3.97-4.15 (m, 2H), 3.80-3.97 (m, 1H), 3.62-3.80 (m, 3H), 3.38 (s, 3H), 3.20-3.32 (m, 1H), 2.88-3.17 (m, 4H), 2.69 (br. s., 1H), 2.44-2.66 (m, 1H), 1.83-1.97 (m, 1H), 1.39 (d, J=7.0 Hz, 1H), 0.99-1.24 (m, 4H), 0.58 (br. s., 1H), 0.52 (br. s., 1H), 0.42 (br. s., 2H); LC-MS: m/z 461.2 (M+H)

(R)-1-cyclopropyl-3-(3-cyclopropyl-4-(3-methoxypropanoyl)piperazin-1-yl)-7-(methylsulfonyl)-5,6,7,8-tetrahydro-2,7-naphthyridine-4-carbonitrile Compound#479
The title compound was prepared from (R)-1-cyclopropyl-3-(3-cyclopropyl-4-(3-methoxypropanoyl) piperazin-1-yl)-5,6,7,8-tetrahydro-2,7-naphthyridine-4-carbonitrile and methanesulfonyl chloride using method G1.
1H NMR (CHLOROFORM-d) □ δ 4.40-4.56 (m, 2H), 4.31 (d, J=12.8 Hz, 1H), 4.21 (d, J=12.5 Hz, 1H), 4.05 (d, J=8.0 Hz, 1H), 3.81 (br. s., 1H), 3.70 (t, J=5.9 Hz, 2H), 3.47-3.62 (m, 2H), 3.36 (s, 3H), 3.27 (s, 1H), 3.03-3.21 (m, 3H), 2.99 (d, J=11.8 Hz, 1H), 2.93 (s, 3H), 2.55-2.77 (m, 2H), 1.78-1.90 (m, 1H), 1.29-1.46 (m, 1H), 1.10-1.21 (m, 2H), 0.99-1.10 (m, 2H), 0.56 (br. s., 1H), 0.50 (br. s., 1H), 0.29-0.48 (m, 2H); LC-MS: m/z 488.6 (M+H)

(R)-1-cyclopropyl-3-(3-cyclopropyl-4-(3-methoxypropanoyl)piperazin-1-yl)-7-(2-hydroxyethyl)-5,6,7,8-tetrahydro-2,7-naphthyridine-4-carbonitrile Compound#484
The title compound was prepared from (R)-1-cyclopropyl-3-(3-cyclopropyl-4-(3-methoxypropanoyl) piperazin-1-yl)-5,6,7,8-tetrahydro-2,7-naphthyridine-4-carbonitrile and 2-chloroethanol using method G1.
1H NMR (CHLOROFORM-d) □ δ 4.62-4.65 (d, J=8.3 Hz, 1H), 4.24 (d, J=13.1 Hz, 1H), 4.14 (d, J=12.5 Hz, 1H), 4.04 (d, J=8.3 Hz, 0.5H), 3.60-3.90 (m, 7H), 3.36 (s, 3H), 3.23 (br. s., 1H), 3.06 (d, J=12.8 Hz, 1H), 2.89-3.02 (m, 3H), 2.74-2.89 (m, 4H), 2.43-2.73 (m, 3H), 1.78-1.89 (m, 1H), 1.34 (br. s., 1H), 1.08-1.19 (m, 2H), 0.93-1.06 (m, 2H), 0.56 (br. s., 1H), 0.49 (br. s., 1H), 0.40 (d, J=5.5 Hz, 2H); LC-MS: m/z 454.6 (M+H)

Compound#485

(R)-7-acryloyl-1-cyclopropyl-3-(3-cyclopropyl-4-(3-methoxypropanoyl)piperazin-1-yl)-5,6,7,8-tetrahydro-2,7-naphthyridine-4-carbonitrile The title compound was prepared from (R)-1-cyclopropyl-3-(3-cyclopropyl-4-(3-methoxypropanoyl) piperazin-1-yl)-5,6,7,8-tetrahydro-2,7-naphthyridine-4-carbonitrile and acryloyl chloride using method G1.
1H NMR (CHLOROFORM-d) □δ 6.67 (dd, J=16.7, 10.7 Hz, 1H), 6.38 (d, J=16.8 Hz, 1H), 5.80 (d, J=10.5 Hz, 1H), 4.75-5.05 (m, 2H), 4.30 (d, J=12.8 Hz, 0.5H), 4.20 (d, J=12.5 Hz, 1H), 4.00-4.13 (m, 1H), 3.80 (d, J=11.0 Hz, 4H), 3.55-3.75 (m, 2H), 3.37 (s, 3H), 3.10 (d, J=12.0 Hz, 1H), 3.01 (br. s., 3H), 2.69 (br. s., 1H), 2.64 (br. s., 1H), 1.99 (br. s., 1H), 1.83 (br. s., 1H), 0.95-1.19 (m, 4H), 0.57 (br. s., 2H), 0.51 (br. s., 1H), 0.41 (br. s., 1H); LC-MS: m/z 464.6 (M+H)

(R)-7-acryloyl-1-cyclopropyl-3-(3-cyclopropyl-4-(3-hydroxypropanoyl)piperazin-1-yl)-5,6,7,8-tetrahydro-2,7-naphthyridine-4-carbonitrile Compound#498
The title compound was prepared from (R)-1-cyclopropyl-3-(3-cyclopropyl-4-(3-hydroxypropanoyl) piperazin-1-yl)-5,6,7,8-tetrahydro-2,7-naphthyridine-4-carbonitrile and acryloyl chloride using method G1.
$^1$H NMR (CHLOROFORM-d) □ δ 6.67 (dd, J=16.7, 10.7 Hz, 1H), 6.37 (dd, J=16.8, 1.8 Hz, 1H), 5.80 (dd, J=10.5, 1.5 Hz, 1H), 4.71-4.96 (m, 2H), 4.29 (d, J=12.8 Hz, 1H), 4.19 (d, J=12.5 Hz, 1H), 3.90 (br. s., 3H), 3.76-3.87 (m, 1H), 3.62-3.76 (m, 1H), 3.49 (br. s., 1H), 3.20-3.33 (m, 1H), 3.06-3.20 (m, 1H), 2.85-3.06 (m, 3H), 2.41-2.66 (m, 2H), 1.88 (br. s., 1H), 1.34 (br. s., 1H), 0.98-1.18 (m, 4H), 0.59 (br. s., 1H), 0.50 (br. s., 1H), 0.43 (d, J=6.3 Hz, 2H);
LC-MS: m/z 450.6 (M+H)

(R)-1-cyclopropyl-3-(3-cyclopropyl-4-(3-hydroxypropanoyl)piperazin-1-yl)-7-propioloyl-5,6,7,8-tetrahydro-2,7-naphthyridine-4-carbonitrile Compound#500
The title compound was prepared from (R)-1-cyclopropyl-3-(3-cyclopropyl-4-(3-hydroxypropanoyl) piperazin-1-yl)-5,6,7,8-tetrahydro-2,7-naphthyridine-4-carbonitrile and propiolic acid using method G2.
1H NMR (CHLOROFORM-d) δ 4.98 (s, 1H), 4.72-4.94 (m, 1H), 4.28-4.39 (m, 1H), 4.21 (d, J=12.8 Hz, 1H), 3.98-4.15 (m, 2H), 3.82-3.98 (m, 2H), 3.61-3.82 (m, 2H), 3.37-3.53 (m, 1H), 3.09-3.35 (m, 2H), 2.90-3.08 (m, 3H), 2.41-2.69 (m, 2H), 1.82-1.96 (m, 1H), 1.72 (br. s., 1H), 1.30-1.40 (m, 1H), 1.01-1.24 (m, 4H), 0.60 (br. s., 1H), 0.52 (br. s., 1H), 0.44 (d, J=6.0 Hz, 2H); LC-MS: m/z 448.5 (M+H)

(R)-1-cyclopropyl-3-(3-cyclopropyl-4-(3-methoxypropanoyl)piperazin-1-yl)-7-methacryloyl-5,6,7,8-tetrahydro-2,7-naphthyridine-4-carbonitrile Compound#502

The title compound was prepared from (R)-1-cyclopropyl-3-(3-cyclopropyl-4-(3-methoxypropanoyl) piperazin-1-yl)-5,6,7,8-tetrahydro-2,7-naphthyridine-4-carbonitrile and methacrylic acid using method G2.

1H NMR (CHLOROFORM-d) δ 5.26 (s, 1H), 5.09 (s, 1H), 4.67-4.86 (m, 2H), 4.25 (d, J=12.8 Hz, 1H), 4.15 (d, J=12.8 Hz, 1H), 4.01 (d, J=8.3 Hz, 1H), 3.58-3.72 (m, 5H), 3.32 (s, 3H), 3.23 (br. s., 1H), 3.02-3.16 (m, 1H), 2.83-3.02 (m, 3H), 2.51-2.73 (m, 2H), 1.86-2.07 (m, 4H), 1.30 (br. s., 1H), 0.94-1.17 (m, 4H), 0.53 (br. s., 1H), 0.46 (br. s., 1H), 0.21-0.42 (m, 2H);
LC-MS: m/z 478.6 (M+H)

(R)-1-cyclopropyl-3-(3-cyclopropyl-4-(3-methoxypropanoyl)piperazin-1-yl)-'7-(3-hydroxypropanoyl)-5,6,7,8-tetrahydro-2,7-naphthyridine-4-carbonitrile Compound#501

The title compound was prepared from (R)-1-cyclopropyl-3-(3-cyclopropyl-4-(3-methoxypropanoyl) piperazin-1-yl)-5,6,7,8-tetrahydro-2,7-naphthyridine-4-carbonitrile and sodium 3-hydroxypropanoate using method G2.

1H NMR (CHLOROFORM-d) δ 4.70-4.91 (m, 1H), 4.65 (s, 1H), 4.30 (d, J=12.8 Hz, 1H), 4.19 (d, J=12.5 Hz, 1H), 4.00-4.11 (m, 1H), 3.87-3.96 (m, 2H), 3.65-3.86 (m, 5H), 3.36 (s, 3H), 3.26 (br. s., 1H), 3.04-3.19 (m, 1H), 2.89-3.04 (m, 3H), 2.45-2.74 (m, 5H), 1.89-2.01 (m, 1H), 1.31 (br. s., 1H), 0.98-1.21 (m, 4H), 0.53-0.74 (m, 1H), 0.50 (br. s., 1H), 0.17-0.46 (m, 2H); LC-MS: m/z 482.6 (M+H)

(R)-7-acetyl-3-(4-(cyclopropanecarbonyl)-3-cyclopropylpiperazin-1-yl)-1-cyclopropyl-5,6,7,8-tetrahydro-2,7-naphthyridine-4-carbonitrile Compound#480

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and acetyl chloride using method G1.

1H NMR (CHLOROFORM-d) □ δ 4.77 (q, J=16.9 Hz, 2H), 4.66 (s, 0.5H), 4.30 (d, J=12.8 Hz, 1H), 4.20 (d, J=12.3 Hz, 1.5H), 3.76-3.91 (m, 1H), 3.62-3.76 (m, 2H), 3.23-3.31 (m, 0.5H), 3.17 (dd, J=11.3, 6.5 Hz, 1.5H), 2.88-3.07 (m, 3H), 2.15-2.26 (m, 4H), 1.89-2.00 (m, 1H), 1.77-1.89 (m, 1H), 1.30-1.55 (m, 1H), 1.10-1.20 (m, 2H), 0.89-1.10 (m, 4H), 0.69-0.82 (m, 2H), 0.59 (br. s., 1H), 0.24-0.54 (m, 3H); LC-MS: m/z 434.6 (M+H)

(R)-3-(4-(cyclopropanecarbonyl)-3-cyclopropylpiperazin-1-yl)-1-cyclopropyl-7-(methylsulfonyl)-5,6,7,8-tetrahydro-2,7-naphthyridine-4-carbonitrile Compound#481

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and methanesulfonyl chloride using method G1.

1H NMR (CHLOROFORM-d) □ δ 4.48 (d, J=2.8 Hz, 2H), 4.33 (d, J=12.5 Hz, 1H), 4.22 (d, J=12.3 Hz, 1H), 3.95-4.12 (m, 1H), 3.43-3.64 (m, 3H), 3.27 (d, J=7.3 Hz, 1H), 3.15 (s, 1H), 2.98-3.12 (m, 3H), 2.92 (s, 3H), 1.88-1.97 (m, 1H), 1.79-1.87 (m, 1H), 1.20-1.27 (m, 1H), 1.12-1.18 (m, 2H), 0.91-1.08 (m, 4H), 0.71-0.84 (m, 2H), 0.35-0.65 (m, 4H); LC-MS: m/z 470.6 (M+H)

(R)-7-acryloyl-3-(4-(cyclopropanecarbonyl)-3-cyclopropylpiperazin-1-yl)-1-cyclopropyl-5,6,7,8-tetrahydro-2,7-naphthyridine-4-carbonitrile Compound#489

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and acryloyl chloride using method G1.

1H NMR (CHLOROFORM-d) □δ 6.67 (dd, J=16.4, 10.7 Hz, 1H), 6.28-6.48 (m, 1H), 5.80 (d, J=10.5 Hz, 1H), 4.72-5.02 (m, 2H), 4.46 (d, J=6.3 Hz, 1H), 4.33 (d, J=12.8 Hz, 1H), 4.23 (d, J=12.5 Hz, 1H), 3.74-4.03 (m, 3H), 3.19 (br. s., 2H), 3.02 (br. s., 3H), 2.00 (br. s., 1H), 1.70 (br. s., 1H), 1.37-1.52 (m, 1H), 1.16 (br. s., 2H), 0.93-1.11 (m, 4H), 0.72-0.87 (m, 2H), 0.62 (br. s., 1H), 0.45-0.55 (m, 2H), 0.29-0.45 (m, 1H); LC-MS: m/z 446.6 (M+H)

(R)-3-(4-(cyclopropanecarbonyl)-3-cyclopropylpiperazin-1-yl)-1-cyclopropyl-7-propioloyl-5,6,7,8-tetrahydro-2,7-naphthyridine-4-carbonitrile Compound#491

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and propiolic acid using method G2.

1H NMR (CHLOROFORM-d) □ δ 4.98 (s, 0.5H), 4.71-4.91 (m, 1.5H), 4.53 (br. s., 1H), 4.34 (d, J=12.5 Hz, 1H), 4.24 (d, J=12.3 Hz, 1H), 3.97-4.16 (m, 2H), 3.81-3.97 (m, 1H), 3.55-3.78 (m, 1H), 3.14-3.35 (m, 2H), 2.90-3.13 (m, 3H), 1.86-1.99 (m, 1H), 1.30-1.58 (m, 2H), 1.13-1.23 (m, 2H), 1.03-1.13 (m, 3H), 1.00 (br. s., 1H), 0.71-0.84 (m, 2H), 0.61 (br. s., 1H), 0.45-0.55 (m, 2H), 0.22-0.45 (m, 1H); LC-MS: m/z 444.5 (M+H)

(R)-3-(4-(cyclopropanecarbonyl)-3-cyclopropylpiperazin-1-yl)-1-cyclopropyl-7-(vinylsulfonyl)-5,6,7,8-tetrahydro-2,7-naphthyridine-4-carbonitrile Compound#493

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and 2-chloroethanesulfonyl chloride using method G1.

1H NMR (CHLOROFORM-d) □ δ 6.52 (dd, J=16.6, 9.8 Hz, 1H), 6.38 (d, J=16.6 Hz, 1H), 6.11 (d, J=9.8 Hz, 1H), 4.39-4.50 (m, 3H), 4.34 (d, J=12.8 Hz, 1H), 4.24 (d, J=12.3 Hz, 1H), 3.58-3.85 (m, 1H), 3.51 (dtd, J=18.9, 12.5, 5.8 Hz, 2.5H), 3.13-3.38 (m, 1.5H), 3.07 (t, J=5.8 Hz, 3H), 1.77-1.88 (m, 1H), 1.31-1.50 (m, 2H), 1.13-1.22 (m, 2H), 0.95-1.11 (m, 4H), 0.76-0.86 (m, 2H), 0.62 (br. s., 1H), 0.29-0.56 (m, 3H); LC-MS: m/z 482.6 (M+H)

(R)-methyl 5-cyano-6-(4-(cyclopropanecarbonyl)-3-cyclopropylpiperazin-1-yl)-8-cyclopropyl-3,4-dihydro-2,7-naphthyridine-2(1H)-carboxylate Compound#494

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and methyl carbonochloridate using method G1.

1H NMR (CHLOROFORM-d) δ 4.61-4.77 (m, 2H), 4.50 (br. s., 0.5H), 4.30 (d, J=12.8 Hz, 1H), 4.21 (d, J=12.5 Hz, 1H), 3.86-4.06 (m, 0.5H), 3.78 (s, 3H), 3.63-3.77 (m, 3H), 3.50 (br. s., 1H), 3.18 (br. s., 1H), 2.84-3.09 (m, 3H), 1.91 (br. s., 1H), 1.36-1.51 (m, 1H), 1.22-1.35 (m, 1H), 1.12-1.20 (m, 2H), 0.94-1.10 (m, 4H), 0.73-0.85 (m, 2H), 0.62 (br. s., 1H), 0.33-0.56 (m, 3H); LC-MS: m/z 450.6 (M+H)

(R)-7-(2-cyanoacetyl)-3-(4-(cyclopropanecarbonyl)-3-cyclopropylpiperazin-1-yl)-1-cyclopropyl-5,6,7,8-tetrahydro-2,7-naphthyridine-4-carbonitrile Compound#497

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and 2-cyanoacetic acid using method G2

¹H NMR (CHLOROFORM-d) δ 4.70-4.91 (m, 1H), 4.67 (s, 1H), 4.33 (d, J=12.5 Hz, 1H), 4.22 (d, J=11.5 Hz, 1H), 3.94-4.15 (m, 0.5H), 3.70-3.94 (m, 2.5H), 3.60-3.69 (m, 1H), 3.43-3.60 (m, 1H), 3.12-3.34 (m, 1H), 2.99-3.12 (m, 2H), 2.89-2.99 (m, 1H), 1.87-1.96 (m, 2H), 1.69 (br. s., 1H), 1.12-1.22 (m, 2H), 0.91-1.11 (m, 4H), 0.71-0.83 (m, 2H), 0.59 (br. s., 1H), 0.29-0.54 (m, 3H); LC-MS: m/z 459.6 (M+H)

(R,E)-7-but-2-enoyl-3-(4-(cyclopropanecarbonyl)-3-cyclopropylpiperazin-1-yl)-1-cyclopropyl-5,6,7,8-tetrahydro-2,7-naphthyridine-4-carbonitrile Compound#499

The title compound was prepared from (R)-3-(4-(cyclopropanecarbonyl)-3-cyclopropylpiperazin-1-yl)-1-cyclopropyl-5,6,7,8-tetrahydro-2,7-naphthyridine-4-carbonitrile and (E)-but-2-enoic acid using method G2

¹H NMR (CHLOROFORM-d) δ 6.85-7.03 (m, 1H), 6.23-6.43 (m, 1H), 4.70-4.99 (m, 2H), 4.53 (br. s., 1H), 4.26-4.37 (m, 1H), 4.20 (d, J=12.5 Hz, 1H), 3.90-4.06 (m, 1H), 3.68-3.90 (m, 2H), 3.39-3.66 (m, 1H), 3.09-3.39 (m, 1H), 2.99 (br. s., 3H), 1.84-2.03 (m, 4H), 1.61-1.79 (m, 1H), 1.36-1.51 (m, 1H), 1.10-1.20 (m, 2H), 0.92-1.10 (m, 4H), 0.74-0.85 (m, 2H), 0.60 (br. s., 1H), 0.27-0.54 (m, 3H); LC-MS: m/z 460.6 (M+H)

(R)-7-acryloyl-1-cyclopropyl-3-(3-cyclopropyl-4-(3,3,3-trifluoropropanoyl)piperazin-1-yl)-5,6,7,8-tetrahydro-2,7-naphthyridine-4-carbonitrile Compound#490

The title compound was prepared from (R)-1-cyclopropyl-3-(3-cyclopropyl-4-(3,3,3-trifluoropropanoyl) piperazin-1-yl)-5,6,7,8-tetrahydro-2,7-naphthyridine-4-carbonitrile and acryloyl chloride using method G1

1H NMR (CHLOROFORM-d) δ 6.66 (dd, J=16.1, 10.8 Hz, 1H), 6.37 (d, J=16.8 Hz, 1H), 5.68-5.97 (m, 1H), 4.72-5.01 (m, 2H), 4.44 (t, J=6.1 Hz, 1H), 4.31 (d, J=12.8 Hz, 1H), 4.21 (d, J=12.3 Hz, 1H), 3.76-3.98 (m, 3H), 3.72 (br. s., 1H), 3.30 (d, J=8.8 Hz, 2H), 3.05-3.20 (m, 2H), 3.01 (br. s., 2H), 1.99 (br. s., 1H), 1.37 (br. s., 1H), 0.95-1.24 (m, 4H), 0.60 (br. s., 1H), 0.52 (br. s., 1H), 0.36-0.48 (m, 2H); LC-MS: m/z 488.5 (M+H)

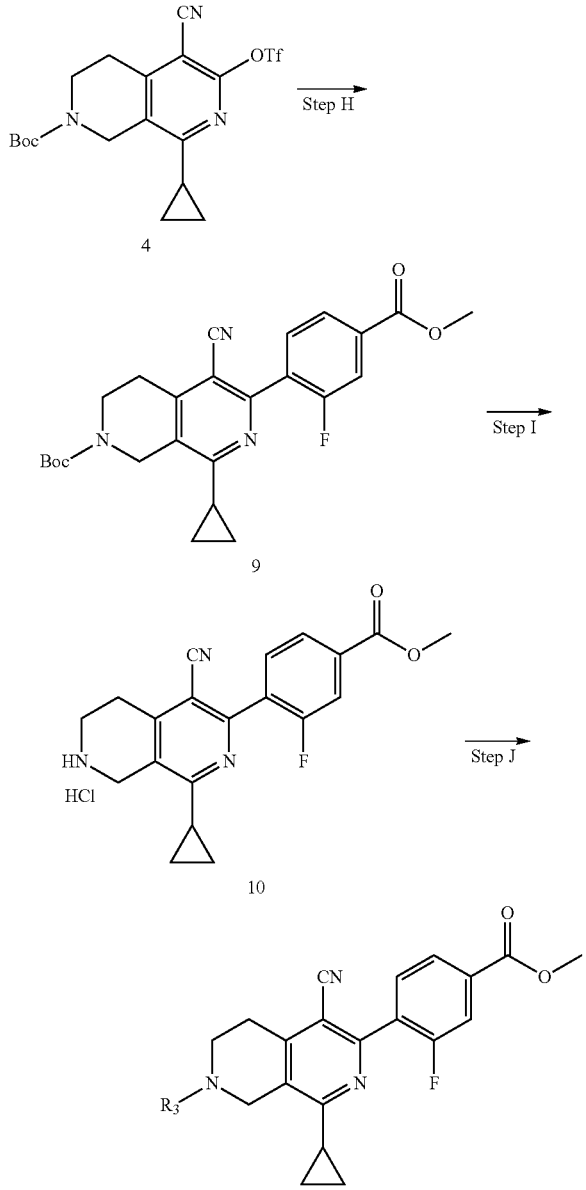

Step H: tert-butyl 5-cyano-8-cyclopropyl-6-(2-fluoro-4-(methoxycarbonyl)phenyl)-3,4-dihydro-2,7-naphthyridine-2(1H)-carboxylate

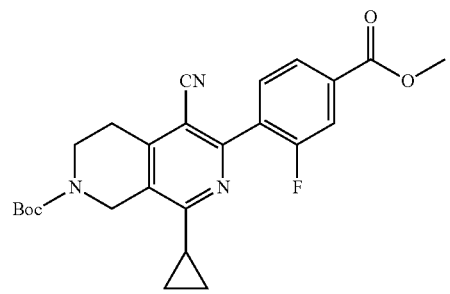 [SMILES: COC(=O)c1ccc(-c2nc(C3CC3)c3c(c2C#N)CCN(C(=O)OC(C)(C)C)C3)c(F)c1]

To a solution of 2-fluoro-4-(methoxycarbonyl)phenylboronic acid (400 mg, 2 mmol) in DMF (150 mL) was added tert-butyl 5-cyano-8-cyclopropyl-6-(trifluoromethylsulfonyloxy)-3,4-dihydro-2,7-naphthyridine-2(1H)-carboxylate (896 mg, 2 mmol), dichloro-bis(triphenylphosphine) palladium (II) (140 mg, 0.2 mmol) and potassium carbonate (420 mg, 6 mmol) and the mixture was stirred at 90° C. for 10 hours under nitrogen. The mixture was diluted with ethyl acetate and water. The organic layer was separated, washed with brine, dried over magnesium sulfate and concentrated in vacuo. Flash column chromatography (10% ethyl acetate/petroleum ether) afforded the title compound as off-white solid (780 mg), which was directly used for the next step without further purification. LC-MS: m/z 352.5 (M+H)

Step J: methyl 4-(4-cyano-1-cyclopropyl-5,6,7,8-tetrahydro-2,7-naphthyridin-3-yl)-3-fluorobenzoate hydrochloride

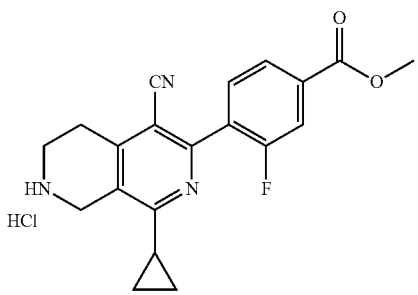 [SMILES: Cl ; COC(=O)c1ccc(-c2nc(C3CC3)c3c(c2C#N)CCNC3)c(F)c1]

To a solution of tert-butyl 5-cyano-8-cyclopropyl-6-(2-fluoro-4-(methoxycarbonyl)phenyl)-3,4-dihydro-2,7-naphthyridine-2(1H)-carboxylate (270 mg 0.5 mmol) in MeOH (5 mL) was added 1N HCl/MeOH solution (20 mL). The mixture was stirred at room temperature until the reaction was complete \. Solvent was removed in vacuo to give the crude product as a light-yellow oil (240 mg), which was used for the next step without further purification. LC-MS: m/z 352.5 (M+H)

Compound#496

To a solution of methyl 4-(4-cyano-1-cyclopropyl-5,6,7, 8-tetrahydro-2,7-naphthyridin-3-yl)-3-fluorobenzoate hydrochloride (97 mg, 0.25 mmol) and Et$_3$N (0.1 mL, 0.75 mmol) in methylene chloride (10 mL) was added 2-chloroethanesulfonyl chloride (62 mg, 0.375 mmol). The mixture was stirred at room temperature for 3 h. After TLC indicated the complete conversion of starting material to the product, the reaction mixture was washed with 1 N HCl aqueous solution (1×20 mL), satd. NaHCO$_3$ and brine, dried over anhy. Na$_2$SO$_4$, and concentrated in vacuo. The crude was purified by preparative HPLC separation (PE:EA/80: 20) to give 55 mg of the title compound as a off-white oil.

1H NMR (CHLOROFORM-d) □δ 7.95 (dd, J=8.0, 1.5 Hz, 1H), 7.87 (dd, J=10.4, 1.4 Hz, 1H), 7.58 (t, J=7.5 Hz, 1H), 6.55 (dd, J=16.6, 9.8 Hz, 1H), 6.41 (d, J=16.6 Hz, 1H), 6.15 (d, J=9.5 Hz, 1H), 4.59 (s, 2H), 3.97 (s, 3H), 3.59 (t, J=5.9 Hz, 2H), 3.20 (t, J=5.8 Hz, 2H), 1.88-2.01 (m, 1H), 1.24-1.31 (m, 2H), 1.08-1.18 (m, 2H); LC-MS: m/z 442.5 (M+H)

Compound#495

To a solution of (methyl 4-(4-cyano-1-cyclopropyl-5,6,7, 8-tetrahydro-2,7-naphthyridin-3-yl)-3-fluorobenzoate hydrochloride (97 mg, 0.25 mmol), propiolic acid (26 mg, 0.375 mmol) and DIPEA (97 mg, 0.75 mmol) in methylene chloride (10 mL) was added HATU (142 mg, 0.375 mmol). The reaction mixture was stirred at room temperature for 2 h. The organic phase was washed with 1N HCl aqueous solution (1×20 mL), satd. NaHCO$_3$ and brine, dried over anhy. Na$_2$SO$_4$, and concentrated in vacuo. The crude product was purified by preparative HPLC (PE: EA/80:20) to afford 52 mg of the title compound as a off-white oil.

1H NMR (CHLOROFORM-d) □ δ 7.95 (d, J=8.0 Hz, 1H), 7.87 (d, J=10.5 Hz, 1H), 7.58 (t, J=7.5 Hz, 1H), 5.14 (s, 0.5H), 4.98 (s, 1.5H), 4.14 (t, J=5.8 Hz, 1.5H), 3.86-4.06 (m, 3.5H), 3.28 (s, 1H), 3.03-3.24 (m, 2H), 2.02-2.12 (m, 1H), 1.21-1.29 (m, 2H), 1.10-1.19 (m, 2H); LC-MS: m/z 404.4 (M+H)

Compound#503

$^1$H NMR (CHLOROFORM-d) δ□□6.50 (dd, J=16.6, 9.8 Hz, 1H), 6.36 (d, J=16.6 Hz, 1H), 6.09 (d, J=9.8 Hz, 1H), 4.41 (s, 2H), 3.62-3.76 (m, 4H), 3.49 (t, J=5.9 Hz, 2H), 3.02 (t, J=5.9 Hz, 2H), 2.46-2.66 (m, 4H), 2.36 (s, 3H), 1.65-1.86 (m, 1H), 1.09-1.20 (m, 2H). LC-MS: m/z 388.2 (M+H)

Core Synthesis 2:

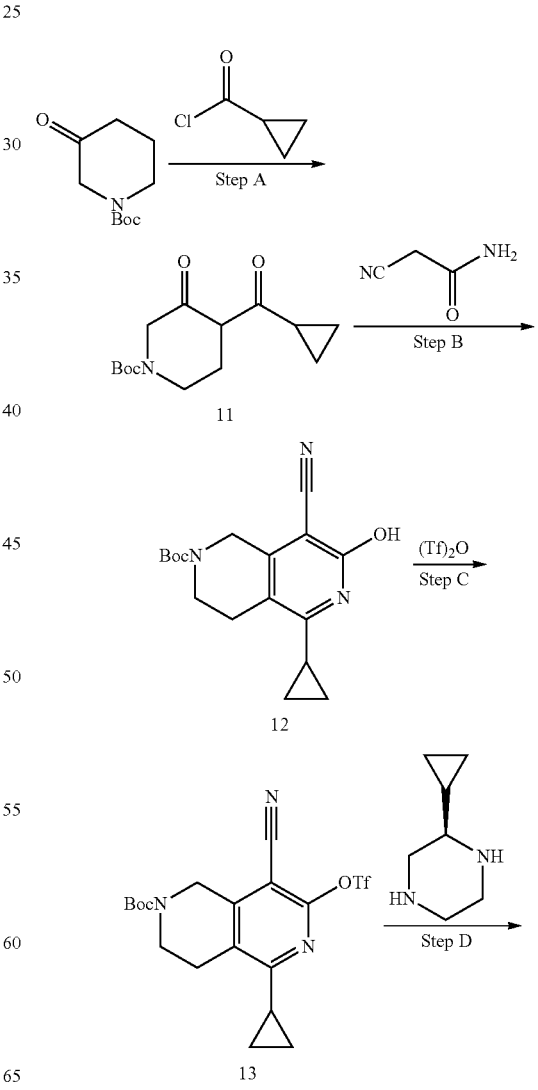

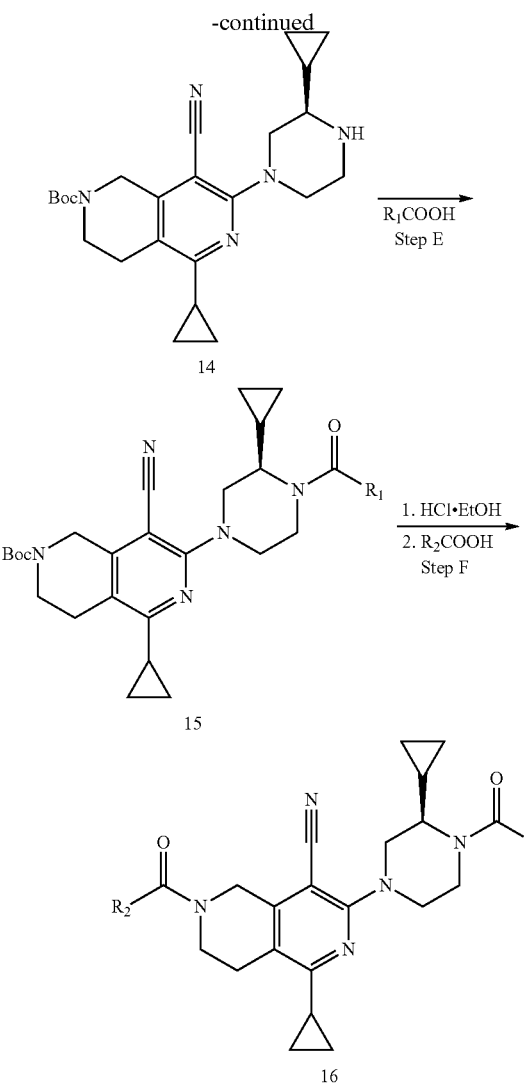

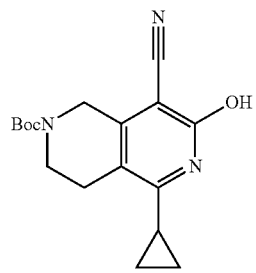 [SMILES: CC(C)(C)OC(=O)N1CCc2c(C3CC3)nc(O)c(C#N)c2C1]

Step B: tert-butyl 8-cyano-5-cyclopropyl-7-hydroxy-3,4-dihydro-2,6-naphthyridine-2(1H)-carboxylate To a solution of compound 11 (3 g, 11.6 mmol) in EtOH (7 ml) was added Et$_2$NH (1 mL) and 2-cyanoacetamide (1.47 g, 17.5 mmol). The mixture was stirred at room temperature for 2 days. The resulting precipitate was filtered and dried to give 1 g of the title compound 12, which was used for the next step without further purification. $^1$H NMR (CHLOROFORM-d) δ: 4.58 (br. s., 2H), 3.66 (t, J=5.6 Hz, 2H), 2.76 (br. s., 2H), 1.49 (s, 9H), 0.92-1.05 (m, 4H). Step C: tert-butyl 8-cyano-5-cyclopropyl-7-(((trifluoromethyl)sulfonyl)oxy)-3,4-dihydro-2,6-naphthyridine-2(1H)-carboxylate

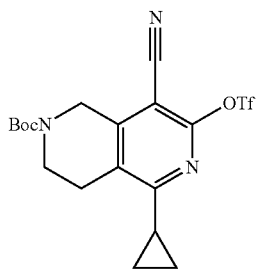 [SMILES: CC(C)(C)OC(=O)N1CCc2c(C3CC3)nc(OS(=O)(=O)C(F)(F)F)c(C#N)c2C1]

At −40° C., Et$_3$N was slowly added into a solution of 12 in DCM (10 ml). Triflic anhydride was then added at the same temperature. The reaction was stirred for further 3 h from −30° C. to 0° C. TLC was used to monitor the complete consumption of the starting material. Water (10 mL) was then added to the reaction and the organic phase was separated, concentrated and purified with PTLC (EA:PE=1:2) to give 600 mg of the title compound 13. 1H NMR (CHLOROFORM-d) δ 4.78 (br. s., 2H), 3.75 (t, J=5.6 Hz, 2H), 3.06 (t, J=5.8 Hz, 2H), 2.01 (br. s., 1H), 1.51 (s, 9H), 1.19-1.31 (m, 4H).

Step D: (R)-tert-butyl 8-cyano-5-cyclopropyl-7-(3-cyclopropylpiperazin-1-yl)-3,4-dihydro-2,6-naphthyridine-2(1H)-carboxylate

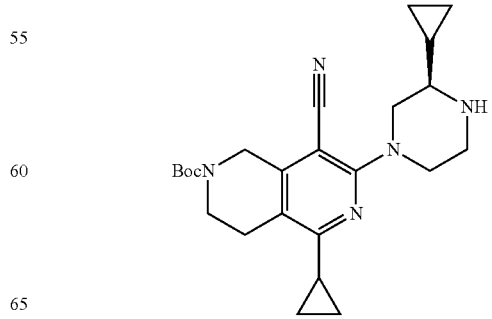

Step A: tert-butyl 4-(cyclopropanecarbonyl)-3-oxopiperidine-1-carboxylate

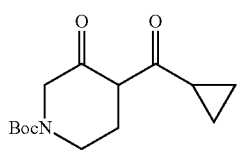

At −70° C., to a solution of tert-butyl 3-oxopiperidine-1-carboxylate (5.5 g, 27.6 mmol) in THF (20 mL) was slowly added LDA (11 mL, 16.8 mmol). After stirring the mixture for 20 min at −70° C., cyclopropanecarbonyl chloride (1.58 ml, 16.2 mmol) was added. The resulting mixture was stirred for another 10 min, allowed to warm to 0° C., and then quenched with saturated NH$_4$Cl in water (10 mL). Then EA (30 mL) was added and the organic phase was separated, dried and concentrated to give a pale oil, which was purified with flash column (PE:EA=5: 1) to obtain 4 g of the title compound 11, which was used directly for the next step without further purification.

A solution of compound 13 (100 mg, 0.223 mmol) and cyclopropyl piperazine (170 mg, 1.35 mmol) was heated to 80° C. in a sealed tube and stirred for further 12 hours at the same temperature. The resulting solution was concentrated and purified with PTLC (EA:PE=1:1) to give 80 mg of the title compound 14. 1H NMR (CHLOROFORM-d) δ 4.62 (br. s., 2H), 4.28 (d, 1H), 4.07-4.18 (m, 1H), 3.58-3.72 (m, 2H), 3.24-3.38 (m, 2H), 3.16 (dd, 10.5 Hz, 1H), 3.00 (td, J=12.0, 3.1 Hz, 1H), 2.89 (t, J=5.3 Hz, 2H), 2.26 (td, J=9.8, 2.8 Hz, 1H), 1.88 (br. s., 1H), 1.52 (s, 9H), 1.08-1.16 (m, 2H), 1.04 (d, J=6.5 Hz, 2H), 0.65-0.69 (m, 2H), 0.49-0.59 (m, 1H), 0.38-0.47 (m, 1H).

Step E: (R)-tert-butyl 8-cyano-5-cyclopropyl-7-(3-cyclopropyl-4-(3-methoxypropanoyl)piperazin-1-yl)-3,4-dihydro-2,6-naphthyridine-2(1H)-carboxylate

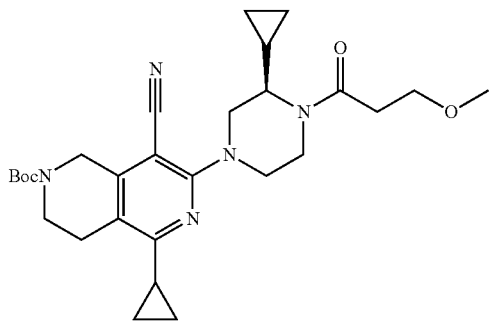 [SMILES: COCCC(=O)N1CCN(c2nc(C3CC3)c3c(c2C#N)CN(C(=O)OC(C)(C)C)CC3)C[C@H]1C1CC1]

A solution of 14 (60 mg, 0.141 mmol), 3-methoxypropanoic acid (22 mg, 0.17 mmol), HATU (8 mg) in DCM (2 mL) was stirred for 2 hours at room temperature. The reaction was washed with water, concentrated and purified with PTLC (EA:PE=2:3) to give 50 mg of the title compound 15. $^1$H NMR (CHLOROFORM-d) δ: 4.65 (br. s., 2H), 3.99-4.29 (m, 3H), 3.58-3.88 (m, 4H), 3.32-3.48 (m, 3H), 2.84 (t, J=5.3 Hz, 2H), 2.58 (t, J=6.3 Hz, 2H), 2.01 (br. s., 1H), 1.81 (m, 1H), 1.47-1.54 (m, 9H), 1.06-1.15 (m, 2H), 1.02 (dt, J=7.7, 2.9 Hz, 2H)

Step F: (R)-6-acryloyl-1-cyclopropyl-3-(3-cyclopropyl-4-(3-methoxypropanoyl)piperazin-1-yl)-5,6,7,8-tetrahydro-2,6-naphthyridine-4-carbonitrile

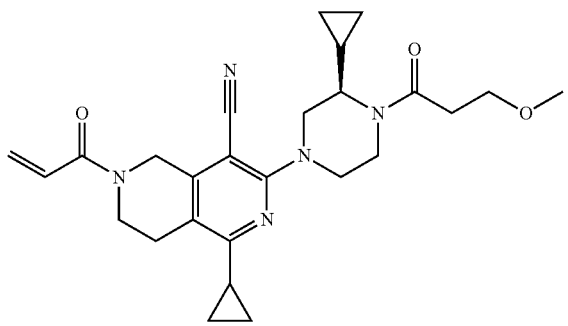 [SMILES: C=CC(=O)N1CCc2c(C3CC3)nc(N3CCN(C(=O)CCOC)[C@H](C4CC4)C3)c(C#N)c2C1]

A solution of 5 (50 mg) in HCl.MTBE (1 N, 5 mL) was stirred for 2 hours. The resulting solution was concentrated to give thick oil, which was dissolved in DCM (2 mL) and treated with acrylic chloride (17 mg) and Et$_3$N (20 mg) and stirred for further 10 min. The title compound was isolated from the reaction using PTLC (PE:EA=1:1) to give 10 mg of Compound#483. 1H NMR (CHLOROFORM-d) δ 6.68 (dd, J=16.8, 10.5 Hz, 1H), 6.38 (d, J=16.8 Hz, 1H), 5.80 (d, J=10.8 Hz, 1H), 4.91 (br. s., 1H), 4.78 (br. s., 1H), 4.29 (d, J=11.8 Hz, 1H), 4.18 (d, J=12.3 Hz, 2H), 3.84 (br. s., 2H), 3.53-3.79 (m, 3H), 3.37 (s, 3H), 2.91 (br. s., 3H), 2.63 (d, J=6.5 Hz, 2H), 2.01 (br. m, H), 1.08-1.20 (m, 2H), 1.04 (br. s., 2H), 0.58 (br. s., 2H), 0.41 (br. s., 2H); LC-MS: m/z 464.8 (M+H)$^+$
Compound#483

(R)-6-acryloyl-1-cyclopropyl-3-(3-cyclopropyl-4-(3-methoxypropanoyl)piperazin-1-yl)-5,6,7,8-tetrahydro-2,6-naphthyridine-4-carbonitrile 1H NMR (CHLOROFORM-d) δ 6.68 (dd, J=16.8, 10.5 Hz, 1H), 6.38 (d, J=16.8 Hz, 1H), 5.80 (d, J=10.8 Hz, 1H), 4.91 (br. s., 1H), 4.78 (br. s., 1H), 4.29 (d, J=11.8 Hz, 1H), 4.18 (d, J=12.3 Hz, 2H), 3.84 (br. s., 2H), 3.53-3.79 (m, 3H), 3.37 (s, 3H), 2.91 (br. s., 3H), 2.63 (d, J=6.5 Hz, 2H), 2.01 (br. m, H), 1.08-1.20 (m, 2H), 1.04 (br. s., 2H), 0.58 (br. s., 2H), 0.41 (br. s., 2H); LC-MS: m/z 464.8 (M+H)$^+$
Compound#482

(R)-6-acryloyl-3-(4-(cyclopropanecarbonyl)-3-cyclopropylpiperazin-1-yl)-1-cyclopropyl-5,6,7,8-tetrahydro-2,6-naphthyridine-4-carbonitrile The title compound was synthesized using the same procedure as Compound#483 except cyclopropanecarbonyl chloride instead of 3-methoxypropanoic acid (Step E).

1H NMR (CHLOROFORM-d) δ 6.69 (dd, J=16.8, 10.5 Hz, 1H), 6.39 (d, J=16.6 Hz, 1H), 5.81 (d, J=11.0 Hz, 1H), 4.92 (br. s., 1H), 4.79 (br. s., 1H), 4.32 (d, J=12.8 Hz, 1H), 4.22 (d, J=12.3 Hz, 2H), 3.85 (br. s., 4H), 2.92 (br. s., 2H), 2.02 (br. s., 2H), 1.23-1.38 (m, 4H), 1.11-1.23 (m, 2H), 0.97-1.10 (m, 4H), 0.73-0.97 (m, 4H), 0.31-0.60 (m, 2H). LC-MS: m/z 446.9 (M+H)$^+$
Compound#487

(R)-1-cyclopropyl-3-(3-cyclopropyl-4-(3-methoxypropanoyl)piperazin-1-yl)-6-(methylsulfonyl)-5,6,7,8-tetrahydro-2,6-naphthyridine-4-carbonitrile 1H NMR (CHLOROFORM-d) δ 4.51 (s, 2H), 4.30 (d, J=12.8 Hz, 1H), 4.21 (d, J=12.5 Hz, 1H), 3.73 (t, J=5.8 Hz, 3H), 3.61 (br. m., 5H), 3.38 (s, 3H), 2.86-3.05 (m, 6H), 2.65 (m, 2H), 1.87-2.11 (m, 2H), 1.04-1.23 (m, 4H), 0.37-0.64 (m, 4H). LC-MS: m/z 462.9 (M+H)$^+$
Compound#486

(R)-1-cyclopropyl-3-(3-cyclopropyl-4-(3-methoxypropanoyl)piperazin-1-yl)-6-propioloyl-5,6,7,8-tetrahydro-2,6-naphthyridine-4-carbonitrile The title compound was synthesized using the same procedure as Compound#483 except Propiolic acid instead of acrylic chloride (Step F).

1H NMR (CHLOROFORM-d) δ 5.00 (d, J=4.0 Hz, 1H), 4.86 (s, 1H), 4.25-4.50 (m, 1H), 4.20 (d, J=12.8 Hz, 1H), 4.02-4.15 (m, 2H), 3.78-4.02 (m, 2H), 3.57-3.78 (m, 3H), 3.33-3.41 (m, 3H), 3.10-3.19 (m, 1H), 2.85-3.10 (m, 3H), 2.46-2.75 (m, 2H), 2.11-2.26 (m, 1H), 1.87-2.11 (m, 1H), 0.97-1.24 (m, 4H), 0.59 (br. s., 1H), 0.52 (br. s., 1H), 0.22-0.48 (m, 2H).
LC-MS: m/z 462.7 (M+H)$^+$

Compound#492

(R)-tert-butyl 8-cyano-5-cyclopropyl-7-(3-cyclopropyl-4-(3-methoxypropanoyl)piperazin-1-yl)-3,4-dihydro-2,6-naphthyridine-2(1H)-carboxylate $^1$H NMR (CHLOROFORM-d) δ: 5.45 (d, J=3.3 Hz, 1H), 5.29-5.40 (m, 1H), 5.24 (dd, J=16.6, 3.0 Hz, 1H), 4.82 (s, 2H), 4.29 (d, J=12.5 Hz, 1H), 4.19 (d, J=12.5 Hz, 1H), 4.06 (br. s., 1H), 3.86 (br. s., 2H), 3.57-3.79 (m, 3H), 3.32-3.48 (m, 3H), 3.27 (br. s., 1H), 3.10 (d, J=13.6 Hz, 1H), 2.86-3.05 (m, 3H), 2.69 (br. s., 1H), 2.64 (br. s., 1H), 2.01 (dd, J=7.5, 3.8 Hz, 1H), 1.58-1.84 (m, 2H), 1.38-1.51 (m, 1H), 1.30-1.38 (m, 2H), 1.27 (br. s., 2H), 0.97-1.20 (m, 4H), 0.89 (t, J=6.5 Hz, 1H), 0.58 (br. s., 1H), 0.52 (br. s., 1H), 0.42 (br. s., 2H). LC-MS: m/z 482.2 (M+H)$^+$

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound having Structural Formula (I) or a pharmaceutically acceptable salt thereof, wherein:

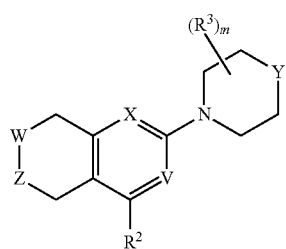

(I)

X is CR$^4$;
Y is —N(R$^5$)— or —CH(R$^5$)—;
Z is —O—, —S—, —C(R)$_2$— or N(R$^7$);
W is C(R$^1$)(R$^1$) or N(R$^7$); provided that (1) when Z is —C(R)$_2$—, then W is not C(R$^1$)(R$_1$); and (2) Z and W are not both N(R$^7$) at the same time;
V is N or C(R);
each R is independently selected from hydrogen, methyl or CF$_3$;
each R$^1$ is independently selected from hydrogen, alkoxy, or alkyl optionally substituted with OH or SH;
or two R$^1$ are taken together with the carbon atom to which they are bound to form a 3-7 membered cycloalkyl, or a 4-7 membered saturated heterocyclyl ring wherein said cycloalkyl or heterocyclyl is optionally substituted with methyl, halo or CF$_3$;
R$^2$ is selected from phenyl, a 3-7 membered cycloalkyl, or C$_2$-C$_4$ alkyl, wherein the phenyl or cycloalkyl is optionally substituted with a single substituent selected from methyl, CF$_3$ or fluoro;
each R$^3$ is independently selected from —C$_1$-C$_4$ alkyl optionally substituted with halo, —(C$_1$-C$_4$ alkyl)-O—(C$_1$-C$_4$ alkyl), —C$_1$-C$_4$ fluoroalkyl, —C(O)—O—(C$_1$-C$_4$ alkyl), -phenyl, -heteroaryl, C$_3$-C$_7$ cycloalkyl, —CH$_2$—N(C$_1$-C$_4$ alkyl)$_2$, C(O)—N—(C$_1$-C$_4$ alkyl)$_2$, —C(O)—NH—(C$_1$-C$_4$ alkyl), or two R$^3$s are taken together to form a 3-8 saturated ring or a fused phenyl wherein said saturated ring or fused phenyl is optionally substituted with 1 to 2 methyl;
R$^4$ is selected from hydrogen, —CN, halo, C$_1$-C$_4$ alkoxy, —CH$_2$NH(C$_1$-C$_4$ alkyl), C$_2$-C$_4$ alkenyl, C$_2$-C$_4$ alkynyl, —(C$_1$-C$_4$ alkyl)-O—(C$_1$-C$_4$ alkyl), C$_1$-C$_4$ fluoroalkyl, C(O)—N—(C$_1$-C$_4$ alkyl)$_2$, C(O)—NH—(C$_2$-C$_4$ alkyl), —S(O)$_2$—(C$_1$-C$_4$ alkyl), or a 5-membered heteroaryl;
R$^5$ is selected from: —C(O)—(C$_1$-C$_4$ alkyl), —C(O)—(C$_0$-C$_2$ alkylene)-Q, —C(O)—(C$_0$-C$_2$ alkylene)-N(R$^6$)—(C$_0$-C$_2$ alkylene)-Q, —C(O)—O—(C$_1$-C$_2$ alkylene)-Q, —C(O)—(C$_1$-C$_2$ alkylene)-O—(C$_0$-C$_2$ alkylene)-Q, —C(O)—C(O)-Q, —S(O)$_2$-Q, —C(O)—(C$_1$-C$_4$ alkylene)-O—C(O)—(C$_1$-C$_4$ alkyl), —C(O)—(C$_1$-C$_4$ alkylene)-C(O)—O—(C$_1$-C$_4$ alkyl), —C(O)—N(R$^6$)—(C$_1$-C$_4$ alkylene)-O—C(O)—(C$_1$-C$_4$ alkyl), —C(O)—N(R$^6$)—(C$_1$-C$_4$ alkylene)-C(O)—O—(C$_1$-C$_4$ alkyl), —C(O)—(C$_0$-C$_2$ alkylene)-N(R$^6$)—(C$_1$-C$_6$ alkyl), —C(O)—(C$_0$-C$_2$ alkylene)N(R$^6$)—(C$_2$-C$_6$ alkynyl), —C(O)—(C$_0$-C$_2$ alkylene)-N(R$^6$)—(C$_2$-C$_6$ alkenyl), —C(O)—(C$_0$-C$_2$ alkylene)-N(R$^6$)—(C$_0$-C$_2$ alkylene)-O—(C$_1$-C$_4$ alkyl), —C(O)—(C$_1$-C$_2$ alkylene)-O—(C$_1$-C$_4$ alkyl), —C(O)—(C$_1$-C$_2$ alkylene)-C(O)C(O)N(R)(C$_1$-C$_4$ alkyl), —C(O)—O—(C$_1$-C$_4$ alkylene)-O—(C$_1$-C$_4$ alkyl), —(C$_0$-C$_4$ alkylene)-O—C(O)—(C$_1$-C$_4$ alkyl), —(C$_0$-C$_4$ alkylene)-C(O)—O—(C$_1$-C$_4$ alkyl), —(C$_0$-C$_4$ alkylene)-O—(C$_1$-C$_4$ alkyl), —C(O)—(C$_1$-C$_2$ alkylene)-S(O)$_{0-2}$—(C$_1$-C$_4$ alkyl), —S(O)$_2$—(C$_1$-C$_4$ alkyl), —C(O)—(C$_1$-C$_4$ alkylene)-C(O)C(O)N(R$^6$) (C$_1$-C$_6$ alkyl), —C(O)—(C$_1$-C$_4$ alkylene)-N(R$^6$)S(O)$_2$—(C$_1$-C$_6$ alkyl), or —C(O)—(C$_1$-C$_4$ alkylene)-N(R$^6$)S(O)$_2$Q, wherein:
any alkylene moiety present in R$^5$ is optionally substituted with OH or F;
any terminal methyl moiety present in R$^5$ is optionally replaced with —CH$_2$OH, CF$_3$, —CH$_2$F, —CH$_2$Cl, C(O)CH$_3$, or C(O)CF$_3$;
each R$^6$ is independently selected from hydrogen and methyl;
Q is selected from aryl, heteroaryl, carbocyclyl and heterocyclyl; and Q is optionally substituted with up to 3 substituents independently selected from C$_1$-C$_4$ alkyl, C$_1$-C$_4$ alkoxy, —CN, fluoro, chloro, and bromo;
each R$^7$ is independently -G-L-M;
G is a bond or a bivalent C$_1$-C$_6$ saturated or unsaturated, straight or branched hydrocarbon chain wherein optionally one, two or three methylene units of the hydrocarbon chain are independently replaced by —NR$^8$—, —O—, —C(O)—, —OC(O)—, —C(O)O—, —S—, —SO—, —SO$_2$—, —C(=S)—, —C(=NR$^8$)—, —N=N—, or —C(=N$_2$)—;
L is a covalent bond or a bivalent C$_{1-8}$ saturated or unsaturated, straight or branched, hydrocarbon chain, wherein one, two, or three methylene units of L are optionally and independently replaced by cyclopropylene, —NR$^8$—, —N(R$^8$)C(O)—, —C(O)N(R$^8$)—, —N(R$^8$)SO$_2$—, SO$_2$N(R$^8$)—, —O—, —C(O)—, —OC(O)—, —C(O)O—, —S—, —SO—, —SO$_2$—, —C(=S)—, —C(=NR$^8$)—, —N=N—, or —C(=N$_2$)—;
M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, NO$_2$, halogen, CN, C$_1$-C$_6$ alkyl, C$_2$-C$_6$ alkenyl, or C$_2$-C$_6$ alkynyl;

D is a covalent bond or a bivalent $C_1$-$C_6$ saturated or unsaturated, straight or branched, hydrocarbon chain, wherein one or two methylene units of D are optionally and independently replaced by —$NR^8$—, —S—, —O—, —C(O)—, —SO—, or —$SO_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN;

each $R^8$ is independently hydrogen, $C_1$-$C_6$ alkyl, $C_2$-$C_6$ alkenyl, $C_2$-$C_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; and m is 0, 1, 2 or 3;

provided that:

when X is —C(CN)—, Y is —N($R^5$)—, m is 0, $R^2$ is phenyl or $C_2$-$C_4$ alkyl, and Z is —O— or —S—, then each $R^1$ is not simultaneously methyl; and when X is —C(CN)—, Y is —N($R^5$)—, m is 0, $R^2$ is phenyl or $C_2$-$C_4$ alkyl, and Z is —$CH_2$—, then each $R^1$ is not simultaneously hydrogen.

2. The compound of claim 1 or a pharmaceutically acceptable salt thereof, wherein X is —C(CN)—.

3. The compound of claim 2 or a pharmaceutically acceptable salt thereof, wherein Z is —O—.

4. The compound of claim 1 or a pharmaceutically acceptable salt thereof, wherein each $R^1$ is the same and is selected from methyl and hydrogen.

5. The compound of claim 1 or a pharmaceutically acceptable salt thereof, wherein Y is —N($R^5$)—.

6. The compound of claim 1 or a pharmaceutically acceptable salt thereof, wherein $R^2$ is selected from phenyl optionally substituted with a single fluoro or a single methyl, cyclohexyl, cyclopentyl, cyclobutyl, cyclopropyl optionally substituted with a single methyl, isopropyl, ethyl and methyl.

7. The compound of claim 6 or a pharmaceutically acceptable salt thereof, wherein $R^2$ is selected from cyclohexyl, cyclobutyl, cyclopropyl, ethyl and isopropyl.

8. The compound of claim 7 or a pharmaceutically acceptable salt thereof, wherein $R^2$ is cyclohexyl; Z is —O—; and each $R^1$ is hydrogen.

9. The compound of claim 7 or a pharmaceutically acceptable salt thereof, wherein $R^2$ is selected from cyclobutyl, cyclopropyl, ethyl and isopropyl; Z is —O—; and each $R^1$ is methyl.

10. The compound of claim 1 or a pharmaceutically acceptable salt thereof, wherein $R^5$ is selected from —C(O)—($C_1$-$C_4$ alkyl), —C(O)—($CH_2$)$_{0-2}$-Q, —C(O)—($CH_2$)$_{1-2}$—O—($CH_2$)$_{0-2}$-Q, —C(O)—($C_1$-$C_4$ alkylene)-C(O)—O—($C_1$-$C_4$ alkyl), —C(O)—N($R^6$)—($C_1$-$C_4$ alkylene)-C(O)—O—($C_1$-$C_4$ alkyl), —C(O)—($CH_2$)$_{0-2}$—N($R^6$)—($C_2$-$C_6$ alkenyl), —C(O)—($CH_2$)$_{1-2}$—O—($C_1$-$C_4$ alkyl), —C(O)—O—($C_1$-$C_4$ alkylene)-O—($C_1$-$C_4$ alkyl), —($CH_2$)$_{0-4}$—C(O)—O—(C1-C4 alkyl), and —C(O)—($CH_2$)$_{1-2}$—S—($C_1$-$C_4$ alkyl).

11. The compound of claim 1, having Structural Formula II or a pharmaceutically acceptable salt thereof, wherein:

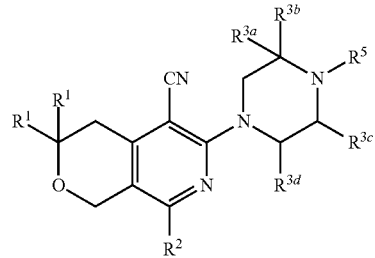

(II)

each $R^1$ is the same and is selected from hydrogen and methyl;

$R^2$ is selected from phenyl optionally substituted with a single fluoro or a single methyl, cyclohexyl, cyclopentyl, cyclobutyl, cyclopropyl optionally substituted with a single methyl, and isopropyl;

$R^{3a}$ is selected from hydrogen and methyl;

$R^{3b}$ is selected from hydrogen, methyl, ethyl, isobutyl, isopropyl, phenyl, —C(O)—O—$CH_2CH_3$, —C(O)—O—$CH_3$, and —$CH_2$—O—$CH_3$;

$R^{3c}$ is selected from hydrogen and methyl; and $R^{3d}$ is selected from hydrogen, phenyl and methyl, wherein one of $R^{3a}$, $R^{3b}$, $R^{3c}$, and $R^{3d}$ is not hydrogen.

12. The compound of claim 11 or a pharmaceutically acceptable salt thereof, wherein:

each $R^1$ is methyl; and $R^2$ is selected from ethyl, isopropyl, cyclopropyl and cyclobutyl.

13. The compound of claim 12 or a pharmaceutically acceptable salt thereof, wherein:

$R^{3a}$, $R^{3c}$ and $R^{3d}$ are simultaneously hydrogen; and $R^{3b}$ is selected from (R)-methyl, (R)-ethyl, (R)-isopropyl, and C(O)—O—$CH_2CH_3$.

14. The compound of claim 13 or a pharmaceutically acceptable salt thereof, wherein $R^{3a}$, $R^{3c}$ and $R^{3d}$ are simultaneously hydrogen; and $R^{3b}$ is (R)-methyl.

15. The compound of claim 11 or a pharmaceutically acceptable salt thereof, wherein:

each $R^1$ is hydrogen; and $R^2$ is cyclohexyl.

16. The compound of claim 11 or a pharmaceutically acceptable salt thereof, wherein $R^5$ is selected from —C(O)—(CH2)$_{0-2}$—$OCH_3$, —C(O)—$CH_2$—$OCH_2CH_3$, —C(O)-furanyl, —C(O)—NH—$CH_2$—CH=$CH_2$, —C(O)—($CH_2$)$_{1-2}$—C(O)—$OCH_3$, —C(O)—($CH_2$)$_2$—$SCH_3$, —C(O)-cyclopropyl, —C(O)—$CH_2$-cyclopropyl, —C(O)—$CH_2CH_3$, —C(O)—($CH_2$)$_2CH_3$, —C(O)—$CH_2Cl$, —C(O)—NH—$CH_3$, —C(O)—$CH_2$-thienyl, —C(O)—NH—($CH_2$)$_2$—C(O)—$OCH_3$, —C(O)—$CH_2$-pyridinyl, —C(O)—($CH_2$)$_2$—O-phenyl, —C(O)—$CH_2$-pyrazolyl, and —C(O)-oxazolyl.

17. A pharmaceutical composition comprising a compound of claim 1 or a pharmaceutically acceptable salt thereof, and a pharmaceutically acceptable carrier.

18. The pharmaceutical composition of claim 17, further comprising a second therapeutic agent.

19. A method of treating a cancer with an IDH1 R132X mutation, the method comprising the step of administering to the patient in need thereof a pharmaceutical composition of claim 17, wherein the cancer is selected from glioma, acute myelogenous leukemia (AML), acute lymphoblastic leukemia (ALL), sarcoma, melanoma, lung cancer, cholangiocarcinoma, myelodysplastic syndrome (MDS), myeloproliferative neoplasm (MPN), colon cancer, prostate cancer and angio-immunoblastic non-Hodgkin's lymphoma (NHL).

20. The method of claim 19, wherein the IDH1 R132X mutation is an IDH1 R132H mutation.

21. The method of claim 20, wherein the cancer is selected from glioblastoma, paraganglioma, non-small cell lung cancer, and chondrosarcoma.

22. The method of claim 19, further comprising administering to the patient in need thereof a second therapeutic agent.

* * * * *

UNITED STATES PATENT AND TRADEMARK OFFICE
CERTIFICATE OF CORRECTION

PATENT NO. : 9,662,327 B2
APPLICATION NO. : 14/126791
DATED : May 30, 2017
INVENTOR(S) : Sheldon Cao et al.

It is certified that error appears in the above-identified patent and that said Letters Patent is hereby corrected as shown below:

Under the Applicant data, replace:

"Cao; Sheldon           San Diego        CA    US
Popovici-Muller; Janeta Windham          NH    US
Salituro; Francesco G.  Marlborough      MA    US
Saunders; Jeffrey O.    Lincoln          MA    US
Tan; Xuefei             Shanghai         N/A   CN
Travins; Jeremy         Southborough     MA    US
Yan; Shunqi             Irvine           CA    US
Ye; Zhixiong            West Windsor     NJ    US"

With:
--AGIOS PHARMACEUTICALS, INC, Cambridge, MA (US)--

Signed and Sealed this
Third Day of October, 2017

Joseph Matal
*Performing the Functions and Duties of the
Under Secretary of Commerce for Intellectual Property and
Director of the United States Patent and Trademark Office*